(12) United States Patent
Nielsen et al.

(10) Patent No.: US 9,051,290 B2
(45) Date of Patent: Jun. 9, 2015

(54) BIARYL PHOSPHODIESTERASE INHIBITORS

(75) Inventors: Simon Feldbæk Nielsen, Ballerup (DK);
Anne Marie Horneman, Ballerup (DK);
Jesper Lau, Farum (DK); Jens Christian Højland Larsen, Ballerup (DK)

(73) Assignee: LEO PHARMA A/S, Ballerup (DK)

( * ) Notice: Subject to any disclaimer, the term of this patent is extended or adjusted under 35 U.S.C. 154(b) by 0 days.

(21) Appl. No.: 13/643,679

(22) PCT Filed: Apr. 28, 2011

(86) PCT No.: PCT/DK2011/000037
§ 371 (c)(1),
(2), (4) Date: Nov. 20, 2012

(87) PCT Pub. No.: WO2011/134468
PCT Pub. Date: Nov. 3, 2011

(65) Prior Publication Data
US 2013/0059853 A1     Mar. 7, 2013

Related U.S. Application Data

(60) Provisional application No. 61/328,920, filed on Apr. 28, 2010.

(51) Int. Cl.
| | | |
|---|---|---|
| A61K 31/5375 | (2006.01) |
| C07C 49/755 | (2006.01) |
| A61K 31/122 | (2006.01) |
| A61P 17/00 | (2006.01) |
| A61P 17/06 | (2006.01) |
| A61P 35/00 | (2006.01) |
| A61P 17/14 | (2006.01) |
| C07C 317/22 | (2006.01) |
| C07D 305/06 | (2006.01) |
| A61K 31/337 | (2006.01) |
| C07C 235/42 | (2006.01) |
| A61K 31/166 | (2006.01) |
| C07C 311/29 | (2006.01) |
| A61K 31/18 | (2006.01) |
| C07D 307/88 | (2006.01) |
| A61K 31/365 | (2006.01) |
| C07D 407/12 | (2006.01) |
| C07D 209/46 | (2006.01) |
| A61K 31/4035 | (2006.01) |
| C07D 405/12 | (2006.01) |
| C07D 265/30 | (2006.01) |
| C07D 307/83 | (2006.01) |

(Continued)

(52) U.S. Cl.
CPC ............. C07D 307/83 (2013.01); C07D 233/34 (2013.01); C07D 233/36 (2013.01); C07D 305/06 (2013.01); C07D 209/46 (2013.01); C07C 49/755 (2013.01); C07C 235/48 (2013.01); C07C 311/29 (2013.01); C07D 307/88 (2013.01)

(58) Field of Classification Search
CPC .. C07D 233/34; C07D 233/36; C07D 305/06; C07D 307/88; C07D 209/46; C07C 49/755; C07C 235/48; C07C 311/39
USPC .......................................... 548/324.1, 323.5
See application file for complete search history.

(56) References Cited

U.S. PATENT DOCUMENTS

| 6,376,535 B2 | 4/2002 | Ohshima et al. |
| 2001/0056117 A1 | 12/2001 | Ohshima et al. |
| 2002/0128290 A1 | 9/2002 | Ohshima et al. |

FOREIGN PATENT DOCUMENTS

| EP | 1 110 961 A1 | 6/2001 |
| WO | WO 94/10118 A1 | 5/1994 |

(Continued)

OTHER PUBLICATIONS

Kende et al. An Unusual Rearrangment During Pyridine Synthesis. Anamolous Condensation of a Beta-Keto Enamine With a Tetronic Acid. Tetrahedron Lett. 1984, 25, 2423-2426.*

(Continued)

*Primary Examiner* — Joseph Kosack
*Assistant Examiner* — Amanda L Aguirre
(74) *Attorney, Agent, or Firm* — Birch, Stewart, Kolasch & Birch, LLP

(57) ABSTRACT

Novel biaryl compounds with phosphodiesterase inhibitory activity of general formula (I) below, wherein R1, R2, R3, X, Y, $Z_1$, $Z_2$, $Z_3$, and $Z_4$ have the meanings defined herein, as well as their use as therapeutic agents in the treatment of inflammatory diseases and conditions are described herein.

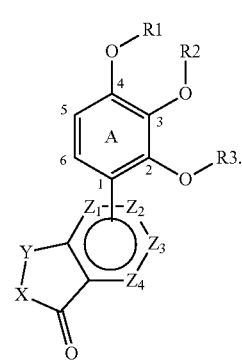

31 Claims, No Drawings

(51) Int. Cl.
*C07D 233/34* (2006.01)
*C07D 233/36* (2006.01)
*C07C 235/48* (2006.01)

(56) References Cited

FOREIGN PATENT DOCUMENTS

| WO | WO 94/12461 A1 | 6/1994 |
|---|---|---|
| WO | WO 95/22520 A1 | 8/1995 |
| WO | WO 95/27692 A1 | 10/1995 |
| WO | WO 00/14085 A1 | 3/2000 |
| WO | WO 03/061655 A1 | 7/2003 |
| WO | WO 2009/006315 A1 | 1/2009 |

OTHER PUBLICATIONS

Saxena et al. Gallic Acid-Based Indanone Derivatives as Anticancer Agents. Bioorg. Med. Chem. Lett. 2008, 18, 3914-3918.*

Boyé et al., "185. Deaminocolchinyl Methyl Ether: Synthesis from 2,3,4,4'-Tetramethoxybiphenyl-2-carbaldehyde. Comparison of Antitubulin Effects of Deaminocolchinyl Methyl Ether and Dehydro Analogs", Helvetica Chimica Acta, XP-002651892, vol. 72, No. 8, pp. 1690-1696, 1989.

Chordia et al., "6-Aryl-8H-indeno[1,2-d]thiazol-2-ylamines: A1 Adenosine Receptor Agonist Allosteric Enhancers Having Improved Potency", Journal of Medicinal Chemistry, XP-002651893, vol. 48, No. 16, pp. 5131-5139, 2005.

International Search Report, dated Aug. 5, 2011, issued in PCT/DK2011/000037.

Wei et al., "Two New Compounds From *Phyllanthus niruri*", Chemistry of Natural Compounds, XP-002651894, vol. 40, No. 5, pp. 460-464, 2004.

Written Opinion of the International Searching Authority, dated Aug. 5, 2011, issued in PCT/DK2011/000037.

Holden et al., "Monocyte Localization of Elevated cAMP Phosphodiesterase Activity in Atopic Dermatitis," Journal of Investigative Dermatology, vol. 87, No. 3, Sep. 1986, pp. 372-376.

Houslay et al., "Keynote Review: Phosphodiesterase-4 as a therapeutic target," Drug Discovery Today, vol. 10, No. 22, Nov. 2005, pp. 1503-1519.

Huang et al., "Phosphodiesterase 4 Inhibitors for the Treatment of Asthma and COPD," Current Medicinal Chemistry, vol. 13, No. 27, 2006, pp. 3253-3262.

Kroegel et al., "Phosphodiesterase-4 inhibitors as a novel approach for the treatment of respiratory disease: cilomilast," Expert Opin. Investig. Drugs, vol. 16, No. 1, 2007, pp. 109-124.

Lipworth, "Phosphodiesterase-4 inhibitors for asthma and chronic obstructive pulmonary disease," Lancet, vol. 365, Jan. 8, 2005, pp. 167-175.

Smith et al., "Selective phosphodiesterase 4 inhibitors in the treatment of allergy and inflammation," Current Opinion in Investigational Drugs, vol. 6, No. 11, 2005, pp. 1136-1141.

* cited by examiner

BIARYL PHOSPHODIESTERASE INHIBITORS

FIELD OF THE INVENTION

The present invention relates to novel compounds with phosphodiesterase inhibitory activity, as well as to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes (Z. Huang and J. A. Mancini, Current Med. Chem. 13, 2006, pp. 3253-3262). As cAMP is a key second messenger in the modulation of inflammatory responses, PDE4 has been found to regulate inflammatory responses of inflammatory cells by modulating proinflammatory cytokines such as TNFα, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, inflammatory bowel disease such as Crohn's disease etc. (M. D. Houslay et al., Drug Discovery Today 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, Curr. Opinion Investig. Drugs 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, Exp. Opinion Investig. Drugs 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, Lancet 365, 2005, pp. 167-175). However, the PDE inhibitors developed so far are not believed to be specific for any of the four PDE4 isoforms.

Numerous PDE4 inhibitors have been studied for their therapeutic effect on inflammatory diseases, primarily asthma and COPD.

The first of these, theophylline, is a weak, non-selective phosphodiesterase inhibitor used in the treatment of respiratory diseases such as asthma and COPD. Treatment with theophylline may, however, give rise to both mild and severe adverse effects, e.g. arrhythmia and convulsions, restricting the clinical utility of theophylline (Kroegel and Foerster, supra). As phosphodiesterase has remained an attractive target for anti-inflammatory therapy, several other, more selective PDE4 inhibitors have been developed and investigated in a clinical setting. The clinical development of many of the first-generation PDE4 inhibitors such as rolipram was discontinued due to dose-limiting side effects, primarily nausea and emesis. Second-generation PDE4 inhibitors with apparently less pronounced adverse effects are currently in clinical trials (Houslay, supra).

WO9410118 discloses tri-substituted phenyl derivatives which may be di-alkoxy substituted, for use as PDE4 inhibitors.

WO9412461 discloses 4-substituted catechol diether compounds as selective PDE4 inhibitors.

WO 9522520 discloses substituted biphenyl derivatives which may be di-alkoxy substituted, for use as PDE4 inhibitors.

WO9527692 discloses substituted biphenyl TNF inhibitors or PDE4 inhibitors.

US2001/0056117, US2002/0128290 and WO2000014085 disclose tri-alkoxy substituted biaryl PDE4 inhibitors, wherein two of the alkoxy substituents are connected to form a ring, thus rigidifying the molecule.

SUMMARY OF THE INVENTION

The inventors have surprisingly found that novel compounds of the present invention which are tri-alkoxy substituted biaryl PDE4 inhibitors, but in which the alkoxy substituents are not connected in a ring system exhibit PDE4 inhibitory activity.

Thus, the compounds may be useful as therapeutic agents for inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

Compounds of the present invention may also be beneficial in preventing, treating or ameliorating a variety of diseases, such as dermal diseases or conditions, such as proliferative and inflammatory skin disorders and in particular psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Accordingly, the present invention relates to a compound according to formula I

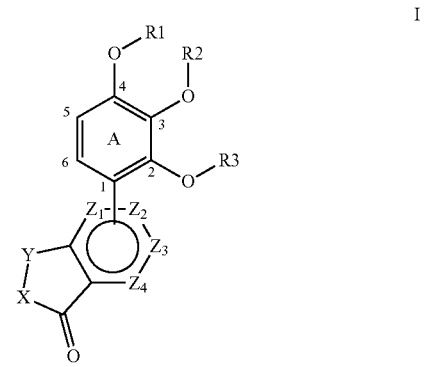

wherein R1 is alkyl, deuterioalkyl, alkenyl, alkynyl, cycloalkyl, heterocycloalkyl, alkylcarbonyl, each of which is optionally substituted with one or more substituents selected from halogen, cyano, alkyl, alkoxy, hydroxy, oxo;

R2 represents alkyl, deuterioalkyl, alkenyl, alkynyl, cycloalkyl, heterocycloalkyl, cycloalkylalkyl, heterocycloalkylalkyl, arylalkyl, alkoxycarbonylalkyl, alkylcarbonyl, arylcarbonyl, or alkoxyalkyl, each of which is optionally substituted by one or more, same or different substituents selected from R4;

R3 represents alkyl, alkenyl, alkynyl, alkylaryl, arylalkyl, cycloalkyl, heterocycloalkyl, cycloalkylalkyl, heterocycloalkylalkyl, alkylcycloalkylalkyl, alkylheterocycloalkylalkyl, alkylalkoxycarbonyl, alkoxycarbonylalkyl, alkylcarbonyl, arylcarbonyl, alkoxyalkyl, heterocycloalkylcarbonyl, cycloalkylcarbonyl, heteroarylcarbonyl, alkoxyalkylcarbonyl, cycloalkoxycarbonylalkyl or cycloalkoxyalkyl, each of which is optionally substituted by one or more, same or different substituents selected from R4;

R4 represents oxo, halogen, cyano, hydroxy or nitro; or

R4 represents alkylaryl, alkyl, alkenyl, cycloalkenyl, alkynyl, haloalkyl, cycloalkyl, heterocycloalkenyl, heterocycloalkyl, hydroxyalkyl, alkoxyalkyl, aryl or heteroaryl, each of which is optionally substituted by one or more, same or different substituents selected from R7;

or R4 represents, —NRaRb, —ORa, —SRa, —SO$_2$Ra, —S(O)Ra, —SO$_2$NRaRb, —NRa SO$_2$Rb, —OC(O)NRaRb, —NRaC(O)ORb, —NRaC(O)NRbRc, —NRaC(O)Rb, —C(O)NRaRb, —C(O)Ra, —OC(O)Ra, —OC(O)ORa, —C(O)ORa, —P(O)RaRb, P(O)(ORa)ORb, —OP(O)RaRb, —OP(O)(ORa)ORb or NraS(O)$_2$NRbRc;

R7 represents halogen, hydroxy, or oxo; or

R7 represents alkyl, cycloalkyl, heterocycloalkyl, aryl or heteroaryl each of which is optionally substituted by one or more, same or different substituents selected from R8;

or R7 represents —ORd, —SRd, —SO$_2$Rd, —SO$_2$NRdRe, —NRd SO$_2$Re, —NRdC(O)Re, —C(O)NRdRe, OC(O)Re, —C(O)Ord, OC(O)Re or NRdC(O)ORe;

R8 represents alkyl, oxo, hydroxy, halogen, alkoxy or haloalkyl;

Ra, Rb, Rc independently represents hydrogen; or

Ra, Rb and Rc independently represents alkylaryl, alkyl, alkenyl, cycloalkenyl, alkynyl, haloalkyl, cycloalkyl, heterocycloalkenyl, heterocycloalkyl, hydroxyalkyl, alkoxyalkyl, aryl or heteroaryl, each of which is optionally substituted by one or more, same or different substituents selected from R7;

Rd and Re independently represents hydrogen; or

Rd and Re independently represents alkyl, alkenyl, cycloalkyl, cycloalkenyl, alkynyl, haloalkyl, heterocycloalkenyl, heterocycloalkyl, aryl, heteroaryl or hydroxyalkyl, each of which is optionally substituted by one or more, same or different substituents selected from R8;

Position 1 of ring A is connected to either $Z_1$ or $Z_2$;

X and Y are CRfRg, NRh, O or S, wherein Rf and Rg independently represent H, halogen, cyano, hydroxy, alkyl, alkoxy, haloalkyl, haloalkoxy; and Rh represents hydrogen, alkyl or haloalkyl; with the proviso that at least one of X and Y represents CRfRg;

$Z_1$, $Z_2$ $Z_3$ and $Z_4$ independently are CRi or N, wherein Ri represents a bond, hydrogen, alkyl, halogen, alkoxy, cyano, haloalkyl, haloalkoxy, or hydroxy; with the proviso that when position 1 of ring A is connected to $Z_1$ then $Z_1$ is CRi; and when position 1 of ring A is connected to $Z_2$ then $Z_2$ is CRi;

and pharmaceutically acceptable and physiologically cleavable esters, pharmaceutically acceptable salts, hydrates, N-oxides or solvates thereof;

with the proviso that when R1=R2=R3=CH$_3$, X=Y=—CH$_2$—, position 1 of ring A is connected to $Z_2$, then at least one of $Z_1$, $Z_3$, and $Z_4$ is different from CH; and with the proviso that when R1=R2=R3=CH$_3$, X=Y=—CH$_2$—, position 1 of ring A is connected to $Z_1$, $Z_4$ is CRi, then Ri is different from methoxy; and with the proviso that when R1=R2=CH$_3$, R3=benzyl, position 1 of ring A is connected to $Z_2$, $Z_1$ is N, $Z_3$=$Z_4$=CRi, Ri=CH$_3$, X=O, Y=CRfRg, Rf=H, then Rg is different from CH$_3$.

In another aspect, the present invention relates to a compound according to formula I for use in therapy.

In another aspect, the present invention relates to a compound according to formula I for use in the prophylaxis, treatment or amelioration of dermal diseases or conditions or acute or chronic cutaneous wound disorders. It is expected that some compounds of formula I may be particularly suitable for topical cutaneous treatment as they may be susceptible to ester hydrolysis in serum to an inactive form after skin permeation following cutaneous application and therefore less likely to result in undesired systemic side effects such as nausea.

In another aspect, the invention relates to a pharmaceutical composition comprising a compound of general formula I as defined herein and pharmaceutically acceptable and physiologically cleavable esters, pharmaceutically acceptable salts, hydrates, N-oxides or solvates thereof together with a pharmaceutically acceptable vehicle or excipient or pharmaceutically acceptable carrier(s), optionally together with one or more other therapeutically active compound(s).

In yet another aspect, the invention relates to a use of a compound according to formula I as defined herein, and pharmaceutically acceptable and physiologically cleavable esters, pharmaceutically acceptable salts, hydrates, N-oxides or solvates thereof in the manufacture of a medicament for the prophylaxis, treatment or amelioration of dermal diseases or conditions, or acute or chronic cutaneous wound disorders.

In yet another aspect, the invention relates to a method of preventing, treating or ameliorating dermal diseases or conditions, or acute or chronic cutaneous wound disorders, the method comprising administering to a person suffering from at least one of said diseases an effective amount of one or more compounds of formula I as defined herein and pharmaceutically acceptable and physiologically cleavable esters, pharmaceutically acceptable salts, hydrates, N-oxides or solvates thereof; optionally together with a pharmaceutically acceptable carrier or one or more excipients, optionally in combination with other therapeutically active compounds.

In yet another aspect, the present invention relates to a method for the preparation or manufacture of a compound of general formula I comprising a method as anywhere described herein, such as method A, B, C, or D, or such as any one of the general methods or procedures described in the examples or preparations herein, and optionally further processing of a compound obtained, to give a compound of general formula I as anywhere defined herein.

DETAILED DESCRIPTION OF THE INVENTION

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12, e.g. 1-6, e.g. 1-4, e.g. 1-3, e.g. 1-2 carbon atoms. The term includes alkyl, alkenyl, cycloalkyl, cycloalkenyl, alkynyl and aryl, as indicated below.

The term "aryl" is intended to indicate a radical of aromatic carbocyclic rings comprising 6-20 carbon atoms, such as 6-14 carbon atoms, preferably 6-10 carbon atoms, in particular 5- or 6-membered rings, including fused carbocyclic rings with at least one aromatic ring, such as phenyl, naphthyl, indenyl and indanyl.

The term "heteroaryl" is intended to indicate radicals of heterocyclic aromatic rings comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms selected from O, S and N, including fused bicyclic rings with 1-4 heteroatoms, and wherein at least one ring is aromatic, e.g. pyridyl, quinolyl, isoquinolyl, indolyl, thiadiazolyl, oxodiazolyl, tetrazolyl, furanyl, pyridyl, thiazolyl, benzooxazolyl, imidazolyl, pyrazolyl, oxazolyl, isoxazolyl, thienyl, pyrazinyl, isothiazolyl, benzimidazolyl, and benzofuranyl.

In the present context, the term "alkyl" is intended to indicate a radical obtained when one hydrogen atom is removed from a hydrocarbon. Said alkyl comprises 1-20, preferably 1-12, such as 1-6, such as 1-4 or such as 1-3 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "cycloalkyl" is intended to indicate a saturated cycloalkane radical comprising 3-20 carbon atoms, preferably 3-10 carbon atoms, in particular 3-8 carbon atoms, such as 3-6 carbon atoms, including fused bicyclic rings, e.g. cyclopropyl, cyclobutyl, cyclopentyl, cyclohexyl, or cycloheptyl.

The term "heterocycloalkyl" is intended to indicate a cycloalkane radical as described above, wherein one or more carbon atoms are replaced by heteroatoms, comprising 1-20 carbon atoms, e.g. 2-5 or 2-4 carbon atoms, further comprising 1-6 heteroatoms, preferably 1, 2, or 3 heteroatoms, selected from O, N, or S, e.g. piperidinyl, pyrrolidinyl, morpholinyl, oxetanyl, [1,3]dioxolanyl and [1,3]dioxolyl, or including fused bicyclic rings with 1-4 heteroatoms, wherein at least one ring comprises a heteroatom, and wherein the other ring may for example be a carbocyclic ring, e.g. isoindolyl.

The term "alkenyl" is intended to indicate a mono-, di-, tri-, tetra- or pentaunsaturated hydrocarbon radical comprising 2-10 carbon atoms, in particular 2-6 carbon atoms, such as 2-4 carbon atoms, e.g. ethenyl, propenyl (allyl), methylbutenyl, butenyl, pentenyl or hexenyl.

The term "cycloalkenyl" is intended to indicate mono-, di- tri- or tetraunsaturated non-aromatic cyclic hydrocarbon radicals, comprising 3-20 carbon atoms, including fused bicyclic rings, typically comprising 3-10 carbon atoms, such as 3, 4, or 6 carbon atoms, e.g. cyclopropenyl, cyclobutenyl, cyclopentenyl, cyclohexenyl, cylcoheptenyl.

The term "heterocycloalkenyl" is intended to indicate a cycloalkene radical as described above, wherein one or more carbon atoms are replaced by heteroatoms, comprising 1-20 carbon atoms, e.g. 2-4 carbon atoms, further comprising 1-6 heteroatoms, preferably 1, 2, or 3 heteroatoms, selected from O, N, or S, including fused bicyclic rings with 1-4 heteroatoms, wherein at least one ring comprises a heteroatom and wherein the other ring may for example be a carbocyclic ring, e.g. dihydrofuranyl, or 2,5-dihydro-1H-pyrrolyl.

The term "alkynyl" is intended to indicate an hydrocarbon radical comprising 1-5 triple C—C bonds and 2-20 carbon atoms, typically comprising 2-10 carbon atoms, in particular 2-6 carbon atoms, such as 2-4 carbon atoms, e.g. ethynyl, propynyl, butynyl, pentynyl or hexynyl.

The term "halogen" is intended to indicate a substituent from the $7^{th}$ main group of the periodic table, such as fluoro, chloro and bromo.

The term "haloalkyl" is intended to indicate an alkyl group as defined above substituted with one or more halogen atoms as defined above, e.g. fluoro or chloro, such as difluoromethyl, or trifluoromethyl.

The term "alkoxy" is intended to indicate a radical of the formula —OR', wherein R' is alkyl as indicated above, e.g. methoxy, ethoxy, n-propoxy, isopropoxy, butoxy, etc.

The term "hydroxyalkyl" is intended to indicate an alkyl group as defined above substituted with one or more hydroxy, e.g. hydroxymethyl, hydroxyethyl, hydroxypropyl.

The term "deuterioalkyl" is intended to indicate an alkyl group as defined above substituted with one or more deuterium, e.g. deuteriomethyl, dideuteriomethyl, trideuteriomethyl, 2-deuterioethyl, 2,2-dideuterioethyl, 2,2,2-trideuterioethyl or 1,1,2,2,2-pentadeuterioethyl.

The term "amino" is intended to indicate a radical of the formula —NR''$_2$, wherein each R'' independently represents hydrogen, or a hydrocarbon radical as indicated above, e.g. —NH$_2$, dimethylamino, —NHMe, —NHEt, tert.-butylamino.

The term "alkoxycarbonyl" is intended to indicate a radical of the formula —C(O)—O—R', wherein R' is alkyl as indicated above, e.g. methoxycarbonyl, ethoxycarbonyl, n-propoxycarbonyl, isopropoxycarbonyl, tert-butoxycarbonyl etc.

The term "alkoxycarbonylalkyl" is intended to indicate a radical of the formula —R—C(O)—O—R', wherein R and R' are alkyl groups as indicated above, e.g. methoxycarbonylmethyl, ethoxycarbonylmethyl, n-propoxycarbonylethyl, isopropoxycarbonylethyl, tert-butoxycarbonylmethyl etc.

The term "cycloalkoxycarbonylalkyl" is intended to indicate a radical of the formula —R—C(O)—O—R', wherein R is an alkyl group as indicated above and R' is a cycloalkyl group as indicated above.

The term "alkylcarbonyl" is intended to indicate a radical of the formula —C(O)—R', wherein R' is alkyl as indicated above, e.g. acetyl.

The term "alkylcarbonyloxy" is intended to indicate a radical of the formula —O—C(O)—R', wherein R' is alkyl as indicated above.

The term "alkoxycarbonyloxy" is intended to indicate a radical of the formula —O—C(O)—O—R', wherein R' is alkyl as indicated above.

The term "heterocycloalkylcarbonyl" is intended to indicate a radical of the formula —C(O)—R', wherein R' is heterocycloalkyl as indicated above.

The term "cycloalkylcarbonyl" is intended to indicate a radical of the formula —C(O)—R', wherein R' is cycloalkyl as indicated above.

The term "heteroarylcarbonyl" is intended to indicate a radical of the formula —C(O)—R', wherein R' is heteroaryl as indicated above.

The term "alkoxyalkylcarbonyl" is intended to indicate a radical of the formula —C(O)—R'—O—R, wherein R' and R are alkyl as indicated above.

The term "cycloalkoxyalkylcarbonyl" is intended to indicate a radical of the formula —C(O)—R'—O—R, wherein R' is alkyl and R is cycloalkyl as indicated above.

The term "cycloalkylcarbonyl" is intended to indicate a radical of the formula —C(O)—R, wherein R is cycloalkyl as indicated above.

The term "heterocycloalkylcarbonyl" is intended to indicate a radical of the formula —C(O)—R'', wherein R'' is heterocycloalkyl as indicated above.

The term "cycloalkoxyalkyl" is intended to indicate a radical of the formula wherein R' is alkyl and R is cycloalkyl as indicated above.

The term "heterocyclic ring" is intended to include the definitions heteroaryl, heterocycloalkyl and heterocylcoalkenyl as defined above, including annelated ring systems with each other or with cyclic hydrocarbons, e.g. 2,5-dihydrobenzo(b)dioxocine, 2,3,5,8-tetrahydro-[1,4]dioxocine, 5,8-dihydro-[1,4]dioxocine, 2,3-dihydro-1H-isoindole.

The term "alkylaryl" is intended to indicate an aryl radical as defined above, which is substituted with an alkyl radical as defined above, e.g. tolyl (=toloyl), ethylbenzene, etc.

The term "arylalkyl" is intended to indicate an alkyl radical as defined above, which is substituted with an aryl radical as defined above, e.g. benzyl, phenylethyl, naphthylmethyl, etc.

The term "alkoxyalkyl" is intended to indicate an alkyl radical as defined above, which is substituted with an alkoxy radical as defined above, i.e. —R'—O—R', wherein each R' is alkyl, same or different, as indicated above, e.g. methoxymethyl, ethoxymethyl.

The term "aryloxy" is intended to indicate —O—R''', wherein R''' is aryl as indicaetd above, e.g. phenoxy.

The term "arylcarbonyl" is intended to indicate —C(O)—R'''', wherein R'''' is an aryl radical as defined above, e.g. benzoyl, naphthylcarbonyl.

When two or more of the above defined terms are used in combination, such as arylalkyl, heteroarylalkyl, cycloalkylalkyl and the like, it is to be understood that the first mentioned radical is a substituent on the latter mentioned radical, where the point of attachment to another part of the molecule, is on the latter radical.

Thus, the term "cycloalkylalkyl" is intended to indicate a radical of the formula —R'-cycloalkyl, wherein R' is alkyl as defined above such as;

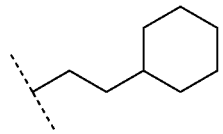

The term "alkylcycloalkylalkyl" is intended to indicate a radical of the formula —R'-cycloalkyl-R, wherein R and R' are alkyl as defined above.

The term "alkylheterocycloalkylalkyl" is intended to indicate a radical of the formula —R'-heterocycloalkyl-R, wherein R and R' are alkyl as defined above.

The term "arylalkyl" is intended to indicate a radical of the formula —R'—Ar, wherein R' is alkyl as defined above and Ar is aryl as defined above such as;

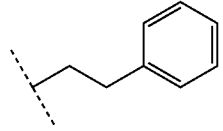

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylene-diamine, and dibenzylamine, or L-arginine or L-lysine. Salts obtained by reaction with a suitable base include, but are not limited to sodium salts, choline salts, 2-(dimethylamino)-ethanol salts, 4-(2-hydroxyethyl)-morpholin salts, L-lysine salts, N-(2-hydroxyethyl)-pyrrolidine salts, ethanolamine salts, potassium salts, tetrabutylammonium salts, benzyltrimethylammonium salts, cetyltrimethylammonium salts, tetramethylammonium salts, tetrapropylammonium salts, tris(hydroxymethyl)aminomethane salts, N-methyl-D-glucamine salts, silver salts, benzethonium salts, and triethanolamine salts.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

Compounds of the invention which comprise free hydroxyl groups or free carboxylic acid groups may also exist in the form of pharmaceutically acceptable, physiologically cleavable esters, and as such are included within the scope of the present invention. Such pharmaceutically acceptable esters are preferably prodrug ester derivatives, such being convertible by solvolysis or cleavage under physiologically conditions to the corresponding compounds of the invention which comprise free hydroxyl groups or free carboxylic acid groups respectively, e.g. in-vivo hydrolysable.

Embodiments of the Present Invention

In an embodiment, the compound of the invention is of general formula I

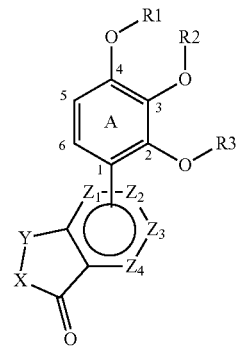

wherein R1 is alkyl, alkenyl, alkynyl, cycloalkyl, heterocloalkyl, alkylcarbonyl, each of which is optionally substituted with one or more substituents selected from halogen, cyano, alkyl, alkoxy, hydroxy, oxo;

R2 represents alkyl, alkenyl, alkynyl, cycloalkyl, heterocycloalkyl, cycloalkylalkyl, heterocycloalkylalkyl, arylalkyl, alkoxycarbonylalkyl, alkylcarbonyl, arylcarbonyl, or alkoxyalkyl, each of which is optionally substituted by one or more, same or different substituents selected from R4;

R3 represents alkyl, alkenyl, alkynyl, alkylaryl, arylalkyl, cycloalkyl, heterocycloalkyl, cycloalkylalkyl, heterocycloalkylalkyl, alkylcycloalkylalkyl, alkylheterocycloalkylalkyl, alkylalkoxycarbonyl, alkoxycarbonylalkyl, alkylcarbonyl, arylcarbonyl, or alkoxyalkyl, each of which is optionally substituted by one or more, same or different substituents selected from R4;

R4 represents oxo, halogen, cyano, hydroxy or nitro; or

R4 represents alkylaryl, alkyl, alkenyl, cycloalkenyl, alkynyl, haloalkyl, cycloalkyl, heterocycloalkenyl, heterocycloalkyl, hydroxyalkyl, alkoxyalkyl, aryl or heteroaryl, each of which is optionally substituted by one or more, same or different substituents selected from R7;

or R4 represents, —NRaRb, —ORa, —SRa, —SO$_2$Ra, —S(O)Ra, —SO$_2$NRaRb, —NRa SO$_2$Rb, —OC(O)NRaRb, —NRaC(O)ORb, —NRaC(O)NRbRc, —NRaC(O)Rb, —C(O)NRaRb, —C(O)Ra, OC(O)Ra, OC(O)ORa, or C(O)ORa;

R7 represents halogen, hydroxy, or oxo; or

R7 represents alkyl, cycloalkyl, heterocycloalkyl, aryl or heteroaryl each of which is optionally substituted by one or more, same or different substituents selected from R8; or R7 represents —ORd, —SO$_2$Rd, —SO$_2$NRdRe, —NRd SO$_2$Re, —NRdC(O)Re, —C(O)NRdRe, OC(O)Re, or —C(O)ORd;

R8 represents alkyl, oxo, hydroxy, halogen, alkoxy or haloalkyl;

Ra, Rb, Rc independently represents hydrogen; or

Ra, Rb and Rc independently represents alkylaryl, alkyl, alkenyl, cycloalkenyl, alkynyl, haloalkyl, cycloalkyl, heterocycloalkenyl, heterocycloalkyl, hydroxyalkyl, alkoxyalkyl, aryl or heteroaryl, each of which is optionally substituted by one or more, same or different substituents selected from R7;

Rd and Re independently represents hydrogen; or

Rd and Re independently represents alkyl, alkenyl, cycloalkyl, cycloalkenyl, alkynyl, haloalkyl, heterocycloalkenyl, heterocycloalkyl, aryl, heteroaryl or hydroxyalkyl, each of which is optionally substituted by one or more, same or different substituents selected from R8;

Position 1 of ring A is connected to either $Z_1$ or $Z_2$;

X and Y are CRfRg, NRh, O or S, wherein Rf and Rg independently represent H, halogen, cyano, hydroxy, alkyl, alkoxy, haloalkyl, haloalkoxy; and Rh represents hydrogen, alkyl or haloalkyl; with the proviso that at least one of X and Y represents CRfRg;

$Z_1$, $Z_2$ $Z_3$ and $Z_4$ independently are CRi or N, wherein Ri represents a bond, hydrogen, alkyl, halogen, alkoxy, cyano, haloalkyl, haloalkoxy, or hydroxy; with the proviso that when position 1 of ring A is connected to $Z_1$ then $Z_1$ is CRi; and when position 1 of ring A is connected to $Z_2$ then $Z_2$ is CRi;

and pharmaceutically acceptable and physiologically cleavable esters, pharmaceutically acceptable salts, hydrates, N-oxides or solvates thereof;

with the proviso that when R1=R2=R3=CH$_3$, X=Y=—CH$_2$—, position 1 of ring A is connected to $Z_2$, then at least one of $Z_1$, $Z_3$, and $Z_4$ is different from CH; and with the proviso that when R1=R2=R3=CH$_3$, X=Y=—CH$_2$—, position 1 of ring A is connected to $Z_1$, Z4 is CRi, then Ri is different from methoxy; and with the proviso that when R1=R2=CH$_3$, R3=benzyl, position 1 of ring A is connected to $Z_2$, $Z_1$ is N, $Z_3$=$Z_4$=CRi, R1=CH$_3$, X=O, Y=CRfRg, Rf=H, then Rg is different from CH$_3$.

In an embodiment the compound according to the invention is of the general formula Ia

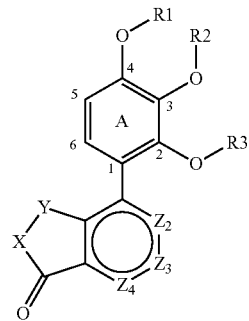

In an embodiment the compound according to the invention is of the general formula Ib

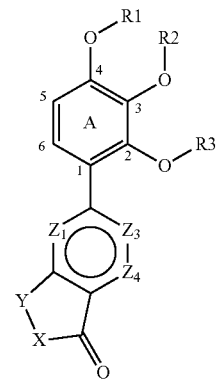

In an embodiment of the compound according to the invention R1 is alkyl, deuterioalkyl, cycloalkyl, or alkylcarbonyl, each of which is optionally substituted with one or more substituents selected from halogen, alkoxy, or oxo;

R2 represents alkyl, deuterioalkyl, cycloalkyl, heterocycloalkyl, cycloalkylalkyl, heterocycloalkylalkyl, alkylheterocycloalkylalkyl or arylalkyl, each of which is optionally substituted by one or more, same or different substituents selected from R4;

R3 represents alkyl, arylalkyl, cycloalkyl, cycloalkylalkyl, heterocycloalkylalkyl, alkylcycloalkylalkyl, alkylheterocycloalkylalkyl, alkoxyalkylcarbonyl, alkylheterocycloalkylalkyl, cycloalkoxycarbonylalkyl, alkylcarbonyl, cycloalkylcarbonyl or alkoxycarbonylalkyl, each of which is optionally substituted by one or more, same or different substituents selected from R4;

R4 represents oxo, halogen, cyano, or hydroxy; or

R4 represents alkyl, cycloalkyl, heterocycloalkyl, aryl or heteroaryl, each of which is optionally substituted by one or more, same or different substituents selected from R7; or R4 represents, —NRaRb, —ORa, —SO$_2$Ra, —S(O)Ra, —SO$_2$NRaRb, —NRaSO$_2$Rb, —OC(O)NRaRb, —NRaC(O)ORb, —NRaC(O)Rb, —C(O)NRaRb, —OC(O)Ra, or C(O)ORa;

R7 represents cyano, halogen or hydroxy; or

R7 represents alkyl or heterocycloalkyl, each of which is optionally substituted by one or more, same or different substituents selected from R8;

or R7 represents —ORd, —SRd, —SO$_2$Rd, —SO$_2$NRdRe, —NRdSO$_2$Re, —NRdC(O)Re, —C(O)NRdRe, OC(O)Re, or —C(O)ORd;

R8 represents alkyl, hydroxy, or halogen;

Ra, Rb, Rc independently represents hydrogen; or

Ra, Rb and Rc independently represents alkyl, cycloalkyl, heterocycloalkyl, aryl or heteroaryl, each of which is optionally substituted by one or more, same or different substituents selected from R7;

Rd and Re independently represents hydrogen; or

Rd and Re independently represents alkyl, cycloalkyl, heterocycloalkyl, aryl, or heteroaryl, each of which is optionally substituted by one or more, same or different substituents selected from R8;

Position 1 of ring A is connected to either $Z_1$ or $Z_2$;

X and Y are CRfRg, NRh, O or S, wherein Rf and Rg independently represent H, halogen, cyano, alkyl, or alkoxy; and Rh represents hydrogen or alkyl; with the proviso that at least one of X and Y represents CRfRg;

$Z_1$, $Z_2$, $Z_3$ and $Z_4$ independently are CRi or N, wherein Ri represents a bond, hydrogen, alkyl, halogen, or alkoxy; with the proviso that when position 1 of ring A is connected to $Z_1$ then $Z_1$ is CRi; and when position 1 of ring A is connected to $Z_2$ then $Z_2$ is CRi.

In an embodiment of the compound according to the invention R1 is methyl, ethyl or difluoromethyl.

In an embodiment of the compound according to the invention R2 is methyl, ethyl, cyclopropylmethyl, isobutyl or difluoromethyl.

In an embodiment of the compound according to the invention R3 is alkyl, arylalkyl, cycloalkylalkyl, heterocycloalkylalkyl, alkylcycloalkylalkyl, alkylheterocycloalkylalkyl, alkoxyalkylcarbonyl, cycloalkoxycarbonylalkyl, alkylcarbonyl, cycloalkylcarbonyl or alkoxycarbonylalkyl each of which is optionally substituted by one or more, same or different substituents selected from R4.

In an embodiment of the compound according to the invention R3 is isobutyl, neopentyl, benzyl, 1-methyl-cyclopropylmethyl, 3-methyl-oxetan-3-ylmethyl, 3,3-dimethylbutyl, isopentyl, cyclobutylmethyl, or 1-methyl-cyclobutylmethyl each of which is optionally substituted by one or more, same or different substituents selected from R4.

In an embodiment of the compound according to the invention R4 is selected from the group consisting of hydroxy, —NRaRb, —ORa, —SO₂Ra, —OC(O)NRaRb, —C(O)NRaRb, —OC(O)Ra, SO₂NRaRb, —NRaSO₂Rb, —NRaC(O)ORb, —NRaC(O)Rb, or C(O)ORa.

In an embodiment of the compound according to the invention Ra, Rb and Rc independently represent hydrogen or alkyl, wherein said alkyl is optionally substituted by one or more substituents selected from halogen, hydroxy and alkoxy.

In an embodiment of the compound according to the invention Ra, Rb and Rc independently represent hydrogen or ($C_1$-$C_5$)alkyl wherein said alkyl is optionally substituted by ($C_1$-$C_5$)alkoxy.

In an embodiment of the compound according to the invention X is CRfRg, NRh, or O.

In an embodiment of the compound according to the invention Y is CRfRg.

In an embodiment of the compound according to the invention Rf, Rg and Rh independently represent hydrogen or alkyl.

In an embodiment of the compound according to the invention Rf, Rg and Rh independently represent hydrogen or ($C_1$-$C_2$)alkyl.

In an embodiment of the compound according to the invention $Z_1$, $Z_2$ $Z_3$ and $Z_4$ independently are CRi.

In an embodiment of the compound according to the invention Ri represents a bond, hydrogen, or alkoxy.

In an embodiment of the compound according to the invention Ri represents a bond, hydrogen or methoxy.

In an embodiment according to the invention the compound of formula I is selected from:

4-[3,4-Dimethoxy-2-(3-methyl-butoxy)-phenyl]-indan-1-one (Compound 101)

4-(2-Cyclobutylmethoxy-3,4-dimethoxy-phenyl)-indan-1-one (Compound 102)

4-[2-(4-Methanesulfonyl-benzyloxy)-3,4-dimethoxy-phenyl]-indan-1-one (Compound 103)

4-[2-(3-Hydroxymethyl-oxetan-3-ylmethoxy)-3,4-dimethoxy-phenyl]-indan-1-one (Compound 104)

4-[2-(3,3-Dimethyl-butoxy)-3,4-dimethoxy-phenyl]-indan-1-one (Compound 105)

4-[2,3-Dimethoxy-6-(1-oxo-indan-4-yl)-phenoxymethyl]-benzamide (Compound 106)

4-[2-(3-Hydroxy-2,2-dimethyl-propoxy)-3,4-dimethoxy-phenyl]-indan-1-one (Compound 107)

4-[2,3-Dimethoxy-6-(1-oxo-indan-4-yl)-phenoxymethyl]-N-methyl-benzamide (Compound 108)

4-[2,3-Dimethoxy-6-(1-oxo-indan-4-yl)-phenoxymethyl]-N,N-dimethyl-benzamide (Compound 109)

3-[2,3-Dimethoxy-6-(1-oxo-indan-4-yl)-phenoxymethyl]-N,N-dimethyl-benzamide (Compound 110)

3-[2,3-Dimethoxy-6-(1-oxo-indan-4-yl)-phenoxymethyl]-N,N-dimethyl-benzenesulfonamide (Compound III)

4-[2,3-Dimethoxy-6-(1-oxo-indan-4-yl)-phenoxymethyl]-benzenesulfonamide (Compound 112)

4-[2-(3-Methanesulfonyl-benzyloxy)-3,4-dimethoxy-phenyl]-indan-1-one (Compound 113)

3-[2,3-Dimethoxy-6-(1-oxo-indan-4-yl)-phenoxymethyl]-benzamide (Compound 114)

4-[2-(4-Methanesulfonyl-benzyloxy)-3,4-dimethoxy-phenyl]-3H-isobenzofuran-1-one (Compound 115)

4-[2,3-Dimethoxy-6-(1-oxo-1,3-dihydro-isobenzofuran-4-yl)-phenoxymethyl]-benzamide (Compound 116)

4-[2,3-Dimethoxy-6-(1-oxo-1,3-dihydro-isobenzofuran-4-yl)-phenoxymethyl]-N-methyl-benzamide (Compound 117)

4-[2,3-Dimethoxy-6-(1-oxo-1,3-dihydro-isobenzofuran-4-yl)-phenoxymethyl]-N,N-dimethyl-benzamide (Compound 118)

4-[2-(3-Hydroxymethyl-oxetan-3-ylmethoxy)-3,4-dimethoxy-phenyl]-3H-isobenzofuran-1-one (Compound 119) 5-[3,4-Dimethoxy-2-(3-methyl-butoxy)-phenyl]-indan-1-one (Compound 120)

5-[2-(2,2-Dimethyl-propoxy)-3,4-dimethoxy-phenyl]-indan-1-one (Compound 121)

5-(2-Cyclobutylmethoxy-3,4-dimethoxy-phenyl)-indan-1-one (Compound 122)

5-[2-(3,3-Dimethyl-butoxy)-3,4-dimethoxy-phenyl]-indan-1-one (Compound 123)

4-[2,3-Dimethoxy-6-(1-oxo-indan-5-yl)-phenoxymethyl]-benzamide (Compound 124)

5-[2-(3-Hydroxy-2,2-dimethyl-propoxy)-3,4-dimethoxy-phenyl]-indan-1-one (Compound 125)

4-[2,3-Dimethoxy-6-(1-oxo-indan-5-yl)-phenoxymethyl]-N-methyl-benzamide (Compound 126)

4-[2,3-Dimethoxy-6-(1-oxo-indan-5-yl)-phenoxymethyl]-N,N-dimethyl-benzamide (Compound 127)

3-[2,3-Dimethoxy-6-(1-oxo-indan-5-yl)-phenoxymethyl]-N,N-dimethyl-benzamide (Compound 128)

5-[2-(3-Hydroxymethyl-oxetan-3-ylmethoxy)-3,4-dimethoxy-phenyl]-indan-1-one (Compound 129)

5-[2-(4-Methanesulfonyl-benzyloxy)-3,4-dimethoxy-phenyl]-indan-1-one (Compound 130)

5-[3,4-Dimethoxy-2-(3-methyl-butoxy)-phenyl]-3H-isobenzofuran-1-one (Compound 131)

5-[2-(2,2-Dimethyl-propoxy)-3,4-dimethoxy-phenyl]-3H-isobenzofuran-1-one (Compound 132)

5-(2-Cyclobutylmethoxy-3,4-dimethoxy-phenyl)-3H-isobenzofuran-1-one (Compound 133)

5-[2-(3-Hydroxymethyl-oxetan-3-ylmethoxy)-3,4-dimethoxy-phenyl]-3H-isobenzofuran-1-one (Compound 134)

5-[2-(3,3-Dimethyl-butoxy)-3,4-dimethoxy-phenyl]-3H-isobenzofuran-1-one (Compound 135)

4-[2,3-Dimethoxy-6-(1-oxo-1,3-dihydro-isobenzofuran-5-yl)-phenoxymethyl]-benzamide (Compound 136)

5-[2-(3-Hydroxy-2,2-dimethyl-propoxy)-3,4-dimethoxy-phenyl]-3H-isobenzofuran-1-one (Compound 137)

4-[2,3-Dimethoxy-6-(1-oxo-1,3-dihydro-isobenzofuran-5-yl)-phenoxymethyl]-N-methyl-benzamide (Compound 138)

4-[2,3-Dimethoxy-6-(1-oxo-1,3-dihydro-isobenzofuran-5-yl)-phenoxymethyl]-N,N-dimethyl-benzamide (Compound 139)

3-[2,3-Dimethoxy-6-(1-oxo-1,3-dihydro-isobenzofuran-5-yl)-phenoxymethyl]-N,N-dimethyl-benzamide (Compound 140)

4-[2,3-Dimethoxy-6-(1-oxo-1,3-dihydro-isobenzofuran-5-yl)-phenoxymethyl]-benzenesulfonamide (Compound 141)

5-[2-(4-Methanesulfonyl-benzyloxy)-3,4-dimethoxy-phenyl]-3H-isobenzofuran-1-one (Compound 142)

5-[2-(3-Methanesulfonyl-benzyloxy)-3,4-dimethoxy-phenyl]-3H-isobenzofuran-1-one (Compound 143)

3-[2,3-Dimethoxy-6-(1-oxo-1,3-dihydro-isobenzofuran-5-yl)-phenoxymethyl]-benzenesulfonamide (Compound 144)

3-[2,3-Dimethoxy-6-(1-oxo-1,3-dihydro-isobenzofuran-5-yl)-phenoxymethyl]-N,N-dimethyl-benzenesulfonamide (Compound 145)

3-[2,3-Dimethoxy-6-(1-oxo-1,3-dihydro-isobenzofuran-5-yl)-phenoxymethyl]-benzamide (Compound 146)

5-[3,4-Dimethoxy-2-(3-methyl-butoxy)-phenyl]-2,3-dihydro-isoindol-1-one (Compound 147)

5-[2-(2,2-Dimethyl-propoxy)-3,4-dimethoxy-phenyl]-2,3-dihydro-isoindol-1-one (Compound 148)

5-(2-Cyclobutylmethoxy-3,4-dimethoxy-phenyl)-2,3-dihydro-isoindol-1-one (Compound 149)

5-[2-(4-Methanesulfonyl-benzyloxy)-3,4-dimethoxy-phenyl]-2,3-dihydro-isoindol-1-one (Compound 150)

5-[2-(3-Hydroxymethyl-oxetan-3-ylmethoxy)-3,4-dimethoxy-phenyl]-2,3-dihydro-isoindol-1-one (Compound 151)

5-[2-(3,3-Dimethyl-butoxy)-3,4-dimethoxy-phenyl]-2,3-dihydro-isoindol-1-one (Compound 152)

4-[2,3-Dimethoxy-6-(1-oxo-2,3-dihydro-1H-isoindol-5-yl)-phenoxymethyl]-benzamide (Compound 153)

5-[2-(3-Hydroxy-2,2-dimethyl-propoxy)-3,4-dimethoxy-phenyl]-2,3-dihydro-isoindol-1-one (Compound 154)

4-[2,3-Dimethoxy-6-(1-oxo-2,3-dihydro-1H-isoindol-5-yl)-phenoxymethyl]-N-methyl-benzamide (Compound 155)

4-[2,3-Dimethoxy-6-(1-oxo-2,3-dihydro-1H-isoindol-5-yl)-phenoxymethyl]-N,N-dimethyl-benzamide (Compound 156)

3-[2,3-Dimethoxy-6-(1-oxo-2,3-dihydro-1H-isoindol-5-yl)-phenoxymethyl]-N,N-dimethyl-benzamide (Compound 157)

3-[2,3-Dimethoxy-6-(1-oxo-2,3-dihydro-1H-isoindol-5-yl)-phenoxymethyl]-benzenesulfonamide (Compound 158)

3-[2,3-Dimethoxy-6-(1-oxo-2,3-dihydro-1H-isoindol-5-yl)-phenoxymethyl]-benzamide (Compound 159)

5-[2-(3-Methanesulfonyl-benzyloxy)-3,4-dimethoxy-phenyl]-2,3-dihydro-isoindol-1-one (Compound 160)

4-[2,3-Dimethoxy-6-(1-oxo-2,3-dihydro-1H-isoindol-5-yl)-phenoxymethyl]-benzenesulfonamide (Compound 161)

3-[2,3-Dimethoxy-6-(1-oxo-indan-4-yl)-phenoxy]-2,2-dimethyl-propionic acid methyl ester (Compound 162)

4-[3,4-Dimethoxy-2-(3-methyl-oxetan-3-ylmethoxy)-phenyl]-indan-1-one (Compound 163)

4-[3,4-Dimethoxy-2-(3-methyl-oxetan-3-ylmethoxy)-phenyl]-3H-isobenzofuran-1-one (Compound 164)

3-[2,3-Dimethoxy-6-(1-oxo-indan-5-yl)-phenoxy]-2,2-dimethyl-propionic acid methyl ester (Compound 165)

4-(2-Isobutoxy-3,4-dimethoxy-phenyl)-indan-1-one (Compound 166)

4-(2-Isobutoxy-3,4-dimethoxy-phenyl)-6,7-dimethoxy-indan-1-one (Compound 167)

4-(2-Isobutoxy-3,4-dimethoxy-phenyl)-7-methoxy-indan-1-one (Compound 168)

5-(2-Isobutoxy-3,4-dimethoxy-phenyl)-indan-1-one (Compound 169)

5-(2-Isobutoxy-3,4-dimethoxy-phenyl)-3H-isobenzofuran-1-one (Compound 170)

5-(2-Isobutoxy-3,4-dimethoxy-phenyl)-2,3-dimethyl-2,3-dihydro-isoindol-1-one (Compound 171)

5-(2-Isobutoxy-3,4-dimethoxy-phenyl)-2-methyl-2,3-dihydro-isoindol-1-one (Compound 172)

4-(2-Isobutoxy-3,4-dimethoxy-phenyl)-2,3-dihydro-isoindol-1-one (Compound 173)

5-(2-Isobutoxy-3,4-dimethoxy-phenyl)-2,3-dihydro-isoindol-1-one (Compound 174)

4-(2-Isobutoxy-3,4-dimethoxy-phenyl)-3H-isobenzofuran-1-one (Compound 175)

6-(2-Isobutoxy-3,4-dimethoxy-phenyl)-benzofuran-3-one (Compound 176)

4-[2-(1-Hydroxymethyl-cyclopropylmethoxy)-3,4-dimethoxy-phenyl]-indan-1-one (Compound 177)

4-[3,4-Dimethoxy-2-(1-methoxymethyl-cyclopropylmethoxy)-phenyl]-indan-1-one (Compound 178)

Ethyl-carbamic acid 1-[2,3-dimethoxy-6-(1-oxo-indan-4-yl)-phenoxymethyl]-cyclopropylmethyl ester (Compound 179)

Isopropyl-carbamic acid 1-[2,3-dimethoxy-6-(1-oxo-indan-4-yl)-phenoxymethyl]-cyclopropylmethyl ester (Compound 180)

Benzyl-carbamic acid 1-[2,3-dimethoxy-6-(1-oxo-indan-4-yl)-phenoxymethyl]-cyclopropylmethyl ester (Compound 181)

4-[2-(1-Aminomethyl-cyclopropylmethoxy)-3,4-dimethoxy-phenyl]-indan-1-one (Compound 182)

N-{1-[2,3-Dimethoxy-6-(1-oxo-indan-4-yl)-phenoxymethyl]-cyclopropylmethyl}-isobutyramide (Compound 183)

N-{1-[2,3-Dimethoxy-6-(1-oxo-indan-4-yl)-phenoxymethyl]-cyclopropylmethyl}-butyramide (Compound 184)

N-{1-[2,3-Dimethoxy-6-(1-oxo-indan-4-yl)-phenoxymethyl]-cyclopropylmethyl}-acetamide (Compound 185)

{1-[2,3-Dimethoxy-6-(1-oxo-indan-4-yl)-phenoxymethyl]-cyclopropylmethyl}-carbamic acid ethyl ester (Compound 186)

{1-[2,3-Dimethoxy-6-(1-oxo-indan-4-yl)-phenoxymethyl]-cyclopropylmethyl}-carbamic acid isopropyl ester (Compound 187)

{1-[2,3-Dimethoxy-6-(1-oxo-indan-4-yl)-phenoxymethyl]-cyclopropylmethyl}-carbamic acid 2-methoxy-ethyl ester (Compound 188)

Ethyl-carbamic acid 3-[2,3-dimethoxy-6-(1-oxo-indan-4-yl)-phenoxymethyl]-oxetan-3-ylmethyl ester (Compound 189)

4-[3,4-Dimethoxy-2-(3-methoxymethyl-oxetan-3-ylmethoxy)-phenyl]-indan-1-one (Compound 190)

4-[2-(3-Aminomethyl-oxetan-3-ylmethoxy)-3,4-dimethoxy-phenyl]-indan-1-one (Compound 191)

N-{3-[2,3-Dimethoxy-6-(1-oxo-indan-4-yl)-phenoxymethyl]-oxetan-3-ylmethyl}-acetamide (Compound 192)

N-{3-[2,3-Dimethoxy-6-(1-oxo-indan-4-yl)-phenoxymethyl]-oxetan-3-ylmethyl}-isobutyramide (Compound 193)

N-{3-[2,3-Dimethoxy-6-(1-oxo-indan-4-yl)-phenoxymethyl]-oxetan-3-ylmethyl}-butyramide (Compound 194)

N-{3-[2,3-Dimethoxy-6-(1-oxo-indan-4-yl)-phenoxymethyl]-oxetan-3-ylmethyl}-2-methoxy-acetamide (Compound 195)

{3-[2,3-Dimethoxy-6-(1-oxo-indan-4-yl)-phenoxymethyl]-oxetan-3-ylmethyl}-carbamic acid ethyl ester (Compound 196)

{3-[2,3-Dimethoxy-6-(1-oxo-indan-4-yl)-phenoxymethyl]-oxetan-3-ylmethyl}-carbamic acid isopropyl ester (Compound 197)

{3-[2,3-Dimethoxy-6-(1-oxo-indan-4-yl)-phenoxymethyl]-oxetan-3-ylmethyl}-carbamic acid 2-methoxy-ethyl ester (Compound 198)

3-[2,3-Dimethoxy-6-(1-oxo-indan-4-yl)-phenoxy]-2,2-dimethyl-propionic acid (Compound 199)

3-[2,3-Dimethoxy-6-(1-oxo-indan-4-yl)-phenoxy]-2,2,N-trimethyl-propionamide (Compound 200)

3-[2,3-Dimethoxy-6-(1-oxo-indan-4-yl)-phenoxy]-N-ethyl-2,2-dimethyl-propionamide (Compound 201)

3-[2,3-Dimethoxy-6-(1-oxo-indan-4-yl)-phenoxy]-2,2,N,N-tetramethyl-propionamide (Compound 202)

N-Cyclopropyl-3-[2,3-dimethoxy-6-(1-oxo-indan-4-yl)-phenoxy]-2,2-dimethyl-propionamide (Compound 203)

4-[2-(2,2-Dimethyl-3-morpholin-4-yl-3-oxo-propoxy)-3,4-dimethoxy-phenyl]-indan-1-one (Compound 204)

3-[2,3-Dimethoxy-6-(1-oxo-indan-5-yl)-phenoxy]-2,2-dimethyl-propionic acid (Compound 205)

3-[2,3-Dimethoxy-6-(1-oxo-indan-5-yl)-phenoxy]-2,2,N-trimethyl-propionamide (Compound 206)

3-[2,3-Dimethoxy-6-(1-oxo-indan-5-yl)-phenoxy]-2,2,N,N-tetramethyl-propionamide (Compound 207)

3-[2,3-Dimethoxy-6-(1-oxo-indan-5-yl)-phenoxy]-N-isopropyl-2,2-dimethyl-propionamide (Compound 208)

3-[2,3-Dimethoxy-6-(1-oxo-indan-5-yl)-phenoxy]-2,2-dimethyl-N-propyl-propionamide (Compound 209)

Ethyl-carbamic acid 3-[2,3-dimethoxy-6-(1-oxo-1,3-dihydro-isobenzofuran-5-yl)-phenoxy]-2,2-dimethyl-propyl ester (Compound 210)

Ethyl-carbamic acid 3-[2,3-dimethoxy-6-(1-oxo-indan-4-yl)-phenoxy]-2,2-dimethyl-propyl ester (Compound 211)

Ethyl-carbamic acid 3-[2,3-dimethoxy-6-(1-oxo-2,3-dihydro-1H-isoindol-5-yl)-phenoxy]-2,2-dimethyl-propyl ester (Compound 212)

Ethyl-carbamic acid 3-[2,3-dimethoxy-6-(1-oxo-1,3-dihydro-isobenzofuran-5-yl)-phenoxymethyl]-oxetan-3-ylmethyl ester (Compound 213)

Ethyl-carbamic acid 3-[2,3-dimethoxy-6-(1-oxo-2,3-dihydro-1H-isoindol-5-yl)-phenoxymethyl]-oxetan-3-ylmethyl ester (Compound 214)

5-[3,4-Dimethoxy-2-(3-methoxymethyl-oxetan-3-ylmethoxy)-phenyl]-3H-isobenzofuran-1-one (Compound 215)

5-[3,4-Dimethoxy-2-(3-methoxymethyl-oxetan-3-ylmethoxy)-phenyl]-2,3-dihydro-isoindol-1-one (Compound 216)

4-[3,4-Dimethoxy-2-(3-methoxy-2,2-dimethyl-propoxy)-phenyl]-indan-1-one (Compound 217)

5-[3,4-Dimethoxy-2-(3-methoxy-2,2-dimethyl-propoxy)-phenyl]-3H-isobenzofuran-1-one (Compound 218)

5-[3,4-Dimethoxy-2-(3-methoxy-2,2-dimethyl-propoxy)-phenyl]-2,3-dihydro-isoindol-1-one (Compound 219)

3-(2,3-dimethoxy-6-(1-oxo-1,3-dihydroisobenzofuran-5-yl)phenoxy)-2,2-dimethylpropanoic acid (Compound 220)

3-(2,3-dimethoxy-6-(1-oxo-1,3-dihydroisobenzofuran-5-yl)phenoxy)-N,2,2-trimethylpropanamide (Compound 221)

3-(2,3-dimethoxy-6-(1-oxo-1,3-dihydroisobenzofuran-5-yl)phenoxy)-N,N,2,2-tetramethylpropanamide (Compound 222)

3-(2,3-dimethoxy-6-(1-oxo-1,3-dihydroisobenzofuran-5-yl)phenoxy)-N-isopropyl-2,2-dimethylpropanamide (Compound 223)

3-(2,3-dimethoxy-6-(1-oxo-1,3-dihydroisobenzofuran-5-yl)phenoxy)-2,2-dimethyl-N-propylpropanamide (Compound 224)

4-(4-Difluoromethoxy-2-ethoxy-3-methoxy-phenyl)-indan-1-one (Compound 225)

4-(4-Difluoromethoxy-3-methoxy-2-propoxy-phenyl)-indan-1-one (Compound 226)

4-(4-Difluoromethoxy-2-isobutoxy-3-methoxy-phenyl)-indan-1-one (Compound 227)

4-[4-Difluoromethoxy-2-(3-hydroxy-2,2-dimethyl-propoxy)-3-methoxy-phenyl]-indan-1-one (Compound 228)

4-[4-Difluoromethoxy-3-methoxy-2-(3-methoxy-2,2-dimethyl-propoxy)-phenyl]-indan-1-one (Compound 229)

4-[4-Difluoromethoxy-2-(3-hydroxymethyl-oxetan-3-ylmethoxy)-3-methoxy-phenyl]-indan-1-one (Compound 230)

4-[4-Difluoromethoxy-3-methoxy-2-(3-methoxymethyl-oxetan-3-ylmethoxy)-phenyl]-indan-1-one (Compound 231)

4-[3-Difluoromethoxy-2-methoxy-6-(1-oxo-indan-4-yl)-phenoxymethyl]-benzenesulfonamide (Compound 232)

4-[4-Difluoromethoxy-2-(4-methanesulfonyl-benzyloxy)-3-methoxy-phenyl]-indan-1-one (Compound 233)

4-((3-(difluoromethoxy)-2-methoxy-6-(1-oxo-2,3-dihydro-1H-inden-4-yl)phenoxy)methyl)benzamide (Compound 234)

5-(4-Difluoromethoxy-2-ethoxy-3-methoxy-phenyl)-3H-isobenzofuran-1-one (Compound 235)

5-(4-Difluoromethoxy-3-methoxy-2-propoxy-phenyl)-3H-isobenzofuran-1-one (Compound 236)

5-(4-Difluoromethoxy-2-isobutoxy-3-methoxy-phenyl)-3H-isobenzofuran-1-one (Compound 237)

5-[4-Difluoromethoxy-2-(3-hydroxy-2,2-dimethyl-propoxy)-3-methoxy-phenyl]-3H-isobenzofuran-1-one (Compound 238)

5-[4-Difluoromethoxy-3-methoxy-2-(3-methoxy-2,2-dimethyl-propoxy)-phenyl]-3H-isobenzofuran-1-one (Compound 239)

5-[4-Difluoromethoxy-2-(3-hydroxymethyl-oxetan-3-ylmethoxy)-3-methoxy-phenyl]-3H-isobenzofuran-1-one (Compound 240)

4-[3-Difluoromethoxy-2-hydroxy-6-(1-oxo-1,3-dihydro-isobenzofuran-5-yl)-phenoxymethyl]-benzenesulfonamide (Compound 241)

5-[4-Difluoromethoxy-3-hydroxy-2-(4-methanesulfonyl-benzyloxy)-phenyl]-3H-isobenzofuran-1-one (Compound 242)

5-(4-(difluoromethoxy)-3-methoxy-2-((3-(methoxymethyl)oxetan-3-yl)methoxy)phenyl)isobenzofuran-1(3H)-one (Compound 243)

5-(4-(Difluoromethoxy)-2-ethoxy-3-methoxyphenyl)isoindolin-1-one (Compound 244)

5-(4-(Difluoromethoxy)-3-methoxy-2-propoxyphenyl)isoindolin-1-one (Compound 245)

5-(4-(Difluoromethoxy)-2-isobutoxy-3-methoxyphenyl)isoindolin-1-one (Compound 246)

5-[4-Difluoromethoxy-3-methoxy-2-(3-hydroxy-2,2-dimethyl-propoxy)-phenyl]-2,3-dihydro-isoindol-1-one (Compound 247)

5-[4-Difluoromethoxy-3-methoxy-2-(3-methyl-oxetan-3-ylmethoxy)-phenyl]-2,3-dihydro-isoindol-1-one (Compound 248)

5-[4-Difluoromethoxy-2-(3-hydroxymethyl-oxetan-3-ylmethoxy)-3-methoxy-phenyl]-2,3-dihydro-isoindol-1-one (Compound 249)

5-[4-Difluoromethoxy-3-methoxy-2-(3-methoxymethyl-oxetan-3-ylmethoxy)-phenyl]-2,3-dihydro-isoindol-1-one (Compound 250)

4-[3-Difluoromethoxy-2-methoxy-6-(1-oxo-2,3-dihydro-1H-isoindol-5-yl)-phenoxymethyl]-benzenesulfonamide (Compound 251)

5-[4-Difluoromethoxy-2-(4-methanesulfonyl-benzyloxy)-3-methoxy-phenyl]-2,3-dihydro-isoindol-1-one (Compound 252)

4-((3-(difluoromethoxy)-2-methoxy-6-(1-oxoisoindolin-5-yl)phenoxy)methyl)benzamide (Compound 253)

2-[3-Difluoromethoxy-2-methoxy-6-(1-oxo-2,3-dihydro-1H-isoindol-5-yl)-phenoxy]-N-propyl-acetamide (Compound 254)

4-(2,4-Diethoxy-3-methoxyphenyl)-2,3-dihydro-1H-inden-1-one 4-(4-Ethoxy-3-methoxy-2-propoxyphenyl)-2,3-dihydro-1H-inden-1-one (Compound 256)

4-(4-Ethoxy-2-isobutoxy-3-methoxyphenyl)-2,3-dihydro-1H-inden-1-one (Compound 257)

4-(4-Ethoxy-2-(3-hydroxy-2,2-dimethylpropoxy)-3-methoxyphenyl)-2,3-dihydro-1H-inden-1-one (Compound 258)

4-(4-Ethoxy-3-methoxy-2-((3-methyloxetan-3-yl)methoxy)phenyl)-2,3-dihydro-1H-inden-1-one (Compound 259)

4-(4-Ethoxy-2-((3-(hydroxymethyl)oxetan-3-yl)methoxy)-3-methoxyphenyl)-2,3-dihydro-1H-inden-1-one (Compound 260)

4-(4-Ethoxy-3-methoxy-2-(4-(methylsulfonyl)benzyloxy)phenyl)-2,3-dihydro-1H-inden-1-one (Compound 261)

5-(2,4-Diethoxy-3-methoxyphenyl)isobenzofuran-1(3H)-one (Compound 262)

5-(4-Ethoxy-2-isobutoxy-3-methoxyphenyl)isobenzofuran-1(3H)-one (Compound 264)

5-(4-Ethoxy-2-(3-hydroxy-2,2-dimethylpropoxy)-3-methoxyphenyl)isobenzofuran-1(3H)-one (Compound 265)

5-(4-Ethoxy-3-methoxy-2-((3-methyloxetan-3-yl)methoxy)phenyl)isobenzofuran-1(3H)-one (Compound 266)

5-[4-Ethoxy-2-(3-hydroxymethyl-oxetan-3-ylmethoxy)-3-methoxy-phenyl]-3H-isobenzofuran-1-one (Compound 267)

5-(4-Ethoxy-3-methoxy-2-(4-(methylsulfonyl)benzyloxy)phenyl)isobenzofuran-1(3H)-one (Compound 268)

4-(3-Ethoxy-2,4-dimethoxyphenyl)-2,3-dihydro-1H-inden-1-one (Compound 269)

4-(2,4-Dimethoxy-3-propoxyphenyl)-2,3-dihydro-1H-inden-1-one (Compound 270)

4-(3-Isobutoxy-2,4-dimethoxyphenyl)-2,3-dihydro-1H-inden-1-one (Compound 271)

4-[3-(3-Hydroxy-2,2-dimethyl-propoxy)-2,4-dimethoxyphenyl]-indan-1-one (Compound 272)

4-(2,4-Dimethoxy-3-((3-methyloxetan-3-yl)methoxy)phenyl)-2,3-dihydro-1H-inden-1-one (Compound 273)

4-(3-((3-(Hydroxymethyl)oxetan-3-yl)methoxy)-2,4-dimethoxyphenyl)-2,3-dihydro-1H-inden-1-one (Compound 274)

4-[2,4-Dimethoxy-3-(3-methoxymethyl-oxetan-3-ylmethoxy)-phenyl]-indan-1-one (Compound 275)

4-[2,6-Dimethoxy-3-(1-oxo-indan-4-yl)-phenoxymethyl]-benzenesulfonamide (Compound 276)

4-(2,4-Dimethoxy-3-(4-(methylsulfonyl)benzyloxy)phenyl)-2,3-dihydro-1H-inden-1-one (Compound 277)

5-(3-Ethoxy-2,4-dimethoxyphenyl)-3H-isobenzofuran-1-one (Compound 278)

5-(2,4-Dimethoxy-3-propoxy-phenyl)-3H-isobenzofuran-1-one (Compound 279)

5-(3-Isobutoxy-2,4-dimethoxyphenyl)-3H-isobenzofuran-1-one (Compound 280)

5-[2,4-Dimethoxy-3-(3-methyl-oxetan-3-ylmethoxy)-phenyl]-3H-isobenzofuran-1-one (Compound 281)

5-(3-((3-(hydroxymethyl)oxetan-3-yl)methoxy)-2,4-dimethoxyphenyl)isobenzofuran-1(3H)-one (Compound 282)

5-[2,4-Dimethoxy-3-(3-methoxymethyl-oxetan-3-ylmethoxy)-phenyl]-3H-isobenzofuran-1-one (Compound 283)

4-[2,6-Dimethoxy-3-(1-oxo-1,3-dihydro-isobenzofuran-5-yl)-phenoxymethyl]-benzenesulfonamide (Compound 284)

5-(2,4-dimethoxy-3-(4-(methylsulfonyl)benzyloxy)phenyl)isobenzofuran-1(3H)-one (Compound 285)

4-[2,6-Dimethoxy-3-(1-oxo-1,3-dihydro-isobenzofuran-5-yl)-phenoxymethyl]-benzamide (Compound 286)

4-(3-Difluoromethoxy-2-ethoxy-4-methoxy-phenyl)-indan-1-one (Compound 287)

4-(3-Difluoromethoxy-4-methoxy-2-propoxy-phenyl)-indan-1-one (Compound 288)

4-(3-Difluoromethoxy-2-isobutoxy-4-methoxy-phenyl)-indan-1-one (Compound 289)

4-[3-Difluoromethoxy-2-(3-hydroxymethyl-oxetan-3-ylmethoxy)-4-methoxy-phenyl]-indan-1-one (Compound 290)

4-[3-Difluoromethoxy-4-methoxy-2-(3-methoxymethyl-oxetan-3-ylmethoxy)-phenyl]-indan-1-one (Compound 291)

4-[2-Difluoromethoxy-3-methoxy-6-(1-oxo-indan-4-yl)-phenoxymethyl]-benzenesulfonamide (Compound 292)

4-[3-Difluoromethoxy-2-(4-methanesulfonyl-benzyloxy)-4-methoxy-phenyl]-indan-1-one (Compound 293)

5-(3-Difluoromethoxy-2-ethoxy-4-methoxy-phenyl)-3H-isobenzofuran-1-one (Compound 294)

5-(3-Difluoromethoxy-4-methoxy-2-propoxy-phenyl)-3H-isobenzofuran-1-one (Compound 295)

5-(3-Difluoromethoxy-2-isobutoxy-4-methoxy-phenyl)-3H-isobenzofuran-1-one (Compound 296)

5-[3-Difluoromethoxy-4-methoxy-2-(3-methyl-oxetan-3-ylmethoxy)-phenyl]-3H-isobenzofuran-1-one (Compound 297)

5-[3-Difluoromethoxy-2-(3-hydroxymethyl-oxetan-3-ylmethoxy)-4-methoxy-phenyl]-3H-isobenzofuran-1-one (Compound 298)

5-[3-Difluoromethoxy-4-methoxy-2-(3-methoxymethyl-oxetan-3-ylmethoxy)-phenyl]-3H-isobenzofuran-1-one (Compound 299)

4-((2-(difluoromethoxy)-3-methoxy-6-(1-oxo-1,3-dihydroisobenzofuran-5-yl)phenoxy)methyl)benzenesulfonamide (Compound 400)

5-(3-(difluoromethoxy)-4-methoxy-2-(4-(methylsulfonyl) benzyloxy)phenyl)isobenzofuran-1(3H)-one (Compound 401)
4-((2-(difluoromethoxy)-3-methoxy-6-(1-oxo-1,3-dihydroisobenzofuran-5-yl)phenoxy)methyl)benzamide (Compound 402)
4-(3-Cyclopropylmethoxy-2-ethoxy-4-methoxy-phenyl)-indan-1-one (Compound 403)
4-(3-Cyclopropylmethoxy-4-methoxy-2-propoxy-phenyl)-indan-1-one (Compound 404)
4-(3-Cyclopropylmethoxy-2-isobutoxy-4-methoxy-phenyl)-indan-1-one (Compound 405)
4-[3-Cyclopropylmethoxy-4-methoxy-2-(3-methyl-oxetan-3-ylmethoxy)-phenyl]-indan-1-one (Compound 406)
4-[3-Cyclopropylmethoxy-2-(3-hydroxymethyl-oxetan-3-ylmethoxy)-4-methoxy-phenyl]-indan-1-one (Compound 407)
4-[3-Cyclopropylmethoxy-4-methoxy-2-(3-methoxymethyl-oxetan-3-ylmethoxy)-phenyl]-indan-1-one (Compound 408)
4-[3-Cyclopropylmethoxy-2-(4-methanesulfonyl-benzyloxy)-4-methoxy-phenyl]-indan-1-one (Compound 409)
2-[2-Cyclopropylmethoxy-3-methoxy-6-(1-oxo-indan-4-yl)-phenoxy]-N-propyl-acetamide (Compound 410)
5-(3-Cyclopropylmethoxy-2-ethoxy-4-methoxy-phenyl)-3H-isobenzofuran-1-one (Compound 411)
5-(3-Cyclopropylmethoxy-4-methoxy-2-propoxy-phenyl)-3H-isobenzofuran-1-one (Compound 412)
5-(3-Cyclopropylmethoxy-2-isobutoxy-4-methoxy-phenyl)-3H-isobenzofuran-1-one (Compound 413)
5-[3-Cyclopropylmethoxy-4-methoxy-2-(3-methyl-oxetan-3-ylmethoxy)-phenyl]-3H-isobenzofuran-1-one (Compound 414)
5-[3-Cyclopropylmethoxy-2-(3-hydroxymethyl-oxetan-3-ylmethoxy)-4-methoxy-phenyl]-3H-isobenzofuran-1-one (Compound 415)
5-[3-Cyclopropylmethoxy-4-methoxy-2-(3-methoxymethyl-oxetan-3-ylmethoxy)-phenyl]-3H-isobenzofuran-1-one (Compound 416)
5-[3-Cyclopropylmethoxy-2-(4-methanesulfonyl-benzyloxy)-4-methoxy-phenyl]-3H-isobenzofuran-1-one (Compound 417)
2-(2-(Cyclopropylmethoxy)-3-methoxy-6-(1-oxo-1,3-dihydroisobenzofuran-5-yl)phenoxy)-N-propylacetamide (Compound 418)
5-(3-(cyclopropylmethoxy)-2,4-dimethoxyphenyl)-2,3-dihydro-1H-inden-1-one (Compound 419)
5-(3-(cyclopropylmethoxy)-2,4-dimethoxyphenyl)isobenzofuran-1(3H)-one (Compound 420)
Methyl 3-[2,3-dimethoxy-6-(1-oxo-3H-isobenzofuran-4-yl)phenoxy]-2,2-dimethyl-propanoate (Compound 421)
Methyl 3-[2,3-dimethoxy-6-(1-oxo-3H-isobenzofuran-5-yl)phenoxy]-2,2-dimethyl-propanoate, (Compound 422)
[2,3-dimethoxy-6-(1-oxoindan-4-yl)phenyl]propanoate
[2,3-dimethoxy-6-(1-oxoindan-4-yl)phenyl]cyclopropanecarboxylate
[2,3-dimethoxy-6-(1-oxoindan-4-yl)phenyl]2-methylpropanoate
[2,3-dimethoxy-6-(1-oxoindan-4-yl)phenyl]butanoate
[2,3-dimethoxy-6-(1-oxoindan-4-yl)phenyl]cyclobutanecarboxylate
[2,3-dimethoxy-6-(1-oxoindan-4-yl)phenyl]2-methylbutanoate
[2,3-dimethoxy-6-(1-oxoindan-4-yl)phenyl]3-methylbutanoate
[2,3-dimethoxy-6-(1-oxoindan-4-yl)phenyl]pentanoate
[2,3-dimethoxy-6-(1-oxoindan-4-yl)phenyl]cyclopentanecarboxylate
[2,3-dimethoxy-6-(1-oxoindan-4-yl)phenyl]hexanoate
[2,3-dimethoxy-6-(1-oxoindan-4-yl)phenyl]2-ethylbutanoate
[2,3-dimethoxy-6-(1-oxoindan-4-yl)phenyl]3,3-dimethylbutanoate
[2,3-dimethoxy-6-(1-oxoindan-4-yl)phenyl]3-methylsulfanylpropanoate
[2,3-dimethoxy-6-(1-oxoindan-4-yl)phenyl]3,3,3-trifluoropropanoate
[2,3-dimethoxy-6-(1-oxoindan-4-yl)phenyl]cyclohexanecarboxylate
[2,3-dimethoxy-6-(1-oxoindan-4-yl)phenyl]2-cyclopentylacetate
[2,3-dimethoxy-6-(1-oxoindan-4-yl)phenyl]2-(2-methoxyethoxy)acetate
[2,3-dimethoxy-6-(1-oxoindan-4-yl)phenyl]3-cyclopentylpropanoate
[2,3-dimethoxy-6-(1-oxoindan-5-yl)phenyl]acetate
[2,3-dimethoxy-6-(1-oxoindan-5-yl)phenyl]cyclopropanecarboxylate
[2,3-dimethoxy-6-(1-oxoindan-5-yl)phenyl]butanoate
[2,3-dimethoxy-6-(1-oxoindan-5-yl)phenyl]2-methylpropanoate
[2,3-dimethoxy-6-(1-oxoindan-5-yl)phenyl]cyclobutanecarboxylate
[2,3-dimethoxy-6-(1-oxoindan-5-yl)phenyl]pentanoate
[2,3-dimethoxy-6-(1-oxoindan-5-yl)phenyl]3-methylbutanoate
[2,3-dimethoxy-6-(1-oxoindan-5-yl)phenyl]2-methylbutanoate
[2,3-dimethoxy-6-(1-oxoindan-5-yl)phenyl]cyclopentanecarboxylate
[2,3-dimethoxy-6-(1-oxoindan-5-yl)phenyl]2-ethylbutanoate
[2,3-dimethoxy-6-(1-oxoindan-5-yl)phenyl]hexanoate
[2,3-dimethoxy-6-(1-oxoindan-5-yl)phenyl]3,3-dimethylbutanoate
[2,3-dimethoxy-6-(1-oxoindan-5-yl)phenyl]3-methylsulfanylpropanoate
[2,3-dimethoxy-6-(1-oxoindan-5-yl)phenyl]3,3,3-trifluoropropanoate
[2,3-dimethoxy-6-(1-oxoindan-5-yl)phenyl]cyclohexanecarboxylate
[2,3-dimethoxy-6-(1-oxoindan-5-yl)phenyl]2-cyclopentylacetate
[2,3-dimethoxy-6-(1-oxoindan-5-yl)phenyl]2-(2-methoxyethoxy)acetate
[2,3-dimethoxy-6-(1-oxoindan-5-yl)phenyl]3-cyclopentylpropanoate
[2,3-dimethoxy-6-(1-oxo-3H-isobenzofuran-4-yl)phenyl]propanoate
[2,3-dimethoxy-6-(1-oxo-3H-isobenzofuran-4-yl)phenyl]cyclopropanecarboxylate
[2,3-dimethoxy-6-(1-oxo-3H-isobenzofuran-4-yl)phenyl]butanoate
[2,3-dimethoxy-6-(1-oxo-3H-isobenzofuran-4-yl)phenyl]2-methylpropanoate
[2,3-dimethoxy-6-(1-oxo-3H-isobenzofuran-4-yl)phenyl]cyclobutanecarboxylate
[2,3-dimethoxy-6-(1-oxo-3H-isobenzofuran-4-yl)phenyl]pentanoate
[2,3-dimethoxy-6-(1-oxo-3H-isobenzofuran-4-yl)phenyl]3-methylbutanoate
[2,3-dimethoxy-6-(1-oxo-3H-isobenzofuran-4-yl)phenyl]cyclopentanecarboxylate

[2,3-dimethoxy-6-(1-oxo-3H-isobenzofuran-4-yl)phenyl]3,3-dimethylbutanoate
[2,3-dimethoxy-6-(1-oxo-3H-isobenzofuran-4-yl)phenyl]hexanoate
[2,3-dimethoxy-6-(1-oxo-3H-isobenzofuran-4-yl)phenyl]2-ethylbutanoate
[2,3-dimethoxy-6-(1-oxo-3H-isobenzofuran-4-yl)phenyl]3-methylsulfanylpropanoate
[2,3-dimethoxy-6-(1-oxo-3H-isobenzofuran-4-yl)phenyl]cyclohexanecarboxylate
[2,3-dimethoxy-6-(1-oxo-3H-isobenzofuran-4-yl)phenyl]2-cyclopentylacetate
[2,3-dimethoxy-6-(1-oxo-3H-isobenzofuran-4-yl)phenyl]2-(2-methoxyethoxy)acetate
[2,3-dimethoxy-6-(1-oxo-3H-isobenzofuran-4-yl)phenyl]3-cyclopentylpropanoate
[2,3-dimethoxy-6-(1-oxo-3H-isobenzofuran-5-yl)phenyl]acetate
[2,3-dimethoxy-6-(1-oxo-3H-isobenzofuran-5-yl)phenyl]cyclopropanecarboxylate
[2,3-dimethoxy-6-(1-oxo-3H-isobenzofuran-5-yl)phenyl]butanoate
[2,3-dimethoxy-6-(1-oxo-3H-isobenzofuran-5-yl)phenyl]2-methylpropanoate
[2,3-dimethoxy-6-(1-oxo-3H-isobenzofuran-5-yl)phenyl]cyclobutanecarboxylate
[2,3-dimethoxy-6-(1-oxo-3H-isobenzofuran-5-yl)phenyl]3-methylbutanoate
[2,3-dimethoxy-6-(1-oxo-3H-isobenzofuran-5-yl)phenyl]pentanoate
[2,3-dimethoxy-6-(1-oxo-3H-isobenzofuran-5-yl)phenyl]2-methylbutanoate
[2,3-dimethoxy-6-(1-oxo-3H-isobenzofuran-5-yl)phenyl]3,3-dimethylbutanoate
[2,3-dimethoxy-6-(1-oxo-3H-isobenzofuran-5-yl)phenyl]2-ethylbutanoate
[2,3-dimethoxy-6-(1-oxo-3H-isobenzofuran-5-yl)phenyl]3-methylsulfanylpropanoate
[2,3-dimethoxy-6-(1-oxo-3H-isobenzofuran-5-yl)phenyl]2-(2-methoxyethoxy)acetate
[2,3-dimethoxy-6-(1-oxo-3H-isobenzofuran-5-yl)phenyl]3-cyclopentylpropanoate
[2,3-dimethoxy-6-(1-oxoisoindolin-5-yl)phenyl]2-methylpropanoate
[2,3-dimethoxy-6-(1-oxoisoindolin-5-yl)phenyl]cyclobutanecarboxylate
[2,3-dimethoxy-6-(1-oxoisoindolin-5-yl)phenyl]pentanoate
[2,3-dimethoxy-6-(1-oxoisoindolin-5-yl)phenyl]3-methylbutanoate
[2,3-dimethoxy-6-(1-oxoisoindolin-5-yl)phenyl]2-methylbutanoate
[2,3-dimethoxy-6-(1-oxoisoindolin-5-yl)phenyl]cyclopentanecarboxylate
[2,3-dimethoxy-6-(1-oxoisoindolin-5-yl)phenyl]hexanoate
[2,3-dimethoxy-6-(1-oxoisoindolin-5-yl)phenyl]3,3-dimethylbutanoate
[2,3-dimethoxy-6-(1-oxoisoindolin-5-yl)phenyl]2-ethylbutanoate
[2,3-dimethoxy-6-(1-oxoisoindolin-5-yl)phenyl]cyclohexanecarboxylate
[2,3-dimethoxy-6-(1-oxoisoindolin-5-yl)phenyl]3-cyclopentylpropanoate
methyl (2R)-3-[2,3-dimethoxy-6-(1-oxoindan-4-yl)phenoxy]-2-methyl-propanoate
methyl (2S)-3-[2,3-dimethoxy-6-(1-oxoindan-4-yl)phenoxy]-2-methyl-propanoate
methyl 1-[[2,3-dimethoxy-6-(1-oxoindan-4-yl)phenoxy]methyl]cyclopropanecarboxylate
ethyl (2S)-3-[2,3-dimethoxy-6-(1-oxoindan-4-yl)phenoxy]-2-methyl-propanoate
ethyl (2R)-3-[2,3-dimethoxy-6-(1-oxoindan-4-yl)phenoxy]-2-methyl-propanoate
ethyl 1-[[2,3-dimethoxy-6-(1-oxoindan-4-yl)phenoxy]methyl]cyclopropanecarboxylate
methyl 1-[[2,3-dimethoxy-6-(1-oxoindan-4-yl)phenoxy]methyl]cyclobutanecarboxylate
ethyl 3-[2,3-dimethoxy-6-(1-oxoindan-4-yl)phenoxy]-2,2-dimethyl-propanoate propyl (2R)-3-[2,3-dimethoxy-6-(1-oxoindan-4-yl)phenoxy]-2-methyl-propanoate
propyl (2S)-3-[2,3-dimethoxy-6-(1-oxoindan-4-yl)phenoxy]-2-methyl-propanoate
isopropyl (2S)-3-[2,3-dimethoxy-6-(1-oxoindan-4-yl)phenoxy]-2-methyl-propanoate
isopropyl (2R)-3-[2,3-dimethoxy-6-(1-oxoindan-4-yl)phenoxy]-2-methyl-propanoate propyl 1-[[2,3-dimethoxy-6-(1-oxoindan-4-yl)phenoxy]methyl]cyclopropanecarboxylate
ethyl 1-[[2,3-dimethoxy-6-(1-oxoindan-4-yl)phenoxy]methyl]cyclobutanecarboxylate
isopropyl 1-[[2,3-dimethoxy-6-(1-oxoindan-4-yl)phenoxy]methyl]cyclopropanecarboxylate
propyl 3-[2,3-dimethoxy-6-(1-oxoindan-4-yl)phenoxy]-2,2-dimethyl-propanoate isopropyl 3-[2,3-dimethoxy-6-(1-oxoindan-4-yl)phenoxy]-2,2-dimethyl-propanoate
cyclobutyl 1-[[2,3-dimethoxy-6-(1-oxoindan-4-yl)phenoxy]methyl]cyclopropanecarboxylate
isobutyl 1-[[2,3-dimethoxy-6-(1-oxoindan-4-yl)phenoxy]methyl]cyclopropanecarboxylate
propyl 1-[[2,3-dimethoxy-6-(1-oxoindan-4-yl)phenoxy]methyl]cyclobutanecarboxylate
butyl 1-[[2,3-dimethoxy-6-(1-oxoindan-4-yl)phenoxy]methyl]cyclopropanecarboxylate
cyclobutyl 3-[2,3-dimethoxy-6-(1-oxoindan-4-yl)phenoxy]-2,2-dimethyl-propanoate
isopropyl 1-[[2,3-dimethoxy-6-(1-oxoindan-4-yl)phenoxy]methyl]cyclobutanecarboxylate
butyl 3-[2,3-dimethoxy-6-(1-oxoindan-4-yl)phenoxy]-2,2-dimethyl-propanoate isobutyl 3-[2,3-dimethoxy-6-(1-oxoindan-4-yl)phenoxy]-2,2-dimethyl-propanoate
3-fluoropropyl 1-[[2,3-dimethoxy-6-(1-oxoindan-4-yl)phenoxy]methyl]cyclopropanecarboxylate
cyclobutyl 1-[[2,3-dimethoxy-6-(1-oxoindan-4-yl)phenoxy]methyl]cyclobutanecarboxylate
cyclopentyl 1-[[2,3-dimethoxy-6-(1-oxoindan-4-yl)phenoxy]methyl]cyclopropanecarboxylate
cyclobutylmethyl 1-[[2,3-dimethoxy-6-(1-oxoindan-4-yl)phenoxy]methyl]cyclopropanecarboxylate
cyclopentyl 3-[2,3-dimethoxy-6-(1-oxoindan-4-yl)phenoxy]-2,2-dimethyl-propanoate cyclobutylmethyl 3-[2,3-dimethoxy-6-(1-oxoindan-4-yl)phenoxy]-2,2-dimethyl-propanoate
1-ethylpropyl 1-[[2,3-dimethoxy-6-(1-oxoindan-4-yl)phenoxy]methyl]cyclopropanecarboxylate
butyl 1-[[2,3-dimethoxy-6-(1-oxoindan-4-yl)phenoxy]methyl]cyclobutanecarboxylate
2,2-dimethylpropyl 1-[[2,3-dimethoxy-6-(1-oxoindan-4-yl)phenoxy]methyl]cyclopropanecarboxylate
isobutyl 1-[[2,3-dimethoxy-6-(1-oxoindan-4-yl)phenoxy]methyl]cyclobutanecarboxylate
2,2-dimethylpropyl 3-[2,3-dimethoxy-6-(1-oxoindan-4-yl)phenoxy]-2,2-dimethyl-propanoate
1-ethylpropyl 3-[2,3-dimethoxy-6-(1-oxoindan-4-yl)phenoxy]-2,2-dimethyl-propanoate (1-cyano-1-methyl-ethyl) 1-[[2,3-dimethoxy-6-(1-oxoindan-4-yl)phenoxy]methyl]cyclobutanecarboxylate cyclohexyl 1-[[2,3-dimethoxy-6-(1-oxoindan-4-yl)phenoxy]methyl]cyclopropanecarboxylate cyclopentyl 1-[[2,3-dimethoxy-6-(1-oxoindan-4-yl)phenoxy]methyl]cyclobutanecarboxylate 1-ethylpropyl 1-[[2,3-dimethoxy-6-(1-oxoindan-4-yl)phenoxy]methyl]cyclobutanecarboxylate 2,2-dimethylpropyl 1-[[2,3-dimethoxy-6-(1-oxoindan-4-yl)phenoxy]methyl]cyclobutanecarboxylate cyclohexyl 3-[2,3-dimethoxy-6-(1-oxoindan-4-yl)phenoxy]-2,2-dimethyl-propanoate and cyclohexyl 1-[([2,3-dimethoxy-6-(1-oxoindan-4-yl)phenoxy]methyl]cyclobutanecarboxylate In one or more embodiments of the present invention, the compounds of formula I as defined above are useful in therapy and in particular useful for the prophylaxis, treatment or amelioration of dermal diseases.

In one or more embodiments of the present invention, the dermal disease or condition is selected from proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula I may or may not comprise asymmetrically substituted (chiral) carbon atoms which give rise to the existence of isomeric forms, e.g. enantiomers and possibly diastereomers. The present invention relates to all such isomers, either in pure form or as mixtures thereof (e.g. racemates). Pure stereoisomeric forms of the compounds and the intermediates of this invention may be obtained by the application of procedures known in the art. The various isomeric forms may be separated by physical separation methods such as selective crystallization and chromatographic techniques, e.g. liquid chromatography using chiral stationary phases. Enantiomers may be separated from each other by the selective crystallization of their diastereomeric salts with optically active amines, such as l-ephedrine. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials.

Compounds of the present invention, optionally in combination with other active compounds, would be useful for the treatment of dermal diseases or conditions, or acute or chronic cutaneous wound disorders, in particular for the treatment of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient, vehicle or carrier(s). The excipient must be "acceptable" in the sense of being compatible with the other ingredients of the composition and not deleterious to the recipient thereof.

Conveniently, the active ingredient comprises from 0.05-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid or liquid pharmaceutical diluents or carriers.

The term "usage unit" in connection with topical use means a unitary, i.e. a single dose, capable of being administered topically to a patient in an application per square centimetre of the infected area of from 0.1 mg to 10 mg and preferably from 0.2 mg to 1 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be pre-pared by any of the methods well known in the art of pharmacy, e.g. as disclosed in Remington, *The Science and Practice of Pharmacy*, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops. Compositions for ophthalmic treatment may preferably additionally contain a cyclodextrin.

For topical administration, the compound of formula I may typically be present in an amount of from 0.01 to 20% by weight of the composition, such as 0.1% to about 10%, but may also be present in an amount of up to about 50% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, 3. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Examples of such additional active components may for example be selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts and salicylazosulfapyridine.

METHODS OF PREPARATION

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected.

Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used. The compounds of the present invention or any intermediate may be purified if required using standard methods well known to a synthetic organist chemist, e.g. methods described in "Purification of Laboratory Chemicals", 5$^{th}$ ed. 2003. Starting materials are either known compounds, commercially available, or they may be prepared by routine synthetic methods well known to a person skilled in the art.

GENERAL PROCEDURES, PREPARATIONS AND EXAMPLES $^1$H nuclear magnetic resonance (NMR) spectra were recorded at 300 MHz or 600 MHz and $^{13}$C NMR spectra at 75.6 MHz or 151 MHz. Chemical shift values (δ, in ppm) are quoted in the specified solvent relative to internal tetramethylsilane (δ=0.00) or chloroform (δ=7.25) or deuteriochloroform (δ=76.81 for $^{13}$C NMR) standards. The value of a multiplet, either defined (doublet (d), triplet (t), quartet (q)) or not (m) at the approximate mid point is given unless a range is quoted. (bs) indicates a broad singlet. The organic solvents used were usually anhydrous. Chromatography was performed on Merck silica gel 60 (0.040-0-063 mm). The solvent ratios indicated refer to v:v unless otherwise noted.
The following abbreviations have been used throughout:
Bu butyl
DCM dichloromethane
DMF N,N'-Dimethylformamide
DMSO dimethyl sulfoxide
EDC.HCl 1-(3-Dimethylaminopropyl)-3-ethylcarbodiimide hydrochloride
Et ethyl
HOAt 1-Hydroxy-7-azabenzotriazole
L litre
m milli
Me methyl
NMR nuclear magnetic resonance
PCy$_3$ tricyclohexylphosphine
PdCl$_2$(dppf)$_2$ [Dichloro-1-1'-bis(diphenylphosphino)ferrocene]palladium(II)
Pd$_2$(dba)$_3$ Di-Palladium-tris(dibenzylideneacetone)
Pet ether Petroleum ether
Ph Phenyl
RT room temperature
THF tetrahydrofuran
v volume
Preparative HPLC/MS Preparative HPLC/MS was performed on a Dionex APS-system with two Shimadzu PP150 prep. pumps and a Thermo MSQ Plus mass spectrometer. Column: Waters XTerra C-18, 150 mm×19 mm, 5 μm; solventsystem: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).
Analytical UPLC/MS Analytical UPLC/MS was performed on a system consisting of a Waters Premier XE mass spectrometer.
Column: Waters Acquity UPLC HSS T3 1.8 μm; 2.1×50 mm. Solvent system: A:10 mM Ammonium acetate+0.1% HCOOH; B: CH3CN+0.1% HCOOH.
Flow rate 0.7 mL/min.
Method (4.8 min): 0.0 min: 99% A and 1% B, 0.5 min: 94% A and 6% B, 1.0 min 94% A and 6% B, 2.6 min: 5% A and 95% B, 3.8 min: 5% A and 95% B, 3.81 min: 99% A and 1% B, 4.8 min: 99% A and 1% B.
Column Temp: 40C.
General Methods and Examples The compounds of the invention may for example be prepared according to the following non-limiting general methods and examples. R1, R1, R3, X, Y and Z$_1$-Z$_4$ are as previously defined for the compounds of Formula I Scheme 1

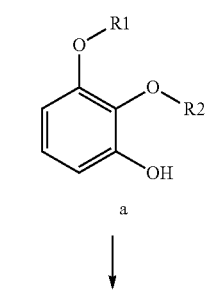

a

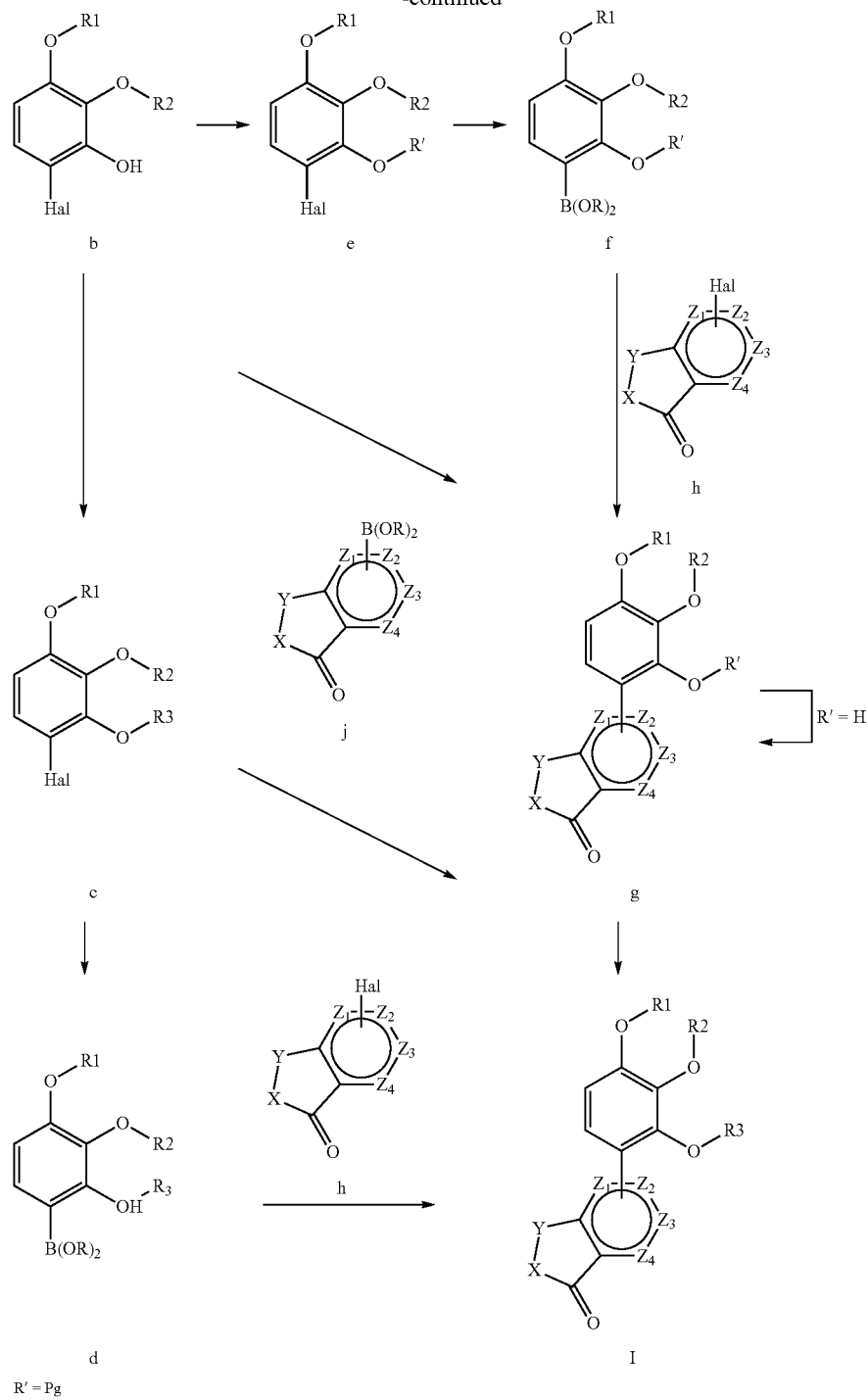

Method A:

Reaction of compounds of general formula a with halogenating agents such as $Br_2$, NBS, $I_2$ or NIS in a suitable solvent such as, but not limited to THF, DMF or HOAc at e.g. minus 78° C. to reflux to yield compounds of the general formula b.

Reaction of compounds of general formula b with suitable alkyl or alkenyl chlorides, bromides, iodides, mesylates or tosylates in the presence of a suitable base, such as $K_2CO_3$, NaOH or NaH in a suitable solvent such as $CH_3CN$, DMSO or DMF at temperatures from room temperature to 180° C. (see also Protective Groups in Organic Chemistry, John Wiley & sons, Ed: T. Greene and P. G. Wuts, $3^{rd}$ edition (1999), p 249-72), or by reaction with suitable alcohols, e.g. alkyl alcohols, using Mitsunobu conditions (see Synthesis (1981), 1; Tet. Lett. (1993), 34, 1639-42 and Eur. J. Org. Chem. (2004), 2763-72), in a suitable solvent such as THF, benzene or DMF to yield compounds of the general formula c.

Reaction of a halogenide of the general formula c with a borylating agent to yield boronic acids or boronic acid esters of the general formula d. This may be accomplished by cross-coupling with a diboron, e.g. bis(pinacolato)diboron in the presence of a Pd catalyst such as PdCl$_2$(dppf) or Pd$_2$(dba)$_3$/PCy$_3$ and in the presence of a suitable base such as KOAc in a suitable solvent such as 1,4-dioxan, THF or DMF at temperatures from room temperature to 180° C. to yield boronic acid esters of the general formula d. (See Hall, D. G: Boronic Acids: Preparation, Applications in Organic Synthesis and Medicines, Wiley-VCH 2005, p 102-105). This may also be accomplished by transmetallation of c, with e.g. n-butyllithium and trapping the arylmetal intermediate with a borate ester such as trimethyl borate in a suitable solvent such as THF at temperatures from −78° C. to room temperature. The boronic acid ester may be hydrolysed to the corresponding boronic acid by reaction with aqueous HCl or aqueous NH$_4$Cl to yield boronic acids of the general formula d. (See Hall, D. G: Boronic Acids: Preparation, Applications in Organic Synthesis and Medicines, Wiley-VCH 2005, p. 28-33)

Reaction of boronic acids or boronic acid esters of the general formula d with a halogenide h under Suzuki coupling conditions using a suitable catalyst (e.g. tetrakistriphenylphosphinepalladium or Pd$_2$(dba)$_3$/PCy$_3$), and a suitable base, such as cesium carbonate, potassium carbonate, sodium hydroxide, triethylamine, K$_3$PO$_4$ in a suitable solvent such as but not limited to DMF, NMP, 1,2-dimethoxyethane, THF, 1,4-dioxane, water or a mixture two or more of these, at temperatures from e.g. minus 78° C. to 180° C. to yield compounds of the general formula I. (For a general review on Suzuki coupling see Suzuki, A. in Hall, D.G: Boronic Acids: Preparation, Applications in Organic Synthesis and Medicines, Wiley-VCH 2005, p. 123-170)

Method B:

Reaction of halogenides of the general formula c with boronic acids or boronic acid ester of the general formula j under Suzuki coupling conditions to yield compounds of the general formula I.

Method C:

Reaction of halogenides of the general formula b with boronic acids or boronic acid ester of the general formula j under Suzuki coupling conditions to yield compounds of the general formula g, wherein R' is hydrogen.

Reaction of compounds of general formula g with suitable alkyl or alkenyl chlorides, bromides, iodides, mesylates or tosylates in the presence of a suitable base, such as K$_2$CO$_3$, NaOH or NaH in a suitable solvent such as CH$_3$CN, DMSO or DMF at temperatures from room temperature to 180° C., or by reaction with suitable alcohols, e.g. alkyl alcohols, using Mitsunobu conditions, in a suitable solvent such as THF, benzene or DMF to yield compounds of the general formula I.

Method D:

Protection of the phenol moiety of compounds of the general formula b with a suitable protecting group, such as but not limited to, methoxymethyl, by reaction with methoxymethyl bromide in the presence of a suitable base such as triethyl amine in a suitable solvent such as methylene chloride (see Protective Groups in Organic Chemistry, John Wiley & sons, Ed: T. Greene and P. G. Wuts, 3$^{rd}$ edition (1999), p 249-72), to yield compounds of the general formula e.

Reaction of halogenides of the general formula e with a borylating agent to yield compounds of the general formula f. This may be accomplished by transmetallation of e, with e.g. n-butyllithium and trapping the arylmetal intermediate with a borate ester such as trimethyl borate in a suitable solvent such as THF at temperatures from −78° C. to room temperature. The boronic acid ester may be hydrolysed to the corresponding boronic acid by reaction with aqueous HCl or aqueous NH$_4$Cl to yield boronic acids of the general formula f.

Reaction of boronic acids or boronic acid ester of the general formula f with a halogenide h under Suzuki coupling conditions to yield compounds of the general formula g, wherein R' is a protecting group. Removal of the protecting group to yield compounds of the general formula g, wherein R' is hydrogen may be accomplished by treating the methoxymethyl protected compound with HCl in MeOH (see also Protective Groups in Organic Chemistry, John Wiley & sons, Ed: T. Greene and P. G. Wuts, 3$^{rd}$ edition (1999), p 249-72).

Reaction of compounds of general formula g wherein R' is hydrogen with suitable alkyl or alkenyl chlorides, bromides, iodides, mesylates or tosylates in the presence of a suitable base, such as K$_2$CO$_3$, NaOH or NaH in a suitable solvent such as CH$_3$CN, DMSO or DMF at temperatures from room temperature to 180° C., or by reaction with suitable alcohols, e.g. alkyl alcohols, using Mitsunobu conditions, in a suitable solvent such as THF, benzene or DMF to yield compounds of the general formula I.

The boronic acid esters of the general formula j may be synthesised from the halogenide h by cross-coupling with a diboron, e.g. bis(pinacolato)diboron in the presence of a Pd catalyst such as PdCl$_2$(dppf) or Pd$_2$(dba)$_3$/PCy$_3$ and in the presence of a suitable base such as KOAc in a suitable solvent such as 1,4-dioxan, THF or DMF at temperatures from room temperature to 180° C.

Preparation 1

3,4-dimethoxy-2-(methoxymethyl)phenylboronic acid (compound 301)

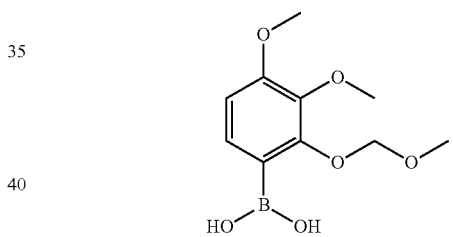

To a stirring solution of 2,3-dimethoxy-phenol (6 g, 38.70 mmol) in tetrahydrofuran (30 mL) at 25° C., was added N-bromosuccinimide (6.89 g, 38.70 mmol) and the resultant reaction mixture was stirred at RT for 1 h. The reaction mixture was diluted with water and extracted with ethyl acetate (3×). The combined ethyl acetate layer was washed with brine and dried over anhydrous sodium sulphate and concentrated under reduced pressure to afford 6-Bromo-2,3-dimethoxyphenol as a solid.

To a stirring solution of 6-bromo-2,3-dimethoxyphenol (1 g, 4.31 mmol) in dichloromethane (20 mL) at 0° C., were added triethyl amine (1.7 mL, 17.47 mmol) and methoxymethyl bromide (0.4 mL, 3.44 mmol) and the resultant reaction mixture was stirred at RT for 1 h. The reaction mixture was quenched with ice water and extracted with dichloromethane (3×). The combined dichloromethane layer was washed with brine, dried over anhydrous sodium sulphate and concentrated under reduced pressure.

Purification by column chromatography (silica gel, 0-10% ethyl acetate in pet ether) afforded 1-Bromo-3,4-dimethoxy-2-methoxymethoxy-benzene as a liquid.

To a stirring solution of 1-bromo-3,4-dimethoxy-2-methoxymethoxy-benzene (1 g, 3.62 mmol) in tetrahydrofuran (15 mL) at −78° C., was added n-butyllithium (5.5 mL, 7.24 mmol) and stirred for 20 min to this trimethylborate (3.76 g, 36.23 mmol) was added and the resultant reaction mixture was stirred for 30 min at −78° C. The reaction mixture was quenched with saturated ammonium chloride solution and extracted with ethyl acetate (3×). The combined ethyl acetate layer was washed with brine, dried over anhydrous sodium sulphate and concentrated under reduced pressure to afford 3,4-dimethoxy-2-(methoxymethyl)phenylboronic acid as a solid.

Preparation 2

3,4-dimethoxy-2-(isobutoxy)phenylboronic acid (Compound 302)

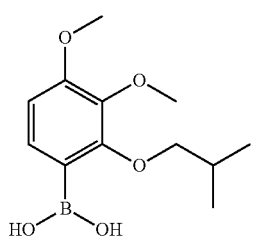 [SMILES: COc1ccc(B(O)O)c(OCC(C)C)c1OC]

Under an argon atmosphere 6-bromo-2,3-dimethoxyphenol (5.8 g, 25 mmol) was dissolved in acetone (40 mL). $K_2CO_3$ (5.2 g, 37.5 mmol) and isobutyl bromide (4.3 g, 31.3 mmol) was added. DMF (20 mL) was added and the suspension was stirred at 50° C. over night. The suspension was partially concentrated in vacuo. $H_2O$ was added and the mixture was extracted with EtOAc (×2). The combined organic phases were washed with H2O and brine, dried ($Na_2SO_4$), filtered and concentrated in vacuo. The crude product was purified by flash chromatography using heptane: EtOAc 96:4 as the eluent to afford 1-bromo-2-isobutoxy-3, 4-dimethoxy-benzene as a liquid.

Under an argon atmosphere 1-bromo-2-isobutoxy-3,4-dimethoxy-benzene (6.7 g, 23.2 mmol) was dissolved in dry THF (50 mL). The solution was cooled to −70° C. while n-BuLi (2.0 M in pentane, 12.8 mL, 25.5 mmol) was added over 10 min. The solution was stirred for 20 min at −70° C. after which trimethyl borate (5.2 mL, 46.4 mmol) was added over 10 min. The solution was kept at −70° C. for 15 min after which it was heated to RT over 15 min and stirred at RT for 30 min. Saturated aq. $NH_4Cl$ (200 mL) was added and the solution was adjusted to pH 1 with 4N HCl (10 mL). The mixture was extracted with EtOAc (×3). The combined organic phases were dried ($Na_2SO4$), filtered and concentrated to afford an oil. The crude product was purified by flash chromatography using heptane:EtOAc 4:1->3:1 as the eluent to afford a crystalline compound which was recrystallised from petroleum ether:$Et_2O$ (90:10) to afford the title compound as a crystalline compound.

Preparation 3

4-(2-Hydroxy-3,4-dimethoxy-phenyl)-indan-1-one (Compound 303)

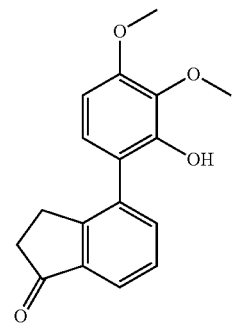 [SMILES: COc1ccc(-c2cccc3c2CCC3=O)c(O)c1OC]

To a stirring solution 3,4-dimethoxy-2-(methoxymethyl) phenylboronic acid (Compound 301)(1 g, 0.186 mmol) in dimethylformamide under nitrogen atmosphere, were added cesium carbonate (4.5 g, 13.84 mmol), tetrakis(triphenylphosphine)palladium(0) (269 mg, 0.232 mmol) and 4-bromo-indan-1-one (1.35 g, 5.57 mmol) and the resultant reaction mixture was heated to 90° C. for 4 h. The reaction mixture was filtered off and the filtrate was extracted with ethyl acetate (3×). The combined ethyl acetate layer was washed with brine and dried over anhydrous sodium sulphate and concentrated under reduced pressure. Purification by column chromatography (silica gel, 0-35% ethyl acetate in pet ether) afforded 4-(3,4-Dimethoxy-2-methoxymethoxy-phenyl)-indan-1-one as a solid.

To a stirring solution of 4-(3,4-Dimethoxy-2-methoxymethoxy-phenyl)-indan-1-one (1.6 g, 4.87 mmol) in methanol (15 mL) at 0° C., was added concentrated hydrochloride acid (3 mL) and the resultant reaction mixture was stirred at 50° C. for 15 min. The reaction mixture was concentrated under reduced pressure and basified with aq sodium bicarbonate solution extracted with ethyl acetate (3×). The combined ethyl acetate layer was washed with brine, dried over anhydrous sodium sulphate and concentrated under reduced pressure. The residue was purified by washing with ether to afford the title compound as a solid.

1H NMR (300 MHz, cdcl3) δ 7.76 (dd, J=7.5, 0.9 Hz, 1H), 7.56 (dd, J=7.4, 1.2 Hz, 1H), 7.43 (t, J=7.5 Hz, 1H), 6.92 (d, J=8.6 Hz, 1H), 6.58 (d, J=8.6 Hz, 1H), 6.04 (s, 1H), 3.97 (s, 3H), 3.93 (s, 3H), 3.11-3.02 (m, 2H), 2.71-2.63 (m, 2H).

Preparation 4

4-(2-hydroxy-3,4-dimethoxyphenyl)isobenzofuran-1(3H)-one (Compound 304)

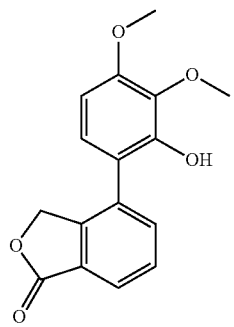 [SMILES: COc1ccc(-c2cccc3c2COC3=O)c(O)c1OC]

To a stirring solution of 3-bromo-2-methyl-benzoic add (1 g) in methanol (10 mL), was added concentrated sulphuric acid (0.4 mL) and the resultant reaction mixture was heated to reflux for 16 h. The reaction mixture was concentrated under reduced pressure and the residue was diluted with water and washed with sodium bicarbonate solution and brine and dried over anhydrous sodium sulphate and concentrated under reduced pressure to afford 3-bromo-2-methyl-benzoic acid methyl ester as a liquid.

To a stirring solution of 3-Bromo-2-methyl-benzoic acid methyl ester (500 mg, 2.22 mmol) in carbon tetrachloride (6 mL) at 0° C., was added chromylchloride (0.36 mL, 4.45 mmol) and the reaction mixture was heated to reflux for 20 h. The reaction mixture was cooled to RT, added ice water and sat sodium bicarbonate solution at 0° C. Extracted with ethyl acetate (3×) the combined ethyl acetate layer was washed with brine and dried over anhydrous sodium sulphate and concentrated under reduced pressure. Purification by column chromatography (silica gel, 0-10% ethyl acetate in pet. ether) afforded 4-bromo-3H-isobenzofuran-1-one as a solid.

To a stirring solution of 3,4-dimethoxy-2-(methoxymethyl)phenylboronic acid (compound 301)(2.3 g, 10.79 mmol) in dimethylformamide (25 mL) under nitrogen atmosphere, were added cesium carbonate (10.52 g, 32.31 mmol), tetrakis(triphenylphosphine)palladium(0) (623 mg, 0.539 mmol) and 4-bromoisobenzofuran-1(3H)-one (5.2 g, 21.5 mmol) and the resultant reaction mixture was heated to 80° C. for 3 h. The reaction mixture was filtered off and the filtrate was extracted with ethyl acetate (3×). The combined ethyl acetate layer was washed with brine and dried over anhydrous sodium sulphate and concentrated under reduced pressure. Purification by column chromatography (silica gel, 0-30% ethyl acetate in pet ether) afforded 4-(3,4-dimethoxy-2-methoxymethoxy-phenyl)-3H-isobenzofuran-1-one as a solid.

To a stirring solution of 4-(3,4-dimethoxy-2-(methoxymethoxy)phenyl)isobenzofuran-1(3H)-one (1.3 g, 3.9 mmol) in methanol (15 mL) at 0° C., was added concentrated hydrochloride acid (3 mL) and the resultant reaction mixture was stirred at 50° C. for 15 min. The reaction mixture was concentrated under reduced pressure and basified with aq. sodium bicarbonate solution extracted with ethyl acetate (3×). The combined ethyl acetate layer was washed with brine, dried over anhydrous sodium sulphate and concen- trated under reduced pressure and purification. The resulting residue purified by washings with pentane to afford the title compound as a solid.

1H NMR (300 MHz, cdcl3) δ 7.90 (d, J=6.8 Hz, 1H), 7.65 (d, J=6.5 Hz, 1H), 7.58 (t, J=7.5 Hz, 1H), 6.94 (d, J=8.7 Hz, 1H), 6.60 (d, J=8.7 Hz, 1H), 6.18 (s, 1H), 5.31 (s, 2H), 3.98 (s, 3H), 3.93 (s, 3H).

Preparation 5

5-(2-hydroxy-3,4-dimethoxyphenyl'-indan-1-one (Compound 305)

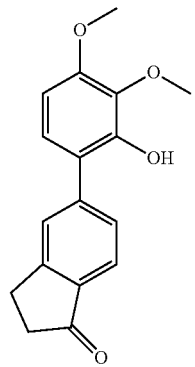

To a stirring solution of 3,4-dimethoxy-2-(methoxymethyl)phenylboronic acid (Compound 301) (3.5 g, 16.58 mmol) in dimethylformamide (50 mL) under nitrogen atmosphere, were added cesium carbonate (16.17 g, 49.75 mmol), tetrakis(triphenylphosphine)palladium(0) (957 mg, 0.828 mmol) and 5-bromo-2,3-indan-1-one (8.02 g, 33.14 mmol) and the resultant reaction mixture was heated to 70° C. for 3 h. The reaction mixture was filtered off and the filtrate was extracted with ethyl acetate (3×). The combined ethyl acetate layer was washed with brine and dried over anhydrous sodium sulphate and concentrated under reduced pressure. Purification by column chromatography (silica gel, 0-30% ethyl acetate in pet ether) afforded 5-(3,4-dimethoxy-2-(methoxymethoxy)phenyl)-indan-1-one as a solid.

To a stirring solution of compound 5-(3,4-dimethoxy-2-(methoxymethoxy)phenyl)-indan-1-one (1.3 g, 3.9 mmol) in methanol (15 mL) at 0° C., was added concentrated hydrochloride acid (3 mL) and the resultant reaction mixture was stirred at 50° C. for 15 min. The reaction mixture was concentrated under reduced pressure and basified with aq sodium bicarbonate solution extracted with ethyl acetate (3×). The combined ethyl acetate layer was washed with brine, dried over anhydrous sodium sulphate and concentrated under reduced pressure. The resulting residue was purified by washings with pentane to afford the title compound as a solid.

1H NMR (300 MHz, cdcl3) δ 7.79 (d, J=8.0 Hz, 1H), 7.70 (s, 1H), 7.59 (d, J=8.0 Hz, 1H), 7.08 (d, J=8.7 Hz, 1H), 6.59

(d, J=8.8 Hz, 1H), 6.19 (s, 1H), 3.96 (s, 3H), 3.92 (s, 3H), 3.23-3.11 (m, 2H), 2.77-2.67 (m, 2H).

Preparation 6

5-(2-hydroxy-3,4-dimethoxyphenyl)isobenzofuran-1(3H)-one (Compound 306)

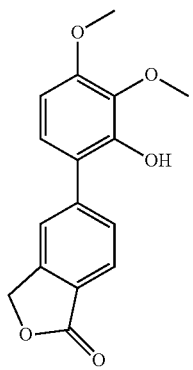 [SMILES: COc1ccc(-c2ccc3c(c2)CCC3=O)c(O)c1OC]

To a stirring solution of 3,4-dimethoxy-2-(methoxymethyl)phenylboronic acid (Compound 301) (3.5 g, 16.58 mmol) in dimethylformamide (50 mL) under nitrogen atmosphere, were added cesium carbonate (16.17 g, 49.75 mmol), tetrakis(triphenylphosphine) palladium(0) (957 mg, 0.828 mmol) and 5-bromoisobenzofuran-1(3H)-one (8.02 g, 33.14 mmol) and the resultant reaction mixture was heated to 70° C. for 3 h. The reaction mixture was filtered off and the filtrate was extracted with ethyl acetate (3×). The combined ethyl acetate layer was washed with brine, dried over anhydrous sodium sulphate and concentrated under reduced pressure. Purification by column chromatography (silica gel, 0-30% ethyl acetate in pet ether) afforded 5-(3,4-dimethoxy-2-(methoxymethoxy)phenyl)isobenzofuran-1(3H)-one as a solid.

To a stirring solution of 5-(3,4-dimethoxy-2-(methoxymethoxy)phenyl)isobenzofuran-1(3H)-one (1.4 g, 4.26 mmol) in methanol (20 mL) at 0° C., was added concentrated hydrochloride acid (3 mL) and the resultant reaction mixture was stirred at 50° C. for 15 min. The reaction mixture was concentrated under reduced pressure and basified with aq sodium bicarbonate solution extracted with ethyl acetate (3×). The combined ethyl acetate layer was washed with brine, dried over anhydrous sodium sulphate and concentrated under reduced pressure. The resulting residue was purified by washings with pentane to afford the title compound as a solid.

1H NMR (300 MHz, cdcl3) δ 7.94 (d, J=8.4 Hz, 1H), 7.73 (m, 2H), 7.08 (d, J=8.8 Hz, 1H), 6.60 (d, J=8.8 Hz, 1H), 6.22 (s, 1H), 5.35 (s, 2H), 3.96 (s, 3H), 3.93 (s, 3H).

Preparation 7

5-(2-hydroxy-3,4-dimethoxyphenyl)isoindolin-1-one (Compound 307)

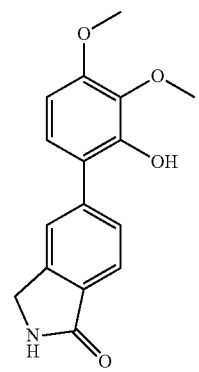 [SMILES: COc1ccc(-c2ccc3c(c2)CNC3=O)c(O)c1OC]

To a stirring solution of 3,4-dimethoxy-2-(methoxymethyl)phenylboronic acid (compound 301) (400 mg, 1.88 mmol) in dimethylformamide (10 mL) under nitrogen atmosphere, were added cesium carbonate (1.8 g, 5.66 mmol), tetrakis(triphenylphosphine)palladium(0) (100 mg, 0.09 mmol) and 5-bromoisoindolin-1-one (913 mg, 3.77 mmol) and the resultant reaction mixture was heated to 90° C. for 6 h. The reaction mixture was filtered off and the filtrate was extracted with ethyl acetate (3×). The combined ethyl acetate layer was washed with brine and dried over anhydrous sodium sulphate and concentrated under reduced pressure. Purification was done by column chromatography (silica gel, 0-3% methanol in dichloromethane) afforded 5-(3,4-dimethoxy-2-(methoxymethoxy)phenyl)isoindolin-1-one as a solid.

To a stirring solution of 5-(3,4-dimethoxy-2-(methoxymethoxy)phenyl)isoindolin-1-one (600 g, 1.81 mmol) in methanol (20 mL) at 0° C., was added concentrated hydrochloride acid (1 mL) and the resultant reaction mixture was stirred at 50° C. for 15 min. The reaction mixture was concentrated under reduced pressure and basified with aq sodium bicarbonate solution extracted with ethyl acetate (3×). The combined ethyl acetate layer was washed with brine, dried over anhydrous sodium sulphate and concentrated under reduced pressure. Purification of the resulting residue by washings with ether afforded the title compound as a solid.

1H NMR (400 MHz, dmso) δ 9.03 (s, 1H), 8.48 (s, 1H), 7.66 (m, 2H), 7.60 (d, J=7.8 Hz, 1H), 7.03 (d, J=8.6 Hz, 1H), 6.63 (d, J=8.6 Hz, 1H), 4.39 (s, 2H), 3.83 (s, 3H), 3.73 (s, 3H).

Preparation 8

4-(4,4,5,5-Tetramethyl-[1,3,2]dioxaborolan-2-yl)-indan-1-one (Compound 308)

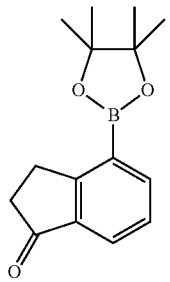 [SMILES: CC1(C)OB(c2cccc3c2CCC3=O)OC1(C)C]

In a screw cap vessel 4-Bromo-1-indanone (1.0 g, 4.9 mmol) was dissolved in 1,4-dioxan (40 mL). Argon was purged through the solution. PdCl$_2$(dppf)$_2$*CH$_2$Cl$_2$ (0.16 g, 0.2 mmol) and bis(pinacolato)diborane (1.3 g, 5.1 mmol) was added followed by addition of KOAc (1.4 g, 14.6 mmol). The vessel was closed and the mixture was stirred at 80° C. for 4 h. The mixture was cooled to RT and diluted with EtOAc (50 mL). The suspension was filtered and washed with EtOAc. The filtrate was concentrated and the crude product was purified by flash chromatography (heptane:EtOAc 100:0->93:7) to afford the title compound as a solid.

1H NMR (300 MHz, CDCl3) δ 8.04 (d, J=7.2 Hz, 1H), 7.84 (d, J=7.7 Hz, 1H), 7.37 (t, J=7.4 Hz, 1H), 3.39-3.29 (m, 2H), 2.70-2.63 (m, 2H), 1.36 (s, 12H).

Preparation 9

5-(4,4,5,5-Tetramethyl-[1,3,2]dioxaborolan-2-yl)-3H-isobenzofuran-1-one (Compound 309)

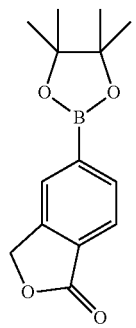 [SMILES: CC1(C)OB(c2ccc3c(c2)COC3=O)OC1(C)C]

The title compound was prepared according to the procedure described in preparation 8, using 5-bromo-3H-isobenzofuran-1-one as the starting material.

1H NMR (300 MHz, CDCl3) δ 7.98-7.89 (m, 3H), 5.31 (s, 2H), 1.37 (s, 12H).

Preparation 10

5-(4,4,5,5-Tetramethyl-[1,3,2]dioxaborolan-2-yl)-2,3-dihydro-isoindol-1-one (Compound 310)

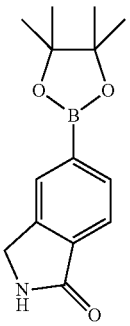 [SMILES: CC1(C)OB(c2ccc3c(c2)CNC3=O)OC1(C)C]

The title compound was prepared according to the procedure described in preparation 8, using 5-bromo-2,3-dihydro-isoindol-1-one as the starting material.

1H NMR (300 MHz, DMSO) δ 8.63 (s, 1H), 7.87 (s, 1H), 7.76 (d, J=7.4 Hz, 1H), 7.70-7.64 (m, 1H), 4.38 (s, 2H), 1.31 (s, 12H).

Example 1

Procedure for Alkylation of Phenols Using Parallel Synthesis

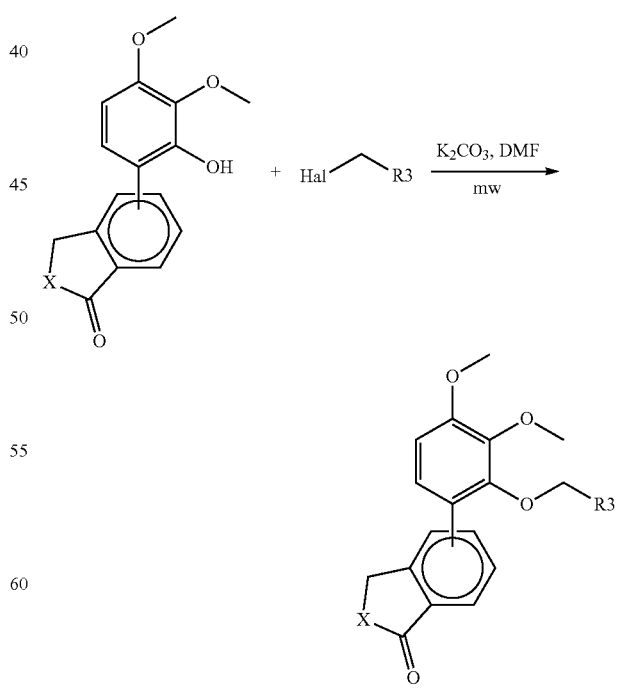

Under an argon atmosphere the phenol (0.035 mmol) and the halogenide (0.07 mmol) were dissolved in DMF (0.5 mL)

in a microwave vial. K₂CO₃ (0.012 g, 0.087 mmol) was added and the suspension was heated in a microwave oven at 120° C. for 10 min. H₂O (2 mL) was added and the mixture was extracted with EtOAc (2×3 mL). The phases were separated using a phase separation cartridge (Chromabond, PTS). The organic phase was concentrated in vacuo and the residue was dissolved in DMSO (0.3 mL) and purified by preparative HPLC/MS.

Following this procedure starting from 4-(2-Hydroxy-3,4-dimethoxy-phenyl)-indan-1-one (compound 303) as the phenol compounds 101-114 were prepared:

4-[3,4-Dimethoxy-2-(3-methyl-butoxy)-phenyl]-indan-1-one (Compound 101)

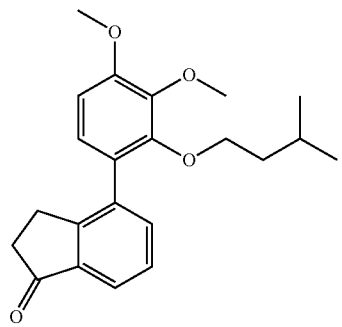 [SMILES: COc1ccc(-c2cccc3c2CCC3=O)c(OCCC(C)C)c1OC]

1H NMR (600 MHz, DMSO-SPE) δ 7.64 (dd, J=7.6, 0.9 Hz, 1H), 7.55 (dd, J=7.3, 1.1 Hz, 1H), 7.48 (t, J=7.5 Hz, 1H), 7.01 (dd, J=8.5, 3.3 Hz, 1H), 6.93-6.89 (m, 1H), 3.85 (s, 3H), 3.80 (s, 3H), 3.64 (t, J=6.2 Hz, 2H), 3.00-2.91 (m, 2H), 2.64-2.57 (m, 2H), 1.30 (dp, J=13.3, 6.7 Hz, 1H), 1.18 (q, J=6.4 Hz, 2H), 0.58 (s, 3H), 0.57 (s, 3H).

4-(2-Cyclobutylmethoxy-3,4-dimethoxy-phenyl)-indan-1-one (Compound 102)

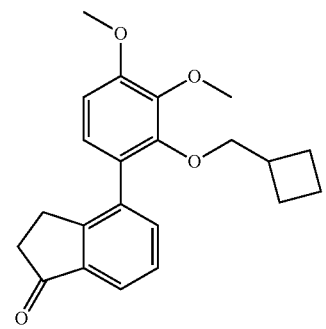 [SMILES: COc1ccc(-c2cccc3c2CCC3=O)c(OCC2CCC2)c1OC]

1H NMR (600 MHz, DMSO-SPE) δ 7.63 (dd, J=7.6, 0.9 Hz, 1H), 7.56 (dd, J=7.4, 1.2 Hz, 1H), 7.48 (t, J=7.5 Hz, 1H), 7.03-6.99 (m, 1H), 6.92-6.89 (m, 1H), 3.85 (s, 3H), 3.80 (s, 3H), 3.60 (d, J=6.3 Hz, 2H), 2.96 (dd, J=14.5, 8.5 Hz, 2H), 2.64-2.58 (m, 2H), 2.35-2.26 (m, 1H), 1.70-1.61 (m, 3H), 1.57-1.49 (m, 1H), 1.37-1.28 (m, 2H).

4-[2-(4-Methanesulfonyl-benzyloxy)-3,4-dimethoxy-phenyl]-indan-1-one (Compound 103)

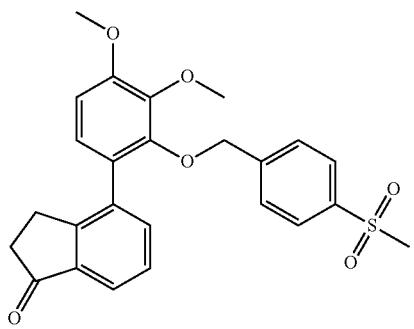 [SMILES: COc1ccc(-c2cccc3c2CCC3=O)c(OCc2ccc(S(C)(=O)=O)cc2)c1OC]

1H NMR (600 MHz, DMSO-SPE) δ 7.71-7.68 (m, 2H), 7.62 (dd, J=7.6, 1.0 Hz, 1H), 7.49 (dd, J=7.3, 1.1 Hz, 1H), 7.43 (t, J=7.5 Hz, 1H), 7.16 (d, J=8.3 Hz, 2H), 7.05-7.02 (m, 1H), 6.97-6.94 (m, 1H), 4.87 (s, 2H), 3.87 (s, 3H), 3.85 (s, 3H), 3.16 (s, 3H), 2.88-2.83 (m, 2H), 2.58-2.52 (m, 2H).

4-[2-(3-Hydroxymethyl-oxetan-3-ylmethoxy)-3,4-dimethoxy-phenyl]-indan-1-one (Compound 104)

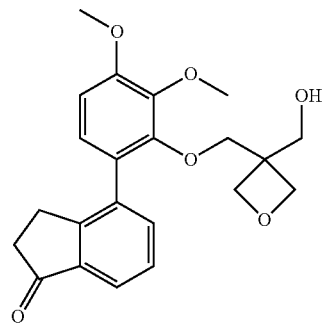 [SMILES: COc1ccc(-c2cccc3c2CCC3=O)c(OCC2(CO)COC2)c1OC]

1H NMR (600 MHz, DMSO-SPE) δ 7.64 (dd, J=7.5, 0.9 Hz, 1H), 7.55 (dd, J=7.4, 1.2 Hz, 1H), 7.48 (t, J=7.5 Hz, 1H), 7.03 (d, J=8.6 Hz, 1H), 6.96-6.92 (m, 1H), 4.74 (t, J=5.3 Hz, 1H), 4.09 (d, J=5.8 Hz, 2H), 3.90 (d, J=5.8 Hz, 2H), 3.86 (s,

3H), 3.81 (s, 3H), 3.81 (s, 2H), 3.29 (t, J=3.8 Hz, 2H), 2.98-2.92 (m, 2H), 2.63-2.57 (m, 2H).

4-[2-(3,3-Dimethyl-butoxy)-3,4-dimethoxy-phenyl]-indan-1-one (Compound 105)

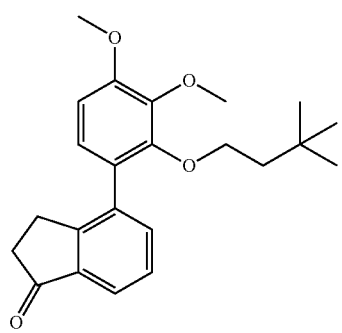 [SMILES: COc1ccc(-c2cccc3c2CCC3=O)c(OCCC(C)(C)C)c1OC]

1H NMR (600 MHz, DMSO-SPE) δ 7.65 (dd, J=7.6, 0.8 Hz, 1H), 7.55 (dd, J=7.3, 1.1 Hz, 1H), 7.49 (t, J=7.5 Hz, 1H), 7.00 (d, J=8.5 Hz, 1H), 6.92-6.89 (m, 1H), 3.85 (s, 3H), 3.81 (s, 3H), 3.69-3.62 (m, 2H), 2.97-2.91 (m, 2H), 2.63-2.56 (m, 2H), 1.22 (t, J=7.2 Hz, 2H), 0.65 (s, 9H).

4-[2,3-Dimethoxy-6-(1-oxo-indan-4-yl)-phenoxymethyl]-benzamide (Compound 106)

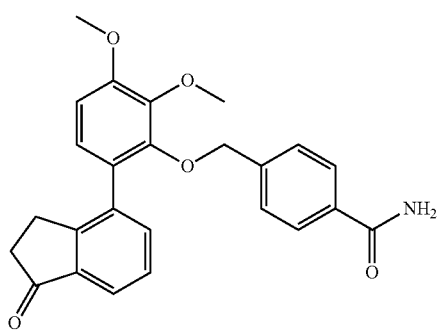 [SMILES: COc1ccc(-c2cccc3c2CCC3=O)c(OCc2ccc(C(N)=O)cc2)c1OC]

1H NMR (600 MHz, DMSO-SPE) δ 7.89 (s, 1H), 7.64 (ddd, J=4.2, 3.3, 1.4 Hz, 3H), 7.51 (dd, J=7.3, 1.1 Hz, 1H), 7.45 (t, J=7.5 Hz, 1H), 7.31 (s, 1H), 7.04-7.00 (m, 1H), 6.93 (dd, J=8.4, 4.6 Hz, 3H), 4.81 (s, 2H), 3.87 (s, 3H), 3.85 (s, 3H), 3.32 (d, J=10.7 Hz, 2H), 2.83-2.78 (m, 2H), 2.52 (dt, J=5.9, 5.4 Hz, 2H).

4-[2-(3-Hydroxy-2,2-dimethyl-propoxy)-3,4-dimethoxy-phenyl]-indan-1-one (Compound 107)

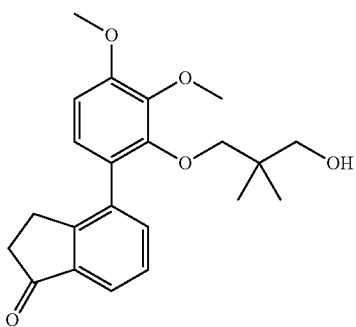 [SMILES: COc1ccc(-c2cccc3c2CCC3=O)c(OCC(C)(C)CO)c1OC]

1H NMR (600 MHz, DMSO-SPE) δ 7.63 (dd, J=7.5, 0.8 Hz, 1H), 7.54 (dd, J=7.3, 1.1 Hz, 1H), 7.47 (t, J=7.5 Hz, 1H), 6.99 (d, J=8.5 Hz, 1H), 6.91-6.87 (m, 1H), 4.28 (t, J=5.4 Hz, 1H), 3.84 (s, 3H), 3.79 (s, 3H), 3.40 (s, 2H), 2.98-2.93 (m, 2H), 2.90 (t, J=3.7 Hz, 2H), 2.60 (dd, J=6.8, 4.9 Hz, 2H).

4-[2,3-Dimethoxy-6-(1-oxo-indan-4-yl)-phenoxymethyl]-N-methyl-benzamide (Compound 108)

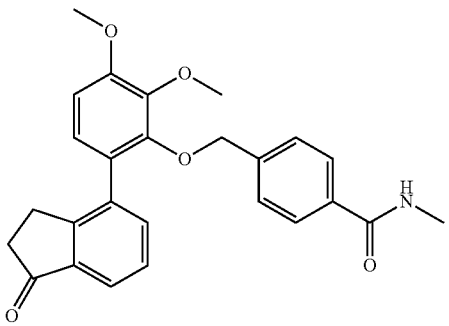 [SMILES: CNC(=O)c1ccc(COc2c(-c3cccc4c3CCC4=O)ccc(OC)c2OC)cc1]

1H NMR (600 MHz, DMSO-SPE) δ 8.34 (q, J=4.2 Hz, 1H), 7.64 (dd, J=7.5, 0.8 Hz, 1H), 7.59 (d, J=8.2 Hz, 2H), 7.51 (dd, J=7.3, 1.0 Hz, 1H), 7.45 (t, J=7.4 Hz, 1H), 7.04-7.00 (m,

1H), 6.93 (m, 3H), 4.80 (s, 2H), 3.87 (s, 3H), 3.85 (s, 3H), 2.85-2.79 (m, 2H), 2.75 (d, J=4.6 Hz, 3H), 2.52 (m, 2H).

4-[2,3-Dimethoxy-6-(1-oxo-indan-4-yl)-phenoxymethyl]-N,N-dimethyl-benzamide (Compound 109)

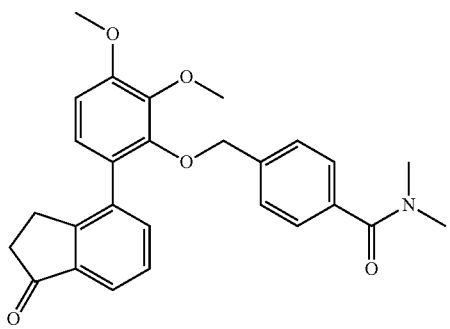 [SMILES: COc1ccc(-c2cccc3c2CCC3=O)c(OCc2ccc(C(=O)N(C)C)cc2)c1OC]

1H NMR (600 MHz, DMSO-SPE) δ 7.62 (dd, J=7.5, 0.8 Hz, 1H), 7.50 (dd, J=7.3, 1.1 Hz, 1H), 7.44 (t, J=7.5 Hz, 1H), 7.16 (d, J=8.1 Hz, 2H), 7.03 (d, J=8.6 Hz, 1H), 6.93 (m, 3H), 4.78 (s, 2H), 3.87 (s, 3H), 3.85 (s, 3H), 2.94 (s, 3H), 2.87-2.78 (m, 5H), 2.54 (dt, J=12.9, 5.6 Hz, 2H).

3-[2,3-Dimethoxy-6-(1-oxo-indan-4-yl)-phenoxymethyl]-N,N-dimethyl-benzamide (Compound 110)

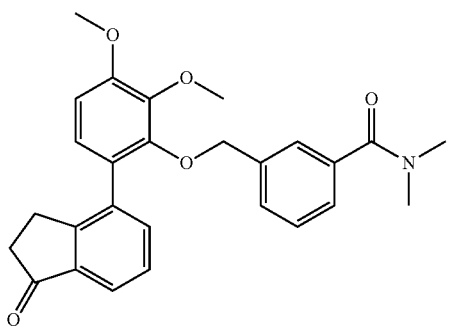 [SMILES: COc1ccc(-c2cccc3c2CCC3=O)c(OCc2cccc(C(=O)N(C)C)c2)c1OC]

1H NMR (600 MHz, DMSO-SPE) δ 7.61 (dd, J=7.5, 0.7 Hz, 1H), 7.51 (dd, J=7.3, 1.0 Hz, 1H), 7.43 (t, J=7.5 Hz, 1H), 7.21-7.18 (m, 2H), 7.02 (d, J=8.5 Hz, 1H), 6.99 (ddd, J=8.8, 4.5, 1.6 Hz, 1H), 6.96-6.91 (m, 1H), 6.80 (s, 1H), 4.79 (s, 2H), 3.87 (s, 3H), 3.85 (s, 3H), 2.94 (s, 3H), 2.85 (dd, J=17.9, 11.8 Hz, 2H), 2.71 (s, 3H), 2.56-2.52 (m, 2H).

3-[2,3-Dimethoxy-6-(1-oxo-indan-4-yl)-phenoxymethyl]-N,N-dimethyl-benzenesulfonamide (Compound 111)

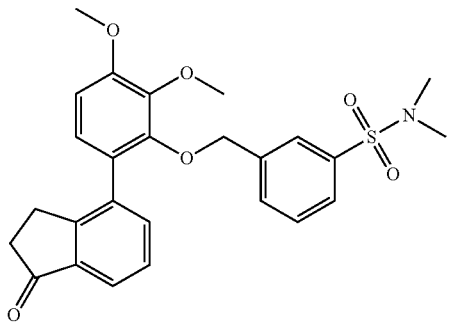 [SMILES: COc1ccc(-c2cccc3c2CCC3=O)c(OCc2cccc(S(=O)(=O)N(C)C)c2)c1OC]

1H NMR (600 MHz, DMSO-SPE) δ 7.62-7.59 (m, 1H), 7.58 (d, J=7.9 Hz, 1H), 7.50 (dd, J=7.3, 0.8 Hz, 1H), 7.43 (t, J=7.6 Hz, 2H), 7.37 (s, 1H), 7.25 (d, J=7.7 Hz, 1H), 7.02 (d, J=8.5 Hz, 1H), 6.96-6.93 (m, 1H), 4.87 (s, 2H), 3.87 (s, 3H), 3.85 (s, 3H), 2.87-2.82 (m, 2H), 2.57-2.53 (m, 2H), 2.48 (s, 6H).

4-[2,3-Dimethoxy-6-(1-oxo-indan-4-yl)-phenoxymethyl]-benzenesulfonamide (Compound 112)

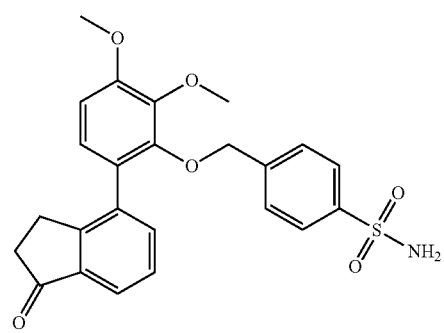 [SMILES: COc1ccc(-c2cccc3c2CCC3=O)c(OCc2ccc(S(N)(=O)=O)cc2)c1OC]

1H NMR (600 MHz, DMSO-SPE) δ 7.65 (dd, J=7.4, 0.9 Hz, 1H), 7.59 (d, J=8.3 Hz, 2H), 7.49 (dd, J=7.3, 1.2 Hz, 1H), 7.45 (t, J=7.4 Hz, 1H), 7.29 (s, 2H), 7.05 (d, J=8.3 Hz, 2H), 7.03 (d, J=8.5 Hz, 1H), 6.95 (d, J=8.6 Hz, 1H), 4.83 (s, 2H), 3.87 (s, 3H), 3.85 (s, 3H), 2.87 (dd, J=13.9, 8.4 Hz, 2H), 2.58 (dd, J=6.7, 4.9 Hz, 2H).

4-[2-(3-Methanesulfonyl-benzyloxy)-3,4-dimethoxy-phenyl]-indan-1-one (Compound 113)

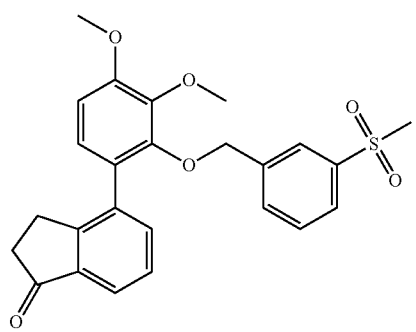 [SMILES: COc1ccc(-c2cccc3c2CCC3=O)c(OCc2cccc(S(C)(=O)=O)c2)c1OC]

1H NMR (600 MHz, DMSO-SPE) δ 7.76 (d, J=7.9 Hz, 1H), 7.62-7.59 (m, 1H), 7.57 (s, 1H), 7.51 (dd, J=7.3, 0.9 Hz, 1H), 7.43 (m, 2H), 7.25 (d, J=7.7 Hz, 1H), 7.04 (d, J=8.5 Hz, 1H), 6.97-6.95 (m, 1H), 4.86 (s, 2H), 3.88 (s, 3H), 3.85 (s, 3H), 3.10 (s, 3H), 2.90-2.86 (m, 2H), 2.57-2.53 (m, 2H).

3-[2,3-Dimethoxy-6-(1-oxo-indan-4-yl)-phenoxymethyl]-benzamide (Compound 114)

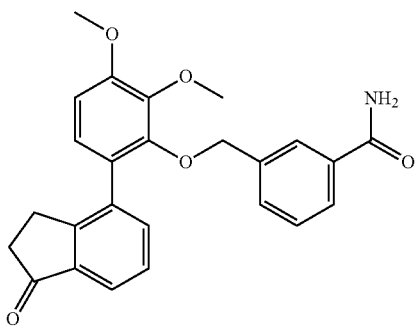 [SMILES: COc1ccc(-c2cccc3c2CCC3=O)c(OCc2cccc(C(N)=O)c2)c1OC]

1H NMR (600 MHz, DMSO-SPE) δ 7.84 (s, 1H), 7.68 (d, J=7.8 Hz, 1H), 7.59 (dd, J=7.6, 0.6 Hz, 1H), 7.54 (s, 1H), 7.48 (dd, J=7.3, 1.0 Hz, 1H), 7.41 (t, J=7.5 Hz, 1H), 7.30 (s, 1H), 7.17 (dd, J=9.5, 5.8 Hz, 1H), 7.01 (d, J=8.5 Hz, 1H), 6.94 (m, 2H), 4.79 (s, 2H), 3.87 (s, 3H), 3.86 (s, 3H), 2.84-2.78 (m, 2H), 2.55-2.51 (m, 2H).

Example 2

Following the procedure described in example 1 starting from 4-(2-hydroxy-3,4-dimethoxyphenyl)isobenzofuran-1 (3H)-one (Compound 304) as the phenol, compounds 115-119 were prepared:

4-[2-(4-Methanesulfonyl-benzyloxy)-3,4-dimethoxy-phenyl]-3H-isobenzofuran-1-one (Compound 115)

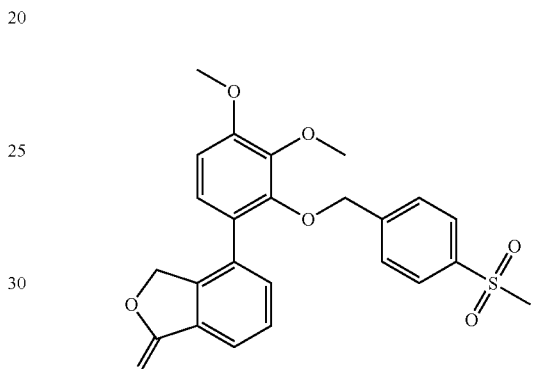

1H NMR (600 MHz, DMSO-SPE) δ 7.82 (dd, J=6.4, 2.2 Hz, 1H), 7.69 (d, J=8.3 Hz, 2H), 7.61-7.57 (m, 2H), 7.19 (d, J=8.3 Hz, 2H), 7.11 (t, J=7.5 Hz, 1H), 6.97 (d, J=8.7 Hz, 1H), 5.25 (s, 2H), 4.88 (s, 2H), 3.87 (s, 3H), 3.86 (s, 3H), 3.17 (s, 3H).

4-[2,3-Dimethoxy-6-(1-oxo-1,3-dihydro-isobenzofuran-4-yl)-phenoxymethyl]-benzamide (Compound 116)

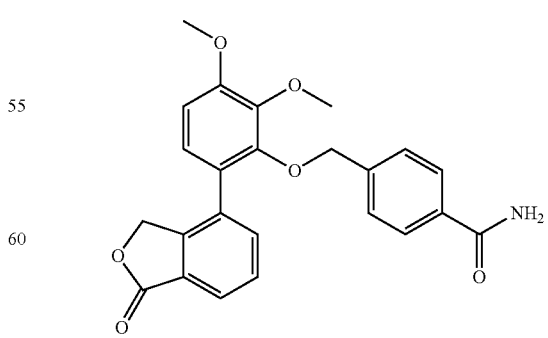

1H NMR (600 MHz, DMSO-SPE) δ 7.88 (s, 1H), 7.84 (dd, J=7.2, 1.2 Hz, 1H), 7.63 (ddd, J=19.4, 12.8, 7.8 Hz, 4H), 7.31

(s, 1H), 7.11 (d, J=8.5 Hz, 1H), 6.97-6.94 (m, 3H), 5.23 (s, 2H), 4.79 (s, 2H), 3.87 (s, 3H), 3.85 (d, J=5.2 Hz, 3H).

4-[2,3-Dimethoxy-6-(1-oxo-1,3-dihydro-isobenzofuran-4-yl)-phenoxymethyl]-N-methyl-benzamide (Compound 117)

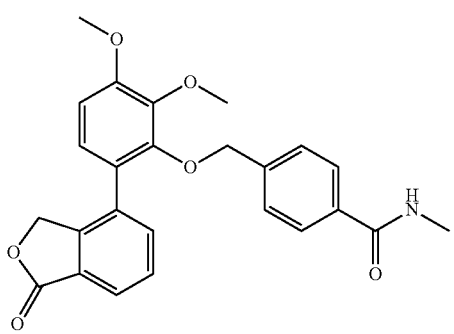 [SMILES: CNC(=O)c1ccc(COc2c(-c3cccc4c3COC4=O)ccc(OC)c2OC)cc1]

1H NMR (600 MHz, DMSO-SPE) δ 8.34 (d, J=4.5 Hz, 1H), 7.84 (dd, J=7.3, 1.1 Hz, 1H), 7.65-7.59 (m, 4H), 7.11 (d, J=8.6 Hz, 1H), 6.96 (dd, J=8.4, 4.1 Hz, 3H), 5.24 (s, 2H), 4.79 (d, J=7.5 Hz, 2H), 3.87 (s, 3H), 3.86 (s, 3H), 2.76 (d, J=7.4 Hz, 3H).

4-[2,3-Dimethoxy-6-(1-oxo-1,3-dihydro-isobenzofuran-4-yl)-phenoxymethyl]-N,N-dimethyl-benzamide (Compound 118)

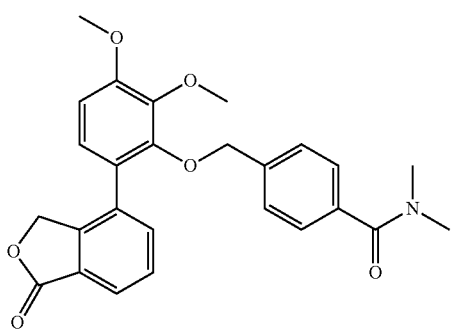 [SMILES: COc1ccc(-c2cccc3c2COC3=O)c(OCc2ccc(C(=O)N(C)C)cc2)c1OC]

1H NMR (600 MHz, DMSO-SPE) δ 7.82 (dd, J=7.2, 1.2 Hz, 1H), 7.65-7.57 (m, 2H), 7.18 (d, J=8.1 Hz, 2H), 7.12 (d, J=8.6 Hz, 1H), 6.96 (d, J=8.4 Hz, 3H), 5.26 (s, 2H), 4.78 (d, J=7.9 Hz, 2H), 3.87 (s, 3H), 3.86 (s, 3H), 2.95 (s, 3H), 2.83 (s, 3H).

4-[2-(3-Hydroxymethyl-oxetan-3-ylmethoxy)-3,4-dimethoxy-phenyl]-3H-isobenzofuran-1-one (Compound 119)

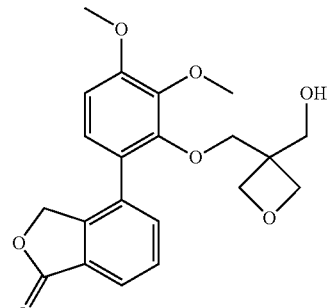

1H NMR (600 MHz, DMSO-SPE) δ 7.87-7.84 (m, 1H), 7.70 (dd, J=7.4, 0.9 Hz, 1H), 7.66 (t, J=7.5 Hz, 1H), 7.13 (d, J=8.6 Hz, 1H), 6.96 (d, J=8.6 Hz, 1H), 5.33 (s, 2H), 4.77 (t, J=5.3 Hz, 1H), 4.10 (d, J=5.8 Hz, 2H), 3.92 (d, J=5.8 Hz, 2H), 3.86 (s, 3H), 3.84 (s, 2H), 3.82 (s, 3H).

Example 3

Following the procedure described in example 1 starting from 5-(2-Hydroxy-3,4-dimethoxy-phenyl)-indan-1-one (Compound 305) as the phenol, compounds 120-130 were prepared:

5-[3,4-Dimethoxy-2-(3-methyl-butoxy)-phenyl]-indan-1-one (Compound 120)

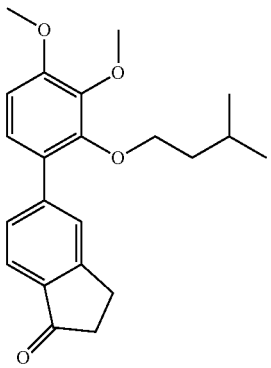 [SMILES: COc1ccc(-c2ccc3c(c2)CCC3=O)c(OCCC(C)C)c1OC]

1H NMR (600 MHz, DMSO-SPE) δ 7.67-7.63 (m, 2H), 7.53-7.49 (m, 1H), 7.12 (d, J=8.7 Hz, 1H), 6.94-6.90 (m, 1H), 3.84 (s, 3H), 3.79 (d, J=3.6 Hz, 3H), 3.74 (q, J=6.6 Hz, 2H), 3.15-3.10 (m, 2H), 2.69-2.63 (m, 2H), 1.59 (dq, J=13.4, 6.7 Hz, 1H), 1.36 (q, J=6.5 Hz, 2H), 0.73 (d, J=6.7 Hz, 6H).

5-[2-(2,2-Dimethyl-propoxy)-3,4-dimethoxy-phenyl]-indan-1-one (Compound 121)

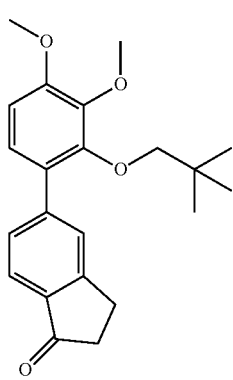 [SMILES: COc1ccc(-c2ccc3c(c2)CCC3=O)c(OCC(C)(C)C)c1OC]

1H NMR (600 MHz, DMSO-SPE) δ 7.67 (s, 1H), 7.64 (d, J=7.9 Hz, 1H), 7.52 (d, J=8.0 Hz, 1H), 7.13 (d, J=8.6 Hz, 1H), 6.92 (d, J=8.7 Hz, 1H), 3.84 (s, 3H), 3.78 (s, 3H), 3.41-3.36 (s, 2H), 3.10 (dd, J=15.3, 9.4 Hz, 2H), 2.70-2.63 (m, 2H), 0.80 (s, 9H).

5-(2-Cyclobutylmethoxy-3,4-dimethoxy-phenyl)-indan-1-one (Compound 122)

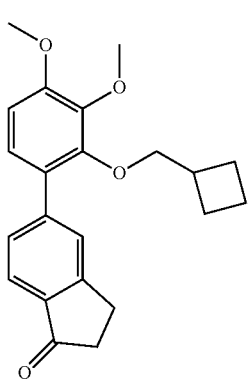 [SMILES: COc1ccc(-c2ccc3c(c2)CCC3=O)c(OCC2CCC2)c1OC]

1H NMR (600 MHz, DMSO-SPE) δ 7.68-7.63 (m, 2H), 7.53 (d, J=7.9 Hz, 1H), 7.13 (d, J=8.6 Hz, 1H), 6.92 (d, J=8.7

Hz, 1H), 3.84 (s, 3H), 3.80 (s, 3H), 3.71 (t, J=6.4 Hz, 2H), 3.16-3.10 (m, 2H), 2.69-2.64 (m, 2H), 2.48-2.39 (m, 1H), 1.85-1.53 (m, 6H).

5-[2-(3,3-Dimethyl-butoxy)-3,4-dimethoxy-phenyl]-indan-1-one (Compound 123)

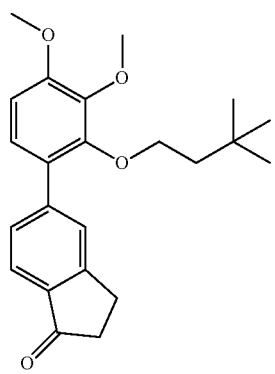 [SMILES: COc1ccc(-c2ccc3c(c2)CCC3=O)c(OCCC(C)(C)C)c1OC]

1H NMR (600 MHz, DMSO-SPE) δ 7.68-7.63 (m, 2H), 7.53-7.49 (m, 1H), 7.11 (d, J=8.6 Hz, 1H), 6.94-6.90 (m, 1H), 3.84 (s, 3H), 3.80 (s, 3H), 3.78 (t, J=7.3 Hz, 2H), 3.17-3.10 (m, 2H), 2.70-2.64 (m, 2H), 1.45 (t, J=7.3 Hz, 2H), 0.79 (s, 9H).

4-[2,3-Dimethoxy-6-(1-oxo-indan-5-yl)-phenoxymethyl]-benzamide Compound 124)

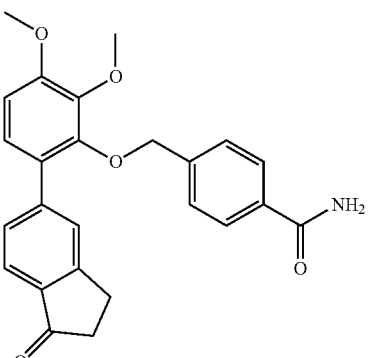

1H NMR (600 MHz, DMSO-SPE) δ 7.93 (s, 1H), 7.74 (d, J=8.2 Hz, 2H), 7.61 (d, J=7.9 Hz, 1H), 7.53 (s, 1H), 7.50-7.46 (m, 1H), 7.34 (s, 1H), 7.20 (d, J=8.2 Hz, 2H), 7.12 (d, J=8.7

Hz, 1H), 6.99-6.95 (m, 1H), 4.88 (s, 2H), 3.87 (s, 3H), 3.84 (s, 3H), 3.07-3.02 (m, 2H), 2.68-2.61 (m, 2H).

5-[2-(3-Hydroxy-2,2-dimethyl-propoxy)-3,4-dimethoxy-phenyl]-indan-1-one (Compound 125)

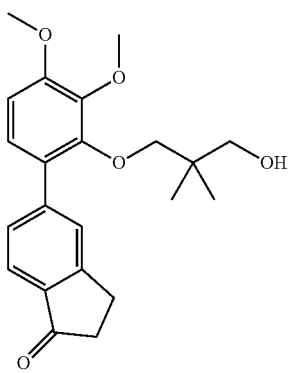 [SMILES: COc1ccc(-c2ccc3c(c2)CCC3=O)c(OCC(C)(C)CO)c1OC]

1H NMR (600 MHz, DMSO-SPE) δ 7.66 (s, 1H), 7.64 (d, J=8.0 Hz, 1H), 7.51 (d, J=8.0 Hz, 1H), 7.12 (d, J=8.7 Hz, 1H), 6.91 (d, J=8.7 Hz, 1H), 4.35 (t, J=5.3 Hz, 1H), 3.84 (s, 3H), 3.78 (s, 3H), 3.50 (s, 2H), 3.13 (dd, J=16.5, 10.9 Hz, 2H), 3.08 (d, J=5.4 Hz, 2H), 2.71-2.63 (m, 2H), 0.74 (s, 6H).

4-[2,3-Dimethoxy-6-(1-oxo-indan-5-yl)-phenoxymethyl]-N-methyl-benzamide (Compound 126)

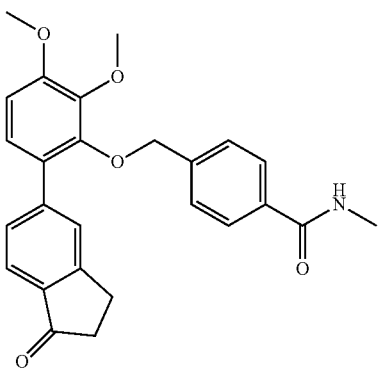 [SMILES: CNC(=O)c1ccc(COc2c(-c3ccc4c(c3)CCC4=O)ccc(OC)c2OC)cc1]

1H NMR (600 MHz, DMSO-SPE) δ 8.39 (q, J=4.3 Hz, 1H), 7.70 (d, J=8.2 Hz, 2H), 7.61 (d, J=7.9 Hz, 1H), 7.54 (s, 1H), 7.51-7.46 (m, 1H), 7.21 (d, J=8.2 Hz, 2H), 7.12 (d, J=8.6 Hz, 1H), 6.99-6.94 (m, 1H), 4.87 (s, 2H), 3.87 (s, 3H), 3.83 (s, 3H), 3.07-3.03 (m, 2H), 2.77 (d, J=4.5 Hz, 3H), 2.68-2.62 (m, 2H).

4-[2,3-Dimethoxy-6-(1-oxo-indan-5-yl)-phenoxymethyl]-N,N-dimethyl-benzamide (Compound 127)

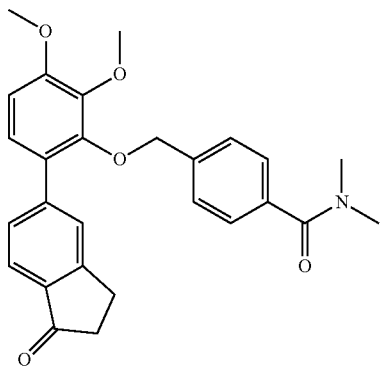 [SMILES: COc1ccc(-c2ccc3c(c2)CCC3=O)c(OCc2ccc(C(=O)N(C)C)cc2)c1OC]

1H NMR (600 MHz, DMSO-SPE) δ 7.63-7.58 (m, 2H), 7.48 (d, J=8.0 Hz, 1H), 7.28 (d, J=8.1 Hz, 2H), 7.20 (d, J=8.1 Hz, 2H), 7.13 (d, J=8.6 Hz, 1H), 6.98-6.95 (m, 1H), 4.86 (s, 2H), 3.87 (s, 3H), 3.84 (s, 3H), 3.09-3.04 (m, 2H), 2.96 (s, 3H), 2.86 (s, 3H), 2.67-2.63 (m, 2H).

3-[2,3-Dimethoxy-6-(1-oxo-indan-5-yl)-phenoxymethyl]-N,N-dimethyl-benzamide (Compound 128)

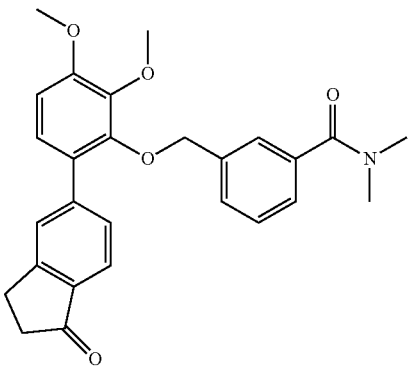 [SMILES: COc1ccc(-c2ccc3c(c2)CCC3=O)c(OCc2cccc(C(=O)N(C)C)c2)c1OC]

1H NMR (600 MHz, DMSO-SPE) δ 7.61-7.58 (m, 2H), 7.48-7.45 (m, 1H), 7.31 (dd, J=9.4, 5.6 Hz, 1H), 7.29-7.25 (m, 1H), 7.23 (t, J=7.3 Hz, 1H), 7.11 (t, J=6.9 Hz, 1H), 7.06 (s,

1H), 6.96 (d, J=8.7 Hz, 1H), 4.87 (s, 2H), 3.87 (s, 3H), 3.84 (s, 3H), 3.08-3.02 (m, 2H), 2.94 (s, 3H), 2.77 (s, 3H), 2.68-2.60 (m, 2H).

5-[2-(3-Hydroxymethyl-oxetan-3-ylmethoxy)-3,4-dimethoxy-phenyl]-indan-1-one (Compound 129)

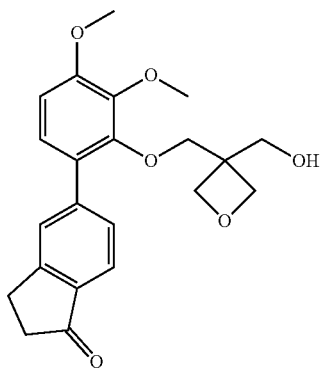 [SMILES: COc1ccc(-c2ccc3c(c2)CCC3=O)c(OCC2(CO)COC2)c1OC]

1H NMR (300 MHz, CDCl3) δ 7.80 (d, J=8.0 Hz, 1H), 7.62 (s, 1H), 7.52 (d, J=8.0 Hz, 1H), 7.11 (d, J=8.7 Hz, 1H), 6.82 (d, J=8.7 Hz, 1H), 4.38 (d, J=6.4 Hz, 2H), 4.23 (d, J=6.4 Hz, 2H), 3.95 (m, 10H), 3.22-3.14 (m, 2H), 2.81-2.68 (m, 2H), 2.35 (s, 1H).

5-[2-(4-Methanesulfonyl-benzyloxy)-3,4-dimethoxy-phenyl]-indan-1-one (Compound 130)

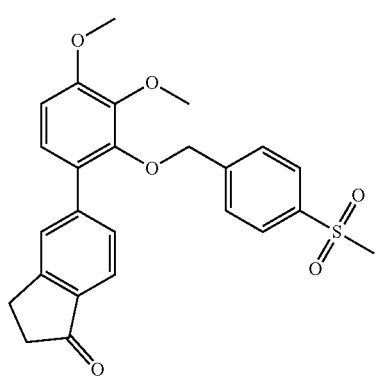 [SMILES: COc1ccc(-c2ccc3c(c2)CCC3=O)c(OCc2ccc(S(C)(=O)=O)cc2)c1OC]

1H NMR (300 MHz, CDCl$_3$) δ 7.79-7.70 (m, 3H), 7.48 (dd, J=10.3, 2.3 Hz, 2H), 7.31 (d, J=8.3 Hz, 2H), 7.06 (d, J=8.7 Hz, 1H), 6.81 (d, J=8.7 Hz, 1H), 4.92 (s, 2H), 3.95 (s, 3H), 3.94 (s, 3H), 3.15-3.06 (m, 2H), 3.01 (s, 3H), 2.74 (ddd, J=6.7, 5.8, 4.6 Hz, 2H).

Example 4

Following the procedure described in example 1 starting from 5-(2-hydroxy-3,4-dimethoxyphenyl)isobenzofuran-1(3H)-one (compound 306) as the phenol, compounds 131-146 were prepared:

5-[3,4-Dimethoxy-2-(3-methyl-butoxy)-phenyl]-3H-isobenzofuran-1-one (Compound 131)

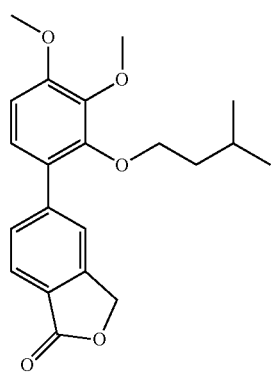 [SMILES: COc1ccc(-c2ccc3c(c2)COC3=O)c(OCCC(C)C)c1OC]

1H NMR (600 MHz, DMSO-SPE) δ 7.87 (d, J=7.9 Hz, 1H), 7.74 (s, 1H), 7.67 (dd, J=7.9, 1.1 Hz, 1H), 7.15-7.10 (m, 1H), 6.96-6.92 (m, 1H), 5.43 (s, 2H), 3.85 (s, 3H), 3.80 (s, 3H), 3.77-3.68 (m, 2H), 1.55 (dh, J=13.4, 6.7 Hz, 1H), 1.35 (q, J=6.5 Hz, 2H), 0.71 (d, J=6.7 Hz, 6H).

5-[2-(2,2-Dimethyl-propoxy)-3,4-dimethoxy-phenyl]-3H-isobenzofuran-1-one (Compound 132)

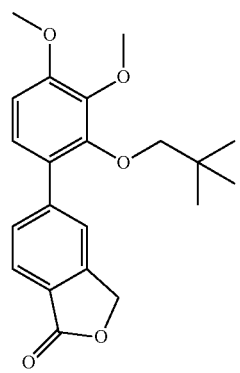 [SMILES: COc1ccc(-c2ccc3c(c2)COC3=O)c(OCC(C)(C)C)c1OC]

1H NMR (600 MHz, DMSO-SPE) δ 7.85 (d, J=7.9 Hz, 1H), 7.75 (s, 1H), 7.68 (dd, J=8.0, 1.0 Hz, 1H), 7.14 (d, J=8.6

Hz, 1H), 6.96-6.92 (m, 1H), 5.42 (s, 2H), 3.85 (s, 3H), 3.79 (s, 3H), 3.38 (s, 2H), 0.79 (s, 9H).

5-(2-Cyclobutylmethoxy-3,4-dimethoxy-phenyl)-3H-isobenzofuran-1-one (Compound 133)

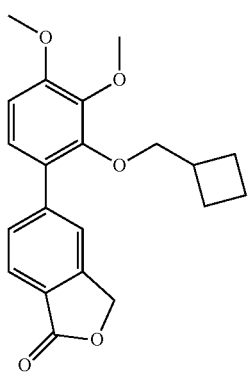 [SMILES: COc1ccc(-c2ccc3c(c2)COC3=O)c(OCC2CCC2)c1OC]

1H NMR (600 MHz, DMSO-SPE) δ 7.86 (d, J=8.0 Hz, 1H), 7.74 (s, 1H), 7.68 (dd, J=7.9, 1.1 Hz, 1H), 7.15-7.11 (m, 1H), 6.96-6.91 (m, 1H), 5.44 (s, 2H), 3.85 (s, 3H), 3.80 (s, 3H), 3.71 (d, J=6.5 Hz, 2H), 2.47-2.38 (m, 1H), 1.85-1.49 (m, 6H).

5-[2-(3-Hydroxymethyl-oxetan-3-ylmethoxy)-3,4-dimethoxy-phenyl]-3H-isobenzofuran-1-one (Compound 134)

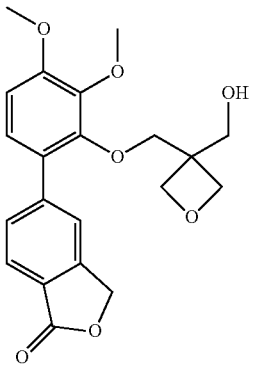 [SMILES: COc1ccc(-c2ccc3c(c2)COC3=O)c(OCC2(CO)COC2)c1OC]

1H NMR (600 MHz, DMSO-SPE) δ 7.86 (d, J=8.0 Hz, 1H), 7.74 (s, 1H), 7.65 (dd, J=8.0, 1.1 Hz, 1H), 7.17-7.14 (m, 1H), 6.99-6.95 (m, 1H), 5.43 (s, 2H), 4.80 (t, J=5.2 Hz, 1H), 4.22 (t, J=6.8 Hz, 2H), 4.14 (d, J=5.8 Hz, 2H), 3.92 (d, J=10.1 Hz, 2H), 3.86 (s, 3H), 3.81 (s, 3H), 3.47 (d, J=5.2 Hz, 2H).

5-[2-(3,3-Dimethyl-butoxy)-3,4-dimethoxy-phenyl]-3H-isobenzofuran-1-one (Compound 135)

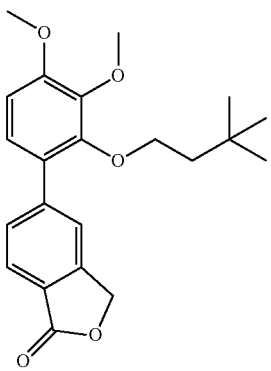 [SMILES: COc1ccc(-c2ccc3c(c2)COC3=O)c(OCCC(C)(C)C)c1OC]

1H NMR (600 MHz, DMSO-SPE) δ 7.88 (d, J=7.9 Hz, 1H), 7.73 (s, 1H), 7.68 (dd, J=8.0, 1.3 Hz, 1H), 7.12 (d, J=8.7 Hz, 1H), 6.95-6.92 (m, 1H), 5.44 (s, 2H), 3.85 (s, 3H), 3.80 (s, 3H), 3.79-3.74 (m, 2H), 1.44 (dd, J=9.8, 4.9 Hz, 2H), 0.78 (s, 9H).

4-[2,3-Dimethoxy-6-(1-oxo-1,3-dihydro-isobenzofuran-5-yl)-phenoxymethyl]-benzamide (Compound 136)

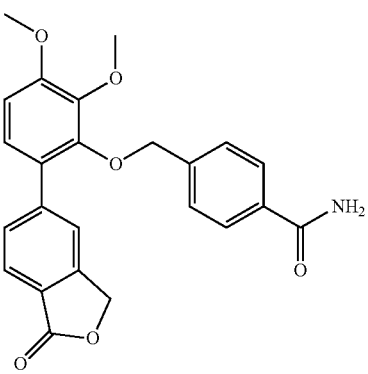

1H NMR (600 MHz, DMSO-SPE) δ 7.93 (s, 1H), 7.84-7.80 (m, 1H), 7.75-7.71 (m, 2H), 7.64-7.60 (m, 2H), 7.34 (s,

1H), 7.18 (d, J=8.2 Hz, 2H), 7.12 (d, J=8.6 Hz, 1H), 7.00-6.96 (m, 1H), 5.37 (s, 2H), 4.89 (s, 2H), 3.87 (s, 3H), 3.84 (s, 3H).

5-[2(3-Hydroxy-2,2-dimethyl-propoxy)-3,4-dimethoxy-phenyl]-3H-isobenzofuran-1-one (Compound 137)

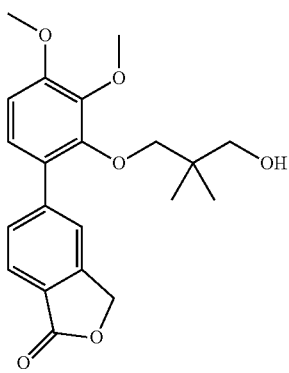 [SMILES: COc1ccc(-c2ccc3c(c2)COC3=O)c(OCC(C)(C)CO)c1OC]

1H NMR (600 MHz, DMSO-SPE) δ 7.85 (d, J=8.0 Hz, 1H), 7.74 (s, 1H), 7.67 (dd, J=8.0, 1.1 Hz, 1H), 7.13 (d, J=8.7 Hz, 1H), 6.95-6.91 (m, 1H), 5.42 (s, 2H), 4.35 (t, J=5.3 Hz, 1H), 3.85 (s, 3H), 3.78 (s, 3H), 3.50 (s, 2H), 3.06 (d, J=5.3 Hz, 2H), 0.73 (s, 6H).

4-[2,3-Dimethoxy-6-(1-oxo-1,3-dihydro-isobenzofuran-5-yl)-phenoxymethyl]-N-methyl-benzamide (Compound 138)

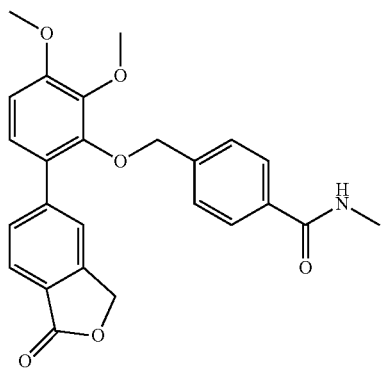 [SMILES: CNC(=O)c1ccc(COc2c(-c3ccc4c(c3)COC4=O)ccc(OC)c2OC)cc1]

1H NMR (600 MHz, DMSO-SPE) δ 8.39 (q, J=4.3 Hz, 1H), 7.84-7.80 (m, 1H), 7.72-7.67 (m, 2H), 7.65-7.61 (m, 2H), 7.19 (d, J=8.2 Hz, 2H), 7.15-7.10 (m, 1H), 6.98 (d, J=8.7 Hz, 1H), 5.37 (s, 2H), 4.88 (s, 2H), 3.87 (s, 3H), 3.84 (s, 3H), 2.77 (d, J=4.5 Hz, 3H).

4-[2,3-Dimethoxy-6-(1-oxo-1,3-dihydro-isobenzofuran-5-yl)-phenoxymethyl]-N,N-dimethyl-benzamide (Compound 139)

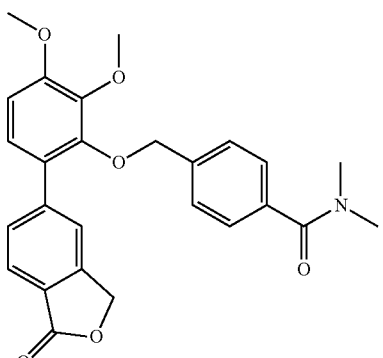

1H NMR (600 MHz, DMSO-SPE) δ 7.80 (d, J=7.9 Hz, 1H), 7.65-7.59 (m, 2H), 7.26 (d, J=8.1 Hz, 2H), 7.17 (d, J=8.1 Hz, 2H), 7.12 (d, J=8.7 Hz, 1H), 6.98 (d, J=8.7 Hz, 1H), 5.39 (s, 2H), 4.87 (s, 2H), 3.87 (s, 3H), 3.85 (s, 3H), 2.96 (s, 3H), 2.85 (s, 3H).

3-[2,3-Dimethoxy-6-(1-oxo-1,3-dihydro-isobenzofuran-5-yl)-phenoxymethyl]-N,N-dimethyl-benzamide (Compound 140)

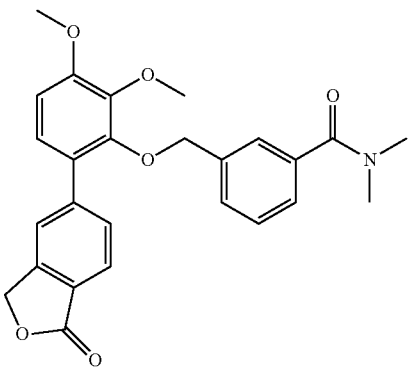 [SMILES: COc1ccc(-c2ccc3c(c2)COC3=O)c(OCc2cccc(C(=O)N(C)C)c2)c1OC]

1H NMR (600 MHz, DMSO-SPE) δ 7.80 (d, J=7.9 Hz, 1H), 7.67 (s, 1H), 7.60 (d, J=7.9 Hz, 1H), 7.32-7.24 (m, 2H), 7.22-7.19 (m, 1H), 7.12 (d, J=8.6 Hz, 1H), 7.03 (s, 1H), 6.99-6.95 (m, 1H), 5.38 (s, 2H), 4.88 (s, 2H), 3.87 (s, 3H), 3.85 (s, 3H), 2.95 (s, 3H), 2.77 (s, 3H).

4-[2,3-Dimethoxy-6-(1-oxo-1,3-dihydro-isobenzofuran-5-yl)-phenoxymethyl]-benzenesulfonamide (Compound 141)

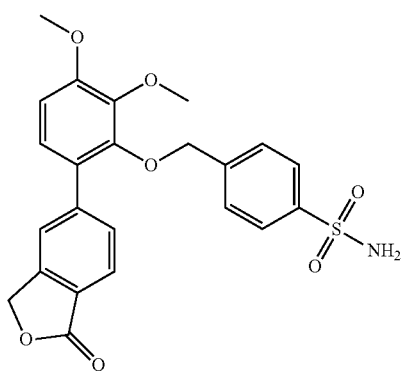 [SMILES: COc1ccc(-c2ccc3c(c2)COC3=O)c(OCc2ccc(S(N)(=O)=O)cc2)c1OC]

1H NMR (600 MHz, DMSO-SPE) δ 7.85-7.82 (m, 1H), 7.71-7.67 (m, 2H), 7.62 (d, J=6.8 Hz, 2H), 7.33 (s, 2H), 7.31 (d, J=8.3 Hz, 2H), 7.13 (d, J=8.6 Hz, 1H), 7.00-6.97 (m, 1H), 5.39 (s, 2H), 4.92 (s, 2H), 3.87 (s, 3H), 3.84 (s, 3H).

5-[2-(4-Methanesulfonyl-benzyloxy)-3,4-dimethoxyphenyl]-3H-isobenzofuran-1-one (Compound 142)

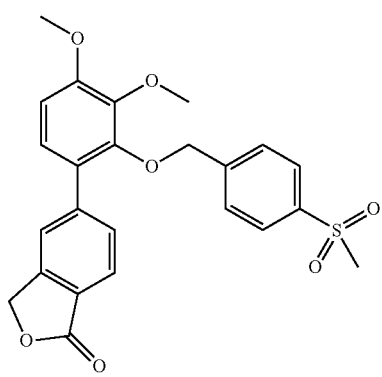 [SMILES: COc1ccc(-c2ccc3c(c2)COC3=O)c(OCc2ccc(S(C)(=O)=O)cc2)c1OC]

1H NMR (600 MHz, DMSO-SPE) δ 7.81 (m, 3H), 7.65 (s, 1H), 7.61 (d, J=8.0 Hz, 1H), 7.40 (d, J=8.3 Hz, 2H), 7.13 (d, J=8.6 Hz, 1H), 7.01-6.98 (m, 1H), 5.39 (s, 2H), 4.95 (s, 2H), 3.88 (s, 3H), 3.84 (s, 3H), 3.18 (s, 3H).

5-[2-(3-Methanesulfonyl-benzyloxy)-3,4-dimethoxyphenyl]-3H-isobenzofuran-1-one (Compound 143)

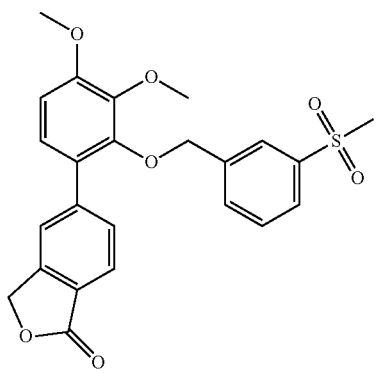 [SMILES: COc1ccc(-c2ccc3c(c2)COC3=O)c(OCc2cccc(S(C)(=O)=O)c2)c1OC]

1H NMR (600 MHz, DMSO-SPE) δ 7.83-7.78 (m, 2H), 7.66 (s, 2H), 7.60 (d, J=7.8 Hz, 1H), 7.53 (t, J=7.6 Hz, 1H), 7.49 (d, J=7.7 Hz, 1H), 7.14-7.11 (m, 1H), 6.99 (d, J=8.7 Hz, 1H), 5.38 (s, 2H), 4.96 (s, 2H), 3.88 (s, 3H), 3.85 (s, 3H), 3.14 (s, 3H).

3-[2,3-Dimethoxy-6-(1-oxo-1,3-dihydro-isobenzofuran-5-yl)-phenoxymethyl]-benzenesulfonamide (Compound 144)

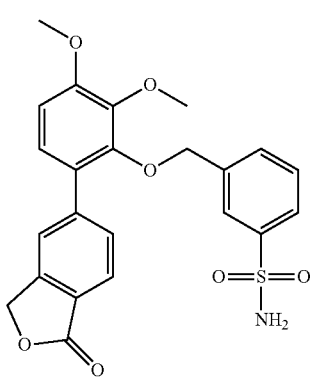 [SMILES: COc1ccc(-c2ccc3c(c2)COC3=O)c(OCc2cccc(S(N)(=O)=O)c2)c1OC]

1H NMR (600 MHz, DMSO-SPE) δ 7.82 (d, J=7.9 Hz, 1H), 7.72 (t, J=7.4 Hz, 1H), 7.68 (m, 2H), 7.65-7.62 (m, 1H), 7.45 (t, J=7.7 Hz, 1H), 7.37-7.33 (m, 3H), 7.14 (t, J=6.8 Hz, 1H), 7.01-6.98 (m, 1H), 5.38 (s, 2H), 4.90 (s, 2H), 3.88 (s, 3H), 3.84 (s, 3H).

3-[2,3-Dimethoxy-6-(1-oxo-1,3-dihydro-isobenzofuran-5-yl)-phenoxymethyl]-N,N-dimethyl-benzenesulfonamide (Compound 145)

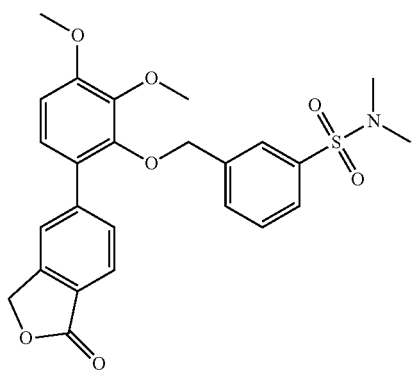 [SMILES: COc1ccc(-c2ccc3c(c2)COC3=O)c(OCc2cccc(S(=O)(=O)N(C)C)c2)c1OC]

1H NMR (600 MHz, DMSO-SPE) δ 7.79 (d, J=7.9 Hz, 1H), 7.65-7.60 (m, 2H), 7.60-7.57 (m, 1H), 7.54-7.50 (m, 1H), 7.49-7.44 (m, 2H), 7.11 (d, J=8.6 Hz, 1H), 7.00-6.97 (m, 1H), 5.38 (s, 2H), 4.97 (s, 2H), 3.87 (s, 3H), 3.84 (s, 3H), 2.51 (s, 6H).

3-[2,3-Dimethoxy-6-(1-oxo-1,3-dihydro-isobenzofuran-5-yl)-phenoxymethyl]-benzamide (Compound 146)

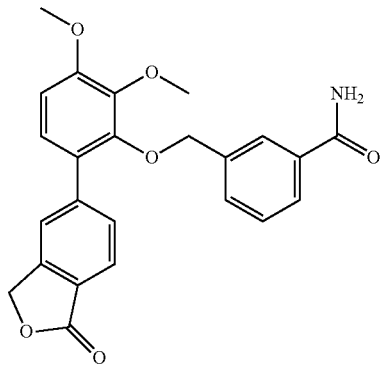 [SMILES: COc1ccc(-c2ccc3c(c2)COC3=O)c(OCc2cccc(C(N)=O)c2)c1OC]

1H NMR (600 MHz, DMSO-SPE) δ 7.90 (s, 1H), 7.79 (d, J=7.9 Hz, 1H), 7.77-7.73 (m, 1H), 7.64 (m, 2H), 7.59 (dd, J=10.5, 2.6 Hz, 1H), 7.34 (s, 1H), 7.31 (dd, J=9.5, 5.7 Hz, 1H), 7.26 (d, J=7.6 Hz, 1H), 7.12 (d, J=8.7 Hz, 1H), 6.98 (d, J=8.7 Hz, 1H), 5.38 (s, 2H), 4.87 (s, 2H), 3.87 (s, 3H), 3.85 (s, 3H).

Example 5

Following the procedure described in example 1 starting from 5-(2-hydroxy-3,4-dimethoxyphenyl)isoindolin-1-one (Compound 307) as the phenol, compounds 147-161 were prepared:

5-[3,4-Dimethoxy-2-(3-methyl-butoxy)-phenyl]-2,3-dihydro-isoindol-1-one (Compound 147)

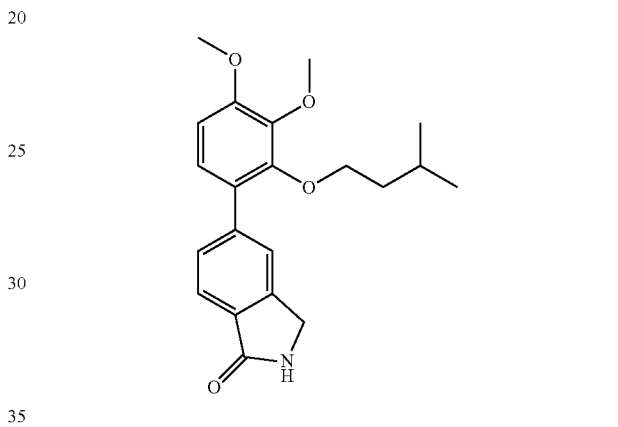

1H NMR (600 MHz, DMSO-SPE) δ 8.53 (s, 1H), 7.70-7.66 (m, 1H), 7.63 (s, 1H), 7.55 (dd, J=7.9, 1.0 Hz, 1H), 7.09 (d, J=8.6 Hz, 1H), 6.93-6.88 (m, 1H), 4.39 (s, 2H), 3.84 (s, 3H), 3.80 (s, 3H), 3.71 (t, J=6.3 Hz, 2H), 1.60-1.48 (m, 1H), 1.33 (q, J=6.5 Hz, 2H), 0.70 (d, J=6.6 Hz, 6H).

5-[2-(2,2-Dimethyl-propoxy)-3,4-dimethoxy-phenyl]-2,3-dihydro-isoindol-1-one (Compound 148)

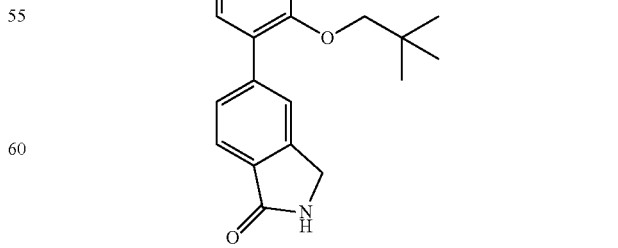

1H NMR (600 MHz, DMSO-SPE) δ 8.53 (s, 1H), 7.67 (d, J=7.8 Hz, 1H), 7.64 (s, 1H), 7.56 (dd, J=7.9, 1.1 Hz, 1H), 7.10

(d, J=8.6 Hz, 1H), 6.91 (d, J=8.7 Hz, 1H), 4.37 (s, 2H), 3.84 (s, 3H), 3.78 (s, 3H), 3.36 (s, 2H), 0.78 (s, 9H).

5-(2-Cyclobutylmethoxy-3,4-dimethoxy-phenyl)-2,3-dihydro-isoindol-1-one (Compound 149)

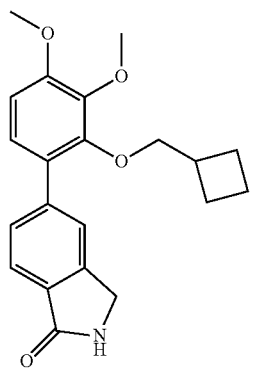 [SMILES: COc1ccc(-c2ccc3c(c2)CNC3=O)c(OCC2CCC2)c1OC]

1H NMR (600 MHz, DMSO-SPE) δ 8.54 (s, 1H), 7.68 (d, J=7.9 Hz, 1H), 7.64 (s, 1H), 7.56 (d, J=7.9 Hz, 1H), 7.10 (d, J=8.6 Hz, 1H), 6.91 (d, J=8.7 Hz, 1H), 4.39 (s, 2H), 3.84 (s, 3H), 3.80 (s, 3H), 3.68 (d, J=6.4 Hz, 2H), 2.47-2.36 (m, 1H), 1.86-1.48 (m, 6H).

5-[2-(4-Methanesulfonyl-benzyloxy)-3,4-dimethoxy-phenyl]-2,3-dihydro-isoindol-1-one (Compound 150)

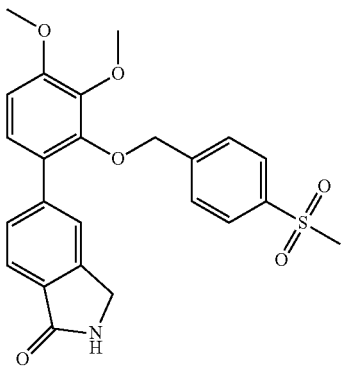 [SMILES: COc1ccc(-c2ccc3c(c2)CNC3=O)c(OCc2ccc(S(C)(=O)=O)cc2)c1OC]

1H NMR (600 MHz, DMSO-SPE) δ 8.54 (s, 1H), 7.82-7.77 (m, 2H), 7.65 (d, J=7.8 Hz, 1H), 7.56 (d, J=9.4 Hz, 1H), 7.52 (dd, J=7.9, 1.2 Hz, 1H), 7.42 (t, J=9.0 Hz, 2H), 7.12 (dd,

J=7.9, 4.6 Hz, 1H), 6.99-6.95 (m, 1H), 4.93 (d, J=7.8 Hz, 2H), 4.34 (s, 2H), 3.87 (s, 3H), 3.83 (s, 3H), 3.18 (s, 3H).

5-[2-(3-Hydroxymethyl-oxetan-3-ylmethoxy)-3,4-dimethoxy-phenyl]-2,3-dihydro-isoindol-1-one (Compound 151)

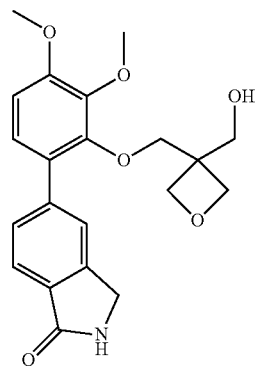 [SMILES: COc1ccc(-c2ccc3c(c2)CNC3=O)c(OCC2(CO)COC2)c1OC]

1H NMR (600 MHz, DMSO-SPE) δ 8.55 (s, 1H), 7.68 (d, J=7.8 Hz, 1H), 7.64 (s, 1H), 7.54 (d, J=7.8 Hz, 1H), 7.12 (d, J=8.7 Hz, 1H), 6.95 (dd, J=8.7, 3.4 Hz, 1H), 4.81 (t, J=5.2 Hz, 1H), 4.39 (s, 2H), 4.20 (t, J=4.3 Hz, 2H), 4.13 (t, J=5.3 Hz, 2H), 3.88 (s, 2H), 3.85 (d, J=10.6 Hz, 3H), 3.81 (s, 3H), 3.47 (t, J=5.7 Hz, 2H).

5-[2-(3,3-Dimethyl-butoxy)-3,4-dimethoxy-phenyl]-2,3-dihydro-isoindol-1-one (Compound 152)

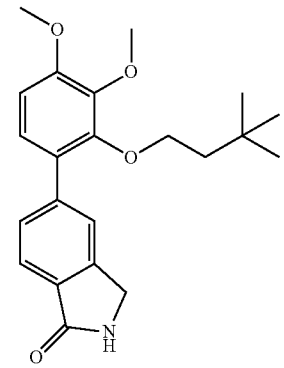 [SMILES: COc1ccc(-c2ccc3c(c2)CNC3=O)c(OCCC(C)(C)C)c1OC]

1H NMR (600 MHz, DMSO-SPE) δ 8.54 (s, 1H), 7.69 (d, J=7.8 Hz, 1H), 7.63 (s, 1H), 7.55 (d, J=7.9 Hz, 1H), 7.09 (t,

J=6.9 Hz, 1H), 6.93-6.88 (m, 1H), 4.40 (s, 2H), 3.84 (s, 3H), 3.80 (s, 3H), 3.78-3.70 (m, 2H), 1.42 (t, J=7.4 Hz, 2H), 0.77 (s, 9H).

4-[2,3-Dimethoxy-6-(1-oxo-2,3-dihydro-1H-isoindol-5-yl)-phenoxymethyl]-benzamide (Compound 153)

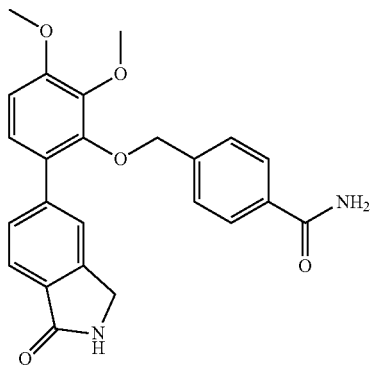 [SMILES: COc1ccc(-c2ccc3c(c2)CNC3=O)c(OCc2ccc(C(N)=O)cc2)c1OC]

1H NMR (600 MHz, DMSO-SPE) δ 8.54 (s, 1H), 7.92 (s, 1H), 7.75 (d, J=8.2 Hz, 2H), 7.66 (d, J=7.8 Hz, 1H), 7.55 (d, J=5.8 Hz, 1H), 7.54 (d, J=7.8 Hz, 1H), 7.33 (s, 1H), 7.20 (d, J=8.2 Hz, 2H), 7.10 (d, J=8.6 Hz, 1H), 6.98-6.93 (m, 1H), 4.86 (s, 2H), 4.33 (s, 2H), 3.87 (s, 3H), 3.83 (s, 3H).

5-[2-(3-Hydroxy-2,2-dimethyl-propoxy)-3,4-dimethoxy-phenyl]-2,3-dihydro-isoindol-1-one (Compound 154)

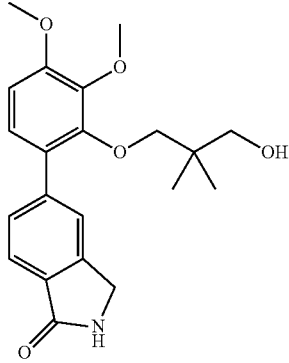 [SMILES: COc1ccc(-c2ccc3c(c2)CNC3=O)c(OCC(C)(C)CO)c1OC]

1H NMR (600 MHz, DMSO-SPE) δ 8.53 (s, 1H), 7.67 (d, J=7.8 Hz, 1H), 7.64 (s, 1H), 7.54 (d, J=7.9 Hz, 1H), 7.09 (d, J=8.6 Hz, 1H), 6.90 (dd, J=8.7, 3.4 Hz, 1H), 4.38 (s, 2H), 4.34 (t, J=5.3 Hz, 1H), 3.84 (s, 3H), 3.78 (d, J=6.5 Hz, 3H), 3.48 (d, J=5.4 Hz, 2H), 3.06 (d, J=5.4 Hz, 2H), 0.71 (s, 6H).

4-[2,3-Dimethoxy-6-(1-oxo-2,3-dihydro-1H-isoindol-5-yl)-phenoxymethyl]-N-methyl-benzamide (Compound 155)

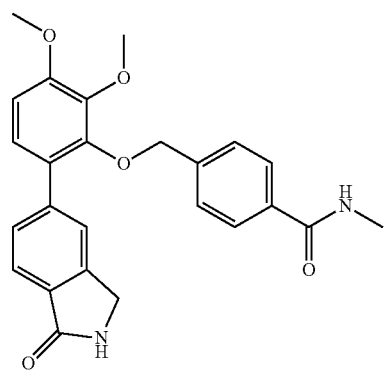 [SMILES: CNC(=O)c1ccc(COc2c(-c3ccc4c(c3)CNC4=O)ccc(OC)c2OC)cc1]

1H NMR (600 MHz, DMSO-SPE) δ 8.54 (s, 1H), 8.39 (q, J=4.2 Hz, 1H), 7.70 (d, J=8.2 Hz, 2H), 7.65 (d, J=7.8 Hz, 1H), 7.56 (s, 1H), 7.54 (d, J=7.9 Hz, 1H), 7.20 (d, J=8.2 Hz, 2H), 7.10 (d, J=8.6 Hz, 1H), 6.96 (dd, J=8.5, 4.2 Hz, 1H), 4.86 (s, 2H), 4.33 (s, 2H), 3.86 (s, 3H), 3.83 (s, 3H), 2.77 (d, J=4.6 Hz, 3H).

4-[2,3-Dimethoxy-6-(1-oxo-2,3-dihydro-1H-isoindol-5-yl)-phenoxymethyl]-N,N-dimethyl-benzamide (Compound 156)

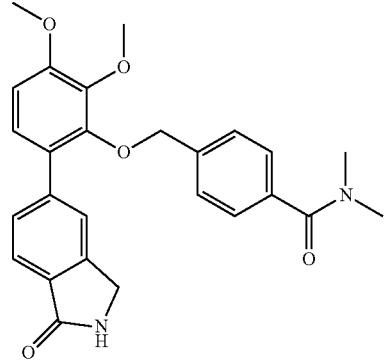 [SMILES: COc1ccc(-c2ccc3c(c2)CNC3=O)c(OCc2ccc(C(=O)N(C)C)cc2)c1OC]

1H NMR (600 MHz, DMSO-SPE) δ 8.52 (s, 1H), 7.64 (d, J=7.8 Hz, 1H), 7.57 (s, 1H), 7.54-7.50 (m, 1H), 7.27 (d, J=8.1 Hz, 2H), 7.18 (d, J=8.1 Hz, 2H), 7.11 (d, J=8.6 Hz, 1H), 6.96

(dd, J=8.6, 4.3 Hz, 1H), 4.84 (s, 2H), 4.34 (s, 2H), 3.87 (s, 3H), 3.84 (s, 3H), 2.93 (d, J=35.2 Hz, 3H), 2.87 (d, J=20.8 Hz, 3H).

3-[2,3-Dimethoxy-6-(1-oxo-2,3-dihydro-1H-isoindol-5-yl)-phenoxymethyl]-N,N-dimethyl-benzamide (Compound 157)

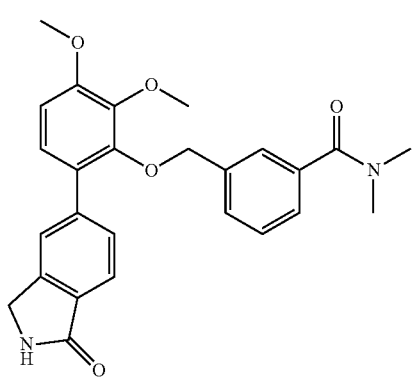 [SMILES: COc1ccc(-c2ccc3c(c2)CNC3=O)c(OCc2cccc(C(=O)N(C)C)c2)c1OC]

1H NMR (600 MHz, DMSO-SPE) δ 8.54 (s, 1H), 7.64 (d, J=7.8 Hz, 1H), 7.60 (s, 1H), 7.51 (dt, J=8.0, 4.1 Hz, 1H), 7.30 (t, J=7.5 Hz, 1H), 7.26 (dt, J=7.4, 1.2 Hz, 1H), 7.21 (d, J=7.5 Hz, 1H), 7.10 (d, J=8.6 Hz, 1H), 7.06 (s, 1H), 6.95 (d, J=8.7 Hz, 1H), 4.85 (s, 2H), 4.33 (s, 2H), 3.86 (s, 3H), 3.84 (s, 3H), 2.95 (s, 3H), 2.75 (s, 3H).

3-[2,3-Dimethoxy-6-(1-oxo-2,3-dihydro-1H-isoindol-5-yl)-phenoxymethyl]-benzenesulfonamide (Compound 158)

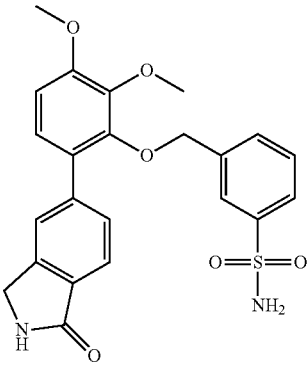

1H NMR (600 MHz, DMSO-SPE) δ 8.52 (s, 1H), 7.76-7.71 (m, 2H), 7.65 (t, J=6.5 Hz, 1H), 7.64 (d, J=7.4 Hz, 1H), 7.55 (dd, J=7.8, 1.2 Hz, 1H), 7.46 (t, J=7.7 Hz, 1H), 7.36 (m, 3H), 7.13 (t, J=6.1 Hz, 1H), 6.97 (dd, J=8.7, 4.4 Hz, 1H), 4.86 (s, 2H), 4.35 (s, 2H), 3.87 (s, 3H), 3.83 (s, 3H).

3-[2,3-Dimethoxy-6-(1-oxo-2,3-dihydro-1H-isoindol-5-yl)-phenoxymethyl]-benzamide (Compound 159)

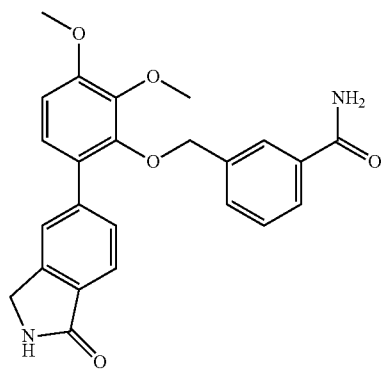 [SMILES: COc1ccc(-c2ccc3c(c2)CNC3=O)c(OCc2cccc(C(N)=O)c2)c1OC]

1H NMR (600 MHz, DMSO-SPE) δ 8.52 (s, 1H), 7.93 (s, 1H), 7.76 (m, 2H), 7.64 (d, J=7.8 Hz, 1H), 7.60 (s, 1H), 7.55-7.51 (m, 1H), 7.35-7.30 (m, 2H), 7.28 (d, J=7.6 Hz, 1H), 7.11 (d, J=8.6 Hz, 1H), 6.96 (d, J=8.7 Hz, 1H), 4.85 (s, 2H), 4.35 (s, 2H), 3.87 (s, 3H), 3.83 (s, 3H).

5-[2-(3-Methanesulfonyl-benzyloxy)-3,4-dimethoxyphenyl]-2,3-dihydro-isoindol-1-one (Compound 160)

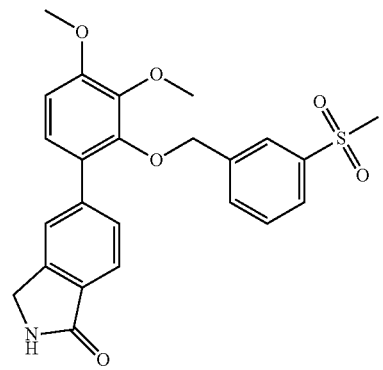 [SMILES: COc1ccc(-c2ccc3c(c2)CNC3=O)c(OCc2cccc(S(C)(=O)=O)c2)c1OC]

1H NMR (600 MHz, DMSO-SPE) δ 8.52 (s, 1H), 7.84-7.79 (m, 1H), 7.74 (s, 1H), 7.64 (d, J=7.9 Hz, 1H), 7.59 (s,

1H), 7.55-7.47 (m, 3H), 7.11 (d, J=8.7 Hz, 1H), 6.98 (dd, J=8.7, 3.4 Hz, 1H), 4.93 (s, 2H), 4.35 (s, 2H), 3.87 (s, 3H), 3.84 (s, 3H), 3.13 (s, 3H).

4-[2,3-Dimethoxy-6-(1-oxo-2,3-dihydro-1H-isoindol-5-yl)-phenoxymethyl]-benzenesulfonamide (Compound 161)

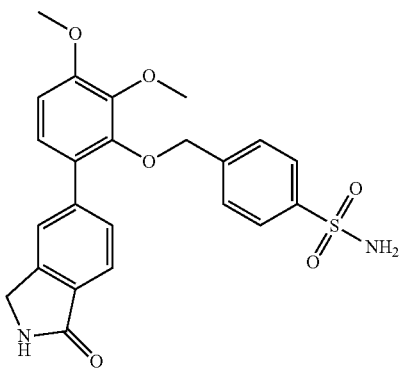

1H NMR (600 MHz, DMSO-SPE) δ 8.54 (s, 1H), 7.72-7.68 (m, 2H), 7.66 (d, J=7.9 Hz, 1H), 7.56 (s, 1H), 7.53 (t, J=8.4 Hz, 1H), 7.31 (m, 4H), 7.10 (t, J=7.7 Hz, 1H), 6.97 (d, J=8.7 Hz, 1H), 4.88 (s, 2H), 4.35 (s, 2H), 3.86 (s, 3H), 3.83 (s, 3H).

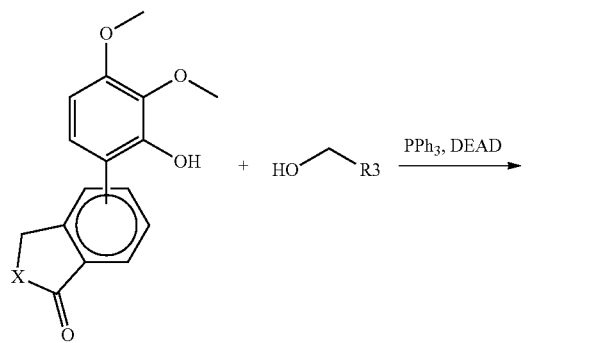

Example 6

General Procedure for Mitsunobu Reaction

In a screw cap vessel under an argon atmosphere the phenol (0.035 mmol) and the alcohol (0.07 mmol) were dissolved in dry THF (2 mL). Triphenyl phosphine resin (0.05 mmol, 0.036 g, 1.5 mmol/g) was added. The mixture was shaken at RT for 30 min after which diethyl azodicarboxylate (40% in toluene, 0.023 mL, 0.07 mmol) was added. The mixture was shaken at RT over night after which it was filtrated and evaporated in vacuo. The crude product was re-dissolved in DMSO (0.3 mL) and purified by preparative HPLC.

Following this procedure starting from 4-(2-Hydroxy-3,4-dimethoxy-phenyl)-indan-1-one (Compound 303) as the phenol compounds 162-163 were prepared:

3-[2,3-Dimethoxy-6-(1-oxo-indan-4-yl)-phenoxy]-2,2-dimethyl-propionic acid methyl ester (Compound 162)

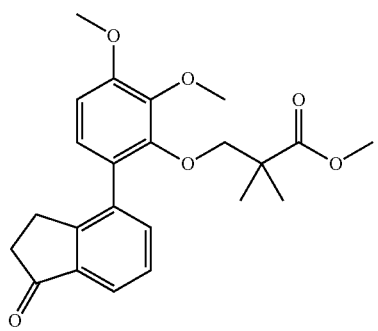 [SMILES: COC(=O)C(C)(C)COc1c(-c2cccc3c2CCC3=O)ccc(OC)c1OC]

1H NMR (600 MHz, DMSO-SPE) δ 7.65-7.62 (m, 1H), 7.52 (dd, J=7.3, 1.1 Hz, 1H), 7.47 (t, J=7.4 Hz, 1H), 6.99 (d, J=8.5 Hz, 1H), 6.92 (d, J=8.6 Hz, 1H), 3.85 (s, 3H), 3.77 (s, 3H), 3.67 (s, 2H), 3.30 (s, 3H), 2.93-2.88 (m, 2H), 2.62-2.56 (m, 2H), 0.86 (s, 6H).

4-[3,4-Dimethoxy-2-(3-methyl-oxetan-3-yl-methoxy)-phenyl]-indan-1-one (Compound 163)

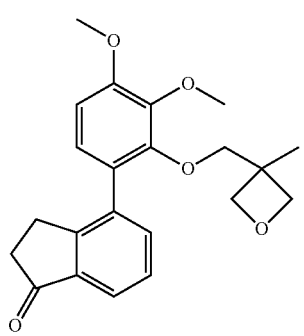 [SMILES: COc1ccc(-c2cccc3c2CCC3=O)c(OCC2(C)COC2)c1OC]

1H NMR (600 MHz, DMSO-SPE) δ 7.64 (dd, J=7.5, 0.7 Hz, 1H), 7.56 (dd, J=7.3, 1.0 Hz, 1H), 7.48 (t, J=7.5 Hz, 1H), 7.05 (d, J=8.5 Hz, 1H), 6.97-6.93 (m, 1H), 4.02-3.97 (m, 4H), 3.86 (s, 3H), 3.82 (s, 3H), 3.70 (s, 2H), 2.98-2.92 (m, 2H), 2.62-2.57 (m, 2H), 0.97 (s, 3H).

Example 7

Following the procedure described in example 6 starting from 4-(2-hydroxy-3,4-dimethoxyphenyl)isobenzofuran-1(3H)-one (Compound 304) as the phenol, compound 164 was prepared:

4-[3,4-Dimethoxy-2-(3-methyl-oxetan-3-yl-methoxy)-phenyl]-3H-isobenzofuran-1-one (Compound 164)

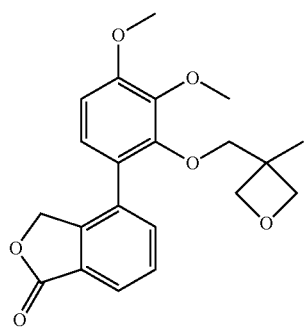 [SMILES: COc1ccc(-c2cccc3c2COC3=O)c(OCC2(C)COC2)c1OC]

1H NMR (300 MHz, CDCl3) δ 7.91 (dd, J=7.0, 1.5 Hz, 1H), 7.66-7.53 (m, 2H), 6.99 (d, J=8.6 Hz, 1H), 6.81 (d, J=8.6 Hz, 1H), 4.14 (q, J=5.9 Hz, 4H), 3.93 (s, 6H), 3.82 (s, 2H), 1.08 (s, 3H).

Example 8

Following the procedure described in example 6 starting from 5-(2-Hydroxy-3,4-dimethoxy-phenyl)-indan-1-one (compound 305) as the phenol, compound 165 was prepared:

3-[2,3-Dimethoxy-6-(1-oxo-indan-5-yl)-phenoxy]-2,2-dimethyl-propionic acid methyl ester (Compound 165)

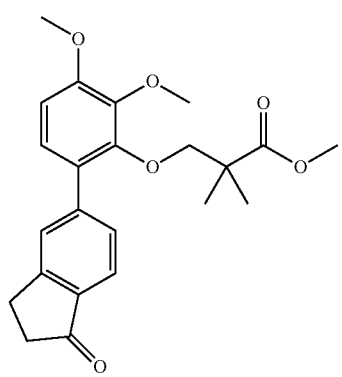 [SMILES: COC(=O)C(C)(C)COc1c(-c2ccc3c(c2)CCC3=O)ccc(OC)c1OC]

1H NMR (600 MHz, DMSO-SPE) δ 7.63 (d, J=7.9 Hz, 1H), 7.61 (s, 1H), 7.46 (d, J=7.8 Hz, 1H), 7.11 (d, J=8.7 Hz, 1H), 6.93 (d, J=8.7 Hz, 1H), 3.85 (s, 3H), 3.78 (s, 2H), 3.76 (s, 3H), 3.40 (d, J=6.8 Hz, 3H), 3.16-3.09 (m, 2H), 2.69-2.64 (m, 2H), 1.04 (2s, 6H).

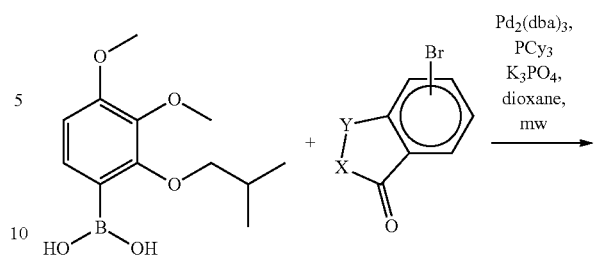

Example 9

General Procedure for parallel Suzuki Coupling

In a microwave vessel under an argon atmosphere 3,4-dimethoxy-2-(isobutoxy)phenylboronic acid (Compound 302) (0.04 g, 0.15 mmol) was dissolved in degassed 1,4-dioxan (0.4 mL). Argon was purged through the solution. The bromide (0.15 mmol) was added. Pd$_2$(dba)$_3$ (0.002 g, 0.002 mmol) and tricyclohexylphosphine (0.001 g, 0.004 mmol) was added. K$_3$PO$_4$ (0.04 g, 0.5 mmol) in degassed H$_2$O (0.2 mL) was added. The suspension was heated in a microwave oven at 145° C. for 15 min. The mixture was filtrated, concentrated in vacuo, re-dissolved in DMSO and purified by preparative HPLC.

Following this procedure compounds 166-173 were prepared:

4-(2-Isobutoxy-3,4-dimethoxy-phenyl)-indan-1-one (Compound 166)

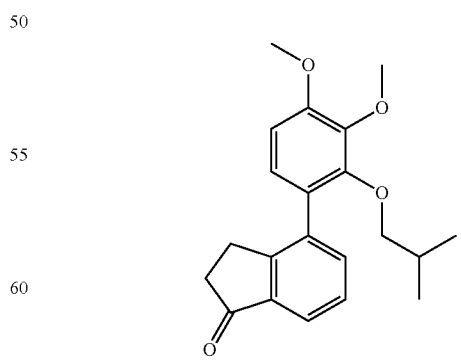

1H NMR (600 MHz, DMSO-SPE) δ 7.63 (dd, J=7.6, 1.0 Hz, 1H), 7.55 (dd, J=7.3, 1.1 Hz, 1H), 7.47 (dd, J=13.2, 5.8 Hz, 1H), 7.02-6.99 (m, 1H), 6.92-6.89 (m, 1H), 3.85 (s, 3H), 3.80 (s, 3H), 3.42 (d, J=6.0 Hz, 2H), 2.98-2.92 (m, 2H), 2.61 (dd, J=6.8, 5.0 Hz, 2H), 1.58 (dp, J=12.9, 6.6 Hz, 1H), 0.57 (d, J=6.7 Hz, 6H).

4-(2-Isobutoxy-3,4-dimethoxy-phenyl)-6,7-dimethoxy-indan-1-one (Compound 167)

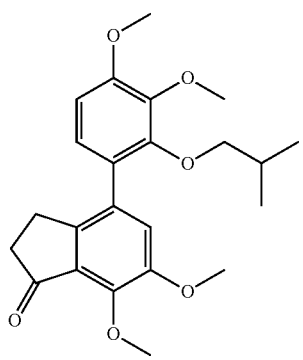 [SMILES: COc1ccc(-c2cc(OC)c(OC)c3c2CCC3=O)c(OCC(C)C)c1OC]

1H NMR (300 MHz, CDCl3) δ 7.13 (s, 1H), 6.93 (d, J=8.5 Hz, 1H), 6.74 (d, J=8.5 Hz, 1H), 4.02 (s, 3H), 3.93 (s, 3H), 3.91 (s, 3H), 3.89 (s, 3H), 3.49 (d, J=6.1 Hz, 2H), 2.91 (dd, J=7.2, 4.9 Hz, 2H), 2.65 (dd, J=7.0, 5.1 Hz, 2H), 1.71 (td, J=13.0, 6.5 Hz, 1H), 0.70 (t, J=8.6 Hz, 6H).

4-(2-Isobutoxy-3,4-dimethoxy-phenyl)-7-methoxy-indan-1-one (Compound 168)

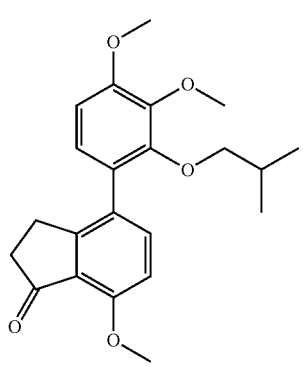 [SMILES: COc1ccc(-c2ccc(OC)c3c2CCC3=O)c(OCC(C)C)c1OC]

1H NMR (300 MHz, CDCl3) δ 7.44 (d, J=8.3 Hz, 1H), 6.89 (d, J=8.6 Hz, 1H), 6.83 (d, J=8.4 Hz, 1H), 6.73 (d, J=8.5 Hz, 1H), 3.99 (s, 3H), 3.92 (s, 3H), 3.91 (s, 3H), 3.46 (d, J=6.2 Hz, 2H), 3.02-2.85 (m, 2H), 2.69-2.55 (m, 2H), 1.78-1.57 (m, 1H), 0.66 (d, J=6.6 Hz, 6H).

5-(2-Isobutoxy-3,4-dimethoxy-phenyl)-indan-1-one (Compound 169)

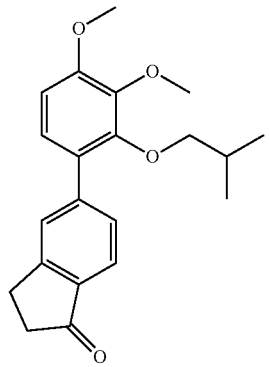 [SMILES: COc1ccc(-c2ccc3c(c2)CCC3=O)c(OCC(C)C)c1OC]

1H NMR (300 MHz, CDCl3) δ 7.76 (d, J=8.0 Hz, 1H), 7.64 (s, 1H), 7.57-7.50 (m, 1H), 7.06 (d, J=8.6 Hz, 1H), 6.79-6.71 (m, 1H), 3.93 (s, 3H), 3.91 (s, 3H), 3.54 (d, J=6.2 Hz, 2H), 3.22-3.10 (m, 2H), 2.82-2.63 (m, 2H), 1.81 (dp, J=13.1, 6.6 Hz, 1H), 0.81 (d, J=6.6 Hz, 6H).

5-(2-Isobutoxy-3,4-dimethoxy-phenyl)-3H-isobenzofuran-1-one (Compound 170)

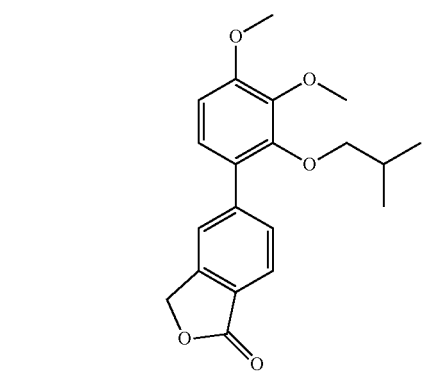 [SMILES: COc1ccc(-c2ccc3c(c2)COC3=O)c(OCC(C)C)c1OC]

1H NMR (300 MHz, CDCl3) δ 7.92 (d, J=8.0 Hz, 1H), 7.69 (dd, J=4.7, 4.1 Hz, 1H), 7.65 (s, 1H), 7.06 (d, J=8.6 Hz, 1H), 6.77 (d, J=8.7 Hz, 1H), 5.34 (s, 2H), 3.93 (s, 3H), 3.91 (s, 3H), 3.55 (d, J=6.3 Hz, 2H), 1.78 (td, J=13.2, 6.6 Hz, 1H), 0.80 (d, J=6.6 Hz, 6H).

5-(2-Isobutoxy-3,4-dimethoxy-phenyl)-2,3-dimethyl-2,3-dihydro-isoindol-1-one (Compound 171)

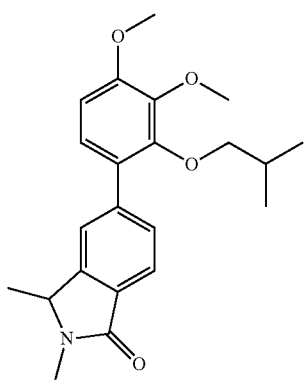 [SMILES: COc1ccc(-c2ccc3c(c2)C(C)N(C)C3=O)c(OCC(C)C)c1OC]

1H NMR (300 MHz, DMSO) δ 7.66 (d, J=8.1 Hz, 2H), 7.52 (dd, J=7.8, 1.2 Hz, 1H), 7.09 (d, J=8.7 Hz, 1H), 6.90 (d, J=8.7 Hz, 1H), 4.56 (q, J=6.6 Hz, 1H), 3.84 (s, 3H), 3.79 (s, 3H), 3.58-3.43 (m, 2H), 3.00 (d, J=8.0 Hz, 3H), 1.72 (dp, J=13.1, 6.5 Hz, 1H), 1.45 (d, J=6.7 Hz, 3H), 0.74 (dd, J=6.7, 3.5 Hz, 6H).

5-(2-Isobutoxy-3,4-dimethoxy-phenyl)-2-methyl-2,3-dihydro-isoindol-1-one (Compound 172)

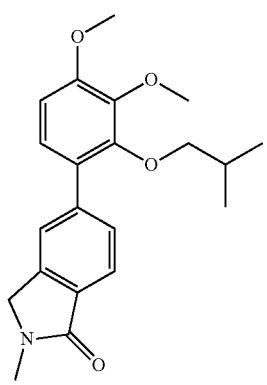 [SMILES: COc1ccc(-c2ccc3c(c2)CN(C)C3=O)c(OCC(C)C)c1OC]

1H NMR (300 MHz, CDCl3) δ 7.84 (d, J=8.5 Hz, 1H), 7.59 (d, J=7.6 Hz, 2H), 7.05 (d, J=8.7 Hz, 1H), 6.79-6.71 (m, 1H), 4.39 (s, 2H), 3.92 (s, 3H), 3.90 (s, 3H), 3.52 (d, J=6.3 Hz, 2H), 3.22 (s, 3H), 1.88-1.69 (m, 1H), 0.78 (d, J=6.6 Hz, 6H).

4-(2-Isobutoxy-3,4-dimethoxy-phenyl)-2,3-dihydro-isoindol-1-one (Compound 173)

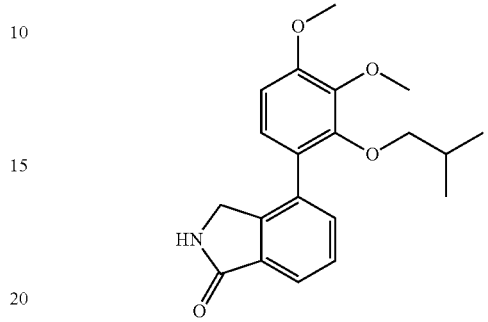

1H NMR (300 MHz, CDCl3) δ 7.85 (dt, J=7.9, 4.0 Hz, 1H), 7.56-7.45 (m, 2H), 6.96 (d, J=8.6 Hz, 1H), 6.76 (d, J=8.5 Hz, 1H), 6.55 (s, 1H), 4.41 (s, 2H), 3.93 (s, 3H), 3.91 (s, 3H), 3.44 (d, J=6.1 Hz, 2H), 1.6 (m, 1H), 0.61 (d, J=6.8 Hz, 6H).

Example 10

General Procedure for Suzuki Coupling

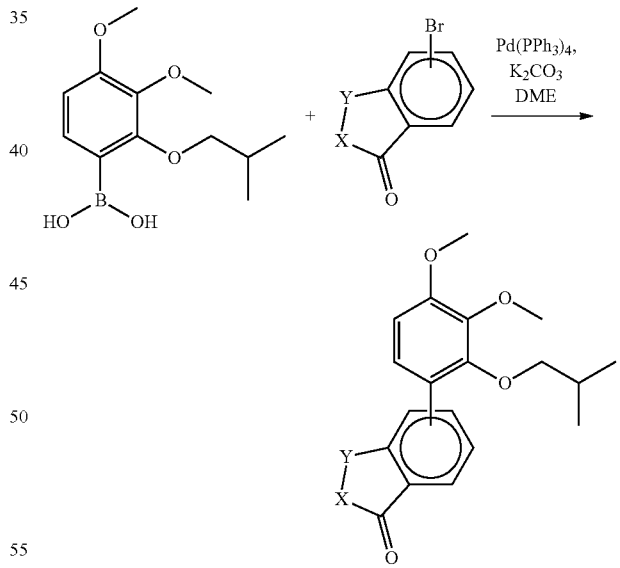

In a screw cap vial under an argon atmosphere 3,4-dimethoxy-2-(isobutoxy)phenylboronic acid (Compound 302) (0.015 g, 0.06 mmol) and the bromide (0.066 mmol) was dissolved in dimethoxyethane (0.35 mL). $K_2CO_3$ (1M solution, 0.12 mL, 0.12 mmol) and $Pd(PPh_3)_4$ (0.004 g, 0.003 mmol) was added. The suspension was shaken at 80° C. for 72 h. Brine (2 mL) was added and the mixture was extracted with $CH_2Cl_2$ (3 mL). The phases were separated using a phase separation cartridge (Chromabond, PTS). The organic phase was concentrated in vacuo and the residue was dissolved in DMF (0.3 mL) and purified by preparative HPLC/MS. Compounds 174-176 were prepared according to this procedure:

5-(2-Isobutoxy-3,4-dimethoxy-phenyl)-2,3-dihydro-isoindol-1-one (Compound 174)

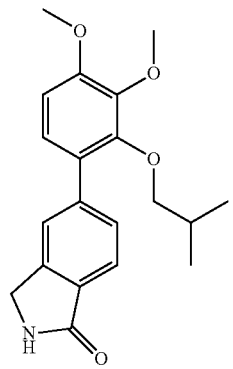 [SMILES: COc1ccc(-c2ccc3c(c2)CNC3=O)c(OCC(C)C)c1OC]

1H NMR (600 MHz, DMSO-SPE) δ 8.53 (s, 1H), 7.68 (d, J=7.8 Hz, 1H), 7.64 (s, 1H), 7.56 (dd, J=7.9, 1.2 Hz, 1H), 7.09 (d, J=8.6 Hz, 1H), 6.93-6.88 (m, 1H), 4.39 (s, 2H), 3.84 (s, 3H), 3.79 (s, 3H), 3.48 (d, J=14.4 Hz, 2H), 1.78-1.67 (m, 1H), 0.75 (d, J=6.7 Hz, 6H).

4-(2-Isobutoxy-3,4-dimethoxy-phenyl)-3H-isobenzofuran-1-one (Compound 175)

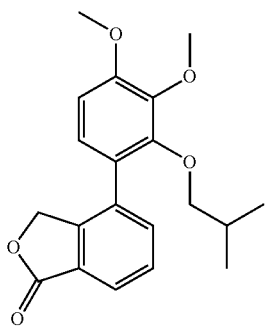 [SMILES: COc1ccc(-c2cccc3c2COC3=O)c(OCC(C)C)c1OC]

1H NMR (600 MHz, DMSO-SPE) δ 7.85 (dd, J=7.4, 0.9 Hz, 1H), 7.71 (dd, J=7.6, 1.0 Hz, 1H), 7.66 (t, J=7.5 Hz, 1H), 7.10 (t, J=6.9 Hz, 1H), 6.94-6.90 (m, 1H), 5.34 (s, 2H), 3.85 (s, 3H), 3.81 (s, 3H), 3.42 (dd, J=19.8, 14.7 Hz, 4H), 1.68-1.50 (m, 1H), 0.60 (d, J=6.8 Hz, 6H).

6-(2-Isobutoxy-3,4-dimethoxy-phenyl)-benzofuran-3-one (Compound 176)

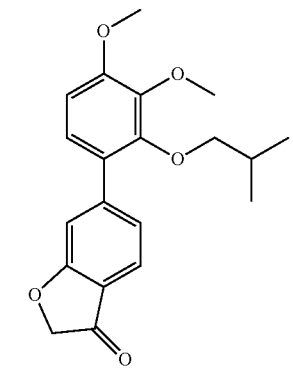 [SMILES: COc1ccc(-c2ccc3c(c2)OCC3=O)c(OCC(C)C)c1OC]

1H NMR (300 MHz, CDCl3) δ 7.66 (dd, J=7.6, 1.2 Hz, 1H), 7.32-7.26 (m, 2H), 7.06 (d, J=8.6 Hz, 1H), 6.75 (d, J=8.6 Hz, 1H), 4.67 (s, 2H), 3.92 (s, 3H), 3.91 (s, 3H), 3.57 (d, J=6.2 Hz, 2H), 1.84 (tt, J=13.2, 6.6 Hz, 1H), 0.84 (d, J=6.7 Hz, 6H).

Example 11

4-[2-(1-Hydroxymethyl-cyclopropylmethoxy)-3,4-dimethoxy-phenyl]-indan-1-one (Compound 177)

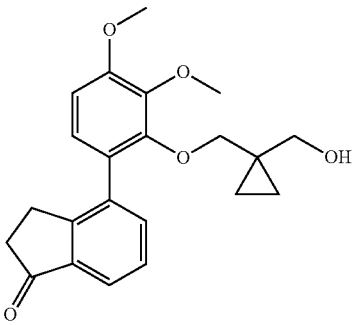 [SMILES: COc1ccc(-c2cccc3c2CCC3=O)c(OCC2(CO)CC2)c1OC]

To a stirring solution of (1-hydroxymethyl-cyclopropyl)-methanol (20 g, 197.05 mmol) in dichloromethane (200 mL) at 0° C., were added N,N-diisopropylethylamine (70 mL, 393.79 mmol) and tert-butyl(chloromethyl)diphenylsilane (15 g, 58.17 mmol) and the resultant reaction mixture was stirred at RT for 16 h. The resultant reaction mixture was quenched with ice water and extracted with dichloromethane (3×). The combined dichloromethane layer was washed with brine, dried over anhydrous sodium sulphate and concentrated under reduced pressure. Purification by column chromatography (silica gel, 0-5% ethyl acetate in pet ether) afforded (1-((tert-butyldiphenylsilyl)methoxy)cyclopropyl)methanol as a yellow liquid.

To a stirring solution of 4-(2-hydroxy-3,4-dimethoxy-phenyl)-indan-1-one (Compound 303) (5 g, 17.60 mmol) in tetrahydrofuran (50 mL), were added triphenylphosphine (9.2 g, 35.21 mmol) and diisopropylazodicarboxylate (7.11 g, 35.21 mmol) and {1-[(tert-Butyl-diphenyl-silanyl)-methoxy]-cyclopropyl}-methanol (7.18 g, 21.12 mmol) and the resultant reaction mixture was stirred at RT for 2 h. The reaction mixture was quenched with water and extracted with ethyl acetate (3×). The combined ethyl acetate layer was washed with brine, dried over anhydrous sodium sulphate and concentrated under reduced pressure. Purification by column chromatography (silica gel, 0-10% ethyl acetate in pet ether) afforded 4-(2-((1-((tert-butyldiphenylsilyl)methoxy)cyclopropyl)methoxy)-3,4-dimethoxyphenyl)-2,3-dihydro-1H-inden-1-one as a liquid.

To a stirring solution of 4-(2-((1-((tert-butyldiphenylsilyl)methoxy)cyclopropyl)methoxy)-3,4-dimethoxyphenyl)-2,3-dihydro-1H-inden-1-one (5 g, 6.25 mmol) in tetrahydrofuran, was added tetrabutylammonium fluoride trihydrate (33 mL, 33 mmol) and the resultant reaction mixture was stirred at RT for 16 h. The reaction mixture was quenched with water and extracted with ethyl acetate (3×). The combined ethyl acetate layer was washed with brine, dried over anhydrous sodium sulphate and concentrated under reduced pressure. Purification was done by column chromatography (silica gel, 0-40% ethyl acetate in pet ether) to afford the title compound as a yellow solid.

1H NMR (600 MHz, DMSO-SPE) δ 7.64 (dd, J=7.6, 0.9 Hz, 1H), 7.54 (dd, J=7.3, 1.1 Hz, 1H), 7.47 (t, J=7.5 Hz, 1H), 7.00 (d, J=8.5 Hz, 1H), 6.90-6.88 (m, 1H), 4.22 (t, J=5.5 Hz, 1H), 3.84 (s, 3H), 3.80 (s, 3H), 3.58 (d, J=10.9 Hz, 2H), 2.97 (t, J=6.1 Hz, 4H), 2.61 (dd, J=6.7, 5.0 Hz, 2H), 0.23-0.16 (m, 2H), 0.0 (m, 2H)

Example 12

4-[3,4-Dimethoxy-2-(1-methoxymethyl-cyclopropyl-methoxy)-phenyl]-indan-1-one (Compound 178)

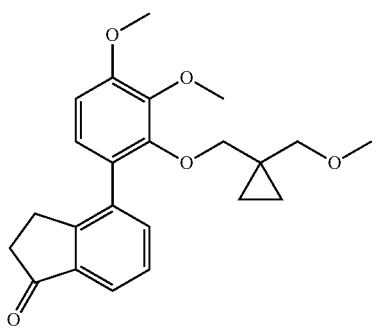 [SMILES: COCC1(COc2c(-c3cccc4c3CCC4=O)ccc(OC)c2OC)CC1]

To a stirring solution of cyclopropane-1,1-diyldimethanol (2 g, 19.60 mmol) in dimethylformamide (30 mL) at 0° C., was added potassium tertiarybutoxide (1.095 g, 9.73 mmol) and stirred for 1 h. To this methyl iodide (5.5 g, 38.73 mmol) was added to the above reaction mixture and the resultant reaction mixture was stirred at 0° C. for 45 min. The reaction mixture was diluted with water and extracted with ethylacetate (3×). The combined ethyl acetate layer was washed with brine and dried over anhydrous sodium sulphate and concentrated under reduced pressure. Purification by column chromatography (silica gel, 0-30% ethyl acetate in pet ether) afforded 1-(methoxymethyl)cyclopropyl)methanol as a solid.

To a stirring solution of 4-(2-hydroxy-3,4-dimethoxy-phenyl)-indan-1-one—(Compound 303) (100 mg, 0.3521 mmol) in tetrahydrofuran (15 mL), were added diisopropylazodicarboxylate (142 mg, 0.702 mmol) and triphenylphosphine (184 mg, 0.702 mmol) and (1-(methoxymethyl)cyclopropyl)methanol (122 mg, 1.051 mmol) and the resultant reaction mixture was heated to 70° C. After completion of reaction (by TLC), the reaction mixture was quenched with water and extracted with ethyl acetate (3×). The combined ethyl acetate layer was washed with brine, dried over anhydrous sodium sulphate and concentrated under reduced pressure. Purification by column chromatography (silica gel, 0-40% ethyl acetate in pet ether) afforded the title compound as a solid.

1H NMR (400 MHz, cdcl3) δ 7.77 (d, J=7.5 Hz, 1H), 7.54 (dd, J=7.4, 1.1 Hz, 1H), 7.43 (t, J=7.5 Hz, 1H), 6.94 (d, J=8.5 Hz, 1H), 6.76 (d, J=8.5 Hz, 1H), 3.95 (s, 3H), 3.90 (s, 3H), 3.60 (d, J=5.3 Hz, 2H), 3.11-3.06 (m, 2H), 3.05 (s, 3H), 2.88 (s, 2H), 2.72-2.64 (m, 2H), 0.31 (t, J=5.3 Hz, 2H), 0.22 (t, J=5.3 Hz, 2H).

Example 13

Ethyl-carbamic acid 1-[2,3-dimethoxy-6-(1-oxo-indan-4-yl)-phenoxymethyl]-cyclopropylmethyl ester (Compound 179)

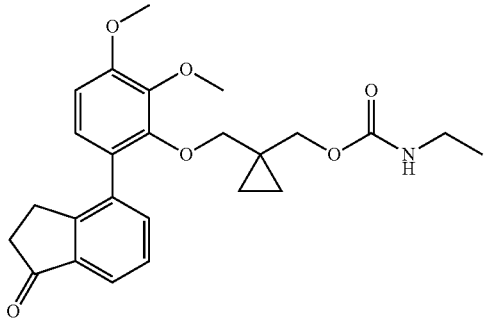 [SMILES: CCNC(=O)OCC1(COc2c(-c3cccc4c3CCC4=O)ccc(OC)c2OC)CC1]

To a stirring solution of 4-[2-(1-Hydroxymethyl-cyclopropylmethoxy)-3,4-dimethoxy-phenyl]-indan-1-one (Compound 177) (150 mg, 0.407 mmol) in dichloromethane (15 mL), were added triethylamine (123 mg, 1.22 mmol) and ethyl isocyanate (86 mg, 1.22 mmol) and the resultant reaction mixture was heated to 50° C. for 16 h. The reaction mixture was quenched with sodium bicarbonate solution and extracted with dichloromethane (3×). The combined dichloromethane layer was washed with brine, dried over anhydrous sodium sulphate and concentrated under reduced pressure. Purification by column chromatography (silica gel, 0-30% ethyl acetate in pet ether) afforded the title compound as a solid.

1H NMR (400 MHz, cdcl3) δ 7.76 (d, J=7.5 Hz, 1H), 7.53 (d, J=7.2 Hz, 1H), 7.42 (t, J=7.3 Hz, 1H), 6.95 (d, J=8.4 Hz, 1H), 6.77 (d, J=7.5 Hz, 1H), 4.40 (s, 1H), 3.94 (s, 3H), 3.92 (s, 3H), 3.73 (s, 2H), 3.52 (s, 2H), 3.17 (s, 2H), 3.12-3.01 (m, 2H), 2.74-2.63 (m, 2H), 1.13 (t, J=16.8 Hz, 3H), 0.37 (d, J=19.4 Hz, 2H), 0.21 (d, J=19.1 Hz, 2H).

Example 14

β Isopropyl-carbamic acid 1-[2,3-dimethoxy-6-(1-oxo-indan-4-yl)-phenoxymethyl]-cyclopropylmethyl ester (Compound 180)

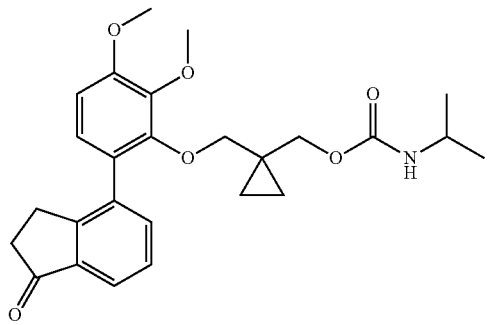 [SMILES: COc1ccc(-c2cccc3c2CCC3=O)c(OCC2(COC(=O)NC(C)C)CC2)c1OC]

To a stirring solution of 4-[2-(1-Hydroxymethyl-cyclopropylmethoxy)-3,4-dimethoxy-phenyl]-indan-1-one (Compound 177) (200 mg, 0.543 mmol) in dichloromethane (20 mL), were added triethylamine (164 mg, 1.623 mmol) and 2-isocyanatopropane (184 mg, 2.164 mmol) and the resultant reaction mixture was subjected to the conditions used in the preparation of Compound 179 to afford the title compound as a solid.

1H NMR (600 MHz, DMSO-SPE) δ 7.62 (d, J=7.5 Hz, 1H), 7.54 (d, J=7.1 Hz, 1H), 7.46 (t, J=7.5 Hz, 1H), 7.02 (d, J=8.5 Hz, 1H), 6.92-6.89 (m, 1H), 6.84 (d, J=7.5 Hz, 1H), 3.84 (s, 3H), 3.80 (s, 3H), 3.56-3.47 (m, 5H), 3.00-2.94 (m, 2H), 2.61 (dd, J=6.7, 5.0 Hz, 2H), 1.06-0.98 (m, 6H), 0.29 (d, J=19.0 Hz, 2H), 0.13 (m, 2H).

Example 15

Benzyl-carbamic acid 1-[2,3-dimethoxy-6-(1-oxo-indan-4-yl)-phenoxymethyl]-cyclopropylmethyl ester (Compound 181)

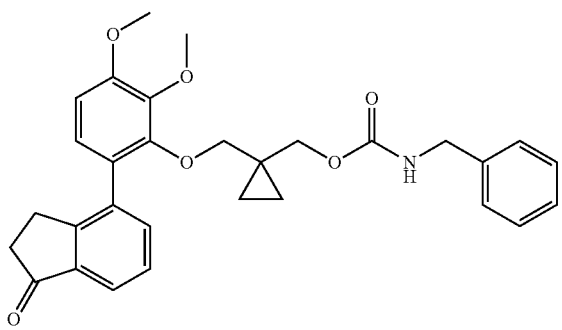 [SMILES: COc1ccc(-c2cccc3c2CCC3=O)c(OCC2(COC(=O)NCc3ccccc3)CC2)c1OC]

To a stirring solution of 4-[2-(1-Hydroxymethyl-cyclopropylmethoxy)-3,4-dimethoxy-phenyl]-indan-1-one (Compound 177) (150 mg, 0.407 mmol) in dichloromethane (15 mL), were added triethylamine (123 mg, 1.222 mmol) and benzyl isocyanate (105 mg, 0.812 mmol) and the resultant reaction mixture was subjected to the conditions used in the preparation of Compound 179 to afforded the title compound as a solid.

1H NMR (600 MHz, DMSO-SPE) δ 7.63-7.59 (m, 1H), 7.55-7.51 (m, 2H), 7.43 (t, J=7.4 Hz, 1H), 7.33-7.28 (m, 2H), 7.23 (t, J=6.7 Hz, 3H), 7.01 (d, J=8.5 Hz, 1H), 6.93-6.89 (m, 1H), 4.12 (t, J=10.3 Hz, 2H), 3.84 (s, 3H), 3.77 (s, 3H), 3.55 (m, 4H), 3.00-2.91 (m, 2H), 2.59 (dd, J=24.5, 18.8 Hz, 2H), 0.34-0.28 (m, 2H), 0.17-0.11 (m, 2H).

Example 16

4-[2-(1-Aminomethyl-cyclopropylmethoxy)-3,4-dimethoxy-phenyl]-indan-1-one (Compound 182)

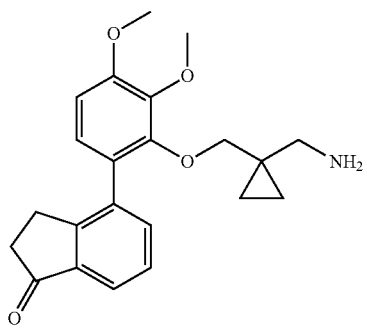 [SMILES: COc1ccc(-c2cccc3c2CCC3=O)c(OCC2(CN)CC2)c1OC]

To a stirring solution of 4-[2-(1-Hydroxymethyl-cyclopropylmethoxy)-3,4-dimethoxy-phenyl]-indan-1-one (Compound 177) (2.5 g, 6.79 mmol) in dichloromethane (30 mL) at 0° C., was added triethylamine (2.7 mL, 20.29 mmol) and methanesulfonyl chloride (1.16 g, 10.19 mmol) and the resultant reaction mixture was stirred at RT for 1 h. The reaction mixture was quenched with water and extracted with dichloromethane (3×). The combined dichloromethane layer was washed with brine, dried over anhydrous sodium sulphate and concentrated under reduced pressure to afford 1-((2,3-dimethoxy-6-(1-oxo-2,3-dihydro-1H-inden-4-yl) phenoxy)methyl)cyclopropyl methanesulfonate as a liquid.

To a stirring solution of 1-((2,3-dimethoxy-6-(1-oxo-2,3-dihydro-1H-inden-4-yl)phenoxy)methyl)cyclopropyl methanesulfonate (3 g, 6.72 mmol) in dimethylformamide (20 mL), was added sodium azide (2.18 g, 33.63 mmol) and the resultant reaction mixture was stirred at RT for 16 h. The reaction mixture was quenched with ice water and extracted with ethyl acetate (3×). The combined ethyl acetate layer was washed with brine, dried over anhydrous sodium sulphate and concentrated under reduced pressure. Purification by column chromatography (silica gel, 0-5% ethyl acetate in pet ether) to afforded 4-(2-((1-(azidomethyl)cyclopropyl)methoxy)-3,4-dimethoxyphenyl)-2,3-dihydro-1H-inden-1-one as a liquid.

To a stirring solution of 4-(2-((1-(azidomethyl)cyclopropyl)methoxy)-3,4-dimethoxyphenyl)-2,3-dihydro-1H-inden-1-one (1.5 g, 3.947 mmol) in tetrahydrofuran (50 mL), were added triphenylphosphine (4.14 g, 15.78 mmol) and the reaction mixture was stirred at RT for 2 h. water (5 mL) was added to the above reaction mixture and the resultant reaction was heated to 80° C. for 1 h. The reaction mixture was concentrated under reduced pressure and the obtained residue was acidified with 1N hydrochloric acid solution. Then extracted with ethyl acetate (3×) and the aq layer was basified with sodium bicarbonate solution and extracted with ethyl acetate and the combined ethyl acetate layer was washed with brine, dried over anhydrous sodium sulphate and concentrated under reduced pressure to afforded the title compound as a liquid.

Example 17

N-{1-[(2,3-Dimethoxy-6-(1-oxo-indan-4-yl)-phenoxymethyl]-cyclopropylmethyl}-isobutyramide (Compound 183)

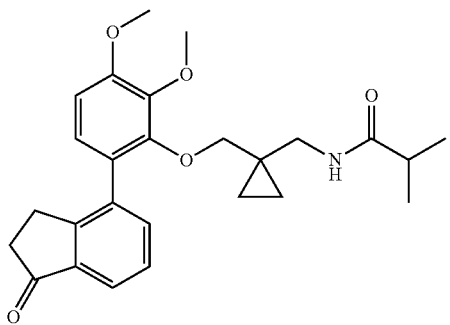 [SMILES: COc1ccc(-c2cccc3c2CCC3=O)c(OCC2(CNC(=O)C(C)C)CC2)c1OC]

To a stirring solution of 4-[2-(1-aminomethyl-cyclopropylmethoxy)-3,4-dimethoxy-phenyl]-indan-1-one (Compound 182) (100 mg, 0.272 mmol) in dichloromethane (10 mL), were added diisopropylethylamine (0.034 g, 0.272 mmol) and isobutyryl chloride (29 mg, 0.272 mmol) and the resultant reaction mixture was stirred at RT for 2 h. The reaction mixture was diluted with water and extracted with dichloromethane (3×). The combined dichloromethane layer was washed with brine and dried over anhydrous sodium sulphate and concentrated under reduced pressure. Purification by column chromatography (silica gel, 0-30% ethyl acetate in pet ether) to afforded the title compound as a solid.

1H NMR (600 MHz, DMSO-SPE) δ 7.63 (dd, J=7.5, 0.7 Hz, 1H), 7.57-7.53 (m, 1H), 7.47 (t, J=7.5 Hz, 1H), 7.35 (t, J=5.7 Hz, 1H), 7.01 (d, J=8.5 Hz, 1H), 6.92-6.89 (m, 1H), 3.84 (s, 3H), 3.79 (s, 3H), 3.49 (s, 2H), 3.01-2.95 (m, 2H), 2.82 (d, J=5.8 Hz, 2H), 2.66-2.60 (m, 2H), 2.27 (hept, J=6.8 Hz, 1H), 0.92 (d, J=6.8 Hz, 6H), 0.22-0.16 (m, 2H), 0.00--0.05 (m, 2H).

Example 18

N-{1-[2,3-Dimethoxy-6-(1-oxo-indan-4-yl)-phenoxymethyl]-cyclopropylmethyl}-butyramide (Compound 184)

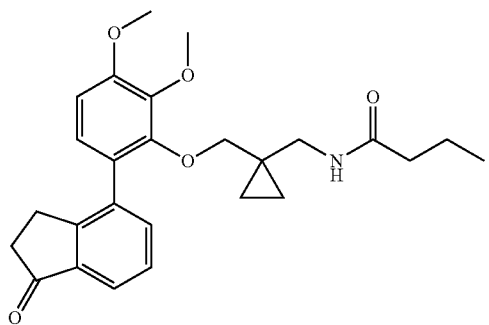 [SMILES: CCCC(=O)NCC1(COc2c(-c3cccc4c3CCC4=O)ccc(OC)c2OC)CC1]

To a stirring solution of 4-[2-(1-Aminomethyl-cyclopropylmethoxy)-3,4-dimethoxy-phenyl]-indan-1-one (Compound 182) (100 mg, 0.272 mmol) in dichloromethane (10 mL), were added diisopropylethylamine (0.034 g, 0.272 mmol) and butyryl chloride (29 mg, 0.272 mmol) and the resultant reaction mixture was subjected to the conditions used in the preparation of compound 183 to afford the title compound as a solid.

1H NMR (600 MHz, DMSO-SPE) δ 7.65-7.59 (m, 1H), 7.57-7.52 (m, 1H), 7.47 (t, J=7.5 Hz, 1H), 7.42-7.35 (m, 1H), 7.01 (d, J=8.5 Hz, 1H), 6.92-6.89 (m, 1H), 3.84 (s, 3H), 3.79 (s, 3H), 3.50 (s, 2H), 3.01-2.95 (m, 2H), 2.80 (d, J=5.8 Hz, 2H), 2.65-2.59 (m, 2H), 1.95 (t, J=7.3 Hz, 2H), 1.44 (h, J=7.4 Hz, 2H), 0.80 (t, J=7.4 Hz, 3H), 0.24-0.17 (m, 2H), 0.0 (m, 2H).

Example 19

N-{1-[2,3-Dimethoxy-6-(1-oxo-indan-4-yl)-phenoxymethyl]-cyclopropylmethyl}-acetamide (Compound 185)

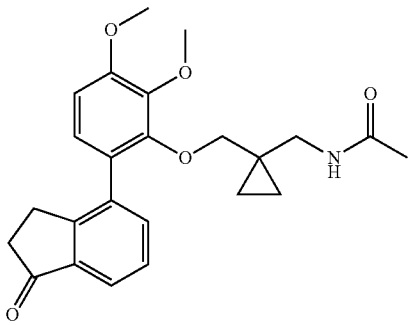 [SMILES: COc1ccc(-c2cccc3c2CCC3=O)c(OCC2(CNC(C)=O)CC2)c1OC]

To a stirring solution of 4-[2-(1-aminomethyl-cyclopropylmethoxy)-3,4-dimethoxy-phenyl]-indan-1-one (Compound 182) (100 mg, 0.272 mmol) in dichloromethane (10 mL), were added triethylamine (0.082 g, 0.811 mmol) and acetyl chloride (42 mg, 0.544 mmol) and the resultant reaction mixture was stirred at RT for 2 h. The reaction mixture was diluted with water and extracted with dichloromethane (3×). The combined dichloromethane layer was washed with brine and dried over anhydrous sodium sulphate and concentrated under reduced pressure. Purification by column chromatography (silica gel, 0-2% methanol in dichloromethane) afforded the title compound as a solid.

1H NMR (600 MHz, DMSO-SPE) δ 7.63 (dd, J=7.6, 0.7 Hz, 1H), 7.55 (dd, J=7.3, 1.0 Hz, 1H), 7.46 (m, 2H), 7.00 (d, J=8.5 Hz, 1H), 6.92-6.88 (m, 1H), 3.84 (s, 3H), 3.79 (s, 3H), 3.49 (s, 2H), 3.00-2.94 (m, 2H), 2.76 (d, J=5.7 Hz, 2H), 2.65-2.59 (m, 2H), 1.71 (s, 3H), 0.23-0.16 (m, 2H), 0.02 (q, J=4.5 Hz, 2H).

Example 20

{1-[2,3-Dimethoxy-6-(1-oxo-indan-4-yl)-phenoxymethyl]-cyclopropylmethyl}-carbamic Acid Ethyl Ester (Compound 186)

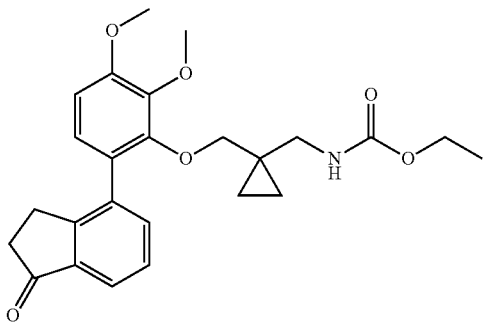 [SMILES: CCOC(=O)NCC1(COc2c(-c3cccc4c3CCC4=O)ccc(OC)c2OC)CC1]

To a stirring solution of 4-[2-(1-Aminomethyl-cyclopropylmethoxy)-3,4-dimethoxy-phenyl]-indan-1-one (Compound 182) (110 mg, 0.272 mmol) in dichloromethane (10 mL), were added triethylamine (0.082 g, 0.811 mmol) and ethyl carbonochloridate (59 mg, 0.544 mmol) and the resultant reaction mixture was subjected to the conditions used in the preparation of Compound 183 and Purification by column chromatography (silica gel, 0-25% ethyl acetate in pet ether) to afford the title compound as a solid.

1H NMR (600 MHz, DMSO-SPE) δ 7.65-7.60 (m, 1H), 7.54 (dd, J=7.4, 1.1 Hz, 1H), 7.47 (t, J=7.5 Hz, 1H), 7.02-6.98 (m, 1H), 6.92-6.89 (m, 1H), 6.69 (t, J=5.6 Hz, 1H), 3.95-3.87 (m, 2H), 3.85 (s, 3H), 3.80 (s, 3H), 3.47 (d, J=15.7 Hz, 2H), 3.01-2.94 (m, 2H), 2.71 (d, J=5.8 Hz, 2H), 2.65-2.60 (m, 2H), 1.15-1.08 (m, 3H), 0.24-0.16 (m, 2H), 0.0 (m, 2H).

Example 21

{1-[2,3-Dimethoxy-6-(1-oxo-indan-4-yl)-phenoxymethyl]-cyclopropylmethyl}-carbamic Acid Isopropyl Ester (Compound 187)

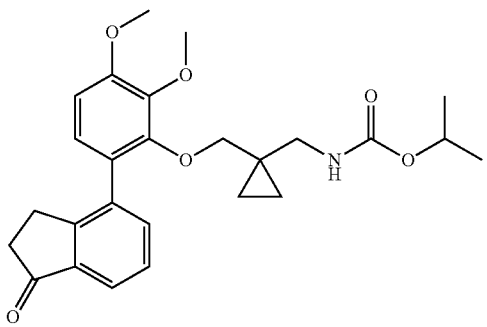 [SMILES: COc1ccc(-c2cccc3c2CCC3=O)c(OCC2(CNC(=O)OC(C)C)CC2)c1OC]

To a stirring solution of 4-[2-(1-Aminomethyl-cyclopropylmethoxy)-3,4-dimethoxy-phenyl]-indan-1-one (Compound 182) (150 mg, 0.272 mmol) in dichloromethane (10 mL), were added triethylamine (0.082 g, 0.811 mmol) and isopropyl carbonochloridate (66 mg, 0.544 mmol) and the resultant reaction mixture was subjected to the conditions used in the preparation of Compound 183 to afford the title compound as a solid.

1H NMR (600 MHz, DMSO-SPE) δ 7.63 (d, J=7.3 Hz, 1H), 7.54 (dt, J=7.9, 4.0 Hz, 1H), 7.47 (t, J=7.5 Hz, 1H), 7.00 (t, J=6.8 Hz, 1H), 6.92-6.88 (m, 1H), 6.63 (t, J=5.7 Hz, 1H), 4.71-4.62 (m, 1H), 3.85 (s, 3H), 3.80 (s, 3H), 3.47 (d, J=14.1 Hz, 2H), 3.02-2.95 (m, 2H), 2.71 (d, J=5.8 Hz, 2H), 2.61 (dd, J=14.0, 8.3 Hz, 2H), 1.16-1.08 (m, 6H), 0.24-0.16 (m, 2H), 0.04-0.07 (m, 2H).

Example 22

{1-[2,3-Dimethoxy-6-(1-oxo-indan-4-yl)-phenoxymethyl]-cyclopropylmethyl}-carbamic acid 2-methoxy-ethyl Ester (Compound 188)

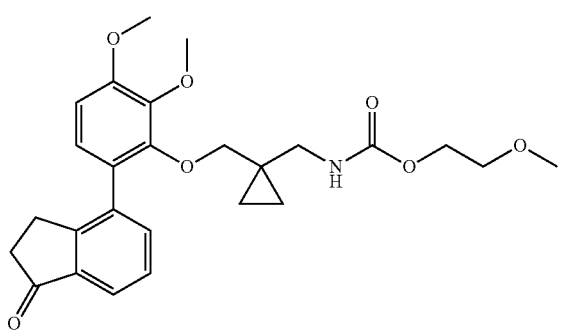 [SMILES: COCCOC(=O)NCC1(COc2c(-c3cccc4c3CCC4=O)ccc(OC)c2OC)CC1]

To a stirring solution of 4-[2-(1-Aminomethyl-cyclopropylmethoxy)-3,4-dimethoxy-phenyl]-indan-1-one (Compound 182) (150 mg, 0.272 mmol) in dichloromethane (10 mL), were added triethylamine (0.082 g, 0.811 mmol) and 2-methoxyethyl carbonochloridate (68 mg, 0.544 mmol) and the resultant reaction mixture was subjected to the conditions used in the preparation of Compound 183 to afford the title compound as a solid 1H NMR (600 MHz, DMSO-SPE) δ 7.65-7.61 (m, 1H), 7.54 (dt, J=7.6, 3.8 Hz, 1H), 7.47 (t, J=7.5 Hz, 1H), 7.02-6.98 (m, 1H), 6.92-6.89 (m, 1H), 6.88-6.83 (m, 1H), 3.99 (dd, J=5.3, 4.1 Hz, 2H), 3.85 (d, J=5.8 Hz, 3H), 3.80 (s, 3H), 3.49

(s, 2H), 3.47-3.42 (m, 2H), 3.23 (s, 3H), 3.00-2.95 (m, 2H), 2.72-2.69 (m, 2H), 2.64-2.59 (m, 2H), 0.22 (t, J=5.0 Hz, 2H), 0.02--0.02 (m, 2H).

Example 23

Ethyl-carbamic acid 3-[2,3-dimethoxy-6-(1-oxo-indan-4-yl)-phenoxymethyl]-oxetan-3-ylmethyl ester (Compound 189)

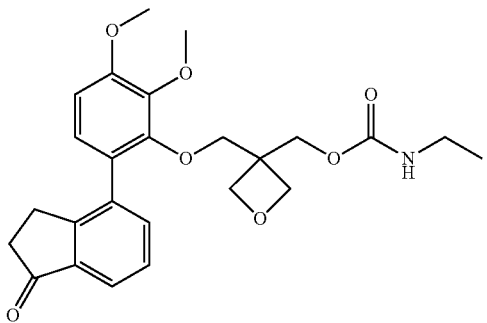 [SMILES: CCNC(=O)OCC1(COc2c(-c3cccc4c3CCC4=O)ccc(OC)c2OC)COC1]

To a stirring solution of 4-[2-(3-Hydroxymethyl-oxetan-3-ylmethoxy)-3,4-dimethoxy-phenyl]-indan-1-one (Compound 104)(100 mg, 0.2604 mmol) in dichloromethane (15 mL), were added triethylamine (0.1 mL, 0.772 mmol) and ethyl isocyanate (55 mg, 0.78 mmol) and the resultant reaction mixture was heated to 50° C. for 16 h. The reaction mixture was quenched with sodium bi carbonate solution and extracted with dichloromethane (3×). The combined dichloromethane layer was washed with brine and dried over anhydrous sodium sulphate and concentrated under reduced pressure. Purification by column chromatography (silica gel, 0-25% ethyl acetate in pet ether) to afforded the title compound as a solid.

1H NMR (600 MHz, DMSO-SPE) δ 7.62 (t, J=9.6 Hz, 1H), 7.55 (d, J=7.0 Hz, 1H), 7.47 (t, J=7.5 Hz, 1H), 7.05 (t, J=6.9 Hz, 2H), 6.96 (d, J=8.6 Hz, 1H), 4.12 (d, J=6.1 Hz, 2H), 3.93 (d, J=6.1 Hz, 2H), 3.88 (m, 7H), 3.81 (s, 3H), 3.00-2.90 (m, 4H), 2.65-2.56 (m, 2H), 1.01-0.96 (tr, 3H).

Example 24

4-[3,4-Dimethoxy-2-(3-methoxymethyl-oxetan-3-ylmethoxy)-phenyl]-indan-1-one (Compound 190)

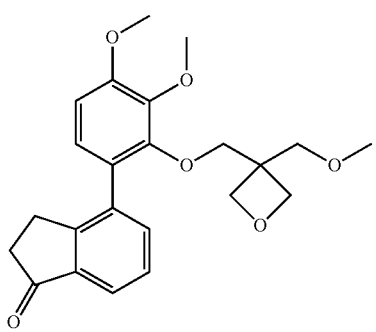 [SMILES: COCC1(COc2c(-c3cccc4c3CCC4=O)ccc(OC)c2OC)COC1]

To a stirring solution of (3-Bromomethyl-oxetan-3-yl)-methanol (200 mg, 1.104 mmol) in tetrahydrofuran (15 mL) at 0° C., was added sodium hydride (63 mg, 2.65 mmol) and stirred for 15 min. To this methyl iodide (629 mg, 4.419 mmol) was added to the above reaction mixture and the resultant reaction mixture was warmed to RT and stirred for 2 h. The reaction mixture was quenched with water and extracted with ethyl acetate (3×). The combined ethyl acetate layer was washed with brine and dried over anhydrous sodium sulphate and concentrated under reduced pressure. Purification by column chromatography (silica gel, 0-20% ethyl acetate in pet ether) afforded 3-(bromomethyl)-3-(methoxymethyl)oxetane as a liquid (120 mg, 55%).

To a stirring solution of 4-(2-Hydroxy-3,4-dimethoxy-phenyl)-indan-1-one (Compound 303) (100 mg, 0.352 mmol) in acetonitrile (15 mL), were added potassium carbonate (145 mg, 1.056 mmol) and 3-(bromomethyl)-3-(methoxymethyl)oxetane (102 mg, 0.528 mmol) and the resultant reaction mixture was heated to 70° C. for 16 h. The reaction mixture was diluted with water and extracted with ethyl acetate (3×). The combined ethyl acetate layer was washed with brine and dried over anhydrous sodium sulphate and concentrated under reduced pressure. Purification by column chromatography (silica gel, 0-25% ethyl acetate in pet ether) to afforded the title compound as a colorless liquid.

1H NMR (600 MHz, DMSO-SPE) δ 7.66 (dd, J=7.5, 0.8 Hz, 1H), 7.55 (dd, J=7.3, 1.1 Hz, 1H), 7.49 (dd, J=9.2, 5.7 Hz, 1H), 7.05-7.02 (m, 1H), 6.97-6.93 (m, 1H), 4.11 (d, J=6.0 Hz, 2H), 3.95 (t, J=7.8 Hz, 2H), 3.86 (s, 3H), 3.83 (s, 2H), 3.82 (s, 3H), 3.17 (s, 2H), 3.08 (s, 3H), 2.94 (dd, J=11.6, 6.0 Hz, 2H), 2.64-2.58 (m, 2H).

Example 25

4-[2-(3-Aminomethyl-oxetan-3-ylmethoxy)-3,4-dimethoxy-phenyl]-indan-1-one (Compound 191)

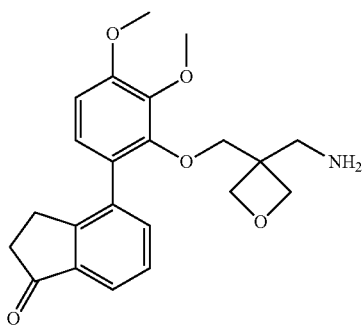 [SMILES: COc1ccc(-c2cccc3c2CCC3=O)c(OCC2(CN)COC2)c1OC]

To a stirring solution of 4-(2-Hydroxy-3,4-dimethoxy-phenyl)-indan-1-one (Compound 303) (500 mg, 1.76 mmol) in acetonitrile, were added potassium carbonate (728 mg, 5.28 mmol) and (3-Bromomethyl-oxetan-3-yl)-methanol (764 mg, 4.28 mmol) and the resultant reaction mixture was heated to 70° C. for 16 h. The reaction mixture was quenched with water and extracted with ethyl acetate (3×). The combined ethyl acetate layer was washed with brine and dried over anhydrous sodium sulphate and concentrated under reduced pressure. Purification by column chromatography (silica gel, 0-70% ethyl acetate in pet ether) afforded 4-(2-((3-(hydroxymethyl)oxetan-3-yl)methoxy)-3,4-dimethoxyphenyl)-indan-1-one (Compound 104) as a white solid.

To a stirring solution of 4-(2-((3-(hydroxymethyl)oxetan-3-yl)methoxy)-3,4-dimethoxyphenyl)-indan-1-one (4 g, 10.41 mmol) in dichloromethane (70 mL) at 0° C., were added triethylamine (3.15 g, 31.25 mmol) and mesyl chloride (1.78 g, 15.614 mmol), the resultant reaction mixture was warmed to RT and stirred for 30 min. The reaction mixture was diluted with water and extracted with dichloromethane (3×). The combined dichloromethane layer was washed with brine and dried over anhydrous sodium sulphate and concentrated under reduced pressure to afford (3-((2,3-dimethoxy-6-(1-oxo-2,3-dihydro-1H-inden-4-yl)phenoxy)methyl)oxetan-3-yl)methyl methanesulfonate as a solid.

To a stirring solution of (3-((2,3-dimethoxy-6-(1-oxo-2,3-dihydro-1H-inden-4-yl)phenoxy)methyl)oxetan-3-yl)methyl methanesulfonate (5 g, 10.82 mmol) in dimethylformamide (40 mL), was added sodium azide (3.5 g, 54.11 mmol) and the resultant reaction mixture was stirred at RT for 16 h. The reaction mixture was quenched with ice water and extracted with ethyl acetate (3×). The combined ethyl acetate layer was washed with brine and dried over anhydrous sodium sulphate and concentrated under reduced pressure to afford 4-(2-((3-(azidomethyl)oxetan-3-yl)methoxy)-3,4-dimethoxyphenyl)-indan-1-one as a solid.

To a stirring solution of 4-(2-((3-(azidomethyl)oxetan-3-yl)methoxy)-3,4-dimethoxyphenyl)-indan-1-one (3 g, 7.57 mmol) in in tetrahydrofuran (30 mL), were added triphenylphosphine (7.6 g, 29.28 mmol) and the reaction mixture was stirred at RT for 2 h. Water (3 mL) was added to the above reaction mixture and the resultant reaction mixture was heated to 80° C. for 1 h. The reaction mixture was concentrated under reduced pressure and the obtained residue was acidified with 1N hydrochloric acid solution. Then extracted with ethyl acetate (3×) and the aq layer was basified with sodium bicarbonate solution and extracted with ethyl acetate and the combined ethyl acetate layer was washed with brine, dried over anhydrous sodium sulphate and concentrated under reduced pressure to afford the title compound as a liquid.

Example 26

N-{3-[2,3-Dimethoxy-6-(1-oxo-indan-4-yl)-phenoxymethyl]-oxetan-3-ylmethyl}-acetamide (Compound 192)

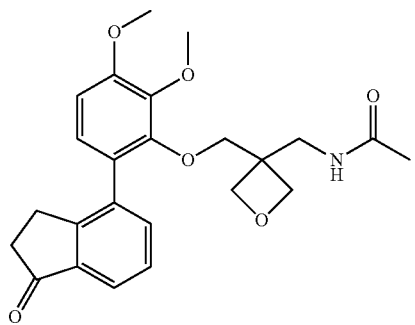 [SMILES: COc1ccc(-c2cccc3c2CCC3=O)c(OCC2(CNC(C)=O)COC2)c1OC]

To a stirring solution of 4-[2-(3-Aminomethyl-oxetan-3-ylmethoxy)-3,4-dimethoxy-phenyl]-indan-1-one (Compound 191) (150 mg, 0.391 mmol) in dichloromethane (15 mL), were added triethylamine (118 mg, 1.174 mmol) and acetyl chloride (61 mg, 0.777 mmol) and the resultant reaction mixture was stirred at RT for 16 h. The reaction mixture was diluted with water and extracted with dichloromethane (3×). The combined dichloromethane layer was washed with brine, dried over anhydrous sodium sulphate and concentrated under reduced pressure. Purification by column chromatography (silica gel, 0-2% methanol in dichloromethane) afforded the title compound as a solid.

1H NMR (600 MHz, DMSO-SPE) δ 7.82 (t, J=6.0 Hz, 1H), 7.64 (t, J=6.1 Hz, 1H), 7.56 (dd, J=7.3, 1.0 Hz, 1H), 7.48 (t, J=7.5 Hz, 1H), 7.06-7.03 (m, 1H), 6.97-6.94 (m, 1H), 4.08 (d, J=6.0 Hz, 2H), 3.90 (d, J=6.0 Hz, 2H), 3.86 (s, 3H), 3.81 (s, 3H), 3.74 (s, 2H), 3.05 (d, J=6.0 Hz, 2H), 2.99-2.93 (m, 2H), 2.62 (dd, J=11.4, 6.3 Hz, 2H), 1.77 (s, 3H).

Example 27

N-{3-[2,3-Dimethoxy-6-(1-oxo-indan-4-yl)-phenoxymethyl]-oxetan-3-ylmethyl}-isobutyramide (Compound 193)

To a stirring solution of 4-[2-(3-Aminomethyl-oxetan-3-ylmethoxy)-3,4-dimethoxy-phenyl]-indan-1-one (Compound 191) (150 mg, 0.3916 mmol) in dichloromethane (15 mL), were added diisopropylethylamine (50 mg, 0.390 mmol) and isobutyryl chloride (41 mg, 0.391 mmol) and the resultant reaction mixture was stirred at RT for 2 h. The reaction mixture was diluted with water and extracted with dichloromethane (3×). The combined dichloromethane layer was washed with brine, dried over anhydrous sodium sulphate and concentrated under reduced pressure. Purification by column chromatography (silica gel, 0-2% methanol in dichloromethane) afforded the title compound as a solid.

1H NMR (600 MHz, DMSO-SPE) δ 7.75 (t, J=6.1 Hz, 1H), 7.65-7.62 (m, 1H), 7.56 (dd, J=7.3, 1.0 Hz, 1H), 7.48 (t, J=7.5 Hz, 1H), 7.05 (d, J=8.5 Hz, 1H), 6.97-6.95 (m, 1H), 4.09 (d, J=6.0 Hz, 2H), 3.89 (t, J=6.1 Hz, 2H), 3.87 (s, 3H), 3.81 (s, 3H), 3.73 (d, J=11.6 Hz, 2H), 3.06 (d, J=6.1 Hz, 2H), 2.99-

2.95 (m, 2H), 2.61 (dd, J=6.7, 4.9 Hz, 2H), 2.32 (dq, J=13.5, 6.8 Hz, 1H), 0.96 (s, 3H), 0.95 (s, 3H).

Example 28

N-{3-[2,3-Dimethoxy-6-(1-oxo-indan-4-yl)-phenoxymethyl]-oxetan-3-ylmethyl}-butyramide (Compound 194)

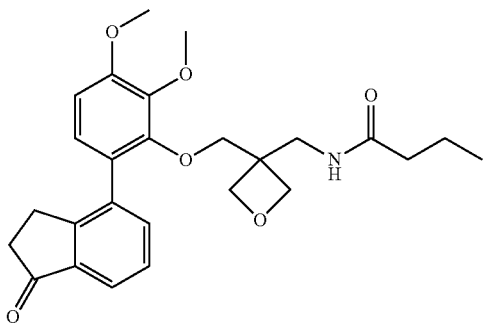 [SMILES: CCCC(=O)NCC1(COc2c(-c3cccc4c3CCC4=O)ccc(OC)c2OC)COC1]

To a stirring solution of 4-[2-(3-Aminomethyl-oxetan-3-ylmethoxy)-3,4-dimethoxy-phenyl]-indan-1-one (Compound 191) (150 mg, 0.3916 mmol) in dichloromethane (15 mL), were added diisopropylethylamine (50 mg, 0.390 mmol) and butyryl chloride (41 mg, 0.391 mmol) and the resultant reaction mixture was subjected to the conditions used in the preparation of Compound 193 and purification by column chromatography (silica gel, 0-3% methanol in dichloromethane) afforded the title compound as a solid.

1H NMR (600 MHz, DMSO-SPE) δ 7.79 (t, J=6.0 Hz, 1H), 7.63 (d, J=7.5 Hz, 1H), 7.58-7.53 (m, 1H), 7.48 (t, J=7.5 Hz, 1H), 7.05 (d, J=8.5 Hz, 1H), 6.96 (d, J=8.6 Hz, 1H), 4.09 (d, J=6.0 Hz, 2H), 3.90 (d, J=6.0 Hz, 2H), 3.85 (s, 3H), 3.81 (s, 3H), 3.73 (s, 2H), 3.05 (d, J=6.1 Hz, 2H), 3.01-2.92 (m, 2H), 2.65-2.57 (m, 2H), 2.01 (t, J=7.3 Hz, 2H), 1.53-1.40 (m, 2H), 0.83 (dt, J=14.8, 4.8 Hz, 3H).

Example 29

N-{3-[2,3-Dimethoxy-6-(1-oxo-indan-4-yl)-phenoxymethyl]-oxetan-3-ylmethyl}-2-methoxy-acetamide (Compound 195)

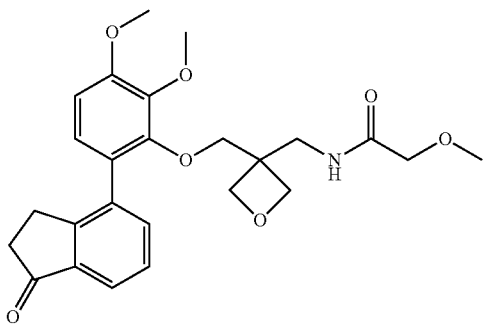 [SMILES: COCC(=O)NCC1(COc2c(-c3cccc4c3CCC4=O)ccc(OC)c2OC)COC1]

To a stirring solution of 4-[2-(3-Aminomethyl-oxetan-3-ylmethoxy)-3,4-dimethoxy-phenyl]-indan-1-one (150 mg, 0.391 mmol) in dichloromethane (15 mL), methoxy-acetic acid (142 mg, 1.56 mmol), 1-(3-Dimethylaminopropyl)-3-ethylcarbodiimide hydrochloride (EDC.HCl) (112 mg, 0.587 mmol) and 1-Hydroxy-7-azabenzotriazole (HOAt) (106 mg, 0.78 mmol) and triethylamine were added and the resultant reaction mixture was stirred at RT for 16 h. The reaction mixture was diluted with water and extracted with dichloromethane (3×). The combined dichloromethane layer was washed with brine and dried over anhydrous sodium sulphate and concentrated under reduced pressure. Purification by column chromatography (silica gel, 0-3% methanol in dichloromethane) afforded the title compound as a solid.

1H NMR (600 MHz, DMSO-SPE) δ 7.84 (t, J=6.3 Hz, 1H), 7.63 (td, J=7.9, 2.2 Hz, 1H), 7.57 (dd, J=7.3, 1.0 Hz, 1H), 7.48 (t, J=7.5 Hz, 1H), 7.05 (d, J=8.5 Hz, 1H), 6.98-6.95 (m, 1H), 4.15 (d, J=6.1 Hz, 2H), 3.88 (d, J=6.1 Hz, 2H), 3.87 (s, 3H), 3.82 (s, 3H), 3.78 (s, 2H), 3.75-3.67 (m, 2H), 3.28 (s, 3H), 3.12 (d, J=6.3 Hz, 2H), 2.99-2.92 (m, 2H), 2.61 (dd, J=6.7, 5.0 Hz, 2H).

Example 30

{3-[2,3-Dimethoxy-6-(1-oxo-indan-4-yl)-phenoxymethyl]-oxetan-3-ylmethyl}-carbamic acid ethyl ester (Compound 196)

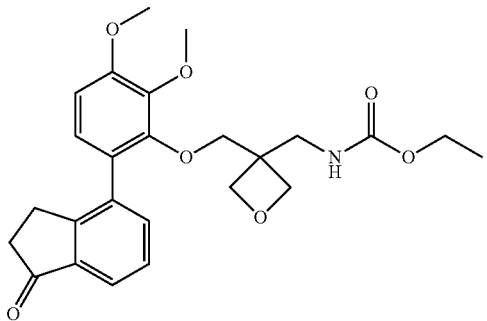 [SMILES: CCOC(=O)NCC1(COc2c(-c3cccc4c3CCC4=O)ccc(OC)c2OC)COC1]

To a stirring solution of 4-[2-(3-Aminomethyl-oxetan-3-ylmethoxy)-3,4-dimethoxy-phenyl]-indan-1-one (Compound 191) (150 mg, 0.3916 mmol) in dichloromethane (15 mL), were added triethylamine (118 mg, 1.174 mmol) and ethyl carbonochloridate (84 mg, 0.783 mmol) and the resultant reaction mixture was subjected to the conditions used in the preparation of Compound 192 to afford the title compound as a solid.

1H NMR (600 MHz, DMSO-SPE) δ 7.63 (t, J=6.6 Hz, 1H), 7.55 (dd, J=7.3, 1.0 Hz, 1H), 7.47 (t, J=7.5 Hz, 1H), 7.14 (t, J=6.0 Hz, 1H), 7.06-7.02 (m, 1H), 6.98-6.94 (m, 1H), 4.10 (d, J=6.1 Hz, 2H), 3.98-3.92 (m, 2H), 3.89 (d, J=6.1 Hz, 2H), 3.86 (s, 3H), 3.81 (s, 3H), 3.75 (s, 2H), 2.96 (dd, J=12.6, 6.0 Hz, 4H), 2.64-2.58 (m, 2H), 1.17-1.11 (m, 3H).

Example 31

{3-[2,3-Dimethoxy-6-(1-oxo-indan-4-yl)-phenoxymethyl]-oxetan-3-ylmethyl}-carbamic acid isopropyl ester (Compound 197)

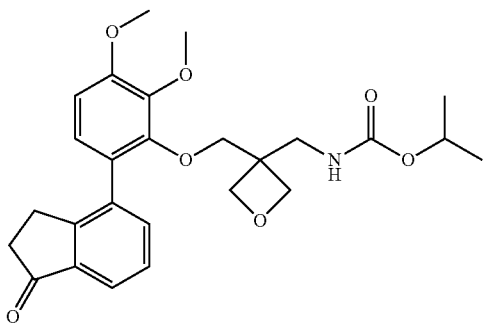 [SMILES: COc1ccc(-c2cccc3c2CCC3=O)c(OCC2(CNC(=O)OC(C)C)COC2)c1OC]

To a stirring solution of 4-[2-(3-Aminomethyl-oxetan-3-ylmethoxy)-3,4-dimethoxy-phenyl]-indan-1-one (Compound 191) (150 mg, 0.3916 mmol) in dichloromethane (15 mL), were added triethylamine (118 mg, 1.174 mmol) and isopropyl carbonochloridate (95 mg, 0.783 mmol) and the resultant reaction mixture was subjected to the conditions used in the preparation of Compound 192 to afford the title compound as a solid.

1H NMR (600 MHz, DMSO-SPE) δ 7.63 (d, J=7.3 Hz, 1H), 7.55 (dd, J=7.3, 0.9 Hz, 1H), 7.48 (t, J=7.5 Hz, 1H), 7.09 (t, J=6.1 Hz, 1H), 7.04 (d, J=8.5 Hz, 1H), 6.95 (dd, J=8.6, 4.3 Hz, 1H), 4.70 (hept, J=6.2 Hz, 1H), 4.10 (d, J=6.1 Hz, 2H), 3.91-3.85 (m, 5H), 3.81 (s, 3H), 3.75 (s, 2H), 2.95 (t, J=5.5 Hz, 4H), 2.61 (dd, J=6.5, 5.1 Hz, 2H), 1.18-1.12 (m, 6H).

Example 32

{3-[2,3-Dimethoxy-6-(1-oxo-indan-4-yl)-phenoxymethyl]-oxetan-3-ylmethyl}-carbamic acid 2-methoxyethyl ester (Compound 198)

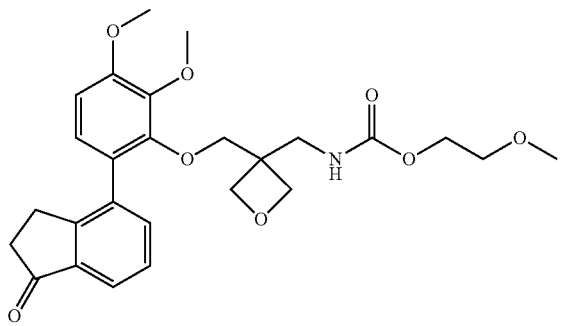 [SMILES: COCCOC(=O)NCC1(COc2c(-c3cccc4c3CCC4=O)ccc(OC)c2OC)COC1]

To a stirring solution of 4-[2-(3-Aminomethyl-oxetan-3-ylmethoxy)-3,4-dimethoxy-phenyl]-indan-1-one (Compound 191) (150 mg, 0.3916 mmol) in dichloromethane (15 mL), were added triethylamine (118 mg, 1.174 mmol) and 2-methoxyethyl carbonochloridate (99 mg, 0.783 mmol) and the resultant reaction mixture was subjected to the conditions used in the preparation of Compound 192 to afford the title compound as a solid.

1H NMR (600 MHz, DMSO-SPE) δ 7.62 (dd, J=13.5, 7.6 Hz, 1H), 7.55 (d, J=6.8 Hz, 1H), 7.48 (t, J=7.5 Hz, 1H), 7.29 (t, J=6.1 Hz, 1H), 7.06-7.02 (m, 1H), 6.97-6.93 (m, 1H), 4.10 (d, J=6.1 Hz, 2H), 4.04 (dd, J=11.7, 7.1 Hz, 2H), 3.89 (d, J=6.1 Hz, 2H), 3.86 (s, 3H), 3.81 (s, 3H), 3.76 (s, 2H), 3.46 (dd, J=10.3, 5.8 Hz, 2H), 3.24 (s, 3H), 3.00-2.90 (m, 4H), 2.61 (dd, J=12.1, 7.2 Hz, 2H).

Example 33

3-[2,3-Dimethoxy-6-(1-oxo-indan-4-yl)-phenoxy]-2,2-dimethyl-propionic acid (Compound 199)

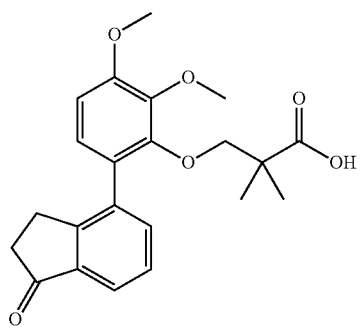 [SMILES: COc1ccc(-c2cccc3c2CCC3=O)c(OCC(C)(C)C(=O)O)c1OC]

To a stirring solution of 4-(2-Hydroxy-3,4-dimethoxy-phenyl)-indan-1-one (Compound 303) (1.3 g, 4.57 mmol), triphenylphosphine (3.5 g, 13.35 mmol), diethylazodicarboxylate (2.4 g, 13.40 mmol) in tetrahydrofuran (30 mL) methyl 3-hydroxy-2,2-dimethylpropanoate (1.2 g, 9.09 mmol) was added portion wise and the resultant reaction mixture was heated to 70° C. The reaction mixture was quenched with water and extracted with ethyl acetate (3×). The combined ethyl acetate layer was washed with brine, dried over anhydrous sodium sulphate and concentrated under reduced pressure. Purification by column chromatography (silica gel, 0-40% ethyl acetate in pet ether) afforded Methyl 3-(2,3-dimethoxy-6-(1-oxo-2,3-dihydro-1H-inden-4-yl)phenoxy)-2,2-dimethyl propanoate as a solid.

To a stirring solution of methyl 3-(2,3-dimethoxy-6-(1-oxo-2,3-dihydro-1H-inden-4-yl)phenoxy)-2,2-dimethyl propanoate (650 mg, 1.641 mmol) in THF (15 mL) lithium hydroxide (689 mg, 16.41 mmol) and water (5 mL) were added and the resultant reaction mixture was stirred for 2 h at room temperature. The reaction mixture was concentrated under reduced pressure and purification by column chromatography (silica gel, 0-60% ethyl acetate in pet ether) afforded the title compound as a solid.

Example 34

3-[2,3-Dimethoxy-6-(1-oxo-indan-4-yl)-phenoxy]-2,2,N-trimethyl-propionamide (Compound 200)

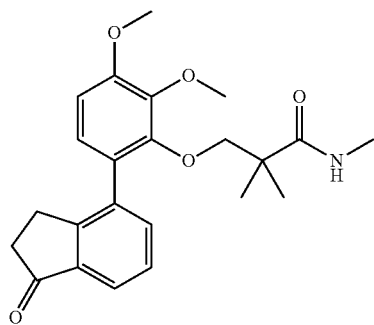 [SMILES: CNC(=O)C(C)(C)COc1c(-c2cccc3c2CCC3=O)ccc(OC)c1OC]

To a stirring solution of 3-[2,3-Dimethoxy-6-(1-oxo-indan-4-yl)-phenoxy]-2,2-dimethyl-propionic acid (Compound 199) (30 mg, 0.078 mmol) in dichloromethane, were added 1-(3-Dimethylaminopropyl)-3-ethylcarbodiimide hydrochloride (EDC.HCl) (22 mg, 0.117 mmol), 1-Hydroxybenzotriazole hydrate (HOBT) (23 mg, 0.156 mmol) and triethylamine (0.1 mL, 0.234 mmolo) and 1M methylamine solution (0.15 mL, 0.156 mmol) and the resultant reaction mixture was stirred at 16 h at RT. The reaction mixture was diluted with water and extracted with dichloromethane (3×). The combined dichloromethane layer was washed with brine and dried over anhydrous sodium sulphate and concentrated under reduced pressure. Purification by column chromatography (silica gel, 0-60% ethyl acetate in pet ether) afforded the title compound as a solid.

1H NMR (400 MHz, cdcl3) δ 7.79 (d, J=7.1 Hz, 1H), 7.54 (dd, J=7.3, 0.9 Hz, 1H), 7.45 (t, J=7.5 Hz, 1H), 6.97 (d, J=8.5 Hz, 1H), 6.82 (m, 2H), 3.95 (s, 3H), 3.95 (s, 3H), 3.53 (s, 2H), 3.05-2.98 (m, 2H), 2.73 (d, J=7.5 Hz, 3H), 2.66 (dd, J=12.3, 7.0 Hz, 2H), 0.87 (s, 6H).

Example 35

3-[2,3-Dimethoxy-6-(1-oxo-indan-4-yl)-phenoxy]-N-ethyl-2,2-dimethyl-propionamide (Compound 201)

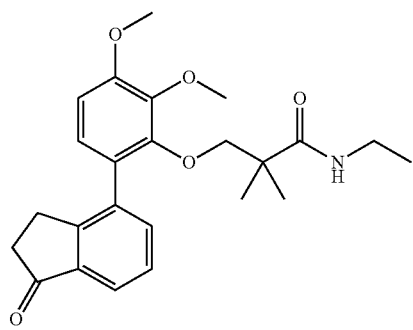 [SMILES: CCNC(=O)C(C)(C)COc1c(-c2cccc3c2CCC3=O)ccc(OC)c1OC]

From 3-[2,3-Dimethoxy-6-(1-oxo-indan-4-yl)-phenoxy]-2,2-dimethyl-propionic acid (Compound 199) and 2-Methylamine solution following the procedure for the preparation of Compound 200. Purification by column chromatography (silica gel, 0-50% ethyl acetate in pet ether) afforded the title compound as a solid.

1H NMR (400 MHz, cdcl3) δ 7.76 (d, J=7.5 Hz, 1H), 7.52 (dd, J=7.3, 0.9 Hz, 1H), 7.42 (dd, J=9.4, 5.5 Hz, 1H), 6.94 (d, J=8.5 Hz, 1H), 6.79 (d, J=8.6 Hz, 1H), 6.73 (s, 1H), 3.93 (s, 3H), 3.92 (s, 3H), 3.53 (s, 2H), 3.24-3.12 (m, 2H), 3.03-2.94 (m, 2H), 2.69-2.59 (m, 2H), 1.11-1.02 (m, 3H), 0.82 (s, 6H).

Example 36

3-[2,3-Dimethoxy-6-(1-oxo-indan-4-yl)-phenoxy]-2,2,N,N-tetramethyl-propionamide (Compound 202)

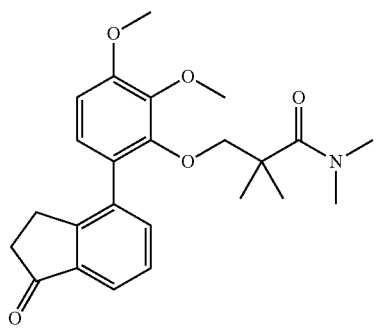 [SMILES: COc1ccc(-c2cccc3c2CCC3=O)c(OCC(C)(C)C(=O)N(C)C)c1OC]

From 3-[2,3-Dimethoxy-6-(1-oxo-indan-4-yl)-phenoxy]-2,2-dimethyl-propionic acid (Compound 199) and 2M dimethylamine solution following the procedure for the preparation of Compound 200. Purification by column chromatography (silica gel, 0-50% ethyl acetate in pet ether) afforded the title compound as a solid.

1H NMR (300 MHz, cdcl3) δ 7.75 (d, J=6.8 Hz, 1H), 7.52 (dd, J=7.3, 1.0 Hz, 1H), 7.40 (t, J=7.5 Hz, 1H), 6.94 (d, J=8.5 Hz, 1H), 6.78 (d, J=8.6 Hz, 1H), 3.92 (s, 3H), 3.91 (s, 3H), 3.77 (s, 2H), 3.02 (d, J=6.1 Hz, 2H), 2.71-2.63 (m, 2H), 1.07 (s, 6H).

Example 37

N-Cyclopropyl-3-[2,3-dimethoxy-6-(1-oxo-indan-4-yl)-phenoxy]-2,2-dimethyl-propionamide (Compound 203)

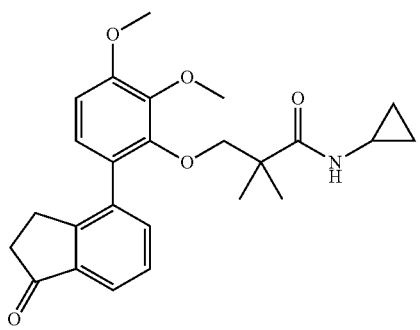 [SMILES: COc1ccc(-c2cccc3c2CCC3=O)c(OCC(C)(C)C(=O)NC2CC2)c1OC]

From 3-[2,3-Dimethoxy-6-(1-oxo-indan-4-yl)-phenoxy]-2,2-dimethyl-propionic acid (Compound 199) and cyclopropylamine following the procedure for the preparation of Compound 200. Purification by column chromatography (silica gel, 0-50% ethyl acetate in pet ether) afforded the title compound as a solid.

1H NMR (300 MHz, cdcl3) δ 7.77 (d, J=7.4 Hz, 1H), 7.52 (dd, J=7.3, 1.1 Hz, 1H), 7.43 (t, J=7.4 Hz, 1H), 6.94 (m, 2H), 6.81 (d, J=8.6 Hz, 2H), 3.96 (s, 3H), 3.94 (s, 3H), 3.49 (s, 2H), 3.05-2.95 (m, 2H), 2.72-2.64 (m, 2H), 0.79 (d, J=8.0 Hz, 6H), 0.77-0.71 (m, 2H), 0.44 (m, 2H).

Example 38

4-[2-(2,2-Dimethyl-3-morpholin-4-yl-3-oxo-propoxy)-3,4-dimethoxy-phenyl]-indan-1-one (Compound 204)

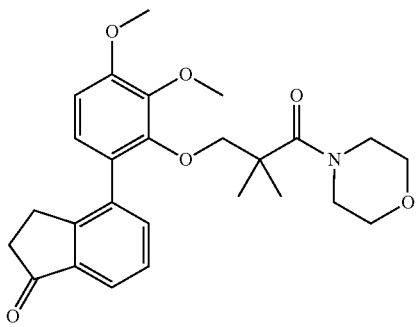 [SMILES: COc1ccc(-c2cccc3c2CCC3=O)c(OCC(C)(C)C(=O)N2CCOCC2)c1OC]

From 3-[2,3-Dimethoxy-6-(1-oxo-indan-4-yl)-phenoxy]-2,2-dimethyl-propionic acid (Compound 199) and morpholine following the procedure for the preparation of Compound 200. Purification by column chromatography (silica gel, 0-50% ethyl acetate in pet ether) afforded the title compound as a solid.

1H NMR (300 MHz, cdcl3) δ 7.76 (d, J=7.5 Hz, 1H), 7.52 (d, J=6.3 Hz, 1H), 7.41 (t, J=7.5 Hz, 1H), 6.94 (d, J=8.5 Hz, 1H), 6.78 (d, J=8.5 Hz, 1H), 3.92 (s, 3H), 3.91 (s, 3H), 3.74 (s, 2H), 3.59-3.51 (m, 4H), 3.45-3.36 (m, 4H), 3.08-2.97 (m, 2H), 2.72-2.63 (m, 2H), 1.04 (s, 6H).

Example 39

3-[2,3-Dimethoxy-6-(1-oxo-indan-5-yl)-phenoxy]-2,2-dimethyl-propionic acid (Compound 205)

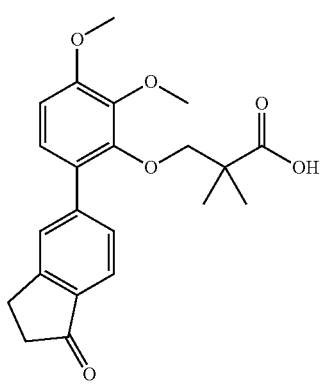 [SMILES: COc1ccc(-c2ccc3c(c2)CCC3=O)c(OCC(C)(C)C(=O)O)c1OC]

To a stirring solution of 5-(2-hydroxy-3,4-dimethoxyphenyl)-indan-1-one (Compound 305) (1.3 g, 4.57 mmol) in tetrahydrofuran (30 mL), were added triphenylphosphine (3.5 g, 13.35 mmol) and diethylazodicarboxylate (2.4 g, 13.40 mmol) and methyl 3-hydroxy-2,2-dimethylpropanoate (1.2 g, 9.09 mmol) was added portion wise and the resultant reaction mixture was heated to 70° C. The reaction mixture was quenched with water and extracted with ethyl acetate (3×). The combined ethyl acetate layer was washed with brine, dried over anhydrous sodium sulphate and concentrated under reduced pressure. Purification by column chromatography (silica gel, 0-40% ethyl acetate in pet ether) afforded methyl 3-(2,3-dimethoxy-6-(1-oxo-2,3-dihydro-1H-inden-5-yl)phenoxy)-2,2-dimethyl propanoate as a solid.

To a stirring solution of methyl 3-(2,3-dimethoxy-6-(1-oxo-2,3-dihydro-1H-inden-5-yl)phenoxy)-2,2-dimethyl propanoate (650 mg, 1.641 mmol) in THF (15 mL), were added lithium hydroxide (689 mg, 16.41 mmol) and water (5 mL) and the resultant reaction mixture was stirred for 2 h. The reaction mixture was concentrated under reduced pressure and purification by column chromatography (silica gel, 0-60% ethyl acetate in pet ether) afforded the title compound as a solid.

Example 40

3-[2,3-Dimethoxy-6-(1-oxo-indan-5-yl)-phenoxy]-2,2,N-trimethyl-propionamide (Compound 206)

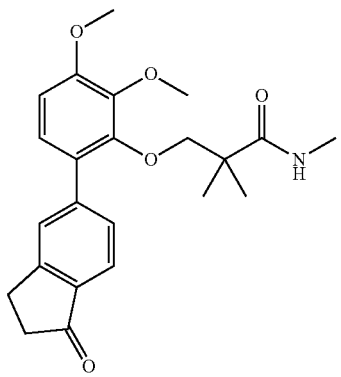 [SMILES: CNC(=O)C(C)(C)COc1c(-c2ccc3c(c2)CCC3=O)ccc(OC)c1OC]

To a stirring solution of 3-[2,3-Dimethoxy-6-(1-oxo-indan-5-yl)-phenoxy]-2,2-dimethyl-propionic acid (Compound 205) (100 mg, 0.260 mmol) in dichloromethane, were added 1-(3-Dimethylaminopropyl)-3-ethylcarbodiimide hydrochloride (EDC.HCl) (75 mg, 3.90 mmol), 1-Hydroxybenzotriazole hydrate (HOBT) (80 mg, 0.520 mmol) and triethylamine (0.1 mL, 0.9814 mmol) and 1M methylamine solution (0.4 mL, 0.520 mmol) and the resultant reaction mixture was stirred at 16 h at room temperature. The reaction mixture was diluted with water and extracted with dichloromethane (3×). The combined dichloromethane layer was washed with brine and dried over anhydrous sodium sulphate and concentrated under reduced pressure. Purification by column chromatography (silica gel, 0-40% ethyl acetate in pet ether) afforded the title compound as a solid.

1H NMR (300 MHz, cdcl3) a 7.79 (d, J=7.9 Hz, 1H), 7.62 (s, 1H), 7.50 (d, J=7.8 Hz, 1H), 7.09 (m, 2H), 6.82 (d, J=8.6 Hz, 1H), 3.96 (s, 3H), 3.94 (s, 3H), 3.56 (s, 2H), 3.23-3.11 (m, 2H), 2.85-2.67 (m, 5H), 1.03 (s, 6H).

Example 41

3-[2,3-Dimethoxy-6-(1-oxo-indan-5-yl)-phenoxy]-2,2,N,N-tetramethyl-propionamide (Compound 207)

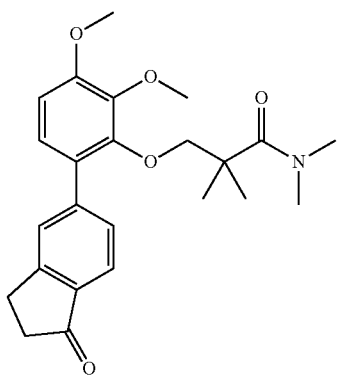 [SMILES: COc1ccc(-c2ccc3c(c2)CCC3=O)c(OCC(C)(C)C(=O)N(C)C)c1OC]

This was obtained from 3-[2,3-Dimethoxy-6-(1-oxo-indan-5-yl)-phenoxy]-2,2-dimethyl-propionic acid (Compound 205) and dimethylamine following the procedure for preparation of Compound 206. Purification by column chromatography (silica gel, 0-50% ethyl acetate in pet ether) afforded the title compound as a solid.

1H NMR (300 MHz, cdcl3) δ 7.75 (d, J=7.9 Hz, 1H), 7.62 (s, 1H), 7.50 (d, J=8.0 Hz, 1H), 7.06 (d, J=8.6 Hz, 1H), 6.77 (d, J=8.6 Hz, 1H), 3.91 (s, 3H), 3.90 (s, 3H), 3.81 (s, 2H), 3.24-3.11 (m, 2H), 2.90 (s, 5H), 2.79-2.66 (m, 2H), 1.22 (s, 6H).

Example 42

3-[2,3-Dimethoxy-6-(1-oxo-indan-5-yl)-phenoxy]-N-isopropyl-2,2-dimethyl-propionamide (Compound 208)

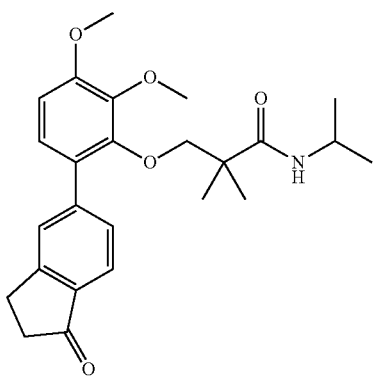 [SMILES: COc1ccc(-c2ccc3c(c2)CCC3=O)c(OCC(C)(C)C(=O)NC(C)C)c1OC]

From 3-[2,3-Dimethoxy-6-(1-oxo-indan-5-yl)-phenoxy]-2,2-dimethyl-propionic acid (Compound 205) and isopropylamine following the procedure for preparation of Compound 206. Purification by column chromatography (silica gel, 0-40% ethyl acetate in pet ether) afforded the title compound as a solid.

1H NMR (300 MHz, cdcl3) δ 7.77 (d, J=7.9 Hz, 1H), 7.59 (s, 1H), 7.48 (d, J=8.0 Hz, 1H), 7.05 (d, J=8.6 Hz, 1H), 6.80 (d, J=8.7 Hz, 1H), 6.52 (d, J=7.0 Hz, 1H), 4.05 (td, J=13.4, 6.7 Hz, 1H), 3.96 (s, 3H), 3.93 (s, 3H), 3.64 (s, 2H), 3.21-3.12 (m, 2H), 2.78-2.66 (m, 2H), 1.14 (d, J=6.6 Hz, 6H), 0.99 (s, 6H).

Example 43

3-[2,3-Dimethoxy-6-(1-oxo-indan-5-yl)-phenoxy]-2,2-dimethyl-N-propyl-propionamide (Compound 209)

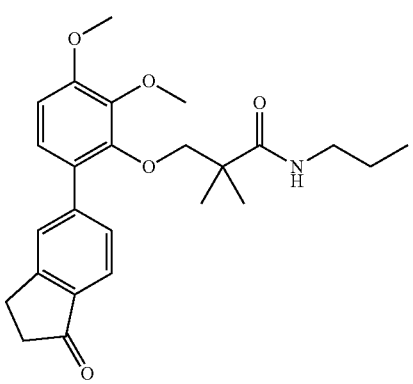 [SMILES: CCCNC(=O)C(C)(C)COc1c(-c2ccc3c(c2)CCC3=O)ccc(OC)c1OC]

From 3-[2,3-Dimethoxy-6-(1-oxo-indan-5-yl)-phenoxy]-2,2-dimethyl-propionic acid (Compound 205) and propan-1-amine following the procedure for preparation of Compound 206. Purification by column chromatography (silica gel, 0-50% ethyl acetate in pet ether) afforded the title compound as a solid.

1H NMR (400 MHz, cdcl3) δ 7.78 (d, J=7.9 Hz, 1H), 7.61 (s, 1H), 7.49 (d, J=8.0 Hz, 1H), 7.07 (d, J=8.6 Hz, 1H), 6.95 (s, 1H), 6.81 (d, J=8.7 Hz, 1H), 3.94 (s, 3H), 3.93 (s, 3H), 3.61 (s, 2H), 3.18 (dd, J=13.3, 6.9 Hz, 4H), 2.78-2.68 (m, 2H), 1.6 (s, 6H), 1.50 (m, 2H), 1.02 (s, 6H), 0.90 (t, J=7.4 Hz, 3H).

Example 44

Ethyl-carbamic acid 3-[2,3-dimethoxy-6-(1-oxo-1,3-dihydro-isobenzofuran-5-yl)-phenoxy]-2,2-dimethyl-propyl Ester (Compound 2101

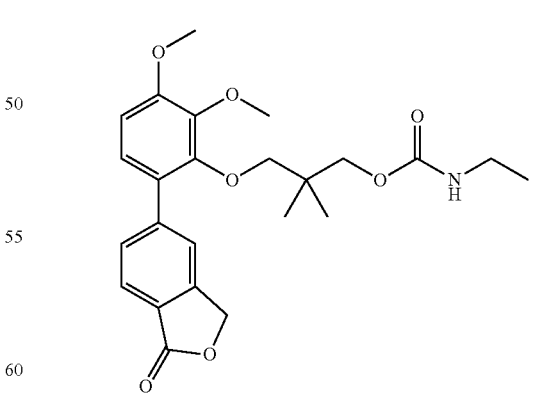

In a screw cap vessel Compound 306 (0.017 g, 0.06 mmol) and 3-bromo-2,2-dimethyl-1-propanol (0.2 g, 0.12 mmol) were dissolved in DMF (0.5 mL) and K₂CO₃ (0.02 g, 0.15 mmol) was added. The suspension was heated at 100° C. for 20 h. 3-Bromo-2,2-dimethyl-1-propanol (0.2 g, 0.12 mmol)

and K₂CO₃ (0.02 g, 0.15 mmol) was added and the suspension was heated at 100° C. for 4 h. H₂O (3 mL) was added and the suspension was extracted with EtOAc (3×3 mL). The combined organic phases were washed with brine, dried (Na₂SO4), filtered and concentrated.

In a screw cap vessel the crude product was dissolved in CH₃CN (0.2 mL). triethyl amine (0.003 mL) and Ethyl isocyanate (0.049 mL, 0.6 mmol) were added. The mixture was heated at 50° C. for 18 h and the solvent was evaporated. The crude product was purified by flash chromatography using toluene:EOAc 3:1 as the eluent. This afforded the title compound as an oil.

1H NMR (300 MHz, DMSO) 67.84 (d, J=7.9 Hz, 1H), 7.72 (s, 1H), 7.64 (d, J=8.0 Hz, 1H), 7.13 (d, J=8.7 Hz, 1H), 6.94 (d, J=8.7 Hz, 1H), 6.88 (s, 1H), 5.42 (s, 2H), 3.85 (s, 3H), 3.79 (s, 3H), 3.62 (s, 2H), 3.56-3.44 (m, 2H), 3.01-2.88 (m, 2H), 1.01-0.93 (m, 3H), 0.79 (s, 6H).

Example 45

Ethyl-carbamic acid 3-[2,3-dimethoxy-6-(1-oxo-indan-4-yl)-phenoxy]-2,2-dimethyl-propyl ester (Compound 211)

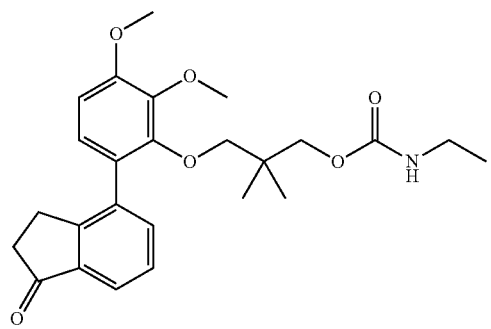 [SMILES: CCNC(=O)OCC(C)(C)COc1c(-c2cccc3c2CCC3=O)ccc(OC)c1OC]

The compound was prepared according to the procedure described in example 44 using compound 303 as the starting material.

1H NMR (300 MHz, DMSO) δ 7.62 (dd, J=7.4, 1.2 Hz, 1H), 7.53 (dd, J=7.3, 1.3 Hz, 1H), 7.47 (d, J=7.4 Hz, 1H), 7.00 (d, J=8.5 Hz, 1H), 6.93-6.84 (m, 2H), 3.85 (s, 3H), 3.78 (s, 3H), 3.46 (s, 2H), 3.44 (s, 2H), 2.98-2.90 (m, 4H), 2.61 (dd, J=6.8, 4.7 Hz, 2H), 0.97 (t, J=7.3 Hz, 3H), 0.58 (s, 6H).

Example 46

Ethyl-carbamic acid 3-[2,3-dimethoxy-6-(1-oxo-2,3-dihydro-1H-isoindol-5-yl)-phenoxy]-2,2-dimethyl-propyl ester (Compound 212)

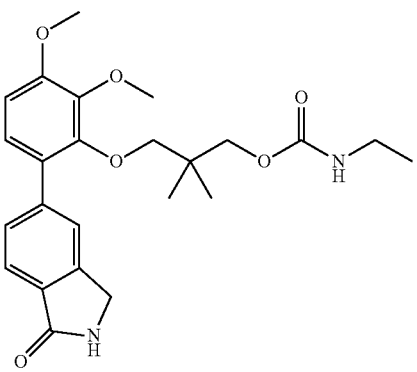 [SMILES: CCNC(=O)OCC(C)(C)COc1c(-c2ccc3c(c2)CNC3=O)ccc(OC)c1OC]

The compound was prepared according to the procedure for the preparation of Compound 210 using compound 307 as the starting material.

1H NMR (300 MHz, DMSO) δ 8.50 (t, J=5.7 Hz, 1H), 7.80 (d, J=8.0 Hz, 1H), 7.74 (s, 1H), 7.61 (d, J=8.0 Hz, 1H), 7.12 (d, J=8.7 Hz, 1H), 6.94 (d, J=8.8 Hz, 1H), 6.85 (s, 1H), 4.81 (s, 2H), 3.85 (s, 3H), 3.79 (d, J=3.0 Hz, 3H), 3.59 (d, J=11.6 Hz, 2H), 3.52 (d, J=11.8 Hz, 2H), 3.00-2.85 (m, 2H), 1.20-1.10 (m, 3H), 0.78 (s, 6H).

Example 47

Ethyl-carbamic acid 3-[2,3-dimethoxy-6-(1-oxo-1,3-dihydro-isobenzofuran-5-yl)-phenoxymethyl]-oxetan-3-ylmethyl ester (Compound 213)

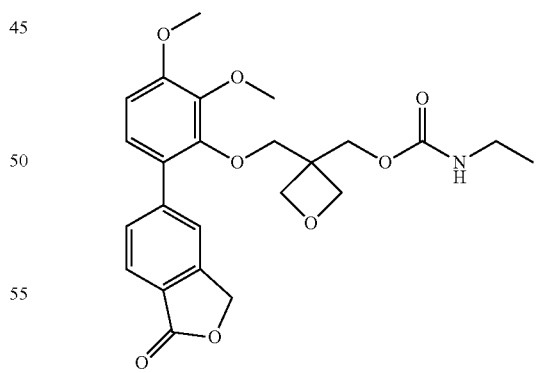

In a screw cap vessel Compound 306 (0.017 g, 0.06 mmol) and 3-bromomethyl-3-hydroxymethyl-oxetane (0.22 g, 0.12 mmol) were dissolved in DMF (0.5 mL) and K₂CO₃ (0.02 g, 0.15 mmol) was added. The suspension was heated at 100° C. for 3 h. H₂O (3 mL) was added and the suspension was extracted with EtOAc (3×3 mL). The combined organic phases were washed with brine, dried (Na₂SO4), filtered and concentrated. In a screw cap vessel the crude product was dissolved in CH₃CN (0.2 mL). Triethyl amine (0.003 mL) and Ethyl isocyanate (0.044 mL, 0.6 mmol) were added. The mixture was heated at 50° C. for 18 h and the solvent was evaporated. The crude product was purified by flash chromatography using toluene:EOAc 60:40->40:60 as the eluent. This afforded the title compound as an oil.

1H NMR (300 MHz, DMSO) δ 7.85 (d, J=8.0 Hz, 1H), 7.72 (s, 1H), 7.63 (d, J=7.9 Hz, 1H), 7.16 (d, J=8.7 Hz, 1H), 7.07 (t, J=5.5 Hz, 1H), 6.99 (d, J=8.8 Hz, 1H), 5.43 (s, 2H), 4.25 (t, J=7.3 Hz, 2H), 4.17 (d, J=6.1 Hz, 2H), 4.08-3.98 (m, 2H), 3.94 (s, 2H), 3.87 (s, 3H), 3.81 (s, 3H), 3.03-2.92 (m, 2H), 1.03-0.92 (m, 3H).

Example 48

Ethyl-carbamic acid 3-[2,3-dimethoxy-6-(1-oxo-2,3-dihydro-1H-isoindol-5-yl)-phenoxymethyl]-oxetan-3-ylmethyl ester (Compound 214)

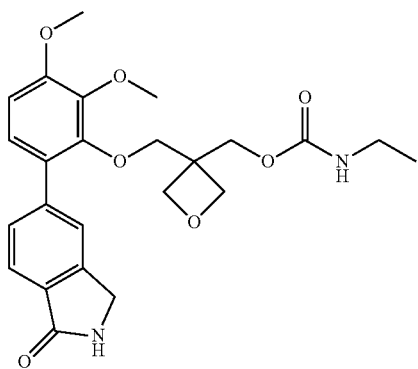 [SMILES: CCNC(=O)OCC1(COc2c(-c3ccc4c(c3)CNC4=O)ccc(OC)c2OC)COC1]

The title compound was prepared following the procedure described in example 47, using compound 307 as the starting material.

1H NMR (300 MHz, DMSO) δ 8.50 (t, J=5.7 Hz, 1H), 7.81 (d, J=8.0 Hz, 1H), 7.73 (s, 1H), 7.60 (d, J=8.0 Hz, 1H), 7.15 (d, J=8.7 Hz, 1H), 7.00 (m, 2H), 4.82 (s, 2H), 4.25 (d, J=6.1 Hz, 2H), 4.17 (d, J=6.1 Hz, 2H), 4.02 (dd, J=8.5, 5.7 Hz, 2H), 3.94 (s, 2H), 3.87 (s, 3H), 3.82 (s, 3H), 3.02-2.85 (m, 2H), 1.15 (dd, J=11.3, 4.1 Hz, 3H).

Example 49

5-[3,4-Dimethoxy-2-(3-methoxymethyl-oxetan-3-ylmethoxy)-phenyl]-3H-isobenzofuran-1-one (Compound 215)

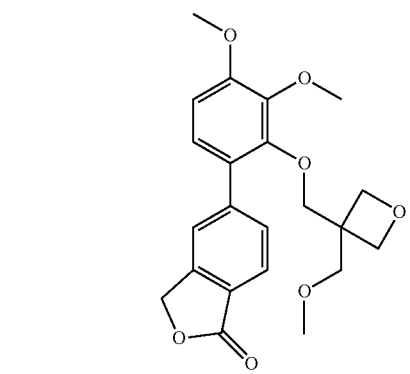 [SMILES: COCC1(COc2c(-c3ccc4c(c3)COC4=O)ccc(OC)c2OC)COC1]

3-(bromomethyl)-3-(methoxymethyl)oxetane (0.35 g, 0.18 mmol) preparation described in example 24) and 6-bromo-2,3-dimethoxyphenol (0.21 g, 0.9 mmol) (preparation described in Preparation 1) were dissolved in DMF (8 mL). K₂CO₃ (0.31 g, 2.2 mmol) was added. The suspension was heated in a microwave oven at 100° C. for 10 min. H₂O was added and the mixture was extracted with EtOAc (×2). The combined organic phases were washed with brine, dried (Na₂SO₄), filtered and concentrated. Purification by flash chromatography (Heptane:EtOAc 100:0->75:25) yielded 3-(6-Bromo-2,3-dimethoxy-phenoxymethyl)-3-methoxymethyl-oxetane as an oil.

3-(6-Bromo-2,3-dimethoxy-phenoxymethyl)-3-methoxymethyl-oxetane (0.02 g, 0.06 mmol) and 5-(4,4,5,5-Tetramethyl-[1,3,2]dioxaborolan-2-yl)-3H-isobenzofuran-1-one (Compound 309) (0.039 g, 0.14 mmol) were dissolved in 1,4-dioxan (0.6 mL). Argon was purged through the solution. Pd₂(dba)₃ 0.001 g, 0.001 mmol) and PCy₃ (0.0008 g, 0.003 mmol) were added followed by addition of K₃PO₄ (0.043 g, 0.2 mmol) in H₂O (0.3 mL). The reaction mixture was heated in a microwave oven at 120° C. for 10 min. The mixture was filtrated, concentrated, redissolved in DMSO and purified by preparative HPLC to afford the title compound.

1H NMR (600 MHz, DMSO-SPE) δ 7.88 (d, J=8.0 Hz, 1H), 7.73 (s, 1H), 7.67-7.63 (m, 1H), 7.15 (d, J=8.7 Hz, 1H), 7.00-6.95 (m, 1H), 5.44 (s, 2H), 4.25-4.19 (m, 2H), 4.15 (d, J=6.0 Hz, 2H), 3.91 (s, 2H), 3.87 (s, 3H), 3.82 (s, 3H), 3.38 (s, 2H), 3.16 (s, 3H).

Example 50

5-[3,4-Dimethoxy-2-(3-methoxymethyl-oxetan-3-ylmethoxy)-phenyl]-2,3-dihydro-isoindol-1-one (Compound 216)

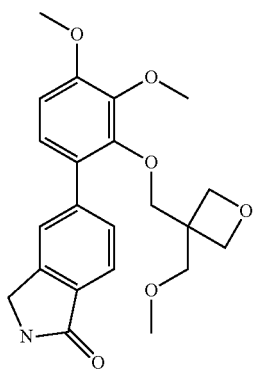 [SMILES: COCC1(COc2c(-c3ccc4c(c3)CNC4=O)ccc(OC)c2OC)COC1]

The title compound was prepared following the procedure described in example 49, using 5(4,4,5,5-Tetramethyl-[1,3,2]dioxaborolan-2-yl)-2,3-dihydro-isoindol-1-one (Compound 310) as the boronic acid ester.

1H NMR (600 MHz, DMSO-SPE) δ 8.55 (s, 1H), 7.69 (d, J=7.8 Hz, 1H), 7.62 (d, J=8.2 Hz, 1H), 7.53 (dd, J=11.6, 3.7 Hz, 1H), 7.11 (d, J=8.6 Hz, 1H), 6.96 (dd, J=10.0, 5.5 Hz, 1H), 4.40 (d, J=9.4 Hz, 2H), 4.21 (d, J=6.0 Hz, 2H), 4.13 (d, J=6.0 Hz, 2H), 3.89 (s, 2H), 3.86 (s, 3H), 3.82 (s, 3H), 3.36 (s, 2H), 3.15 (s, 3H).

Example 51

4-[3,4-Dimethoxy-2-(3-methoxy-2,2-dimethyl-propoxy)-phenyl]-indan-1-one (Compound 217)

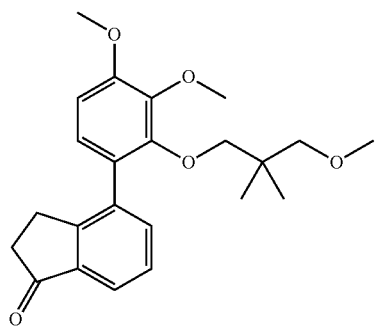 [SMILES: COCC(C)(C)COc1c(-c2cccc3c2CCC3=O)ccc(OC)c1OC]

Under an argon atmosphere 3-Bromo-2,2-dimethyl-propan-1-ol (1.1 g, 6.9 mmol) was dissolved in dry THF (50 mL) and cooled to 0° C. NaH (0.4 g, 16.5 mmol) was added and the suspension was stirred at 0° C. for 15 min. MeI (1.7 mL, 27.6 mmol) was added at 0° C. The reaction mixture was allowed to stir at RT for 2 h. H$_2$O (100 mL) was added and the aqueous phase was extracted with EtOAc (×2). The combined organic phases were washed with brine, dried (Na$_2$SO$_4$), filtered and concentrated to afford 1-bromo-3-methoxy-2,2-dimethyl-propane as an oil.

Compound 303 (0.02 g, 0.07 mmol) and 1-bromo-3-methoxy-2,2-dimethyl-propane (0.12 g, 0.56 mmol) were dissolved in dry DMF (0.8 mL). K$_2$CO$_3$ (0.1 g, 0.68 mmol) were added. The suspension was heated at 100° C. for 18 h. H$_2$O was added and the mixture was extracted with EtOAc (×2). The combined organic phases were washed with brine, dried (Na$_2$SO$_4$), filtered and concentrated. Purification by preparative HPLC afforded the title compound as an oil.

1H NMR (300 MHz, CDCl3) δ 7.76 (d, J=7.6 Hz, 1H), 7.52 (dd, J=7.4, 1.2 Hz, 1H), 7.42 (t, J=7.5 Hz, 1H), 6.92 (d, J=8.5 Hz, 1H), 6.75 (d, J=8.5 Hz, 1H), 3.92 (s, 6H), 3.49 (s, 2H), 3.11-3.01 (m, 5H), 2.81 (s, 2H), 2.73-2.61 (m, 2H), 0.66 (s, 6H).

Example 52

5-[3,4-Dimethoxy-2-(3-methoxy-2,2-dimethyl-propoxy)-phenyl]-3H-isobenzofuran-1-one (Compound 218)

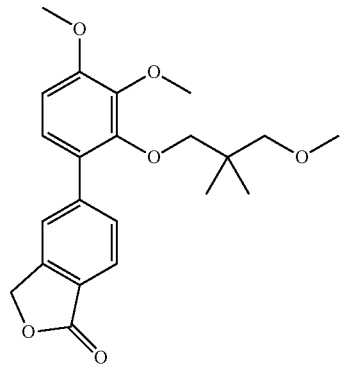 [SMILES: COCC(C)(C)COc1c(-c2ccc3c(c2)COC3=O)ccc(OC)c1OC]

The title compound was prepared following the procedure described in example 51, using compound 306 as the starting material.

1H NMR (300 MHz, CDCl3) δ 7.93 (d, J=8.0 Hz, 1H), 7.71-7.65 (m, 1H), 7.62 (s, 1H), 7.04 (d, J=8.7 Hz, 1H), 6.76 (d, J=8.7 Hz, 1H), 5.34 (s, 2H), 3.91 (s, 6H), 3.56 (s, 2H), 3.15 (s, 3H), 3.00 (s, 2H), 0.81 (s, 6H).

Example 53

5-[3,4-Dimethoxy-2-(3-methoxy-2,2-dimethyl-propoxy)-phenyl]-2,3-dihydro-isoindol-1-one (Compound 219)

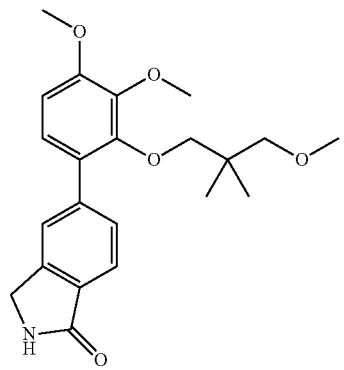 [SMILES: COCC(C)(C)COc1c(-c2ccc3c(c2)CNC3=O)ccc(OC)c1OC]

The title compound was prepared following the procedure described in example 51, using compound 307 as the starting material.

1H NMR (300 MHz, CDCl3) δ 7.89 (d, J=8.3 Hz, 1H), 7.62 (d, J=6.5 Hz, 2H), 7.04 (d, J=8.7 Hz, 1H), 6.75 (d, J=8.7 Hz, 1H), 6.29 (s, 1H), 4.48 (s, 2H), 3.91 (s, 6H), 3.54 (s, 2H), 3.15 (s, 3H), 2.99 (s, 2H), 0.80 (s, 6H).

Example 54

3-(2,3-dimethoxy-6-(1-oxo-1,3-dihydroisobenzofuran-5-yl)phenoxy)-2,2-dimethylpropanoic acid (Compound 220)

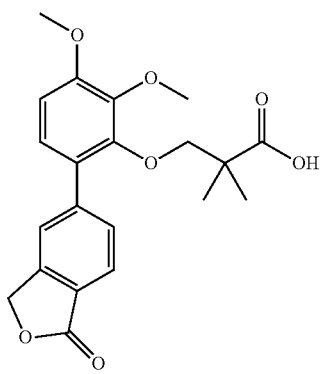 [SMILES: COc1ccc(-c2ccc3c(c2)COC3=O)c(OCC(C)(C)C(=O)O)c1OC]

To a stirring solution of methyl 3-hydroxy-2,2-dimethylpropanoate (2.76 g, 20.94 mmol, in portions) in tetrahydrofuran (25 mL) was added diethylazodicarboxylate (2.43 g, 13.96 mmol), triphenylphosphine (3.59 g, 13.96 mmol) and 5-(2-hydroxy-3,4-dimethoxyphenyl)isobenzofuran-1(3H)-one (2 g, 6.98 mmol) and the resultant reaction mixture was heated to 70° C. for 6 h. The reaction mixture was diluted with ethyl acetate layer, washed with water, dried over anhydrous sodium sulphate and concentrated under reduced pressure. Purification of the residue by flash, column chromatography (silica gel, 0-20% ethyl acetate in pet ether) to afford Methyl 3-(2,3-dimethoxy-6-(1-oxo-1,3-dihydroisobenzofuran-5-yl)phenoxy)-2,2-dimethylpropanoate as a solid (800 mg, 28.6%)

To a stirring solution of methyl 3-(2,3-dimethoxy-6-(1-oxo-1,3-dihydroisobenzofuran-5-yl)phenoxy)-2,2-dimethylpropanoate (200 mg, 0.49 mmol) in tetrahydrofuran (15 mL) was added lithium hydroxide (102.5 mg, 2.45 mmol) in water (5 mL) and the resultant reaction mixture was stirred at RT for 4 h. The reaction mixture was concentrated under reduced pressure, the residue was acidified using 1N HCl solution to pH 5 and then extracted with ethyl acetate (3×). The combined ethyl acetate layers were washed with brine, dried over anhydrous sodium sulphate and concentrated under reduced pressure to afford the title compound as a solid (120 mg, 63%).

Example 55

3-(2,3-dimethoxy-6-(1-oxo-1,3-dihydroisobenzofuran-5-yl)phenoxy)-N,2,2-trimethylpropanamide (Compound 221)

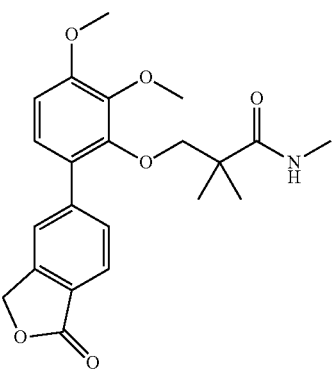 [SMILES: CNC(=O)C(C)(C)COc1c(-c2ccc3c(c2)COC3=O)ccc(OC)c1OC]

To a stirring solution of 3-(2,3-dimethoxy-6-(1-oxo-1,3-dihydroisobenzofuran-5-yl)phenoxy)-2,2-dimethylpropanoic acid (100 mg, 0.259 mmol) in dichloromethane (10 mL) was added 1-(3-dimethylaminopropyl)-3-ethylcarbodiimide hydrochloride (EDC.HCl) (74 mg, 0.388 mmol), triethylamine (0.1 mL, 0.77 mmol) and 1-hydroxybenzotriazole hydrate (HOBt) (79 mg, 0.518 mmol) and stirred for 10 min. To this methyl amine solution in THF (0.518 mmol) was added and the resultant reaction mixture was stirred at RT for 16 h. The reaction mixture was diluted with water and extracted with dichloromethane (3×). The combined dichloromethane layers were washed with brine, dried over anhydrous sodium sulphate and concentrated under reduced pressure. Purification of the residue by column chromatography (silica gel, 0-80% ethyl acetate in pet ether) afforded the title compound as a solid (50 mg, 50%).

UPLC-MS (M+1): 400.16; UPLC-MS RT (min): 2.2

Example 56

3-(2,3-dimethoxy-6-(1-oxo-1,3-dihydroisobenzofuran-5-yl)phenoxy)-N,N,2,2-tetramethylpropanamide (Compound 222)

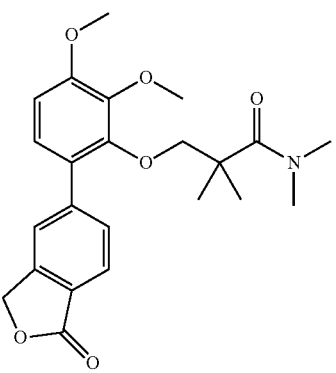 [SMILES: COc1ccc(-c2ccc3c(c2)COC3=O)c(OCC(C)(C)C(=O)N(C)C)c1OC]

To a stirring solution of 3-(2,3-dimethoxy-6-(1-oxo-1,3-dihydroisobenzofuran-5-yl)phenoxy)-2,2-dimethylpropanoic acid (100 mg, 0.259 mmol) in dichloromethane (10 mL) was added 1-(3-Dimethylaminopropyl)-3-ethylcarbodiimide hydrochloride (EDC.HCl) (74.1 mg, 0.388 mmol), triethylamine (1 mL, 0.77 mmol) and 1-hydroxybenzotriazole hydrate (HOBt) (79.2 mg, 0.518 mmol) and stirred for 10 min. To this dimethylamine (23 mg, 0.518 mmol) was added and the resultant reaction mixture was stirred at RT for 16 h. The reaction mixture was diluted with water and extracted with dichloromethane (3×). The combined dichloromethane layers were washed with brine, dried over anhydrous sodium sulphate and concentrated under reduced pressure. Purification of the residue by column chromatography (silica gel, 0-45% ethyl acetate in pet ether) afforded the title compound as a solid (30 mg, 30%).

UPLC-MS (M+1): 414.19; UPLC-MS RT (min): 2.3

Example 57

3-(2,3-dimethoxy-6-(1-oxo-1,3-dihydroisobenzofuran-5-yl)phenoxy)-N-isopropyl-2,2-dimethylpropanamide (Compound 223)

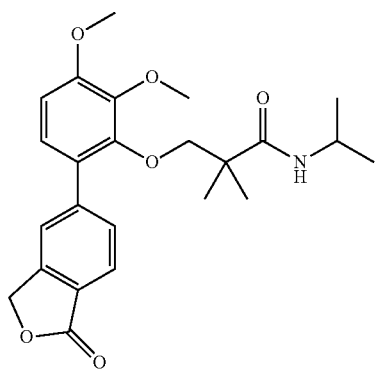 [SMILES: COc1ccc(-c2ccc3c(c2)COC3=O)c(OCC(C)(C)C(=O)NC(C)C)c1OC]

To a stirring solution of 3-(2,3-dimethoxy-6-(1-oxo-1,3-dihydroisobenzofuran-5-yl)phenoxy)-2,2-dimethylpropanoic acid (100 mg, 0.25 mmol) in dichloromethane (10 mL) was added 1-(3-Dimethylaminopropyl)-3-ethylcarbodiimide hydrochloride (EDC. HCl) (71.6 mg, 0.375 mmol), triethylamine (1 mL, 0.75 mmol) and 1-hydroxybenzotriazole hydrate (HOBT) (76.5 mg, 0.50 mmol) and stirred for 10 min. To this isopropyl amine (59 mg, 1.00 mmol) was added and the resultant reaction mixture was stirred at RT for 16 h. The reaction mixture was diluted with water and extracted with dichloromethane (3×). The combined dichloromethane layers were washed with brine, dried over anhydrous sodium sulphate and concentrated under reduced pressure. Purification of the residue by column chromatography (silica gel, 0-50% ethyl acetate in pet ether) afforded the title compound as a solid (27 mg, 27%).

UPLC-MS (M+1): 428.19; UPLC-MS RT (min): 2.4

Example 58

3-(2,3-dimethoxy-6-(1-oxo-1,3-dihydroisobenzofuran-5-yl)phenoxy)-2,2-dimethyl-N-propylpropanamide (Compound 224)

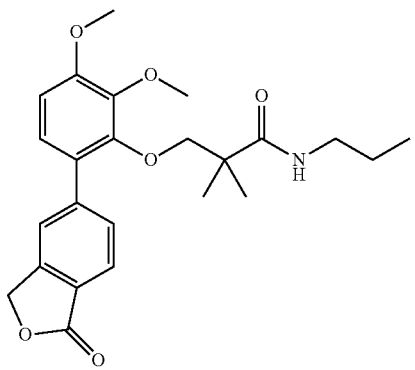 [SMILES: CCCNC(=O)C(C)(C)COc1c(-c2ccc3c(c2)COC3=O)ccc(OC)c1OC]

To a stirring solution of 3-(2,3-dimethoxy-6-(1-oxo-1,3-dihydroisobenzofuran-5-yl)phenoxy)-2,2-dimethylpropanoic acid (100 mg, 0.25 mmol) in dichloromethane (10 mL) was added 1-(3-Dimethylaminopropyl)-3-ethylcarbodiimide hydrochloride (EDC.HCl) (71.6 mg, 0.375 mmol), triethylamine (0.1 mL, 0.75 mmol) and 1-hydroxybenzotriazole hydrate (HOBT) (76.5 mg, 0.50 mmol) and stirred for 10 min. To this propylamine (59 mg, 1.0 mmol) was added and the resultant reaction mixture was stirred at RT for 16 h. The reaction mixture was diluted with water and extracted with dichloromethane (3×). The combined dichloromethane layers were washed with brine, dried over anhydrous sodium sulphate and concentrated under reduced pressure. Purification of the residue by column chromatography (silica gel, 0-40% ethyl acetate in pet ether) afforded the title compound as a solid (40 mg, 36%).

UPLC-MS (M+1): 428.19; UPLC-MS RT (min): 2.4

Preparation 11

4-(4-(Difluoromethoxy)-2-hydroxy-3-methoxyphenyl)-2,3-dihydro-1H-inden-1-one (Compound 311)

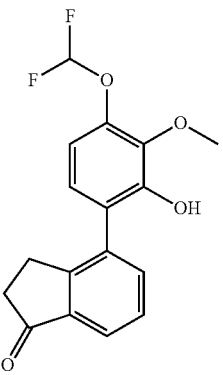 [SMILES: COc1c(OC(F)F)ccc(-c2cccc3c2CCC3=O)c1O]

To a stirring solution of benzene-1,2,3-triol (2 g, 15.87 mmol) in acetone was added potassium bicarbonate (1.90 g, 19.04 mmol) and methyl iodide (3.38 g, 23.80 mmol) and the resultant reaction mixture was heated to reflux for 16 h. The reaction mixture was cooled to RT and filtered through celite bed. The filtrate was concentrated under reduced pressure, triturated with diethyl ether and the obtained solid was separated and the filtrate was concentrated under reduced pressure. Purification of the residue by flash chromatography (silica gel, 0-15% ethyl acetate in pet ether) afforded 2-Methoxybenzene-1,3-diol as a solid (600 mg, 27.2%). 4-Bromo-2-methoxybenzene-1,3-diol: To a stirring solution of 2-methoxybenzene-1,3-diol (3.0 g, 21.42 mmol) in tetrahydrofuran (30 mL) at −78° C. was added N-bromosuccinimide (4.57 g, 25.71 mmol) and the reaction mixture was stirred at −78° C. for 2 h. The reaction mixture was diluted with ice-cold water and extracted with ethyl acetate (3×). The combined ethyl acetate layers were washed with brine, dried over anhydrous sodium sulphate and concentrated under reduced pressure. The obtained residue has mixture of products (mono and dibromo) which was used as such for further reactions (4.2 g).

To a stirring solution of 4-bromo-2-methoxybenzene-1,3-diol (4.5 g, 20.54 mmol) in acetone (40 mL) at 0° C. was added potassium carbonate (2.83 g, 20.54 mmol) and methoxymethyl chloride (1.32 mg, 16.43 mmol) and the resultant reaction mixture was stirred at RT for 7 h. The reaction mixture was quenched with ice-cold water, filtered and the filtrate was concentrated under reduced pressure. Purification of the residue by column chromatography (silica gel, 0-10% ethyl acetate in pet ether) afforded 4-Bromo-2-methoxy-3-(methoxymethoxy)phenol as a liquid (2 g, 37%).

To a stirring solution of 4-bromo-2-methoxy-3-(methoxymethoxy)phenol (700 mg, 2.66 mmol) in N,N-dimethylformamide (15 mL) was added potassium carbonate (734 mg, 5.32 mmol) cooled to −45° C. and chlorodifluoromethane (gas) was passed for 10 min and the resultant reaction mixture was heated to 80° C. for 2 h. The reaction mixture was quenched with ice-cold water and extracted with ethyl acetate (3×). The combined ethyl acetate layers were dried over anhy. sodium sulphate and concentrated under reduced pressure. Purification of the residue by flash column chromatography (silica gel, 0-5% ethyl acetate in pet ether) afforded 1-Bromo-4-(difluoromethoxy)-3-methoxy-2-(methoxymethoxy)benzene as a liquid (250 mg, 30%).

A stirring solution of 1-bromo-4-(difluoromethoxy)-3-methoxy-2-(methoxymethoxy)benzene (3.0 g, 9.58 mmol) in N,N-dimethylformamide (30 mL) was purged with argon for 1 h, to this cesium carbonate (9.34 g, 28.74 mmol), tetrakis(triphenylphosphine) palladium(0) (553 mg, 0.48 mmol) and 4-(4,4,5,5-tetramethyl-1,3,2-dioxaborolan-2-yl)-2,3-dihydro-1H-inden-1-one (2.96 g, 11.50 mmol) were added and the resultant reaction mixture was heated to 90° C. for 4 h. The reaction mixture was cooled to RT, filtered and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-20% ethyl acetate in pet ether) afforded 4-(4-(difluoromethoxy)-3-methoxy-2-(methoxymethoxy)phenyl)-2,3-dihydro-1H-inden-1-one as a solid (1.5 g, 43%).

To a stirring solution of 4-(4-(difluoromethoxy)-3-methoxy-2-(methoxymethoxy)phenyl)-2,3-dihydro-1H-inden-1-one (1 g, 2.74 mmol) in methanol (75 mL) was added concentrated hydrochloride (5 mL) and the reaction mixture was heated to 50° C. for 1 h. The reaction mixture was cooled to RT and concentrated under reduced pressure and the obtained residue was basified with sodium bicarbonate solution and extracted with dichloromethane (3×). The combined dichloromethane layers were washed with brine, dried over sodium sulphate and concentrated under reduced pressure to afford the title compound as a solid (700 mg, 80%).

Example 59

4-(4-Difluoromethoxy-2-ethoxy-3-methoxy-phenyl)-indan-1-one (Compound 225)

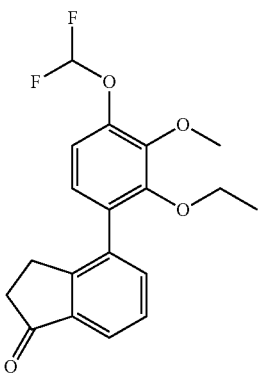 [SMILES: CCOc1c(-c2cccc3c2CCC3=O)ccc(OC(F)F)c1OC]

To a stirring solution of 4-(4-(difluoromethoxy)-2-hydroxy-3-methoxyphenyl)-2,3-dihydro-1H-inden-1-one (75 mg, 0.234 mmol) in acetonitrile (10 mL) was added potassium carbonate (96 mg, 0.702 mmol) and ethyl iodide (109 mg, 0.702 mmol) and the resultant reaction mixture was heated to 80° C. for 4 h. The reaction mixture was cooled to RT, filtered through celite and the filtrate was concentrated under reduced pressure. The residue was purified by column chromatography (silica gel, 0-20% ethyl acetate in pet ether) to afford title compound as a solid (20 mg, 24%).

UPLC-MS (M+1): 349.13; UPLC-MS RT (min): 2.6

Example 60

4-(4-Difluoromethoxy-3-methoxy-2-propoxy-phenyl)-indan-1-one (Compound 226)

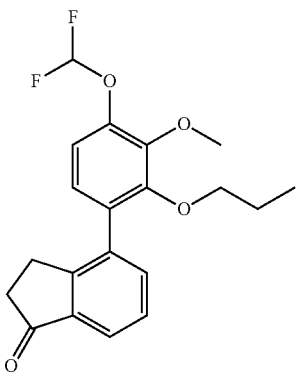 [SMILES: CCCOc1c(-c2cccc3c2CCC3=O)ccc(OC(F)F)c1OC]

To a stirring solution of 4-(4-(difluoromethoxy)-2-hydroxy-3-methoxyphenyl)-2,3-dihydro-1H-inden-1-one (80 mg, 0.25 mmol) in acetonitrile (10 mL) was added potassium carbonate (104 mg, 0.75 mmol) and propyl bromide (92 mg, 0.75 mmol) and the resultant reaction mixture was heated to 80° C. for 3 h. The reaction mixture was cooled to RT, filtered through celite and the filtrate was concentrated under reduced pressure. The residue was purified by column chromatography (silica gel, 0-20% ethyl acetate in pet ether) to afford title compound as a solid (30 mg, 33.3%).
UPLC-MS (M+1): 363.14; UPLC-MS RT (min): 2.7

Example 61

4-(4-Difluoromethoxy-2-isobutoxy-3-methoxy-phenyl)-indan-1-one (Compound 227)

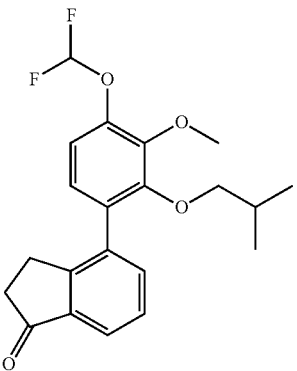 [SMILES: COc1c(OC(F)F)ccc(-c2cccc3c2CCC3=O)c1OCC(C)C]

To a stirring solution of 4-(4-(difluoromethoxy)-2-hydroxy-3-methoxyphenyl)-2,3-dihydro-1H-inden-1-one (80 mg, 0.25 mmol) in acetonitrile (10 mL) was added potassium carbonate (104 mg, 0.75 mmol) and isobutyl bromide (102 mg, 0.75 mmol) and the resultant reaction mixture was heated to 80° C. for 16 h. The reaction mixture was cooled to RT, filtered through celite and the filtrate was concentrated under reduced pressure. The residue was purified by column chromatography (silica gel, 0-20% ethyl acetate in pet ether) to afford title compound as a solid (40 mg, 43%).
UPLC-MS (M+1): 377.16; UPLC-MS RT (min): 2.8

Example 62

4-[4-Difluoromethoxy-2-(3-hydroxy-2,2-dimethyl-propoxy)-3-methoxy-phenyl]-indan-1-one (Compound 228)

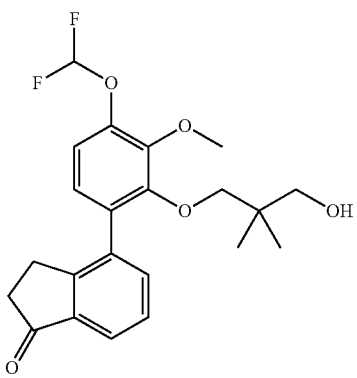 [SMILES: COc1c(OC(F)F)ccc(-c2cccc3c2CCC3=O)c1OCC(C)(C)CO]

To a stirring solution of 4-(4-(difluoromethoxy)-2-hydroxy-3-methoxyphenyl)-2,3-dihydro-1H-inden-1-one (80 mg, 0.25 mmol) in acetonitrile (10 mL) was added potassium carbonate (104 mg, 0.75 mmol) and followed by 3-bromo-2,2-dimethyl-propan-1-ol (125 mg, 0.75 mmol) and the resultant reaction mixture was heated to 80° C. for 16 h. The reaction mixture was cooled to RT, filtered through celite and the filtrate was concentrated under reduced pressure. The residue was purified by column chromatography (silica gel, 0-70% ethyl acetate in pet ether) to afford title compound as a solid (30 mg, 30%).

Example 63

4-[4-Difluoromethoxy-3-methoxy-2-(3-methoxy-2,2-dimethyl-propoxy)-phenyl]-indan-1-one (Compound 229)

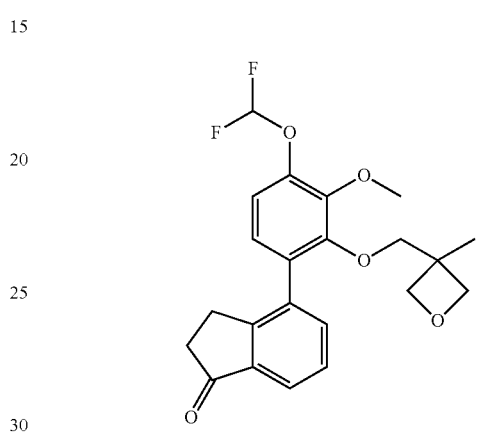

To a stirring solution of 4-(4-(difluoromethoxy)-2-hydroxy-3-methoxyphenyl)-2,3-dihydro-1H-inden-1-one (75 mg, 0.234 mmol) in acetonitrile (10 mL) was added potassium carbonate (96.8 mg, 0.702 mmol) and 3-bromomethyl-3-methyl-oxetane (115 mg, 0.702 mmol) and the resultant reaction mixture was heated to 80° C. for 16 h. The reaction mixture was cooled to RT and filtered through celite and the filtrate was concentrated under reduced pressure. The residue was purified by column chromatography (silica gel, 0-20% ethyl acetate in pet ether) to afford title compound as a solid (25 mg, 26%).
UPLC-MS (M+1): 405.15; UPLC-MS RT (min): 2.5

Example 64

4-[4-Difluoromethoxy-2-(3-hydroxymethyl-oxetan-3-ylmethoxy)-3-methoxy-phenyl]-indan-1-one (Compound 230

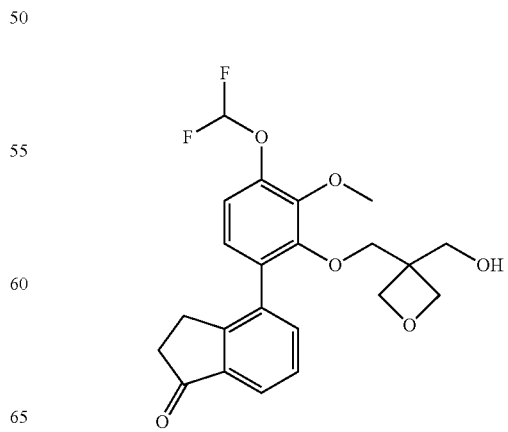

To a stirring solution of 4-(4-(difluoromethoxy)-2-hydroxy-3-methoxyphenyl)-2,3-dihydro-1H-inden-1-one (80 mg, 0.25 mmol) in acetonitrile (10 mL) was added potassium carbonate (103.5 mg, 0.75 mmol) and (3-bromomethyl-oxetan-3-yl)-methanol (135.7 mg, 0.75 mmol) and the resultant reaction mixture was heated to 80° C. for 16 h. The reaction mixture was cooled to RT and filtered through celite and the filtrate was concentrated under reduced pressure. The residue was purified by column chromatography (silica gel, 0-40% ethyl acetate in pet ether) to afford title compound as a solid (40 mg, 38%).

Example 65

4-[4-Difluoromethoxy-3-methoxy-2-(3-methoxymethyl-oxetan-3-ylmethoxy)-phenyl]-indan-1-one (Compound 231)

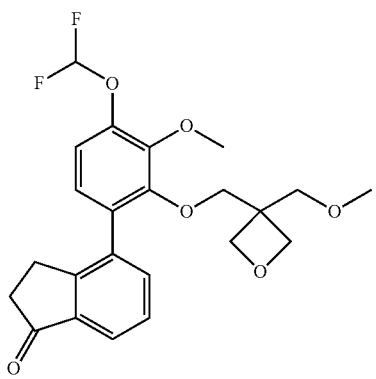 [SMILES: COCC1(COc2c(-c3cccc4c3CCC4=O)ccc(OC(F)F)c2OC)COC1]

To a stirring solution of 4-(4-(difluoromethoxy)-2-hydroxy-3-methoxyphenyl)-2,3-dihydro-1H-inden-1-one (80 mg, 0.25 mmol) in acetonitrile (10 mL) was added potassium carbonate (103.5 mg, 0.75 mmol) and 3-bromomethyl-3-methoxymethyl-oxetane (146 mg, 0.75 mmol) and the resultant reaction mixture was heated to 80° C. for 16 h. The reaction mixture was cooled to RT and filtered through celite and the filtrate was concentrated under reduced pressure. The residue was purified by column chromatography (silica gel, 0-40% ethyl acetate in pet ether) to afford title compound as a solid (25 mg, 23%).

UPLC-MS (M+1): 435.16; UPLC-MS RT (min): 2.5

Example 66

4-[3-Difluoromethoxy-2-methoxy-6-(1-oxo-indan-4-yl)-phenoxymethyl]-benzenesulfonamide (Compound 232)

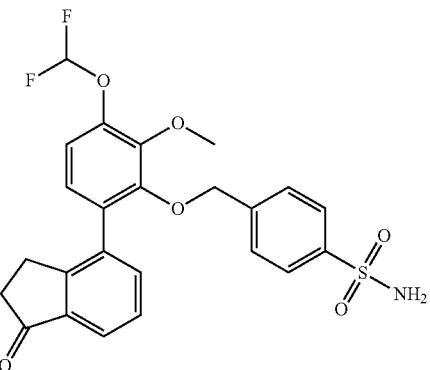 [SMILES: COc1c(OC(F)F)ccc(-c2cccc3c2CCC3=O)c1OCc1ccc(S(N)(=O)=O)cc1]

To a stirring solution of 4-(4-(difluoromethoxy)-2-hydroxy-3-methoxyphenyl)-2,3-dihydro-1H-inden-1-one (80 mg, 0.25 mmol) in acetonitrile (10 mL), was added potassium carbonate (104 mg, 0.75 mmol) and 4-bromomethyl-benzenesulfonamide (125 mg, 0.5 mmol) and the resultant reaction mixture was heated to 80° C. for 16 h. The reaction mixture was cooled to RT and filtered through celite and the filtrate was concentrated under reduced pressure. The residue was purified by column chromatography (silica gel, 0-70° A) ethyl acetate in pet ether) to afford title compound as a solid (40 mg, 33%).

UPLC-MS (M+1): 490.11; UPLC-MS RT (min): 2.4

Example 67

4-[4-Difluoromethoxy-2-(4-methanesulfonyl-benzyloxy)-3-methoxy-phenyl]-indan-1-one (Compound 233)

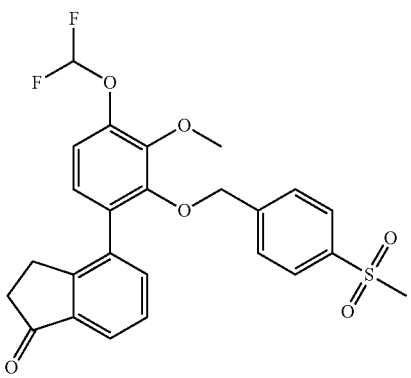 [SMILES: COc1c(OC(F)F)ccc(-c2cccc3c2CCC3=O)c1OCc1ccc(S(C)(=O)=O)cc1]

To a stirring solution of 4-(4-(difluoromethoxy)-2-hydroxy-3-methoxyphenyl)-2,3-dihydro-1H-inden-1-one (80 mg, 0.25 mmol) in acetonitrile (10 mL), was added potassium carbonate (103.5 mg, 0.75 mmol) and 1-bromomethyl-4-methanesulfonyl-benzene (186 mg, 0.75 mmol) and the resultant reaction mixture was heated to 80° C. for 16 h. The reaction mixture was cooled to RT and filtered through celite and the filtrate was concentrated under reduced pressure. The residue was purified by column chromatography (silica gel, 0-50% ethyl acetate in pet ether) to afford title compound as a solid (40 mg, 24%).

UPLC-MS (M+1): 489.1; UPLC-MS RT (min): 2.5

Example 68

4-((3-(difluoromethoxy)-2-methoxy-6-(1-oxo-2,3-dihydro-1H-inden-4-yl)phenoxy)methyl)benzamide (Compound 234)

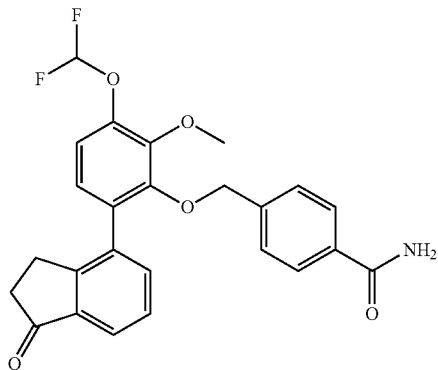 [SMILES: COc1c(OC(F)F)ccc(-c2cccc3c2CCC3=O)c1OCc1ccc(C(N)=O)cc1]

To a stirring solution of 1-bromo-4-(difluoromethoxy)-3-methoxy-2-(methoxymethoxy)benzene (1 g, 3.19 mmol) in methanol (15 mL) was added concentrated hydrochloride (2 mL) and the reaction mixture was heated to 50° C. for 1 h. The reaction mixture was cooled to RT, concentrated under reduced pressure and the obtained residue was basified with sodium bicarbonate solution and extracted with dichloromethane (3x). The combined dichloromethane layers were washed with brine, dried over sodium sulphate and concentrated under reduced pressure to afford 6-Bromo-3-(difluoromethoxy)-2-methoxyphenol as a solid (800 mg, 93%).

To a stirring solution of 6-bromo-3-(difluoromethoxy)-2-methoxyphenol (1.0 g, 3.71 mmol) in acetonitrile (10 mL), was added potassium carbonate (1.53 g, 11.08 mmol) and followed by 4-(bromomethyl)benzamide (795 mg, 3.71 mmol) and the resultant reaction mixture was heated to 80° C. for 16 h. The reaction mixture was cooled to RT and filtered through celite and the filtrate was concentrated under reduced pressure to afford 4-((6-Bromo-3-(difluoromethoxy)-2-methoxyphenoxy)methyl)benzamide as a solid (1 g, 67%).

A stirring solution of 4-((6-bromo-3-(difluoromethoxy)-2-methoxyphenoxy)methyl)benzamide (500 mg, 1.24 mmol) in dimethylformamide (10 mL) was purged with argon for 1 h, to this cesium carbonate (1.2 g, 3.73 mmol), tetrakis(triphenylphosphine) palladium(0) (72 mg, 0.06 mmol) and 4-(4,4,5,5-tetramethyl-1,3,2-dioxaborolan-2-yl)-2,3-dihydro-1H-inden-1-one (641 mg, 2.48 mmol) was added and the resultant reaction mixture was heated to 80° C. for 16 h. The reaction mixture was cooled to RT and filtered through celite and the filtrate was concentrated under reduced pressure. The residue was purified by column chromatography (silica gel, 0-80% ethyl acetate in pet ether) to afford title compound as a solid (150 mg, 26.7%).

UPLC-MS (M+1): 454.13; UPLC-MS RT (min): 2.3

Preparation 12

5-(4-(difluoromethoxy)-2-hydroxy-3-methoxyphenyl)isobenzofuran-1(3H)-one (Compound 312)

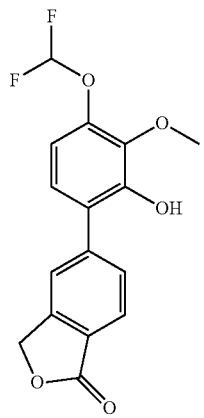 [SMILES: COc1c(OC(F)F)ccc(-c2ccc3c(c2)COC3=O)c1O]

A stirring solution of 1-bromo-4-(difluoromethoxy)-3-methoxy-2-(methoxymethoxy)benzene (3 g, 9.58 mmol) in N,N-dimethylformamide (30 mL) was purged with argon for 1 h, to this cesium carbonate (9.36 g, 28.74 mmol), tetrakis(triphenylphosphine) palladium(0) (553 mg, 0.479 mmol) and 5-(4,4,5,5-tetramethyl-1,3,2-dioxaborolan-2-yl)isobenzofuran-1(3H)-one (2.98 g, 11.49 mol) were added and the resultant reaction mixture was heated to 90° C. for 4 h. The reaction mixture was cooled to RT, filtered and the filtrate was diluted with water and extracted with ethyl acetate (3x). The combined ethyl acetate layers were washed with brine, dried over anhydrous sodium sulphate and concentrated under reduced pressure. Purification of the residue by column chromatography (silica gel, 0-20% ethyl acetate in pet ether) afforded 5-(4-(difluoromethoxy)-3-methoxy-2-(methoxymethoxy)phenyl)isobenzofuran-1(3H)-one as a solid (1.5 g, 42%).

To a stirring solution of 5-(4-(difluoromethoxy)-3-methoxy-2-(methoxymethoxy)phenyl) isobenzofuran-1(3H)-one (1 g, 2.73 mmol) in methanol (75 mL) was added concentrated hydrochloride (5 mL) and the reaction mixture was heated to 50° C. for 1 h. The reaction mixture was cooled to RT and concentrated under reduced pressure. The obtained residue was basified with sodium bicarbonate solution and extracted with dichloromethane (3x). The combined dichloromethane layers were washed with brine, dried over sodium sulphate and concentrated under reduced pressure to afford the title compound as a solid (800 mg, 91%).

Example 69

5-(4-Difluoromethoxy-2-ethoxy-3-methoxy-phenyl)-3H-isobenzofuran-1-one (Compound 235)

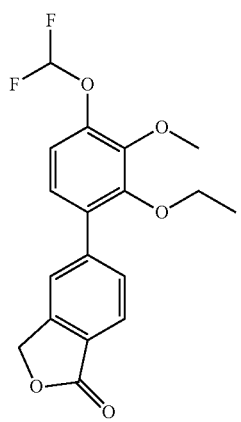 [SMILES: CCOc1c(-c2ccc3c(c2)COC3=O)ccc(OC(F)F)c1OC]

To a stirring solution of 5-(4-(difluoromethoxy)-2-hydroxy-3-methoxyphenyl)isobenzofuran-1(3H)-one (80 mg, 0.25 mmol) in acetonitrile (10 mL) was added potassium carbonate (103.5 mg, 0.75 mmol) and ethyl iodide (0.1 mL, 0.75 mmol) and the resultant reaction mixture was heated to 70° C. for 3 h. The reaction mixture was cooled to RT, filtered through celite and the filtrate was concentrated under reduced pressure. The residue was purified by column chromatography (silica gel, 100-200 mesh, 0-30% ethyl acetate in pet ether) to afford title compound as a solid (50 mg, 58%).

Example 70

5-(4-Difluoromethoxy-3-methoxy-2-propoxy-phenyl)-3H-isobenzofuran-1-one (Compound 236)

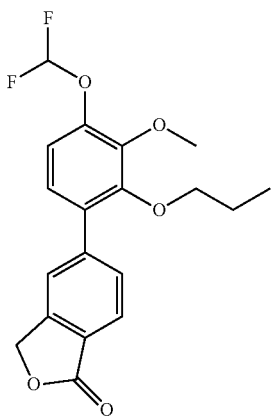 [SMILES: CCCOc1c(-c2ccc3c(c2)COC3=O)ccc(OC(F)F)c1OC]

To a stirring solution of 5-(4-(difluoromethoxy)-2-hydroxy-3-methoxyphenyl)isobenzofuran-1(3H)-one (80 mg, 0.25 mmol) in acetonitrile (10 mL) was added potassium carbonate (103.5 mg, 0.75 mmol) and propyl bromide (92.2 mg, 0.75 mmol) and the resultant reaction mixture was heated to 80° C. for 3 h. The reaction mixture was cooled to RT and filtered through celite and the filtrate was concentrated under reduced pressure. The residue was purified by column chromatography (silica gel, 0-20% ethyl acetate in pet ether) to afford title compound as a solid (20 mg, 22%).

UPLC-MS (M+1): 365.13; UPLC-MS RT (min): 2.6

Example 71

5-(4-Difluoromethoxy-2-isobutoxy-3-methoxy-phenyl)-3H-isobenzofuran-1-one (Compound 237)

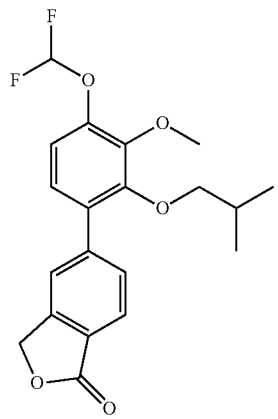 [SMILES: COc1c(OC(F)F)ccc(-c2ccc3c(c2)COC3=O)c1OCC(C)C]

To a stirring solution of 5-(4-(difluoromethoxy)-2-hydroxy-3-methoxyphenyl)isobenzofuran-1(3H)-one (80 mg, 0.25 mmol) in acetonitrile (10 mL) was added potassium carbonate (103 mg, 0.75 mmol) and isobutyl bromide (102 mg, 0.75 mmol) and the resultant reaction mixture was heated to 80° C. for 16 h. The reaction mixture was cooled to RT, filtered through celite and the filtrate was concentrated under reduced pressure. The residue was purified by column chromatography (silica gel, 0-20% ethyl acetate in pet ether) to afford title compound as a solid (30 mg, 32%).

UPLC-MS (M+1): 379.14; UPLC-MS RT (min): 2.7

Example 72

5-[4-Difluoromethoxy-2-(3-hydroxy-2,2-dimethyl-propoxy)-3-methoxy-phenyl]-3H-isobenzofuran-1-one (Compound 238)

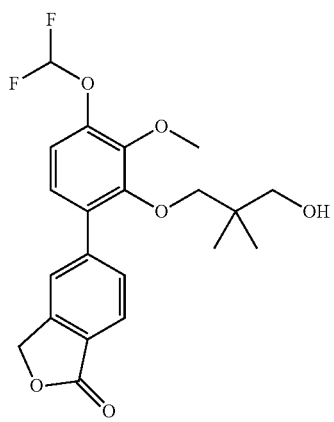 [SMILES: COc1c(OC(F)F)ccc(-c2ccc3c(c2)COC3=O)c1OCC(C)(C)CO]

To a stirring solution of 5-(4-(difluoromethoxy)-2-hydroxy-3-methoxyphenyl)isobenzofuran-1(3H)-one (100 mg, 0.31 mmol) in acetonitrile (10 mL) was added potassium carbonate (128 mg, 0.930 mmol) and 3-bromo-2,2-dimethyl-propan-1-ol (155 mg, 0.930 mmol) and the resultant reaction mixture was heated to 80° C. for 16 h. The reaction mixture was cooled to RT, filtered through celite and the filtrate was concentrated under reduced pressure. The residue was purified by prep TLC to afford title compound as a solid (10 mg, 8%).

Example 73

5-[4-Difluoromethoxy-3-methoxy-2-(3-methoxy-2,2-dimethyl-propoxy)-phenyl]-3H-isobenzofuran-1-one (Compound 239)

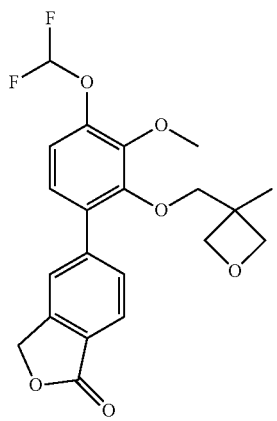 [SMILES: COc1c(OC(F)F)ccc(-c2ccc3c(c2)COC3=O)c1OCC1(C)COC1]

To a stirring solution of 5-(4-(difluoromethoxy)-2-hydroxy-3-methoxyphenyl)isobenzofuran-1(3H)-one (80 mg, 0.25 mmol) in acetonitrile (10 mL), was added potassium carbonate (103.5 mg, 0.75 mmol) and 3-bromomethyl-3-methyl-oxetane (123 mg, 0.75 mmol) and the resultant reaction mixture was heated to 80° C. for 3 h. The reaction mixture was cooled to RT, filtered through celite and the filtrate was concentrated under reduced pressure. The residue was purified by column chromatography (silica gel, 0-40° A) ethyl acetate in pet ether) to afford title compound as a solid (30 mg, 30%).

UPLC-MS (M+1): 407.13; UPLC-MS RT (min): 2.5

Example 74

5-[4-Difluoromethoxy-2-(3-hydroxymethyl-oxetan-3-ylmethoxy)-3-methoxy-phenyl]-3H-isobenzofuran-1-one (Compound 240)

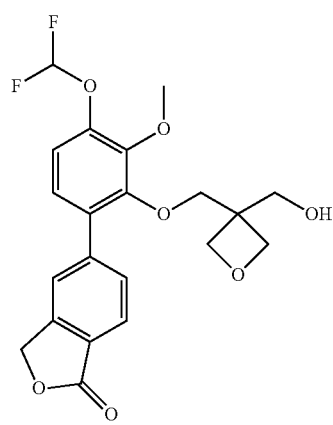

To a stirring solution of 5-(4-(difluoromethoxy)-2-hydroxy-3-methoxyphenyl)isobenzofuran-1(3H)-one (80 mg, 0.25 mmol) in acetonitrile (10 mL), was added potassium carbonate (103.5 mg, 0.75 mmol) and (3-bromomethyl-oxetan-3-yl)-methanol (135.7 mg, 0.75 mmol) and the resultant reaction mixture was heated to 80° C. for 16 h. The reaction mixture was cooled to RT, filtered through celite and the filtrate was concentrated under reduced pressure. The residue was purified by column chromatography (silica gel, 0-30% ethyl acetate in pet ether) to afford title compound as a solid (30 mg, 28.8%).

Example 75

4-[3-Difluoromethoxy-2-hydroxy-6-(1-oxo-1,3-dihydro-isobenzofuran-5-yl)-phenoxymethyl]-benzenesulfonamide (Compound 241)

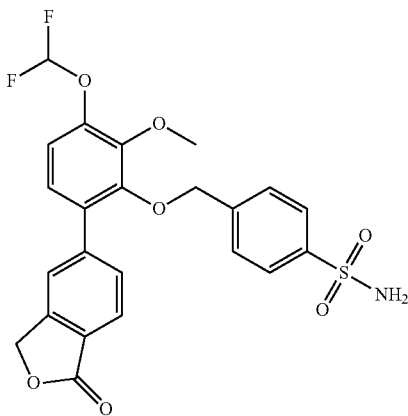 [SMILES: COc1c(OC(F)F)ccc(-c2ccc3c(c2)COC3=O)c1OCc1ccc(S(N)(=O)=O)cc1]

To a stirring solution of 5-(4-(difluoromethoxy)-2-hydroxy-3-methoxyphenyl)isobenzofuran-1(3H)-one (100 mg, 0.310 mmol) in acetonitrile (20 mL), was added potassium carbonate (128.3 mg, 0.930 mmol) and 4-bromomethyl-benzenesulfonamide (155.2 mg, 0.620 mmol) and the resultant reaction mixture was heated to 80° C. for 16 h. The reaction mixture was cooled to RT, filtered through celite and the filtrate was concentrated under reduced pressure. The residue was purified by column chromatography (silica gel, 0-70% ethyl acetate in pet ether) to afford title compound as a solid (70 mg, 46%).

UPLC-MS (M+1): 492.96; UPLC-MS RT (min): 2.3

Example 76

5-[4-Difluoromethoxy-3-hydroxy-2-(4-methanesulfonyl-benzyloxy)-phenyl]-3H-isobenzofuran-1-one (Compound 242)

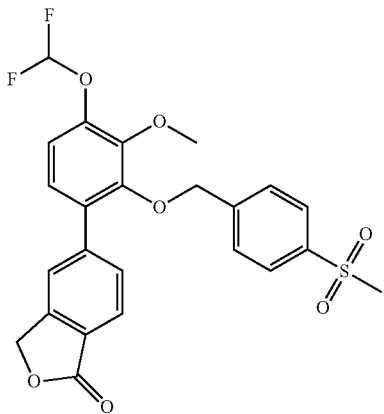 [SMILES: COc1c(OC(F)F)ccc(-c2ccc3c(c2)COC3=O)c1OCc1ccc(S(C)(=O)=O)cc1]

To a stirring solution of 5-(4-(difluoromethoxy)-2-hydroxy-3-methoxyphenyl)isobenzofuran-1(3H)-one (80 mg, 0.25 mmol) in acetonitrile (5 mL), was added potassium carbonate (103.5 mg, 0.75 mmol) and 1-bromomethyl-4-methanesulfonyl-benzene (186.8 mg, 0.75 mmol) and the resultant reaction mixture was heated to 80° C. for 16 h. The reaction mixture was cooled to RT, filtered through celite and the filtrate was concentrated under reduced pressure. The residue was purified by column chromatography (silica gel, 100-200 mesh, 0-20% ethyl acetate in pet ether) to afford title compound as a solid (50 mg, 41%).

UPLC-MS (M+1): 491.09; UPLC-MS RT (min): 2.4

Example 77

5-(4-(difluoromethoxy)-3-methoxy-2-((3-(methoxymethyl)oxetan-3-yl)methoxy)phenyl)isobenzofuran-1(3H)-one (Compound 243)

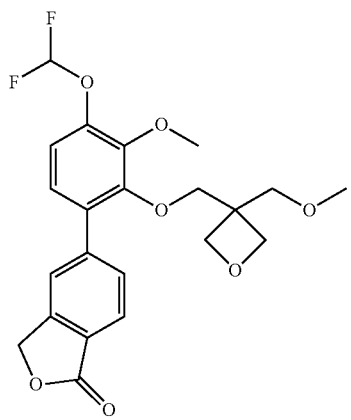

To a stirring solution of 1-bromo-4-(difluoromethoxy)-3-methoxy-2-(methoxymethoxy)benzene (1 g, 3.19 mmol) in methanol (15 mL) was added concentrated hydrochloride (2 mL) and the reaction mixture was heated to 50° C. for 1 h. The reaction mixture was cooled to RT, concentrated under reduced pressure and the obtained residue was basified with sodium bicarbonate solution and extracted with dichloromethane (3×). The combined dichloromethane layers were washed with brine, dried over sodium sulphate and concentrated under reduced pressure to afford 6-Bromo-3-(difluoromethoxy)-2-methoxyphenol as a solid (800 mg, 93%).

To a stirring solution of 6-bromo-3-(difluoromethoxy)-2-methoxyphenol (0.3 g, 1.11 mmol) in acetonitrile (10 mL) was added potassium carbonate (0.46 g, 3.34 mmol) and followed by 3-(bromomethyl)-3-(methoxymethyl)oxetane (0.43 g, 2.22 mmol) and the resultant reaction mixture was heated to 80° C. for 16 h. The reaction mixture was cooled to RT, filtered through celite and the filtrate was concentrated under reduced pressure to afford 3-((6-bromo-3-(difluoromethoxy)-2-methoxyphenoxy)methyl)-3-(methoxymethyl)oxetane as a solid (0.3 g, 70%).

A stirring solution of 3-((6-bromo-3-(difluoromethoxy)-2-methoxyphenoxy)methyl)-3-(methoxymethyl)oxetane (220 mg, 0.574 mmol) in dimethylformamide (10 mL) was purged with argon for 1 h, to this cesium carbonate (561 mg, 1.72 mmol), tetrakis(triphenylphosphine) palladium(0) (19 mg, 0.017 mmol) and 5-(4,4,5,5-tetramethyl-1,3,2-dioxaborolan-2-yl)isobenzofuran-1(3H)-one (178 mg, 0.686 mmol) was added and the resultant reaction mixture was heated to 80° C.

for 16 h. The reaction mixture was cooled to RT and filtered through celite and the filtrate was concentrated under reduced pressure. The residue was purified by column chromatography (silica gel, 0-80% ethyl acetate in pet ether) to afford title compound as a solid (30 mg, 12%).

Preparation 13

6-Bromo-3-(difluoromethoxy)-2-methoxyphenol (Compound 313)

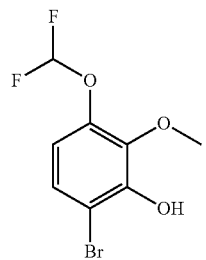

To a stirring solution of 1-bromo-4-(difluoromethoxy)-3-methoxy-2-(methoxymethoxy)benzene (1 g, 3.19 mmol) in methanol (15 mL) was added concentrated hydrochloride (2 mL) and the reaction mixture was heated to 50° C. for 1 h. The reaction mixture was cooled to RT, concentrated under reduced pressure and the obtained residue was basified with sodium bicarbonate solution and extracted with dichloromethane (3×). The combined dichloromethane layers were washed with brine, dried over sodium sulphate and concentrated under reduced pressure to afford the title compound as a solid (800 mg, 93%).

Preparation 14

5-(4,4,5,5-tetramethyl-1,3,2-dioxaborolan-2-yl)isoindolin-1-one

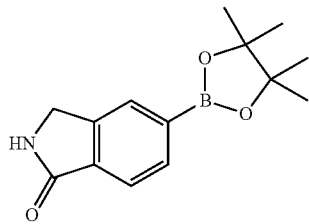 [SMILES: CC1(C)OB(c2ccc3c(c2)CNC3=O)OC1(C)C]

To a stirring solution of 4-bromo-2-methylbenzoic acid (3 g) in methanol (70 mL) was added concentrated hydrochloric acid (5 mL) and the reaction mixture was heated to 60° C. for 16 h. The reaction mixture was concentrated under reduced pressure, the residue was basified with sodium bicarbonate solution and extracted with dichloromethane (3×). The combined dichloromethane layers were washed with brine, dried over sodium sulphate and concentrated under reduced pressure to afford Methyl 4-bromo-2-methylbenzoate as a solid (2 g, 62%).

To a stirring solution of methyl 4-bromo-2-methylbenzoate (600 mg, 2.62 mmol) in carbon tetrachloride (70 mL) was added N-bromo succinimide (466 mg, 2.62 mmol) and benzoyl peroxide (12 mg) and the resultant reaction mixture was stirred in presence of sodium lamp at RT for 4 h. The reaction mixture was filtered through celite and washed with 2N sodium hydroxide solution, dried over sodium sulphate and concentrated under reduced pressure to afford Methyl 4-bromo-2-(bromomethyl)benzoate as a solid (300 mg, 37.5%).

Ammonia gas was purged to a stirring solution of methyl 4-bromo-2-(bromomethyl)benzoate (200 mg, 0.649 mmol) in methanol at 0° C. for 10 min. To the resulting reaction mixture ammonium hydroxide (0.5 mL) was added and the reaction mixture was stirred at RT for 16 h. The obtained solid was separated by filtration and dried to afford 5-Bromoisoindolin-1-one as a solid (100 mg, 72%).

Argon was purged to a stirring solution of 5-bromoisoindolin-1-one (200 mg, 0.943 mmol) in dimethylformamide for 30 min, to this bis(pinacolato)diboron (477 mg, 1.886 mmol) and tetrakis(triphenylphosphine) palladium(0) (13 mg, 0.018 mmol) and potassium acetate (277 mg, 2.829 mmol) were added and the reaction mixture was heated to 70° C. for 16 h. The reaction mixture was cooled to RT, filtered through celite and the filtrate was extracted with ethyl acetate (3×). The combined ethyl acetate layers were washed with brine, dried over sodium sulphate and concentrated under reduced pressure to afford the title compound as a solid (100 mg, 41%).

Example 78

5-(4-(Difluoromethoxy)-2-ethoxy-3-methoxyphenyl)isoindolin-1-one (Compound 244)

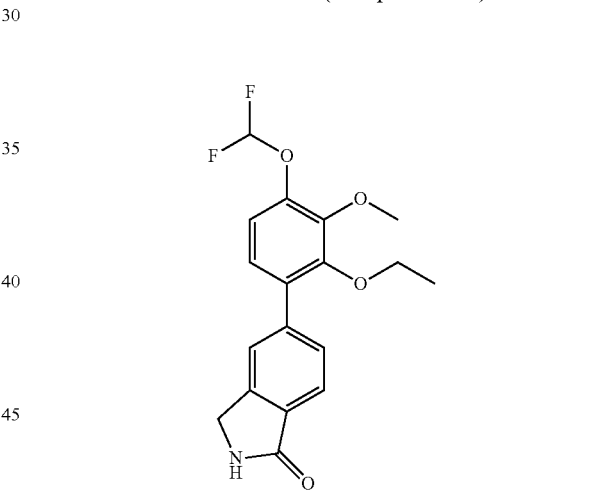

To a stirring solution of 6-bromo-3-(difluoromethoxy)-2-methoxyphenol (200 mg, 0.74 mmol) in acetonitrile (10 mL) was added potassium carbonate (307 mg, 2.23 mmol) and ethyl bromide (0.6 mL, 2.23 mmol) and the resultant reaction mixture was heated to 80° C. for 2 h. The reaction mixture was cooled to RT, filtered through celite and the filtrate was concentrated under reduced pressure to afford 200 mg of crude product, 1-Bromo-4-difluoromethoxy-2-ethoxy-3-methoxybenzene, as a solid. A stirring solution of 1-bromo-4-(difluoromethoxy)-2-ethoxy-3-methoxybenzene (200 mg, 0.673 mmol) in N,N-dimethylformamide (5 mL) was purged with argon for 1 h, to this cesium carbonate (656 mg, 2.019 mmol), tetrakis(triphenylphosphine) palladium(0) (38 mg, 0.033 mmol) and 5-(4,4,5,5-tetramethyl-1,3,2-dioxaborolan-2-yl) isoindolin-1-one (209 mg, 0.807 mmol) were added and the resultant reaction mixture was heated to 80-90° C. for 3 h. The reaction mixture was cooled to RT, filtered and the filtrate was diluted with water and extracted with ethyl acetate (3×). The

Example 79

5-(4-(Difluoromethoxy)-3-methoxy-2-propoxyphenyl)isoindolin-1-one (Compound 245)

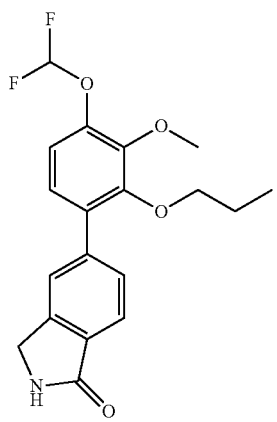 [SMILES: CCCOc1c(-c2ccc3c(c2)CNC3=O)ccc(OC(F)F)c1OC]

To a stirring solution of 6-bromo-3-(difluoromethoxy)-2-methoxyphenol (300 mg, 1.115 mmol) in acetonitrile (10 mL) was added potassium carbonate (495 mg, 2.334 mmol) and propyl bromide (411 mg, 3.34 mmol) and the resultant reaction mixture was heated to 80° C. for 3 h. The reaction mixture was cooled to RT, filtered through celite and the filtrate was concentrated under reduced pressure to afford 300 mg of 1-Bromo-4-(difluoromethoxy)-3-methoxy-2-propoxybenzene (Int14-F2) as a solid. A stirring solution of 1-bromo-4-(difluoromethoxy)-3-methoxy-2-propoxybenzene (300 mg, 0.964 mmol) in dimethylformamide (5 mL) was purged with argon for 1 h, to this cesium carbonate (625 mg, 1.926 mmol), tetrakis(triphenylphosphine) palladium(0) (37 mg, 0.032 mmol) and 5-(4,4,5,5-tetramethyl-1,3,2-dioxaborolan-2-yl)isoindolin-1-one (199 mg, 0.771 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a solid (30 mg, 13%).

UPLC-MS (M+1): 408.16; UPLC-MS RT (min): 2.2

Example 80

5(4-(Difluoromethoxy)-2-isobutoxy-3-methoxyphenyl)isoindolin-1-one (Compound 246)

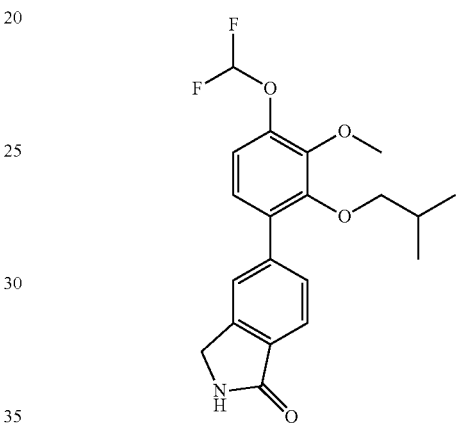

To a stirring solution of 6-bromo-3-(difluoromethoxy)-2-methoxyphenol (100 mg, 0.371 mmol) in acetonitrile (10 mL), was added potassium carbonate (153.8 mg, 1.114 mmol) and isobutyl bromide (152.6 mg, 1.114 mmol) and the resultant reaction mixture was heated to 80° C. for 3 h. The reaction mixture was cooled to RT, filtered through celite and the filtrate was concentrated under reduced pressure to afford 300 mg of 1-Bromo-4-(difluoromethoxy)-2-isobutoxy-3-methoxybenzene as a solid. To a stirring solution of 1-bromo-4-(difluoromethoxy)-2-isobutoxy-3-methoxybenzene (200 mg, 0.615 mmol) in dimethylformamide (5 mL) was purged with argon for 1 h. To this cesium carbonate (599 mg, 1.84 mmol), tetrakis(triphenylphosphine) palladium(0) (35 mg, 0.030 mmol) and 5-(4,4,5,5-tetramethyl-1,3,2-dioxaborolan-2-yl)isoindolin-1-one (191 mg, 0.738 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a (30 mg, 13%)

UPLC-MS (M+1): 378.16; UPLC-MS RT (min): 2.5 .

Example 81

5-[4-Difluoromethoxy-3-methoxy-2-(3-hydroxy-2,2-dimethyl-propoxy)-phenyl]-2,3-dihydro-isoindol-1-one (Compound 247)

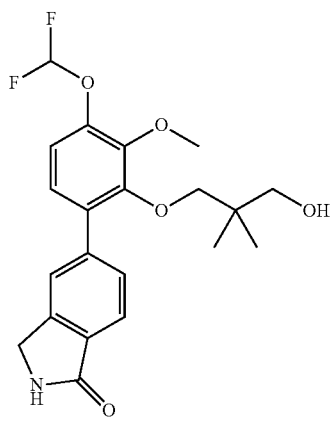 [SMILES: COc1c(OC(F)F)ccc(-c2ccc3c(c2)CNC3=O)c1OCC(C)(C)CO]

To a stirring solution of 6-bromo-3-(difluoromethoxy)-2-methoxyphenol (200 mg, 0.743 mmol) in dimethylformamide (10 mL) was added potassium carbonate (307 mg, 2.229 mmol) and 3-bromo-2,2-dimethylpropan-1-ol (248 mg, 1.486 mmol) and the resultant reaction mixture was heated to 80° C. for 2 h. The reaction mixture was cooled to RT, filtered through celite and the filtrate was concentrated under reduced pressure to afford 200 mg of 3-(6-Bromo-3-(difluoromethoxy)-2-methoxyphenoxy)-2,2-dimethylpropan-1-ol as a solid.

To a stirring solution of 3-(6-bromo-3-(difluoromethoxy)-2-methoxyphenoxy)-2,2-dimethylpropan-1-ol (200 mg, 0.563 mmol) in dimethylformamide (10 mL) was purged with argon for 1 h. To this cesium carbonate (548 mg, 1.689 mmol), tetrakis(triphenylphosphine) palladium(0) (32 mg, 0.028 mmol) and 5-(4,4,5,5-tetramethyl-1,3,2-dioxaborolan-2-yl)isoindolin-1-one (175 mg, 0.675 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a (50 mg, 22%).

UPLC-MS (M+1): 408.16; UPLC-MS RT (min): 2.2

Example 82

5-[4-Difluoromethoxy-3-methoxy-2-(3-methyl-oxetan-3-ylmethoxy)-phenyl]-2,3-dihydro-isoindol-1-one (Compound 248)

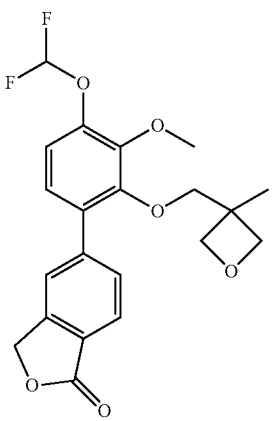

To a stirring solution of 6-bromo-3-(difluoromethoxy)-2-methoxyphenol (200 mg, 0.743 mmol) in acetonitrile (10 mL) was added potassium carbonate (307 mg, 2.229 mmol) and followed by 3-(bromomethyl)-3-methyloxetane (244 mg, 1.48 mmol) and the resultant reaction mixture was heated to 80° C. for 16 h. The reaction mixture was cooled to RT, filtered through celite and the filtrate was concentrated under reduced pressure to afford 200 mg 3-((6-Bromo-3-(difluoromethoxy)-2-methoxyphenoxy)methyl)-3-methyloxetane (Int14-F6) as a solid.

To a stirring solution of 3-((6-bromo-3-(difluoromethoxy)-2-methoxyphenoxy)methyl)-3-methyloxetane (200 mg, 0.566 mmol) in dimethylformamide (10 mL) was purged with argon for 1 h. To this cesium carbonate (551 mg, 1.698 mmol), tetrakis(triphenylphosphine) palladium(0) (32 mg, 0.028 mmol) and 5-(4,4,5,5-tetramethyl-1,3,2-dioxaborolan-2-yl)isoindolin-1-one (176 mg, 0.679 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a solid (50 mg, 22%).

UPLC-MS (M+1): 406.13; UPLC-MS RT (min): 2.2

Example 83

5-[4-Difluoromethoxy-2-(3-hydroxymethyl-oxetan-3-ylmethoxy)-3-methoxy-phenyl]-2,3-dihydro-isoindol-1-one (Compound 249)

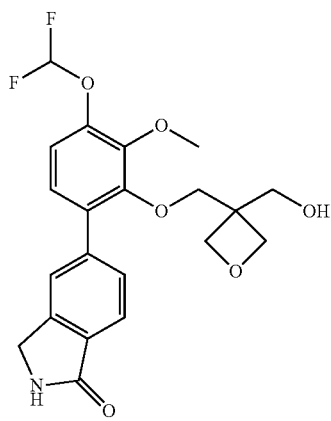 [SMILES: COc1c(OC(F)F)ccc(-c2ccc3c(c2)CNC3=O)c1OCC1(CO)COC1]

To a stirring solution of 6-bromo-3-(difluoromethoxy)-2-methoxyphenol (200 mg, 0.743 mmol) in acetonitrile (10 mL) was added potassium carbonate (307 mg, 2.23 mmol) and (3-(bromomethyl)oxetan-3-yl)methanol (267 mg, 1.48 mmol) and the resultant reaction mixture was heated to 80° C. for 16 h. The reaction mixture was cooled to RT, filtered through celite and the filtrate was concentrated under reduced pressure to afford 30 mg of (3-((6-Bromo-3-(difluoromethoxy)-2-methoxyphenoxy)methyl)oxetan-3-yl)methanol as a solid.

To a stirring solution of (3-((6-bromo-3-(difluoromethoxy)-2-methoxyphenoxy)methyl)oxetan-3-yl)methanol (200 mg, 0.541 mmol) in dimethylformamide (10 mL) was purged with argon for 1 h. To this cesium carbonate (527 mg, 1.623 mmol), tetrakis(triphenylphosphine) palladium(0) (31 mg, 0.027 mmol) and 5(4,4,5,5-tetramethyl-1,3,2-dioxaborolan-2-yl)isoindolin-1-one (168 mg, 0.650 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a solid (50 mg, 21%).

UPLC-MS (M+1): 422.14; UPLC-MS RT (min): 2.0

Example 84

5-[4-Difluoromethoxy-3-methoxy-2-(3-methoxymethyl-oxetan-3-ylmethoxy)-phenyl]-2,3-dihydro-isoindol-1-one (Compound 2501

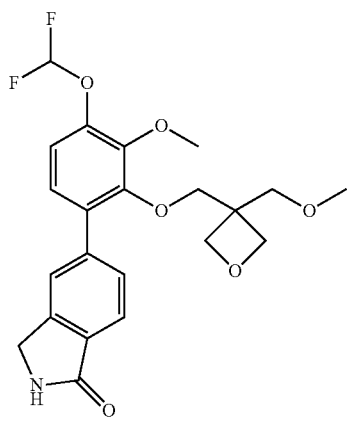 [SMILES: COCC1(COc2c(-c3ccc4c(c3)CNC4=O)ccc(OC(F)F)c2OC)COC1]

To a stirring solution of 6-bromo-3-(difluoromethoxy)-2-methoxyphenol (200 mg, 0.743 mmol) in acetonitrile (10 mL) was added potassium carbonate (307 mg, 2.228 mmol) and 3-(bromomethyl)-3-(methoxymethyl)oxetane (288 mg, 1.48 mmol) and the resultant reaction mixture was heated to 80° C. for 16 h. The reaction mixture was cooled to RT, filtered through celite and the filtrate was concentrated under reduced pressure to afford 200 mg of 3-((6-Bromo-3-(difluoromethoxy)-2-methoxyphenoxy)methyl)-3-(methoxymethyl)oxetane as a solid.

To a stirring solution of 3-((6-bromo-3-(difluoromethoxy)-2-methoxyphenoxy)methyl)-3-(methoxymethyl)oxetane (200 mg, 0.521 mmol) in dimethylformamide (10 mL) was purged with argon for 1 h. To this cesium carbonate (507 mg, 1.563 mmol), tetrakis(triphenylphosphine) palladium(0) (30 mg, 0.026 mmol) and 5-(4,4,5,5-tetramethyl-1,3,2-dioxaborolan-2-yl)isoindolin-1-one (162 mg, 0.626 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a solid (50 mg, 22%).

UPLC-MS (M+1): 436.15; UPLC-MS RT (min): 2.2

Example 85

4-[3-Difluoromethoxy-2-methoxy-6-(1-oxo-2,3-dihydro-1H-isoindol-5-yl)-phenoxymethyl]-benzenesulfonamide (Compound 251)

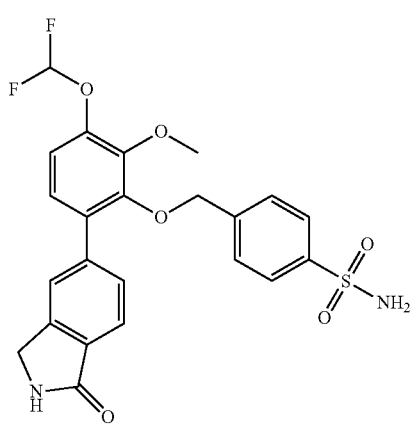 [SMILES: COc1c(OC(F)F)ccc(-c2ccc3c(c2)CNC3=O)c1OCc1ccc(S(N)(=O)=O)cc1]

To a stirring solution of 6-bromo-3-(difluoromethoxy)-2-methoxyphenol (200 mg, 0.743 mmol) in acetonitrile (10 mL) was added potassium carbonate (307 mg, 2.228 mmol) and 4-(bromomethyl)benzenesulfonamide (370 mg, 1.48 mmol) and the resultant reaction mixture was heated to 80° C. for 16 h. The reaction mixture was cooled to RT, filtered through celite and the filtrate was concentrated under reduced pressure to afford 300 mg of 4-((6-Bromo-3-(difluoromethoxy)-2-methoxyphenoxy)methyl)benzenesulfonamide crude product as a solid.

To a stirring solution of 4-((6-bromo-3-(difluoromethoxy)-2-methoxyphenoxy)methyl)benzenesulfonamide (200 mg, 0.456 mmol) in dimethylformamide (10 mL) was purged with argon for 1 h. To this cesium carbonate (444 mg, 1.368 mmol), tetrakis(triphenylphosphine) palladium(0) (26 mg, 0.022 mmol) and 5-(4,4,5,5-tetramethyl-1,3,2-dioxaborolan-2-yl)isoindolin-1-one (141 mg, 0.547 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a solid (40 mg, 18%).

UPLC-MS (M+1): 491.09; UPLC-MS RT (min): 2.2

Example 86

5-[4-Difluoromethoxy-2-(4-methanesulfonyl-benzyloxy)-3-methoxy-phenyl]-2,3-dihydro-isoindol-1-one (Compound 252)

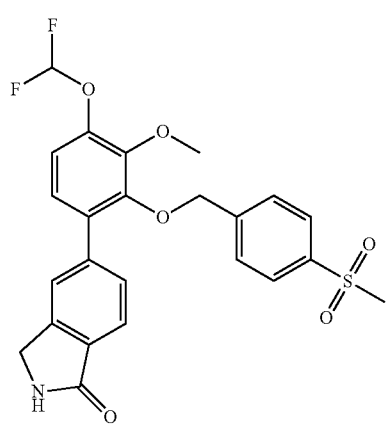 [SMILES: COc1c(OC(F)F)ccc(-c2ccc3c(c2)CNC3=O)c1OCc1ccc(S(C)(=O)=O)cc1]

To a stirring solution of 6-bromo-3-(difluoromethoxy)-2-methoxyphenol (200 mg, 0.743 mmol) in acetonitrile (10 mL) was added potassium carbonate (307 mg, 2.228 mmol) and 1-(bromomethyl)-4-(methylsulfonyl)benzene (368.6 mg, 1.48 mmol) and the resultant reaction mixture was heated to 80° C. for 16 h. The reaction mixture was cooled to RT, filtered through celite and the filtrate was concentrated under reduced pressure to afford 300 mg of 1-Bromo-4-(difluoromethoxy)-3-methoxy-2-(4-(methylsulfonyl)benzyloxy)benzene crude product as a solid.

To a stirring solution of 1-bromo-4-(difluoromethoxy)-3-methoxy-2-(4-(methylsulfonyl)benzyloxy)benzene (200 mg, 0.457 mmol) in dimethylformamide (10 mL) was purged with argon for 1 h. To this cesium carbonate (445 mg, 1.371 mmol), tetrakis(triphenylphosphine) palladium(0) (26 mg, 0.022 mmol) and 5-(4,4,5,5-tetramethyl-1,3,2-dioxaborolan-2-yl)isoindolin-1-one (142 mg, 0.548 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a solid (50 mg, 22%).

UPLC-MS (M+1): 490.08; UPLC-MS RT (min): 2.2

Example 87

4-((3-(difluoromethoxy)-2-methoxy-6-(1-oxoisoindolin-5-yl)phenoxy)methyl)benzamide (Compound 253)

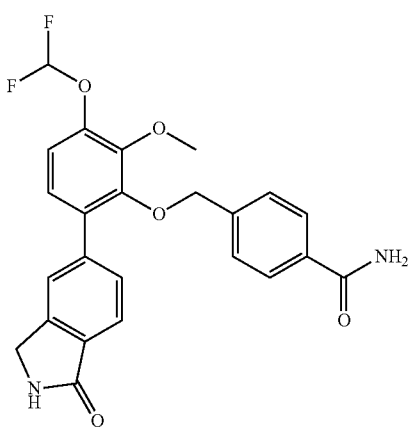 [SMILES: COc1c(OC(F)F)ccc(-c2ccc3c(c2)CNC3=O)c1OCc1ccc(C(N)=O)cc1]

To a stirring solution of 6-bromo-3-(difluoromethoxy)-2-methoxyphenol (1.0 g, 3.71 mmol) in acetonitrile (10 mL) was added potassium carbonate (1.53 g, 11.08 mmol) and 4-(bromomethyl)benzamide (795 mg, 3.71 mmol) and the resultant reaction mixture was heated to 80° C. for 16 h. The reaction mixture was cooled to RT, filtered through celite and the filtrate was concentrated under reduced pressure to afford 4-((6-bromo-3-(difluoromethoxy)-2-methoxyphenoxy)methyl)benzamide as a solid (1 g, 67%).

To a stirring solution of 4-((6-bromo-3-(difluoromethoxy)-2-methoxyphenoxy)methyl)benzamide (500 mg, 1.24 mmol) in dimethylformamide (10 mL) was purged with argon for 1 h. To this cesium carbonate (1.2 g, 3.73 mmol), tetrakis(triphenylphosphine) palladium(0) (72 mg, 0.06 mmol) and 5-(4,4,5,5-tetramethyl-1,3,2-dioxaborolan-2-yl)isoindolin-1-one (386 mg, 1.49 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a solid (100 mg, 17.7%).

UPLC-MS (M+1):455.13; UPLC-MS RT (min): 2.3

Example 88

2-[3-Difluoromethoxy-2-methoxy-6-(1-oxo-2,3-dihydro-1H-isoindol-5-yl)-phenoxy]-N-propyl-acetamide (Compound 254)

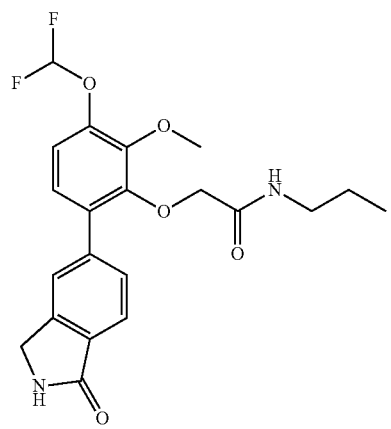 [SMILES: CCCNC(=O)COc1c(-c2ccc3c(c2)CNC3=O)ccc(OC(F)F)c1OC]

To a stirring solution of 6-bromo-3-(difluoromethoxy)-2-methoxyphenol (500 mg, 1.858 mmol) in acetonitrile (20 mL) was added potassium carbonate (769 mg, 5.57 mmol) and ethyl 2-bromoacetate (568 mg, 3.71 mmol) and the resultant reaction mixture was heated to 70° C. for 16 h. The reaction mixture was cooled to RT, filtered through celite and the filtrate was concentrated under reduced pressure to afford 300 mg of Ethyl 2-(6-bromo-3-(difluoromethoxy)-2-methoxyphenoxy)acetate as solid.

To a stirring solution of ethyl 2-(6-bromo-3-(difluoromethoxy)-2-methoxyphenoxy)acetate (300 mg, 0.845 mmol) in tetrahydrofuran was added lithium hydroxide in water and the reaction mixture was stirred at RT for 1 h. The reaction mixture was concentrated under reduced pressure and the obtained residue was acidified to pH 2 and then extracted with ethyl acetate. The combined ethyl acetate layers were dried over sodium sulphate and concentrated under reduced pressure to afford 2-(6-Bromo-3-(difluoromethoxy)-2-methoxyphenoxy)acetic acid as a solid (180 mg, 66%).

To a stirring solution of 2-(6-bromo-3-(difluoromethoxy)-2-methoxyphenoxy)acetic acid (420 mg, 1.284 mmol) in dichloromethane (20 mL) at 0° C. was added triethylamine (0.54 mL, 5.20 mmol), EDC.HCl (369 mg, 1.921 mmol), HOBt (393 mg, 2.56 mmol) and propylamine (227 mg, 3.85 mmol) and the reaction mixture was stirred at RT for 16 h. The reaction mixture was diluted with water and extracted with dichloromethane (3×). The combined dichloromethane layers were washed with brine, dried over anhydrous sodium sulphate and concentrated under reduced pressure to afford 2-(6-Bromo-3-(difluoromethoxy)-2-methoxyphenoxy)-N-propylacetamide as a liquid (300 mg, 63%).

A stirring solution of 2-(6-bromo-3-difluoromethoxy-2-methoxy-phenoxy)-N-propyl-acetamide (100 mg, 0.271 mmol) in dimethylformamide (10 mL) was purged with argon for 1 h, to this cesium carbonate (266 mg, 0.813 mmol), tetrakis(triphenylphosphine) palladium(0) (22 mg, 0.019 mmol) and 5-(4,4,5,5-tetramethyl-1,3,2-dioxaborolan-2-yl) isoindolin-1-one (105.5 mg, 0.407 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layer was washed with brine and dried over anhydrous sodium sulphate and concentrated under reduced pressure. Purification of the residue by column chromatography (silica gel, 0-20% ethyl acetate in pet ether) afforded the title compound as a solid. (20 mg, 18%).

UPLC-MS (M+1): 421.16; UPLC-MS RT (min): 2.1

Preparation 15

4(4-Ethoxy-2-hydroxy-3-methoxyphenyl)-2,3-dihydro-1H-inden-1-one (Compound 315)

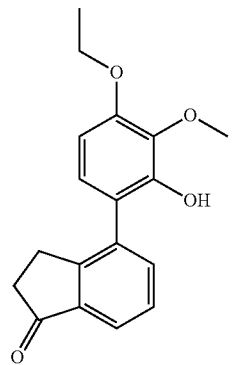 [SMILES: CCOc1ccc(-c2cccc3c2CCC3=O)c(O)c1OC]

To a stirring solution of benzene-1,2,3-triol (2 g, 15.87 mmol) in acetone was added potassium bicarbonate (1.9 g, 19.04 mmol) and methyl iodide (3.3 g, 23.8 mmol) and the resultant reaction mixture was heated to reflux for 16 h. The reaction mixture was cooled to RT, filtered through celite and the filtrate was concentrated under reduced pressure. The residue was diluted with ether, solid separated out was filtered and the filtrate was concentrated under reduced pressure to afford the crude product. The crude product was purified by flash column chromatography (silica gel, 0-15% ethyl acetate in pet ether) to afford 2-Methoxybenzene-1,3-diol as a solid (600 mg, 27%).

To a stirring solution of 2-methoxybenzene-1,3-diol (3 g, 21.42 mmol) in THF (30 mL) at −78° C. was added N-bromosuccinimide (4.5 g, 25.71 mmol) and the resultant reaction mixture was stirred at −78° C. for 2 h. The reaction mixture was diluted with ice-cold water and extracted with ethyl acetate (3×). The combined ethyl acetate layers were washed with brine, dried over anhydrous sodium sulphate and concentrated under reduced pressure. The obtained residue has mixture of products (4-Bromo-2-methoxybenzene-1,3-diol) which was used as such for further reactions (4.2 g).

To a stirring solution of 4-bromo-2-methoxybenzene-1,3-diol (4.5 g, 20.54 mmol) in acetone (40 mL) at 0° C. was added potassium carbonate (2.83 g, 20.54 mmol) and methoxymethyl chloride (1.32 g, 17.39 mmol). The resultant reaction mixture was stirred at RT for 7 h. The reaction mixture was quenched with ice-cold water, the solid was filtered and the filtrate was concentrated under reduced pressure to leave a residue having the crude product. The crude product was purified by column chromatography (silica gel, 0-10% ethyl acetate in pet ether) to afford 4-Bromo-2-methoxy-3-(methoxymethoxy)phenol as a liquid (2 g, 37%).

To a stirring solution of 4-bromo-2-methoxy-3-(methoxymethoxy)phenol (600 mg, 2.28 mmol) in acetonitrile (20 mL) was added potassium carbonate (944 mg, 6.84 mmol) and ethyl iodide (711 mg, 4.56 mmol) and the resultant reaction mixture was heated to 70° C. for 3 h. The reaction mixture was filtered through celite and the filtrate was concentrated under reduced pressure. The obtained residue was purified by column chromatography (silica gel, 0-7% ethyl acetate in pet ether) to afford 1-Bromo-4-ethoxy-3-methoxy-2-(methoxymethoxy)benzene as a solid (525 mg, 79%).

A stirring solution of 1-bromo-4-ethoxy-3-methoxy-2-(methoxymethoxy)benzene (300 mg, 1.030 mmol) in dimethylformamide (10 mL) was purged with argon for 1 h, to this cesium carbonate (1 g, 3.092 mmol), Pd(PPh$_3$)$_4$ (59 mg, 0.051 mmol) and 4-(4,4,5,5-tetramethyl-1,3,2-dioxaborolan-2-yl)-2,3-dihydro-1H-inden-1-one (265 mg, 1.030 mmol) were added and the resultant reaction mixture was heated to 80-90° C. for 2 h. The reaction mixture was cooled to RT, filtered through celite and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-10% ethyl acetate in pet ether) afforded 4-(4-Ethoxy-3-methoxy-2-(methoxymethoxy)phenyl)-2,3-dihydro-1H-inden-1-one as a solid (200 mg, 56%).

To a stirring solution of 5-(4-ethoxy-3-methoxy-2-(methoxymethoxy)phenyl)-2,3-dihydro-1H-inden-1-one (1 g, 2.92 mmol) in methanol (20 mL) was added conc. hydrochloric acid (3 mL) and heated to 60° C. for 1 h. The reaction mixture was cooled to RT and concentrated under reduced pressure. The residue was basified with sodium bicarbonate solution and extracted with ethyl acetate (3×). The combined ethyl acetate layers were washed with brine, dried over sodium sulphate and concentrated under reduced pressure to afford the title compound as a solid (850 mg, 97.7%).

Example 89

4-(2,4-Diethoxy-3-methoxyphenyl)-2,3-dihydro-1H-inden-1-one

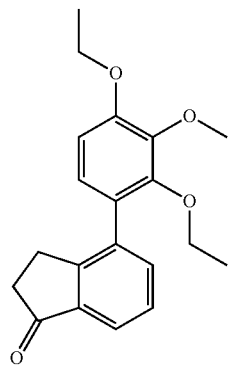 [SMILES: CCOc1ccc(-c2cccc3c2CCC3=O)c(OCC)c1OC]

To a stirring solution of 4-(4-ethoxy-2-hydroxy-3-methoxyphenyl)-2,3-dihydro-1H-inden-1-one (90 mg, 0.302 mmol) in acetonitrile was added potassium carbonate (126 mg, 0.906 mmol) and ethyl iodide (141 mg, 0.906 mmol) and the resultant reaction mixture was heated to 80° C. for 4 h. The reaction mixture was cooled to RT, filtered through celite and the filtrate was concentrated under reduced pressure. Purification of the residue by flash column chromatography (silica gel, 0-20% ethyl acetate in pet ether) afforded title compound as a solid (45 mg, 46%).

UPLC-MS (M+1): 327.16; UPLC-MS RT (min): 2.5

Example 90

4-(4-Ethoxy-3-methoxy-2-propoxyphenyl)-2,3-dihydro-1H-inden-1-one (Compound 256)

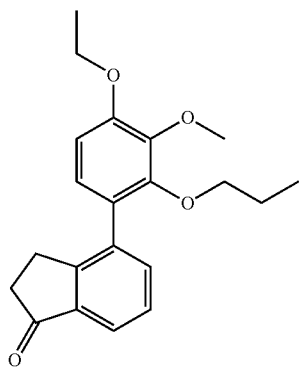 [SMILES: CCCOc1c(-c2cccc3c2CCC3=O)ccc(OCC)c1OC]

To a stirring solution of 4-(4-ethoxy-2-hydroxy-3-methoxyphenyl)-2,3-dihydro-1H-inden-1-one (80 mg, 0.268 mmol) in acetonitrile was added potassium carbonate (111 mg, 0.805 mmol) and propyl bromide (99 mg, 0.805 mmol) and the resultant reaction mixture was heated to 80° C. for 4 h. The reaction mixture was cooled to RT, filtered through celite and the filtrate was concentrated under reduced pressure. Purification of the residue by flash column chromatography (silica gel, 0-20% ethyl acetate in pet ether) afforded title compound as a solid (7 mg, 7.7%).

Example 91

4-(4-Ethoxy-2-isobutoxy-3-methoxyphenyl)-2,3-dihydro-1H-inden-1-one (Compound 257)

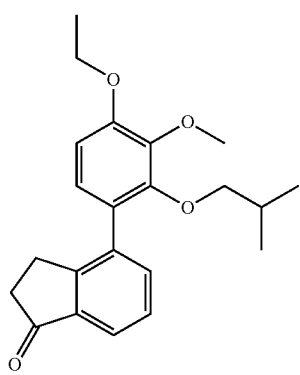 [SMILES: CCOc1ccc(-c2cccc3c2CCC3=O)c(OCC(C)C)c1OC]

To a stirring solution of 4-(4-ethoxy-2-hydroxy-3-methoxyphenyl)-2,3-dihydro-1H-inden-1-one (80 mg, 0.268 mmol) in acetonitrile was added potassium carbonate (111 mg, 0.805 mmol) and isobutyl bromide (110 mg, 0.805 mmol) and the resultant reaction mixture was heated to 80° C. for 2 h. The reaction mixture was cooled to RT, filtered through celite and the filtrate was concentrated under reduced pressure. Purification of the residue by flash column chromatography (silica gel, 0-20% ethyl acetate in pet ether) afforded title compound as a solid (20 mg, 21%).
UPLC-MS (M+1): 355.19; UPLC-MS RT (min): 2.8

Example 92

4-(4-Ethoxy-2-(3-hydroxy-2,2-dimethylpropoxy)-3-methoxyphenyl)-2,3-dihydro-1H-inden-1-one (Compound 258)

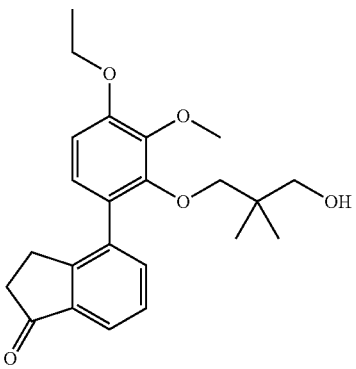 [SMILES: CCOc1ccc(-c2cccc3c2CCC3=O)c(OCC(C)(C)CO)c1OC]

To a stirring solution of 4-(4-ethoxy-2-hydroxy-3-methoxyphenyl)-2,3-dihydro-1H-inden-1-one (80 mg, 0.268 mmol) in acetonitrile (7 mL) was added potassium carbonate (110 mg, 0.80 mmol) and 3-bromo-2,2-dimethylpropan-1-ol (133 mg, 0.80 mmol) and the resultant reaction mixture was heated to 80° C. for 16 h. The reaction mixture was cooled to RT, filtered through celite and the filtrate was concentrated under reduced pressure. Purification of the residue by flash column chromatography (silica gel, 0-25% ethyl acetate in pet ether) afforded title compound as a solid (20 mg, 19%).

Example 93

4-(4-Ethoxy-3-methoxy-2-((3-methyloxetan-3-yl)methoxy)phenyl)-2,3-dihydro-1H-inden-1-one (Compound 259)

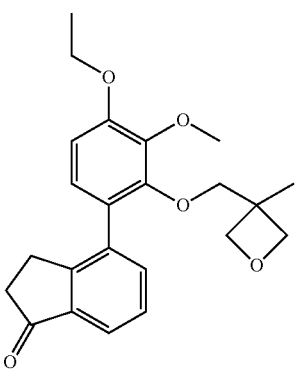 [SMILES: CCOc1ccc(-c2cccc3c2CCC3=O)c(OCC2(C)COC2)c1OC]

To a stirring solution of 4-(4-ethoxy-2-hydroxy-3-methoxyphenyl)-2,3-dihydro-1H-inden-1-one (80 mg, 0.268 mmol) in acetonitrile (7 mL) was added potassium carbonate (111 mg, 0.80 mmol) and 3-(bromomethyl)-3-methyloxetane (132 mg, 0.80 mmol) and the resultant reaction mixture was heated to 80° C. for 16 h. The reaction mixture was cooled to RT, filtered through celite and the filtrate was concentrated under reduced pressure. Purification of the residue by flash column chromatography (silica gel, 0-25% ethyl acetate in pet ether) afforded title compound as a solid (20 mg, 19%).
UPLC-MS (M+1): 383.18; UPLC-MS RT (min): 2.5

Example 94

4-(4-Ethoxy-2-((3-(hydroxymethyl)oxetan-3-yl)methoxy)-3-methoxyphenyl)-2,3-dihydro-1H-inden-1-one (Compound 260)

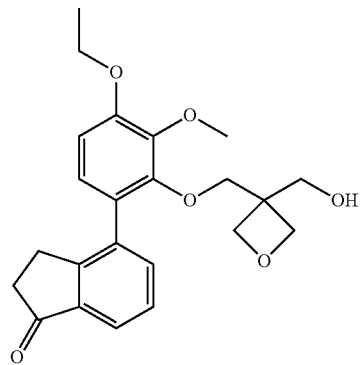 [SMILES: CCOc1ccc(-c2cccc3c2CCC3=O)c(OCC2(CO)COC2)c1OC]

To a stirring solution of 4-(4-ethoxy-2-hydroxy-3-methoxyphenyl)-2,3-dihydro-1H-inden-1-one (80 mg, 0.268 mmol) in acetonitrile (7 mL) was added potassium carbonate (111 mg, 0.80 mmol) and (3-(bromomethyl)oxetan-3-yl)methanol (97 mg, 0.536 mmol) and the resultant reaction mixture was heated to 80° C. for 16 h. The reaction mixture was cooled to RT, filtered through celite and the filtrate was concentrated under reduced pressure. Purification of the residue by flash column chromatography (silica gel, 0-25% ethyl acetate in pet ether) afforded title compound as a solid (20 mg, 19%).
UPLC-MS (M+1): 399.18; UPLC-MS RT (min): 2.2

Example 95

4-(4-Ethoxy-3-methoxy-2-(4-(methylsulfonyl)benzyloxy)phenyl)-2,3-dihydro-1H-inden-1-one (Compound 261)

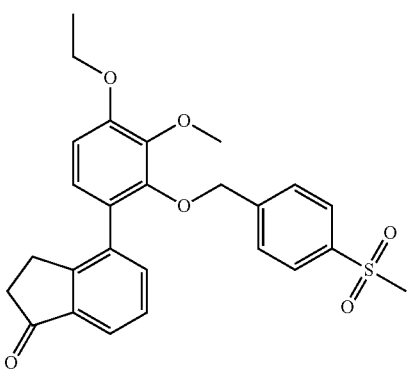 [SMILES: CCOc1ccc(-c2cccc3c2CCC3=O)c(OCc2ccc(S(C)(=O)=O)cc2)c1OC]

To a stirring solution of 4-(4-ethoxy-2-hydroxy-3-methoxyphenyl)-2,3-dihydro-1H-inden-1-one (80 mg, 0.268 mmol) in acetonitrile (7 mL) was added potassium carbonate (111 mg, 0.80 mmol) and 1-(bromomethyl)-4-(methylsulfonyl)benzene (100 mg, 0.402 mmol) and the resultant reaction mixture was heated to 80° C. for 16 h. The reaction mixture was cooled to RT, filtered through celite and the filtrate was concentrated under reduced pressure. Purification of the residue by flash column chromatography (silica gel, 0-30% ethyl acetate in pet ether) afforded title compound as a solid (30 mg, 24%).
UPLC-MS (M+1): 467.14; UPLC-MS RT (min): 2.5

Preparation 16

5-(4-Ethoxy-2-hydroxy-3-methoxyphenyl)isobenzofuran-1(3H)-one (Compound 316)

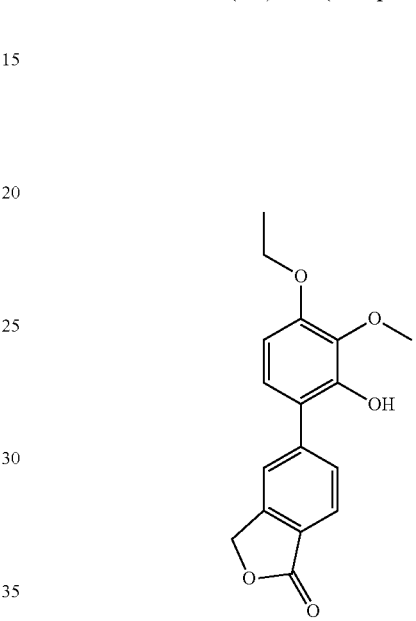

A stirring solution of 1-bromo-4-ethoxy-3-methoxy-2-(methoxymethoxy)benzene (200 mg, 0.722 mmol) in dimethylformamide (5 mL) was purged with argon for 1 h, to this cesium carbonate (700 mg, 2.166 mmol), Pd(PPh$_3$)$_4$ (41 mg, 0.036 mmol) and 5-(4,4,5,5-tetramethyl-1,3,2-dioxaborolan-2-yl)isobenzofuran-1(3H)-one (280 mg, 1.08 mmol) were added and the resultant reaction mixture was heated to 80-90° C. for 3 h. The reaction mixture was cooled to RT, filtered and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-20% ethyl acetate in pet ether) afforded 5-(4-Ethoxy-3-methoxy-2-(methoxymethoxy)phenyl)isobenzofuran-1(3H)-one as a solid (100 mg, 40%).

To a stirring solution of 5-(4-ethoxy-3-methoxy-2-(methoxymethoxy)phenyl)isobenzofuran-1(3H)-one (100 mg, 0.292 mmol) in methanol (5 mL) was added conc. hydrochloric acid (0.5 mL) and heated to 50° C. for 1 h. The reaction mixture was concentrated under reduced pressure; the residue was basified with sodium bicarbonate solution and extracted with ethyl acetate (3×). The combined ethyl acetate layers were washed with brine, dried over sodium sulphate and concentrated under reduced pressure to afford the title compound as a solid (60 mg, 68%).

Example 96

5-(2,4-Diethoxy-3-methoxyphenyl)isobenzofuran-1(3H)-one (Compound 262)

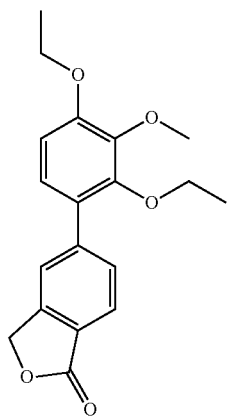 [SMILES: CCOc1ccc(-c2ccc3c(c2)COC3=O)c(OCC)c1OC]

To a stirring solution of 5-(4-ethoxy-2-hydroxy-3-methoxyphenyl)isobenzofuran-1(3H)-one (30 mg, 0.1 mmol) in acetonitrile (5 mL) was added potassium carbonate (41 mg, 0.30 mmol) and ethyl iodide (62 mg, 0.40 mmol) and the resultant reaction mixture was heated to 75° C. for 2 h. The reaction mixture was cooled to RT, filtered through celite and the filtrate was concentrated under reduced pressure. Purification of the residue by flash column chromatography (silica gel, 0-20% ethyl acetate in pet ether) afforded the title compound as a solid (20 mg, 61%).

UPLC-MS (M+1): 329.14; UPLC-MS RT (min): 2.4

Example 97

5-(4-Ethoxy-3-methoxy-2-propoxyphenyl)isobenzofuran-1(3H)-one (Compound 263)

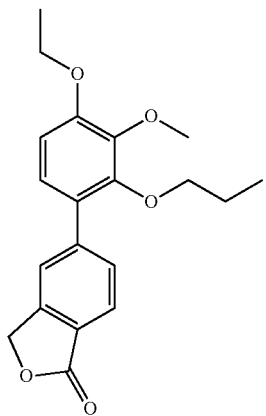 [SMILES: CCCOc1c(-c2ccc3c(c2)COC3=O)ccc(OCC)c1OC]

To a stirring solution of 5-(4-ethoxy-2-hydroxy-3-methoxyphenyl)isobenzofuran-1(3H)-one (80 mg, 0.266 mmol) in acetonitrile was added potassium carbonate (110 mg, 0.798 mmol) and propyl bromide (130 mg, 1.066 mmol) and the resultant reaction mixture was heated to 70° C. for 2 h. The reaction mixture was cooled to RT, filtered through celite and the filtrate was concentrated under reduced pressure. Purification of the residue by flash column chromatography (silica gel, 0-25% ethyl acetate in pet ether) afforded the title compound as a solid (20 mg, 22%).

UPLC-MS (M+1): 343.15; UPLC-MS RT (min): 2.6

Example 98

5-(4-Ethoxy-2-isobutoxy-3-methoxyphenyl)isobenzofuran-1(3H)-one (Compound 264)

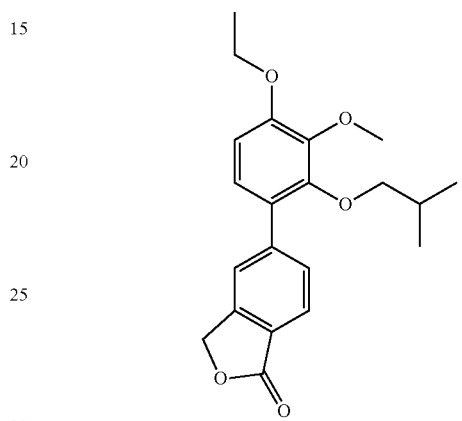

To a stirring solution of 5-(4-ethoxy-2-hydroxy-3-methoxyphenyl)isobenzofuran-1(3H)-one (80 mg, 0.266 mmol) in acetonitrile was added potassium carbonate (110 mg, 0.798 mmol) and isobutyl bromide (146 mg, 1.064 mmol) and the resultant reaction mixture was heated to 80° C. for 2 h. The reaction mixture was cooled to RT, filtered through celite and the filtrate was concentrated under reduced pressure. Purification of the residue by flash column chromatography (silica gel, 0-20% ethyl acetate in pet ether) afforded the title compound as a solid (20 mg, 21%).

UPLC-MS (M+1): 357.17; UPLC-MS RT (min): 2.7

Example 99

5-(4-Ethoxy-2-(3-hydroxy-2,2-dimethylpropoxy)-3-methoxyphenyl)isobenzofuran-1(3H)-one (Compound 265)

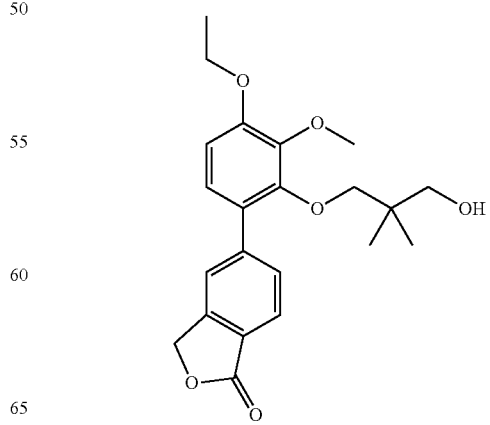

To a stirring solution of 5-(4-ethoxy-2-hydroxy-3-methoxyphenyl)isobenzofuran-1(3H)-one (80 mg, 0.266 mmol) in acetonitrile (7 mL) was added potassium carbonate (110 mg, 0.798 mmol) and 3-bromo-2,2-dimethylpropan-1-ol (134 mg, 0.798 mmol) and the resultant reaction mixture was heated to 80° C. for 16 h. The reaction mixture was cooled to RT, filtered through celite and the filtrate was concentrated under reduced pressure. Purification of the residue by flash column chromatography (silica gel, 0-25% ethyl acetate in pet ether) afforded title compound as a solid (15 mg, 14.7%).

Example 100

5-(4-Ethoxy-3-methoxy-2-((3-methyloxetan-3-yl)methoxy)phenyl)isobenzofuran-1(3H)-one (Compound 266)

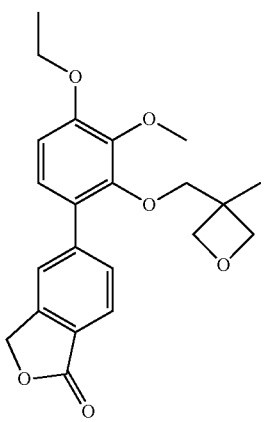 [SMILES: CCOc1ccc(-c2ccc3c(c2)COC3=O)c(OCC2(C)COC2)c1OC]

To a stirring solution of 5-(4-ethoxy-2-hydroxy-3-methoxyphenyl)isobenzofuran-1(3H)-one (80 mg, 0.266 mmol) in acetonitrile (7 mL) was added potassium carbonate (110 mg, 0.798 mmol) and 3-(bromomethyl)-3-methyloxetane (132 mg, 0.798 mmol) and the resultant reaction mixture was heated to 80° C. for 16 h. The reaction mixture was cooled to RT, filtered through celite and the filtrate was concentrated under reduced pressure. Purification of the residue by flash column chromatography (silica gel, 0-25% ethyl acetate in pet ether) afforded title compound as a solid (30 mg, 29%).

UPLC-MS (M+1): 385.16; UPLC-MS RT (min): 2.5

Example 101

5-[4-Ethoxy-2-(3-hydroxymethyl-oxetan-3-yl-methoxy)-3-methoxy-phenyl]-3H-isobenzofuran-1-one (Compound 267)

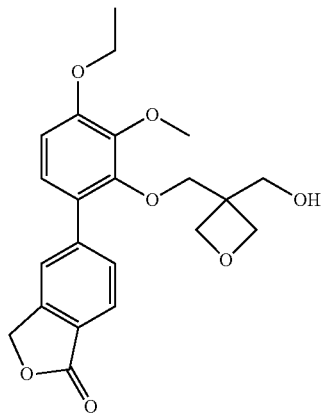 [SMILES: CCOc1ccc(-c2ccc3c(c2)COC3=O)c(OCC2(CO)COC2)c1OC]

To a stirring solution of 5-(4-ethoxy-2-hydroxy-3-methoxyphenyl)isobenzofuran-1(3H)-one (80 mg, 0.266 mmol) in acetonitrile (7 mL) was added potassium carbonate (110 mg, 0.798 mmol) and (3-Bromomethyl-oxetan-3-yl)-methanol (96 mg, 0.532 mmol) and the resultant reaction mixture was heated to 80° C. for 16 h. The reaction mixture was cooled to RT, filtered through celite and the filtrate was concentrated under reduced pressure. Purification of the residue by flash column chromatography (silica gel, 0-25% ethyl acetate in pet ether) afforded title compound as a solid (30 mg, 28%).

UPLC-MS (M+1): 401.16; UPLC-MS RT (min): 2.2

Example 102

5-(4-Ethoxy-3-methoxy-2-(4-(methylsulfonyl)benzyloxy)phenyl)isobenzofuran-1(3H)-one (Compound 268)

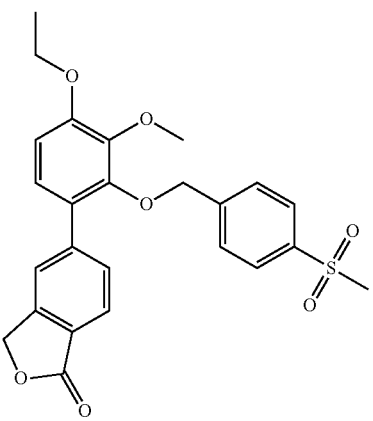 [SMILES: CCOc1ccc(-c2ccc3c(c2)COC3=O)c(OCc2ccc(S(C)(=O)=O)cc2)c1OC]

To a stirring solution of 5-(4-ethoxy-2-hydroxy-3-methoxyphenyl)isobenzofuran-1(3H)-one (80 mg, 0.266 mmol) in acetonitrile (7 mL) was added potassium carbonate (110 mg, 0.80 mmol) and 1-(bromomethyl)-4-(methylsulfonyl)benzene (99 mg, 0.399 mmol) and the resultant reaction mixture was heated to 80° C. for 16 h. The reaction mixture was cooled to RT, filtered through celite and the filtrate was concentrated under reduced pressure. Purification of the residue by flash column chromatography (silica gel, 0-40% ethyl acetate in pet ether) afforded title compound as a solid (20 mg, 16%).

UPLC-MS (M+1): 469.11; UPLC-MS RT (min): 2.5

Preparation 17

4-(3-Hydroxy-2,4-dimethoxyphenyl)-2,3-dihydro-1H-inden-1-one (Compound 317)

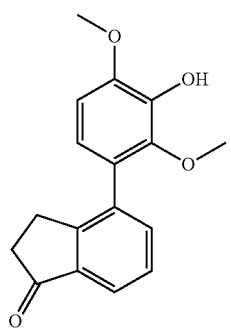 [SMILES: COc1ccc(-c2cccc3c2CCC3=O)c(OC)c1O]

To a stirring solution of 2,6-dimethoxy-phenol (2 g, 12.98 mmol) in CCl$_4$ (70 mL) at −10° C. was added bromine (2.07 g, 12.98 mmol) and stirred for 2 h. The reaction mixture was diluted with CCl$_4$, washed with water and the combined CCl$_4$ layers were washed with brine, dried over anhydrous sodium sulphate and concentrated under reduced pressure to afford 3-Bromo-2,6-dimethoxy-phenol as a solid (2 g, 66%).

A stirring solution of 4-(4,4,5,5-tetramethyl-1,3,2-dioxaborolan-2-yl)-2,3-dihydro-1H-inden-1-one (3 g, 12.87 mmol) in dimethylformamide (30 mL) was purged with argon for 1 h, to this cesium carbonate (12.58 g, 38.61 mmol), Pd(PPh$_3$)$_4$ (743 mg, 0.64 mmol) and 3-bromo-2,6-dimethoxyphenol (3.32 g, 12.87 mmol) were added and the resultant reaction mixture was heated to 80-90° C. for 16 h. The reaction mixture was cooled to RT, filtered through celite and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-10% ethyl acetate in pet ether) afforded the title compound as a solid (1.5 g, 41%).

Example 103

4-(3-Ethoxy-2,4-dimethoxyphenyl)-2,3-dihydro-1H-inden-1-one (Compound 269)

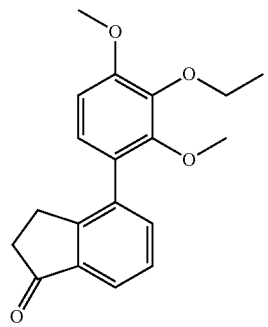 [SMILES: CCOc1c(OC)ccc(-c2cccc3c2CCC3=O)c1OC]

To a stirring solution of 4-(3-hydroxy-2,4-dimethoxyphenyl)-2,3-dihydro-1H-inden-1-one (80 mg, 0.281 mmol) in acetonitrile (5 mL) was added potassium carbonate (116 mg, 0.843 mmol) and ethyl iodide (131 mg, 0.843 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (25 mg, 28.7%).

UPLC-MS (M+1): 313.14; UPLC-MS RT (min): 2.4

Example 104

4-(2,4-Dimethoxy-3-propoxyphenyl)-2,3-dihydro-1H-inden-1-one (Compound 2701

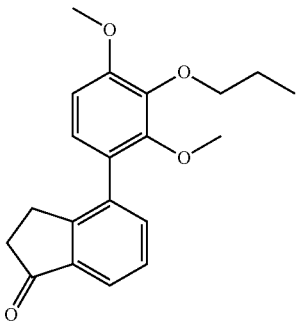 [SMILES: CCCOc1c(OC)ccc(-c2cccc3c2CCC3=O)c1OC]

To a stirring solution of 4-(3-hydroxy-2,4-dimethoxyphenyl)-2,3-dihydro-1H-inden-1-one (80 mg, 0.281 mmol) in acetonitrile (5 mL) was added potassium carbonate (116 mg, 0.843 mmol) and propyl bromide (103 mg, 0.843 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (30 mg, 33.3%).

UPLC-MS (M+1): 327.16; UPLC-MS RT (min): 2.5

Example 105

4(3-Isobutoxy-2,4-dimethoxyphenyl)-2,3-dihydro-1H-inden-1-one (Compound 271)

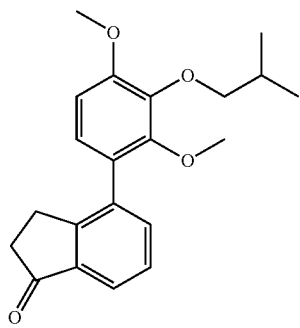 [SMILES: COc1ccc(-c2cccc3c2CCC3=O)c(OC)c1OCC(C)C]

To a stirring solution of 4-(3-hydroxy-2,4-dimethoxyphenyl)-2,3-dihydro-1H-inden-1-one (80 mg, 0.281 mmol) in acetonitrile (10 mL) was added potassium carbonate (115 mg, 0.843 mmol) and isobutyl bromide (115 mg, 0.843 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (15 mg, 15.7%).

UPLC-MS (M+1): 341.17; UPLC-MS RT (min): 2.6

Example 106

4-[3-(3-Hydroxy-2,2-dimethyl-propoxy)-2,4-dimethoxy-phenyl]-indan-1-one (Compound 272)

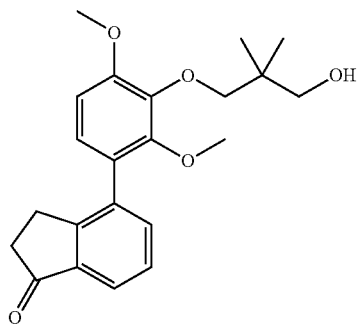 [SMILES: COc1ccc(-c2cccc3c2CCC3=O)c(OC)c1OCC(C)(C)CO]

To a stirring solution of 4-(3-hydroxy-2,4-dimethoxyphenyl)-2,3-dihydro-1H-inden-1-one (80 mg, 0.281 mmol) in acetonitrile (10 mL) was added potassium carbonate (155 mg, 1.124 mmol) and 3-bromo-2,2-dimethyl-propan-1-ol (141 mg, 0.843 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (20 mg, 20%).

UPLC-MS (M+1): 371.19; UPLC-MS RT (min): 2.5

Example 107

4(2,4-Dimethoxy-3-((3-methyloxetan-3-yl)methoxy)phenyl)-2,3-dihydro-1H-inden-1-one (Compound 273)

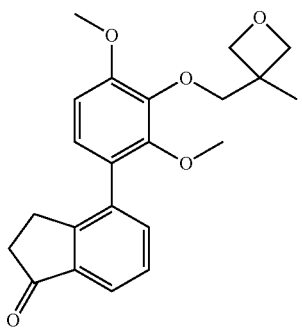 [SMILES: COc1ccc(-c2cccc3c2CCC3=O)c(OC)c1OCC1(C)COC1]

To a stirring solution of 4-(3-hydroxy-2,4-dimethoxyphenyl)-2,3-dihydro-1H-inden-1-one (80 mg, 0.281 mmol) in acetonitrile (5 mL) was added potassium carbonate (115 mg, 0.843 mmol) and 3-(bromomethyl)-3-methyloxetane (139 mg, 0.843 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (40 mg, 38.5%).

UPLC-MS (M+1): 369.17; UPLC-MS RT (min): 2.7

Example 108

4-(3-((3-(Hydroxymethyl)oxetan-3-yl)methoxy)-2,4-dimethoxyphenyl)-2,3-dihydro-1H-inden-1-one (Compound 274)

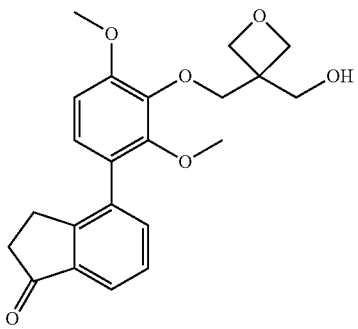 [SMILES: COc1ccc(-c2cccc3c2CCC3=O)c(OC)c1OCC1(CO)COC1]

To a stirring solution of 4-(3-hydroxy-2,4-dimethoxyphenyl)-2,3-dihydro-1H-inden-1-one (80 mg, 0.281 mmol) in acetonitrile (5 mL) was added potassium carbonate (115 mg, 0.843 mmol) and (3-(bromomethyl)oxetan-3-yl)methanol (153 mg, 0.843 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (30 mg, 27.6%).

UPLC-MS (M+1): 385.17; UPLC-MS RT (min): 2.0

Example 110

4-[2,4-Dimethoxy-3-(3-methoxymethyl-oxetan-3-ylmethoxy)-phenyl]-indan-1-one (Compound 275)

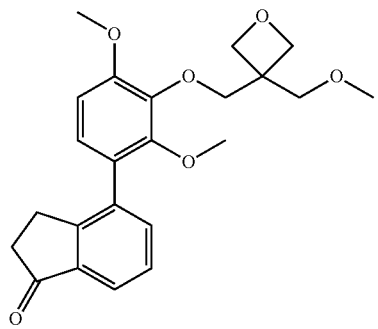 [SMILES: COCC1(COc2c(OC)ccc(-c3cccc4c3CCC4=O)c2OC)COC1]

To a stirring solution of 4-(3-hydroxy-2,4-dimethoxyphenyl)-2,3-dihydro-1H-inden-1-one (80 mg, 0.281 mmol) in acetonitrile (5 mL) was added potassium carbonate (155 mg, 1.124 mmol) and 3-bromomethyl-3-methoxymethyl-oxetane (82 mg, 0.422 mmol) and the resultant reaction mixture was heated to 80° C. for 16 h. The reaction mixture was filtered through celite and the filtrate was concentrated under reduced pressure. The obtained residue was purified by column chromatography (silica gel, 0-50% ethyl acetate in pet ether) to afford the title compound as a solid (20 mg, 17.9%).

Example 111

4-[2,6-Dimethoxy-3-(1-oxo-indan-4-yl)-phenoxymethyl]-benzenesulfonamide (Compound 276)

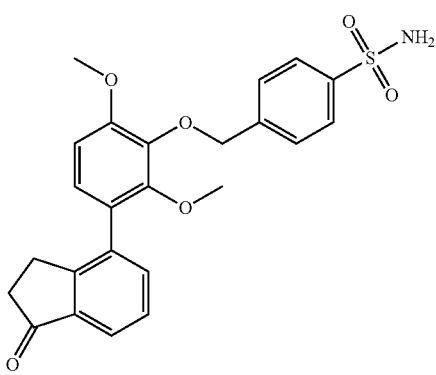 [SMILES: COc1ccc(-c2cccc3c2CCC3=O)c(OC)c1OCc1ccc(S(N)(=O)=O)cc1]

To a stirring solution of 4-(3-hydroxy-2,4-dimethoxyphenyl)-2,3-dihydro-1H-inden-1-one (80 mg, 0.281 mmol) in acetonitrile (5 mL) was added potassium carbonate (155 mg, 1.126 mmol) and 4-bromomethyl-benzenesulfonamide (84 mg, 0.337 mmol) and the resultant reaction mixture was heated to 80° C. for 16 h. The reaction mixture was filtered through celite and the filtrate was concentrated under reduced pressure. The obtained residue was purified by column chromatography (silica gel, 0-50% ethyl acetate in pet ether) to afford the title compound as a solid (20 mg, 15.7%).

UPLC-MS (M+1): 454.14; UPLC-MS RT (min): 2.3

Example 112

4-(2,4-Dimethoxy-3-(4-(methylsulfonyl)benzyloxy)phenyl)-2,3-dihydro-1H-inaen-1-one (Compound 277)

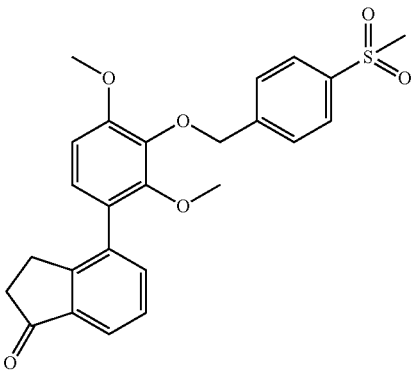 [SMILES: COc1ccc(-c2cccc3c2CCC3=O)c(OC)c1OCc1ccc(S(C)(=O)=O)cc1]

To a stirring solution of 4-(3-hydroxy-2,4-dimethoxyphenyl)-2,3-dihydro-1H-inden-1-one (80 mg, 0.281 mmol) in acetonitrile (5 mL) was added potassium carbonate (155 mg, 0.843 mmol) and 1-(bromomethyl)-4-(methylsulfonyl)benzene (210 mg, 0.843 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (50 mg, 39.3%).

UPLC-MS (M+1): 453.14; UPLC-MS RT (min): 2.3

Preparation 18

5-(3-Hydroxy-2,4-dimethoxy-phenyl)-3H-isobenzofuran-1-one (Compound 318)

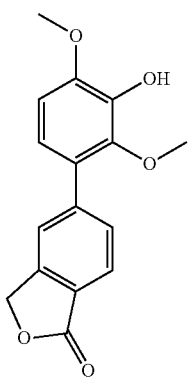 [SMILES: COc1ccc(-c2ccc3c(c2)COC3=O)c(OC)c1O]

To a stirring solution of 2,6-dimethoxy-phenol (2 g, 12.98 mmol) in carbon tetrachloride (70 mL) at −10° C. was added bromine (2 g, 12.98 mmol) in carbon tetrachloride and stirred for 2 h. The reaction mixture was diluted with carbon tetrachloride, washed with water, brine, dried over anhydrous sodium sulphate and concentrated under reduced pressure to afford 3-Bromo-2,6-dimethoxy-phenol as a mixture (2 g).

A stirring solution of 5-(4,4,5,5-Tetramethyl-[1,3,2]dioxaborolan-2-yl)-3H-isobenzofuran-1-one (2.23 g, 8.58 mmol) in dimethylformamide (30 mL) was purged with argon for 1 h, to this cesium carbonate (8.37 g, 25.74 mmol), Pd(PPh$_3$)$_4$ (495 mg, 0.429 mmol) and 3-bromo-2,6-dimethoxy-phenol (2.0 g, 8.58 mmol) were added and the resultant reaction mixture was heated to 80-90° C. for 16 h. The reaction mixture was cooled to RT, filtered through celite and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-10% ethyl acetate in pet ether) afforded the title compound as a solid (1 g, 40.7%).

Example 113

5-(3-Ethoxy-2,4-dimethoxy-phenyl)-3H-isobenzofuran-1-one (Compound 278)

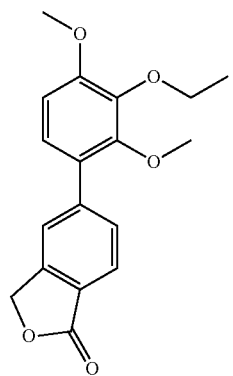 [SMILES: CCOc1c(OC)ccc(-c2ccc3c(c2)COC3=O)c1OC]

To a stirring solution of 5-(3-Hydroxy-2,4-dimethoxy-phenyl)-3H-isobenzofuran-1-one (80 mg, 0.279 mmol) in acetonitrile (10 mL) was added potassium carbonate (115 mg, 0.837 mmol) and ethyl iodide (130 mg, 0.837 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (50 mg, 57%).

UPLC-MS (M+1): 315.13; UPLC-MS RT (min): 2.3

Example 114

5-(2,4-Dimethoxy-3-propoxy-phenyl)-3H-isobenzofuran-1-one (Compound 279)

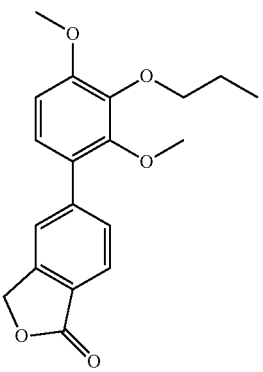 [SMILES: CCCOc1c(OC)ccc(-c2ccc3c(c2)COC3=O)c1OC]

To a stirring solution of 5-(3-Hydroxy-2,4-dimethoxy-phenyl)-3H-isobenzofuran-1-one (80 mg, 0.279 mmol) in acetonitrile (10 mL) was added potassium carbonate (115 mg, 0.837 mmol) and propyl bromide (103 mg, 0.837 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (30 mg, 32.8%).

UPLC-MS (M+1): 329.14; UPLC-MS RT (min): 2.5

Example 115

5-(3-Isobutoxy-2,4-dimethoxy-phenyl)-3H-isobenzofuran-1-one (Compound 280)

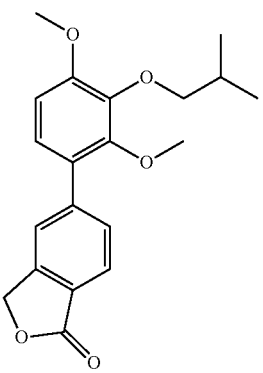 [SMILES: COc1ccc(-c2ccc3c(c2)COC3=O)c(OC)c1OCC(C)C]

To a stirring solution of 5-(3-Hydroxy-2,4-dimethoxy-phenyl)-3H-isobenzofuran-1-one (80 mg, 0.279 mmol) in acetonitrile (10 mL) was added potassium carbonate (115 mg, 0.837 mmol) and isobutyl bromide (115 mg, 0.837 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (30 mg, 31.4%)

UPLC-MS (M+1): 343.16; UPLC-MS RT (min): 2.6

Example 116

5-[2,4-Dimethoxy-3-(3-methyl-oxetan-3-yl-methoxy)-phenyl]-3H-isobenzofuran-1-one (Compound 281)

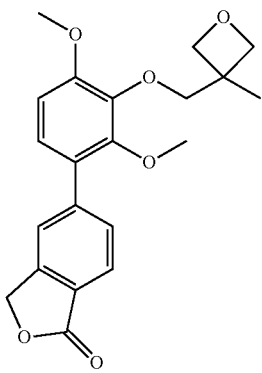 [SMILES: COc1ccc(-c2ccc3c(c2)COC3=O)c(OC)c1OCC1(C)COC1]

To a stirring solution of 5-(3-Hydroxy-2,4-dimethoxy-phenyl)-3H-isobenzofuran-1-one (80 mg, 0.279 mmol) in acetonitrile (10 mL) was added potassium carbonate (115 mg, 0.837 mmol) and 3-bromomethyl-3-methyl-oxetane (138 mg, 0.837 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (50 mg, 48.4%).

Example 117

5-(3-((3-(hydroxymethyl)oxetan-3-yl)methoxy)-2,4-dimethoxyphenyl)isobenzofuran-1(3H)-one (Compound 282)

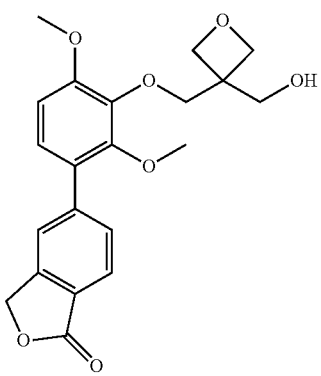 [SMILES: COc1ccc(-c2ccc3c(c2)COC3=O)c(OC)c1OCC1(CO)COC1]

To a stirring solution of 5-(3-Hydroxy-2,4-dimethoxy-phenyl)-3H-isobenzofuran-1-one (80 mg, 0.279 mmol) in acetonitrile (10 mL) was added potassium carbonate (115 mg, 0.837 mmol) and (3-(bromomethyl)oxetan-3-yl)methanol (151 mg, 0.837 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (25 mg, 23.2%).

UPLC-MS (M+1): 387.18; UPLC-MS RT (min): 2.2

Example 118

5-[2,4-Dimethoxy-3-(3-methoxymethyl-oxetan-3-ylmethoxy)-phenyl]-3H-isobenzofuran-1-one (Compound 283)

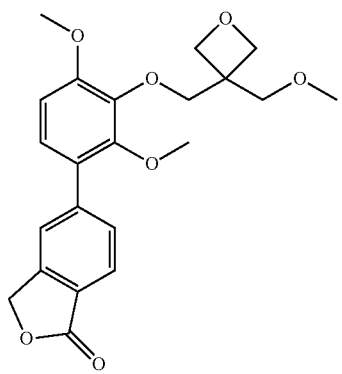 [SMILES: COCC1(COc2c(OC)ccc(-c3ccc4c(c3)COC4=O)c2OC)COC1]

To a stirring solution of 5-(3-Hydroxy-2,4-dimethoxy-phenyl)-3H-isobenzofuran-1-one (80 mg, 0.279 mmol) in acetonitrile (10 mL) was added potassium carbonate (154 mg, 1.118 mmol) and 3-bromomethyl-3-methoxymethyl-oxetane (107 mg, 0.558 mmol) and the resultant reaction mixture was heated to 80° C. for 16 h. The reaction mixture was filtered through celite and the filtrate was concentrated under reduced pressure. The obtained residue was purified by column chromatography (silica gel, 0-50% ethyl acetate in pet ether) to afford the title compound as a solid (20 mg, 18%).

UPLC-MS (M+1): 401.13; UPLC-MS RT (min): 2.3

Example 119

4-[2,6-Dimethoxy-3-(1-oxo-1,3-dihydro-isobenzofuran-5-yl)-phenoxymethyl]-benzenesulfonamide (Compound 284)

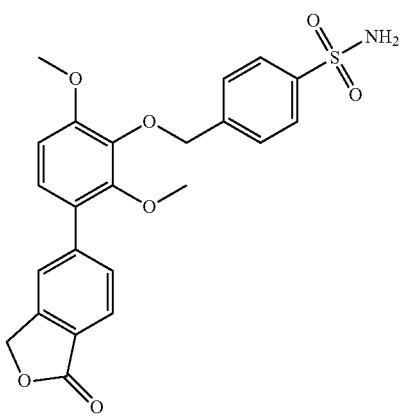 [SMILES: COc1ccc(-c2ccc3c(c2)COC3=O)c(OC)c1OCc1ccc(S(N)(=O)=O)cc1]

To a stirring solution of 5-(3-Hydroxy-2,4-dimethoxy-phenyl)-3H-isobenzofuran-1-one (80 mg, 0.279 mmol) in acetonitrile (10 mL) was added potassium carbonate (154 mg, 1.118 mmol) and 4-bromomethyl-benzenesulfonamide (104 mg, 0.418 mmol) and the resultant reaction mixture was heated to 80° C. for 16 h. The reaction mixture was filtered through celite and the filtrate was concentrated under reduced pressure. The obtained residue was purified by column chromatography (silica gel, 0-25% ethyl acetate in pet ether) to afford the title compound as a solid (20 mg, 15.7%).

UPLC-MS (M+1): 456.11; UPLC-MS RT (min): 2.3

Example 120

5-(2,4-dimethoxy-3-(4-(methylsulfonyl)benzyloxy)phenyl)isobenzofuran-1(3H)-one (Compound 285)

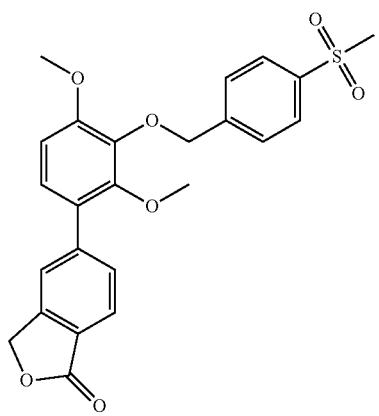 [SMILES: COc1ccc(-c2ccc3c(c2)COC3=O)c(OC)c1OCc1ccc(S(C)(=O)=O)cc1]

To a stirring solution of 5-(3-Hydroxy-2,4-dimethoxyphenyl)-3H-isobenzofuran-1-one (80 mg, 0.279 mmol) in acetonitrile (10 mL) was added potassium carbonate (115 mg, 0.837 mmol) and 1-(bromomethyl)-4-(methylsulfonyl)benzene (208 mg, 0.837 mmol) and the resultant reaction mixture was heated to 80° C. for 4 h. The reaction mixture was filtered through celite and the filtrate was concentrated under reduced pressure. The obtained residue was purified by column chromatography (silica gel, 0-50% ethyl acetate in pet ether) to afford the title compound as a solid (25 mg, 19.7%).

UPLC-MS (M+1): 455.11; UPLC-MS RT (min): 2.3

Example 121

4-[2,6-Dimethoxy-3-(1-oxo-1,3-dihydro-isobenzofuran-5-yl)-phenoxymethyl]-benzamide (Compound 286)

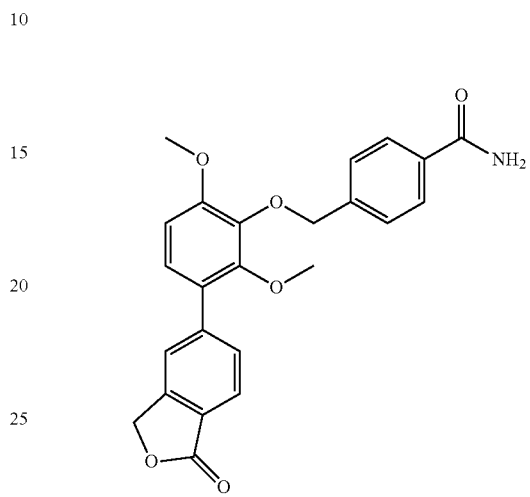

To a stirring solution of 5-(3-Hydroxy-2,4-dimethoxyphenyl)-3H-isobenzofuran-1-one (80 mg, 0.279 mmol) in acetonitrile (10 mL) was added potassium carbonate (154 mg, 1.118 mmol) and 4-bromomethyl-benzamide (89 mg, 0.419 mmol) and the resultant reaction mixture was heated to 80° C. for 4 h. The reaction mixture was filtered through celite and the filtrate was concentrated under reduced pressure. The obtained residue was purified by column chromatography (silica gel, 0-25% ethyl acetate in pet ether) to afford the title compound as a solid (20 mg, 17%).

UPLC-MS (M+1): 420.14; UPLC-MS RT (min): 2.2

Preparation 19

4-(3-(Difluoromethoxy)-2-hydroxy-4-methoxyphenyl)-2,3-dihydro-1H-inden-1-one (Compound 319)

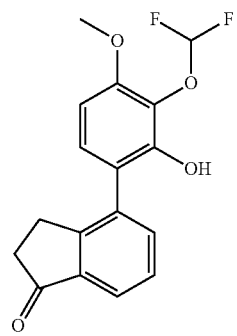 [SMILES: COc1ccc(-c2cccc3c2CCC3=O)c(O)c1OC(F)F]

To a stirring solution of 3-methoxybenzene-1,2-diol (3 g, 21.42 mmol) in carbon tetrachloride (30 mL) was added N-bromosuccinimide (4.5 g, 25.28 mmol) and the reaction mixture was stirred at RT for 2 h. The reaction mixture was diluted with ice-cold water and extracted with dichloromethane (3×). The combined dichloromethane layers were washed with brine, dried over anhydrous sodium sulphate and concentrated under reduced pressure. The obtained residue has mixture of products (3-Bromo-6-methoxybenzene-1,2-diol) which was used as such for further reactions (4.2 g).

To a stirring solution of 3-bromo-6-methoxybenzene-1,2-diol (500 mg, 2.28 mmol) in acetone (40 mL) at 0° C. was added potassium carbonate (314 mg, 2.28 mmol) and methoxymethyl chloride (184 mg, 2.28 mmol) and the resultant reaction mixture was stirred at RT for 2 h. The reaction mixture was filtered and the filtrate was concentrated under reduced pressure Purification by column chromatography (silica gel, 0-8% ethyl acetate in pet ether) afforded 3-Bromo-6-methoxy-2-(methoxymethoxy)phenol as a liquid (230 mg, 38%).

To a stirring solution of 3-bromo-6-methoxy-2-(methoxymethoxy)phenol (700 mg, 2.64 mmol) in dimethylformamide (15 mL) was added potassium carbonate (729 mg, 5.28 mmol), cooled to −45° C. and chlorodifluoromethane gas was passed for 10 min and the resultant reaction mixture was heated to 80° C. for 2 h. The reaction mixture was quenched with ice-cold water and extracted with ethyl acetate (3×). The combined ethyl acetate layers were dried over sodium sulphate and concentrated under reduced pressure. Purification of the residue by flash column chromatography (silica gel, 0-5% ethyl acetate in pet ether) afforded 1-Bromo-3-(difluoromethoxy)-4-methoxy-2-(methoxymethoxy)benzene as a liquid (250 mg, 30%).

A solution of 1-bromo-3-(difluoromethoxy)-4-methoxy-2-(methoxymethoxy)benzene (3 g, 9.58 mmol) in dimethylformamide (50 mL) was purged with argon for 1 h, to this cesium carbonate (9.34 g, 28.74 mmol), tetrakis(triphenylphosphine) palladium (0) (1.1 g, 0.958 mmol) and 4-(4,4,5,5-tetramethyl-1,3,2-dioxaborolan-2-yl)-2,3-dihydro-1H-inden-1-one (2.96 g, 11.49 mmol) were added and the resultant reaction mixture was heated to 80° C. for 4 h. The reaction mixture was cooled to RT and filtered and the filtrate was diluted with water and extracted with ethyl acetate (3×). The combined ethyl acetate layers were washed with brine and dried over anhydrous sodium sulphate and concentrated under reduced pressure. Purification by column chromatography (silica gel, 0-20% ethyl acetate in pet ether) afforded 4-(3-(Difluoromethoxy)-4-methoxy-2-(methoxymethoxy)phenyl)-2,3-dihydro-1H-inden-1-one as a solid (1.8 g, 51.6%).

To a stirring solution of 4-(3-(difluoromethoxy)-4-methoxy-2-(methoxymethoxy)phenyl)-2,3-dihydro-1H-inden-1-one (1 g, 2.747 mmol) in methanol (75 mL) was added concentrated hydrochloride (5 mL) and the reaction mixture was heated to 50° C. for 1 h. The reaction mixture was cooled to RT, concentrated under reduced pressure, the obtained residue was basified with sodium bicarbonate solution and extracted with dichloromethane (3×). The combined dichloromethane layers were washed with brine, dried over sodium sulphate and concentrated under reduced pressure to afford the title compound as a solid (700 mg, 79.6%).

Example 122

4(3-Difluoromethoxy-2-ethoxy-4-methoxy-phenyl)-indan-1-one (Compound 287)

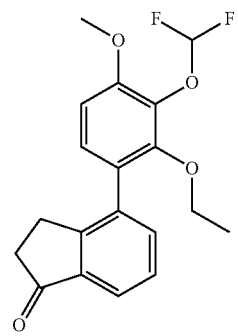 [SMILES: CCOc1c(-c2cccc3c2CCC3=O)ccc(OC)c1OC(F)F]

To a stirring solution of 4-(3-(difluoromethoxy)-2-hydroxy-4-methoxyphenyl)-2,3-dihydro-1H-inden-1-one (80 mg, 0.25 mmol) in acetonitrile (10 mL) was added potassium carbonate (103 mg, 0.75 mmol) and ethyl iodide (156 mg, 1.0 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-15% ethyl acetate in pet ether) to afford title compound as a solid (20 mg, 23%).

UPLC-MS (M+1): 349.13; UPLC-MS RT (min): 2.6

Example 123

4-(3-Difluoromethoxy-4-methoxy-2-propoxy-phenyl)-indan-1-one (Compound 288)

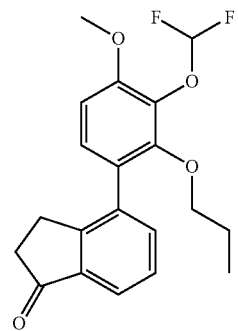 [SMILES: CCCOc1c(-c2cccc3c2CCC3=O)ccc(OC)c1OC(F)F]

To a stirring solution of 4-(3-(difluoromethoxy)-2-hydroxy-4-methoxyphenyl)-2,3-dihydro-1H-inden-1-one (80 mg, 0.25 mmol) in acetonitrile (10 mL) was added potassium carbonate (102 mg, 0.75 mmol) and propyl bromide (92 mg, 0.75 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-20% ethyl acetate in pet ether) to afford the title compound as a solid (20 mg, 22%).

UPLC-MS (M+1): 363.14; UPLC-MS RT (min): 2.6

Example 124

4-(3-Difluoromethoxy-2-isobutoxy-4-methoxy-phenyl)-indan-1-one (Compound 289)

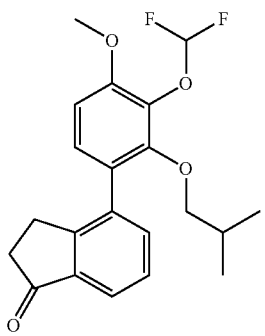 [SMILES: COc1ccc(-c2cccc3c2CCC3=O)c(OCC(C)C)c1OC(F)F]

To a stirring solution of 4-(3-(difluoromethoxy)-2-hydroxy-4-methoxyphenyl)-2,3-dihydro-1H-inden-1-one (80 mg, 0.25 mmol) in acetonitrile (10 mL) was added potassium carbonate (102 mg, 0.75 mmol) and isobutylbromide (102 mg, 0.75 mmol) and the resultant reaction mixture was heated to 80° C. for 16 h. The reaction mixture was cooled to RT, filtered through celite and the filtrate was concentrated under reduced pressure. The residue was purified by column chromatography (silica gel, 0-30% ethyl acetate in pet ether) to afford title compound as a solid (20 mg, 21.2%).

UPLC-MS (M+1): 377.16; UPLC-MS RT (min): 2.7

Example 125

4-[3-Difluoromethoxy-2-(3-hydroxymethyl-oxetan-3-ylmethoxy)-4-methoxy-phenyl]-indan-1-one (Compound 290)

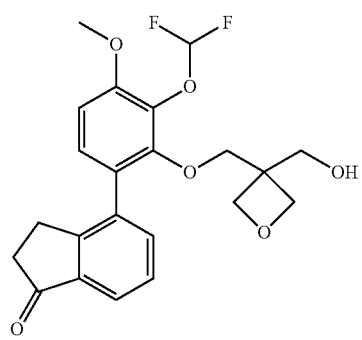 [SMILES: COc1ccc(-c2cccc3c2CCC3=O)c(OCC2(CO)COC2)c1OC(F)F]

To a stirring solution of 4-(3-(difluoromethoxy)-2-hydroxy-4-methoxyphenyl)-2,3-dihydro-1H-inden-1-one (80 mg, 0.25 mmol) in acetonitrile (10 mL) was added potassium carbonate (102 mg, 0.75 mmol) and (3-bromomethyl-oxetan-3-yl)-methanol (68 mg, 0.375 mmol) and the resultant reaction mixture was heated to 80° C. for 16 h. The reaction mixture was cooled to RT, filtered through celite and the filtrate was concentrated under reduced pressure. The residue was purified by column chromatography (silica gel, 0-40% ethyl acetate in pet ether) to afford the title compound as a solid (20 mg, 19%).

UPLC-MS (M+1): 421.15; UPLC-MS RT (min): 2.3

Example 126

4-[3-Difluoromethoxy-4-methoxy-2-(3-methoxymethyl-oxetan-3-ylmethoxy)-phenyl]-indan-1-one (Compound 291)

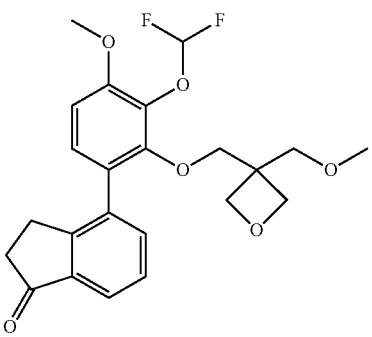 [SMILES: COCC1(COc2c(-c3cccc4c3CCC4=O)ccc(OC)c2OC(F)F)COC1]

To a stirring solution of 4-(3-(difluoromethoxy)-2-hydroxy-4-methoxyphenyl)-2,3-dihydro-1H-inden-1-one (80 mg, 0.25 mmol) in acetonitrile (10 mL) was added potassium carbonate (138 mg, 0.75 mmol) and 3-bromomethyl-3-methoxymethyl-oxetane (97.5 mg, 0.5 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-40% ethyl acetate in pet ether) to afford title compound as a solid (20 mg, 18%).

UPLC-MS (M+1): 435.16; UPLC-MS RT (min): 2.4

Example 127

4-[2-Difluoromethoxy-3-methoxy-6-(1-oxo-indan-4-yl)-phenoxymethyl]-benzenesulfonamide (Compound 292)

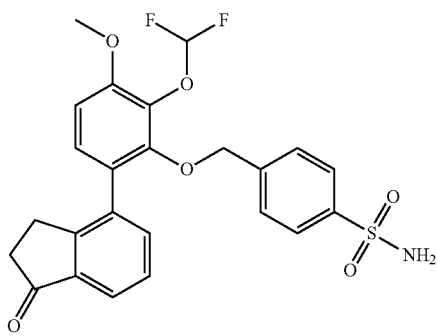 [SMILES: COc1ccc(-c2cccc3c2CCC3=O)c(OCc2ccc(S(N)(=O)=O)cc2)c1OC(F)F]

To a stirring solution of 4-(3-(difluoromethoxy)-2-hydroxy-4-methoxyphenyl)-2,3-dihydro-1H-inden-1-one (80 mg, 0.25 mmol) in acetonitrile (10 mL) was added potassium carbonate (102 mg, 0.75 mmol) and 4-bromomethyl-benzenesulfonamide (94 mg, 0.375 mmol) and the resultant reaction mixture was heated to 70° C. for 16 h. The reaction mixture was cooled to RT, filtered through celite and the filtrate was concentrated under reduced pressure. The residue

Example 128

4-[3-Difluoromethoxy-2-(4-methanesulfonyl-benzyloxy)-4-methoxy-phenyl]-indan-1-one (Compound 293)

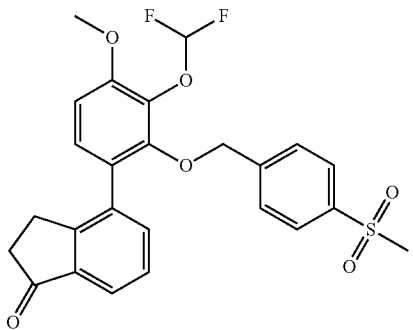 [SMILES: COc1ccc(-c2cccc3c2CCC3=O)c(OCc2ccc(S(C)(=O)=O)cc2)c1OC(F)F]

To a stirring solution of 4-(3-(difluoromethoxy)-2-hydroxy-4-methoxyphenyl)-2,3-dihydro-1H-inden-1-one (80 mg, 0.25 mmol) in acetonitrile (10 mL) was added potassium carbonate (105 mg, 0.75 mmol) and 1-bromomethyl-4-methanesulfonyl-benzene (93 mg, 0.375 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-40% ethyl acetate in pet ether) to afford the title compound as a solid (25 mg, 20%).

UPLC-MS (M+1): 489.09; UPLC-MS RT (min): 2.4

Preparation 20

5-(3-(Difluoromethoxy)-2-hydroxy-4-methoxyphenyl)isobenzofuran-1(3H)-one (Compound 320)

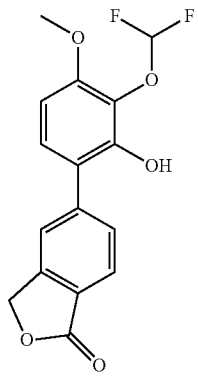 [SMILES: COc1ccc(-c2ccc3c(c2)COC3=O)c(O)c1OC(F)F]

A stirring solution of 1-bromo-3-(difluoromethoxy)-4-methoxy-2-(methoxymethoxy)benzene (1.5 g, 4.79 mmol) in dimethylformamide (30 mL) was purged with argon gas for 1 h, to this cesium carbonate (4.7 g, 14.37 mmol), tetrakis(triphenylphosphine) palladium (0) (553 mg, 0.479 mmol) and 5-(4,4,5,5-tetramethyl-1,3,2-dioxaborolan-2-yl)isobenzofuran-1(3H)-one (1.49 g, 5.74 mmol) were added and the resultant reaction mixture was heated to 80° C. for 4 h. The reaction mixture was cooled to RT, filtered and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-20% ethyl acetate in pet ether) afforded 5-(3-(Difluoromethoxy)-4-methoxy-2-(methoxymethoxy)phenyl)isobenzofuran-1(3H)-one as a solid (1 g, 56.8%).

To a stirring solution of 5-(3-(difluoromethoxy)-4-methoxy-2-(methoxymethoxy)phenyl)isobenzofuran-1(3H)-one (1 g, 2.7 mmol) in methanol (75 mL) was added concentrated hydrochloride (5 mL) and the reaction mixture was heated to 50° C. for 1 h. The reaction mixture was cooled to RT and concentrated under reduced pressure. The obtained residue was basified with sodium bicarbonate solution and extracted with dichloromethane (3×). The combined dichloromethane layers were washed with brine, dried over sodium sulphate and concentrated under reduced pressure to afford the title compound as a solid (600 mg, 68%).

Example 129

5-(3-Difluoromethoxy-2-ethoxy-4-methoxy-phenyl)-3H-isobenzofuran-1-one (Compound 294)

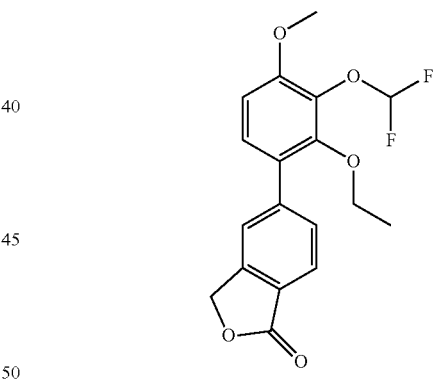

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and ethyl iodide (153 mg, 0.98 mmol) and the resultant reaction mixture was heated to 70° C. for 16 h. The reaction mixture was cooled to RT, filtered through celite and the filtrate was concentrated under reduced pressure. The obtained residue was purified by column chromatography (silica gel, 0-15% ethyl acetate in pet ether) to afford the title compound as a solid (20 mg, 23%).

UPLC-MS (M+1): 351.11; UPLC-MS RT (min): 2.5

Example 130

5-(3-Difluoromethoxy-4-methoxy-2-propoxy-phenyl)-3H-isobenzofuran-1-one (Compound 295)

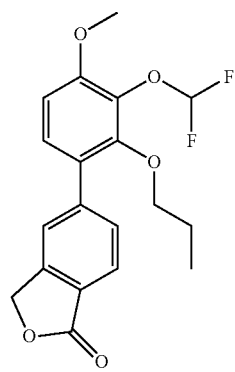 [SMILES: CCCOc1c(-c2ccc3c(c2)COC3=O)ccc(OC)c1OC(F)F]

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and propyl bromide (60 mg, 0.492 mmol) and the resultant reaction mixture was heated to 70° C. for 16 h. The reaction mixture was cooled to RT, filtered through celite and the filtrate was concentrated under reduced pressure. The obtained residue was purified by column chromatography (silica gel, 0-20% ethyl acetate in pet ether) to afford the title compound as a solid (20 mg, 22%).

UPLC-MS (M+1): 365.12; UPLC-MS RT (min): 2.6

Example 131

5-(3-Difluoromethoxy-2-isobutoxy-4-methoxy-phenyl)-3H-isobenzofuran-1-one (Compound 296)

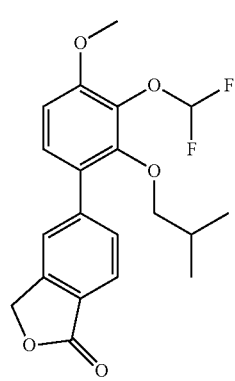 [SMILES: COc1ccc(-c2ccc3c(c2)COC3=O)c(OCC(C)C)c1OC(F)F]

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and isobutylbromide (67 mg, 0.492 mmol) and the resultant reaction mixture was heated to 70° C. for 16 h. The reaction mixture was cooled to RT, filtered through celite and the filtrate was concentrated under reduced pressure. The obtained residue was purified by column chromatography (silica gel, 0-30% ethyl acetate in pet ether) to afford the title compound as a solid (20 mg, 21.4%).

UPLC-MS (M+1): 379.14; UPLC-MS RT (min): 2.7

Example 132

5-[3-Difluoromethoxy-4-methoxy-2-(3-methyl-oxetan-3-ylmethoxy)-phenyl]-3H-isobenzofuran-1-one (Compound 297)

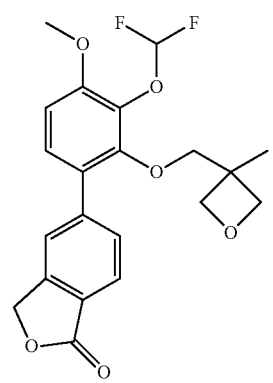 [SMILES: COc1ccc(-c2ccc3c(c2)COC3=O)c(OCC2(C)COC2)c1OC(F)F]

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and 3-bromomethyl-3-methyl-oxetane (122 mg, 0.740 mmol) and the resultant reaction mixture was heated to 70° C. for 16 h. The reaction mixture was cooled to RT, filtered through celite and the filtrate was concentrated under reduced pressure. The obtained residue was purified by column chromatography (silica gel, 0-30% ethyl acetate in pet ether) to afford the title compound as a solid (20 mg, 20%).

UPLC-MS (M+1): 407.18; UPLC-MS RT (min): 2.3

Example 133

5-[3-Difluoromethoxy-2-(3-hydroxymethyl-oxetan-3-ylmethoxy)-4-methoxy-phenyl]-3H-isobenzofuran-1-one (Compound 298)

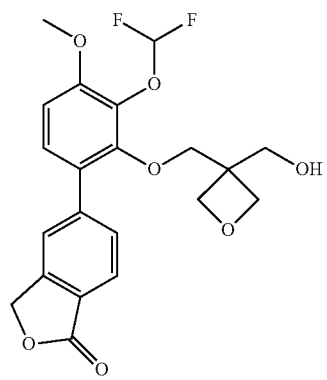 [SMILES: COc1ccc(-c2ccc3c(c2)COC3=O)c(OCC2(CO)COC2)c1OC(F)F]

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and (3-bromomethyl-oxetan-3-yl)-methanol (89 mg, 0.493 mmol) and the resultant reaction mixture was heated to 80° C. for 16 h. The reaction mixture was cooled to RT, filtered through celite and the filtrate was concentrated under reduced pressure. The obtained residue was purified by column chromatography (silica gel, 0-40% ethyl acetate in pet ether) to afford title compound as a solid (20 mg, 19%).

UPLC-MS (M+1): 423.12; UPLC-MS RT (min): 2.2

Example 134

5-[3-Difluoromethoxy-4-methoxy-2-(3-methoxymethyl-oxetan-3-ylmethoxy)-phenyl]-3H-isobenzofuran-1-one (Compound 299)

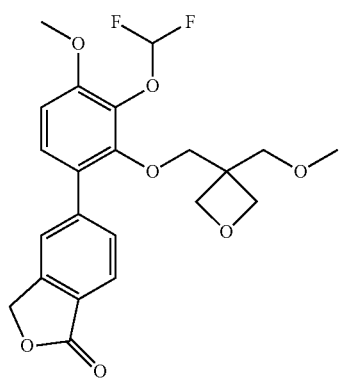 [SMILES: COCC1(COc2c(-c3ccc4c(c3)COC4=O)ccc(OC)c2OC(F)F)COC1]

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and 3-bromomethyl-3-methoxymethyl-oxetane (144 mg, 0.740 mmol) and the resultant reaction mixture was heated to 70° C. for 16 h. The reaction mixture was cooled to RT, filtered through celite and the filtrate was concentrated under reduced pressure. The obtained residue was purified by column chromatography (silica gel, 0-40% ethyl acetate in pet ether) to afford the title compound as a solid (20 mg, 18%).

UPLC-MS (M+1): 437.14; UPLC-MS RT (min): 2.4

Example 135

4-((2-(difluoromethoxy)-3-methoxy-6-(1-oxo-1,3-dihydroisobenzofuran-5-yl)phenoxy)methyl)benzenesulfonamide (Compound 400)

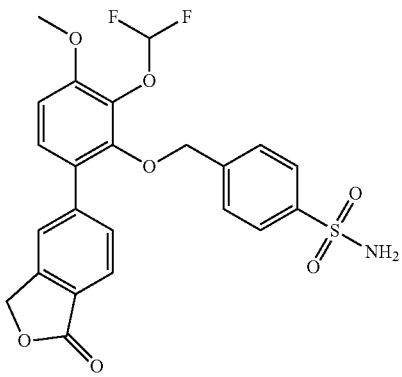 [SMILES: COc1ccc(-c2ccc3c(c2)COC3=O)c(OCc2ccc(S(N)(=O)=O)cc2)c1OC(F)F]

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and 4-(bromomethyl)benzenesulfonamide (124 mg, 0.496 mmol) and the resultant reaction mixture was heated to 70° C. for 16 h. The reaction mixture was cooled to RT, filtered through celite and the filtrate was concentrated under reduced pressure. The obtained residue was purified by column chromatography (silica gel, 0-70% ethyl acetate in pet ether) to afford the title compound as a solid (40 mg, 33%).

UPLC-MS (M+1): 492.08; UPLC-MS RT (min): 2.3

Example 136

5-(3-(difluoromethoxy)-4-methoxy-2-(4-(methylsulfonyl)benzyloxy)phenyl)isobenzofuran-1(3H)-one (Compound 401)

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and 1-(bromomethyl)-4-(methylsulfonyl)benzene (123 mg, 0.496 mmol) and the resultant reaction mixture was heated to 70° C. for 16 h. The reaction mixture was cooled to RT, filtered through celite and the filtrate was concentrated under reduced pressure. The obtained residue was purified by column chromatography (silica gel, 0-70% ethyl acetate in pet ether) to afford the title compound as a solid (40 mg, 33%).

UPLC-MS (M+1): 491.08; UPLC-MS RT (min): 2.4

Example 137

4-((2-(difluoromethoxy)-3-methoxy-6-(1-oxo-1,3-dihydroisobenzofuran-5-yl)phenoxy)methyl)benzamide (Compound 402)

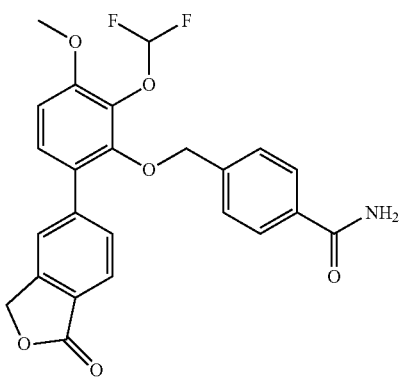 [SMILES: COc1ccc(-c2ccc3c(c2)COC3=O)c(OCc2ccc(C(N)=O)cc2)c1OC(F)F]

To a stirring solution of 5-(3-(difluoromethoxy)-2-hydroxy-4-methoxyphenyl)isobenzofuran-1(3H)-one (80 mg, 0.246 mmol) in acetonitrile (10 mL) was added potassium carbonate (102 mg, 0.738 mmol) and 4-(bromomethyl)benzamide (106 mg, 0.496 mmol) and the resultant reaction mixture was heated to 70° C. for 16 h. The reaction mixture was cooled to RT, filtered through celite and the filtrate was concentrated under reduced pressure. The obtained residue was purified by column chromatography (silica gel, 0-70% ethyl acetate in pet ether) to afford the title compound as a solid (35 mg, 30.9%).

UPLC-MS (M+1): 456.11; UPLC-MS RT (min): 2.3

Preparation 21

4(3-(Cyclopropylmethoxy)-2-hydroxy-4-methoxyphenyl)-2,3-dihydro-1H-inden-1-one (Compound 321)

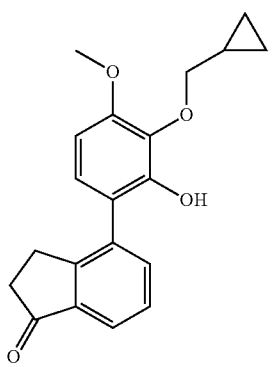 [SMILES: COc1ccc(-c2cccc3c2CCC3=O)c(O)c1OCC1CC1]

To a stirring solution of 3-methoxybenzene-1,2-diol (3 g, 21.42 mmol) in carbon tetrachloride (30 mL) was added N-bromosuccinimide (4.5 g, 25.71 mmol) and the reaction mixture was stirred at RT for 2 h. The reaction mixture was diluted with ice-cold water and extracted with dichloromethane (3×). The combined dichloromethane layers were washed with brine, dried over anhydrous sodium sulphate and concentrated under reduced pressure. The obtained residue has mixture of products (3-Bromo-6-methoxybenzene-1,2-diol) which was used as such for further reactions (4.2 g).

To a stirring solution of 3-bromo-6-methoxybenzene-1,2-diol (500 mg, 2.27 mmol) in acetone (40 mL) at 0° C. was added potassium carbonate (313 mg, 2.27 mmol) and methoxymethyl chloride (183 mg, 2.27 mmol) and the resultant reaction mixture was stirred at RT for 2 h. The reaction mixture was filtered and filtrate was concentrated under reduced pressure. Purification of the residue by column chromatography (silica gel, 0-8% ethyl acetate in pet ether) afforded 3-Bromo-6-methoxy-2-(methoxymethoxy)phenol as a liquid (230 mg, 38%).

To a stirring solution of 3-bromo-6-methoxy-2-(methoxymethoxy)phenol (12 g, 0.045 mol) in acetonitrile (100 mL) at 0° C. was added potassium carbonate (18 g, 0.135 mol) and cyclopropylmethyl bromide (9 g, 0.067 mol) and the resultant reaction mixture was stirred for 1 h at RT. The reaction mixture was filtered through celite and the filtrate was concentrated under reduced pressure. The residue was purified by column chromatography (silica gel, 0-12% ethyl acetate in pet ether) to afford 1-Bromo-3-(cyclopropylmethoxy)-4-methoxy-2-(methoxymethoxy)benzene as a solid (5.5 g, 38%).

A stirring solution of 1-bromo-3-(cyclopropylmethoxy)-4-methoxy-2-(methoxymethoxy)benzene (3 g, 9.46 mmol) in dimethylformamide (50 mL) was purged with argon for 1 h, to this cesium carbonate (9.23 g, 28.39 mmol), water (3 mL), tetrakis triphenylphosphine palladium (546 mg, 0.472 mmol) and 4-(4,4,5,5-tetramethyl-1,3,2-dioxaborolan-2-yl)-2,3-dihydro-1H-inden-1-one (2.93 g, 11.35 mmol) were added and the resultant reaction mixture was heated to 80° C. for 5 h. The reaction mixture was cooled to RT, filtered through celite and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-20% ethyl acetate in pet ether) afforded 4-(3-(Cyclopropylmethoxy)-4-methoxy-2-(methoxymethoxy)phenyl)-2,3-dihydro-1H-inden-1-one as a solid (1.8 g, 51%).

To a stirring solution of 4-(3-(cyclopropylmethoxy)-4-methoxy-2-(methoxymethoxy)phenyl)-2,3-dihydro-1H-inden-1-one (1.5 g, 4.076 mmol) in methanol (25 mL) was added concentrated hydrochloride (5 mL) and the reaction mixture was stirred at RT for 2 h. The reaction mixture was concentrated under reduced pressure the obtained residue was basified with sodium bicarbonate solution and extracted with dichloromethane (3×). The combined dichloromethane layers were washed with brine, dried over sodium sulphate and concentrated under reduced pressure to afford the title compound as a solid (1 g, 75.7%).

Example 138

4-(3-Cyclopropylmethoxy-2-ethoxy-4-methoxy-phenyl)-indan-1-one (Compound 403)

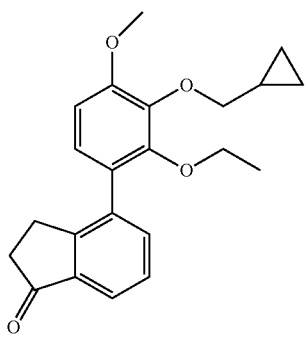 [SMILES: CCOc1c(-c2cccc3c2CCC3=O)ccc(OC)c1OCC1CC1]

To a stirring solution of 4-(3-(cyclopropylmethoxy)-2-hydroxy-4-methoxyphenyl)-2,3-dihydro-1H-inden-1-one (80 mg, 0.246 mmol) in acetonitrile (10 mL) was added potassium carbonate (102 mg, 0.740 mmol) and ethyl iodide (153 mg, 0.984 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-15% ethyl acetate in pet ether) to afford title compound as a solid (20 mg, 23%).
UPLC-MS (M+1): 353.15; UPLC-MS RT (min): 2.7

Example 139

4(3-Cyclopropylmethoxy-4-methoxy-2-propoxy-phenyl)-indan-1-one (Compound 404)

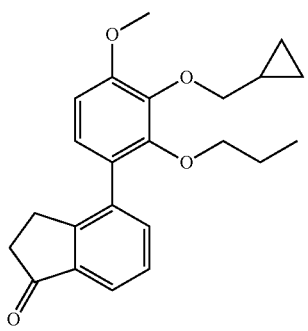 [SMILES: CCCOc1c(-c2cccc3c2CCC3=O)ccc(OC)c1OCC1CC1]

To a stirring solution of 4-(3-(cyclopropylmethoxy)-2-hydroxy-4-methoxyphenyl)-2,3-dihydro-1H-inden-1-one (80 mg, 0.246 mmol) in acetonitrile (10 mL) was added potassium carbonate (102 mg, 0.740 mmol) and n-propyl bromide (91 mg, 0.740 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-15% ethyl acetate in pet ether) to afford title compound as a solid (20 mg, 22%).
UPLC-MS (M+1): 367.17; UPLC-MS RT (min): 2.8

Example 140

4-(3-Cyclopropylmethoxy-2-isobutoxy-4-methoxy-phenyl)-indan-1-one (Compound 405)

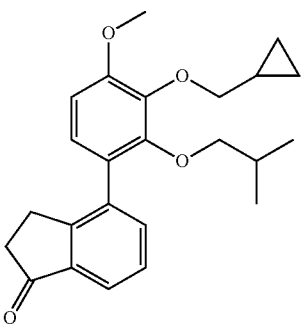 [SMILES: COc1ccc(-c2cccc3c2CCC3=O)c(OCC(C)C)c1OCC1CC1]

To a stirring solution of 4-(3-(cyclopropylmethoxy)-2-hydroxy-4-methoxyphenyl)-2,3-dihydro-1H-inden-1-one (80 mg, 0.246 mmol) in acetonitrile (10 mL) was added potassium carbonate (102 mg, 0.740 mmol) and isobutylbromide (101 mg, 0.740 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-20% ethyl acetate in pet ether) to afford title compound as a solid (20 mg, 21%).
UPLC-MS (M+1): 381.2; UPLC-MS RT (min): 2.9

Example 141

4-[3-Cyclopropylmethoxy-4-methoxy-2-(3-methyl-oxetan-3-ylmethoxy)-phenyl]-indan-1-one (Compound 406)

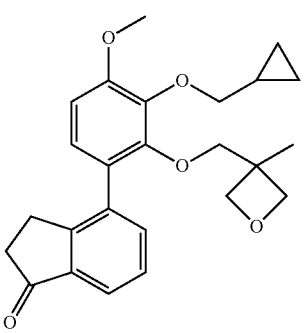 [SMILES: COc1ccc(-c2cccc3c2CCC3=O)c(OCC2(C)COC2)c1OCC1CC1]

To a stirring solution of 4-(3-(cyclopropylmethoxy)-2-hydroxy-4-methoxyphenyl)-2,3-dihydro-1H-inden-1-one (80 mg, 0.246 mmol) in acetonitrile (10 mL) was added potassium carbonate (102 mg, 0.740 mmol) and 3-bromomethyl-3-methyl-oxetane (122 mg, 0.740 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-40% ethyl acetate in pet ether) to afford the title compound as a solid (20 mg, 20%).
UPLC-MS (M+1): 409.19; UPLC-MS RT (min): 2.6

Example 142

4-[3-Cyclopropylmethoxy-2-(3-hydroxymethyl-oxetan-3-ylmethoxy)-4-methoxy-phenyl]-indan-1-one (Compound 407)

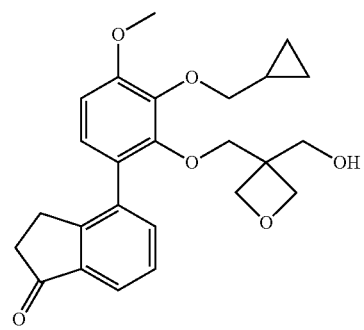 [SMILES: COc1ccc(-c2cccc3c2CCC3=O)c(OCC2(CO)COC2)c1OCC1CC1]

To a stirring solution of 4-(3-(cyclopropylmethoxy)-2-hydroxy-4-methoxyphenyl)-2,3-dihydro-1H-inden-1-one (80 mg, 0.246 mmol) in acetonitrile (10 mL) was added potassium carbonate (102 mg, 0.740 mmol) and (3-bromomethyl-oxetan-3-yl)-methanol (134 mg, 0.740 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-50% ethyl acetate in pet ether) to afford the title compound as a solid (20 mg, 19.2%).

UPLC-MS (M+1): 425.18; UPLC-MS RT (min): 2.3

Example 143

4-[3-Cyclopropylmethoxy-4-methoxy-2-(3-methoxymethyl-oxetan-3-ylmethoxy)-phenyl]-indan-1-one (Compound 408)

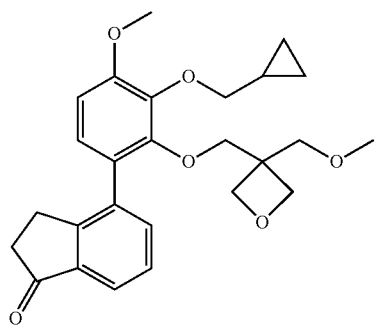 [SMILES: COCC1(COc2c(-c3cccc4c3CCC4=O)ccc(OC)c2OCC2CC2)COC1]

To a stirring solution of 4(3-(cyclopropylmethoxy)-2-hydroxy-4-methoxyphenyl)-2,3-dihydro-1H-inden-1-one (80 mg, 0.246 mmol) in acetonitrile (150 mL) was added potassium carbonate (102 mg, 0.740 mmol) and 3-bromomethyl-3-methoxymethyl-oxetane (120 mg, 0.615 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-50% ethyl acetate in pet ether) to afford the title compound as a solid (25 mg, 23%).

UPLC-MS (M+1): 439.19; UPLC-MS RT (min): 2.6

Example 144

4-[3-Cyclopropylmethoxy-2-(4-methanesulfonyl-benzyloxy)-4-methoxy-phenyl]-indan-1-one (Compound 409)

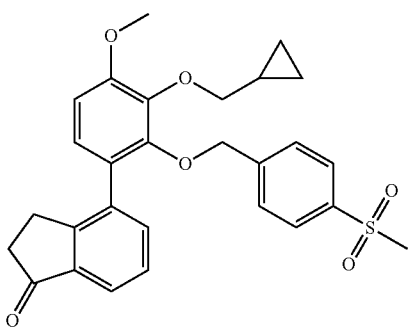 [SMILES: COc1ccc(-c2cccc3c2CCC3=O)c(OCc2ccc(S(C)(=O)=O)cc2)c1OCC1CC1]

To a stirring solution of 4-(3-(cyclopropylmethoxy)-2-hydroxy-4-methoxyphenyl)-2,3-dihydro-1H-inden-1-one (80 mg, 0.246 mmol) in acetonitrile (15 mL) was added potassium carbonate (102 mg, 0.740 mmol) and 1-bromomethyl-4-methanesulfonyl-benzene (122 mg, 0.493 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-45% ethyl acetate in pet ether) to afford the title compound as a solid (20 mg, 16%).

UPLC-MS (M+1): 493.11; UPLC-MS RT (min): 2.6

Example 145

2-[2-Cyclopropylmethoxy-3-methoxy-6-(1-oxo-indan-4-yl)-phenoxy]-N-propyl-acetamide (Compound 410)

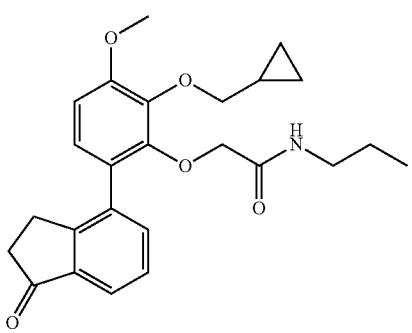 [SMILES: CCCNC(=O)COc1c(-c2cccc3c2CCC3=O)ccc(OC)c1OCC1CC1]

To a stirring solution of n-propylamine (1.18 g, 20 mmol) in dichloroethane (10 mL) at 0° C. was added bromo acetyl bromide (2 g, 10 mmol) and further stirred for 10 min. The reaction mixture was diluted with dichloroethane, filtered and the filtrate was concentrated under reduce pressure to afford 2-Bromo-N-propylacetamide as a solid (1 g, 55.8%).

4-(3-(cyclopropylmethoxy)-2-hydroxy-4-methoxyphenyl)-2,3-dihydro-1H-inden-1-one (100 mg, 0.308 mmol) in acetonitrile (15 mL) was added potassium carbonate (127 mg, 0.925 mmol) and 2-bromo-N-propylacetamide (110 mg, 0.616 mmol) and the resultant reaction mixture was heated to 70° C. for 16 h. The reaction mixture was cooled to RT, filtered through celite and the filtrate was concentrated under reduced pressure. The residue was purified by column chromatography (silica gel, 0-45% ethyl acetate in pet ether) to afford the title compound as a solid (40 mg, 30.7%).

UPLC-MS (M+1): 424.2; UPLC-MS RT (min): 2.5

Preparation 22

5-(3-(Cyclopropylmethoxy)-2-hydroxy-4-methoxyphenyl)isobenzofuran-1(3H)-one (Compound 322)

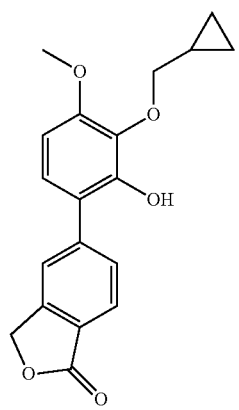 [SMILES: COc1ccc(-c2ccc3c(c2)COC3=O)c(O)c1OCC1CC1]

A stirring solution of 1-bromo-3-(cyclopropylmethoxy)-4-methoxy-2-(methoxymethoxy)benzene (3 g, 9.46 mmol) in dimethylformamide (50 mL) was purged with argon for 1 h, to this cesium carbonate (9.23 g, 28.39 mmol), water (3 mL), tetrakis(triphenylphosphine) palladium(0) (546 mg, 0.472 mmol) and 5-(4,4,5,5-tetramethyl-1,3,2-dioxaborolan-2-yl) isobenzofuran-1(3H)-one (2.96 g, 11.47 mmol) were added and the resultant reaction mixture was heated to 80° C. for 5 h. The reaction mixture was cooled to RT, filtered and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-20% ethyl acetate in pet ether) afforded 5-(3-(Cyclopropylmethoxy)-4-methoxy-2-(methoxymethoxy)phenyl)isobenzofuran-1(3H)-one as a solid (1.8 g, 51%).

To a stirring solution of 5-(3-(cyclopropylmethoxy)-4-methoxy-2-(methoxymethoxy)phenyl)isobenzofuran-1(3H)-one (1.5 g, 4.05 mmol) in methanol (25 mL) was added concentrated hydrochloride (5 mL) and the reaction mixture was stirred for 2 h at RT. The reaction mixture was concentrated under reduced pressure and the obtained residue was basified with sodium bicarbonate solution and then extracted with dichloromethane (3×). The combined dichloromethane layers were washed with brine, dried over sodium sulphate and concentrated under reduced pressure to afford the title compound as a solid (1 g, 76%).

Example 146

5-(3-Cyclopropylmethoxy-2-ethoxy-4-methoxyphenyl)-3H-isobenzofuran-1-one (Compound 411)

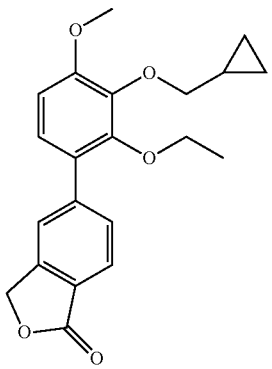 [SMILES: CCOc1c(-c2ccc3c(c2)COC3=O)ccc(OC)c1OCC1CC1]

To a stirring solution of 5-(3-(cyclopropylmethoxy)-2-hydroxy-4-methoxyphenyl) isobenzofuran-1(3H)-one (80 mg, 0.246 mmol) in acetonitrile (10 mL) was added potassium carbonate (102 mg, 0.745 mmol) and ethyl iodide (156 mg, 0.987 mmol) and the resultant reaction mixture was heated to 70° C. for 16 h. The reaction mixture was cooled to RT and filtered through celite. The filtrate was concentrated under reduced pressure and the residue was purified by column chromatography (silica gel, 0-15% ethyl acetate in pet ether) to afford title compound as a solid (20 mg, 23%).

UPLC-MS (M+1): 455.15; UPLC-MS RT (min): 2.6

Example 147

5(3-Cyclopropylmethoxy-4-methoxy-2-propoxyphenyl)-3H-isobenzofuran-1-one (Compound 412)

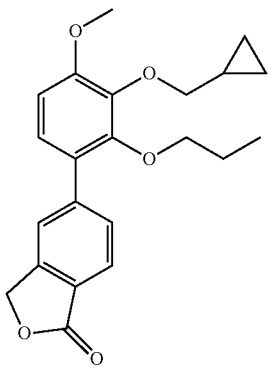 [SMILES: CCCOc1c(-c2ccc3c(c2)COC3=O)ccc(OC)c1OCC1CC1]

To a stirring solution of 5-(3-(cyclopropylmethoxy)-2-hydroxy-4-methoxyphenyl)isobenzofuran-1(3H)-one (80 mg, 0.246 mmol) in acetonitrile (10 mL) was added potassium carbonate (102 mg, 0.745 mmol) and propyl bromide (91 mg, 0.745 mmol) and the resultant reaction mixture was heated to 70° C. for 16 h. The reaction mixture was cooled to RT and filtered through celite. The filtrate was concentrated under reduced pressure and the residue was purified by column

Example 148

5-(3-Cyclopropylmethoxy-2-isobutoxy-4-methoxy-phenyl)-3H-isobenzofuran-1-one (Compound 413)

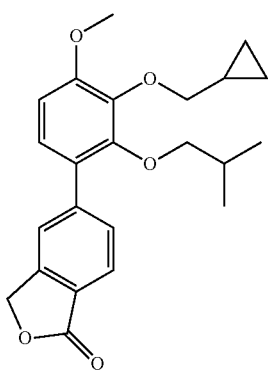 [SMILES: COc1ccc(-c2ccc3c(c2)COC3=O)c(OCC(C)C)c1OCC1CC1]

To a stirring solution of 5-(3-(cyclopropylmethoxy)-2-hydroxy-4-methoxyphenyl) isobenzofuran-1(3H)-one (80 mg, 0.246 mmol) in acetonitrile (10 mL) was added potassium carbonate (102 mg, 0.745 mmol) and isobutylbromide (102 mg, 0.745 mmol) and the resultant reaction mixture was heated to 70° C. for 16 h. The reaction mixture was cooled to RT and filtered through celite. The filtrate was concentrated under reduced pressure and the residue was purified by column chromatography (silica gel, 0-20% ethyl acetate in pet ether) to afford the title compound as a solid (20 mg, 21%).
UPLC-MS (M+1): 383.19; UPLC-MS RT (min): 2.8

Example 149

5-[3-Cyclopropylmethoxy-4-methoxy-2-(3-methyl-oxetan-3-ylmethoxy)-phenyl]-3H-isobenzofuran-1-one (Compound 414)

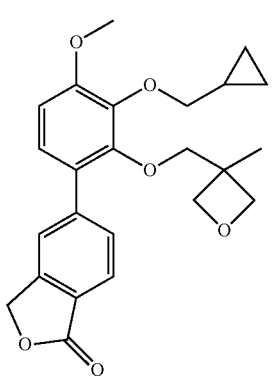 [SMILES: COc1ccc(-c2ccc3c(c2)COC3=O)c(OCC2(C)COC2)c1OCC1CC1]

To a stirring solution of 5-(3-(cyclopropylmethoxy)-2-hydroxy-4-methoxyphenyl)isobenzofuran-1(3H)-one (80 mg, 0.246 mmol) in acetonitrile (10 mL), was added potassium carbonate (102 mg, 0.745 mmol) and 3-bromomethyl-3-methyl-oxetane (122 mg, 0.740 mmol) and the resultant reaction mixture was heated to 70° C. for 16 h. The reaction mixture was cooled to RT and filtered through celite. The filtrate was concentrated under reduced pressure and the residue was purified by column chromatography (silica gel, 0-40% ethyl acetate in pet ether) to afford title compound as a solid (20 mg, 20%)
UPLC-MS (M+1): 411.18; UPLC-MS RT (min): 2.6

Example 150

5-[3-Cyclopropylmethoxy-2-(3-hydroxymethyl-oxetan-3-ylmethoxy)-4-methoxy-phenyl]-3H-isobenzofuran-1-one (Compound 415)

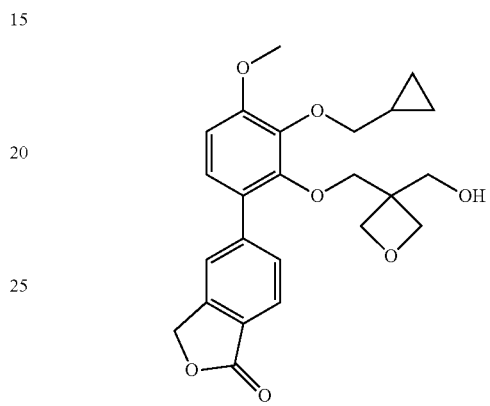

To a stirring solution of 5-(3-(cyclopropylmethoxy)-2-hydroxy-4-methoxyphenyl)isobenzofuran-1(3H)-one (80 mg, 0.246 mmol) in acetonitrile (10 mL), was added potassium carbonate (102 mg, 0.745 mmol) and (3-bromomethyl-oxetan-3-yl)-methanol (134 mg, 0.745 mmol) and the resultant reaction mixture was heated to 70° C. for 16 h. The reaction mixture was cooled to RT and filtered through celite. The filtrate was concentrated under reduced pressure and the residue was purified by column chromatography (silica gel, 0-50% ethyl acetate in pet ether) to afford the title compound as a solid (20 mg, 19.2%).
UPLC-MS (M+1): 427.18; UPLC-MS RT (min): 2.3

Example 151

5-[3-Cyclopropylmethoxy-4-methoxy-2-(3-methoxymethyl-oxetan-3-ylmethoxy)-phenyl]-3H-isobenzofuran-1-one (Compound 416)

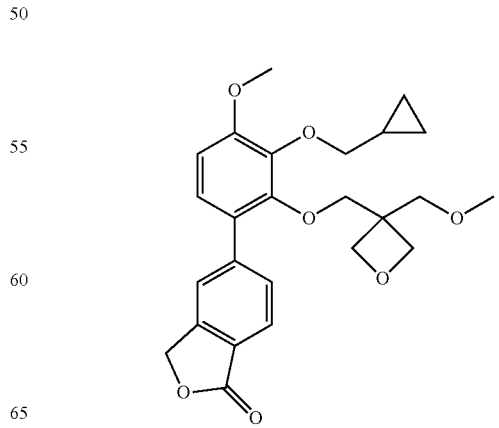

To a stirring solution of 5-(3-(cyclopropylmethoxy)-2-hydroxy-4-methoxyphenyl)isobenzofuran-1(3H)-one (80 mg, 0.246 mmol) in acetonitrile (15 mL), was added potassium carbonate (101 mg, 0.736 mmol) and 3-bromomethyl-3-methoxymethyl-oxetane (95 mg, 0.490 mmol) and the resultant reaction mixture was heated to 70° C. for 16 h. The reaction mixture was cooled to RT and filtered through celite. The filtrate was concentrated under reduced pressure and the residue was purified by column chromatography (silica gel, 0-40% ethyl acetate in pet ether) to afford the title compound as a solid (30 mg, 28%).

UPLC-MS (M+1): 441.19; UPLC-MS RT (min): 2.5

Example 152

5-[3-Cyclopropylmethoxy-2-(4-methanesulfonyl-benzyloxy)-4-methoxy-phenyl]-3H-isobenzofuran-1-one (Compound 417)

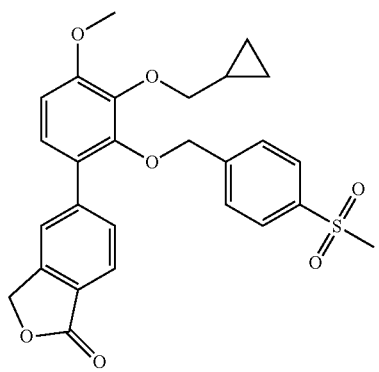 [SMILES: COc1ccc(-c2ccc3c(c2)COC3=O)c(OCc2ccc(S(C)(=O)=O)cc2)c1OCC1CC1]

To a stirring solution of 5-(3-(cyclopropylmethoxy)-2-hydroxy-4-methoxyphenyl)isobenzofuran-1(3H)-one (80 mg, 0.246 mmol) in acetonitrile (15 mL), was added potassium carbonate (102 mg, 0.740 mmol) and 1-bromomethyl-4-methanesulfonyl-benzene (122 mg, 0.490 mmol) and the resultant reaction mixture was heated to 70° C. for 16 h. The reaction mixture was cooled to RT and filtered through celite. The filtrate was concentrated under reduced pressure and the residue was purified by column chromatography (silica gel, 0-45% ethyl acetate in pet ether) to afford the title compound as a solid (20 mg, 16.5%).

UPLC-MS (M+1): 495.15; UPLC-MS RT (min): 2.5

Example 153

2(2-(Cyclopropylmethoxy)-3-methoxy-6-(1-oxo-1,3-dihydroisobenzofuran-5-yl)phenoxy)-N-propylacetamide (Compound 418)

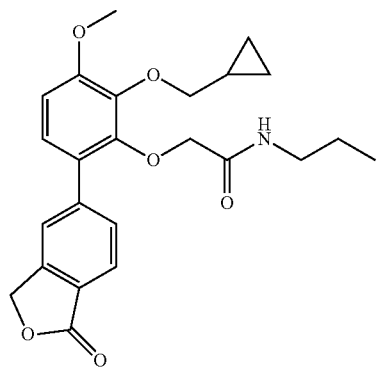 [SMILES: CCCNC(=O)COc1c(-c2ccc3c(c2)COC3=O)ccc(OC)c1OCC1CC1]

To a stirring solution of 5-(3-(cyclopropylmethoxy)-2-hydroxy-4-methoxyphenyl)isobenzofuran-1(3H)-one (250 mg, 0.766 mmol) in acetonitrile (20 mL) was added potassium carbonate (312 mg, 2.3 mmol) and ethylbromoacetate (256 mg, 1.533 mmol) and the reaction mixture was heated to 80° C. for 16 h. The reaction mixture was cooled to RT and filtered through celite. The filtrate was concentrated under reduced pressure to afford Ethyl 2-(2-(cyclopropylmethoxy)-3-methoxy-6-(1-oxo-1,3-dihydroisobenzofuran-5-yl)phenoxy)acetate as a crude product which was used as such in further reaction (300 mg).

To a stirring solution of ethyl 2-(2-(cyclopropylmethoxy)-3-methoxy-6-(1-oxo-1,3-dihydroisobenzofuran-5-yl)phenoxy)acetate (300 mg, 0.726 mmol) in tetrahydrofuran (15 mL) was added lithium hydroxide (152 mg, 3.631 mmol) in water (5 mL) and the reaction mixture was stirred at RT for 4 h. The reaction mixture was diluted with water and extracted with ethyl acetate (3x). The combined ethyl acetate layers were washed with water, dried over sodium sulphate and concentrated under reduced pressure to afford the 2-(2-(Cyclopropylmethoxy)-3-methoxy-6-(1-oxo-1,3-dihydroisobenzofuran-5-yl)phenoxy)acetic acid as a solid (200 mg, 71.5%).

To a stirring solution of 2-(2-(cyclopropylmethoxy)-3-methoxy-6-(1-oxo-1,3-dihydroisobenzofuran-5-yl)phenoxy)acetic acid (200 mg, 0.519 mmol) in dichloromethane (20 mL) was added EDCI.HCl (150 mg, 0.779 mmol), triethylamine (156 mg, 1.55 mmol), HOBt (158 mg, 1.038 mmol) and propylamine (91 mg, 1.553 mmol) and the resultant reaction mixture was stirred at RT for 16 h. The reaction mixture was diluted with water and extracted with dichloromethane (3x). The combined dichloromethane layers were washed with brine, dried over sodium sulphate and concentrated under reduced pressure. Purification of the residue by flash column chromatography (silica gel, 5-40% ethyl acetate in pet ether) afforded the title compound as a solid (30 mg, 14%).

UPLC-MS (M+1): 426.18; UPLC-MS RT (min): 2.5

Example 154

5-(3-(cyclopropylmethoxy)-2,4-dimethoxyphenyl)-2,3-dihydro-1H-inden-1-one (Compound 419)

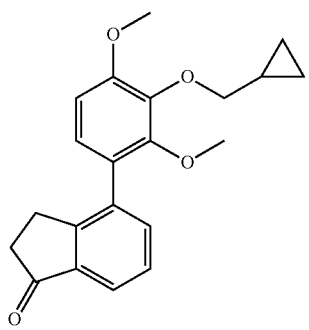 [SMILES: COc1ccc(-c2cccc3c2CCC3=O)c(OC)c1OCC1CC1]

To a stirring solution of 2,6-dimethoxyphenol (2 g, 12.9 mmol) in acetonitrile (50 mL) was added potassium carbonate (3.5 g, 25.8 mmol) and (bromomethyl)cyclopropane (3.5 g, 25.8 mmol) and the resultant reaction mixture was heated to 80° C. for 16 h. The reaction mixture was cooled to RT, filtered through celite and the filtrate was concentrated under reduced pressure. The obtained residue was purified by column chromatography (silica gel, 0-10% ethyl acetate in pet ether) to afford 2-(Cyclopropylmethoxy)-1,3-dimethoxybenzene as a solid (2 g, 74%).

To a stirring solution of 2-(cyclopropylmethoxy)-1,3-dimethoxybenzene (500 mg, 2.40 mmol) in THF (25 mL) was added N-bromosuccinimide (430 mg, 2.40 mmol) and the resultant reaction mixture was stirred at RT for 4 h. The reaction mixture was concentrated under reduced pressure and the obtained residue was diluted with water and extracted with ethyl acetate (3×). The combined ethyl acetate layers were washed with brine, dried over anhydrous sodium sulphate and concentrated under reduced pressure to afford 1-Bromo-3-(cyclopropylmethoxy)-2,4-dimethoxybenzene as a solid (500 mg, 73%).

To a stirring solution of 5-bromo-2,3-dihydro-1H-inden-1-one (4 g, 18.957 mmol) in dioxane (80 mL) purged with argon was added bis(triphenylphosphine)palladium(II)chloride (398 mg, 0.568 mmol) and heated to 70° C. To this was added bis(pinacolato)diboron (9.6 g, 37.91 mmol) and potassium acetate (3.7 g, 37.91 mmol) and the resultant reaction mixture was stirred at 80° C. for 16 h. The reaction mixture was cooled to RT, filtered through celite and the filtrate was concentrated under reduced pressure. The obtained residue was purified by column chromatography (silica gel, 0-15% ethyl acetate in pet ether) to afford 5-(4,4,5,5-tetramethyl-1,3,2-dioxaborolan-2-yl)-2,3-dihydro-1H-inden-1-one (Compound A) as a solid (3.5 g, 71%).

A solution of 5-(4,4,5,5-tetramethyl-1,3,2-dioxaborolan-2-yl)-2,3-dihydro-1H-inden-1-one (180 mg, 0.69 mmol) in dioxane (25 mL) was purged with argon for 1 h, to this was added cesium carbonate (672 mg, 2.07 mmol), Pd(PPh$_3$)$_4$ (40 mg, 0.034 mmol) and 1-bromo-3-(cyclopropylmethoxy)-2,4-dimethoxybenzene (200 mg, 0.69 mmol) and the resultant reaction mixture was heated to 80-90° C. for 16 h. The reaction mixture was cooled to RT, filtered through celite and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-10% ethyl acetate in pet ether) afforded the title compound as a solid (100 mg and 42.3%).

Example 155

5-(3-(cyclopropylmethoxy)-2,4-dimethoxyphenyl)isobenzofuran-1(3H)-one (Compound 420)

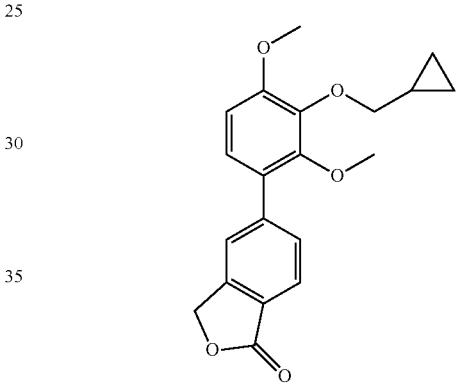

To a stirring solution of 5-bromoisobenzofuran-1(3H)-one (500 mg, 2.34 mmol) in dioxane (30 mL) purged with argon was added bis(triphenylphosphine)palladium(II)chloride (50 mg, 0.070 mmol) and heated to 50° C. To this was added bis(pinacolato)diboron (1.2 g, 4.6 mmol) and potassium acetate (460 mg, 4.69 mmol) and the resultant reaction mixture was stirred at 80° C. for 16 h. The reaction mixture was cooled to RT, filtered through celite bed and the filtrate was concentrated under reduced pressure. The obtained residue was purified by column chromatography (silica gel, 0-15% ethyl acetate in pet ether) to afford 5-(4,4,5,5-tetramethyl-1,3,2-dioxaborolan-2-yl)isobenzofuran-1(3H)-one (Compound-B) as a solid (400 mg, 65.7%).

A solution of 5(4,4,5,5-tetramethyl-1,3,2-dioxaborolan-2-yl)isobenzofuran-1(3H)-one (325 mg, 1.25 mmol) in dioxane (25 mL) was purged with argon for 1 h, to this was added cesium carbonate (1 g, 3.12 mmol), Pd(PPh$_3$)$_4$ (36 mg, 0.031 mmol) and 1-bromo-3-(cyclopropylmethoxy)-2,4-dimethoxybenzene (300 mg, 1.04 mmol) and the resultant reaction mixture was heated to 80-90° C. for 16 h. The reaction mixture was cooled to RT, filtered through celite and the filtrate was diluted with water and extracted with ethyl acetate (3×). The combined ethyl acetate layers were washed with brine, dried over anhydrous sodium sulphate and concentrated under reduced pressure. Purification of the residue by column chromatography (silica gel, 0-10% ethyl acetate in pet ether) afforded a solid (150 mg, 42.5%).

Example 156

Methyl 3-[2,3-dimethoxy-6-(1-oxo-3H-isobenzofuran-4-yl)phenoxy]-2,2-dimethyl-propanoate (Compound 421)

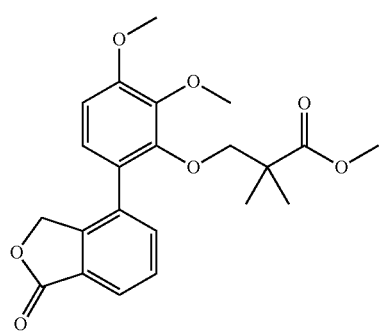 [SMILES: COC(=O)C(C)(C)COc1c(-c2cccc3c2COC3=O)ccc(OC)c1OC]

Following the procedure described in example 6 starting from 4-(2-hydroxy-3,4-dimethoxyphenyl)isobenzofuran-1(3H)-one (Compound 304) as the phenol, the title compound was prepared.

UPLC-MS (M+1): 401.16; UPLC-MS RT (min): 2.5

Example 157

Methyl 3-[2,3-dimethoxy-6-(1-oxo-3H-isobenzofuran-5-yl)phenoxy]-2,2-dimethyl-propanoate, (Compound 422)

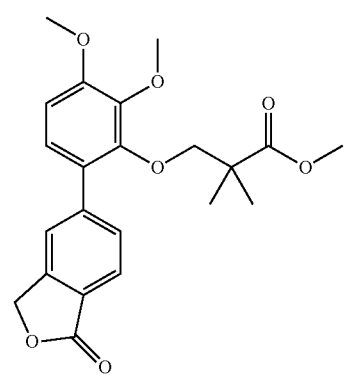 [SMILES: COC(=O)C(C)(C)COc1c(-c2ccc3c(c2)COC3=O)ccc(OC)c1OC]

To a stirring solution of methyl 3-hydroxy-2,2-dimethyl-propanoate (2.76 g, 20.94 mmol, in portions) in tetrahydrofuran (25 mL) was added diethylazodicarboxylate (2.43 g, 13.96 mmol), triphenylphosphine (3.59 g, 13.96 mmol) and 5-(2-hydroxy-3,4-dimethoxyphenyl)isobenzofuran-1(3H)-one (2 g, 6.98 mmol) and the resultant reaction mixture was heated to 70° C. for 6 h. The reaction mixture was diluted with ethyl acetate layer, washed with water, dried over anhydrous sodium sulphate and concentrated under reduced pressure. Purification of the residue by flash, column chromatography (silica gel, 0-20% ethyl acetate in pet ether) to afford the title compound as a solid (800 mg, 28.6%).

UPLC-MS (M+1): 401.16; UPLC-MS RT (min): 2.5

Example 158

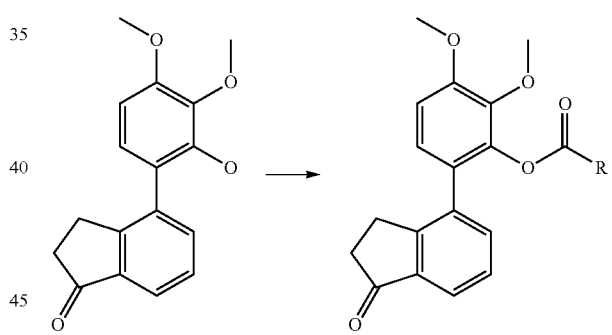

Acid chlorides (53 µmol) were added to solutions of 4-(2-hydroxy-3,4-dimethoxy-phenyl)-indan-1-one (Compound 303) (35 µmol) and DIPEA (53 µmol) in dichloroethane (0.5 mL). The mixtures were shanked at room temperature overnight and subsequently evaporated to dryness. The crude reaction mixtures were re-dissolved in DMF (0.3 mL), and HPLC purification yielded the below compounds, which were characterized by analytical UPLC-MS

| Compound | Structure | Compound Name | Retention Time (minutes) | Detected Mass (M) |
|---|---|---|---|---|
| 423 | 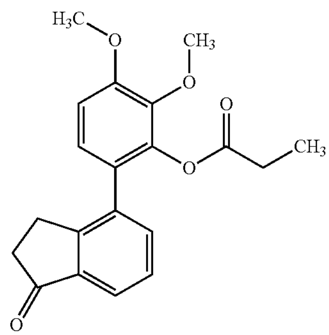 [SMILES: CCC(=O)Oc1c(-c2cccc3c2CCC3=O)ccc(OC)c1OC] | [2,3-dimethoxy-6-(1-oxoindan-4-yl)phenyl] propanoate | 2.41 | 340.13 |
| 424 | 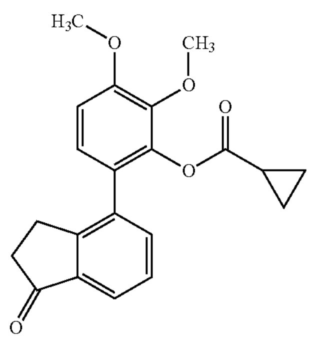 [SMILES: COc1ccc(-c2cccc3c2CCC3=O)c(OC(=O)C2CC2)c1OC] | [2,3-dimethoxy-6-(1-oxoindan-4-yl)phenyl] cyclopropanecarboxylate | 2.41 | 352.13 |
| 425 | 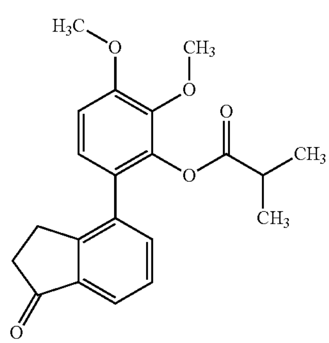 [SMILES: COc1ccc(-c2cccc3c2CCC3=O)c(OC(=O)C(C)C)c1OC] | [2,3-dimethoxy-6-(1-oxoindan-4-yl)phenyl] 2-methylpropanoate | 2.50 | 354.15 |
| 426 | 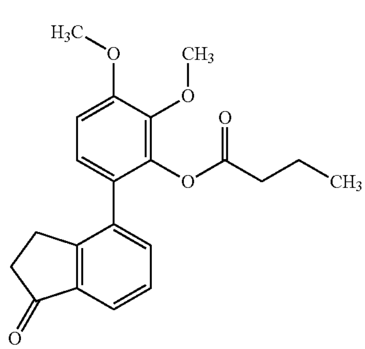 [SMILES: CCCC(=O)Oc1c(-c2cccc3c2CCC3=O)ccc(OC)c1OC] | [2,3-dimethoxy-6-(1-oxoindan-4-yl)phenyl] butanoate | 2.50 | 354.15 |

| Compound | Structure | Compound Name | Retention Time (minutes) | Detected Mass (M) |
|---|---|---|---|---|
| 427 | 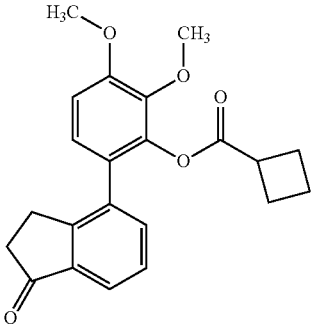 [SMILES: COc1ccc(-c2cccc3c2CCC3=O)c(OC(=O)C2CCC2)c1OC] | [2,3-dimethoxy-6-(1-oxoindan-4-yl)phenyl] cyclobutanecarboxylate | 2.52 | 366.15 |
| 428 | 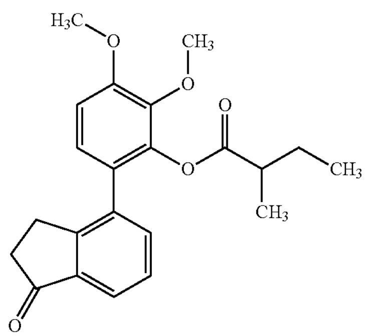 [SMILES: CCC(C)C(=O)Oc1c(-c2cccc3c2CCC3=O)ccc(OC)c1OC] | [2,3-dimethoxy-6-(1-oxoindan-4-yl)phenyl] 2-methylbutanoate | 2.59 | 368.16 |
| 429 | 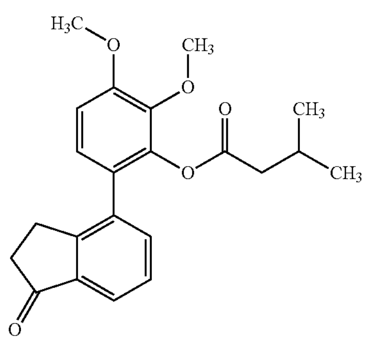 [SMILES: COc1ccc(-c2cccc3c2CCC3=O)c(OC(=O)CC(C)C)c1OC] | [2,3-dimethoxy-6-(1-oxoindan-4-yl)phenyl] 3-methylbutanoate | 2.58 | 368.16 |
| 430 | 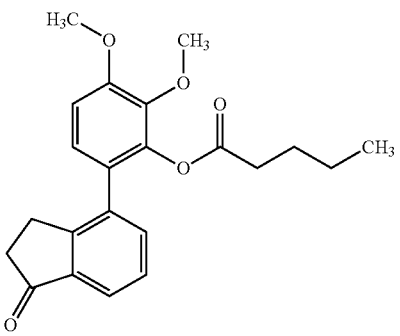 [SMILES: CCCCC(=O)Oc1c(-c2cccc3c2CCC3=O)ccc(OC)c1OC] | [2,3-dimethoxy-6-(1-oxoindan-4-yl)phenyl] pentanoate | 2.58 | 368.16 |

-continued

| Compound | Structure | Compound Name | Retention Time (minutes) | Detected Mass (M) |
|---|---|---|---|---|
| 431 | 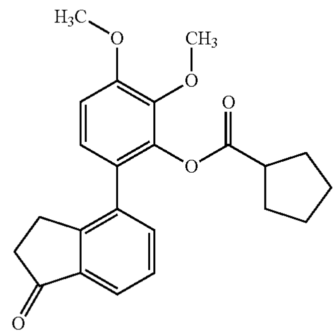 [SMILES: COc1ccc(-c2cccc3c2CCC3=O)c(OC(=O)C2CCCC2)c1OC] | [2,3-dimethoxy-6-(1-oxoindan-4-yl)phenyl] cyclopentanecarboxylate | 2.61 | 380.16 |
| 432 | 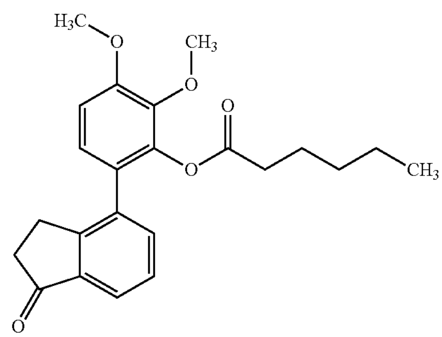 [SMILES: CCCCCC(=O)Oc1c(-c2cccc3c2CCC3=O)ccc(OC)c1OC] | [2,3-dimethoxy-6-(1-oxoindan-4-yl)phenyl] hexanoate | 2.67 | 382.18 |
| 433 | 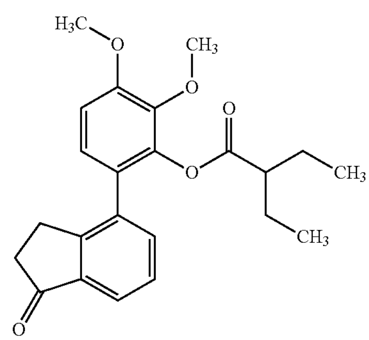 [SMILES: CCC(CC)C(=O)Oc1c(-c2cccc3c2CCC3=O)ccc(OC)c1OC] | [2,3-dimethoxy-6-(1-oxoindan-4-yl)phenyl] 2-ethylbutanoate | 2.67 | 382.18 |
| 434 | 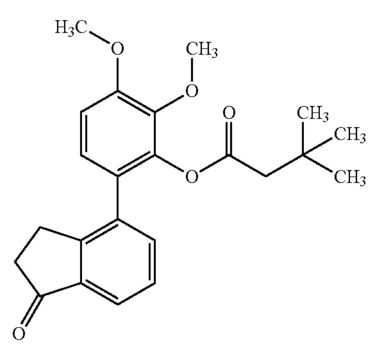 [SMILES: COc1ccc(-c2cccc3c2CCC3=O)c(OC(=O)CC(C)(C)C)c1OC] | [2,3-dimethoxy-6-(1-oxoindan-4-yl)phenyl] 3,3-dimethylbutanoate | 2.67 | 382.18 |

-continued

| Compound | Structure | Compound Name | Retention Time (minutes) | Detected Mass (M) |
|---|---|---|---|---|
| 435 | 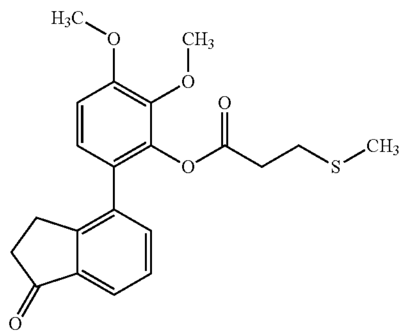 [SMILES: COc1ccc(-c2cccc3c2CCC3=O)c(OC(=O)CCSC)c1OC] | [2,3-dimethoxy-6-(1-oxoindan-4-yl)phenyl] 3-methylsulfanylpropanoate | 2.46 | 386.12 |
| 436 | 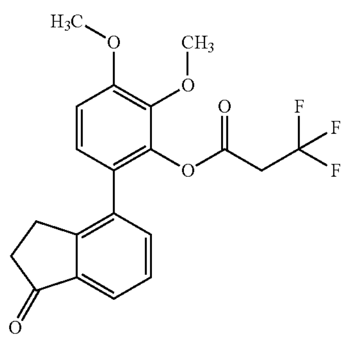 [SMILES: COc1ccc(-c2cccc3c2CCC3=O)c(OC(=O)CC(F)(F)F)c1OC] | [2,3-dimethoxy-6-(1-oxoindan-4-yl)phenyl] 3,3,3-trifluoropropanoate | 2.46 | 394.10 |
| 437 | 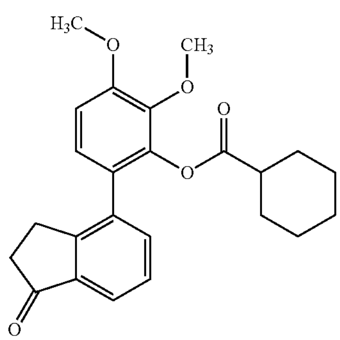 [SMILES: COc1ccc(-c2cccc3c2CCC3=O)c(OC(=O)C2CCCCC2)c1OC] | [2,3-dimethoxy-6-(1-oxoindan-4-yl)phenyl] cyclohexanecarboxylate | 2.70 | 394.18 |
| 438 | 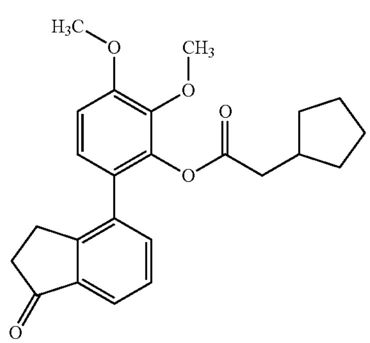 [SMILES: COc1ccc(-c2cccc3c2CCC3=O)c(OC(=O)CC2CCCC2)c1OC] | [2,3-dimethoxy-6-(1-oxoindan-4-yl)phenyl] 2-cyclopentylacetate | 2.70 | 394.18 |

-continued

| Compound | Structure | Compound Name | Retention Time (minutes) | Detected Mass (M) |
|---|---|---|---|---|
| 439 | 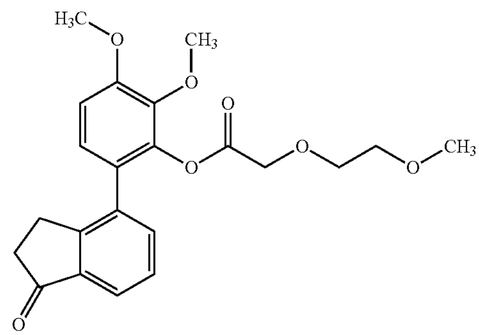 [SMILES: COCCOCC(=O)Oc1c(-c2cccc3c2CCC3=O)ccc(OC)c1OC] | [2,3-dimethoxy-6-(1-oxoindan-4-yl)phenyl] 2-(2-methoxyethoxy)acetate | 2.28 | 400.15 |
| 440 | 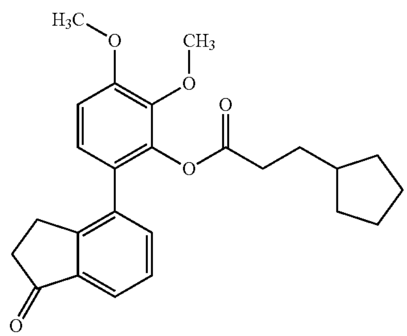 [SMILES: COc1ccc(-c2cccc3c2CCC3=O)c(OC(=O)CCC2CCCC2)c1OC] | [2,3-dimethoxy-6-(1-oxoindan-4-yl)phenyl] 3-cyclopentylpropanoate | 2.77 | 408.19 |

Example 159

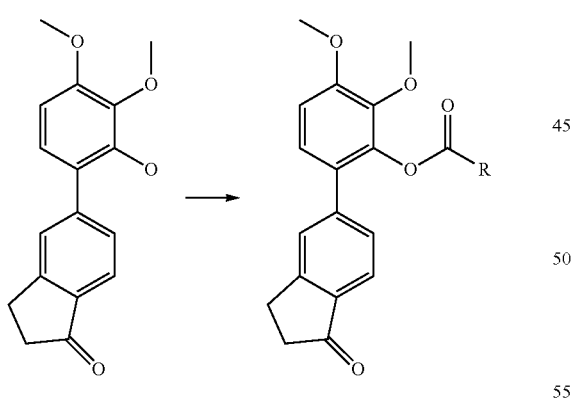

Acid chlorides (53 μmol) were added to solutions of 5-(2-hydroxy-3,4-dimethoxyphenyl)-indan-1-one (Compound 305) (35 μmol) and DIPEA (53 μmol) in dichloroethane (0.5 mL). The mixtures were shanked at room temperature overnight and subsequently evaporated to dryness. The crude reaction mixtures were re-dissolved in DMF (0.3 mL), and HPLC purification yielded the below compounds, which were characterized by analytical UPLC-MS

| Compound | Structure | Compound Name | Retention Time (minutes) | Detected Mass (M) |
|---|---|---|---|---|
| 441 | 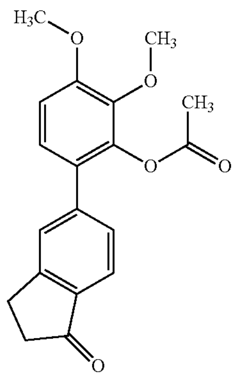 [SMILES: COc1ccc(-c2ccc3c(c2)CCC3=O)c(OC(C)=O)c1OC] | [2,3-dimethoxy-6-(1-oxoindan-5-yl)phenyl] acetate | 2.33 | 326.12 |
| 442 | 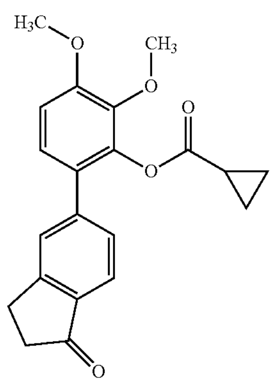 [SMILES: COc1ccc(-c2ccc3c(c2)CCC3=O)c(OC(=O)C2CC2)c1OC] | [2,3-dimethoxy-6-(1-oxoindan-5-yl)phenyl] cyclopropanecarboxylate | 2.42 | 352.13 |
| 443 | 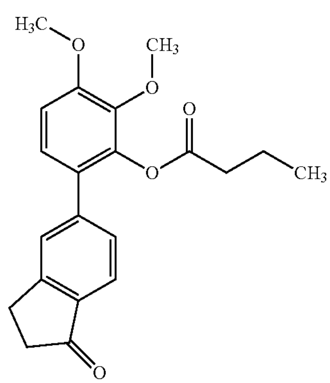 [SMILES: CCCC(=O)Oc1c(-c2ccc3c(c2)CCC3=O)ccc(OC)c1OC] | [2,3-dimethoxy-6-(1-oxoindan-5-yl)phenyl] butanoate | 2.52 | 354.15 |
| 444 | 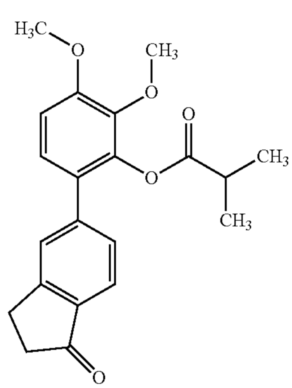 [SMILES: COc1ccc(-c2ccc3c(c2)CCC3=O)c(OC(=O)C(C)C)c1OC] | [2,3-dimethoxy-6-(1-oxoindan-5-yl)phenyl] 2-methylpropanoate | 2.52 | 354.15 |

-continued
| Compound | Structure | Compound Name | Retention Time (minutes) | Detected Mass (M) |
|---|---|---|---|---|
| 445 | 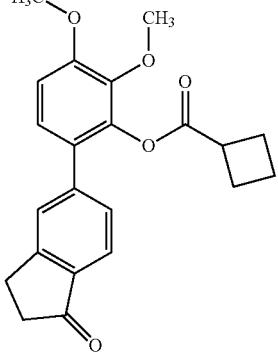 | [2,3-dimethoxy-6-(1-oxoindan-5-yl)phenyl] cyclobutanecarboxylate | 2.54 | 366.15 |
| 446 | 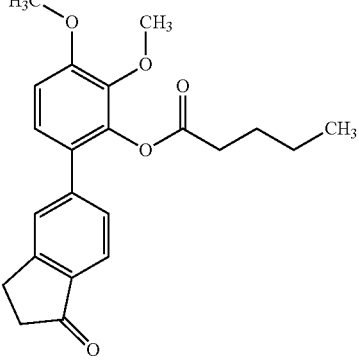 | [2,3-dimethoxy-6-(1-oxoindan-5-yl)phenyl] pentanoate | 2.21 | 314.08 |
| 447 | 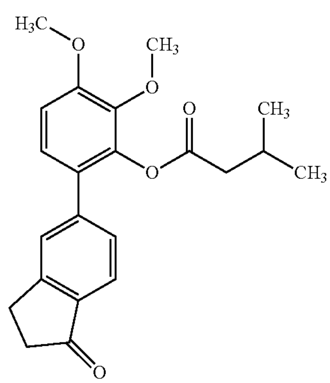 [SMILES: COc1ccc(-c2ccc3c(c2)CCC3=O)c(OC(=O)CC(C)C)c1OC] | [2,3-dimethoxy-6-(1-oxoindan-5-yl)phenyl] 3-methylbutanoate | 2.61 | 368.16 |
| 448 | 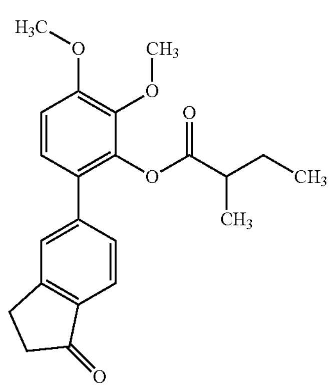 [SMILES: CCC(C)C(=O)Oc1c(-c2ccc3c(c2)CCC3=O)ccc(OC)c1OC] | [2,3-dimethoxy-6-(1-oxoindan-5-yl)phenyl] 2-methylbutanoate | 2.60 | 368.16 |

-continued
| Compound | Structure | Compound Name | Retention Time (minutes) | Detected Mass (M) |
|---|---|---|---|---|
| 449 | 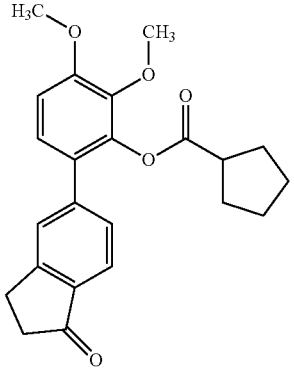 [SMILES: COc1ccc(-c2ccc3c(c2)CCC3=O)c(OC(=O)C2CCCC2)c1OC] | [2,3-dimethoxy-6-(1-oxoindan-5-yl)phenyl] cyclopentanecarboxylate | 2.63 | 380.16 |
| 450 | 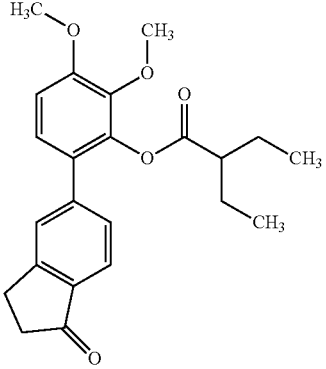 | [2,3-dimethoxy-6-(1-oxoindan-5-yl)phenyl] 2-ethylbutanoate | 2.69 | 382.18 |
| 451 | 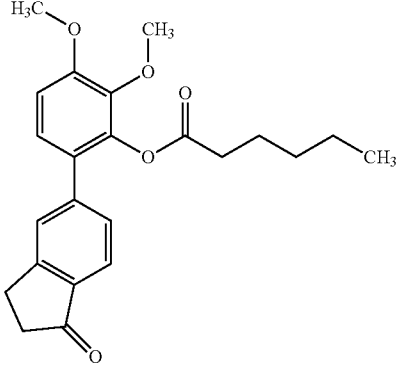 [SMILES: CCCCCC(=O)Oc1c(-c2ccc3c(c2)CCC3=O)ccc(OC)c1OC] | [2,3-dimethoxy-6-(1-oxoindan-5-yl)phenyl] hexanoate | 2.69 | 382.18 |
| 452 | 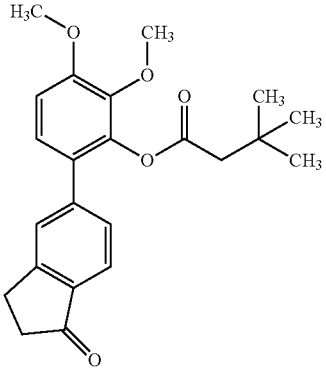 [SMILES: COc1ccc(-c2ccc3c(c2)CCC3=O)c(OC(=O)CC(C)(C)C)c1OC] | [2,3-dimethoxy-6-(1-oxoindan-5-yl)phenyl] 3,3-dimethylbutanoate | 2.69 | 382.18 |

-continued

| Compound | Structure | Compound Name | Retention Time (minutes) | Detected Mass (M) |
|---|---|---|---|---|
| 453 | 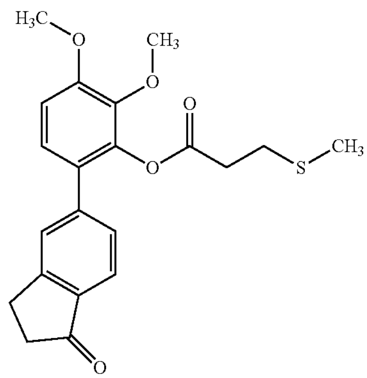 [SMILES: COc1ccc(-c2ccc3c(c2)CCC3=O)c(OC(=O)CCSC)c1OC] | [2,3-dimethoxy-6-(1-oxoindan-5-yl)phenyl] 3-methylsulfanylpropanoate | 2.48 | 386.12 |
| 454 | 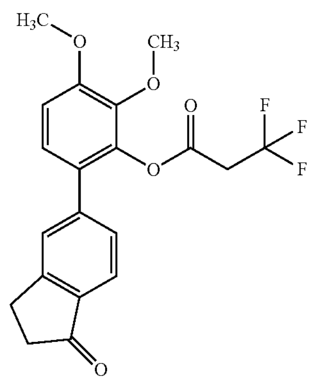 [SMILES: COc1ccc(-c2ccc3c(c2)CCC3=O)c(OC(=O)CC(F)(F)F)c1OC] | [2,3-dimethoxy-6-(1-oxoindan-5-yl)phenyl] 3,3,3-trifluoropropanoate | 2.47 | 394.10 |
| 455 | 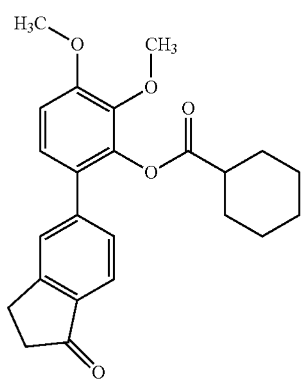 [SMILES: COc1ccc(-c2ccc3c(c2)CCC3=O)c(OC(=O)C2CCCCC2)c1OC] | [2,3-dimethoxy-6-(1-oxoindan-5-yl)phenyl] cyclohexanecarboxylate | 2.72 | 394.18 |
| 456 | 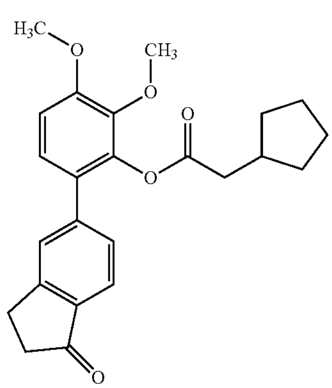 [SMILES: COc1ccc(-c2ccc3c(c2)CCC3=O)c(OC(=O)CC2CCCC2)c1OC] | [2,3-dimethoxy-6-(1-oxoindan-5-yl)phenyl] 2-cyclopentylacetate | 2.72 | 394.18 |

-continued

| Compound | Structure | Compound Name | Retention Time (minutes) | Detected Mass (M) |
|---|---|---|---|---|
| 457 | 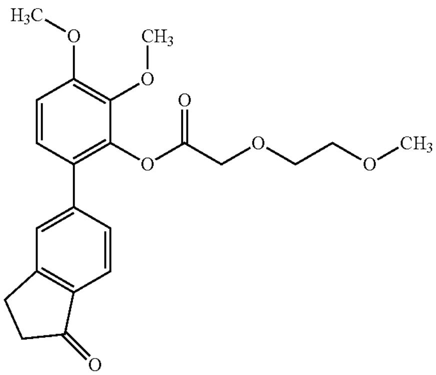 [SMILES: COCCOCC(=O)Oc1c(-c2ccc3c(c2)CCC3=O)ccc(OC)c1OC] | [2,3-dimethoxy-6-(1-oxoindan-5-yl)phenyl] 2-(2-methoxyethoxy)acetate | 2.30 | 400.15 |
| 458 | 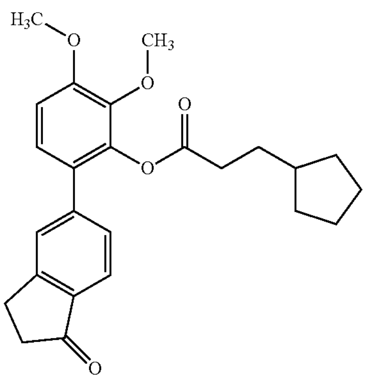 [SMILES: COc1ccc(-c2ccc3c(c2)CCC3=O)c(OC(=O)CCC2CCCC2)c1OC] | [2,3-dimethoxy-6-(1-oxoindan-5-yl)phenyl] 3-cyclopentylpropanoate | 2.80 | 408.19 |

Example 160

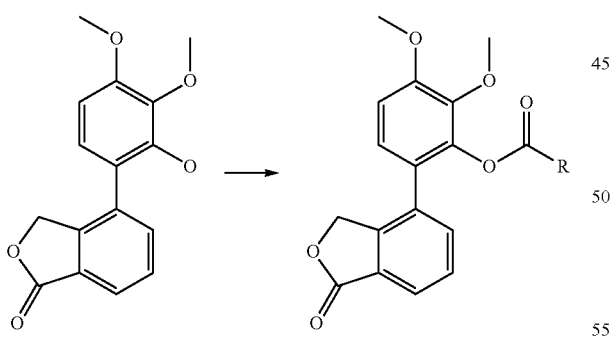

Acid chlorides (53 µmol) were added to solutions of 4-(2-hydroxy-3,4-dimethoxyphenyl)isobenzofuran-1(3H)-one (Compound 304)(35 µmol) and DIPEA (53 µmol) in dichloroethane (0.5 mL). The mixtures were shanked at room temperature overnight and subsequently evaporated to dryness- The crude reaction mixtures were re-dissolved in DMF (0.3 mL), and HPLC purification yielded the below compounds, which were characterised by analytical UPLC-MS.

| Compound | Structure | Compound Name | Retention Time (minutes) | Detected Mass (M) |
|---|---|---|---|---|
| 459 | 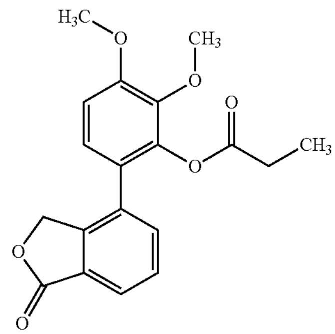 [SMILES: CCC(=O)Oc1c(-c2cccc3c2COC3=O)ccc(OC)c1OC] | [2,3-dimethoxy-6-(1-oxo-3H-isobenzofuran-4-yl)phenyl] propanoate | 2.37 | 342.11 |
| 460 | 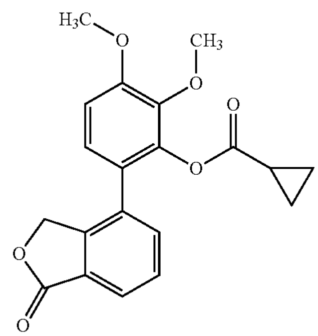 [SMILES: COc1ccc(-c2cccc3c2COC3=O)c(OC(=O)C2CC2)c1OC] | [2,3-dimethoxy-6-(1-oxo-3H-isobenzofuran-4-yl)phenyl] cyclopropanecarboxylate | 2.37 | 354.11 |
| 461 | 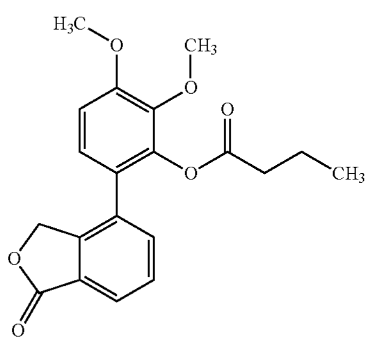 [SMILES: CCCC(=O)Oc1c(-c2cccc3c2COC3=O)ccc(OC)c1OC] | [2,3-dimethoxy-6-(1-oxo-3H-isobenzofuran-4-yl)phenyl] butanoate | 2.46 | 356.13 |
| 462 | 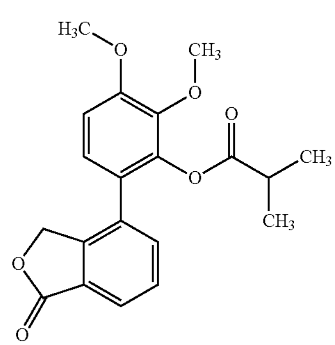 [SMILES: COc1ccc(-c2cccc3c2COC3=O)c(OC(=O)C(C)C)c1OC] | [2,3-dimethoxy-6-(1-oxo-3H-isobenzofuran-4-yl)phenyl] 2-methylpropanoate | 2.46 | 356.13 |

-continued

| Compound | Structure | Compound Name | Retention Time (minutes) | Detected Mass (M) |
|---|---|---|---|---|
| 463 | 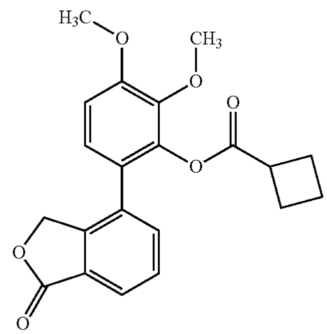 [SMILES: COc1ccc(-c2cccc3c2COC3=O)c(OC(=O)C2CCC2)c1OC] | [2,3-dimethoxy-6-(1-oxo-3H-isobenzofuran-4-yl)phenyl] cyclobutanecarboxylate | 2.48 | 368.13 |
| 464 | 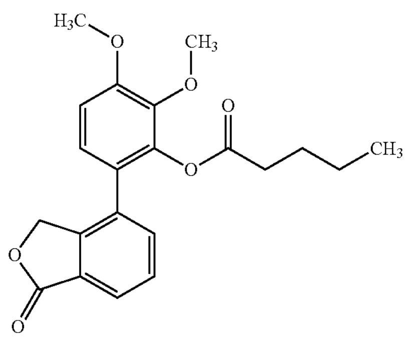 [SMILES: CCCCC(=O)Oc1c(-c2cccc3c2COC3=O)ccc(OC)c1OC] | [2,3-dimethoxy-6-(1-oxo-3H-isobenzofuran-4-yl)phenyl] pentanoate | 2.54 | 370.14 |
| 465 | 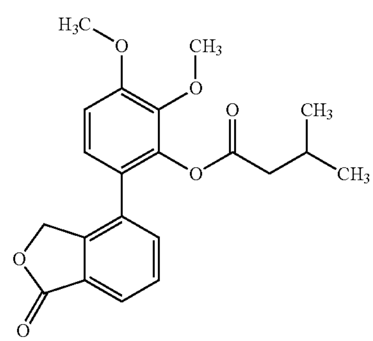 [SMILES: COc1ccc(-c2cccc3c2COC3=O)c(OC(=O)CC(C)C)c1OC] | [2,3-dimethoxy-6-(1-oxo-3H-isobenzofuran-4-yl)phenyl] 3-methylbutanoate | 2.54 | 370.14 |
| 466 | 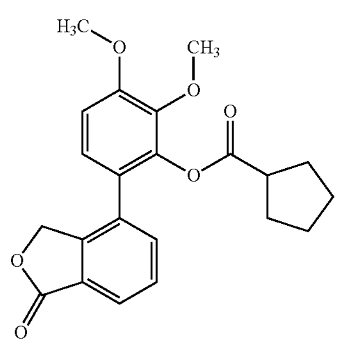 [SMILES: COc1ccc(-c2cccc3c2COC3=O)c(OC(=O)C2CCCC2)c1OC] | [2,3-dimethoxy-6-(1-oxo-3H-isobenzofuran-4-yl)phenyl] cyclopentanecarboxylate | 2.57 | 382.14 |

-continued

| Compound | Structure | Compound Name | Retention Time (minutes) | Detected Mass (M) |
|---|---|---|---|---|
| 467 | 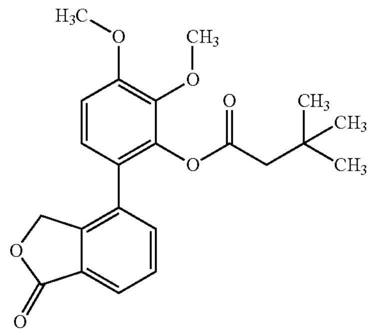 [SMILES: COc1ccc(-c2cccc3c2COC3=O)c(OC(=O)CC(C)(C)C)c1OC] | [2,3-dimethoxy-6-(1-oxo-3H-isobenzofuran-4-yl)phenyl] 3,3-dimethylbutanoate | 2.62 | 384.16 |
| 468 | 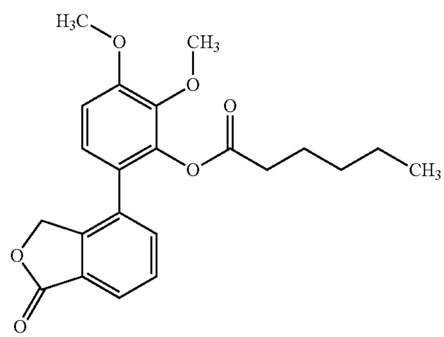 [SMILES: CCCCCC(=O)Oc1c(-c2cccc3c2COC3=O)ccc(OC)c1OC] | [2,3-dimethoxy-6-(1-oxo-3H-isobenzofuran-4-yl)phenyl] hexanoate | 2.63 | 384.16 |
| 469 | 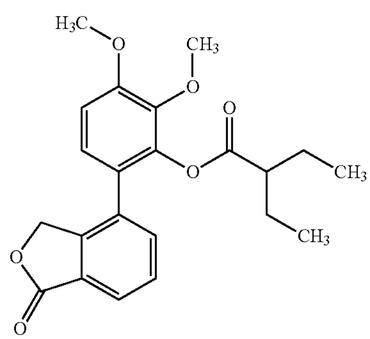 [SMILES: CCC(CC)C(=O)Oc1c(-c2cccc3c2COC3=O)ccc(OC)c1OC] | [2,3-dimethoxy-6-(1-oxo-3H-isobenzofuran-4-yl)phenyl] 2-ethylbutanoate | 2.62 | 384.16 |
| 470 | 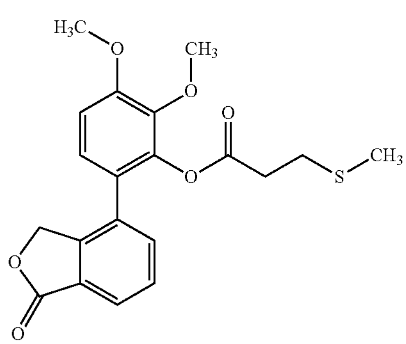 [SMILES: COc1ccc(-c2cccc3c2COC3=O)c(OC(=O)CCSC)c1OC] | [2,3-dimethoxy-6-(1-oxo-3H-isobenzofuran-4-yl)phenyl] 3-methylsulfanylpropanoate | 2.41 | 388.10 |

-continued

| Compound | Structure | Compound Name | Retention Time (minutes) | Detected Mass (M) |
|---|---|---|---|---|
| 471 | 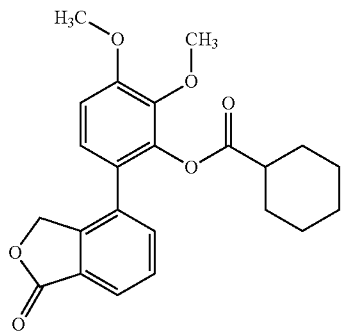 [SMILES: COc1ccc(-c2cccc3c2COC3=O)c(OC(=O)C2CCCCC2)c1OC] | [2,3-dimethoxy-6-(1-oxo-3H-isobenzofuran-4-yl)phenyl] cyclohexanecarboxylate | 2.65 | 396.16 |
| 472 | 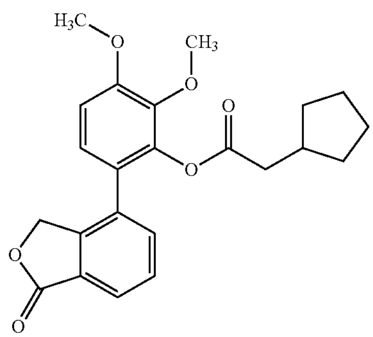 [SMILES: COc1ccc(-c2cccc3c2COC3=O)c(OC(=O)CC2CCCC2)c1OC] | [2,3-dimethoxy-6-(1-oxo-3H-isobenzofuran-4-yl)phenyl] 2-cyclopentylacetate | 2.65 | 396.16 |
| 473 | 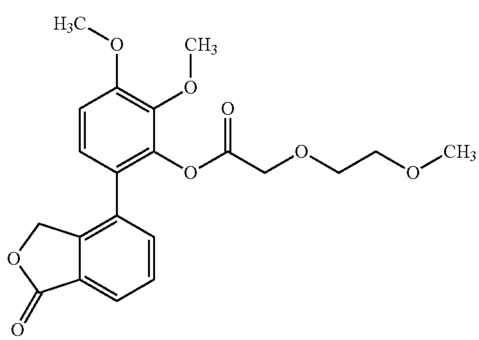 [SMILES: COCCOCC(=O)Oc1c(-c2cccc3c2COC3=O)ccc(OC)c1OC] | [2,3-dimethoxy-6-(1-oxo-3H-isobenzofuran-4-yl)phenyl] 2-(2-methoxyethoxy)acetate | 2.25 | 402.13 |
| 474 | 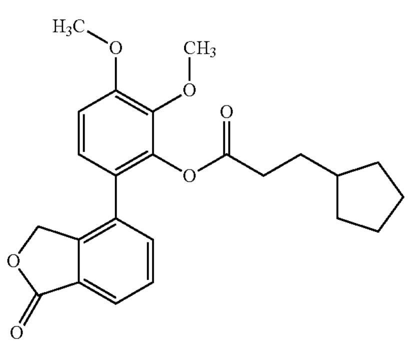 [SMILES: COc1ccc(-c2cccc3c2COC3=O)c(OC(=O)CCC2CCCC2)c1OC] | [2,3-dimethoxy-6-(1-oxo-3H-isobenzofuran-4-yl)phenyl] 3-cyclopentylpropanoate | 2.72 | 410.17 |

Example 161

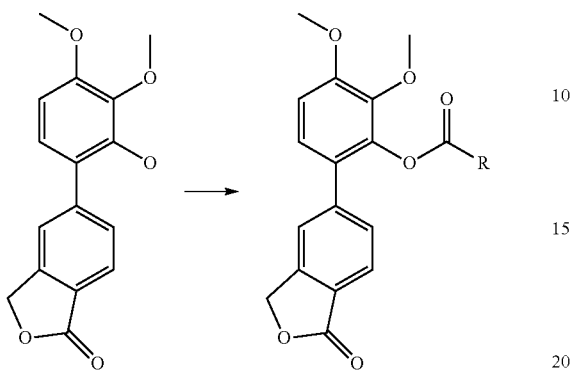

Acid chlorides (53 µmol) were added to solutions of 5-(2-hydroxy-3,4-dimethoxyphenyl)isobenzofuran-1(3H)-one (Compound 306) (35 µmol) and DIPEA (53 µmol) in dichloroethane (0.5 mL). The mixtures were shanked at room temperature overnight and subsequently evaporated to dryness. The crude reaction mixtures were re-dissolved in DMF (0.3 mL), and HPLC purification yielded the below compounds, which were characterized by analytical UPLC-MS

| Compound | Structure | Compound Name | Retention Time (minutes) | Detected Mass (M) |
|---|---|---|---|---|
| 475 | 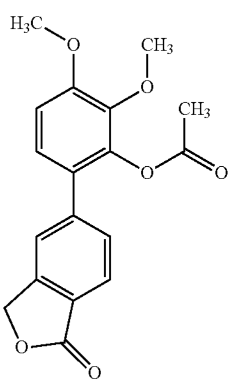 [SMILES: COc1ccc(-c2ccc3c(c2)COC3=O)c(OC(C)=O)c1OC] | [2,3-dimethoxy-6-(1-oxo-3H-isobenzofuran-5-yl)phenyl] acetate | 2.27 | 328.09 |
| 476 | 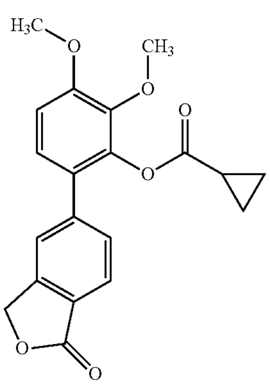 [SMILES: COc1ccc(-c2ccc3c(c2)COC3=O)c(OC(=O)C2CC2)c1OC] | [2,3-dimethoxy-6-(1-oxo-3H-isobenzofuran-5-yl)phenyl] cyclopropanecarboxylate | 2.36 | 354.11 |

-continued

| Compound | Structure | Compound Name | Retention Time (minutes) | Detected Mass (M) |
|---|---|---|---|---|
| 477 | 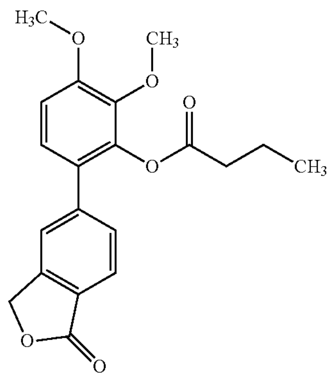 [SMILES: CCCC(=O)Oc1c(-c2ccc3c(c2)COC3=O)ccc(OC)c1OC] | [2,3-dimethoxy-6-(1-oxo-3H-isobenzofuran-5-yl)phenyl] butanoate | 2.45 | 356.13 |
| 478 | 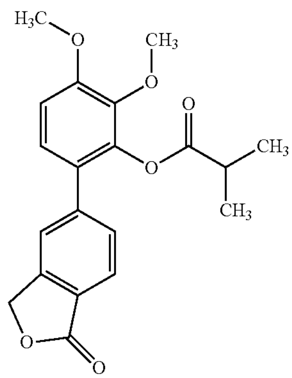 [SMILES: COc1ccc(-c2ccc3c(c2)COC3=O)c(OC(=O)C(C)C)c1OC] | [2,3-dimethoxy-6-(1-oxo-3H-isobenzofuran-5-yl)phenyl] 2-methylpropanoate | 2.44 | 356.13 |
| 479 | 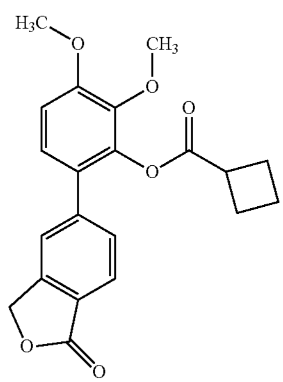 | [2,3-dimethoxy-6-(1-oxo-3H-isobenzofuran-5-yl)phenyl] cyclobutanecarboxylate | 2.47 | 368.13 |
| 480 | 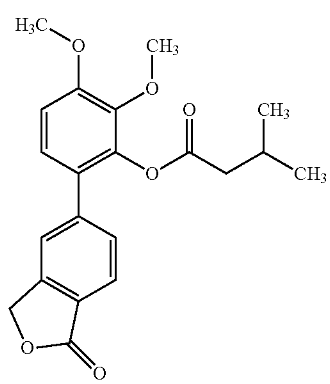 [SMILES: COc1ccc(-c2ccc3c(c2)COC3=O)c(OC(=O)CC(C)C)c1OC] | [2,3-dimethoxy-6-(1-oxo-3H-isobenzofuran-5-yl)phenyl] 3-methylbutanoate | 2.53 | 370.14 |

-continued
| Compound | Structure | Compound Name | Retention Time (minutes) | Detected Mass (M) |
|---|---|---|---|---|
| 481 | 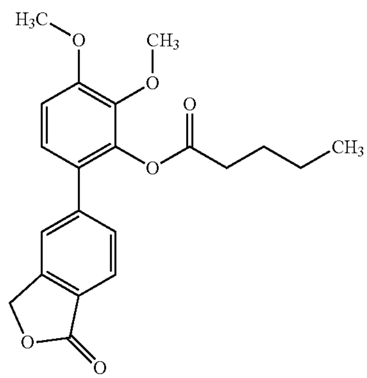 | [2,3-dimethoxy-6-(1-oxo-3H-isobenzofuran-5-yl)phenyl] pentanoate | 2.53 | 370.14 |
| 482 | 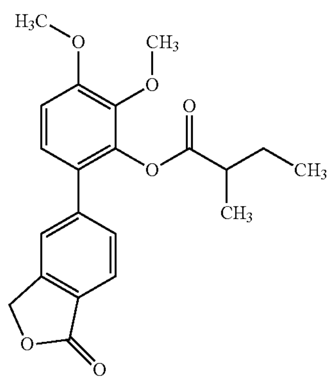 [SMILES: CCC(C)C(=O)Oc1c(-c2ccc3c(c2)COC3=O)ccc(OC)c1OC] | [2,3-dimethoxy-6-(1-oxo-3H-isobenzofuran-5-yl)phenyl] 2-methylbutanoate | 2.52 | 370.14 |
| 483 | 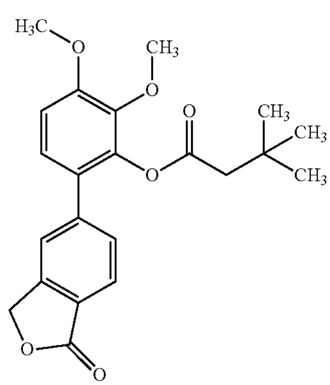 [SMILES: COc1ccc(-c2ccc3c(c2)COC3=O)c(OC(=O)CC(C)(C)C)c1OC] | [2,3-dimethoxy-6-(1-oxo-3H-isobenzofuran-5-yl)phenyl] 3,3-dimethylbutanoate | 2.61 | 384.16 |
| 484 | 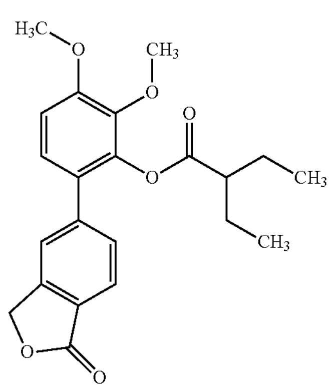 [SMILES: CCC(CC)C(=O)Oc1c(-c2ccc3c(c2)COC3=O)ccc(OC)c1OC] | [2,3-dimethoxy-6-(1-oxo-3H-isobenzofuran-5-yl)phenyl] 2-ethylbutanoate | 2.60 | 384.16 |

-continued

| Compound | Structure | Compound Name | Retention Time (minutes) | Detected Mass (M) |
|---|---|---|---|---|
| 485 | 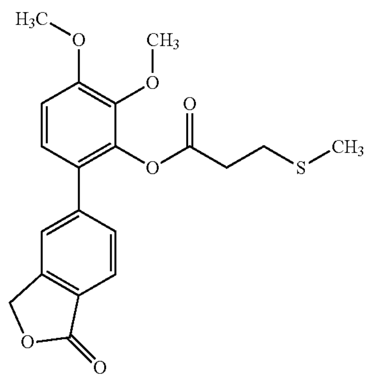 [SMILES: COc1ccc(-c2ccc3c(c2)COC3=O)c(OC(=O)CCSC)c1OC] | [2,3-dimethoxy-6-(1-oxo-3H-isobenzofuran-5-yl)phenyl] 3-methylsulfanylpropanoate | 2.41 | 388.10 |
| 486 | 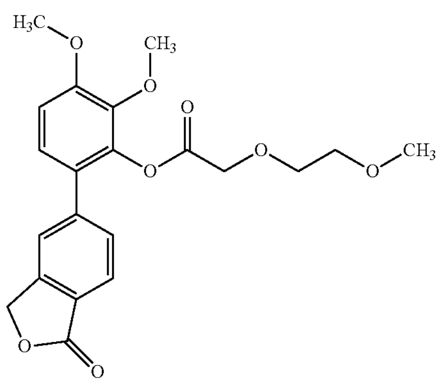 [SMILES: COCCOCC(=O)Oc1c(-c2ccc3c(c2)COC3=O)ccc(OC)c1OC] | [2,3-dimethoxy-6-(1-oxo-3H-isobenzofuran-5-yl)phenyl] 2-(2-methoxyethoxy)acetate | 2.25 | 402.13 |
| 487 | 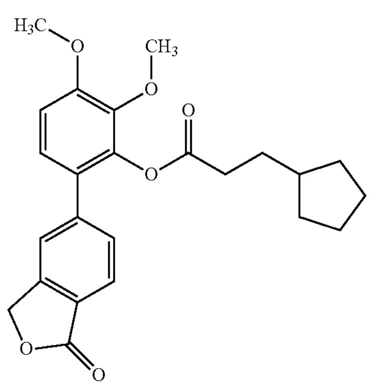 [SMILES: COc1ccc(-c2ccc3c(c2)COC3=O)c(OC(=O)CCC2CCCC2)c1OC] | [2,3-dimethoxy-6-(1-oxo-3H-isobenzofuran-5-yl)phenyl] 3-cyclopentylpropanoate | 2.71 | 410.17 |

Example 162

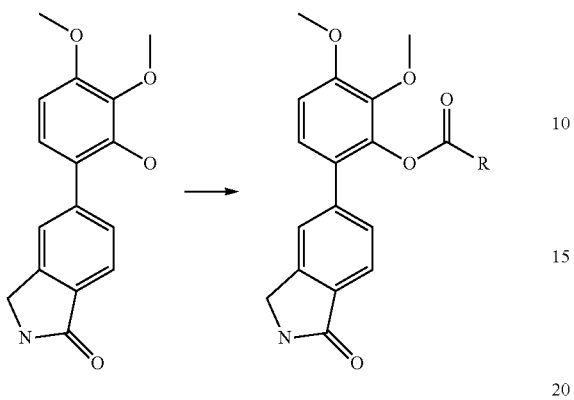

Acid chlorides (53 μmol) were added to solutions of 5-(2-hydroxy-3,4-dimethoxyphenyl)isoindolin-1-one (Compound 307) (35 μmol) and DIPEA (53 μmol) in dichloroethane (0.5 mL). The mixtures were shanked at room temperature overnight and subsequently evaporated to dryness. The crude reaction mixtures were re-dissolved in DMF (0.3 mL), and HPLC purification yielded the below compounds, which were characterized by analytical UPLC-MS

| Compound | Structure | Compound Name | Retention Time (minutes) | Detected Mass (M) |
|---|---|---|---|---|
| 488 | 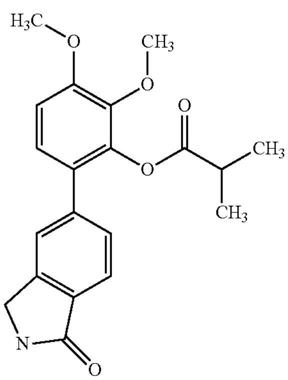 [SMILES: COc1ccc(-c2ccc3c(c2)CNC3=O)c(OC(=O)C(C)C)c1OC] | [2,3-dimethoxy-6-(1-oxoisoindolin-5-yl)phenyl] 2-methylpropanoate | 2.48 | 355.14 |
| 489 | 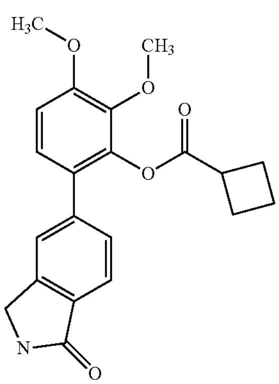 | [2,3-dimethoxy-6-(1-oxoisoindolin-5-yl)phenyl] cyclobutanecarboxylate | 2.52 | 367.14 |

-continued
| Compound | Structure | Compound Name | Retention Time (minutes) | Detected Mass (M) |
|---|---|---|---|---|
| 490 | 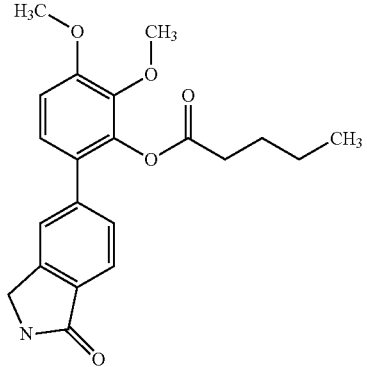 | [2,3-dimethoxy-6-(1-oxoisoindolin-5-yl)phenyl] pentanoate | 2.57 | 369.16 |
| 491 | 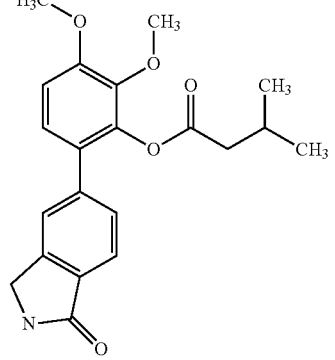 | [2,3-dimethoxy-6-(1-oxoisoindolin-5-yl)phenyl] 3-methylbutanoate | 2.56 | 369.16 |
| 492 | 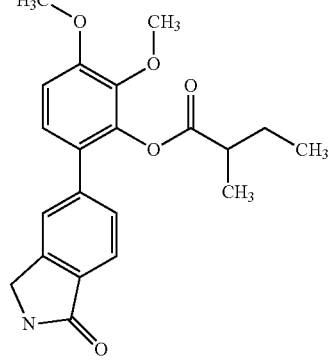 | [2,3-dimethoxy-6-(1-oxoisoindolin-5-yl)phenyl] 2-methylbutanoate | 2.56 | 369.16 |
| 493 | 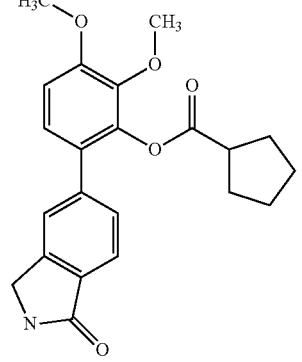 | [2,3-dimethoxy-6-(1-oxoisoindolin-5-yl)phenyl] cyclopentanecarboxylate | 2.61 | 381.16 |

-continued

| Compound | Structure | Compound Name | Retention Time (minutes) | Detected Mass (M) |
|---|---|---|---|---|
| 494 | 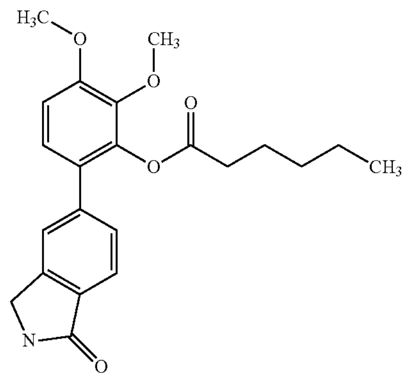 | [2,3-dimethoxy-6-(1-oxoisoindolin-5-yl)phenyl] hexanoate | 2.67 | 383.17 |
| 495 | 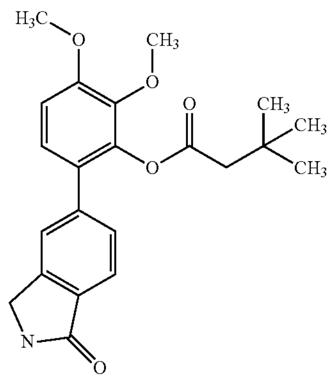 | [2,3-dimethoxy-6-(1-oxoisoindolin-5-yl)phenyl] 3,3-dimethylbutanoate | 2.66 | 383.17 |
| 496 | 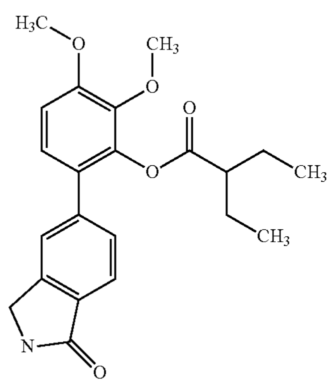 [SMILES: CCC(CC)C(=O)Oc1c(-c2ccc3c(c2)CNC3=O)ccc(OC)c1OC] | [2,3-dimethoxy-6-(1-oxoisoindolin-5-yl)phenyl] 2-ethylbutanoate | 2.64 | 383.17 |
| 497 | 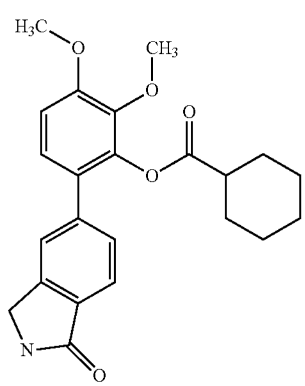 [SMILES: COc1ccc(-c2ccc3c(c2)CNC3=O)c(OC(=O)C2CCCCC2)c1OC] | [2,3-dimethoxy-6-(1-oxoisoindolin-5-yl)phenyl] cyclohexanecarboxylate | 2.69 | 395.17 |

| Compound | Structure | Compound Name | Retention Time (minutes) | Detected Mass (M) |
|---|---|---|---|---|
| 498 | 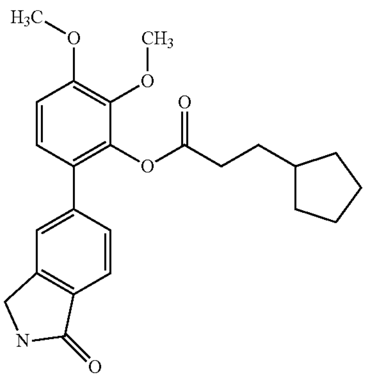 | [2,3-dimethoxy-6-(1-oxoisoindolin-5-yl)phenyl] 3-cyclopentylpropanoate | 2.78 | 409.19 |

Example 163

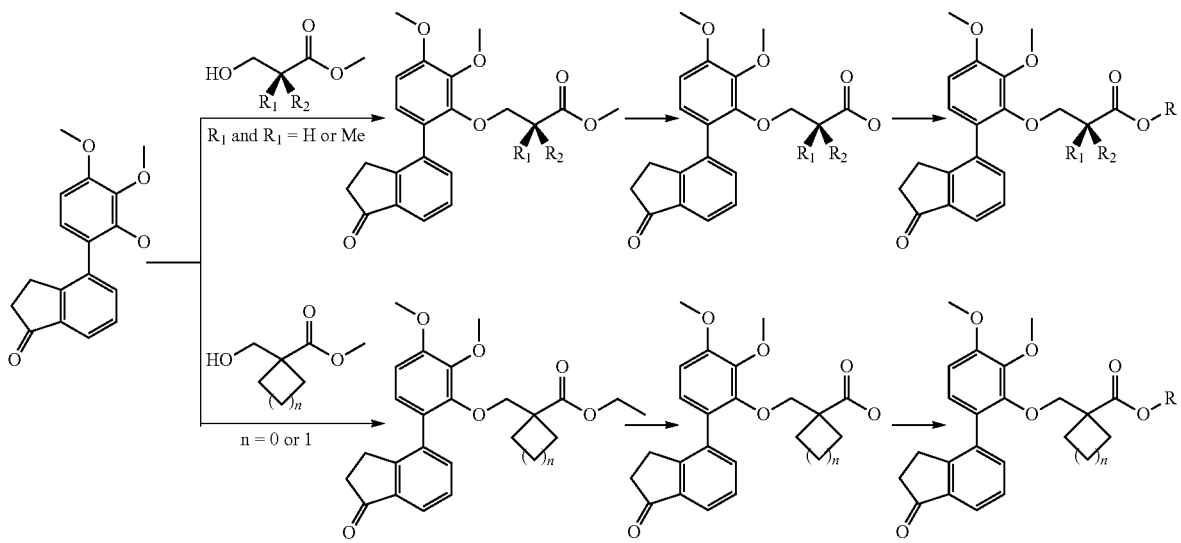

A solution of 4-(2-hydroxy-3,4-dimethoxy-phenyl)-indan-1-one (Compound 303) (1.00 mmol), the alkyl 3-hydroxypropanoate derivative (1.00 mmol) and triphenylphosphine (3.00 mmol) in THF (4 mL) was flushed with argon and cooled in an icebath, before a solution of DEAD (3.00 mmol) in THF (3.2 mL) was added dropwise. Subsequently the icebath was removed and the mixture was stirred at room temperature for 3 hours. The crude reaction mixture was diluted with DCM, washed with 1M HCl, water and evaporated to dryness. Column chromatography (silica gel, 0-100% ethyl acetate in pet ether) afforded the desired ester intermediate.

The ester intermediate was stirred in a mixture of 1 N aqueous LiOH (4 mL) and THF (4 mL) at room temperature overnight. Then water was added and the aqueous phase washed with EtOAc, acidified to pH 1 with concentrated HCl and extracted four times with DCM. Evaporation to dryness of the organic phase afforded the desired carboxylic acid.

Solutions of the carboxylic acid (40 µmol), EDCI (80 µmol), DMAP (80 µmol) and the selected alcohols in DCM (700 µL) were stirred overnight at room temperature, before they were evaporated to dryness. The crude reaction mixtures were re-dissolved in DMF (0.3 mL), and HPLC purification yielded the below compounds, which were characterized by analytical UPLC-MS

| Compound | Structure | Compound Name | Retention Time (minutes) | Detected Mass |
|---|---|---|---|---|
| 499 | 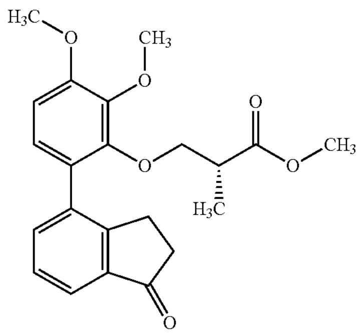 [SMILES: COC(=O)[C@H](C)COc1c(-c2cccc3c2CCC3=O)ccc(OC)c1OC] | methyl (2R)-3-[2,3-dimethoxy-6-(1-oxoindan-4-yl)phenoxy]-2-methyl-propanoate | 2.46 | 384.16 |
| 500 | 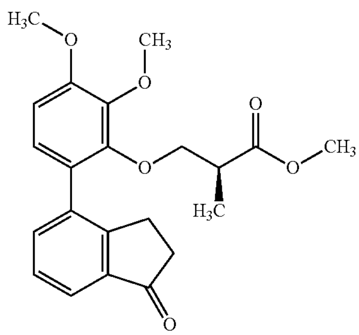 [SMILES: COC(=O)[C@@H](C)COc1c(-c2cccc3c2CCC3=O)ccc(OC)c1OC] | methyl (2S)-3-[2,3-dimethoxy-6-(1-oxoindan-4-yl)phenoxy]-2-methyl-propanoate | 2.46 | 384.16 |
| 501 | 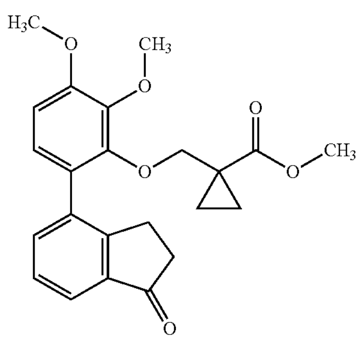 [SMILES: COC(=O)C1(COc2c(-c3cccc4c3CCC4=O)ccc(OC)c2OC)CC1] | methyl 1-[[2,3-dimethoxy-6-(1-oxoindan-4-yl)phenoxy]methyl]cyclopropanecarboxylate | 2.47 | 396.16 |
| 502 | 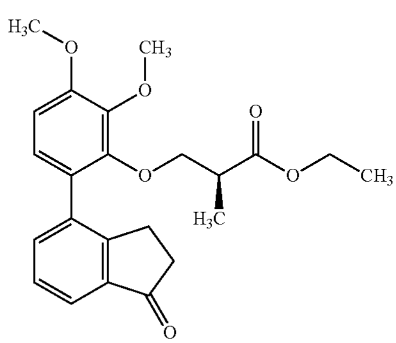 [SMILES: CCOC(=O)[C@@H](C)COc1c(-c2cccc3c2CCC3=O)ccc(OC)c1OC] | ethyl (2S)-3-[2,3-dimethoxy-6-(1-oxoindan-4-yl)phenoxy]-2-methyl-propanoate | 2.55 | 398.17 |

-continued

| Compound | Structure | Compound Name | Retention Time (minutes) | Detected Mass |
|---|---|---|---|---|
| 503 | 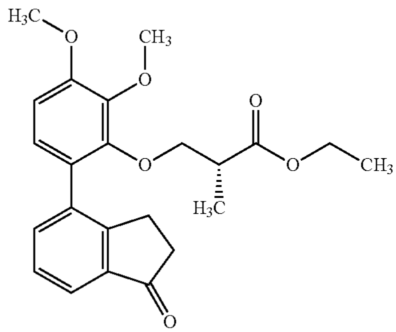 [SMILES: CCOC(=O)[C@H](C)COc1c(-c2cccc3c2CCC3=O)ccc(OC)c1OC] | ethyl (2R)-3-[2,3-dimethoxy-6-(1-oxoindan-4-yl)phenoxy]-2-methyl-propanoate | 2.55 | 398.17 |
| 504 | 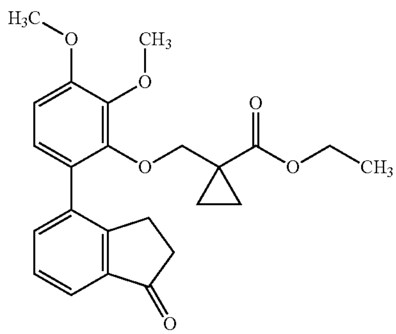 [SMILES: CCOC(=O)C1(COc2c(-c3cccc4c3CCC4=O)ccc(OC)c2OC)CC1] | ethyl 1-[[2,3-dimethoxy-6-(1-oxoindan-4-yl)phenoxy]methyl]cyclopropanecarboxylate | 2.56 | 410.17 |
| 505 | 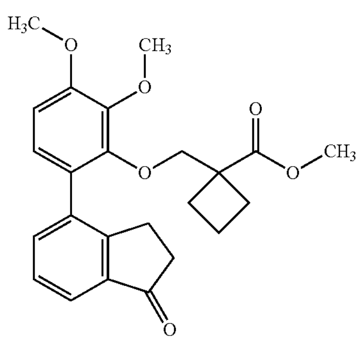 [SMILES: COC(=O)C1(COc2c(-c3cccc4c3CCC4=O)ccc(OC)c2OC)CCC1] | methyl 1-[[2,3-dimethoxy-6-(1-oxoindan-4-yl)phenoxy]methyl]cyclobutanecarboxylate | 2.58 | 410.17 |
| 506 | 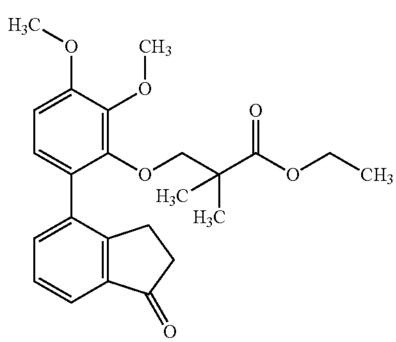 [SMILES: CCOC(=O)C(C)(C)COc1c(-c2cccc3c2CCC3=O)ccc(OC)c1OC] | ethyl 3-[2,3-dimethoxy-6-(1-oxoindan-4-yl)phenoxy]-2,2-dimethyl-propanoate | 2.65 | 412.19 |

-continued

| Compound | Structure | Compound Name | Retention Time (minutes) | Detected Mass |
|---|---|---|---|---|
| 507 | 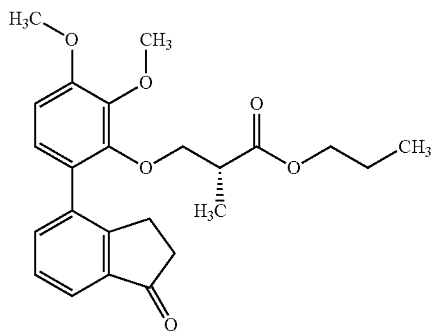 [SMILES: CCCOC(=O)[C@H](C)COc1c(-c2cccc3c2CCC3=O)ccc(OC)c1OC] | propyl (2R)-3-[2,3-dimethoxy-6-(1-oxoindan-4-yl)phenoxy]-2-methyl-propanoate | 2.65 | 412.19 |
| 508 | 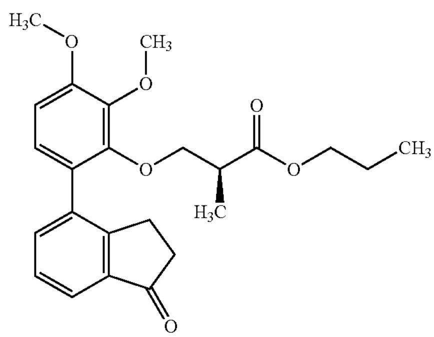 [SMILES: CCCOC(=O)[C@@H](C)COc1c(-c2cccc3c2CCC3=O)ccc(OC)c1OC] | propyl (2S)-3-[2,3-dimethoxy-6-(1-oxoindan-4-yl)phenoxy]-2-methyl-propanoate | 2.65 | 412.19 |
| 509 | 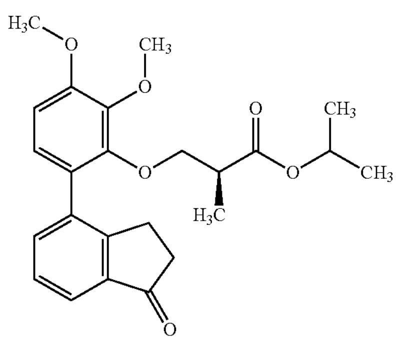 [SMILES: COc1ccc(-c2cccc3c2CCC3=O)c(OC[C@H](C)C(=O)OC(C)C)c1OC] | isopropyl (2S)-3-[2,3-dimethoxy-6-(1-oxoindan-4-yl)phenoxy]-2-methyl-propanoate | 2.64 | 412.19 |
| 510 | 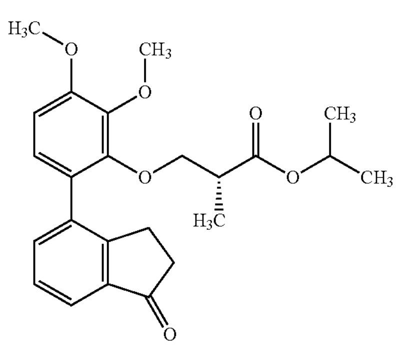 [SMILES: COc1ccc(-c2cccc3c2CCC3=O)c(OC[C@@H](C)C(=O)OC(C)C)c1OC] | isopropyl (2R)-3-[2,3-dimethoxy-6-(1-oxoindan-4-yl)phenoxy]-2-methyl-propanoate | 2.64 | 412.19 |

-continued

| Compound | Structure | Compound Name | Retention Time (minutes) | Detected Mass |
|---|---|---|---|---|
| 511 | 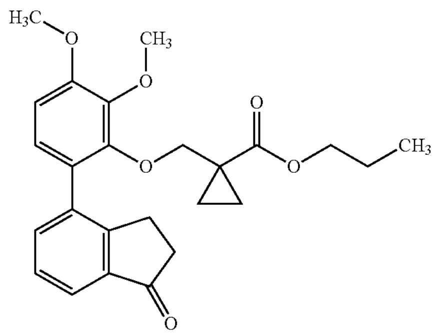 [SMILES: CCCOC(=O)C1(COc2c(-c3cccc4c3CCC4=O)ccc(OC)c2OC)CC1] | propyl 1-[[2,3-dimethoxy-6-(1-oxoindan-4-yl)phenoxy]methyl]cyclopropanecarboxylate | 2.66 | 424.19 |
| 512 | 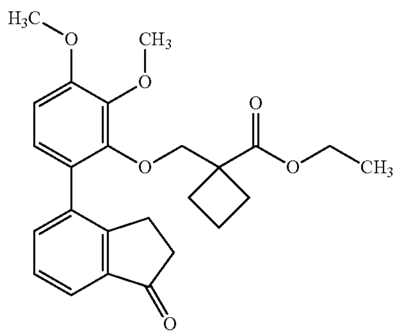 [SMILES: CCOC(=O)C1(COc2c(-c3cccc4c3CCC4=O)ccc(OC)c2OC)CCC1] | ethyl 1-[[2,3-dimethoxy-6-(1-oxoindan-4-yl)phenoxy]methyl]cyclobutanecarboxylate | 2.67 | 424.19 |
| 513 | 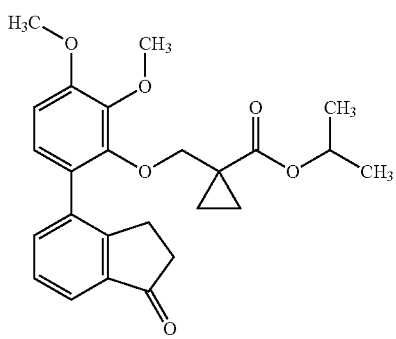 [SMILES: COc1ccc(-c2cccc3c2CCC3=O)c(OCC2(C(=O)OC(C)C)CC2)c1OC] | isopropyl 1-[[2,3-dimethoxy-6-(1-oxoindan-4-yl)phenoxy]methyl]cyclobutanecarboxylate | 2.65 | 424.19 |
| 514 | 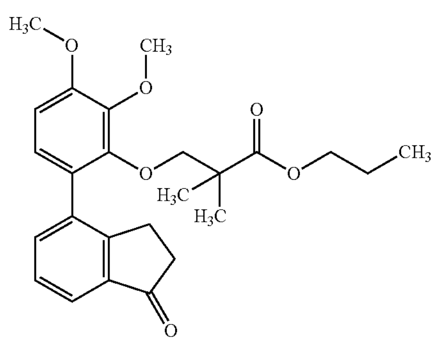 [SMILES: CCCOC(=O)C(C)(C)COc1c(-c2cccc3c2CCC3=O)ccc(OC)c1OC] | propyl 3-[2,3-dimethoxy-6-(1-oxoindan-4-yl)phenoxy]-2,2-dimethyl-propanoate | 2.74 | 426.2 |

-continued

| Compound | Structure | Compound Name | Retention Time (minutes) | Detected Mass |
|---|---|---|---|---|
| 515 | 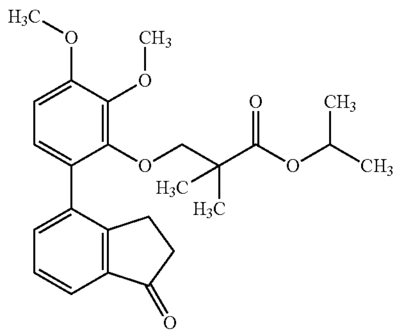 [SMILES: COc1ccc(-c2cccc3c2CCC3=O)c(OCC(C)(C)C(=O)OC(C)C)c1OC] | isopropyl 3-[2,3-dimethoxy-6-(1-oxoindan-4-yl)phenoxy]-2,2-dimethyl-propanoate | 2.74 | 426.2 |
| 516 | 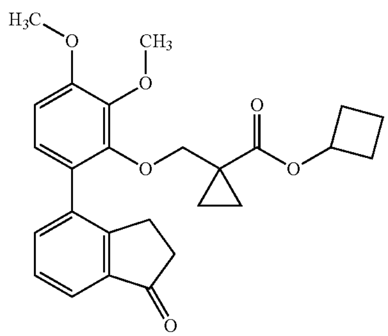 [SMILES: COc1ccc(-c2cccc3c2CCC3=O)c(OCC2(C(=O)OC3CCC3)CC2)c1OC] | cyclobutyl 1-[[2,3-dimethoxy-6-(1-oxoindan-4-yl)phenoxy]methyl]cyclopropanecarboxylate | 2.69 | 436.19 |
| 517 | 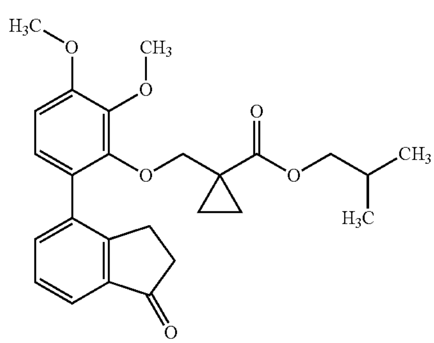 [SMILES: COc1ccc(-c2cccc3c2CCC3=O)c(OCC2(C(=O)OCC(C)C)CC2)c1OC] | isobutyl 1-[[2,3-dimethoxy-6-(1-oxoindan-4-yl)phenoxy]methyl]cyclopropanecarboxylate | 2.74 | 438.2 |
| 518 | 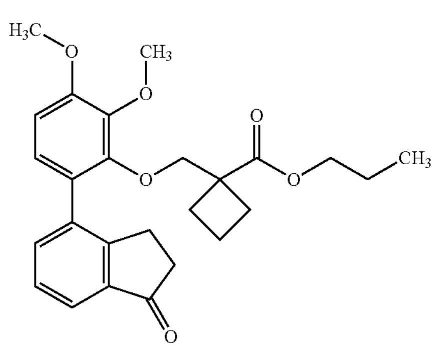 [SMILES: CCCOC(=O)C1(COc2c(-c3cccc4c3CCC4=O)ccc(OC)c2OC)CCC1] | propyl 1-[[2,3-dimethoxy-6-(1-oxoindan-4-yl)phenoxy]methyl]cyclobutanecarboxylate | 2.76 | 438.2 |

-continued
| Compound | Structure | Compound Name | Retention Time (minutes) | Detected Mass |
|---|---|---|---|---|
| 519 | 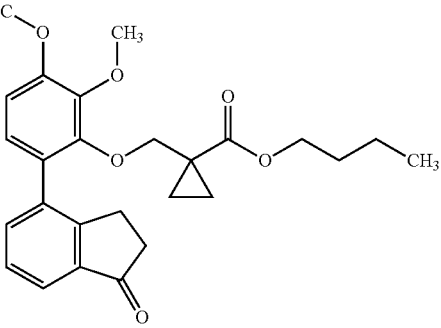 | butyl 1-[[2,3-dimethoxy-6-(1-oxoindan-4-yl)phenoxy]methyl]cyclopropanecarboxylate | 2.75 | 438.2 |
| 520 | 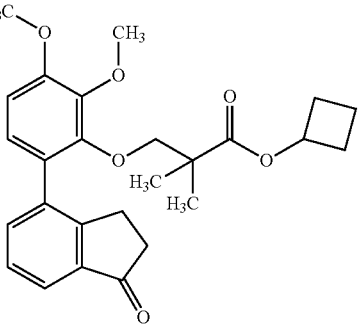 | cyclobutyl 3-[2,3-dimethoxy-6-(1-oxoindan-4-yl)phenoxy]-2,2-dimethyl-propanoate | 2.78 | 438.2 |
| 521 | 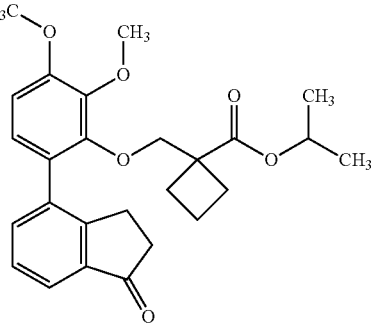 | isopropyl 1-[[2,3-dimethoxy-6-(1-oxoindan-4-yl)phenoxy]methyl]cyclobutanecarboxylate | 2.76 | 438.2 |
| 522 | 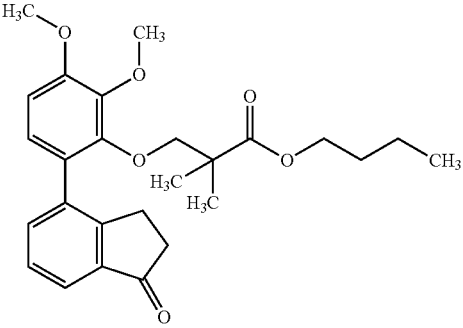 [SMILES: CCCCOC(=O)C(C)(C)COc1c(-c2cccc3c2CCC3=O)ccc(OC)c1OC] | butyl 3-[2,3-dimethoxy-6-(1-oxoindan-4-yl)phenoxy]-2,2-dimethyl-propanoate | 2.83 | 440.22 |

-continued

| Compound | Structure | Compound Name | Retention Time (minutes) | Detected Mass |
|---|---|---|---|---|
| 523 | 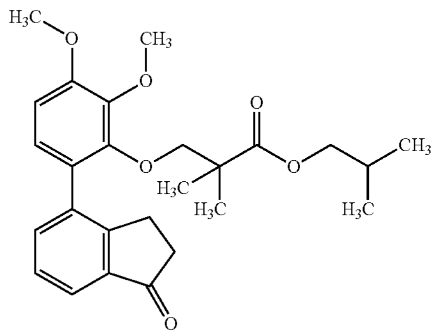 [SMILES: COc1ccc(-c2cccc3c2CCC3=O)c(OCC(C)(C)C(=O)OCC(C)C)c1OC] | isobutyl 3-[2,3-dimethoxy-6-(1-oxoindan-4-yl)phenoxy]-2,2-dimethyl-propanoate | 2.83 | 440.22 |
| 524 | 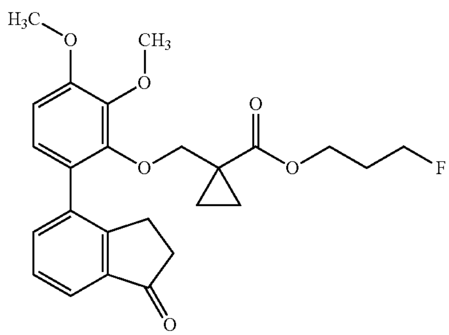 [SMILES: COc1ccc(-c2cccc3c2CCC3=O)c(OCC2(C(=O)OCCCF)CC2)c1OC] | 3-fluoropropyl 1-[[2,3-dimethoxy-6-(1-oxoindan-4-yl)phenoxy]methyl]cyclopropanecarboxylate | 2.54 | 442.18 |
| 525 | 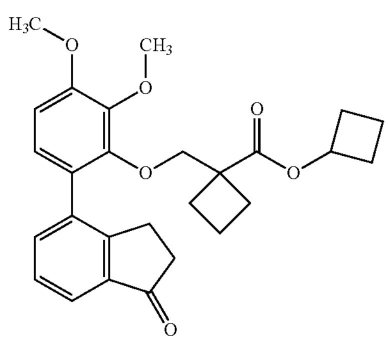 [SMILES: COc1ccc(-c2cccc3c2CCC3=O)c(OCC2(C(=O)OC3CCC3)CCC2)c1OC] | cyclobutyl 1-[[2,3-dimethoxy-6-(1-oxoindan-4-yl)phenoxy]methyl]cyclobutanecarboxylate | 2.79 | 450.2 |
| 526 | 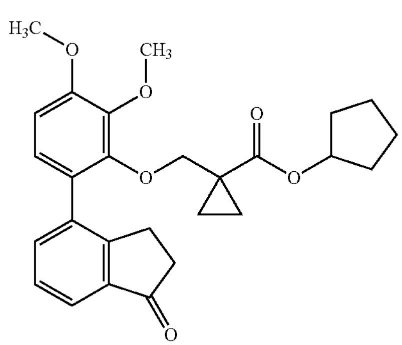 [SMILES: COc1ccc(-c2cccc3c2CCC3=O)c(OCC2(C(=O)OC3CCCC3)CC2)c1OC] | cyclopentyl 1-[[2,3-dimethoxy-6-(1-oxoindan-4-yl)phenoxy]methyl]cyclopropanecarboxylate | 2.76 | 450.2 |

| Compound | Structure | Compound Name | Retention Time (minutes) | Detected Mass |
|---|---|---|---|---|
| 527 | 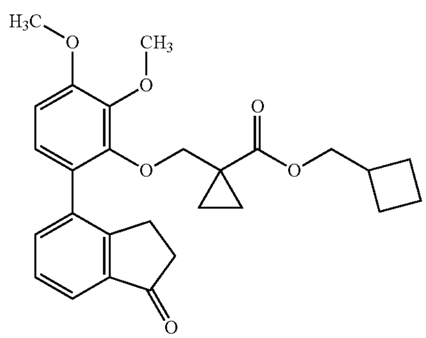 [SMILES: COc1ccc(-c2cccc3c2CCC3=O)c(OCC2(C(=O)OCC3CCC3)CC2)c1OC] | cyclobutylmethyl 1-[[2,3-dimethoxy-6-(1-oxoindan-4-yl)phenoxy]methyl]cyclopropanecarboxylate | 2.78 | 450.2 |
| 528 | 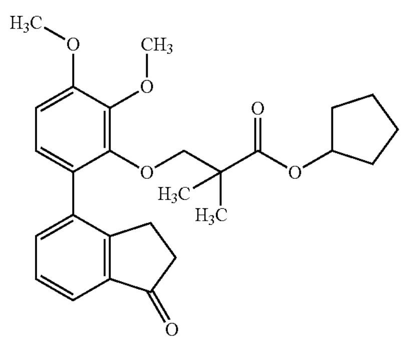 [SMILES: COc1ccc(-c2cccc3c2CCC3=O)c(OCC(C)(C)C(=O)OC2CCCC2)c1OC] | cyclopentyl 3-[2,3-dimethoxy-6-(1-oxoindan-4-yl)phenoxy]-2,2-dimethyl-propanoate | 2.85 | 452.22 |
| 529 | 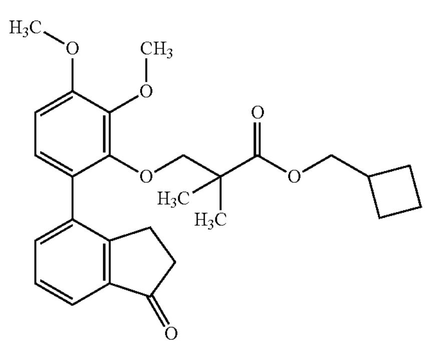 [SMILES: COc1ccc(-c2cccc3c2CCC3=O)c(OCC(C)(C)C(=O)OCC2CCC2)c1OC] | cyclobutylmethyl 3-[2,3-dimethoxy-6-(1-oxoindan-4-yl)phenoxy]-2,2-dimethyl-propanoate | 2.87 | 452.22 |
| 530 | 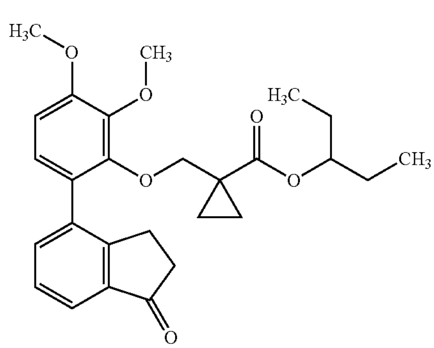 [SMILES: CCC(CC)OC(=O)C1(COc2c(-c3cccc4c3CCC4=O)ccc(OC)c2OC)CC1] | 1-ethylpropyl 1-[[2,3-dimethoxy-6-(1-oxoindan-4-yl)phenoxy]methyl]cyclopropanecarboxylate | 2.83 | 452.22 |

-continued

| Compound | Structure | Compound Name | Retention Time (minutes) | Detected Mass |
|---|---|---|---|---|
| 531 | 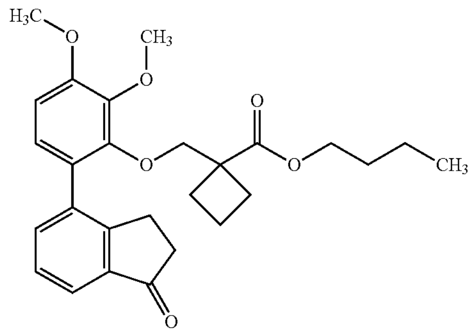 [SMILES: CCCCOC(=O)C1(COc2c(-c3cccc4c3CCC4=O)ccc(OC)c2OC)CCC1] | butyl 1-[[2,3-dimethoxy-6-(1-oxoindan-4-yl)phenoxy]methyl]cyclobutanecarboxylate | 2.85 | 452.22 |
| 532 | 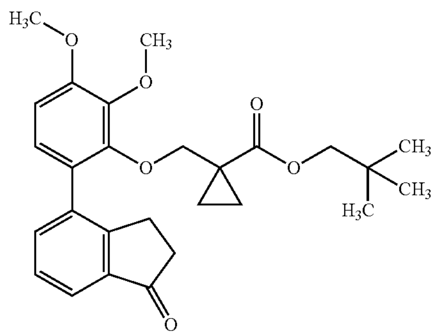 [SMILES: COc1ccc(-c2cccc3c2CCC3=O)c(OCC2(C(=O)OCC(C)(C)C)CC2)c1OC] | 2,2-dimethylpropyl 1-[[2,3-dimethoxy-6-(1-oxoindan-4-yl)phenoxy]methyl]cyclopropanecarboxylate | 2.81 | 452.22 |
| 533 | 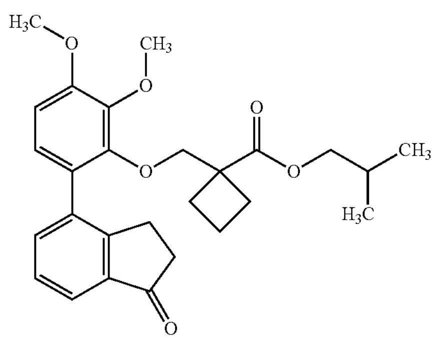 [SMILES: COc1ccc(-c2cccc3c2CCC3=O)c(OCC2(C(=O)OCC(C)C)CCC2)c1OC] | isobutyl 1-[[2,3-dimethoxy-6-(1-oxoindan-4-yl)phenoxy]methyl]cyclobutanecarboxylate | 2.85 | 452.22 |
| 534 | 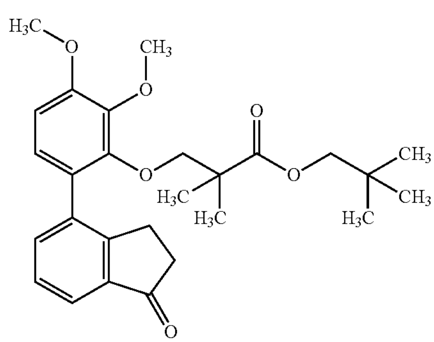 [SMILES: COc1ccc(-c2cccc3c2CCC3=O)c(OCC(C)(C)C(=O)OCC(C)(C)C)c1OC] | 2,2-dimethylpropyl 3-[2,3-dimethoxy-6-(1-oxoindan-4-yl)phenoxy]-2,2-dimethyl-propanoate | 2.89 | 454.24 |

-continued

| Compound | Structure | Compound Name | Retention Time (minutes) | Detected Mass |
|---|---|---|---|---|
| 535 | 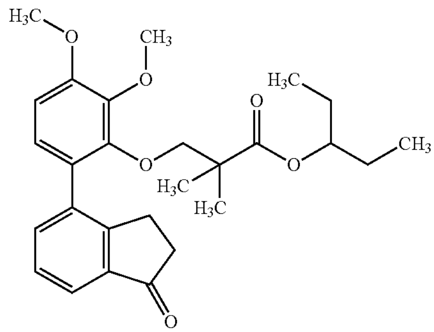 [SMILES: CCC(CC)OC(=O)C(C)(C)COc1c(-c2cccc3c2CCC3=O)ccc(OC)c1OC] | 1-ethylpropyl 3-[2,3-dimethoxy-6-(1-oxoindan-4-yl)phenoxy]-2,2-dimethyl-propanoate | 2.90 | 454.24 |
| 536 | 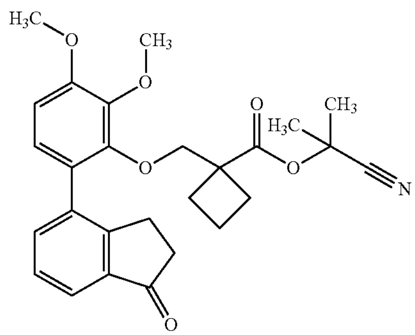 [SMILES: COc1ccc(-c2cccc3c2CCC3=O)c(OCC2(C(=O)OC(C)(C)C#N)CCC2)c1OC] | (1-cyano-1-methyl-ethyl) 1-[[2,3-dimethoxy-6-(1-oxoindan-4-yl)phenoxy]methyl]cyclobutanecarboxylate | 2.64 | 463.2 |
| 537 | 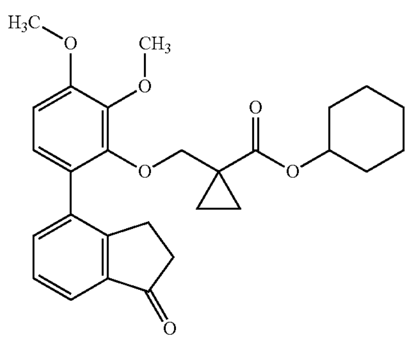 [SMILES: COc1ccc(-c2cccc3c2CCC3=O)c(OCC2(C(=O)OC3CCCCC3)CC2)c1OC] | cyclohexyl 1-[[2,3-dimethoxy-6-(1-oxoindan-4-yl)phenoxy]methyl]cyclopropanecarboxylate | 2.85 | 464.22 |
| 538 | 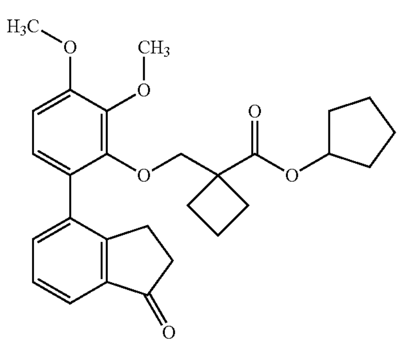 [SMILES: COc1ccc(-c2cccc3c2CCC3=O)c(OCC2(C(=O)OC3CCCC3)CCC2)c1OC] | cyclopentyl 1-[[2,3-dimethoxy-6-(1-oxoindan-4-yl)phenoxy]methyl]cyclobutanecarboxylate | 2.87 | 464.22 |

-continued

| Compound | Structure | Compound Name | Retention Time (minutes) | Detected Mass |
|---|---|---|---|---|
| 539 | 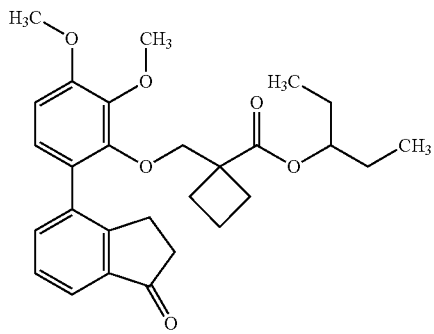 [SMILES: CCC(CC)OC(=O)C1(COc2c(-c3cccc4c3CCC4=O)ccc(OC)c2OC)CCC1] | 1-ethylpropyl 1-[[2,3-dimethoxy-6-(1-oxoindan-4-yl)phenoxy]methyl]cyclobutanecarboxylate | 2.92 | 466.24 |
| 540 | 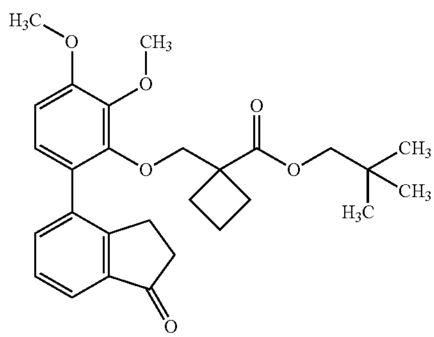 [SMILES: COc1ccc(-c2cccc3c2CCC3=O)c(OCC2(C(=O)OCC(C)(C)C)CCC2)c1OC] | 2,2-dimethylpropyl 1-[[2,3-dimethoxy-6-(1-oxoindan-4-yl)phenoxy]methyl]cyclobutanecarboxylate | 2.91 | 466.24 |
| 541 | 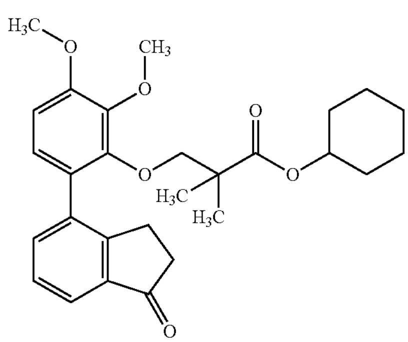 [SMILES: COc1ccc(-c2cccc3c2CCC3=O)c(OCC(C)(C)C(=O)OC2CCCCC2)c1OC] | cyclohexyl 3-[2,3-dimethoxy-6-(1-oxoindan-4-yl)phenoxy]-2,2-dimethyl-propanoate | 2.94 | 466.24 |
| 542 | 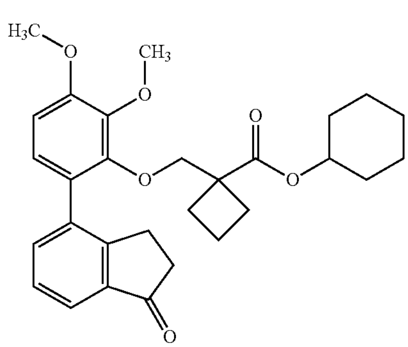 [SMILES: COc1ccc(-c2cccc3c2CCC3=O)c(OCC2(C(=O)OC3CCCCC3)CCC2)c1OC] | cyclohexyl 1-[[2,3-dimethoxy-6-(1-oxoindan-4-yl)phenoxy]methyl]cyclobutanecarboxylate | 2.95 | 478.24 |

Example 164

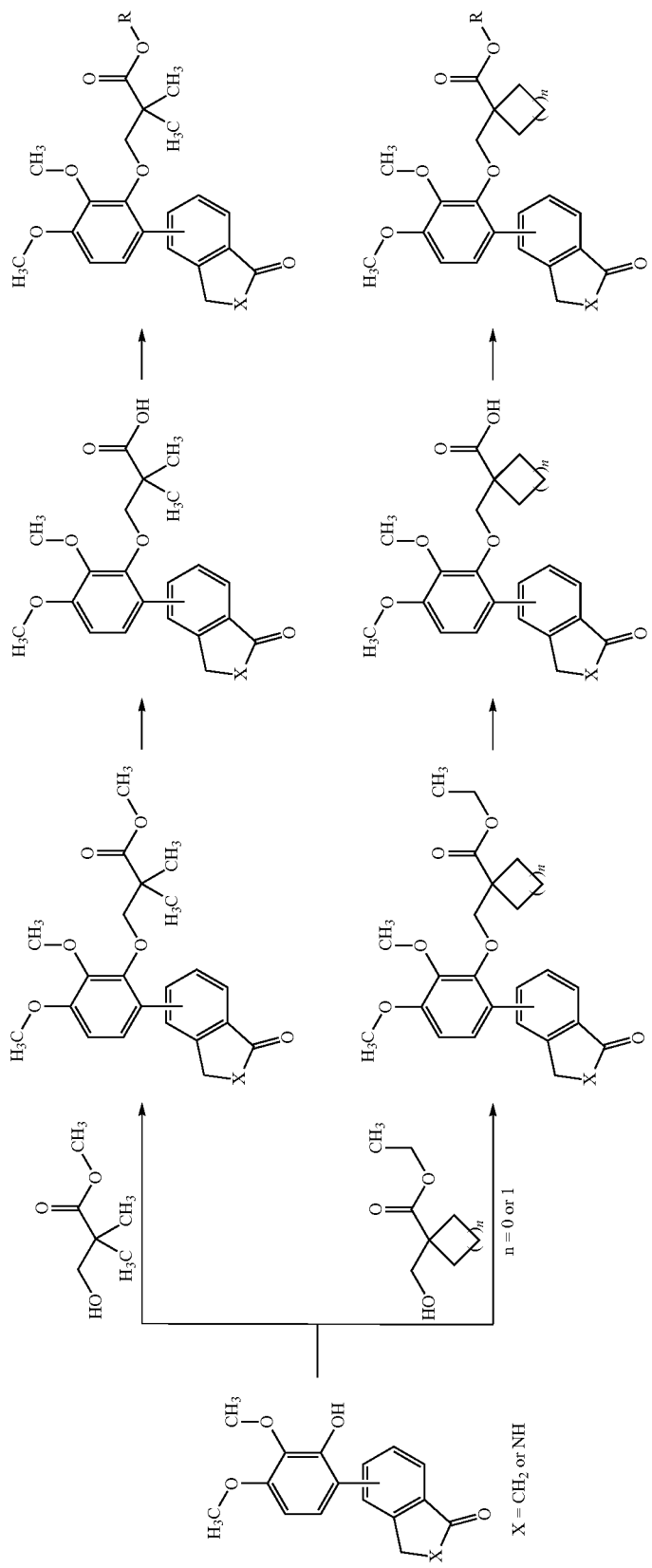

4-(2-Hydroxy-3,4-dimethoxy-phenyl)isoindolin-1-one is synthesized following the same procedure as the one described for the synthesis of Compound 307 using 4-bromo-2,3-dihydro-1H-isoindol-1-one as starting material.

Compounds 543-735 are synthesized following the experimental procedure described for the preparation of Compounds 499-542.

| Compound | Structure | IUPAC name |
|---|---|---|
| 543 | 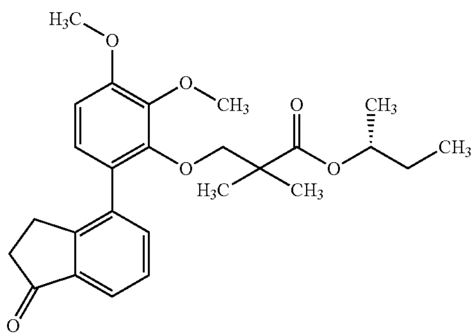 [SMILES: CC[C@@H](C)OC(=O)C(C)(C)COc1c(-c2cccc3c2CCC3=O)ccc(OC)c1OC] | [(1R)-1-methylpropyl] 3-[2,3-dimethoxy-6-(1-oxoindan-4-yl)phenoxy]-2,2-dimethyl-propanoate |
| 544 | 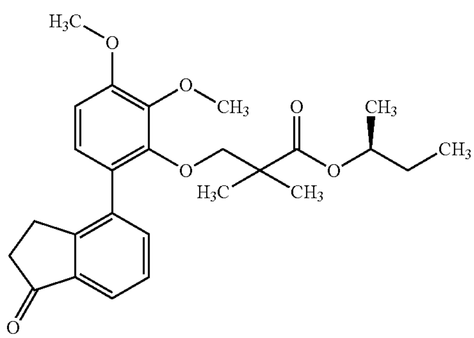 [SMILES: CC[C@H](C)OC(=O)C(C)(C)COc1c(-c2cccc3c2CCC3=O)ccc(OC)c1OC] | [(1S)-1-methylpropyl] 3-[2,3-dimethoxy-6-(1-oxoindan-4-yl)phenoxy]-2,2-dimethyl-propanoate |
| 545 | 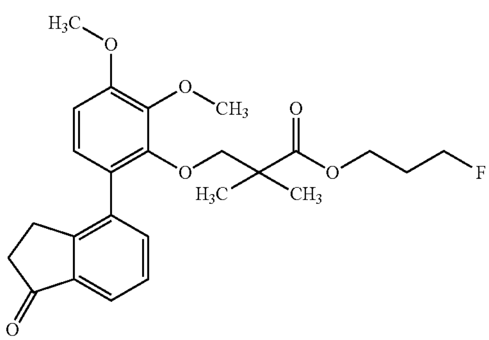 [SMILES: COc1ccc(-c2cccc3c2CCC3=O)c(OCC(C)(C)C(=O)OCCCF)c1OC] | 3-fluoropropyl 3-[2,3-dimethoxy-6-(1-oxoindan-4-yl)phenoxy]-2,2-dimethyl-propanoate |
| 546 | 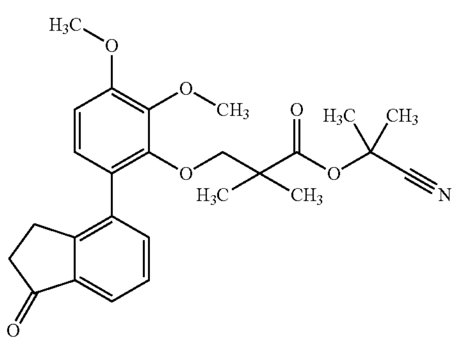 [SMILES: COc1ccc(-c2cccc3c2CCC3=O)c(OCC(C)(C)C(=O)OC(C)(C)C#N)c1OC] | (1-cyano-1-methyl-ethyl) 3-[2,3-dimethoxy-6-(1-oxoindan-4-yl)phenoxy]-2,2-dimethyl-propanoate |

-continued

| Compound | Structure | IUPAC name |
|---|---|---|
| 547 | 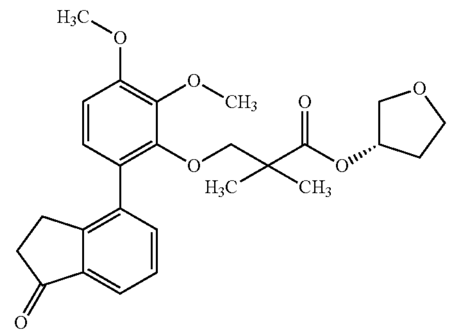 [SMILES: COc1ccc(-c2cccc3c2CCC3=O)c(OCC(C)(C)C(=O)O[C@H]2CCOC2)c1OC] | [(3S)-tetrahydrofuran-3-yl] 3-[2,3-dimethoxy-6-(1-oxoindan-4-yl)phenoxy]-2,2-dimethyl-propanoate |
| 548 | 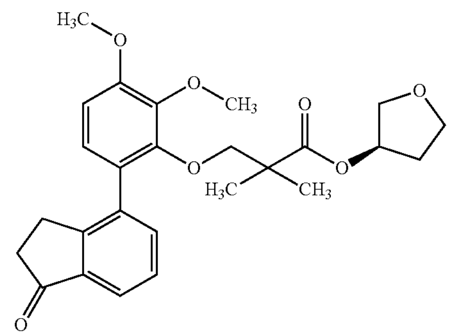 [SMILES: COc1ccc(-c2cccc3c2CCC3=O)c(OCC(C)(C)C(=O)O[C@@H]2CCOC2)c1OC] | [(3R)-tetrahydrofuran-3-yl] 3-[2,3-dimethoxy-6-(1-oxoindan-4-yl)phenoxy]-2,2-dimethyl-propanoate |
| 549 | 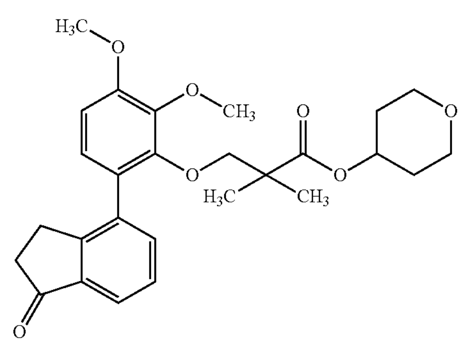 [SMILES: COc1ccc(-c2cccc3c2CCC3=O)c(OCC(C)(C)C(=O)OC2CCOCC2)c1OC] | tetrahydropyran-4-yl 3-[2,3-dimethoxy-6-(1-oxoindan-4-yl)phenoxy]-2,2-dimethyl-propanoate |
| 550 | 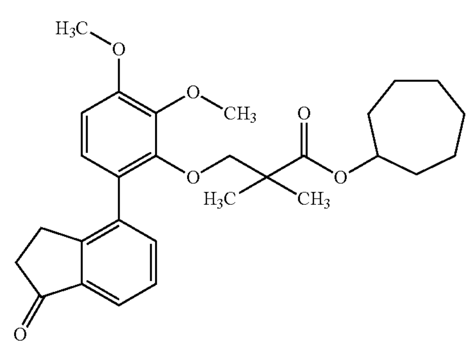 [SMILES: COc1ccc(-c2cccc3c2CCC3=O)c(OCC(C)(C)C(=O)OC2CCCCCC2)c1OC] | cycloheptyl 3-[2,3-dimethoxy-6-(1-oxoindan-4-yl)phenoxy]-2,2-dimethyl-propanoate |

| Compound | Structure | Compound name |
|---|---|---|
| 551 | 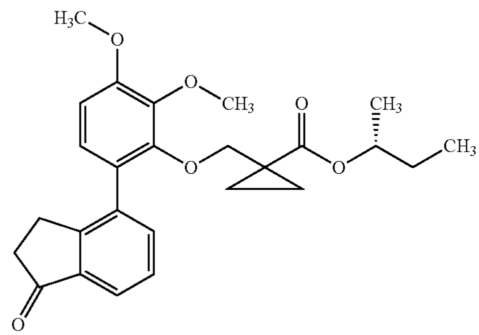 [SMILES: CC[C@@H](C)OC(=O)C1(COc2c(-c3cccc4c3CCC4=O)ccc(OC)c2OC)CC1] | [(1R)-1-methylpropyl] 1-[[2,3-dimethoxy-6-(1-oxoindan-4-yl)phenoxy]methyl]cyclopropanecarboxylate |
| 552 | 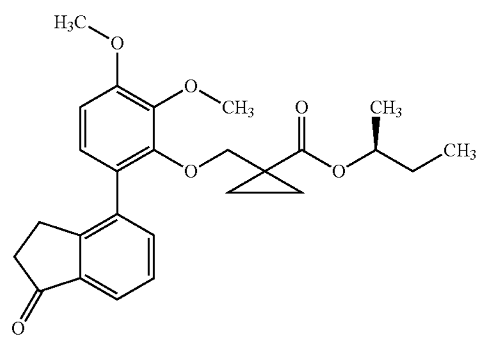 [SMILES: CC[C@H](C)OC(=O)C1(COc2c(-c3cccc4c3CCC4=O)ccc(OC)c2OC)CC1] | [(1S)-1-methylpropyl] 1-[[2,3-dimethoxy-6-(1-oxoindan-4-yl)phenoxy]methyl]cyclopropanecarboxylate |
| 553 | 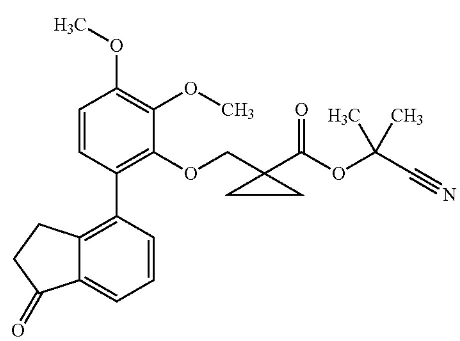 [SMILES: COc1ccc(-c2cccc3c2CCC3=O)c(OCC2(C(=O)OC(C)(C)C#N)CC2)c1OC] | (1-cyano-1-methyl-ethyl) 1-[[2,3-dimethoxy-6-(1-oxoindan-4-yl)phenoxy]methyl]cyclopropanecarboxylate |
| 554 | 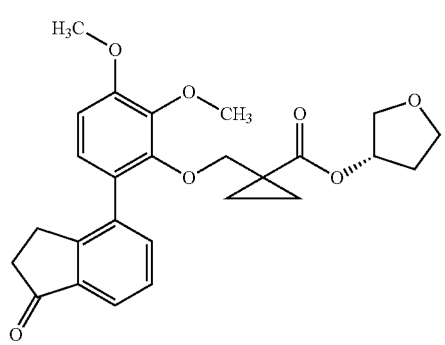 [SMILES: COc1ccc(-c2cccc3c2CCC3=O)c(OCC2(C(=O)O[C@H]3CCOC3)CC2)c1OC] | [(3S)-tetrahydrofuran-3-yl] 1-[[2,3-dimethoxy-6-(1-oxoindan-4-yl)phenoxy]methyl]cyclopropanecarboxylate |

-continued

| Compound | Structure | Compound name |
|---|---|---|
| 555 | 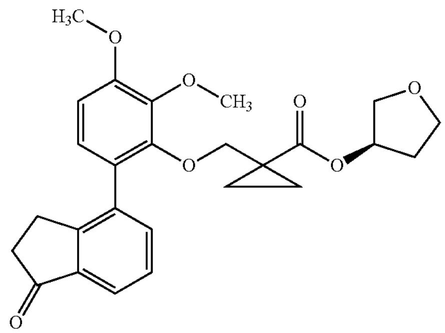 [SMILES: COc1ccc(-c2cccc3c2CCC3=O)c(OCC2(C(=O)O[C@@H]3CCOC3)CC2)c1OC] | [(3R)-tetrahydrofuran-3-yl] 1-[[2,3-dimethoxy-6-(1-oxoindan-4-yl)phenoxy]methyl]cyclopropanecarboxylate |
| 556 | 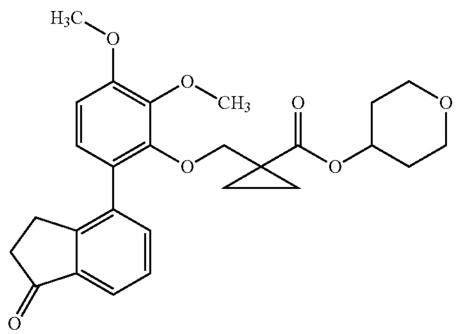 [SMILES: COc1ccc(-c2cccc3c2CCC3=O)c(OCC2(C(=O)OC3CCOCC3)CC2)c1OC] | tetrahydropyran-4-yl 1-[[2,3-dimethoxy-6-(1-oxoindan-4-yl)phenoxy]methyl]cyclopropanecarboxylate |
| 557 | 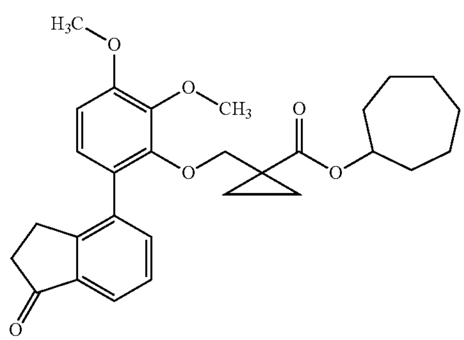 [SMILES: COc1ccc(-c2cccc3c2CCC3=O)c(OCC2(C(=O)OC3CCCCCC3)CC2)c1OC] | cycloheptyl 1-[[2,3-dimethoxy-6-(1-oxoindan-4-yl)phenoxy]methyl]cyclopropanecarboxylate |
| 558 | 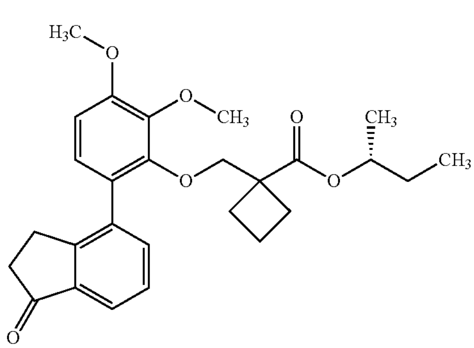 [SMILES: CC[C@@H](C)OC(=O)C1(COc2c(-c3cccc4c3CCC4=O)ccc(OC)c2OC)CCC1] | [(1R)-1-methylpropyl] 1-[[2,3-dimethoxy-6-(1-oxoindan-4-yl)phenoxy]methyl]cyclobutanecarboxylate |

-continued

| Compound | Structure | Compound name |
|---|---|---|
| 559 | 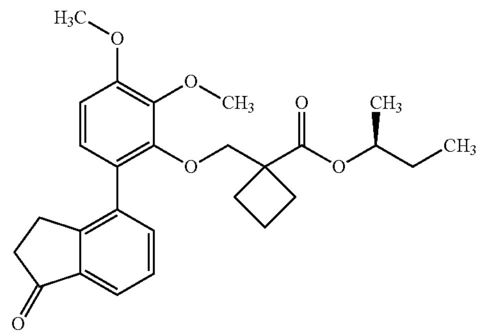 [SMILES: CC[C@H](C)OC(=O)C1(COc2c(-c3cccc4c3CCC4=O)ccc(OC)c2OC)CCC1] | [(1S)-1-methylpropyl] 1-[[2,3-dimethoxy-6-(1-oxoindan-4-yl)phenoxy]methyl]cyclobutanecarboxylate |
| 560 | 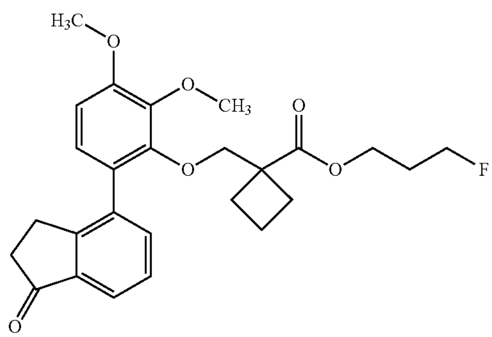 [SMILES: COc1ccc(-c2cccc3c2CCC3=O)c(OCC2(C(=O)OCCCF)CCC2)c1OC] | 3-fluoropropyl 1-[[2,3-dimethoxy-6-(1-oxoindan-4-yl)phenoxy]methyl]cyclobutanecarboxylate |
| 561 | 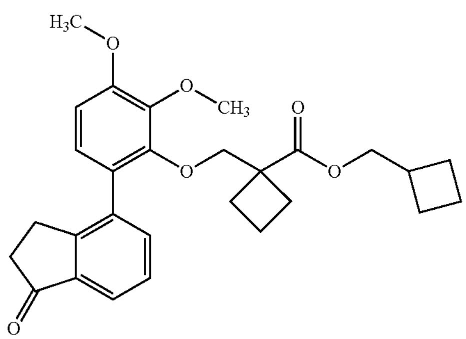 [SMILES: COc1ccc(-c2cccc3c2CCC3=O)c(OCC2(C(=O)OCC3CCC3)CCC2)c1OC] | cyclobutylmethyl 1-[[2,3-dimethoxy-6-(1-oxoindan-4-yl)phenoxy]methyl]cyclobutanecarboxylate |
| 562 | 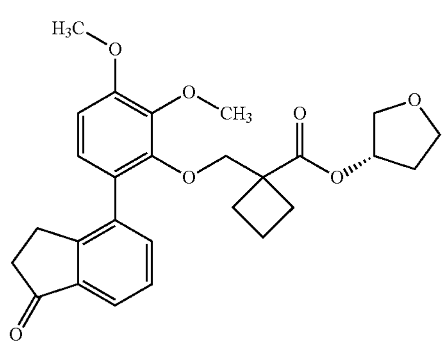 [SMILES: COc1ccc(-c2cccc3c2CCC3=O)c(OCC2(C(=O)O[C@H]3CCOC3)CCC2)c1OC] | [(3S)-tetrahydrofuran-3-yl] 1-[[2,3-dimethoxy-6-(1-oxoindan-4-yl)phenoxy]methyl]cyclobutanecarboxylate |

| Compound | Structure | Compound name |
|---|---|---|
| 563 | 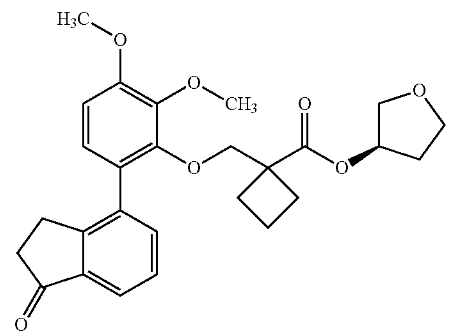 [SMILES: COc1ccc(-c2cccc3c2CCC3=O)c(OCC2(C(=O)O[C@@H]3CCOC3)CCC2)c1OC] | [(3R)-tetrahydrofuran-3-yl] 1-[[2,3-dimethoxy-6-(1-oxoindan-4-yl)phenoxy]methyl]cyclobutanecarboxylate |
| 564 | 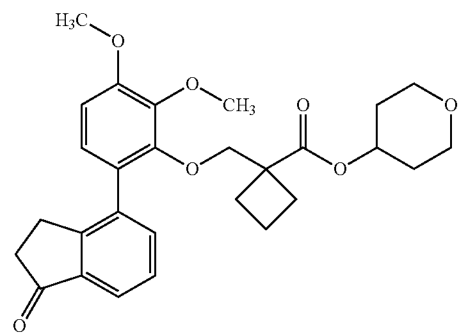 [SMILES: COc1ccc(-c2cccc3c2CCC3=O)c(OCC2(C(=O)OC3CCOCC3)CCC2)c1OC] | tetrahydropyran-4-yl 1-[[2,3-dimethoxy-6-(1-oxoindan-4-yl)phenoxy]methyl]cyclobutanecarboxylate |
| 565 | 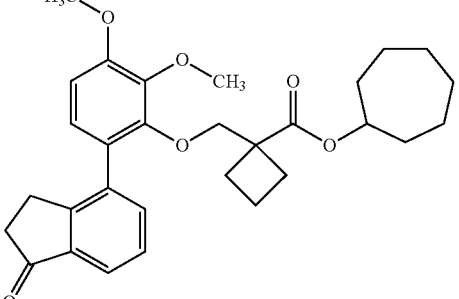 | cycloheptyl 1-[[2,3-dimethoxy-6-(1-oxoindan-4-yl)phenoxy]methyl]cyclobutanecarboxylate |
| 566 | 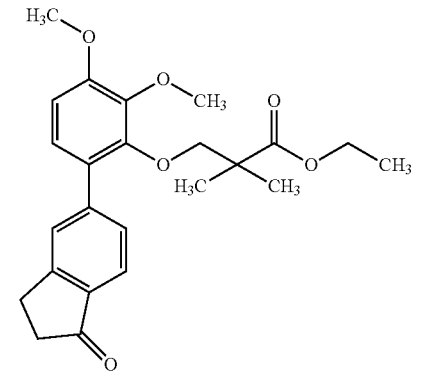 [SMILES: CCOC(=O)C(C)(C)COc1c(-c2ccc3c(c2)CCC3=O)ccc(OC)c1OC] | ethyl 3-[2,3-dimethoxy-6-(1-oxoindan-5-yl)phenoxy]-2,2-dimethyl-propanoate |

-continued

| Compound | Structure | Compound name |
|---|---|---|
| 567 | 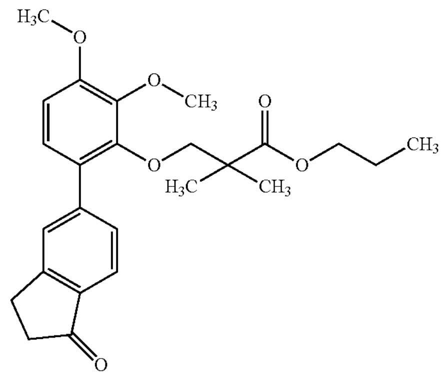 [SMILES: CCCOC(=O)C(C)(C)COc1c(-c2ccc3c(c2)CCC3=O)ccc(OC)c1OC] | propyl 3-[2,3-dimethoxy-6-(1-oxoindan-5-yl)phenoxy]-2,2-dimethyl-propanoate |
| 568 | 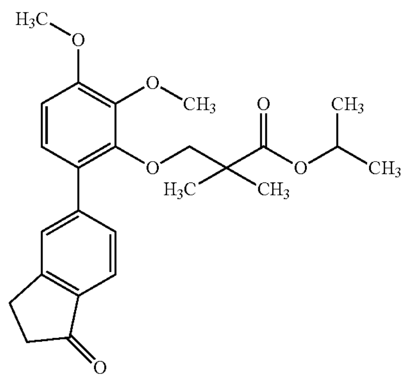 [SMILES: COc1ccc(-c2ccc3c(c2)CCC3=O)c(OCC(C)(C)C(=O)OC(C)C)c1OC] | isopropyl 3-[2,3-dimethoxy-6-(1-oxoindan-5-yl)phenoxy]-2,2-dimethyl-propanoate |
| 569 | 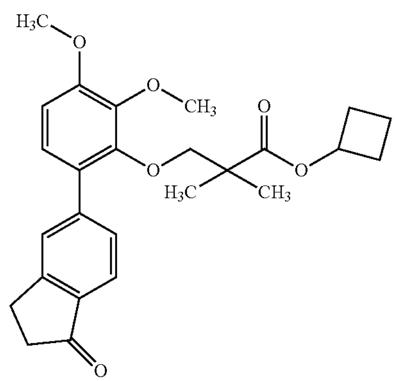 [SMILES: COc1ccc(-c2ccc3c(c2)CCC3=O)c(OCC(C)(C)C(=O)OC2CCC2)c1OC] | cyclobutyl 3-[2,3-dimethoxy-6-(1-oxoindan-5-yl)phenoxy]-2,2-dimethyl-propanoate |
| 570 | 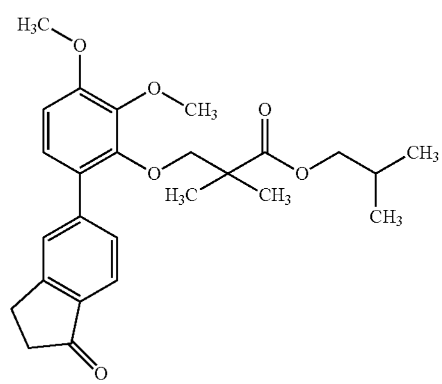 [SMILES: COc1ccc(-c2ccc3c(c2)CCC3=O)c(OCC(C)(C)C(=O)OCC(C)C)c1OC] | isobutyl 3-[2,3-dimethoxy-6-(1-oxoindan-5-yl)phenoxy]-2,2-dimethyl-propanoate |

-continued
| Compound | Structure | Compound name |
|---|---|---|
| 571 | 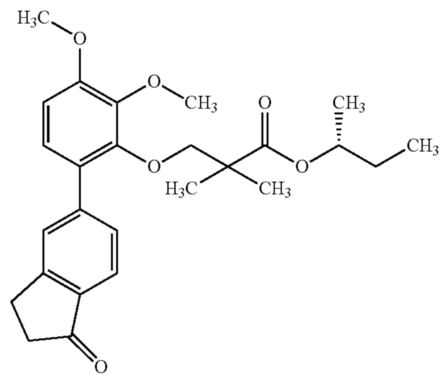 [SMILES: CC[C@@H](C)OC(=O)C(C)(C)COc1c(-c2ccc3c(c2)CCC3=O)ccc(OC)c1OC] | [(1R)-1-methylpropyl] 3-[2,3-dimethoxy-6-(1-oxoindan-5-yl)phenoxy]-2,2-dimethyl-propanoate |
| 572 | 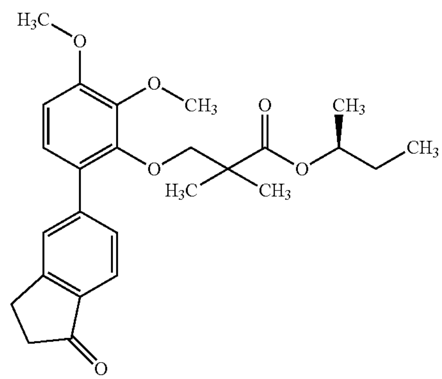 [SMILES: CC[C@H](C)OC(=O)C(C)(C)COc1c(-c2ccc3c(c2)CCC3=O)ccc(OC)c1OC] | [(1S)-1-methylpropyl] 3-[2,3-dimethoxy-6-(1-oxoindan-5-yl)phenoxy]-2,2-dimethyl-propanoate |
| 573 | 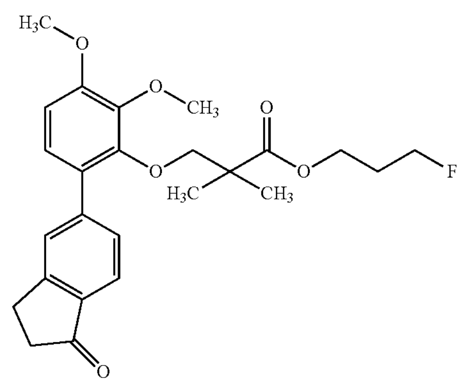 [SMILES: COc1ccc(-c2ccc3c(c2)CCC3=O)c(OCC(C)(C)C(=O)OCCCF)c1OC] | 3-fluoropropyl 3-[2,3-dimethoxy-6-(1-oxoindan-5-yl)phenoxy]-2,2-dimethyl-propanoate |
| 574 | 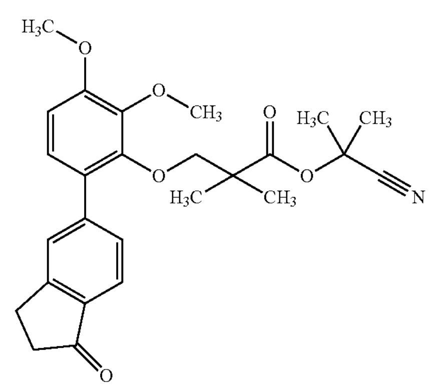 [SMILES: COc1ccc(-c2ccc3c(c2)CCC3=O)c(OCC(C)(C)C(=O)OC(C)(C)C#N)c1OC] | (1-cyano-1-methyl-ethyl) 3-[2,3-dimethoxy-6-(1-oxoindan-5-yl)phenoxy]-2,2-dimethyl-propanoate |

-continued
| Compound | Structure | Compound name |
|---|---|---|
| 575 | 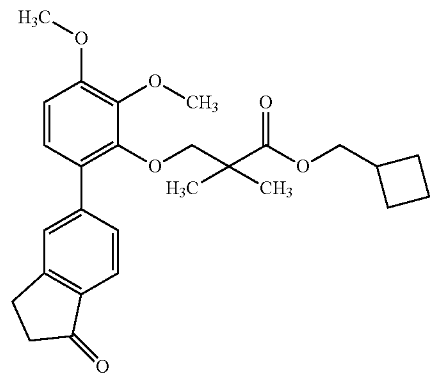 [SMILES: COc1ccc(-c2ccc3c(c2)CCC3=O)c(OCC(C)(C)C(=O)OCC2CCC2)c1OC] | cyclobutylmethyl 3-[2,3-dimethoxy-6-(1-oxoindan-5-yl)phenoxy]-2,2-dimethyl-propanoate |
| 576 | 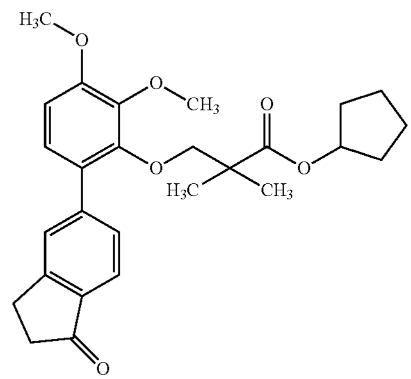 [SMILES: COc1ccc(-c2ccc3c(c2)CCC3=O)c(OCC(C)(C)C(=O)OC2CCCC2)c1OC] | cyclopentyl 3-[2,3-dimethoxy-6-(1-oxoindan-5-yl)phenoxy]-2,2-dimethyl-propanoate |
| 577 | 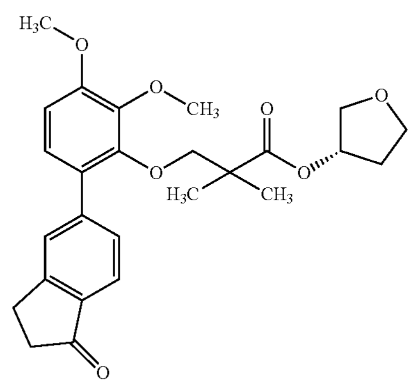 [SMILES: COc1ccc(-c2ccc3c(c2)CCC3=O)c(OCC(C)(C)C(=O)O[C@H]2CCOC2)c1OC] | [(3S)-tetrahydrofuran-3-yl] 3-[2,3-dimethoxy-6-(1-oxoindan-5-yl)phenoxy]-2,2-dimethyl-propanoate |
| 578 | 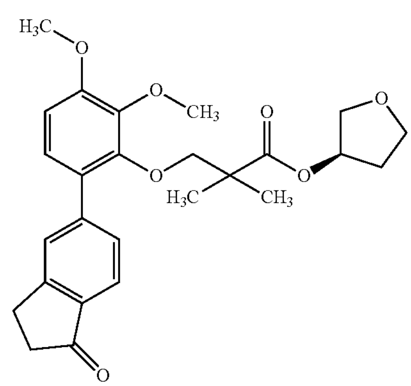 [SMILES: COc1ccc(-c2ccc3c(c2)CCC3=O)c(OCC(C)(C)C(=O)O[C@@H]2CCOC2)c1OC] | [(3R)-tetrahydrofuran-3-yl] 3-[2,3-dimethoxy-6-(1-oxoindan-5-yl)phenoxy]-2,2-dimethyl-propanoate |

-continued
| Compound | Structure | Compound name |
|---|---|---|
| 579 | 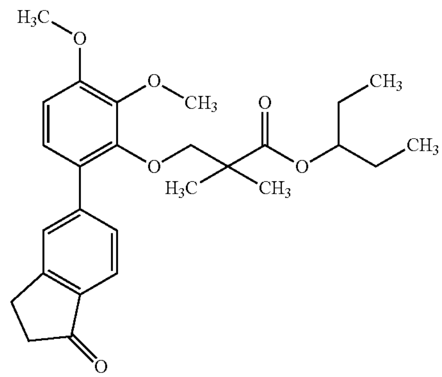 [SMILES: CCC(CC)OC(=O)C(C)(C)COc1c(-c2ccc3c(c2)CCC3=O)ccc(OC)c1OC] | 1-ethylpropyl 3-[2,3-dimethoxy-6-(1-oxoindan-5-yl)phenoxy]-2,2-dimethyl-propanoate |
| 580 | 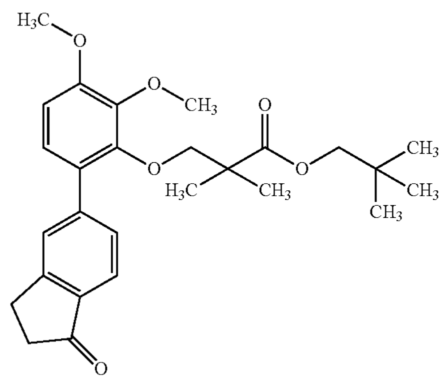 [SMILES: COc1ccc(-c2ccc3c(c2)CCC3=O)c(OCC(C)(C)C(=O)OCC(C)(C)C)c1OC] | 2,2-dimethylpropyl 3-[2,3-dimethoxy-6-(1-oxoindan-5-yl)phenoxy]-2,2-dimethyl-propanoate |
| 581 | 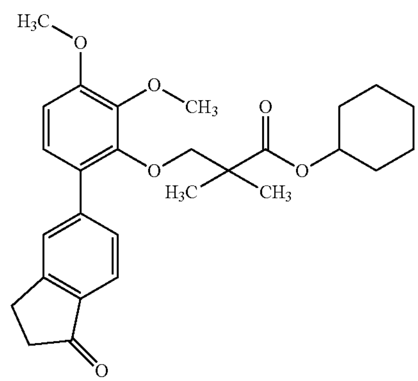 [SMILES: COc1ccc(-c2ccc3c(c2)CCC3=O)c(OCC(C)(C)C(=O)OC2CCCCC2)c1OC] | cyclohexyl 3-[2,3-dimethoxy-6-(1-oxoindan-5-yl)phenoxy]-2,2-dimethyl-propanoate |
| 582 | 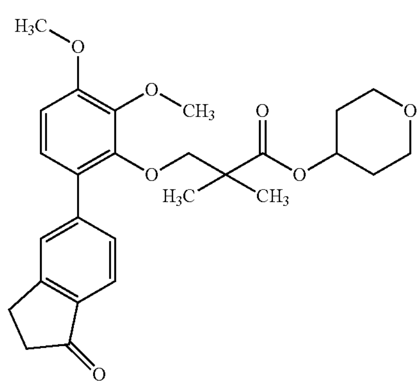 [SMILES: COc1ccc(-c2ccc3c(c2)CCC3=O)c(OCC(C)(C)C(=O)OC2CCOCC2)c1OC] | tetrahydropyran-4-yl 3-[2,3-dimethoxy-6-(1-oxoindan-5-yl)phenoxy]-2,2-dimethyl-propanoate |

-continued
| Compound | Structure | Compound name |
|---|---|---|
| 583 | 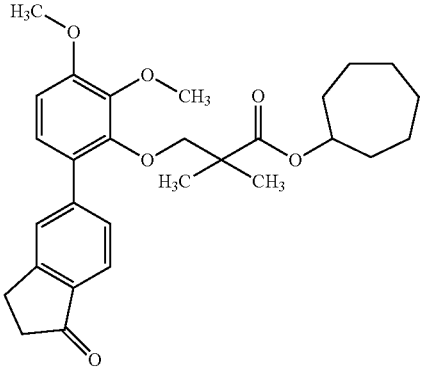 [SMILES: COc1ccc(-c2ccc3c(c2)CCC3=O)c(OCC(C)(C)C(=O)OC2CCCCCC2)c1OC] | cycloheptyl 3-[2,3-dimethoxy-6-(1-oxoindan-5-yl)phenoxy]-2,2-dimethyl-propanoate |
| 584 | 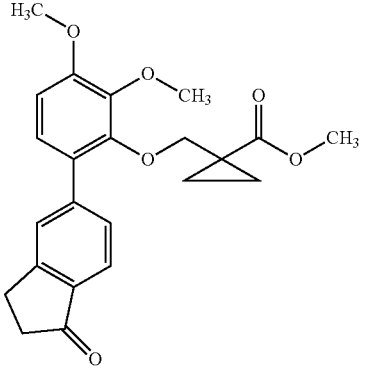 [SMILES: COC(=O)C1(COc2c(-c3ccc4c(c3)CCC4=O)ccc(OC)c2OC)CC1] | methyl 1-[[2,3-dimethoxy-6-(1-oxoindan-5-yl)phenoxy]methyl]cyclopropanecarboxylate |
| 585 | 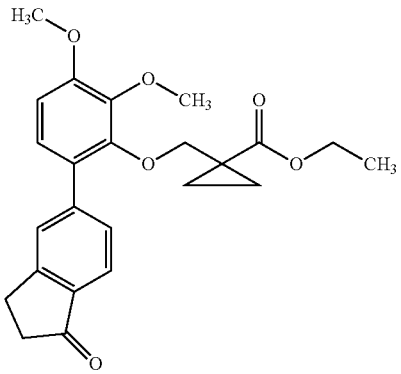 [SMILES: CCOC(=O)C1(COc2c(-c3ccc4c(c3)CCC4=O)ccc(OC)c2OC)CC1] | ethyl 1-[[2,3-dimethoxy-6-(1-oxoindan-5-yl)phenoxy]methyl]cyclopropanecarboxylate |
| 586 | 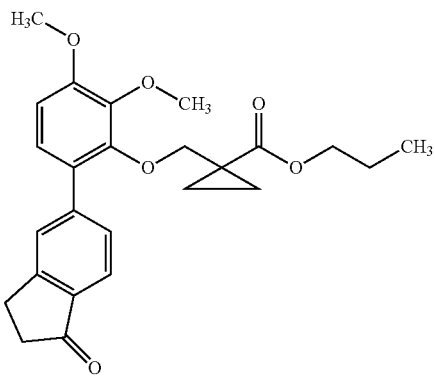 [SMILES: CCCOC(=O)C1(COc2c(-c3ccc4c(c3)CCC4=O)ccc(OC)c2OC)CC1] | propyl 1-[[2,3-dimethoxy-6-(1-oxoindan-5-yl)phenoxy]methyl]cyclopropanecarboxylate |

-continued

| Compound | Structure | Compound name |
|---|---|---|
| 587 | 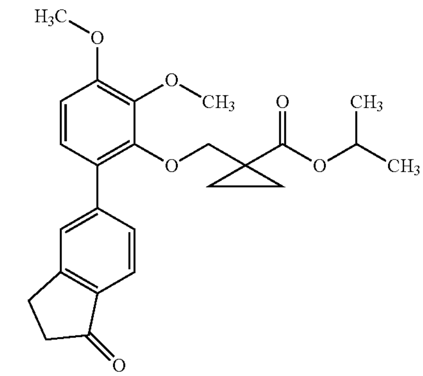 [SMILES: COc1ccc(-c2ccc3c(c2)CCC3=O)c(OCC2(C(=O)OC(C)C)CC2)c1OC] | isopropyl 1-[[2,3-dimethoxy-6-(1-oxoindan-5-yl)phenoxy]methyl]cyclopropanecarboxylate |
| 588 | 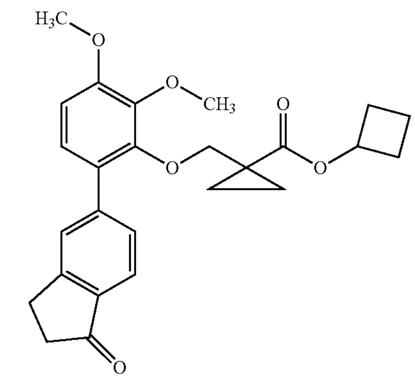 [SMILES: COc1ccc(-c2ccc3c(c2)CCC3=O)c(OCC2(C(=O)OC3CCC3)CC2)c1OC] | cyclobutyl 1-[[2,3-dimethoxy-6-(1-oxoindan-5-yl)phenoxy]methyl]cyclopropanecarboxylate |
| 589 | 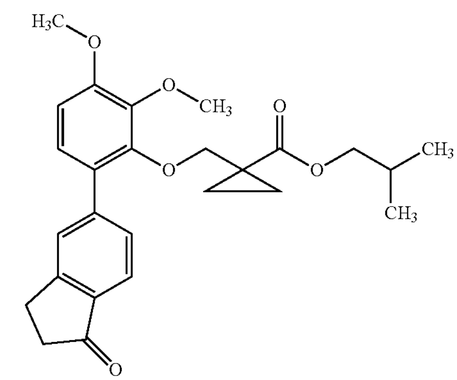 [SMILES: COc1ccc(-c2ccc3c(c2)CCC3=O)c(OCC2(C(=O)OCC(C)C)CC2)c1OC] | isobutyl 1-[[2,3-dimethoxy-6-(1-oxoindan-5-yl)phenoxy]methyl]cyclopropanecarboxylate |
| 590 | 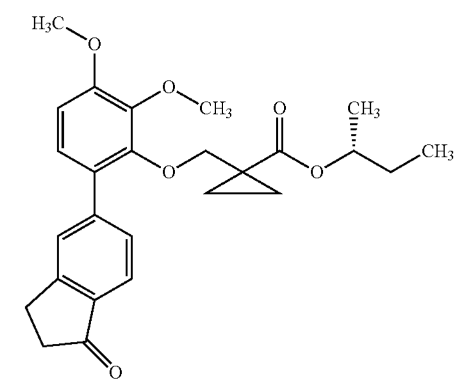 [SMILES: CC[C@@H](C)OC(=O)C1(COc2c(-c3ccc4c(c3)CCC4=O)ccc(OC)c2OC)CC1] | [(1R)-1-methylpropyl] 1-[[2,3-dimethoxy-6-(1-oxoindan-5-yl)phenoxy]methyl]cyclopropanecarboxylate |

| Compound | Structure | Compound name |
|---|---|---|
| 591 | 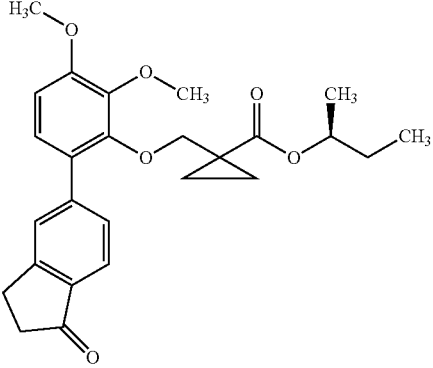 [SMILES: CC[C@H](C)OC(=O)C1(COc2c(-c3ccc4c(c3)CCC4=O)ccc(OC)c2OC)CC1] | [(1S)-1-methylpropyl] 1-[[2,3-dimethoxy-6-(1-oxoindan-5-yl)phenoxy]methyl]cyclopropanecarboxylate |
| 592 | 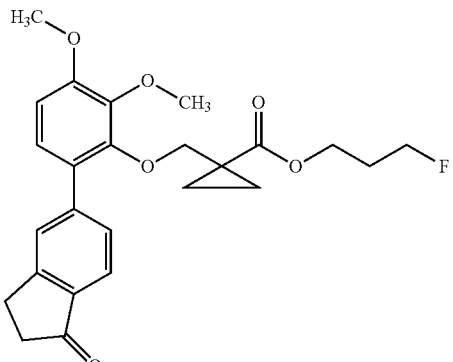 | 3-fluoropropyl 1-[[2,3-dimethoxy-6-(1-oxoindan-5-yl)phenoxy]methyl]cyclopropanecarboxylate |
| 593 | 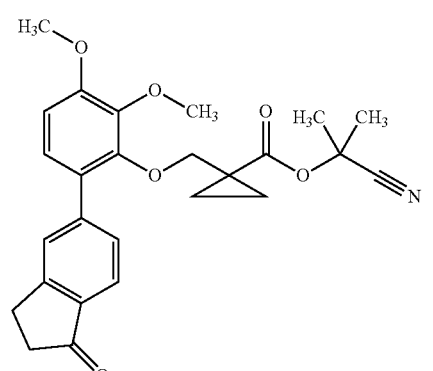 | (1-cyano-1-methyl-ethyl) 1-[[2,3-dimethoxy-6-(1-oxoindan-5-yl)phenoxy]methyl]cyclopropanecarboxylate |
| 594 | 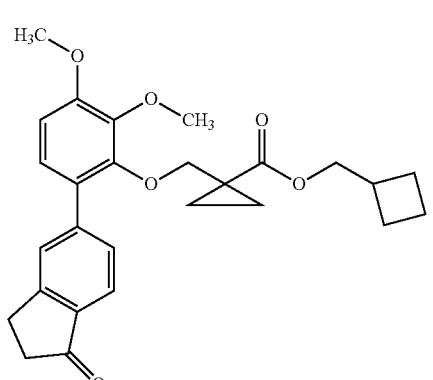 | cyclobutylmethyl 1-[[2,3-dimethoxy-6-(1-oxoindan-5-yl)phenoxy]methyl]cyclopropanecarboxylate |

| Compound | Structure | Compound name |
|---|---|---|
| 595 | 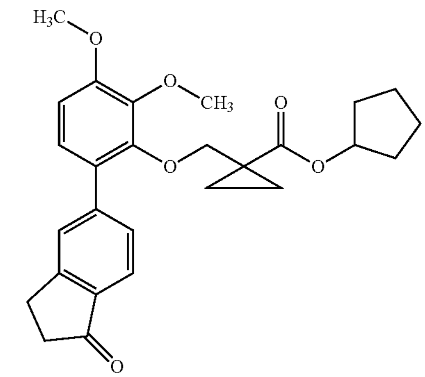 [SMILES: COc1ccc(-c2ccc3c(c2)CCC3=O)c(OCC2(C(=O)OC3CCCC3)CC2)c1OC] | cyclopentyl 1-[[2,3-dimethoxy-6-(1-oxoindan-5-yl)phenoxy]methyl]cyclopropanecarboxylate |
| 596 | 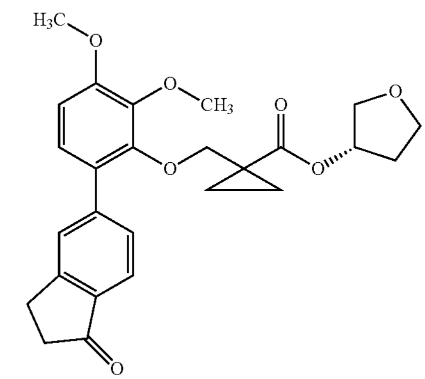 [SMILES: COc1ccc(-c2ccc3c(c2)CCC3=O)c(OCC2(C(=O)O[C@H]3CCOC3)CC2)c1OC] | [(3S)-tetrahydrofuran-3-yl] 1-[[2,3-dimethoxy-6-(1-oxoindan-5-yl)phenoxy]methyl]cyclopropanecarboxylate |
| 597 | 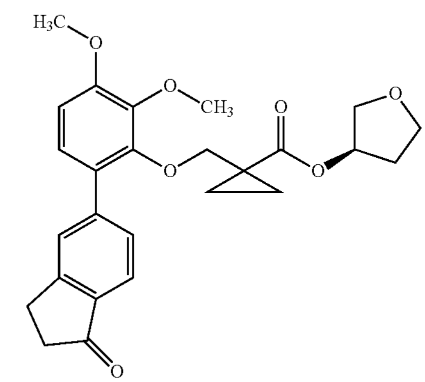 [SMILES: COc1ccc(-c2ccc3c(c2)CCC3=O)c(OCC2(C(=O)O[C@@H]3CCOC3)CC2)c1OC] | [(3R)-tetrahydrofuran-3-yl] 1-[[2,3-dimethoxy-6-(1-oxoindan-5-yl)phenoxy]methyl]cyclopropanecarboxylate |
| 598 | 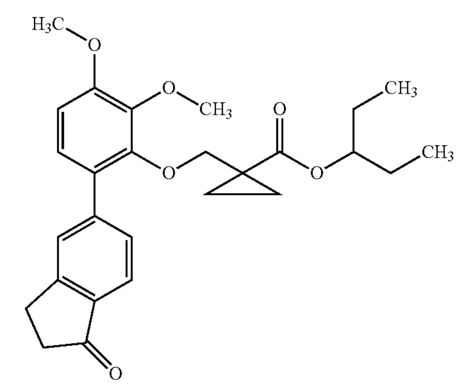 [SMILES: CCC(CC)OC(=O)C1(COc2c(-c3ccc4c(c3)CCC4=O)ccc(OC)c2OC)CC1] | 1-ethylpropyl 1-[[2,3-dimethoxy-6-(1-oxoindan-5-yl)phenoxy]methyl]cyclopropanecarboxylate |

-continued

| Compound | Structure | Compound name |
|---|---|---|
| 599 | 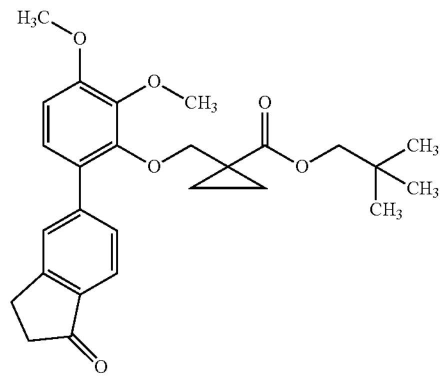 [SMILES: COc1ccc(-c2ccc3c(c2)CCC3=O)c(OCC2(C(=O)OCC(C)(C)C)CC2)c1OC] | 2,2-dimethylpropyl 1-[[2,3-dimethoxy-6-(1-oxoindan-5-yl)phenoxy]methyl]cyclopropanecarboxylate |
| 600 | 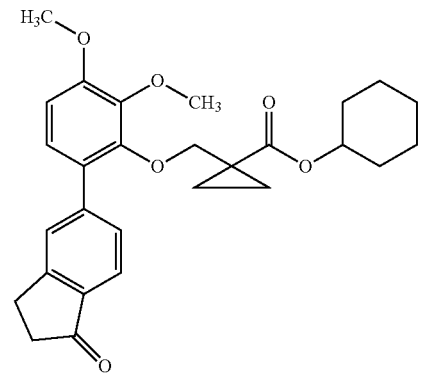 [SMILES: COc1ccc(-c2ccc3c(c2)CCC3=O)c(OCC2(C(=O)OC3CCCCC3)CC2)c1OC] | cyclohexyl 1-[[2,3-dimethoxy-6-(1-oxoindan-5-yl)phenoxy]methyl]cyclopropanecarboxylate |
| 601 | 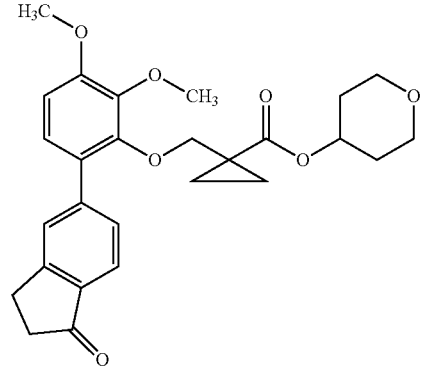 [SMILES: COc1ccc(-c2ccc3c(c2)CCC3=O)c(OCC2(C(=O)OC3CCOCC3)CC2)c1OC] | tetrahydropyran-4-yl 1-[[2,3-dimethoxy-6-(1-oxoindan-5-yl)phenoxy]methyl]cyclopropanecarboxylate |
| 602 | 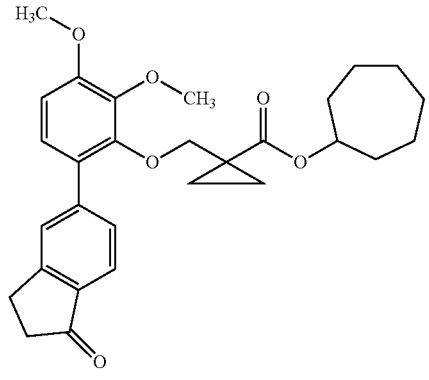 [SMILES: COc1ccc(-c2ccc3c(c2)CCC3=O)c(OCC2(C(=O)OC3CCCCCC3)CC2)c1OC] | cycloheptyl 1-[[2,3-dimethoxy-6-(1-oxoindan-5-yl)phenoxy]methyl]cyclopropanecarboxylate |

| Compound | Structure | Structure name |
|---|---|---|
| 603 | 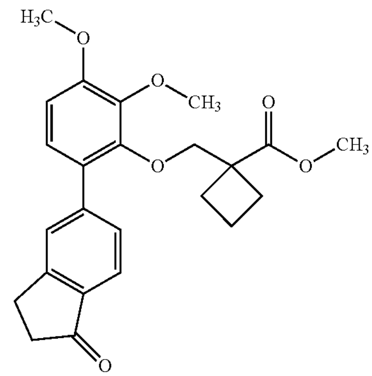 [SMILES: COC(=O)C1(COc2c(-c3ccc4c(c3)CCC4=O)ccc(OC)c2OC)CCC1] | methyl 1-[[2,3-dimethoxy-6-(1-oxoindan-5-yl)phenoxy]methyl]cyclobutanecarboxylate |
| 604 | 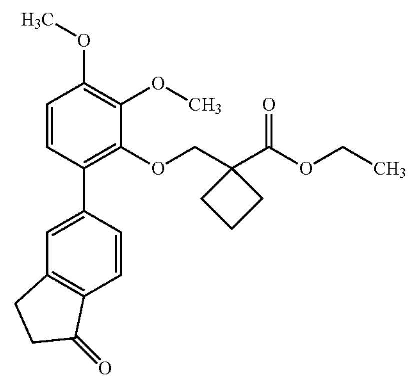 [SMILES: CCOC(=O)C1(COc2c(-c3ccc4c(c3)CCC4=O)ccc(OC)c2OC)CCC1] | ethyl 1-[[2,3-dimethoxy-6-(1-oxoindan-5-yl)phenoxy]methyl]cyclobutanecarboxylate |
| 605 | 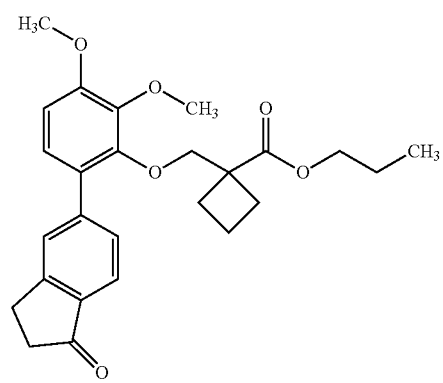 | propyl 1-[[2,3-dimethoxy-6-(1-oxoindan-5-yl)phenoxy]methyl]cyclobutanecarboxylate |
| 606 | 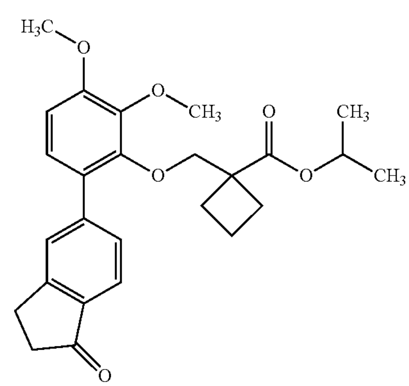 [SMILES: COc1ccc(-c2ccc3c(c2)CCC3=O)c(OCC2(C(=O)OC(C)C)CCC2)c1OC] | isopropyl 1-[[2,3-dimethoxy-6-(1-oxoindan-5-yl)phenoxy]methyl]cyclobutanecarboxylate |

-continued

| Compound | Structure | Structure name |
|---|---|---|
| 607 | 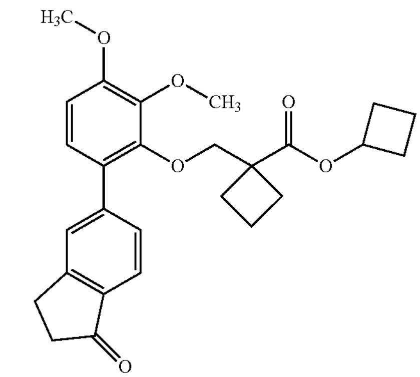 | cyclobutyl 1-[[2,3-dimethoxy-6-(1-oxoindan-5-yl)phenoxy]methyl]cyclobutanecarboxylate |
| 608 | 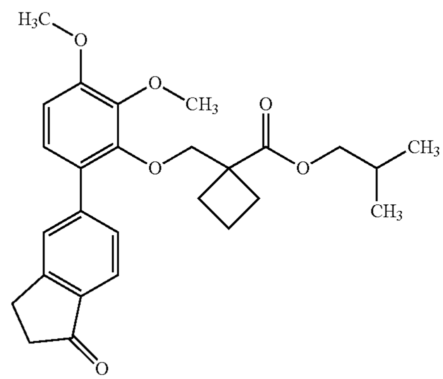 [SMILES: COc1ccc(-c2ccc3c(c2)CCC3=O)c(OCC2(C(=O)OCC(C)C)CCC2)c1OC] | isobutyl 1-[[2,3-dimethoxy-6-(1-oxoindan-5-yl)phenoxy]methyl]cyclobutanecarboxylate |
| 609 | 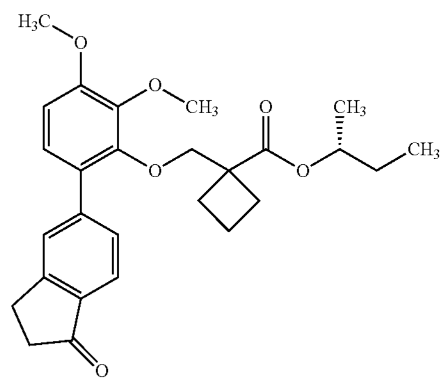 [SMILES: CC[C@@H](C)OC(=O)C1(COc2c(-c3ccc4c(c3)CCC4=O)ccc(OC)c2OC)CCC1] | [(1R)-1-methylpropyl] 1-[[2,3-dimethoxy-6-(1-oxoindan-5-yl)phenoxy]methyl]cyclobutanecarboxylate |
| 610 | 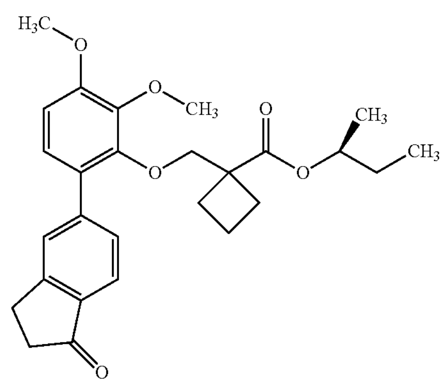 [SMILES: CC[C@H](C)OC(=O)C1(COc2c(-c3ccc4c(c3)CCC4=O)ccc(OC)c2OC)CCC1] | [(1S)-1-methylpropyl] 1-[[2,3-dimethoxy-6-(1-oxoindan-5-yl)phenoxy]methyl]cyclobutanecarboxylate |

| Compound | Structure | Structure name |
|---|---|---|
| 611 | 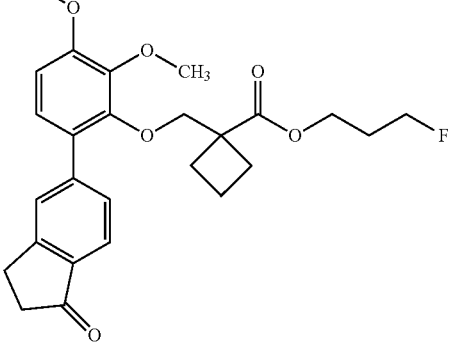 | 3-fluoropropyl 1-[[2,3-dimethoxy-6-(1-oxoindan-5-yl)phenoxy]methyl]cyclobutanecarboxylate |
| 612 | 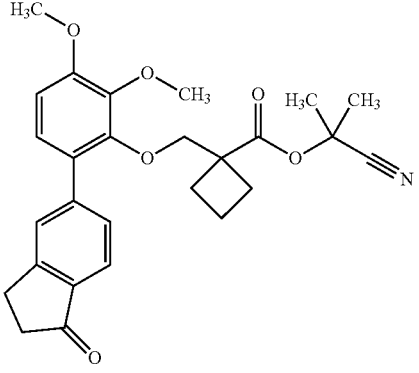 [SMILES: COc1ccc(-c2ccc3c(c2)CCC3=O)c(OCC2(C(=O)OC(C)(C)C#N)CCC2)c1OC] | (1-cyano-1-methyl-ethyl) 1-[[2,3-dimethoxy-6-(1-oxoindan-5-yl)phenoxy]methyl]cyclobutanecarboxylate |
| 613 | 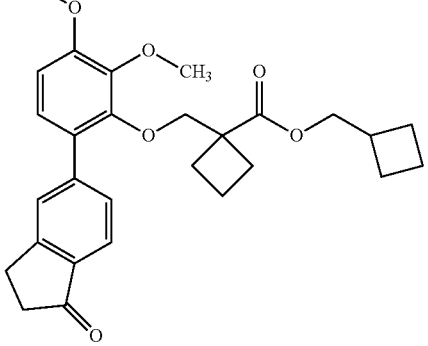 | cyclobutylmethyl 1-[[2,3-dimethoxy-6-(1-oxoindan-5-yl)phenoxy]methyl]cyclobutanecarboxylate |
| 614 | 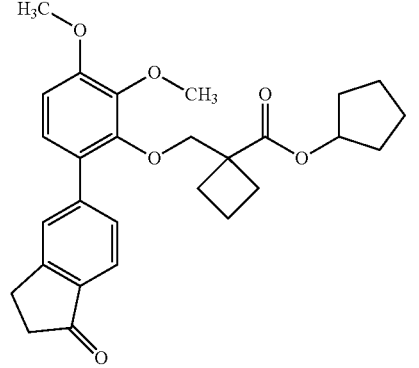 | cyclopentyl 1-[[2,3-dimethoxy-6-(1-oxoindan-5-yl)phenoxy]methyl]cyclobutanecarboxylate |

-continued

| Compound | Structure | Structure name |
| --- | --- | --- |
| 615 | 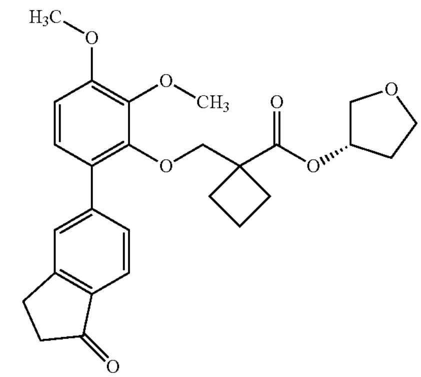 | [(3S)-tetrahydrofuran-3-yl] 1-[[2,3-dimethoxy-6-(1-oxoindan-5-yl)phenoxy]methyl]cyclobutanecarboxylate |
| 616 | 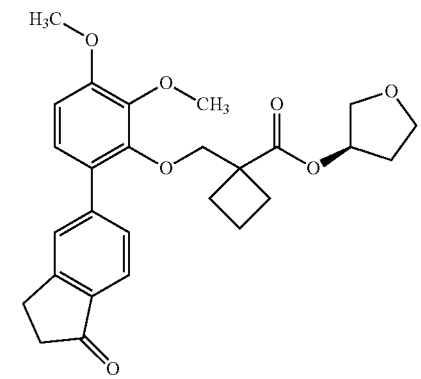 | [(3R)-tetrahydrofuran-3-yl] 1-[[2,3-dimethoxy-6-(1-oxoindan-5-yl)phenoxy]methyl]cyclobutanecarboxylate |
| 617 | 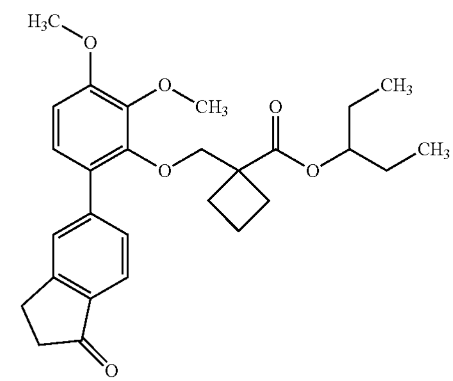 [SMILES: CCC(CC)OC(=O)C1(COc2c(-c3ccc4c(c3)CCC4=O)ccc(OC)c2OC)CCC1] | 1-ethylpropyl 1-[[2,3-dimethoxy-6-(1-oxoindan-5-yl)phenoxy]methyl]cyclobutanecarboxylate |
| 618 | 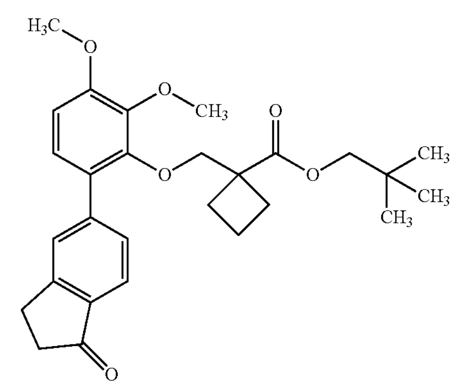 [SMILES: COc1ccc(-c2ccc3c(c2)CCC3=O)c(OCC2(C(=O)OCC(C)(C)C)CCC2)c1OC] | 2,2-dimethylpropyl 1-[[2,3-dimethoxy-6-(1-oxoindan-5-yl)phenoxy]methyl]cyclobutanecarboxylate |

| Compound | Structure | Structure name |
|---|---|---|
| 619 | 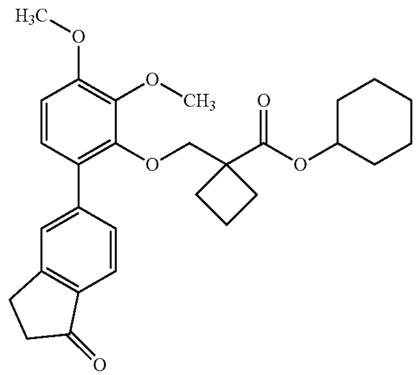 | cyclohexyl 1-[[2,3-dimethoxy-6-(1-oxoindan-5-yl)phenoxy]methyl]cyclobutanecarboxylate |
| 620 | 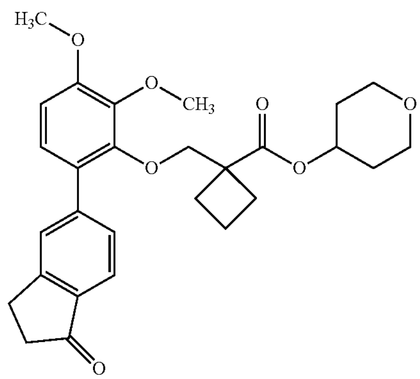 | tetrahydropyran-4-yl 1-[[2,3-dimethoxy-6-(1-oxoindan-5-yl)phenoxy]methyl]cyclobutanecarboxylate |
| 621 | 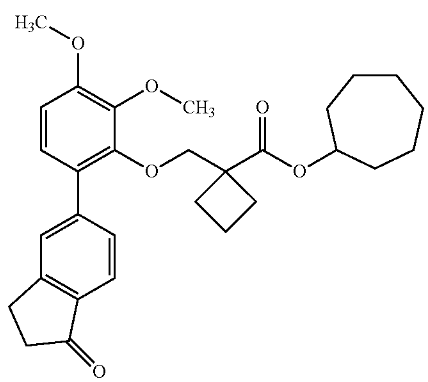 | cycloheptyl 1-[[2,3-dimethoxy-6-(1-oxoindan-5-yl)phenoxy]methyl]cyclobutanecarboxylate |

| Compound | Structure | Compound name |
|---|---|---|
| 622 | 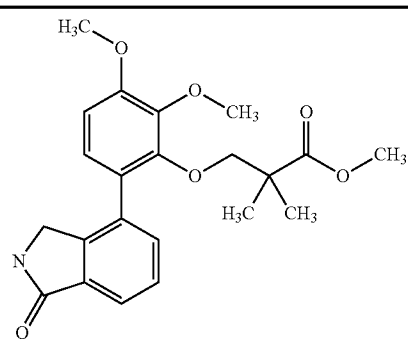 | methyl 3-[2,3-dimethoxy-6-(1-oxoisoindolin-4-yl)phenoxy]-2,2-dimethyl-propanoate |

| Compound | Structure | Compound name |
|---|---|---|
| 623 | 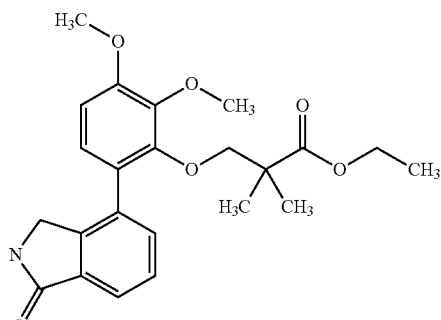 | ethyl 3-[2,3-dimethoxy-6-(1-oxoisoindolin-4-yl)phenoxy]-2,2-dimethoxy-propanoate |
| 624 | 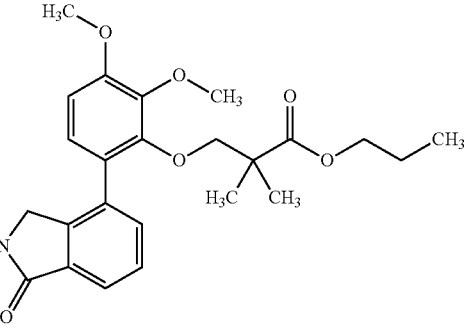 | propyl 3-[2,3-dimethoxy-6-(1-oxoisoindolin-4-yl)phenoxy]-2,2-dimethyl-propanoate |
| 625 | 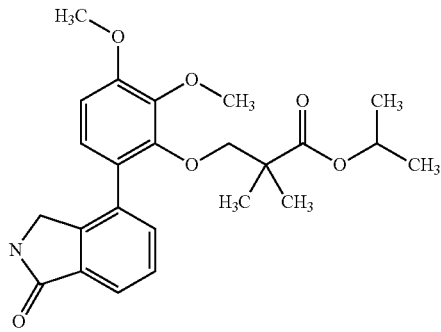 [SMILES: COc1ccc(-c2cccc3c2CNC3=O)c(OCC(C)(C)C(=O)OC(C)C)c1OC] | isopropyl 3-[2,3-dimethoxy-6-(1-oxoisoindolin-4-yl)phenoxy]-2,2-dimethyl-propanoate |
| 626 | 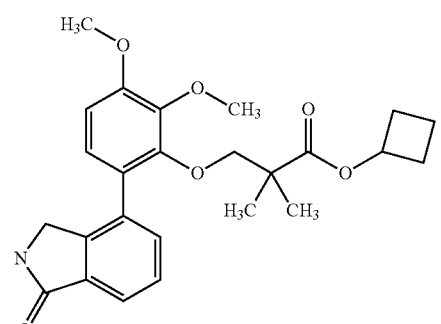 | cyclobutyl 3-[2,3-dimethoxy-6-(1-oxoisoindolin-4-yl)phenoxy]-2,2-dimethyl-propanoate |

| Compound | Structure | Compound name |
| --- | --- | --- |
| 627 | 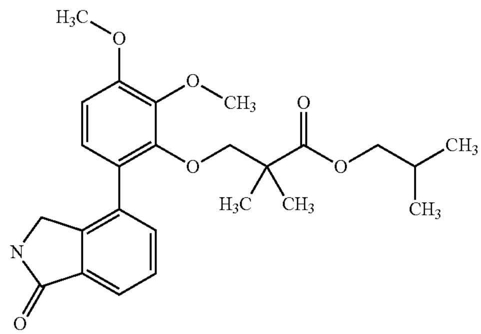 [SMILES: COc1ccc(-c2cccc3c2CNC3=O)c(OCC(C)(C)C(=O)OCC(C)C)c1OC] | isobutyl 3-[2,3-dimethoxy-6-(1-oxoisoindolin-4-yl)phenoxy]-2,2-dimethyl-propanoate |
| 628 | 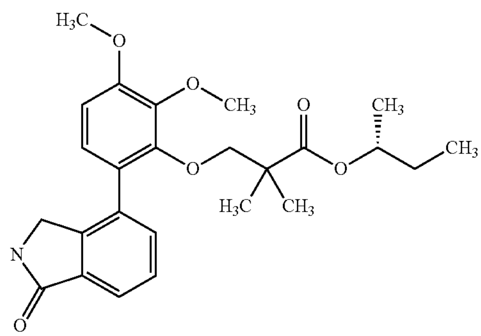 [SMILES: CC[C@@H](C)OC(=O)C(C)(C)COc1c(-c2cccc3c2CNC3=O)ccc(OC)c1OC] | [(1R)-1-methylpropyl] 3-[2,3-dimethoxy-6-(1-oxoisoindolin-4-yl)phenoxy]-2,2-dimethyl-propanoate |
| 629 | 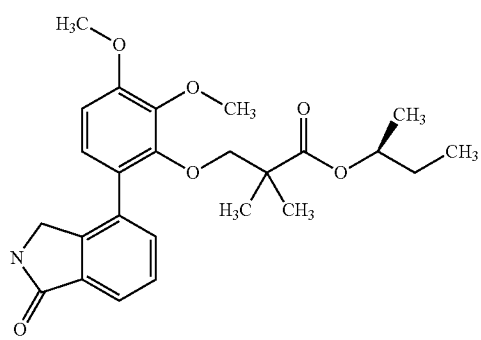 [SMILES: CC[C@H](C)OC(=O)C(C)(C)COc1c(-c2cccc3c2CNC3=O)ccc(OC)c1OC] | [(1S)-1-methylpropyl] 3-[2,3-dimethoxy-6-(1-oxoisoindolin-4-yl)phenoxy]-2,2-dimethyl-propanoate |
| 630 | 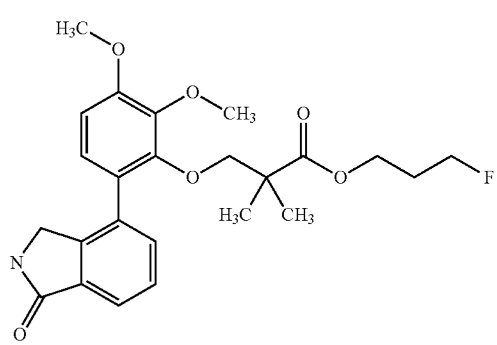 [SMILES: COc1ccc(-c2cccc3c2CNC3=O)c(OCC(C)(C)C(=O)OCCCF)c1OC] | 3-fluoropropyl 3-[2,3-dimethoxy-6-(1-oxoisoindolin-4-yl)phenoxy]-2,2-dimethyl-propanoate |

| Compound | Structure | Compound name |
|---|---|---|
| 631 | 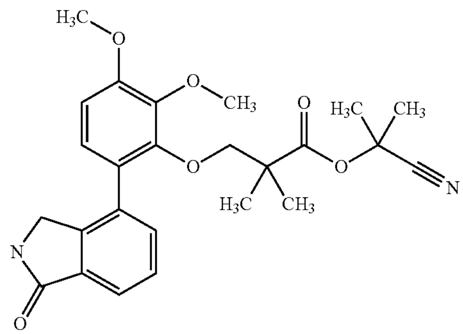 [SMILES: COc1ccc(-c2cccc3c2CNC3=O)c(OCC(C)(C)C(=O)OC(C)(C)C#N)c1OC] | (1-cyano-1-methyl-ethyl) 3-[2,3-dimethoxy-6-(1-oxoisoindolin-4-yl)phenoxy]-2,2-dimethyl-propanoate |
| 632 | 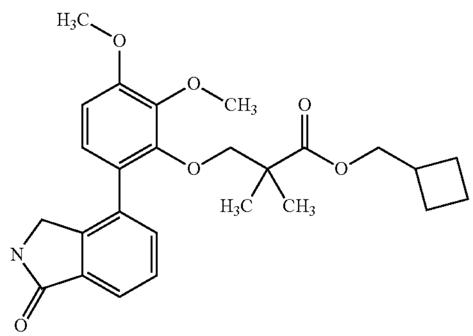 [SMILES: COc1ccc(-c2cccc3c2CNC3=O)c(OCC(C)(C)C(=O)OCC2CCC2)c1OC] | cyclobutylmethyl 3-[2,3-dimethoxy-6-(1-oxoisoindolin-4-yl)phenoxy]-2,2-dimethyl-propanoate |
| 633 | 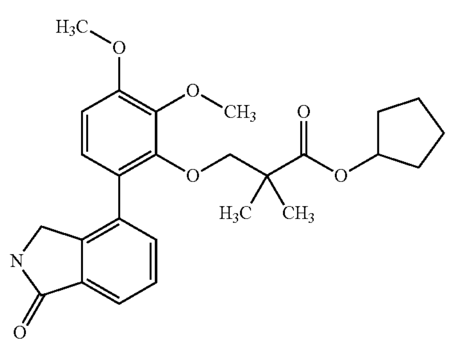 [SMILES: COc1ccc(-c2cccc3c2CNC3=O)c(OCC(C)(C)C(=O)OC2CCCC2)c1OC] | cyclopentyl 3-[2,3-dimethoxy-6-(1-oxoisoindolin-4-yl)phenoxy]-2,2-dimethyl-propanoate |
| 634 | 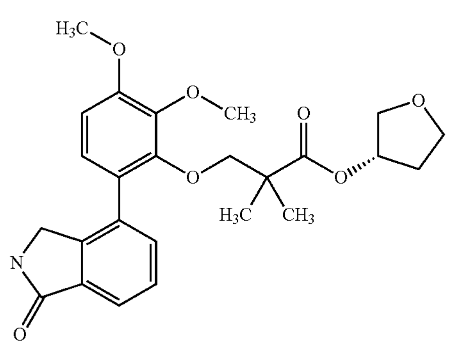 [SMILES: COc1ccc(-c2cccc3c2CNC3=O)c(OCC(C)(C)C(=O)O[C@H]2CCOC2)c1OC] | [(3S)-tetrahydrofuran-3-yl] 3-[2,3-dimethoxy-6-(1-oxoisoindolin-4-yl)phenoxy]-2,2-dimethyl-propanoate |

-continued

| Compound | Structure | Compound name |
|---|---|---|
| 635 | 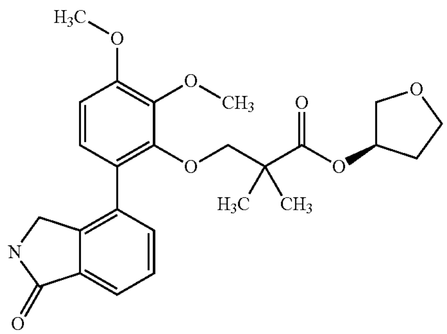 [SMILES: COc1ccc(-c2cccc3c2CNC3=O)c(OCC(C)(C)C(=O)O[C@@H]2CCOC2)c1OC] | [(3R)-tetrahydrofuran-3-yl] 3-[2,3-dimethoxy-6-(1-oxoisoindolin-4-yl)phenoxy]-2,2-dimethyl-propanoate |
| 636 | 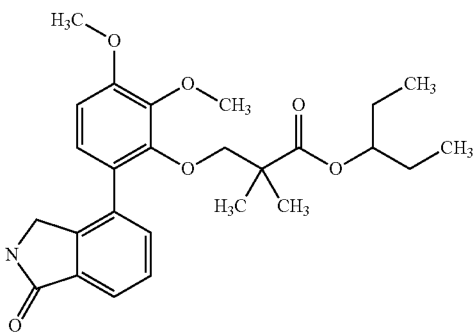 [SMILES: CCC(CC)OC(=O)C(C)(C)COc1c(-c2cccc3c2CNC3=O)ccc(OC)c1OC] | 1-ethylpropyl 3-[2,3-dimethoxy-6-(1-oxoisoindolin-4-yl)phenoxy]-2,2-dimethyl-propanoate |
| 637 | 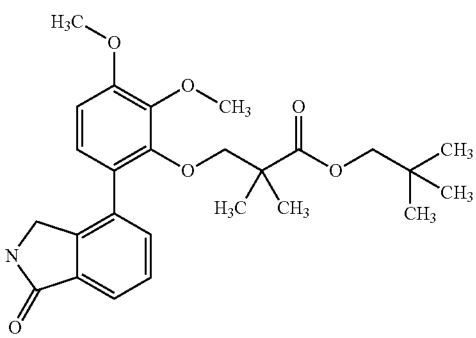 [SMILES: COc1ccc(-c2cccc3c2CNC3=O)c(OCC(C)(C)C(=O)OCC(C)(C)C)c1OC] | 2,2-dimethylpropyl 3-[2,3-dimethoxy-6-(1-oxoisoindolin-4-yl)phenoxy]-2,2-dimethyl-propanoate |
| 638 | 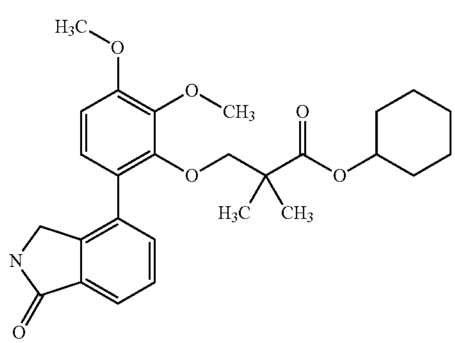 [SMILES: COc1ccc(-c2cccc3c2CNC3=O)c(OCC(C)(C)C(=O)OC2CCCCC2)c1OC] | cyclohexyl 3-[2,3-dimethoxy-6-(1-oxoisoindolin-4-yl)phenoxy]-2,2-dimethyl-propanoate |

| Compound | Structure | Compound name |
|---|---|---|
| 639 | 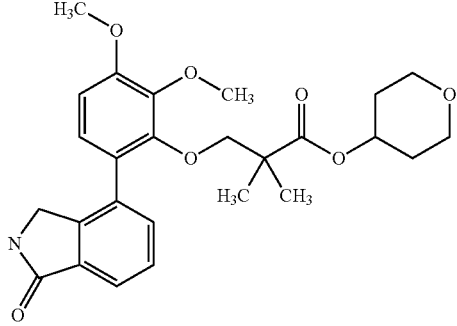 [SMILES: COc1ccc(-c2cccc3c2CNC3=O)c(OCC(C)(C)C(=O)OC2CCOCC2)c1OC] | tetrahydropyran-4-yl 3-[2,3-dimethoxy-6-(1-oxoisoindolin-4-yl)phenoxy]-2,2-dimethyl-propanoate |
| 640 | 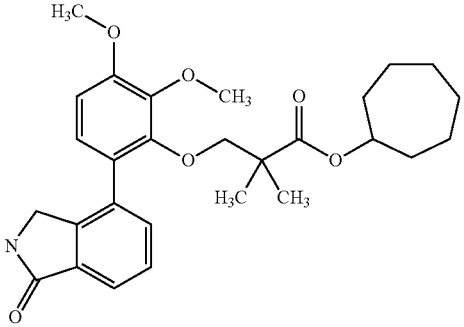 [SMILES: COc1ccc(-c2cccc3c2CNC3=O)c(OCC(C)(C)C(=O)OC2CCCCCC2)c1OC] | cycloheptyl 3-[2,3-dimethoxy-6-(1-oxoisoindolin-4-yl)phenoxy]-2,2-dimethyl-propanoate |
| 641 | 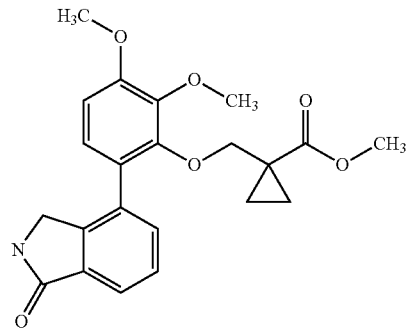 [SMILES: COC(=O)C1(COc2c(-c3cccc4c3CNC4=O)ccc(OC)c2OC)CC1] | methyl 1-[[2,3-dimethoxy-6-(1-oxoisoindolin-4-yl)phenoxy]methyl]cycloprpanecarboxylate |
| 642 | 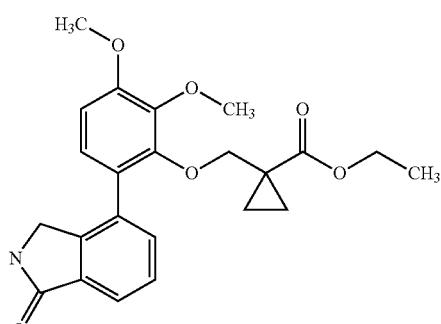 | ethyl 1-[[2,3-dimethoxy-6-(1-oxoisoindolin-4-yl)phenoxy]methyl]cyclopropanecarboxylate |

| Compound | Structure | Compound name |
|---|---|---|
| 643 | 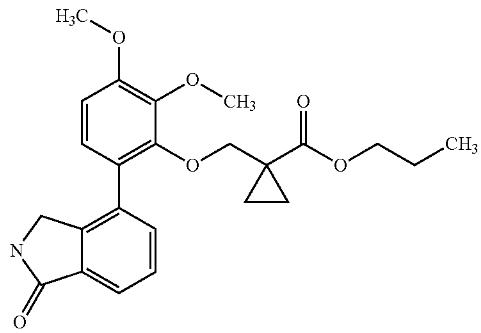 [SMILES: CCCOC(=O)C1(COc2c(-c3cccc4c3CNC4=O)ccc(OC)c2OC)CC1] | propyl 1-[[2,3-dimethoxy-6-(1-oxoisoindolin-4-yl)phenoxy]methyl]cyclopropanecarboxylate |
| 644 | 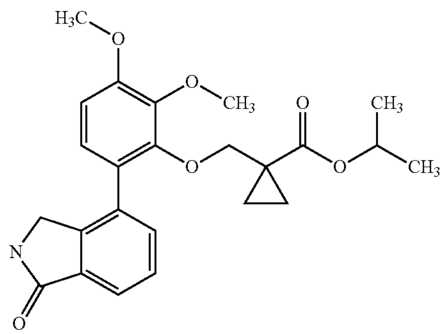 [SMILES: COc1ccc(-c2cccc3c2CNC3=O)c(OCC2(C(=O)OC(C)C)CC2)c1OC] | isopropyl 1-[[2,3-dimethoxy-6-(1-oxoisoindolin-4-yl)phenoxy]methyl]cyclopropanecarboxylate |
| 645 | 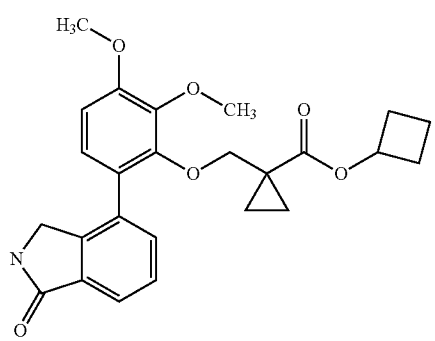 [SMILES: COc1ccc(-c2cccc3c2CNC3=O)c(OCC2(C(=O)OC3CCC3)CC2)c1OC] | cyclobutyl 1-[[2,3-dimethoxy-6-(1-oxoisoindolin-4-yl)phenoxy]methyl]cyclopropanecarboxylate |
| 646 | 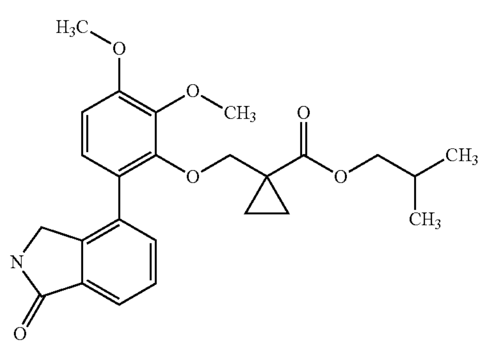 [SMILES: COc1ccc(-c2cccc3c2CNC3=O)c(OCC2(C(=O)OCC(C)C)CC2)c1OC] | isobutyl 1-[[2,3-dimethoxy-6-(1-oxoisoindolin-4-yl)phenoxy]methyl]cyclopropanecarboxylate |

-continued

| Compound | Structure | Compound name |
|---|---|---|
| 647 | 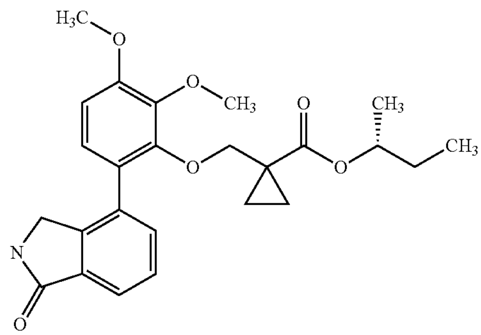 [SMILES: CC[C@@H](C)OC(=O)C1(COc2c(-c3cccc4c3CNC4=O)ccc(OC)c2OC)CC1] | [(1R)-1-methylpropyl] 1[[2,3-dimethoxy-6-(1-oxoisoindolin-4-yl)phenoxy]methyl]cyclopropanecarboxylate |
| 648 | 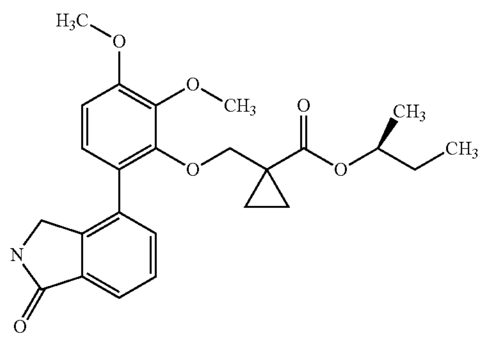 [SMILES: CC[C@H](C)OC(=O)C1(COc2c(-c3cccc4c3CNC4=O)ccc(OC)c2OC)CC1] | [(1S)-1-methylpropyl] 1-[[2,3-dimethoxy-6-(1-oxoisoindolin-4-yl)phenoxy]methyl]cyclopropanecarboxylate |
| 649 | 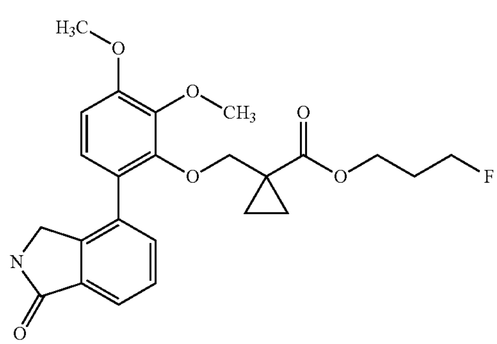 [SMILES: COc1ccc(-c2cccc3c2CNC3=O)c(OCC2(C(=O)OCCCF)CC2)c1OC] | 3-fluoropropyl 1-[[2,3-dimethoxy-6-(1-oxoisoindolin-4-yl)phenoxy]methyl]cyclopropanecarboxylate |
| 650 | 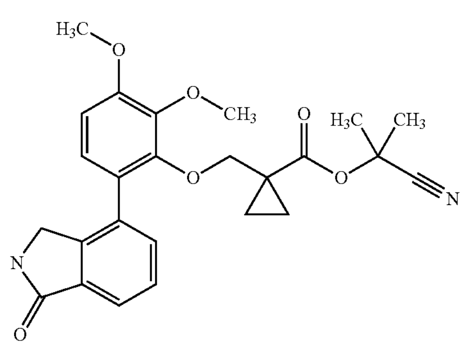 [SMILES: COc1ccc(-c2cccc3c2CNC3=O)c(OCC2(C(=O)OC(C)(C)C#N)CC2)c1OC] | (1-cyano-1-methyl-ethyl) 1-[[2,3-dimethoxy-6-(1-oxoisoindolin-4-yl)phenoxy]methyl]cyclopropanecarboxylate |

| Compound | Structure | Compound name |
|---|---|---|
| 651 | 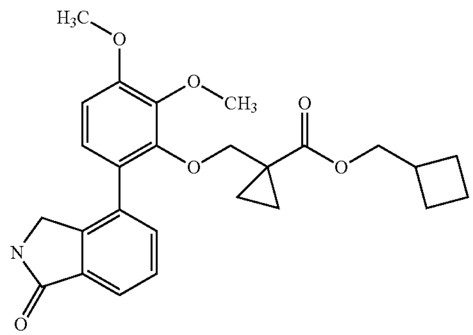 [SMILES: COc1ccc(-c2cccc3c2CNC3=O)c(OCC2(C(=O)OCC3CCC3)CC2)c1OC] | cyclobutylmethyl 1-[[2,3-dimethoxy-6-(1-oxoisoindolin-4-yl)phenoxy]methyl]cyclopropanecarboxylate |
| 652 | 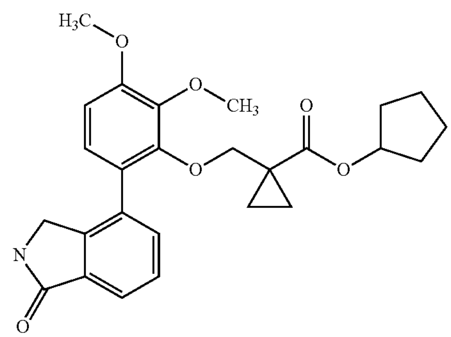 [SMILES: COc1ccc(-c2cccc3c2CNC3=O)c(OCC2(C(=O)OC3CCCC3)CC2)c1OC] | cyclopentyl 1-[[2,3-dimethoxy-6-(1-oxoisoindolin-4-yl)phenoxy]methyl]cyclopropanecarboxylate |
| 653 | 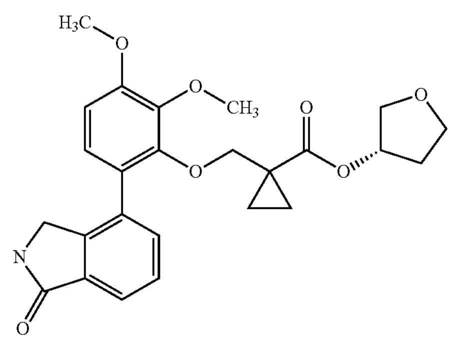 [SMILES: COc1ccc(-c2cccc3c2CNC3=O)c(OCC2(C(=O)O[C@H]3CCOC3)CC2)c1OC] | [(3S)-tetrahydrofuran-3-yl] 1-[[2,3-dimethoxy-6-(1-oxoisoindolin-4-yl)phenoxy]methyl]cyclopropanecarboxylate |
| 654 | 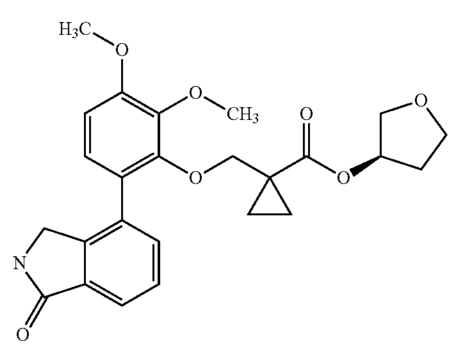 [SMILES: COc1ccc(-c2cccc3c2CNC3=O)c(OCC2(C(=O)O[C@@H]3CCOC3)CC2)c1OC] | [(3R)-tetrahydrofuran-3-yl] 1-[[2,3-dimethoxy-6-(1-oxoisoindolin-4-yl)phenoxy]methyl]cyclopropanecarboxylate |

-continued

| Compound | Structure | Compound name |
|---|---|---|
| 655 | 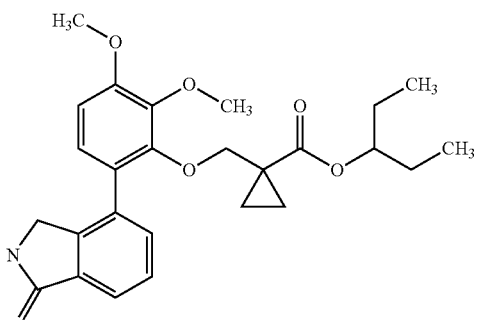 | 1-ethylpropyl 1-[[2,3-dimethoxy-6-(1-oxoisoindolin-4-yl)phenoxy]methyl]cyclopropanecarboxylate |
| 656 | 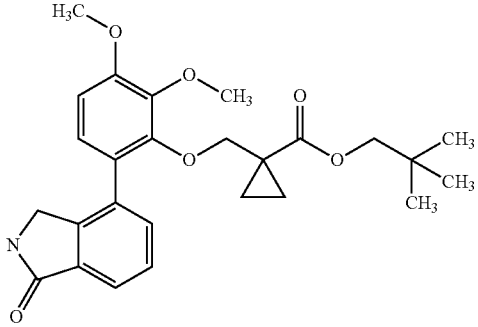 [SMILES: COc1ccc(-c2cccc3c2CNC3=O)c(OCC2(C(=O)OCC(C)(C)C)CC2)c1OC] | 2,2-dimethylpropyl 1-[[2,3-dimethoxy-6-(1-oxoisoindolin-4-yl)phenoxy]methyl]cyclopropanecarboxylate |
| 657 | 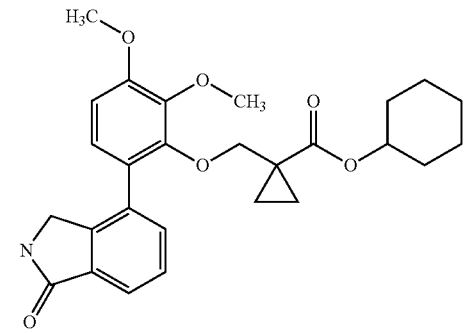 [SMILES: COc1ccc(-c2cccc3c2CNC3=O)c(OCC2(C(=O)OC3CCCCC3)CC2)c1OC] | cyclohexyl 1-[[2,3-dimethoxy-6-(1-oxoisoindolin-4-yl)phenoxy]methyl]cyclopropanecarboxylate |
| 658 | 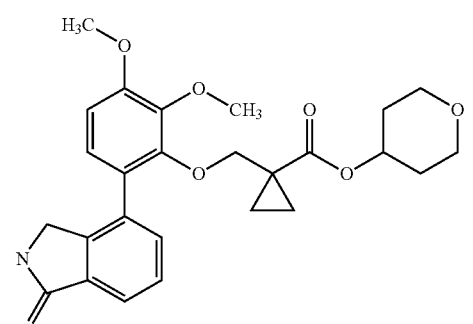 | tetrahydrofuran-4-yl 1-[[2,3-dimethoxy-6-(1-oxoisoindolin-4-yl)phenoxy]methyl]cyclopropanecarboxylate |

-continued

| Compound | Structure | Compound name |
|---|---|---|
| 659 | 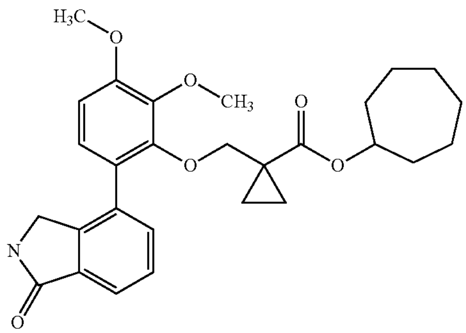 [SMILES: COc1ccc(-c2cccc3c2CNC3=O)c(OCC2(C(=O)OC3CCCCCC3)CC2)c1OC] | cycloheptyl 1-[[2,3-dimethoxy-6-(1-oxoisoindolin-4-yl)phenoxy]methyl]cyclopropanecarboxylate |
| 660 | 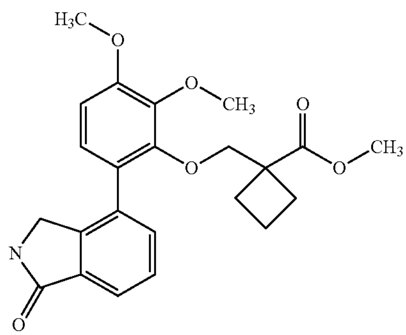 [SMILES: COC(=O)C1(COc2c(-c3cccc4c3CNC4=O)ccc(OC)c2OC)CCC1] | methyl 1-[[2,3-dimethoxy-6-(1-oxoisoindolin-4-yl)phenoxy]methyl]cyclobutanecarboxylate |
| 661 | 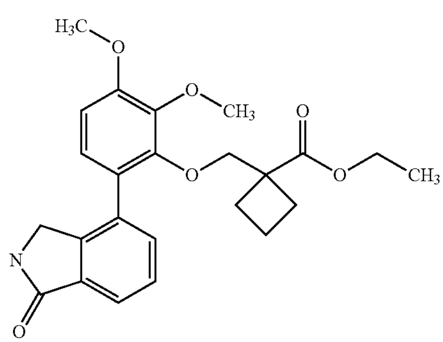 [SMILES: CCOC(=O)C1(COc2c(-c3cccc4c3CNC4=O)ccc(OC)c2OC)CCC1] | ethyl 1-[[2,3-dimethoxy-6-(1-oxoisoindolin-4-yl)phenoxy]methyl]cyclobutanecarboxylate |
| 662 | 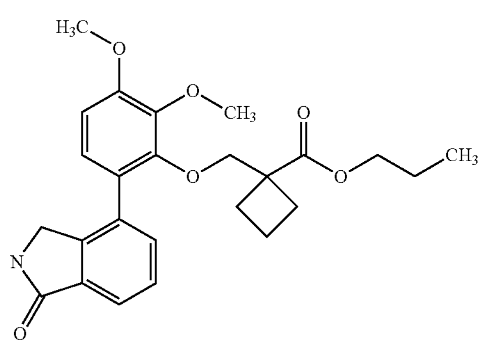 [SMILES: CCCOC(=O)C1(COc2c(-c3cccc4c3CNC4=O)ccc(OC)c2OC)CCC1] | propyl 1-[[2,3-dimethoxy-6-(1-oxoisoindolin-4-yl)phenoxy]methyl]cyclobutanecarboxylate |

| Compound | Structure | Compound name |
|---|---|---|
| 663 | 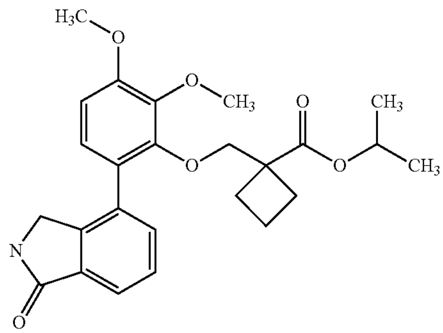 [SMILES: COc1ccc(-c2cccc3c2CNC3=O)c(OCC2(C(=O)OC(C)C)CCC2)c1OC] | isopropyl 1-[[2,3-dimethoxy-6-(1-oxoisoindolin-4-yl)phenoxy]methyl]cyclobutanecarboxylate |
| 664 | 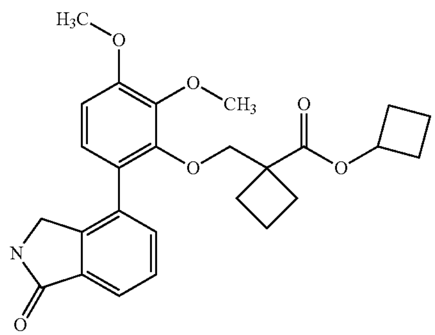 [SMILES: COc1ccc(-c2cccc3c2CNC3=O)c(OCC2(C(=O)OC3CCC3)CCC2)c1OC] | cyclobutyl 1-[[2,3-dimethoxy-6-(1-oxoisoindolin-4-yl)phenoxy]methyl]cyclobutanecarboxylate |
| 665 | 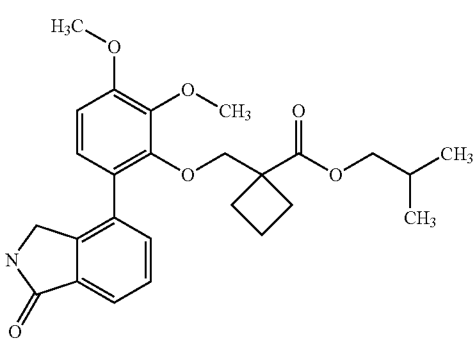 [SMILES: COc1ccc(-c2cccc3c2CNC3=O)c(OCC2(C(=O)OCC(C)C)CCC2)c1OC] | isobutyl 1-[[2,3-dimethoxy-6-(1-oxoisoindolin-4-yl)phenoxy]methyl]cyclobutanecarboxylate |
| 666 | 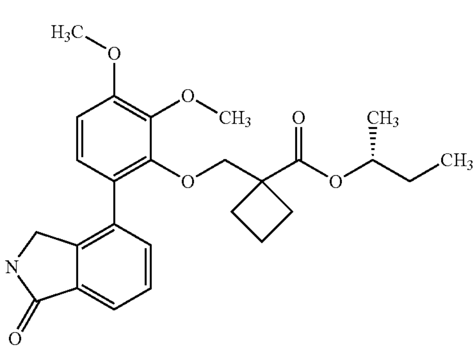 [SMILES: CC[C@@H](C)OC(=O)C1(COc2c(-c3cccc4c3CNC4=O)ccc(OC)c2OC)CCC1] | [(1R)-1-methylpropyl] 1-[[2,3-dimethoxy-6-(1-oxoisoindolin-4-yl)phenoxy]methyl]cyclobutanecarboxylate |

| Compound | Structure | Compound name |
|---|---|---|
| 667 | 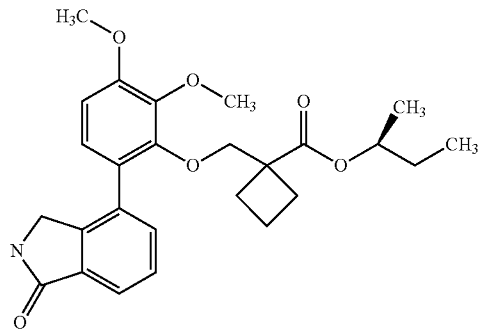 [SMILES: CC[C@H](C)OC(=O)C1(COc2c(-c3cccc4c3CNC4=O)ccc(OC)c2OC)CCC1] | [(1S)-1-methylpropyl] 1-[[2,3-dimethoxy-6-(1-oxoisoindolin-4-yl)phenoxy]methyl]cyclobutanecarboxylate |
| 668 | 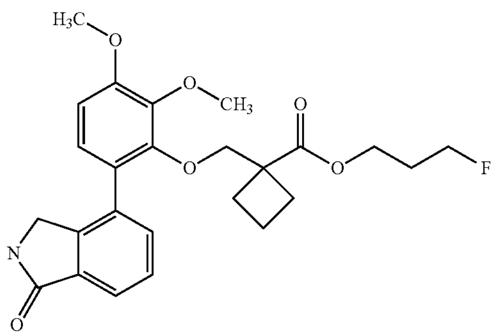 [SMILES: COc1ccc(-c2cccc3c2CNC3=O)c(OCC2(C(=O)OCCCF)CCC2)c1OC] | 3-fluoropropyl 1-[[2,3-dimethoxy-6-(1-oxoisoindolin-4-yl)phenoxy]methyl]cyclobutanecarboxylate |
| 669 | 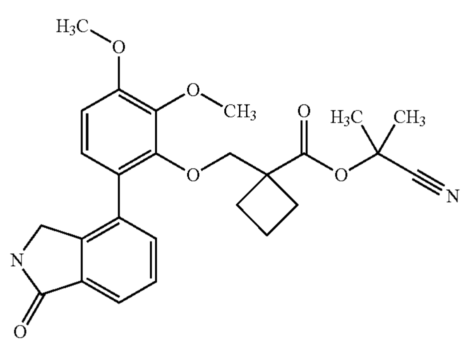 [SMILES: COc1ccc(-c2cccc3c2CNC3=O)c(OCC2(C(=O)OC(C)(C)C#N)CCC2)c1OC] | (1-cyano-1-methyl-ethyl) 1-[[2,3-dimethoxy-6-oxoisoindolin-4-yl)phenoxy]methyl]cyclobutanecarboxylate |
| 670 | 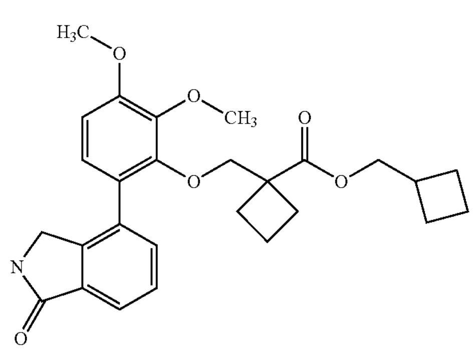 [SMILES: COc1ccc(-c2cccc3c2CNC3=O)c(OCC2(C(=O)OCC3CCC3)CCC2)c1OC] | cyclobutylmethyl 1-[[2,3-dimethoxy-6-(1-oxoisoindolin-4-yl)phenoxy]methyl]cyclobutanecarboxylate |

-continued

| Compound | Structure | Compound name |
|---|---|---|
| 671 | 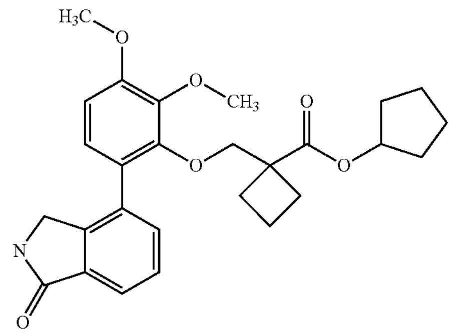 [SMILES: COc1ccc(-c2cccc3c2CNC3=O)c(OCC2(C(=O)OC3CCCC3)CCC2)c1OC] | cyclopentyl 1-[[2,3-dimethoxy-6-(1-oxoisoindolin-4-yl)phenoxy]methyl]cyclobutanecarboxylate |
| 672 | 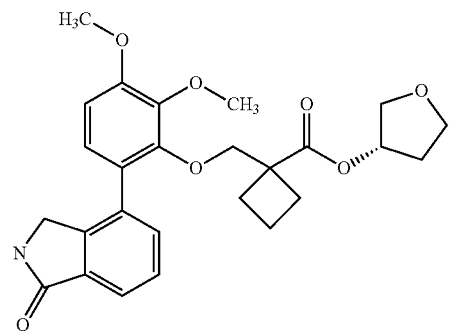 [SMILES: COc1ccc(-c2cccc3c2CNC3=O)c(OCC2(C(=O)O[C@H]3CCOC3)CCC2)c1OC] | [(3S)-tetrahydrofuran-3-yl] 1-[[2,3-dimethoxy-6-(1-oxoisoindolin-4-yl)phenoxy]methyl]cyclobutanecarboxylate |
| 673 | 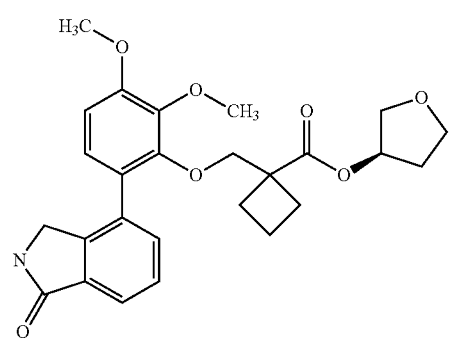 [SMILES: COc1ccc(-c2cccc3c2CNC3=O)c(OCC2(C(=O)O[C@@H]3CCOC3)CCC2)c1OC] | [(3R)-tetrahydrofuran-3-yl] 1-[[2,3-dimethoxy-6-(1-oxoisoindolin-4-yl)phenoxy]methyl]cyclobutanecarboxylate |
| 674 | 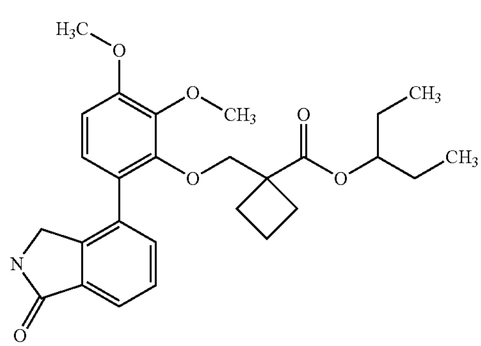 [SMILES: CCC(CC)OC(=O)C1(COc2c(-c3cccc4c3CNC4=O)ccc(OC)c2OC)CCC1] | 1-ethylpropyl 1-[[2,3-dimethoxy-6-(1-oxoisoindolin-4-yl)phenoxy]methyl]cyclobutanecarboxylate |

-continued

| Compound | Structure | Compound name |
|---|---|---|
| 675 | 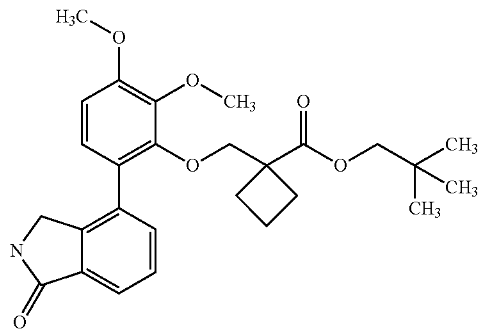 [SMILES: COc1ccc(-c2cccc3c2CNC3=O)c(OCC2(C(=O)OCC(C)(C)C)CCC2)c1OC] | 2,2-dimethylpropyl 1-[[2,3-dimethoxy-6-(1-oxoisoindolin-4-yl)phenoxy]methyl]cyclobutanecarboxylate |
| 676 | 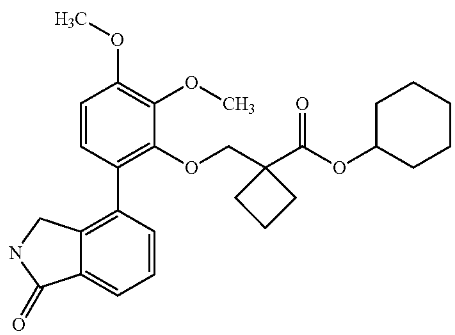 [SMILES: COc1ccc(-c2cccc3c2CNC3=O)c(OCC2(C(=O)OC3CCCCC3)CCC2)c1OC] | cyclohexyl 1-[[2,3-dimethoxy-6-(1-oxoisoindolin-4-yl)phenoxy]methyl]cyclobutanecarboxylate |
| 677 | 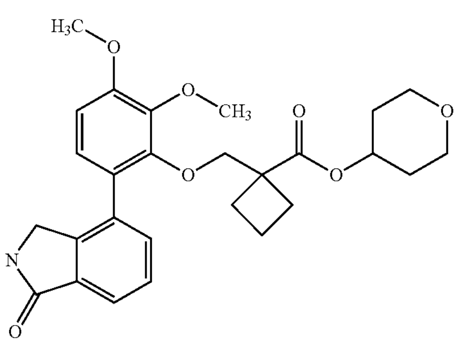 [SMILES: COc1ccc(-c2cccc3c2CNC3=O)c(OCC2(C(=O)OC3CCOCC3)CCC2)c1OC] | tetrahydropyran-4-yl 1-[[2,3-dimethoxy-6-(1-oxoisoindolin-4-yl)phenoxy]methyl]cyclobutanecarboxylate |
| 678 | 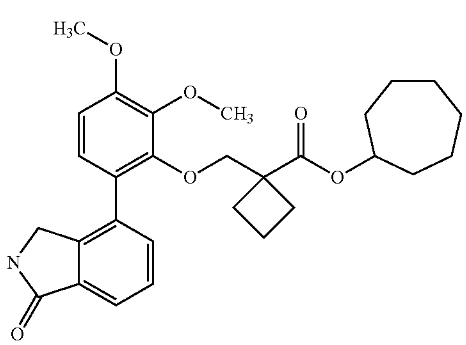 [SMILES: COc1ccc(-c2cccc3c2CNC3=O)c(OCC2(C(=O)OC3CCCCCC3)CCC2)c1OC] | cycloheptyl 1-[[2,3-dimethoxy-6-(1-oxoisoindolin-4-yl)phenoxy]methyl]cyclobutanecarboxylate |

| Compound | Structure | Compound name |
|---|---|---|
| 679 | 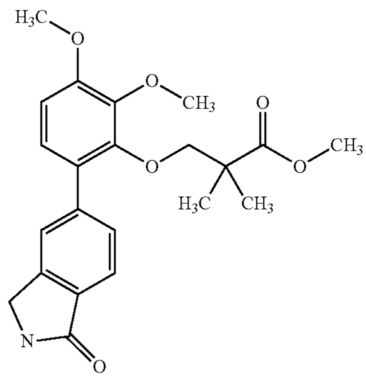 [SMILES: COC(=O)C(C)(C)COc1c(-c2ccc3c(c2)CNC3=O)ccc(OC)c1OC] | methyl 3-[2,3-dimethoxy-6-(1-oxoisoindolin-5-yl)phenoxy]-2,2-dimethyl-propanoate |
| 680 | 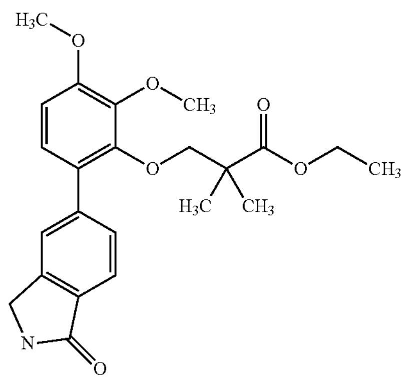 [SMILES: CCOC(=O)C(C)(C)COc1c(-c2ccc3c(c2)CNC3=O)ccc(OC)c1OC] | ethyl 3-[2,3-dimethoxy-6-(1-oxoisoindolin-5-yl)phenoxy]-2,2-dimethyl-propanoate |
| 681 | 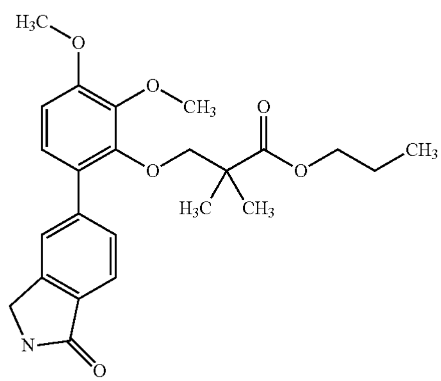 [SMILES: CCCOC(=O)C(C)(C)COc1c(-c2ccc3c(c2)CNC3=O)ccc(OC)c1OC] | propyl 3-[2,3-dimethoxy-6-(1-oxoisoindolin-5-yl)phenoxy]-2,2-dimethyl-propanoate |
| 682 | 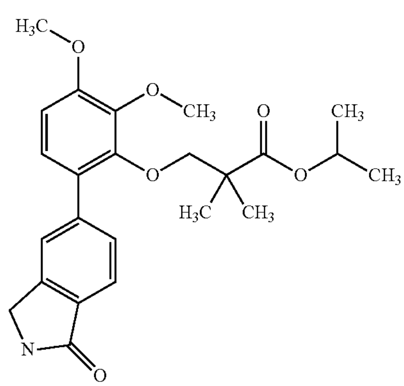 | isopropyl 3-[2,3-dimethoxy-6-(1-oxoisoindolin-5-yl)phenoxy]-2,2-dimethyl-propanoate |

| Compound | Structure | Compound name |
|---|---|---|
| 683 | 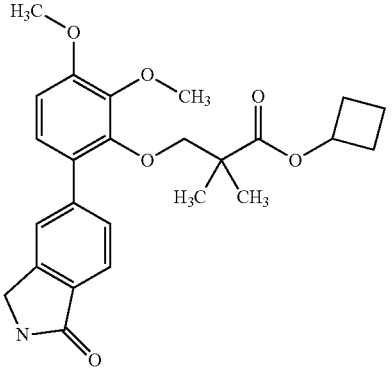 [SMILES: COc1ccc(-c2ccc3c(c2)CNC3=O)c(OCC(C)(C)C(=O)OC2CCC2)c1OC] | cyclobutyl 3-[2,3-dimethoxy-6-(1-oxoisoindolin-5-yl)phenoxy]-2,2-dimethyl-propanoate |
| 684 | 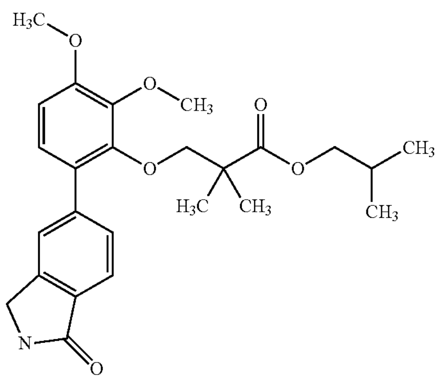 | isobutyl 3-[2,3-dimethoxy-6-(1-oxoisoindolin-5-yl)phenoxy]-2,2-dimethyl-propanoate |
| 685 | 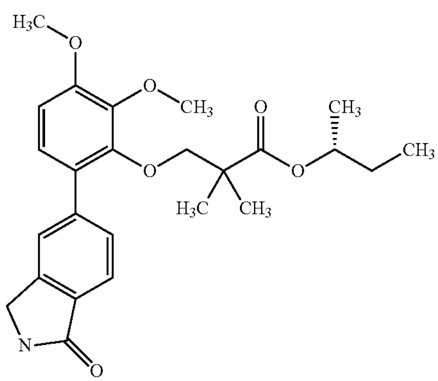 [SMILES: CC[C@@H](C)OC(=O)C(C)(C)COc1c(-c2ccc3c(c2)CNC3=O)ccc(OC)c1OC] | [(1R)-1-methylpropyl] 3-[2,3-dimethoxy-6-(1-oxoisoindolin-5-yl)phenoxy]-2,2-dimethyl-propanoate |
| 686 | 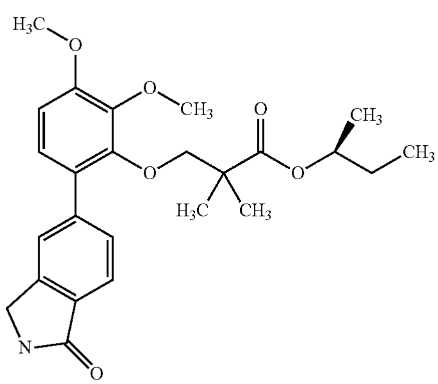 [SMILES: CC[C@H](C)OC(=O)C(C)(C)COc1c(-c2ccc3c(c2)CNC3=O)ccc(OC)c1OC] | [(1S)-1-methylpropyl] 3-[2,3-dimethoxy-6-(1-oxoisoindolin-5-yl)phenoxy]-2,2-dimethyl-propanoate |

| Compound | Structure | Compound name |
|---|---|---|
| 687 | 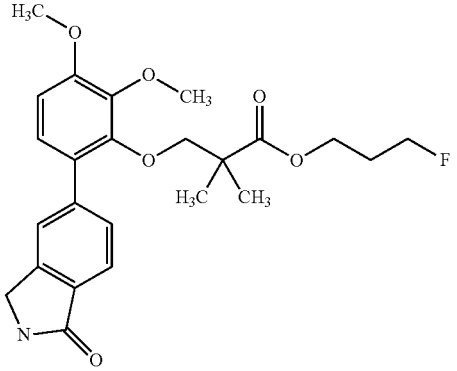 [SMILES: COc1ccc(-c2ccc3c(c2)CNC3=O)c(OCC(C)(C)C(=O)OCCCF)c1OC] | 3-fluoropropyl 3-[2,3-dimethoxy-6-(1-oxoisoindolin-5-yl)phenoxy]-2,2-dimethyl-propanoate |
| 688 | 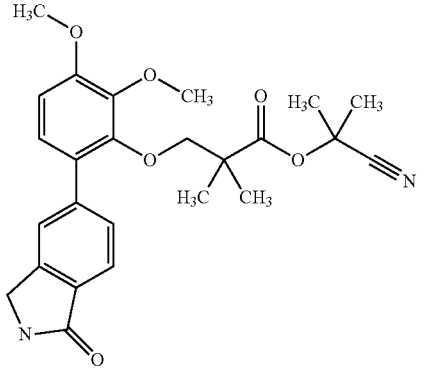 [SMILES: COc1ccc(-c2ccc3c(c2)CNC3=O)c(OCC(C)(C)C(=O)OC(C)(C)C#N)c1OC] | (1-cyano-1-methyl-ethyl) 3-[2,3-dimethoxy-6-(1-oxoisoindolin-5-yl)phenoxy]-2,2-dimethyl-propanoate |
| 689 | 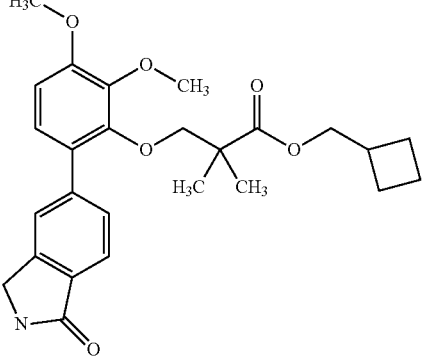 | cyclobutylmethyl 3-[2,3-dimethoxy-6-(1-oxoisoindolin-5-yl)phenoxy]-2,2-dimethyl-propanoate |
| 690 | 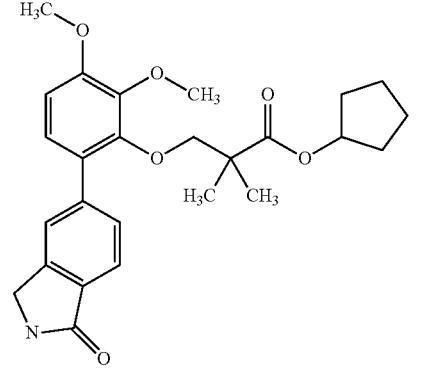 [SMILES: COc1ccc(-c2ccc3c(c2)CNC3=O)c(OCC(C)(C)C(=O)OC2CCCC2)c1OC] | cyclopentyl 3-[2,3-dimethoxy-6-(1-oxoisoindolin-5-yl)phenoxy]-2,2-dimethyl-propanoate |

-continued

| Compound | Structure | Compound name |
|---|---|---|
| 691 | 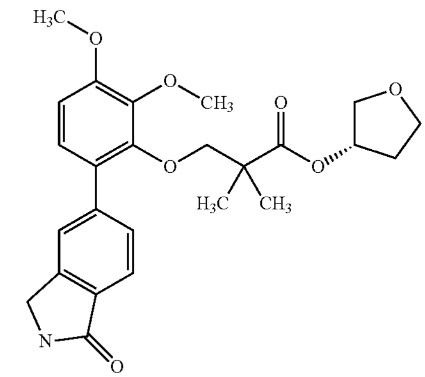 [SMILES: COc1ccc(-c2ccc3c(c2)CNC3=O)c(OCC(C)(C)C(=O)O[C@H]2CCOC2)c1OC] | [(3S)-tetrahydrofuran-3-yl] 3-[2,3-dimethoxy-6-(1-oxoisoindolin-5-yl)phenoxy]-2,2-dimethyl-propanoate |
| 692 | 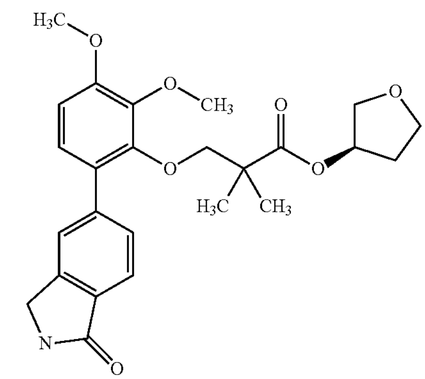 [SMILES: COc1ccc(-c2ccc3c(c2)CNC3=O)c(OCC(C)(C)C(=O)O[C@@H]2CCOC2)c1OC] | [(3R)-tetrahydrofuran-3-yl] 3-[2,3-dimethoxy-6-(1-oxoisoindolin-5-yl)phenoxy]-2,2-dimethyl-propanoate |
| 693 | 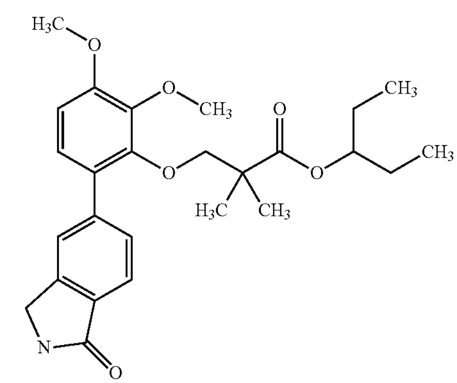 [SMILES: CCC(CC)OC(=O)C(C)(C)COc1c(-c2ccc3c(c2)CNC3=O)ccc(OC)c1OC] | 1-ethylpropyl 3-[2,3-dimethoxy-6-(1-oxoisoindolin-5-yl)phenoxy]-2,2-dimethyl-propanoate |
| 694 | 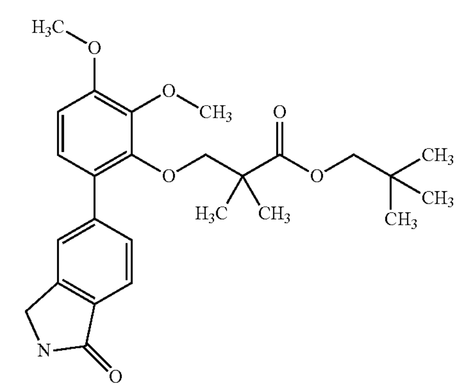 [SMILES: COc1ccc(-c2ccc3c(c2)CNC3=O)c(OCC(C)(C)C(=O)OCC(C)(C)C)c1OC] | 2,2-dimethylpropyl 3-[2,3-dimethoxy-6-(1-oxoisoindolin-5-yl)phenoxy]-2,2-dimethyl-propanoate |

-continued
| Compound | Structure | Compound name |
|---|---|---|
| 695 | 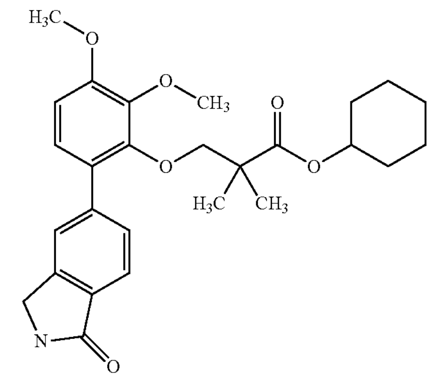 [SMILES: COc1ccc(-c2ccc3c(c2)CNC3=O)c(OCC(C)(C)C(=O)OC2CCCCC2)c1OC] | cyclohexyl 3-[2,3-dimethoxy-6-(1-oxoisoindolin-5-yl)phenoxy]-2,2-dimethyl-propanoate |
| 696 | 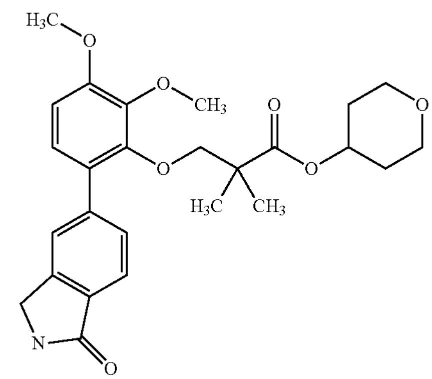 [SMILES: COc1ccc(-c2ccc3c(c2)CNC3=O)c(OCC(C)(C)C(=O)OC2CCOCC2)c1OC] | tetrahydropyran-4-yl 3-[2,3-dimethoxy-6-(1-oxoisoindolin-5-yl)phenoxy]-2,2-dimethyl-propanoate |
| 697 | 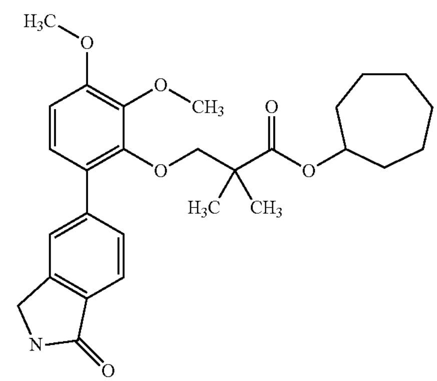 [SMILES: COc1ccc(-c2ccc3c(c2)CNC3=O)c(OCC(C)(C)C(=O)OC2CCCCCC2)c1OC] | cycloheptyl 3-[2,3-dimethoxy-6-(1-oxoisoindolin-5-yl)phenoxy]-2,2-dimethyl-propanoate |
| 698 | 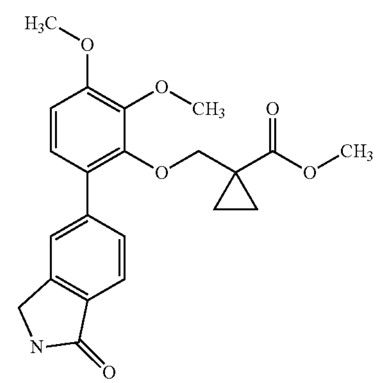 | methyl 1-[[2,3-dimethoxy-6-(1-oxoisoindolin-5-yl)phenoxy]methyl]cyclopropanecarboxylate |

-continued

| Compound | Structure | Compound name |
|---|---|---|
| 699 | 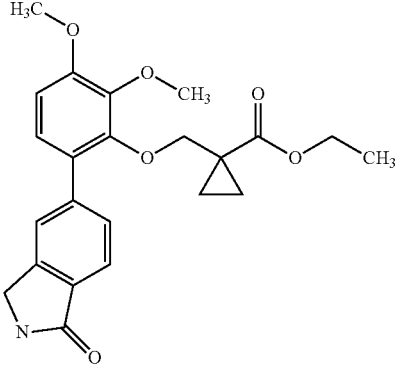 [SMILES: CCOC(=O)C1(COc2c(-c3ccc4c(c3)CNC4=O)ccc(OC)c2OC)CC1] | ethyl 1-[[2,3-dimethoxy-6-(1-oxoisoindolin-5-yl)phenoxy]methyl]cyclopropanecarboxylate |
| 700 | 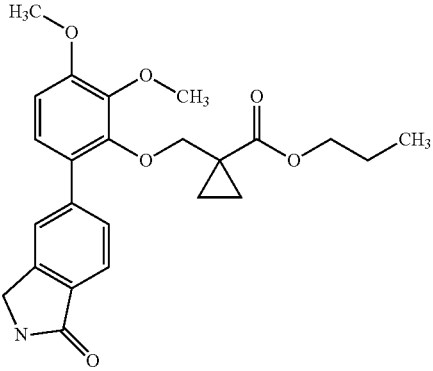 | propyl 1-[[2,3-dimethoxy-6-(1-oxoisoindolin-5-yl)phenoxy]methyl]cyclopropanecarboxylate |
| 701 | 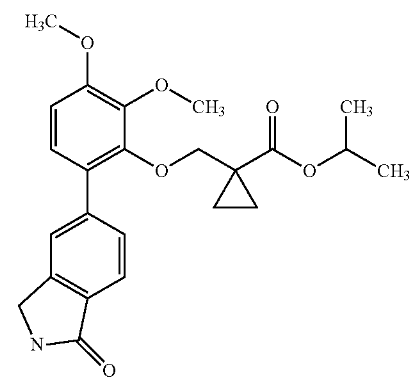 | isopropyl 1-[[2,3-dimethoxy-6-(1-oxoisoindolin-5-yl)phenoxy]methyl]cyclopropanecarboxylate |
| 702 | 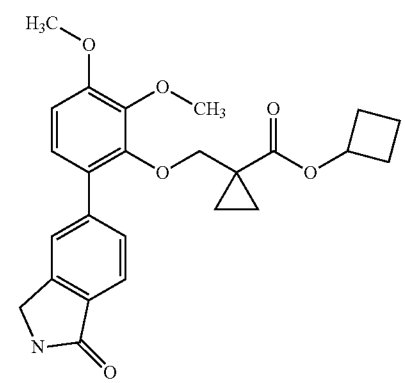 | cyclobutyl 1-[[2,3-dimethoxy-6-(1-oxoisoindolin-5-yl)phenoxy]methyl]cyclopropanecarboxylate |

-continued

| Compound | Structure | Compound name |
|---|---|---|
| 703 | 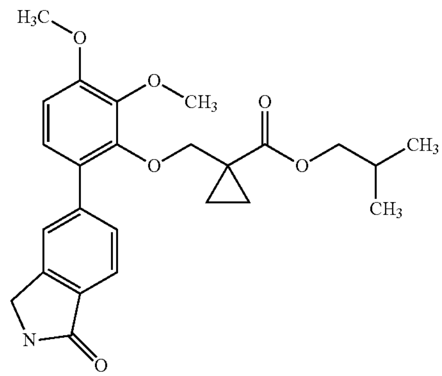 [SMILES: COc1ccc(-c2ccc3c(c2)CNC3=O)c(OCC2(C(=O)OCC(C)C)CC2)c1OC] | isobutyl 1-[[2,3-dimethoxy-6-(1-oxoisoindolin-5-yl)phenoxy]methyl]cyclopropanecarboxylate |
| 704 | 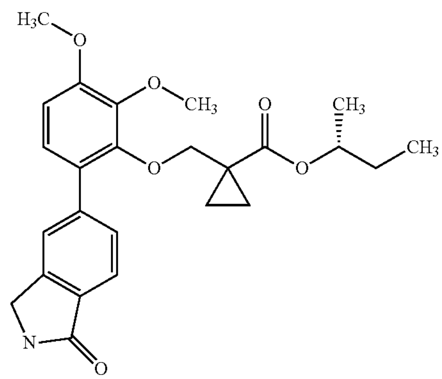 | [(1R)-methylpropyl] 1-[[2,3-dimethoxy-6-(1-oxoisoindolin-5-yl)phenoxy]methyl]cyclopropanecarboxylate |
| 705 | 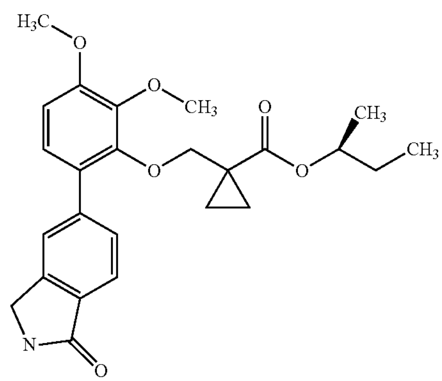 | [(1S)-1-methylpropyl] 1-[[2,3-dimethoxy-6-(1-oxoisoindolin-5-yl)phenoxy]methyl]cyclopropanecarboxylate |
| 706 | 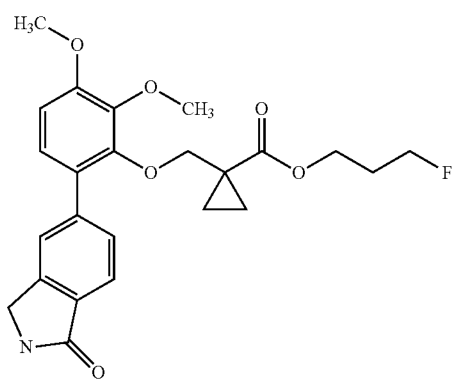 [SMILES: COc1ccc(-c2ccc3c(c2)CNC3=O)c(OCC2(C(=O)OCCCF)CC2)c1OC] | 3-fluoropropyl 1-[[2,3-dimethoxy-6-(1-oxoisoindolin-5-yl)phenoxy]methyl]cyclopropanecarboxylate |

-continued

| Compound | Structure | Compound name |
|---|---|---|
| 707 | 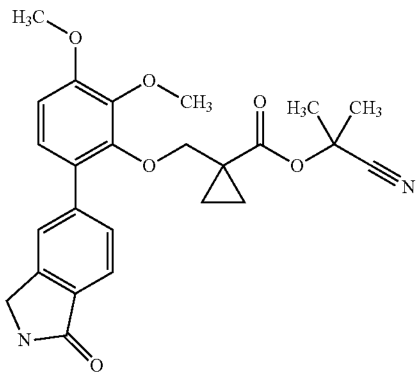 [SMILES: COc1ccc(-c2ccc3c(c2)CNC3=O)c(OCC2(C(=O)OC(C)(C)C#N)CC2)c1OC] | (1-cyano-1-methyl-ethyl) 1-[[2,3-dimethoxy-6-(1-oxoisoindolin-5-yl)phenoxy]methyl]cyclopropanecarboxylate |
| 708 | 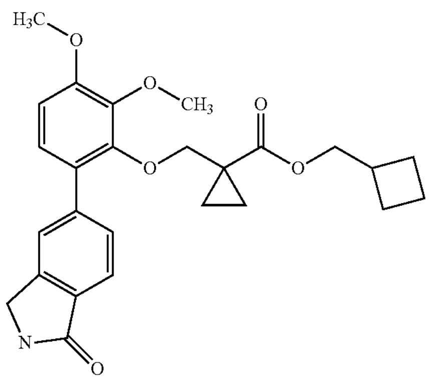 | cyclobutylmethyl 1-[[2,3-dimethoxy-6-(1-oxoisoindolin-5-yl)phenoxy]methyl]cyclopropanecarboxylate |
| 709 | 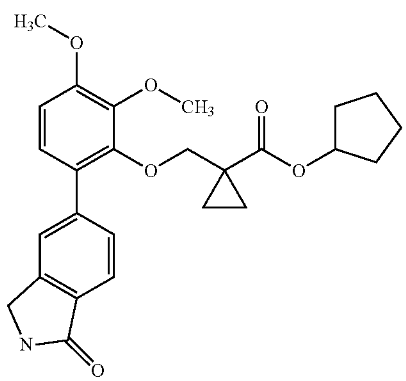 | cyclopentyl 1-[[2,3-dimethoxy-6-(1-oxoisoindolin-5-yl)phenoxy]methyl]cyclopropanecarboxylate |
| 710 | 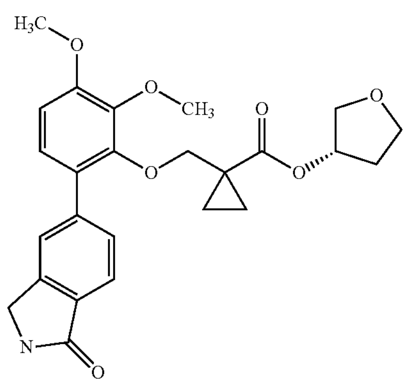 | [(3S)-tetrahydrofuran-3-yl] 1-[[2,3-dimethoxy-6-(1-oxoisoindolin-5-yl)phenoxy]methyl]cyclopropanecarboxylate |

| Compound | Structure | Compound name |
|---|---|---|
| 711 | 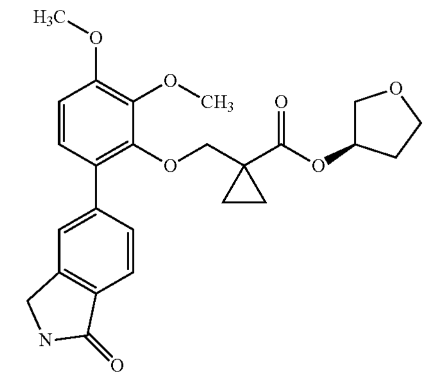 | [(3R)-tetrahydrofuran-3-yl] 1-[[2,3-dimethoxy-6-oxoisoindolin-5-yl)phenoxy]methyl]cyclopropanecarboxylate |
| 712 | 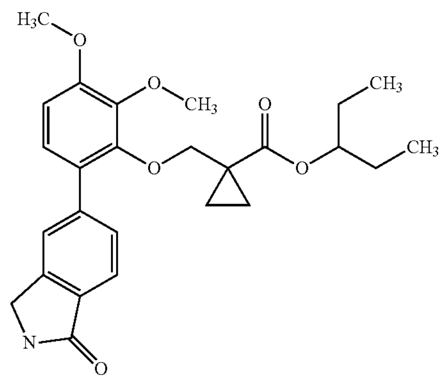 | 1-ethylpropyl 1-[[2,3-dimethoxy-6-(1-oxoisoindolin-5-yl)phenoxy]methyl]cyclopropanecarboxylate |
| 713 | 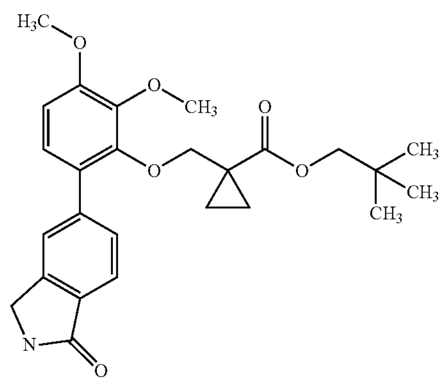 | 2,2-dimethylpropyl 1-[[2,3-dimethoxy-6-(1-oxoisoindolin-5-yl)phenoxy]methyl]cyclopropanecarboxylate |
| 714 | 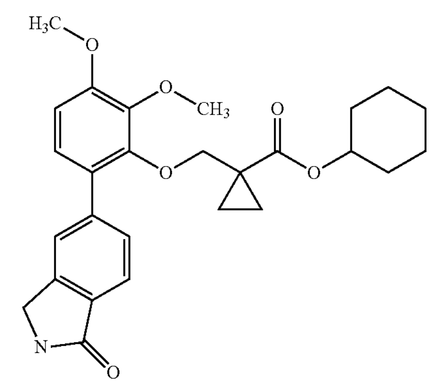 | cyclohexyl 1-[[2,3-dimethoxy-6-(1-oxoisoindolin-5-yl)phenoxy]methyl]cyclopropanecarboxylate |

-continued

| Compound | Structure | Compound name |
|---|---|---|
| 715 | 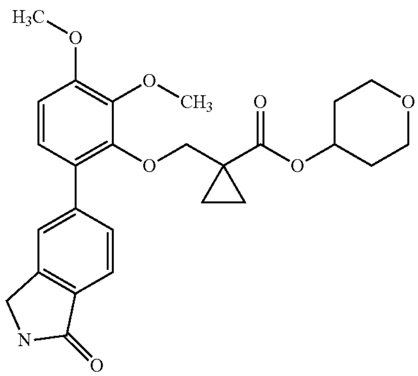 | tetrahydrofuran-4-yl 1-[[2,3-dimethoxy-6-(1-oxoisoindolin-5-yl)phenoxy]methyl]cyclopropanecarboxylate |
| 716 | 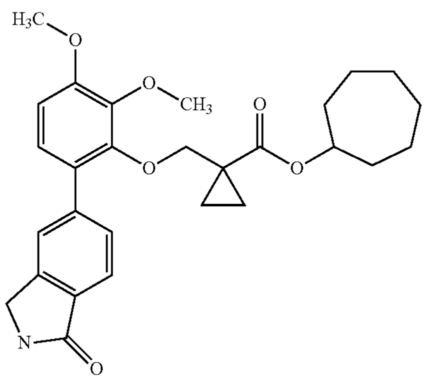 [SMILES: COc1ccc(-c2ccc3c(c2)CNC3=O)c(OCC2(C(=O)OC3CCCCCC3)CC2)c1OC] | cycloheptyl 1-[[2,3-dimethoxy-6-(1-oxoisoindolin-5-yl)phenoxy]methyl]cyclopropanecarboxylate |
| 717 | 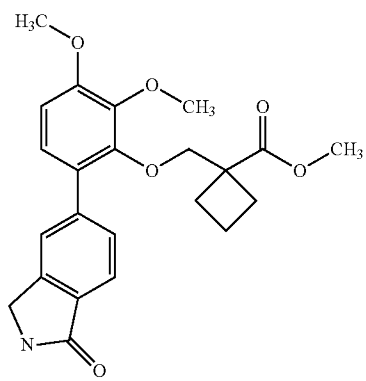 | methyl 1-[[2,3-dimethoxy-6-(1-oxoisoindolin-5-yl)phenoxy]methyl]cyclobutanecarboxylate |
| 718 | 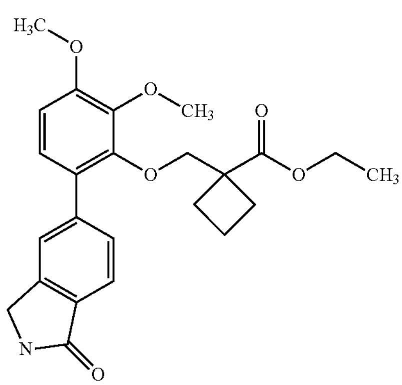 [SMILES: CCOC(=O)C1(COc2c(-c3ccc4c(c3)CNC4=O)ccc(OC)c2OC)CCC1] | ethyl 1-[[2,3-dimethoxy-6-(1-oxoisoindolin-5-yl)phenoxy]methyl]cyclobutanecarboxylate |

-continued

| Compound | Structure | Compound name |
|---|---|---|
| 719 | 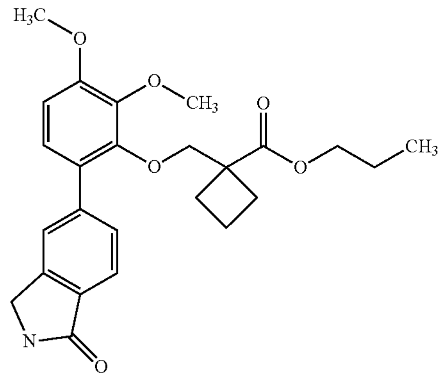 [SMILES: CCCOC(=O)C1(COc2c(-c3ccc4c(c3)CNC4=O)ccc(OC)c2OC)CCC1] | propyl 1-[[2,3-dimethoxy-6-(1-oxoisoindolin-5-yl)phenoxy]methyl]cyclobutanecarboxylate |
| 720 | 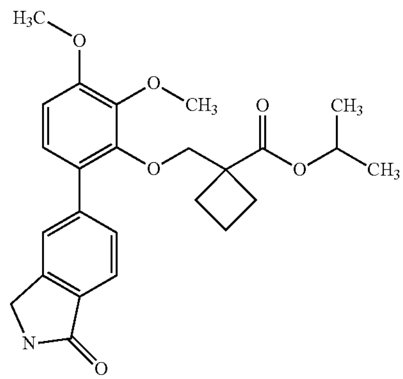 [SMILES: COc1ccc(-c2ccc3c(c2)CNC3=O)c(OCC2(C(=O)OC(C)C)CCC2)c1OC] | isopropyl 1-[[2,3-dimethoxy-6-(1-oxoisoindolin-5-yl)phenoxy]methyl]cyclobutanecarboxylate |
| 721 | 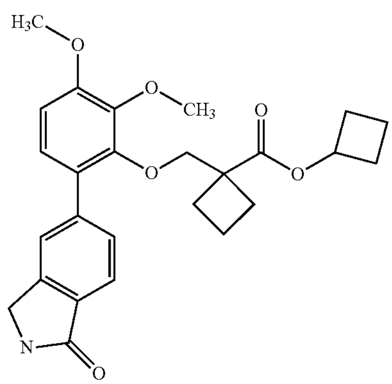 [SMILES: COc1ccc(-c2ccc3c(c2)CNC3=O)c(OCC2(C(=O)OC3CCC3)CCC2)c1OC] | cyclobutyl 1-[[2,3-dimethoxy-6-(1-oxoisoindolin-5-yl)phenoxy]methyl]cyclobutanecarboxylate |
| 722 | 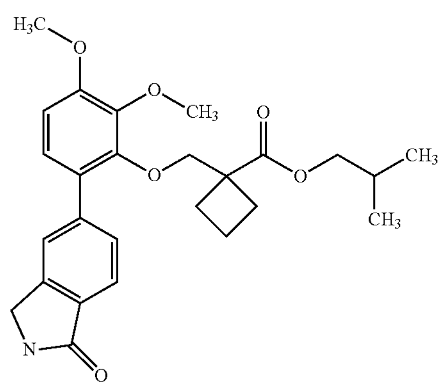 [SMILES: COc1ccc(-c2ccc3c(c2)CNC3=O)c(OCC2(C(=O)OCC(C)C)CCC2)c1OC] | isobutyl 1-[[2,3-dimethoxy-6-(1-oxoisoindolin-5-yl)phenoxy]methyl]cyclobutanecarboxylate |

-continued

| Compound | Structure | Compound name |
|---|---|---|
| 723 | 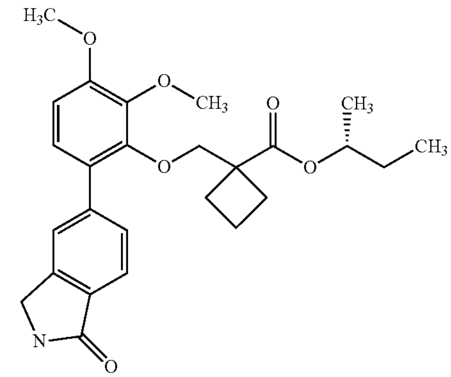 [SMILES: CC[C@@H](C)OC(=O)C1(COc2c(-c3ccc4c(c3)CNC4=O)ccc(OC)c2OC)CCC1] | [(1R)-1-methylpropyl] 1-[[2,3-dimethoxy-6-(1-oxoisoindolin-5-yl)phenoxy]methyl]cyclobutanecarboxylate |
| 724 | 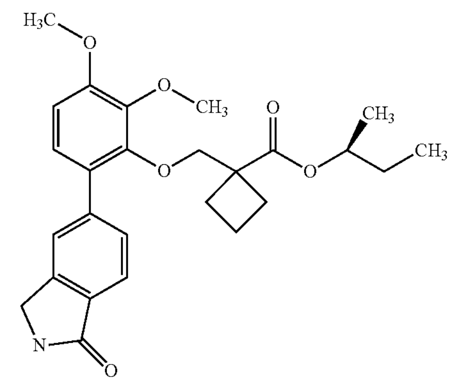 [SMILES: CC[C@H](C)OC(=O)C1(COc2c(-c3ccc4c(c3)CNC4=O)ccc(OC)c2OC)CCC1] | [(1S)-1-methylpropyl] 1-[[2,3-dimethoxy-6-(1-oxoisoindolin-5-yl)phenoxy]methyl]cyclobutanecarboxylate |
| 725 | 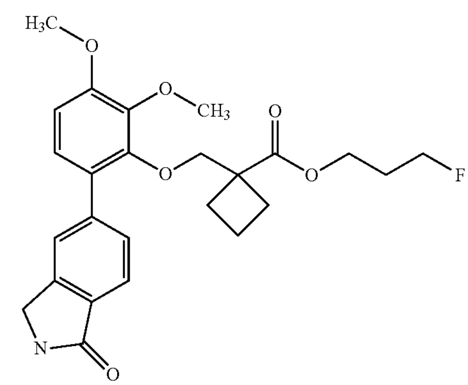 [SMILES: COc1ccc(-c2ccc3c(c2)CNC3=O)c(OCC2(C(=O)OCCCF)CCC2)c1OC] | 3-fluoropropyl 1-[[2,3-dimethoxy-6-(1-oxoisoindolin-5-yl)phenoxy]methyl]cyclobutanecarboxylate |
| 726 | 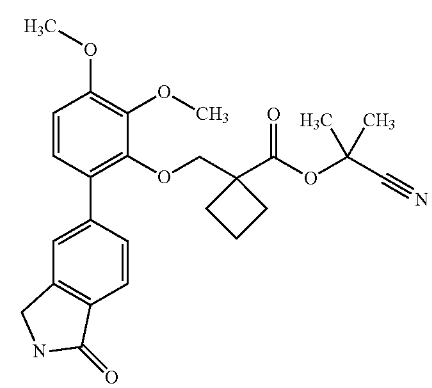 [SMILES: COc1ccc(-c2ccc3c(c2)CNC3=O)c(OCC2(C(=O)OC(C)(C)C#N)CCC2)c1OC] | (1-cyano-1-methyl-ethyl) 1-[[2,3-dimethoxy-6-(1-oxoisoindolin-5-yl)phenoxy]methyl]cyclobutanecarboxylate |

-continued

| Compound | Structure | Compound name |
|---|---|---|
| 727 | 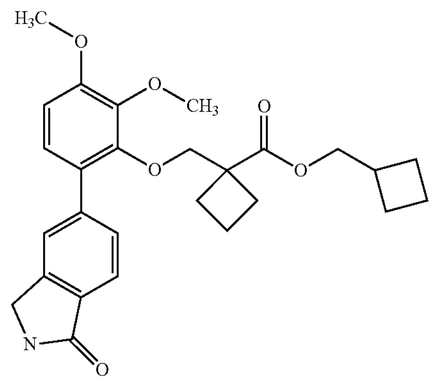 [SMILES: COc1ccc(-c2ccc3c(c2)CNC3=O)c(OCC2(C(=O)OCC3CCC3)CCC2)c1OC] | cyclobutylmethyl 1-[[2,3-dimethoxy-6-(1-oxoisoindolin-5-yl)phenoxy]methyl]cyclobutanecarboxylate |
| 728 | 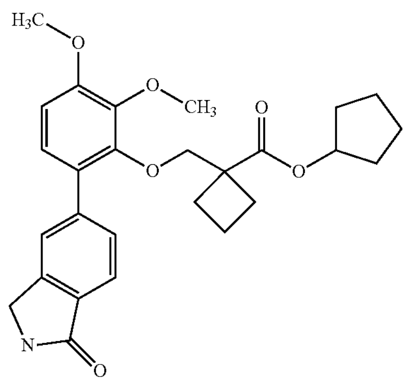 [SMILES: COc1ccc(-c2ccc3c(c2)CNC3=O)c(OCC2(C(=O)OC3CCCC3)CCC2)c1OC] | cyclopentyl 1-[[2,3-dimethoxy-6-(1-oxoisoindolin-5-yl)phenoxy]methyl]cyclobutanecarboxylate |
| 729 | 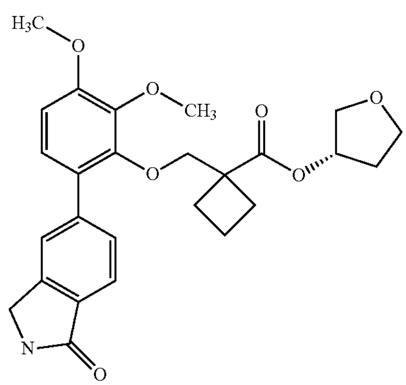 [SMILES: COc1ccc(-c2ccc3c(c2)CNC3=O)c(OCC2(C(=O)O[C@H]3CCOC3)CCC2)c1OC] | [(3S)-tetrahydrofuran-3-yl] 1-[[2,3-dimethoxy-6-(1-oxoisoindolin-5-yl)phenoxy]methyl]cyclobutanecarboxylate |
| 730 | 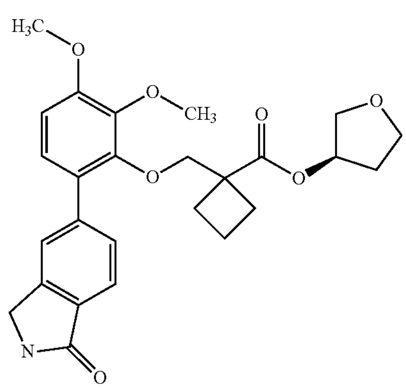 [SMILES: COc1ccc(-c2ccc3c(c2)CNC3=O)c(OCC2(C(=O)O[C@@H]3CCOC3)CCC2)c1OC] | [(3R)-tetrahydrofuran-3-yl] 1-[[2,3-dimethoxy-6-(1-oxoisoindolin-5-yl)phenoxy]methyl]cyclobutanecarboxylate |

-continued

| Compound | Structure | Compound name |
|---|---|---|
| 731 | 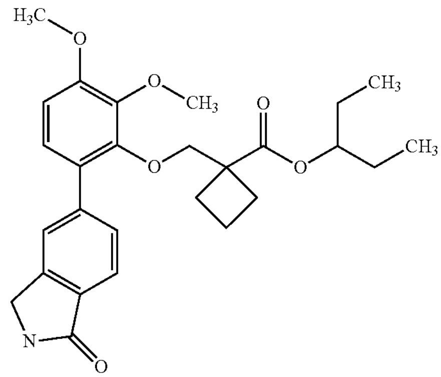 [SMILES: CCC(CC)OC(=O)C1(COc2c(-c3ccc4c(c3)CNC4=O)ccc(OC)c2OC)CCC1] | 1-ethylpropyl 1-[[2,3-dimethoxy-6-(1-oxoisoindolin-5-yl)phenoxy]methyl]cyclobutanecarboxylate |
| 732 | 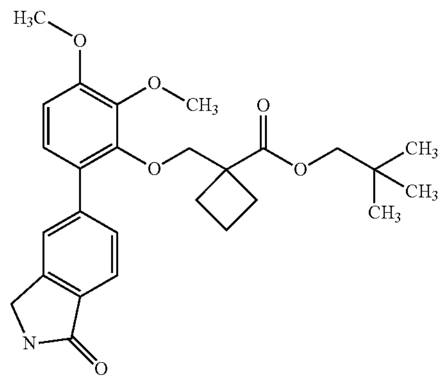 [SMILES: COc1ccc(-c2ccc3c(c2)CNC3=O)c(OCC2(C(=O)OCC(C)(C)C)CCC2)c1OC] | 2,2-dimethylpropyl 1-[[2,3-dimethoxy-6-(1-oxoisoindolin-5-yl)phenoxy]methyl]cyclobutanecarboxylate |
| 733 | 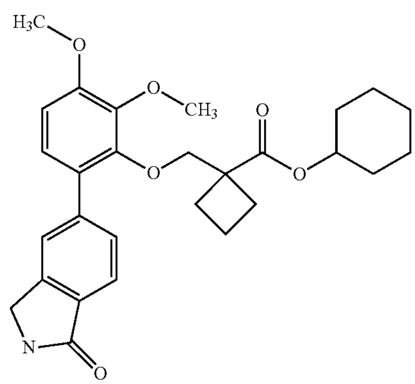 [SMILES: COc1ccc(-c2ccc3c(c2)CNC3=O)c(OCC2(C(=O)OC3CCCCC3)CCC2)c1OC] | cyclohexyl 1-[[2,3-dimethoxy-6-(1-oxoisoindolin-5-yl)phenoxy]methyl]cyclobutanecarboxylate |
| 734 | 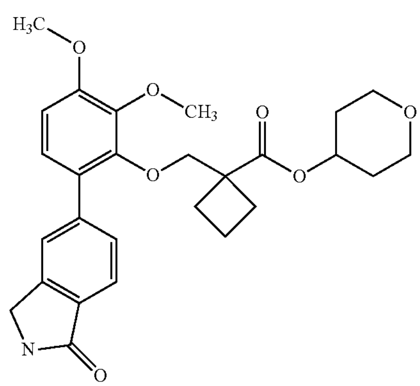 [SMILES: COc1ccc(-c2ccc3c(c2)CNC3=O)c(OCC2(C(=O)OC3CCOCC3)CCC2)c1OC] | tetrahydrofuran-4-yl 1-[[2,3-dimethoxy-6-(1-oxoisoindolin-5-yl)phenoxy]methyl]cyclobutanecarboxylate |

-continued

| Compound | Structure | Compound name |
|---|---|---|
| 735 | 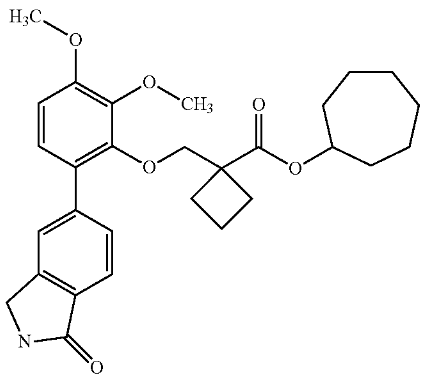 [SMILES: COc1ccc(-c2ccc3c(c2)CNC3=O)c(OCC2(C(=O)OC3CCCCCC3)CCC2)c1OC] | cycloheptyl 1-[[2,3-dimethoxy-6-(1-oxoisoindolin-5-yl)phenoxy]methyl]cyclobutanecarboxylate |

Example 165

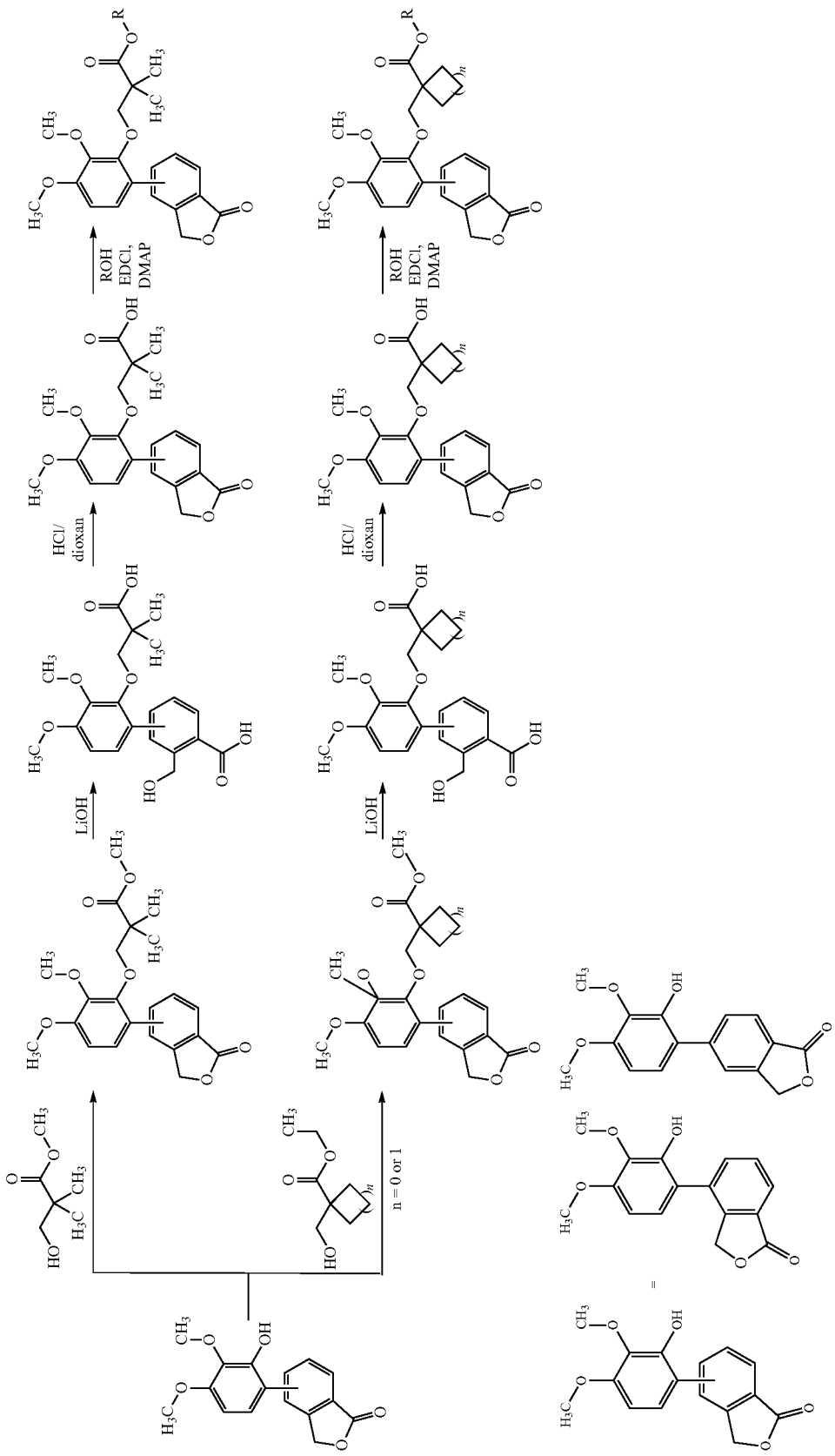

Compounds 736-842 are synthesized as described below. A solution of the appropriate biaryl-alcohol, Compound 304 or 306, the appropriate alcohol ester, for example methyl 3-hydroxy-2,2-dimethyl-propanoate, and triphenylphosphine in THF is flushed with argon and cooled in an icebath, before a solution of DEAD in THF is added dropwise. The mixture is stirred at room temperature. The crude reaction mixture is then diluted with DCM, washed with 1M HCl, water and evaporated to dryness. Column chromatography (silica gel, 0-100% ethyl acetate in pet ether) affords the corresponding O-alkylated bi-aryl compound, for example methyl 3-[2,3-dimethoxy-6-(1-oxo-3H-isobenzofuran-5-yl)phenoxy]-2,2-dimethyl-propanoate, which is stirred in a mixture of 1 N aqueous LiOH and THF at room temperature.

Water is added and the aqueous phase is washed with EtOAc, acidified to pH 1 with concentrated HCl and extracted with DCM. The organic phase is evaporated to dryness and the crude reaction mixture is stirred at room temperature in a HCl/dioxane suspension before it is evaporated to dryness. The obtained carboxylic acid, for example 3-[2,3-dimethoxy-6-(1-oxo-3H-isobenzofuran-5-yl)phenoxy]-2,2-dimethyl-propanoic acid, EDCI, DMAP and the appropriate alcohol, for example isopropanol, in DCM is stirred overnight at room temperature, before it is evaporated to dryness. The crude reaction mixture is re-dissolved in DMF and purified by HPLC purification to obtain the title compound, for example isopropyl 3-[2,3-dimethoxy-6-(1-oxo-3H-isobenzofuran-5-yl)phenoxy]-2,2-dimethyl-propanoate

| Compound | Structure | Compound name |
|---|---|---|
| 736 | 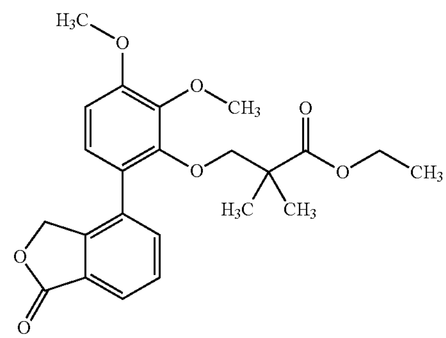 [SMILES: CCOC(=O)C(C)(C)COc1c(-c2cccc3c2COC3=O)ccc(OC)c1OC] | ethyl 3-[2,3-dimethoxy-6-(1-oxo-3H-isobenzofuran-4-yl)phenoxy]-2,2-dimethyl-propanoate |
| 737 | 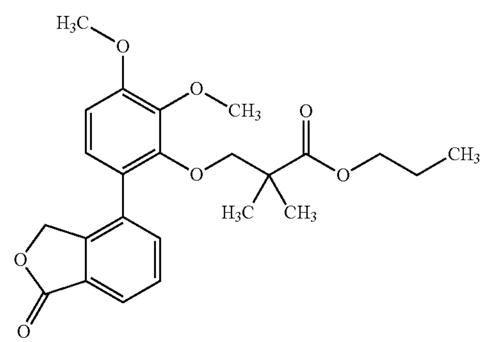 [SMILES: CCCOC(=O)C(C)(C)COc1c(-c2cccc3c2COC3=O)ccc(OC)c1OC] | propyl 3-[2,3-dimethoxy-6-(1-oxo-3H-isobenzofuran-4-yl)phenoxy]-2,2-dimethyl-propanoate |
| 738 | 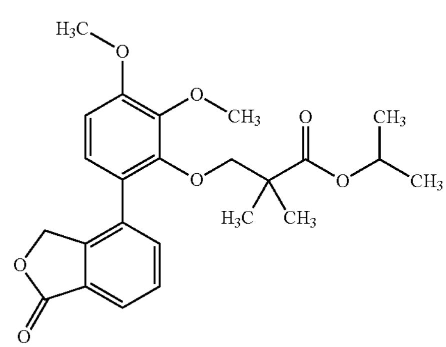 [SMILES: COc1ccc(-c2cccc3c2COC3=O)c(OCC(C)(C)C(=O)OC(C)C)c1OC] | isopropyl 3-[2,3-dimethoxy-6-(1-oxo-3H-isobenzofuran-4-yl)phenoxy]-2,2-dimethyl-propanoate |

-continued

| Compound | Structure | Compound name |
|---|---|---|
| 739 | 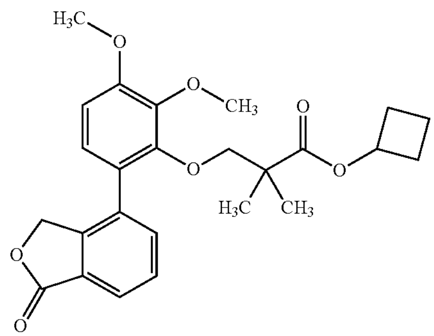 [SMILES: COc1ccc(-c2cccc3c2COC3=O)c(OCC(C)(C)C(=O)OC2CCC2)c1OC] | cyclobutyl 3-[2,3-dimethoxy-6-(1-oxo-3H-isobenzofuran-4-yl)phenoxy]-2,2-dimethyl-propanoate |
| 740 | 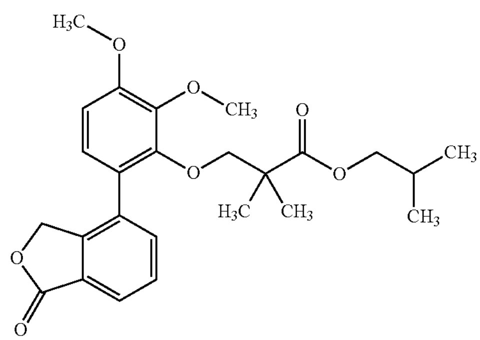 [SMILES: COc1ccc(-c2cccc3c2COC3=O)c(OCC(C)(C)C(=O)OCC(C)C)c1OC] | isobutyl 3-[2,3-dimethoxy-6-(1-oxo-3H-isobenzofuran-4-yl)phenoxy]-2,2-dimethyl-propanoate |
| 741 | 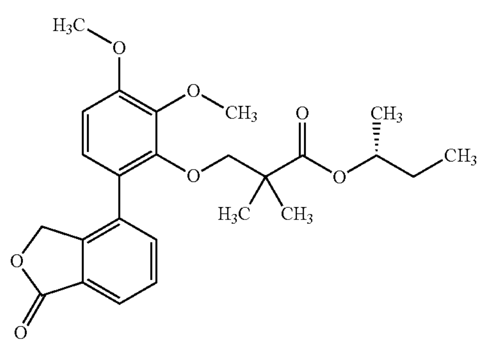 [SMILES: CC[C@@H](C)OC(=O)C(C)(C)COc1c(-c2cccc3c2COC3=O)ccc(OC)c1OC] | [(1R)-1-methylpropyl] 3-[2,3-dimethoxy-6-(1-oxo-3H-isobenzofuran-4-yl)phenoxy]-2,2-dimethyl-propanoate |
| 742 | 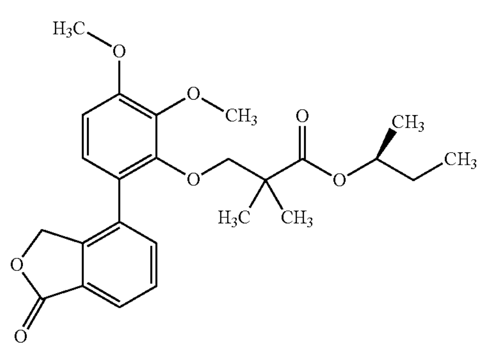 [SMILES: CC[C@H](C)OC(=O)C(C)(C)COc1c(-c2cccc3c2COC3=O)ccc(OC)c1OC] | [(1S)-1-methylpropyl] 3-[2,3-dimethoxy-6-(1-oxo-3H-isobenzofuran-4-yl)phenoxy]-2,2-dimethyl-propanoate |

-continued

| Compound | Structure | Compound name |
|---|---|---|
| 743 | 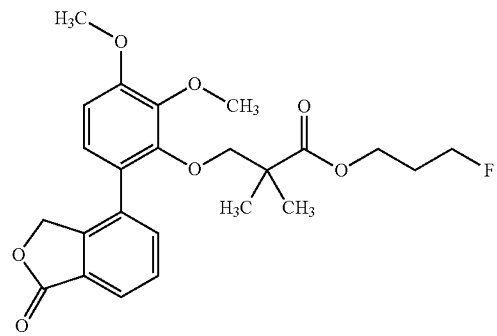 [SMILES: COc1ccc(-c2cccc3c2COC3=O)c(OCC(C)(C)C(=O)OCCCF)c1OC] | 3-fluoropropyl 3-[2,3-dimethoxy-6-(1-oxo-3H-isobenzofuran-4-yl)phenoxy]-2,2-dimethyl-propanoate |
| 744 | 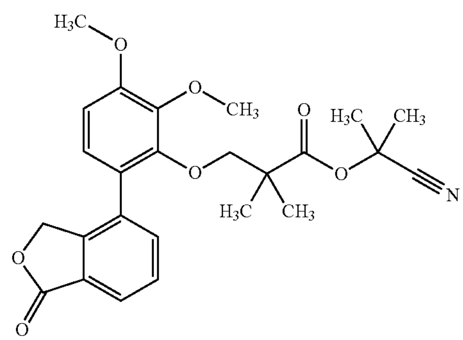 [SMILES: COc1ccc(-c2cccc3c2COC3=O)c(OCC(C)(C)C(=O)OC(C)(C)C#N)c1OC] | (1-cyano-1-methyl-ethyl) 3-[2,3-dimethoxy-6-(1-oxo-3H-isobenzofuran-4-yl)phenoxy]-2,2-dimethyl-propanoate |
| 745 | 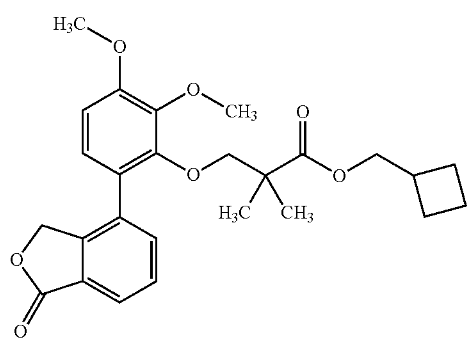 [SMILES: COc1ccc(-c2cccc3c2COC3=O)c(OCC(C)(C)C(=O)OCC2CCC2)c1OC] | cyclobutylmethyl 3-[2,3-dimethoxy-6-(1-oxo-3H-isobenzofuran-4-yl)phenoxy]-2,2-dimethyl-propanoate |
| 746 | 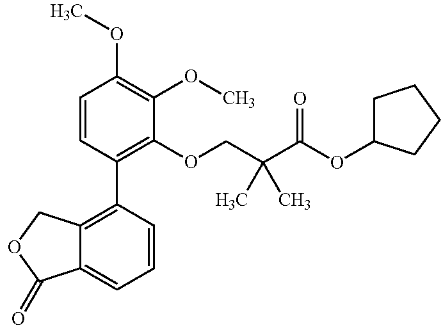 [SMILES: COc1ccc(-c2cccc3c2COC3=O)c(OCC(C)(C)C(=O)OC2CCCC2)c1OC] | cyclopentyl 3-[2,3-dimethoxy-6-(1-oxo-3H-isobenzofuran-4-yl)phenoxy]-2,2-dimethyl-propanoate |

-continued

| Compound | Structure | Compound name |
|---|---|---|
| 747 | 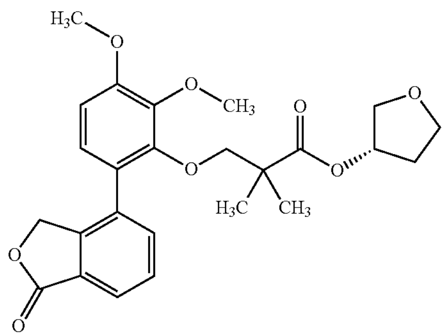 [SMILES: COc1ccc(-c2cccc3c2COC3=O)c(OCC(C)(C)C(=O)O[C@H]2CCOC2)c1OC] | [(3S)-tetrahydrofuran-3-yl] 3-[2,3-dimethoxy-6-(1-oxo-3H-isobenzofuran-4-yl)phenoxy]-2,2-dimethyl-propanoate |
| 748 | 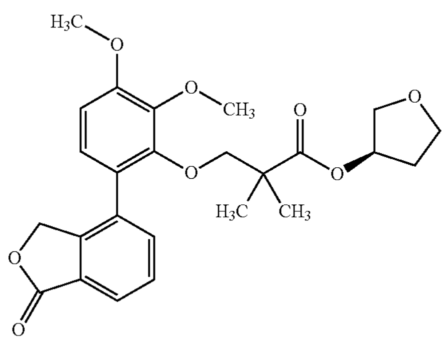 [SMILES: COc1ccc(-c2cccc3c2COC3=O)c(OCC(C)(C)C(=O)O[C@@H]2CCOC2)c1OC] | [(3R)-tetrahydrofuran-3-yl] 3-[2,3-dimethoxy-6-(1-oxo-3H-isobenzofuran-4-yl)phenoxy]-2,2-dimethyl-propanoate |
| 749 | 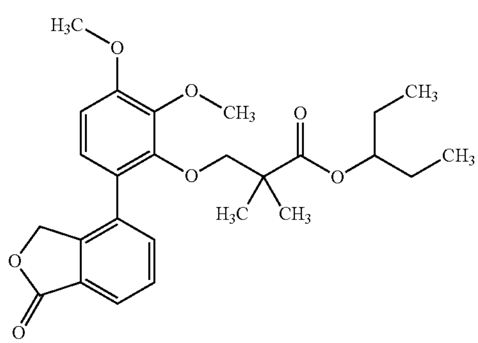 [SMILES: CCC(CC)OC(=O)C(C)(C)COc1c(-c2cccc3c2COC3=O)ccc(OC)c1OC] | 1-ethylpropyl 3-[2,3-dimethoxy-6-(1-oxo-3H-isobenzofuran-4-yl)phenoxy]-2,2-dimethyl-propanoate |
| 750 | 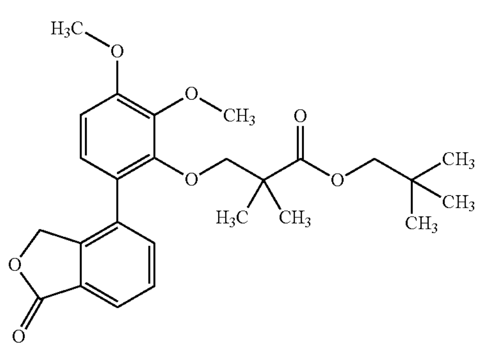 [SMILES: COc1ccc(-c2cccc3c2COC3=O)c(OCC(C)(C)C(=O)OCC(C)(C)C)c1OC] | 2,2-dimethylpropyl 3-[2,3-dimethoxy-6-(1-oxo-3H-isobenzofuran-4-yl)phenoxy]-2,2-dimethyl-propanoate |

-continued

| Compound | Structure | Compound name |
|---|---|---|
| 751 | 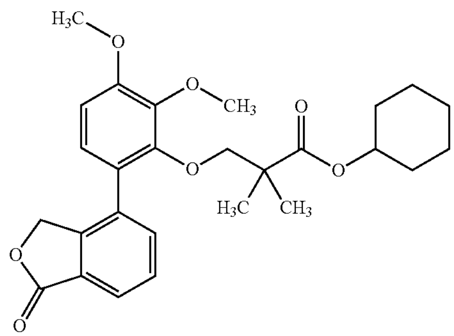 [SMILES: COc1ccc(-c2cccc3c2COC3=O)c(OCC(C)(C)C(=O)OC2CCCCC2)c1OC] | cyclohexyl 3-[2,3-dimethoxy-6-(1-oxo-3H-isobenzofuran-4-yl)phenoxy]-2,2-dimethyl-propanoate |
| 752 | 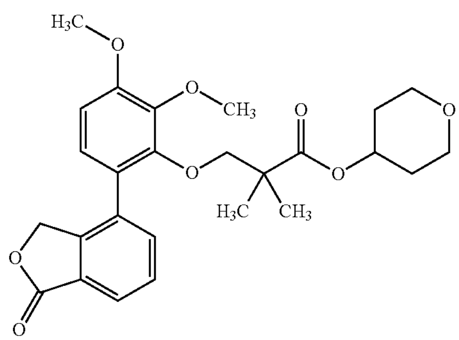 [SMILES: COc1ccc(-c2cccc3c2COC3=O)c(OCC(C)(C)C(=O)OC2CCOCC2)c1OC] | tetrahydropyran-4-yl 3-[2,3-dimethoxy-6-(1-oxo-3H-isobenzofuran-4-yl)phenoxy]-2,2-dimethyl-propanoate |
| 753 | 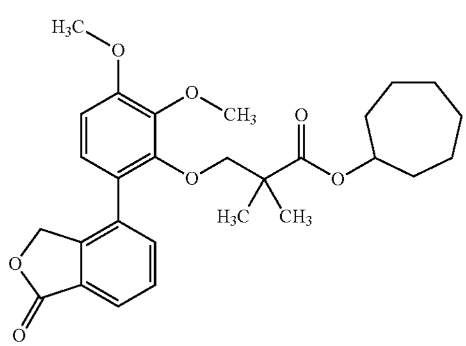 [SMILES: COc1ccc(-c2cccc3c2COC3=O)c(OCC(C)(C)C(=O)OC2CCCCCC2)c1OC] | cycloheptyl 3-[2,3-dimethoxy-6-(1-oxo-3H-isobenzofuran-4-yl)phenoxy]-2,2-dimethyl-propanoate |
| 754 | 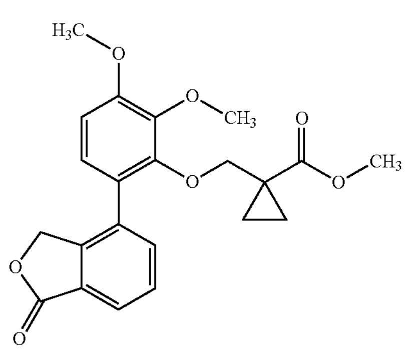 [SMILES: COC(=O)C1(COc2c(-c3cccc4c3COC4=O)ccc(OC)c2OC)CC1] | methyl 1-[[2,3-dimethoxy-6-(1-oxo-3H-isobenzofuran-4-yl)phenoxy]methyl]cyclopropanecarboxylate |

-continued

| Compound | Structure | Compound name |
|---|---|---|
| 755 | 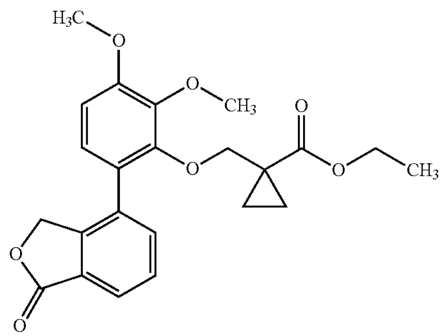 [SMILES: CCOC(=O)C1(COc2c(-c3cccc4c3COC4=O)ccc(OC)c2OC)CC1] | ethyl 1-[[2,3-dimethoxy-6-(1-oxo-3H-isobenzofuran-4-yl)phenoxy]methyl]cyclopropanecarboxylate |
| 756 | 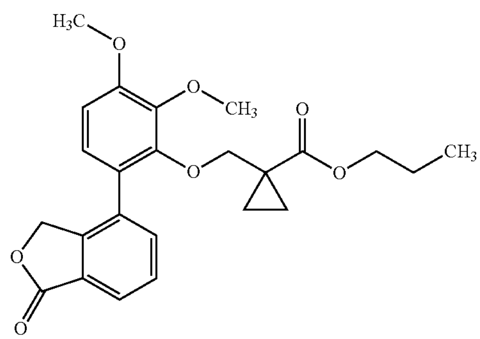 [SMILES: CCCOC(=O)C1(COc2c(-c3cccc4c3COC4=O)ccc(OC)c2OC)CC1] | propyl 1-[[2,3-dimethoxy-6-(1-oxo-3H-isobenzofuran-4-yl)phenoxy]methyl]cyclopropanecarboxylate |
| 757 | 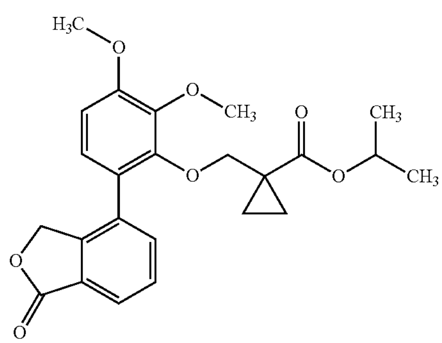 [SMILES: COc1ccc(-c2cccc3c2COC3=O)c(OCC2(C(=O)OC(C)C)CC2)c1OC] | isopropyl 1-[[2,3-dimethoxy-6-(1-oxo-3H-isobenzofuran-4-yl)phenoxy]methyl]cyclopropanecarboxylate |
| 758 | 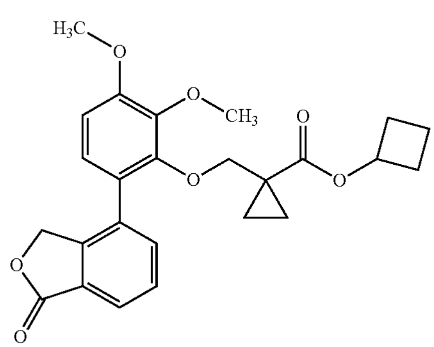 [SMILES: COc1ccc(-c2cccc3c2COC3=O)c(OCC2(C(=O)OC3CCC3)CC2)c1OC] | cyclobutyl 1-[[2,3-dimethoxy-6-(1-oxo-3H-isobenzofuran-4-yl)phenoxy]methyl]cyclopropanecarboxylate |

| Compound | Structure | Compound name |
|---|---|---|
| 759 | 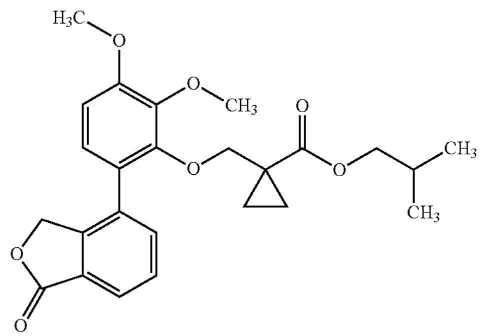 [SMILES: COc1ccc(-c2cccc3c2COC3=O)c(OCC2(C(=O)OCC(C)C)CC2)c1OC] | isobutyl 1-[[2,3-dimethoxy-6-(1-oxo-3H-isobenzofuran-4-yl)phenoxy]methyl]cyclopropanecarboxylate |
| 760 | 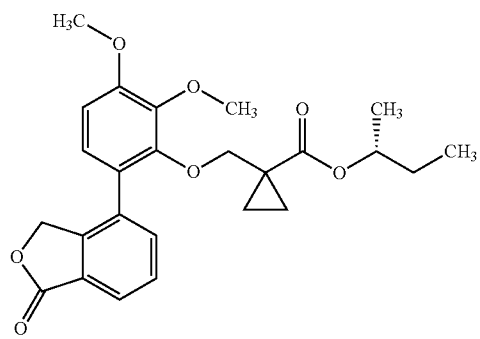 [SMILES: CC[C@@H](C)OC(=O)C1(COc2c(-c3cccc4c3COC4=O)ccc(OC)c2OC)CC1] | [(1R)-1-methylpropyl] 1-[[2,3-dimethoxy-6-(1-oxo-3H-isobenzofuran-4-yl)phenoxy]methyl]cyclopropanecarboxylate |
| 761 | 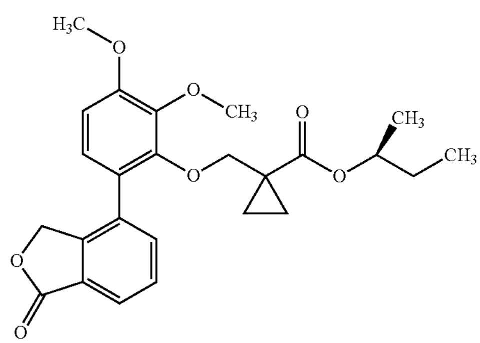 [SMILES: CC[C@H](C)OC(=O)C1(COc2c(-c3cccc4c3COC4=O)ccc(OC)c2OC)CC1] | [(1S)-1-methylpropyl] 1-[[2,3-dimethoxy-6-(1-oxo-3H-isobenzofuran-4-yl)phenoxy]methyl]cyclopropanecarboxylate |
| 762 | 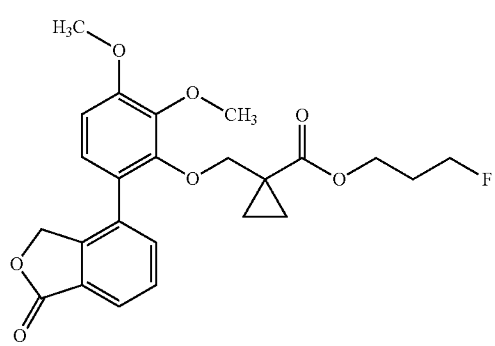 [SMILES: COc1ccc(-c2cccc3c2COC3=O)c(OCC2(C(=O)OCCCF)CC2)c1OC] | 3-fluoropropyl 1-[[2,3-dimethoxy-6-(1-oxo-3H-isobenzofuran-4-yl)phenoxy]methyl]cyclopropanecarboxylate |

-continued

| Compound | Structure | Compound name |
|---|---|---|
| 763 | 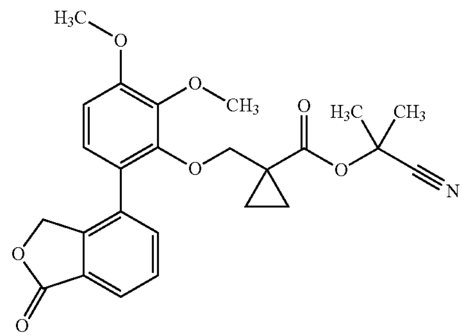 [SMILES: COc1ccc(-c2cccc3c2COC3=O)c(OCC2(C(=O)OC(C)(C)C#N)CC2)c1OC] | (1-cyano-1-methyl-ethyl) 1-[[2,3-dimethoxy-6-(1-oxo-3H-isobenzofuran-4-yl)phenoxy]methyl]cyclopropanecarboxylate |
| 764 | 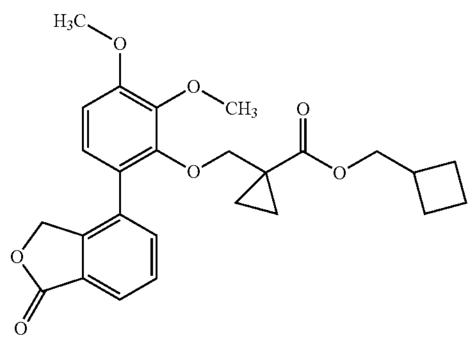 [SMILES: COc1ccc(-c2cccc3c2COC3=O)c(OCC2(C(=O)OCC3CCC3)CC2)c1OC] | cyclobutylmethyl 1-[[2,3-dimethoxy-6-(1-oxo-3H-isobenzofuran-4-yl)phenoxy]methyl]cyclopropanecarboxylate |
| 765 | 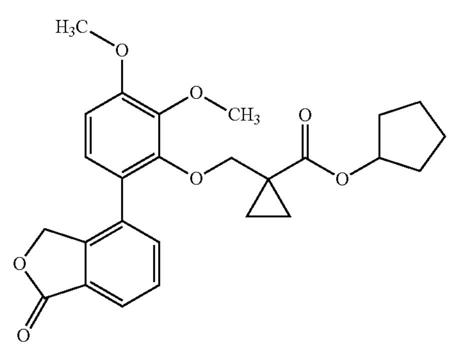 [SMILES: COc1ccc(-c2cccc3c2COC3=O)c(OCC2(C(=O)OC3CCCC3)CC2)c1OC] | cyclopentyl 1-[[2,3-dimethoxy-6-(1-oxo-3H-isobenzofuran-4-yl)phenoxy]methyl]cyclopropanecarboxylate |
| 766 | 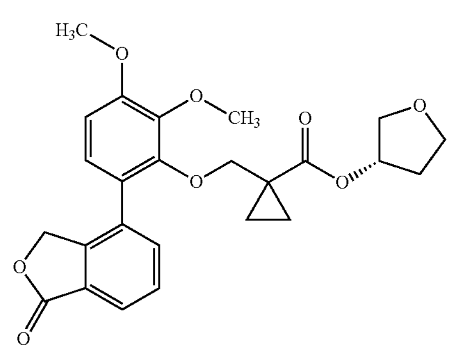 [SMILES: COc1ccc(-c2cccc3c2COC3=O)c(OCC2(C(=O)O[C@H]3CCOC3)CC2)c1OC] | [(3S)-tetrahydrofuran-3-yl] 1-[[2,3-dimethoxy-6-(1-oxo-3H-isobenzofuran-4-yl)phenoxy]methyl]cyclopropanecarboxylate |

-continued

| Compound | Structure | Compound name |
|---|---|---|
| 767 | 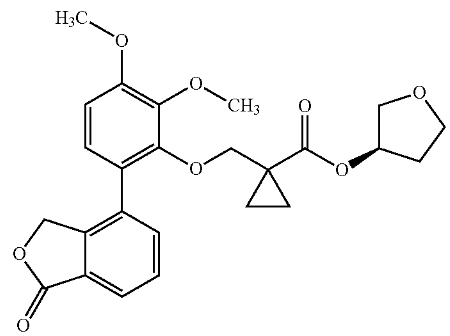 [SMILES: COc1ccc(-c2cccc3c2COC3=O)c(OCC2(C(=O)O[C@@H]3CCOC3)CC2)c1OC] | [(3R)-tetrahydrofuran-3-yl] 1-[[2,3-dimethoxy-6-(1-oxo-3H-isobenzofuran-4-yl)phenoxy]methyl]cyclopropanecarboxylate |
| 768 | 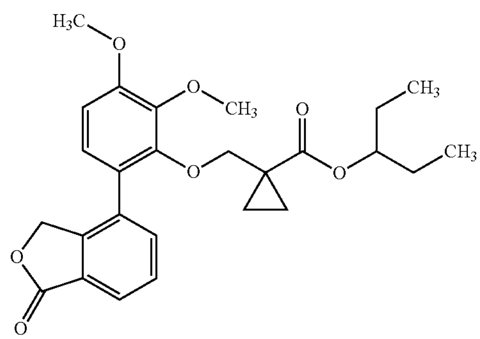 [SMILES: CCC(CC)OC(=O)C1(COc2c(-c3cccc4c3COC4=O)ccc(OC)c2OC)CC1] | 1-ethylpropyl 1-[[2,3-dimethoxy-6-(1-oxo-3H-isobenzofuran-4-yl)phenoxy]methyl]cyclopropanecarboxylate |
| 769 | 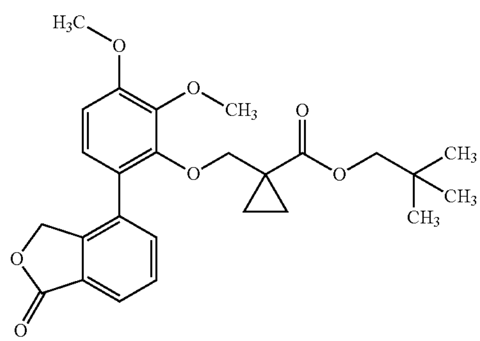 [SMILES: COc1ccc(-c2cccc3c2COC3=O)c(OCC2(C(=O)OCC(C)(C)C)CC2)c1OC] | 2,2-dimethylpropyl 1-[[2,3-dimethoxy-6-(1-oxo-3H-isobenzofuran-4-yl)phenoxy]methyl]cyclopropanecarboxylate |
| 770 | 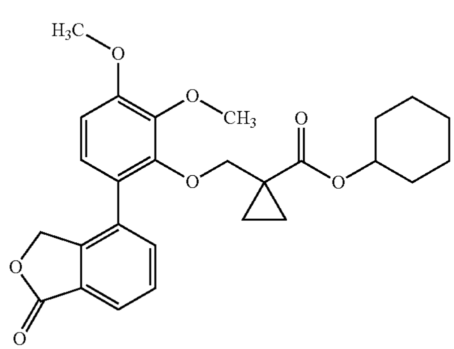 [SMILES: COc1ccc(-c2cccc3c2COC3=O)c(OCC2(C(=O)OC3CCCCC3)CC2)c1OC] | cyclohexyl 1-[[2,3-dimethoxy-6-(1-oxo-3H-isobenzofuran-4-yl)phenoxy]methyl]cyclopropanecarboxylate |

-continued

| Compound | Structure | Compound name |
|---|---|---|
| 771 | 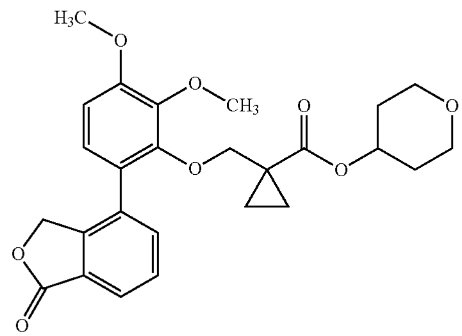 [SMILES: COc1ccc(-c2cccc3c2COC3=O)c(OCC2(C(=O)OC3CCOCC3)CC2)c1OC] | tetrahydropyran-4-yl 1-[[2,3-dimethoxy-6-(1-oxo-3H-isobenzofuran-4-yl)phenoxy]methyl]cyclopropanecarboxylate |
| 772 | 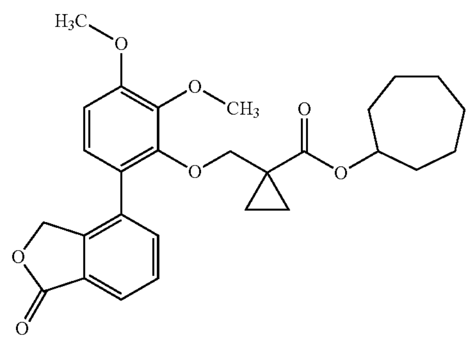 [SMILES: COc1ccc(-c2cccc3c2COC3=O)c(OCC2(C(=O)OC3CCCCCC3)CC2)c1OC] | cycloheptyl 1-[[2,3-dimethoxy-6-(1-oxo-3H-isobenzofuran-4-yl)phenoxy]methyl]cyclopropanecarboxylate |
| 843 | 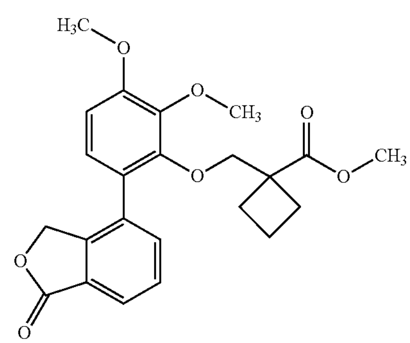 [SMILES: COC(=O)C1(COc2c(-c3cccc4c3COC4=O)ccc(OC)c2OC)CCC1] | methyl 1-[[2,3-dimethoxy-6-(1-oxo-3H-isobenzofuran-4-yl)phenoxy]methyl]cyclobutanecarboxylate |
| 844 | 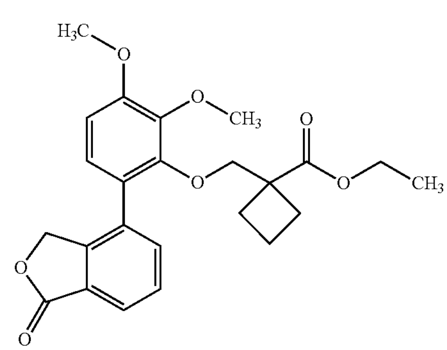 [SMILES: CCOC(=O)C1(COc2c(-c3cccc4c3COC4=O)ccc(OC)c2OC)CCC1] | ethyl 1-[[2,3-dimethoxy-6-(1-oxo-3H-isobenzofuran-4-yl)phenoxy]methyl]cyclobutanecarboxylate |

-continued

| Compound | Structure | Compound name |
|---|---|---|
| 845 | 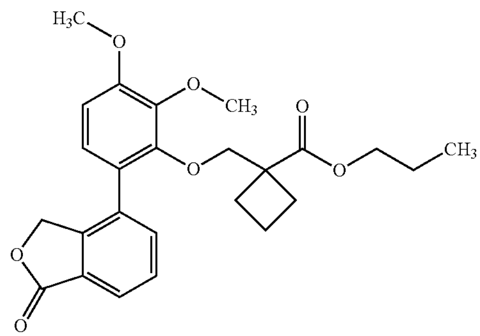 [SMILES: CCCOC(=O)C1(COc2c(-c3cccc4c3COC4=O)ccc(OC)c2OC)CCC1] | propyl 1-[[2,3-dimethoxy-6-(1-oxo-3H-isobenzofuran-4-yl)phenoxy]methyl]cyclobutanecarboxylate |
| 846 | 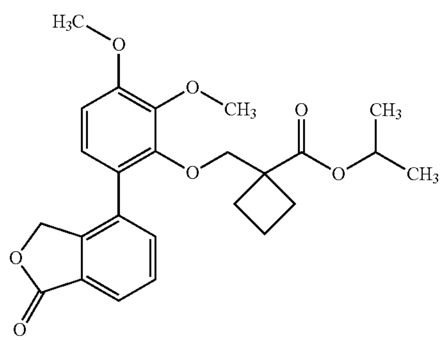 [SMILES: COc1ccc(-c2cccc3c2COC3=O)c(OCC2(C(=O)OC(C)C)CCC2)c1OC] | isopropyl 1-[[2,3-dimethoxy-6-(1-oxo-3H-isobenzofuran-4-yl)phenoxy]methyl]cyclobutanecarboxylate |
| 847 | 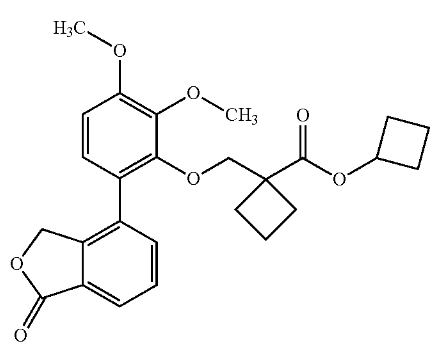 [SMILES: COc1ccc(-c2cccc3c2COC3=O)c(OCC2(C(=O)OC3CCC3)CCC2)c1OC] | cyclobutyl 1-[[2,3-dimethoxy-6-(1-oxo-3H-isobenzofuran-4-yl)phenoxy]methyl]cyclobutanecarboxylate |
| 773 | 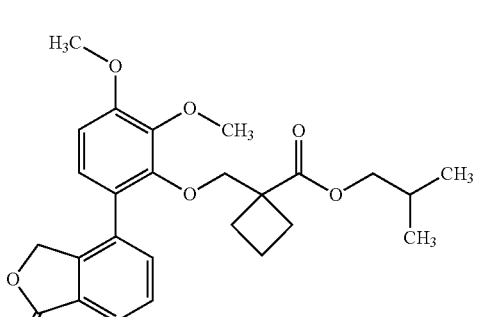 | isobutyl 1-[[2,3-dimethoxy-6-(1-oxo-3H-isobenzofuran-4-yl)phenoxy]methyl]cyclobutanecarboxylate |

-continued

| Compound | Structure | Compound name |
|---|---|---|
| 774 | 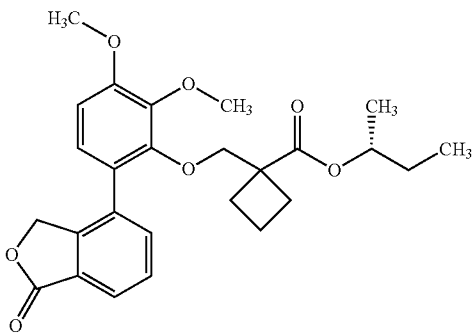 [SMILES: CC[C@@H](C)OC(=O)C1(COc2c(-c3cccc4c3COC4=O)ccc(OC)c2OC)CCC1] | [(1R)-1-methylpropyl] 1-[[2,3-dimethoxy-6-(1-oxo-3H-isobenzofuran-4-yl)phenoxy]methyl]cyclobutanecarboxylate |
| 775 | 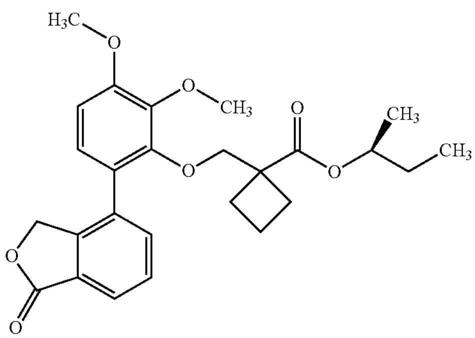 [SMILES: CC[C@H](C)OC(=O)C1(COc2c(-c3cccc4c3COC4=O)ccc(OC)c2OC)CCC1] | [(1S)-1-methylpropyl] 1-[[2,3-dimethoxy-6-(1-oxo-3H-isobenzofuran-4-yl)phenoxy]methyl]cyclobutanecarboxylate |
| 776 | 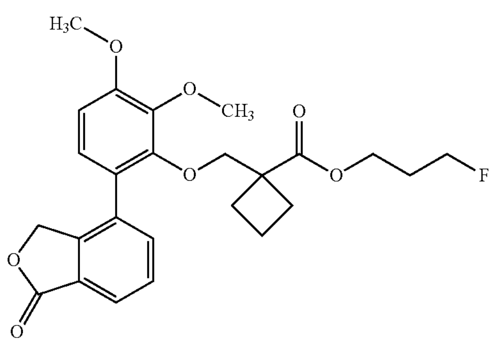 [SMILES: COc1ccc(-c2cccc3c2COC3=O)c(OCC2(C(=O)OCCCF)CCC2)c1OC] | 3-fluoropropyl 1-[[2,3-dimethoxy-6-(1-oxo-3H-isobenzofuran-4-yl)phenoxy]methyl]cyclobutanecarboxylate |
| 777 | 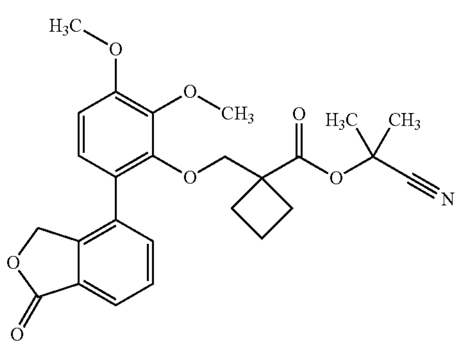 [SMILES: COc1ccc(-c2cccc3c2COC3=O)c(OCC2(C(=O)OC(C)(C)C#N)CCC2)c1OC] | (1-cyano-1-methyl-ethyl) 1-[[2,3-dimethoxy-6-(1-oxo-3H-isobenzofuran-4-yl)phenoxy]methyl]cyclobutanecarboxylate |

-continued

| Compound | Structure | Compound name |
|---|---|---|
| 778 | 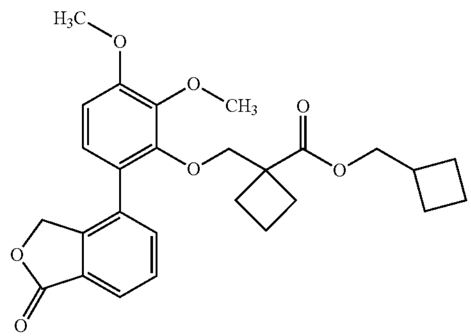 [SMILES: COc1ccc(-c2cccc3c2COC3=O)c(OCC2(C(=O)OCC3CCC3)CCC2)c1OC] | cyclobutylmethyl 1-[[2,3-dimethoxy-6-(1-oxo-3H-isobenzofuran-4-yl)phenoxy]methyl]cyclobutanecarboxylate |
| 779 | 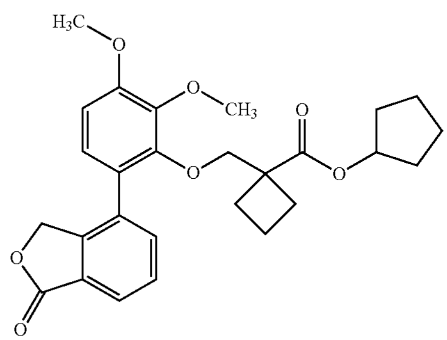 [SMILES: COc1ccc(-c2cccc3c2COC3=O)c(OCC2(C(=O)OC3CCCC3)CCC2)c1OC] | cyclopentyl 1-[[2,3-dimethoxy-6-(1-oxo-3H-isobenzofuran-4-yl)phenoxy]methyl]cyclobutanecarboxylate |
| 780 | 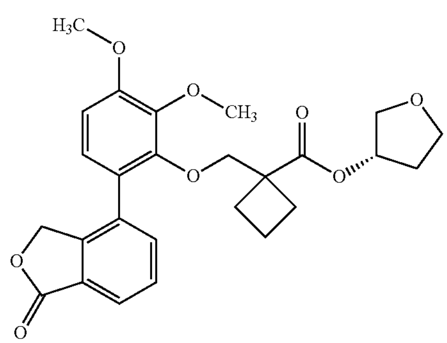 [SMILES: COc1ccc(-c2cccc3c2COC3=O)c(OCC2(C(=O)O[C@H]3CCOC3)CCC2)c1OC] | [(3S)-tetrahydrofuran-3-yl] 1-[[2,3-dimethoxy-6-(1-oxo-3H-isobenzofuran-4-yl)phenoxy]methyl]cyclobutanecarboxylate |
| 781 | 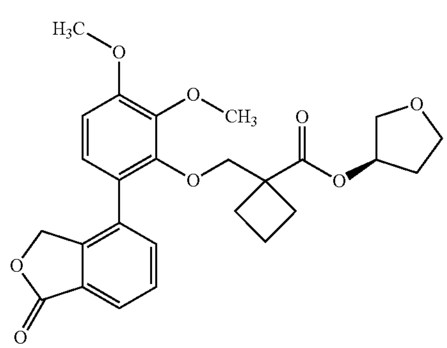 [SMILES: COc1ccc(-c2cccc3c2COC3=O)c(OCC2(C(=O)O[C@@H]3CCOC3)CCC2)c1OC] | [(3R)-tetrahydrofuran-3-yl] 1-[[2,3-dimethoxy-6-(1-oxo-3H-isobenzofuran-4-yl)phenoxy]methyl]cyclobutanecarboxylate |

-continued

| Compound | Structure | Compound name |
|---|---|---|
| 782 | 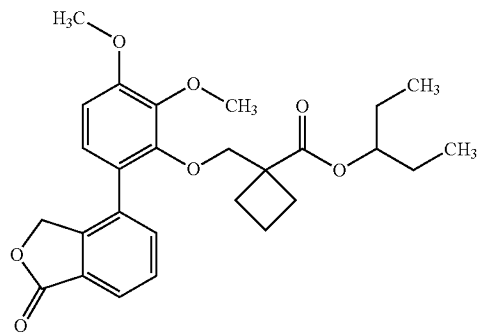 [SMILES: CCC(CC)OC(=O)C1(COc2c(-c3cccc4c3COC4=O)ccc(OC)c2OC)CCC1] | 1-ethylpropyl 1-[[2,3-dimethoxy-6-(1-oxo-3H-isobenzofuran-4-yl)phenoxy]methyl]cyclobutanecarboxylate |
| 783 | 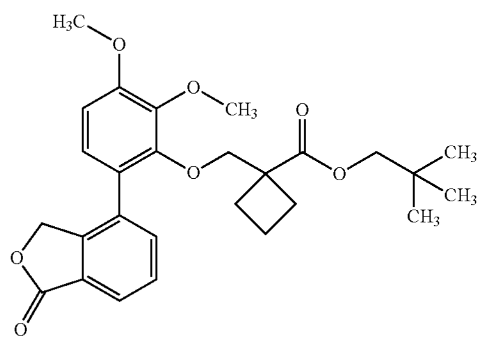 [SMILES: COc1ccc(-c2cccc3c2COC3=O)c(OCC2(C(=O)OCC(C)(C)C)CCC2)c1OC] | 2,2-dimethylpropyl 1-[[2,3-dimethoxy-6-(1-oxo-3H-isobenzofuran-4-yl)phenoxy]methyl]cyclobutanecarboxylate |
| 784 | 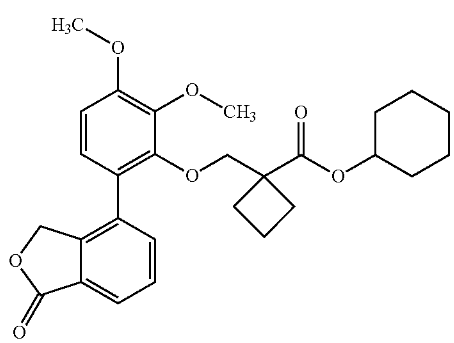 [SMILES: COc1ccc(-c2cccc3c2COC3=O)c(OCC2(C(=O)OC3CCCCC3)CCC2)c1OC] | cyclohexyl 1-[[2,3-dimethoxy-6-(1-oxo-3H-isobenzofuran-4-yl)phenoxy]methyl]cyclobutanecarboxylate |
| 785 | 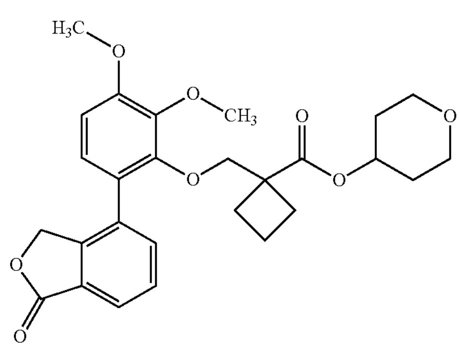 [SMILES: COc1ccc(-c2cccc3c2COC3=O)c(OCC2(C(=O)OC3CCOCC3)CCC2)c1OC] | tetrahydrofuran-4-yl 1-[[2,3-dimethoxy-6-(1-oxo-3H-isobenzofuran-4-yl)phenoxy]methyl]cyclobutanecarboxylate |

| Compound | Structure | Compound name |
|---|---|---|
| 786 | 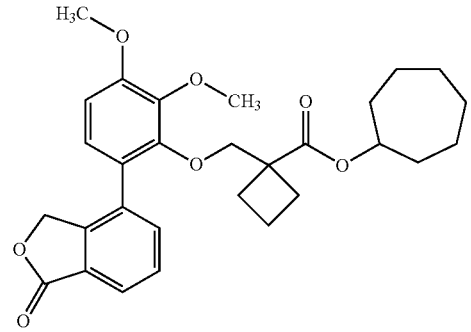 [SMILES: COc1ccc(-c2cccc3c2COC3=O)c(OCC2(C(=O)OC3CCCCCC3)CCC2)c1OC] | cycloheptyl 1-[[2,3-dimethoxy-6-(1-oxo-3H-isobenzofuran-4-yl)phenoxy]methyl]cyclobutanecarboxylate |
| 787 | 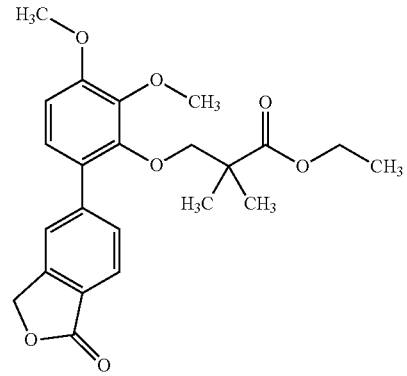 [SMILES: CCOC(=O)C(C)(C)COc1c(-c2ccc3c(c2)COC3=O)ccc(OC)c1OC] | ethyl 3-[2,3-dimethoxy-6-(1-oxo-3H-isobenzofuran-5-yl)phenoxy]-2,2-dimethyl-propanoate |
| 788 | 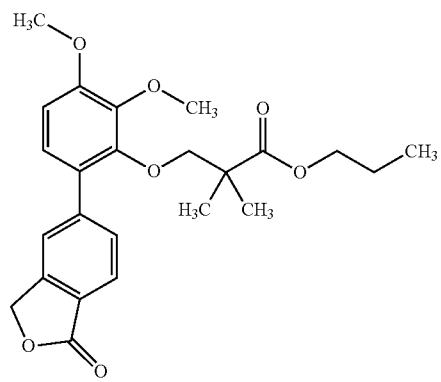 [SMILES: CCCOC(=O)C(C)(C)COc1c(-c2ccc3c(c2)COC3=O)ccc(OC)c1OC] | propyl 3-[2,3-dimethoxy-6-(1-oxo-3H-isobenzofuran-5-yl)phenoxy]-2,2-dimethyl-propanoate |
| 789 | 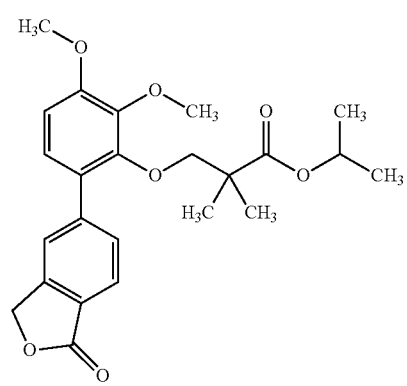 | isopropyl 3-[2,3-dimethoxy-6-(1-oxo-3H-isobenzofuran-5-yl)phenoxy]-2,2-dimethyl-propanoate |

| Compound | Structure | Compound name |
|---|---|---|
| 790 | 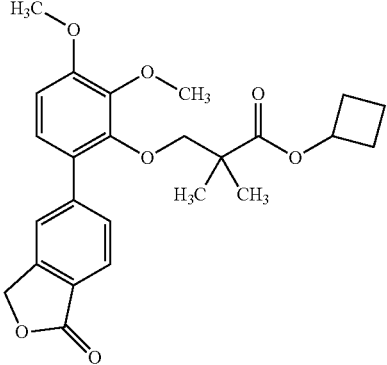 | cyclobutyl 3-[2,3-dimethoxy-6-(1-oxo-3H-isobenzofuran-5-yl)phenoxy]-2,2-dimethyl-propanoate |
| 791 | 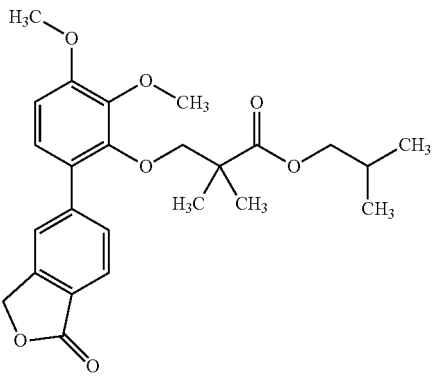 | isobutyl 3-[2,3-dimethoxy-6-(1-oxo-3H-isobenzofuran-5-yl)phenoxy]-2,2-dimethyl-propanoate |
| 792 | 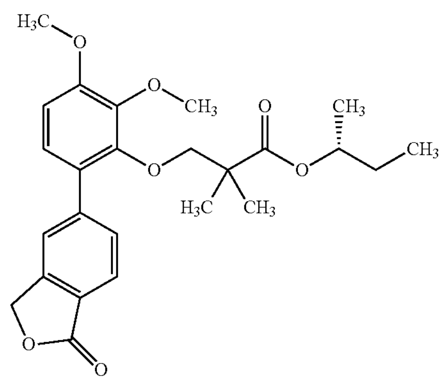 | [(1R)-1-methylpropyl] 3-[2,3-dimethoxy-6-(1-oxo-3H-isobenzofuran-5-yl)phenoxy]-2,2-dimethyl-propanoate |
| 793 | 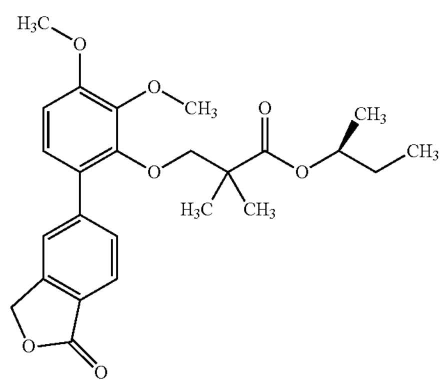 [SMILES: CC[C@H](C)OC(=O)C(C)(C)COc1c(-c2ccc3c(c2)COC3=O)ccc(OC)c1OC] | [(1S)-1-methylpropyl] 3-[2,3-dimethoxy-6-(1-oxo-3H-isobenzofuran-5-yl)phenoxy]-2,2-dimethyl-propanoate |

-continued

| Compound | Structure | Compound name |
|---|---|---|
| 794 | 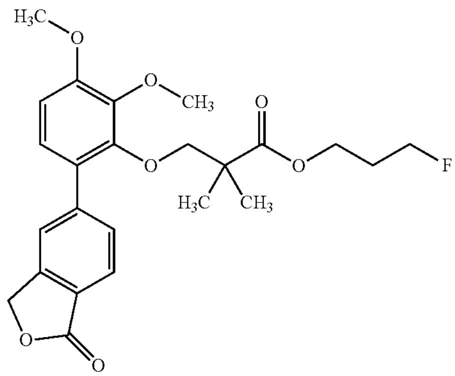 [SMILES: COc1ccc(-c2ccc3c(c2)COC3=O)c(OCC(C)(C)C(=O)OCCCF)c1OC] | 3-fluoropropyl 3-[2,3-dimethoxy-6-(1-oxo-3H-isobenzofuran-5-yl)phenoxy]-2,2-dimethyl-propanoate |
| 795 | 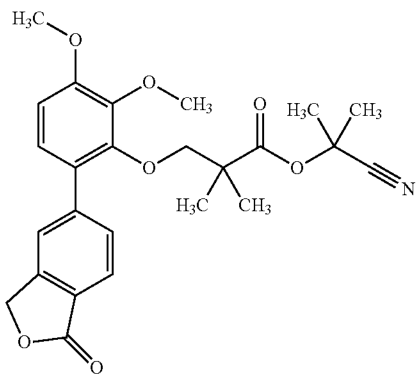 | (1-cyano-3-methyl-ethyl) 3-[2,3-dimethoxy-6-(1-oxo-3H-isobenzofuran-5-yl)phenoxy]-2,2-dimethyl-propanoate |
| 796 | 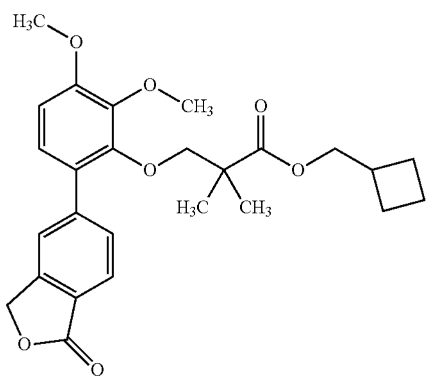 | cyclobutylmethyl 3-[2,3-dimethoxy-6-(1-oxo-3H-isobenzofuran-5-yl)phenoxy]-2,2-dimethyl-propanoate |
| 797 | 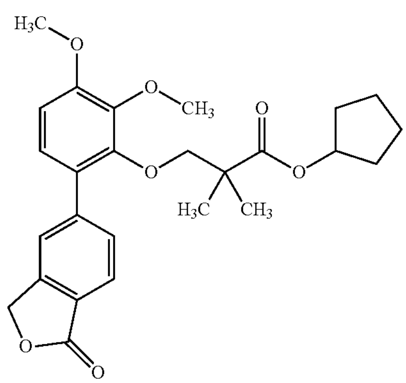 | cyclopentyl 3-[2,3-dimethoxy-6-(1-oxo-3H-isobenzofuran-5-yl)phenoxy]-2,2-dimethyl-propanoate |

-continued

| Compound | Structure | Compound name |
|---|---|---|
| 798 | 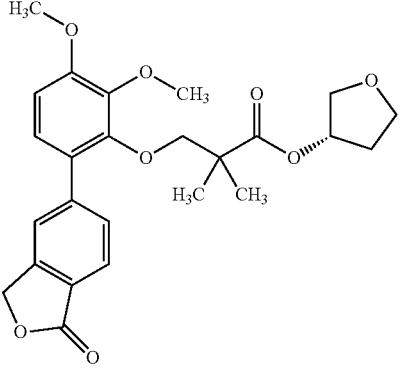 | [(3S)-tetrahydrofuran-3-yl] 3-[2,3-dimethoxy-6-(1-oxo-3H-isobenzofuran-5-yl)phenoxy]-2,2-dimethyl-propanoate |
| 799 | 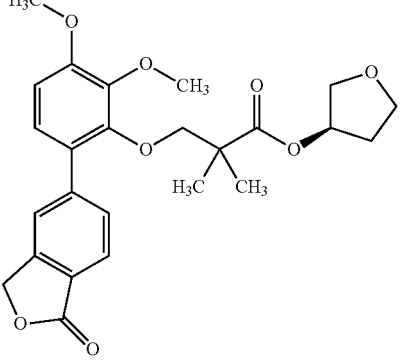 | [(3R)-tetrahydrofuran-3-yl] 3-[2,3-dimethoxy-6-(1-oxo-3H-isobenzofuran-5-yl)phenoxy]-2,2-dimethyl-propanoate |
| 800 | 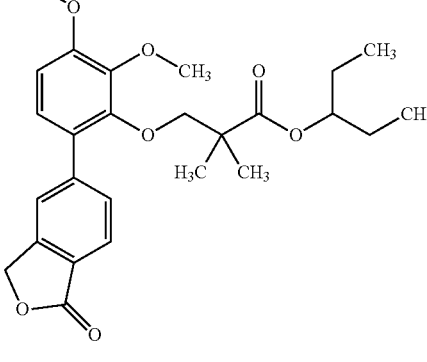 | 1-ethylpropyl 3-[2,3-dimethoxy-6-(1-oxo-3H-isobenzofuran-5-yl)phenoxy]-2,2-dimethyl-propanoate |
| 801 | 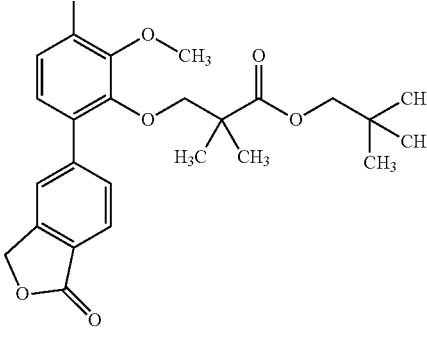 | 2,2-dimethylpropyl 3-[2,3-dimethoxy-6-(1-oxo-3H-isobenzofuran-5-yl)phenoxy]-2,2-dimethyl-propanoate |

-continued

| Compound | Structure | Compound name |
|---|---|---|
| 802 | 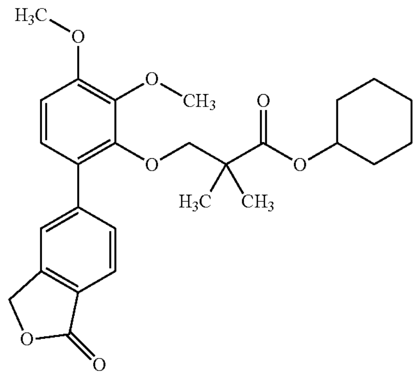 | cyclohexyl 3-[2,3-dimethoxy-6-(1-oxo-3H-isobenzofuran-5-yl)phenoxy]-2,2-dimethyl-propanoate |
| 803 | 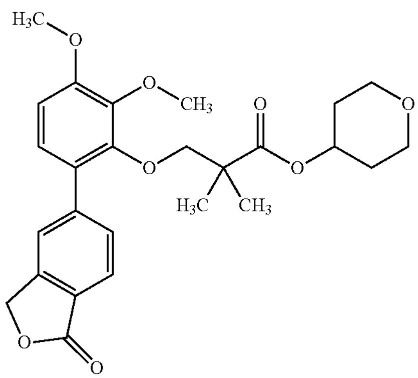 [SMILES: COc1ccc(-c2ccc3c(c2)COC3=O)c(OCC(C)(C)C(=O)OC2CCOCC2)c1OC] | tetrahydrofuran-4-yl 3-[2,3-dimethoxy-6-(1-oxo-3H-isobenzofuran-5-yl)phenoxy]-2,2-dimethyl-propanoate |
| 804 | 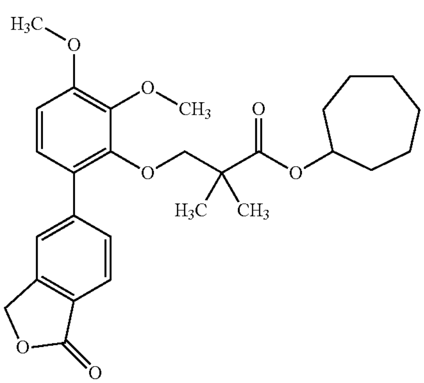 | cycloheptyl 3-[2,3-dimethoxy-6-(1-oxo-3H-isobenzofuran-5-yl)phenoxy]-2,2-dimethyl-propanoate |
| 805 | | methyl 1-[[2,3-dimethoxy-6-(1-oxo-3H-isobenzofuran-5-yl)phenoxy]methyl]cyclopropanecarboxylate |

6B

-continued

| Compound | Structure | Compound name |
|---|---|---|
| 806 | 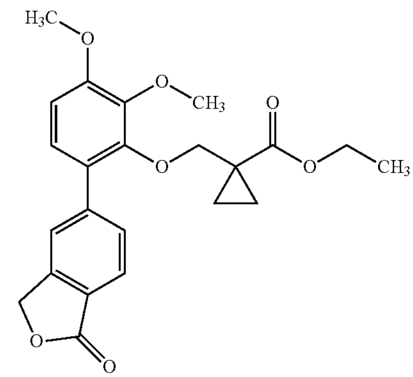 | ethyl 1-[[2,3-dimethoxy-6-(1-oxo-3H-isobenzofuran-5-yl)phenoxy]methyl]cyclopropanecarboxylate |
| 807 | 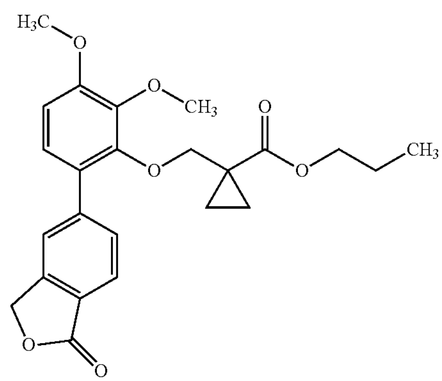 [SMILES: CCCOC(=O)C1(COc2c(-c3ccc4c(c3)COC4=O)ccc(OC)c2OC)CC1] | propyl 1-[[2,3-dimethoxy-6-(1-oxo-3H-isobenzofuran-5-yl)phenoxy]methyl]cyclopropanecarboxylate |
| 808 | 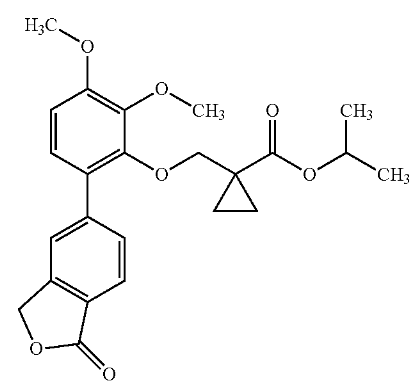 [SMILES: COc1ccc(-c2ccc3c(c2)COC3=O)c(OCC2(C(=O)OC(C)C)CC2)c1OC] | isopropyl 1-[[2,3-dimethoxy-6-(1-oxo-3H-isobenzofuran-5-yl)phenoxy]methyl]cyclopropanecarboxylate |
| 809 | 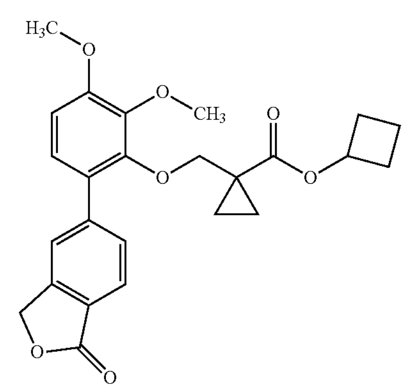 [SMILES: COc1ccc(-c2ccc3c(c2)COC3=O)c(OCC2(C(=O)OC3CCC3)CC2)c1OC] | cyclobutyl 1-[[2,3-dimethoxy-6-(1-oxo-3H-isobenzofuran-5-yl)phenoxy]methyl]cyclopropanecarboxylate |

| Compound | Structure | Compound name |
|---|---|---|
| 810 | 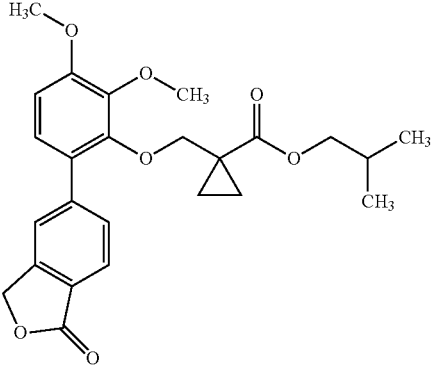 | isobutyl 1-[[2,3-dimethoxy-6-(1-oxo-3H-isobenzofuran-5-yl)phenoxy]methyl]cyclopropanecarboxylate |
| 811 | 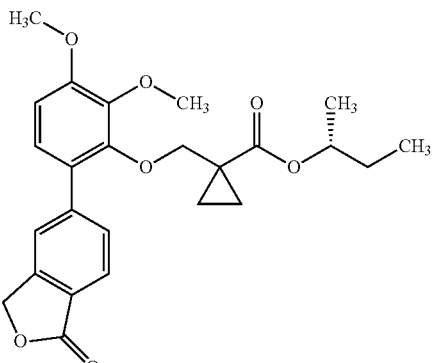 | [(1R)-1-methylpropyl] 1-[[2,3-dimethoxy-6-(1-oxo-3H-isobenzofuran-5-yl)phenoxy]methyl]cyclopropanecarboxylate |
| 812 | 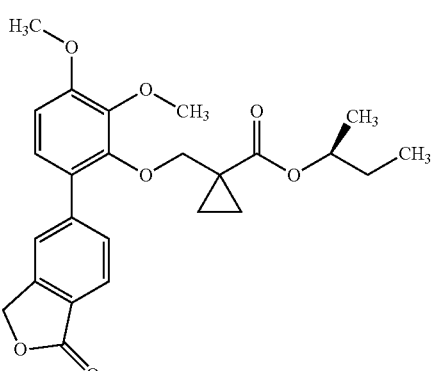 | [(1S)-1-methylpropyl] 1-[[2,3-dimethoxy-6-(1-oxo-3H-isobenzofuran-5-yl)phenoxy]methyl]cyclopropanecarboxylate |
| 813 | 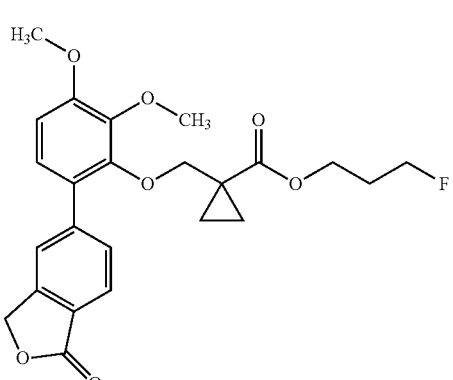 | 3-fluorophenyl 1-[[2,3-dimethoxy-6-(1-oxo-3H-isobenzofuran-5-yl)phenoxy]methyl]cyclopropanecarboxylate |

-continued

| Compound | Structure | Compound name |
|---|---|---|
| 814 | 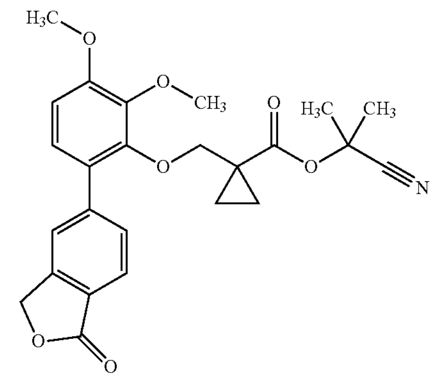 | (1-cyano-1-methyl-ethyl) 1-[[2,3-dimethoxy-6-(1-oxo-3H-isobenzofuran-5-yl)phenoxy]methyl]cyclopropanecarboxylate |
| 815 | 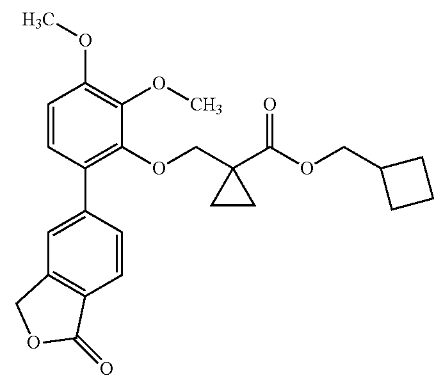 [SMILES: COc1ccc(-c2ccc3c(c2)COC3=O)c(OCC2(C(=O)OCC3CCC3)CC2)c1OC] | cyclobutylmethyl 1-[[2,3-dimethoxy-6-(1-oxo-3H-isobenzofuran-5-yl)phenoxy]methyl]cyclopropanecarboxylate |
| 816 | 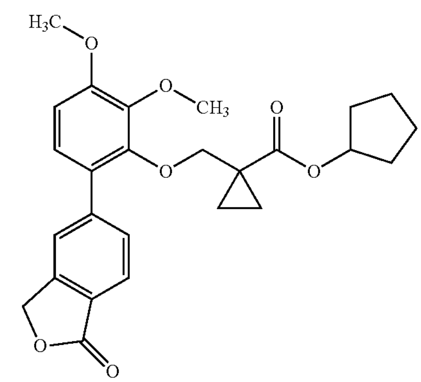 [SMILES: COc1ccc(-c2ccc3c(c2)COC3=O)c(OCC2(C(=O)OC3CCCC3)CC2)c1OC] | cyclopentyl 1-[[2,3-dimethoxy-6-(1-oxo-3H-isobenzofuran-5-yl)phenoxy]methyl]cyclopropanecarboxylate |
| 817 | 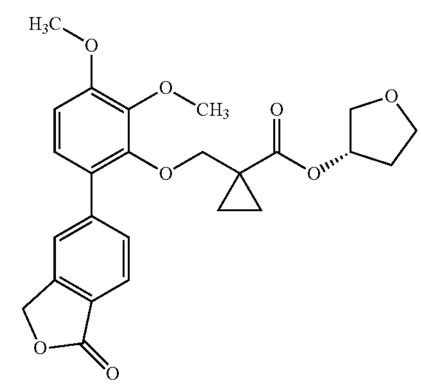 [SMILES: COc1ccc(-c2ccc3c(c2)COC3=O)c(OCC2(C(=O)O[C@H]3CCOC3)CC2)c1OC] | [(3S)-tetrahydrofuran-3-yl] 1-[[2,3-dimethoxy-6-(1-oxo-3H-isobenzofuran-5-yl)phenoxy]methyl]cyclopropanecarboxylate |

| Compound | Structure | Compound name |
|---|---|---|
| 818 | 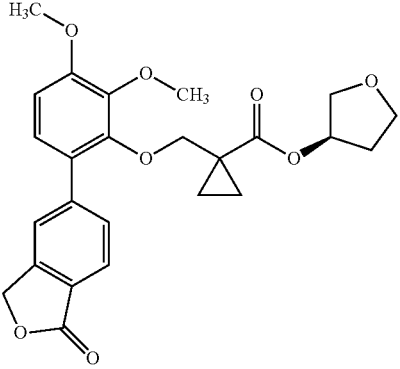 [SMILES: COc1ccc(-c2ccc3c(c2)COC3=O)c(OCC2(C(=O)O[C@@H]3CCOC3)CC2)c1OC] | [(3R)-tetrahydrofuran-3-yl] 1-[[2,3-dimethoxy-6-(1-oxo-3H-isobenzofuran-5-yl)phenoxy]methyl]cyclopropanecarboxylate |
| 819 | 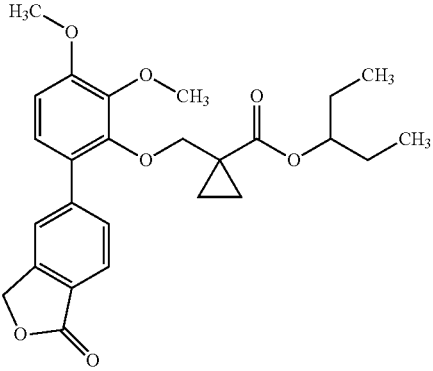 [SMILES: CCC(CC)OC(=O)C1(COc2c(-c3ccc4c(c3)COC4=O)ccc(OC)c2OC)CC1] | 1-ethylpropyl 1-[[2,3-dimethoxy-6-(1-oxo-3H-isobenzofuran-5-yl)phenoxy]methyl]cyclopropanecarboxylate |
| 820 | 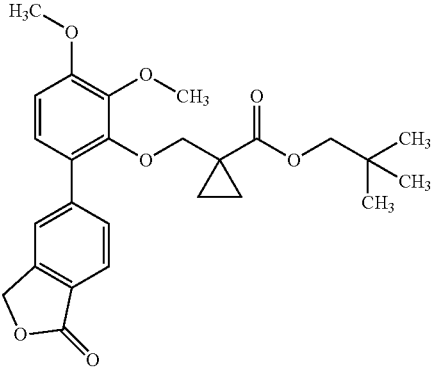 [SMILES: COc1ccc(-c2ccc3c(c2)COC3=O)c(OCC2(C(=O)OCC(C)(C)C)CC2)c1OC] | 2,2-dimethylpropyl 1-[[2,3-dimethoxy-6-(1-oxo-3H-isobenzofuran-5-yl)phenoxy]methyl]cyclopropanecarboxylate |
| 821 | 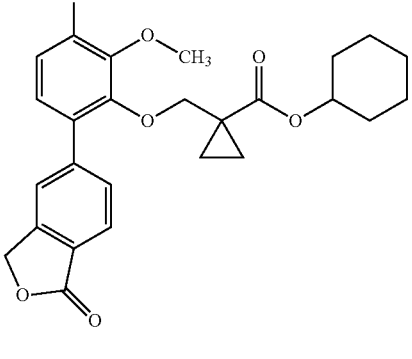 | cyclohexyl 1-[[2,3-dimethoxy-6-(1-oxo-3H-isobenzofuran-5-yl)phenoxy]methyl]cyclopropanecarboxylate |

-continued

| Compound | Structure | Compound name |
|---|---|---|
| 822 | 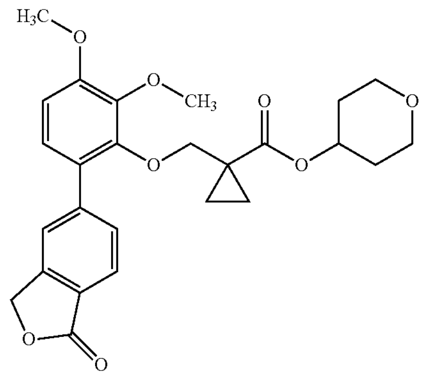 | tetrahydrofuran-4-yl 1-[[2,3-dimethoxy-6-(1-oxo-3H-isobenzofuran-5-yl)phenoxy]methyl]cyclopropanecarboxylate |
| 823 | 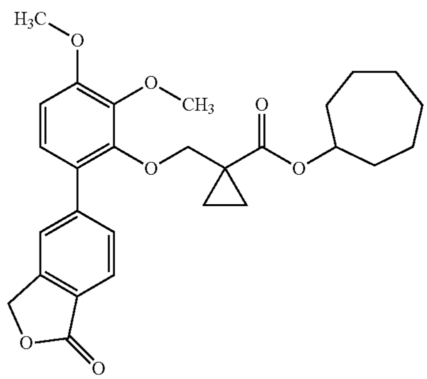 | cycloheptyl 1-[[2,3-dimethoxy-6-(1-oxo-3H-isobenzofuran-5-yl)phenoxy]methyl]cyclopropanecarboxylate |
| 824 | | methyl 1-[[2,3-dimethoxy-6-(1-oxo-3H-isobenzofuran-5-yl)phenoxy]methyl]cyclobutanecarboxylate |
| 825 | | ethyl 1-[[2,3-dimethoxy-6-(1-oxo-3H-isobenzofuran-5-yl)phenoxy]methyl]cyclobutanecarboxylate |

6C

-continued

| Compound | Structure | Compound name |
|---|---|---|
| 826 | 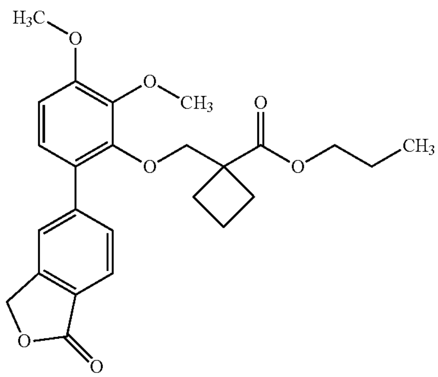 [SMILES: CCCOC(=O)C1(COc2c(-c3ccc4c(c3)COC4=O)ccc(OC)c2OC)CCC1] | propyl 1-[[2,3-dimethoxy-6-(1-oxo-3H-isobenzofuran-5-yl)phenoxy]methyl]cyclobutanecarboxylate |
| 827 | 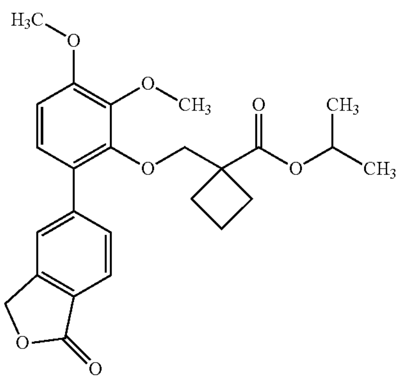 [SMILES: COc1ccc(-c2ccc3c(c2)COC3=O)c(OCC2(C(=O)OC(C)C)CCC2)c1OC] | isopropyl 1-[[2,3-dimethoxy-6-(1-oxo-3H-isobenzofuran-5-yl)phenoxy]methyl]cyclobutanecarboxylate |
| 828 | 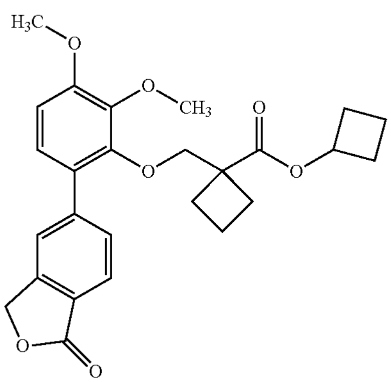 [SMILES: COc1ccc(-c2ccc3c(c2)COC3=O)c(OCC2(C(=O)OC3CCC3)CCC2)c1OC] | cyclobutyl 1-[[2,3-dimethoxy-6-(1-oxo-3H-isobenzofuran-5-yl)phenoxy]methyl]cyclobutanecarboxylate |
| 829 | 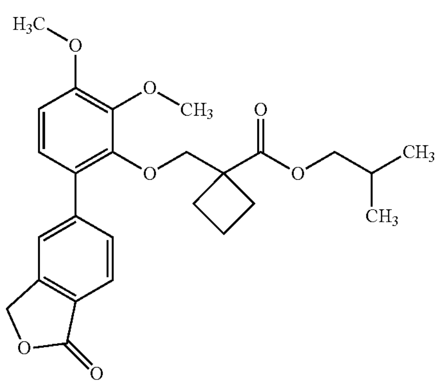 [SMILES: COc1ccc(-c2ccc3c(c2)COC3=O)c(OCC2(C(=O)OCC(C)C)CCC2)c1OC] | isobutyl 1-[[2,3-dimethoxy-6-(1-oxo-3H-isobenzofuran-5-yl)phenoxy]methyl]cyclobutanecarboxylate |

| Compound | Structure | Compound name |
|---|---|---|
| 830 | 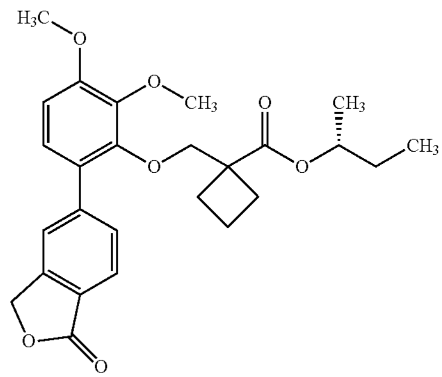 [SMILES: CC[C@@H](C)OC(=O)C1(COc2c(-c3ccc4c(c3)COC4=O)ccc(OC)c2OC)CCC1] | [(1R)-1-methylpropyl 1-[[2,3-dimethoxy-6-(1-oxo-3H-isobenzofuran-5-yl)phenoxy]methyl]cyclobutanecarboxylate |
| 831 | 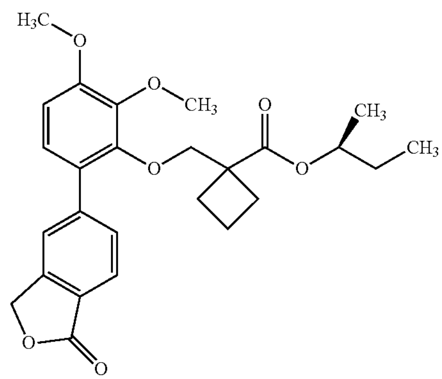 [SMILES: CC[C@H](C)OC(=O)C1(COc2c(-c3ccc4c(c3)COC4=O)ccc(OC)c2OC)CCC1] | [(1S)-1-methylpropyl 1-[[2,3-dimethoxy-6-(1-oxo-3H-isobenzofuran-5-yl)phenoxy]methyl]cyclobutanecarboxylate |
| 832 | 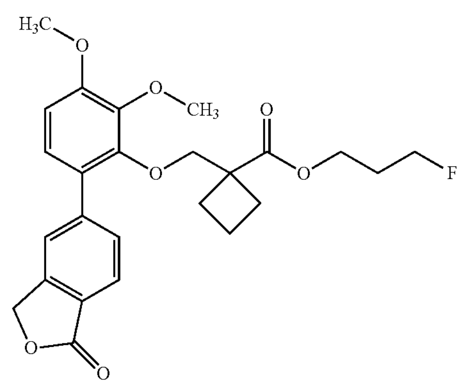 [SMILES: COc1ccc(-c2ccc3c(c2)COC3=O)c(OCC2(C(=O)OCCCF)CCC2)c1OC] | 3-fluoropropyl 1-[[2,3-dimethoxy-6-(1-oxo-3H-isobenzofuran-5-yl)phenoxy]methyl]cyclobutanecarboxylate |
| 833 | 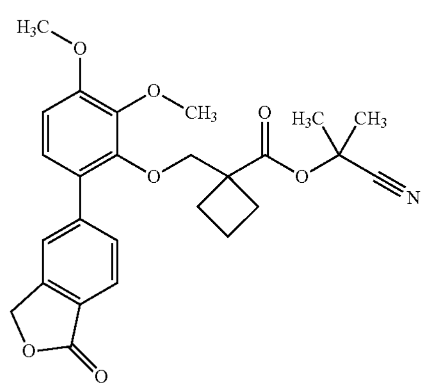 [SMILES: COc1ccc(-c2ccc3c(c2)COC3=O)c(OCC2(C(=O)OC(C)(C)C#N)CCC2)c1OC] | (1-cyano-1-methyl-ethyl) 1-[[2,3-dimethoxy-6-(1-oxo-3H-isobenzofuran-5-yl)phenoxy]methyl]cyclobutanecarboxylate |

-continued

| Compound | Structure | Compound name |
|---|---|---|
| 834 | 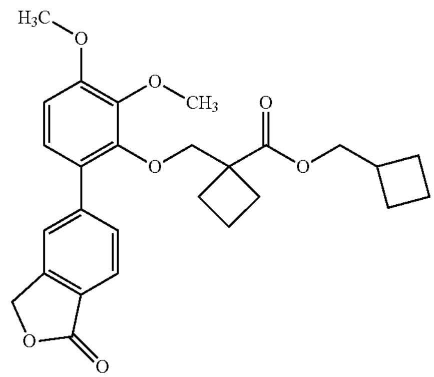 | cyclobutylmethyl 1-[[2,3-dimethoxy-6-(1-oxo-3H-isobenzofuran-5-yl)phenoxy]methyl]cyclobutanecarboxylate |
| 835 | 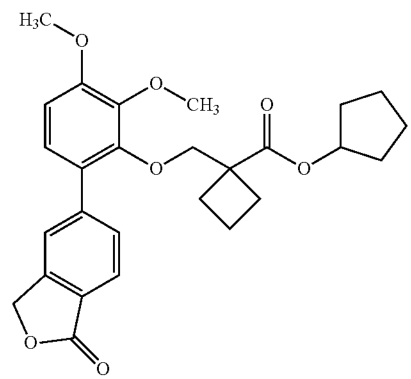 [SMILES: COc1ccc(-c2ccc3c(c2)COC3=O)c(OCC2(C(=O)OC3CCCC3)CCC2)c1OC] | cyclopentyl 1-[[2,3-dimethoxy-6-(1-oxo-3H-isobenzofuran-5-yl)phenoxy]methyl]cyclobutanecarboxylate |
| 836 | 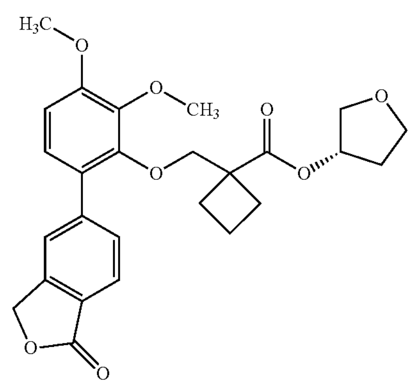 [SMILES: COc1ccc(-c2ccc3c(c2)COC3=O)c(OCC2(C(=O)O[C@H]3CCOC3)CCC2)c1OC] | [(3S)-tetrahydrofuran-3-yl] 1-[[2,3-dimethoxy-6-(1-oxo-3H-isobenzofuran-5-yl)phenoxy]methyl]cyclobutanecarboxylate |
| 837 | 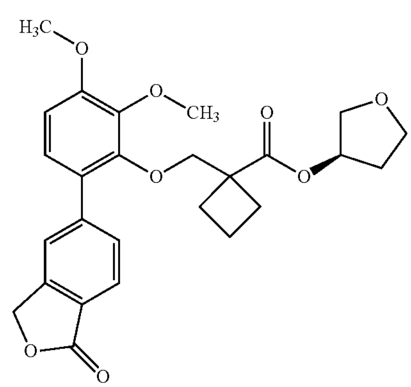 [SMILES: COc1ccc(-c2ccc3c(c2)COC3=O)c(OCC2(C(=O)O[C@@H]3CCOC3)CCC2)c1OC] | [(3R)-tetrahydrofuran-3-yl] 1-[[2,3-dimethoxy-6-(1-oxo-3H-isobenzofuran-5-yl)phenoxy]methyl]cyclobutanecarboxylate |

| Compound | Structure | Compound name |
|---|---|---|
| 838 | 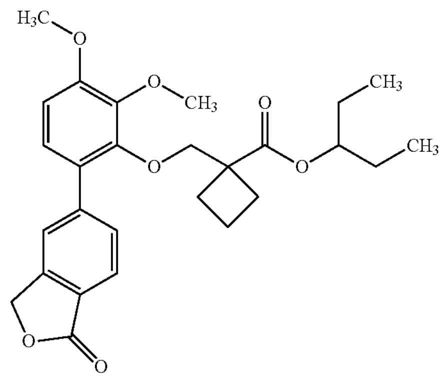 [SMILES: CCC(CC)OC(=O)C1(COc2c(-c3ccc4c(c3)COC4=O)ccc(OC)c2OC)CCC1] | 1-ethylpropyl 1-[[2,3-dimethoxy-6-(1-oxo-3H-isobenzofuran-5-yl)phenoxy]methyl]cyclobutanecarboxylate |
| 839 | 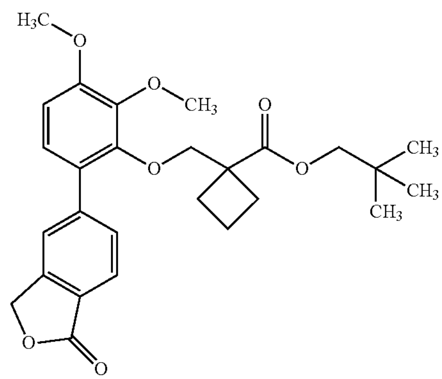 [SMILES: COc1ccc(-c2ccc3c(c2)COC3=O)c(OCC2(C(=O)OCC(C)(C)C)CCC2)c1OC] | 2,2-dimethylpropyl 1-[[2,3-dimethoxy-6-(1-oxo-3H-isobenzofuran-5-yl)phenoxy]methyl]cyclobutanecarboxylate |
| 840 | 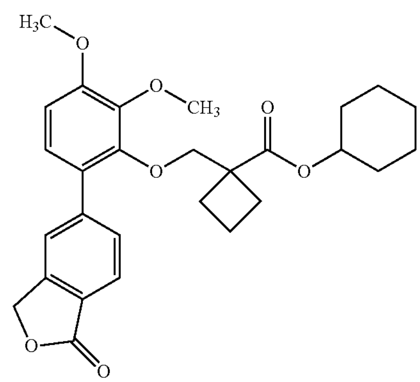 [SMILES: COc1ccc(-c2ccc3c(c2)COC3=O)c(OCC2(C(=O)OC3CCCCC3)CCC2)c1OC] | cyclohexyl 1-[[2,3-dimethoxy-6-(1-oxo-3H-isobenzofuran-5-yl)phenoxy]methyl]cyclobutanecarboxylate |
| 841 | 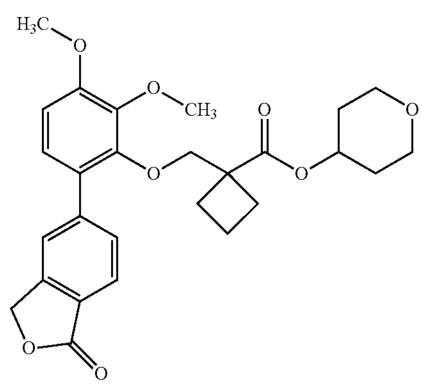 [SMILES: COc1ccc(-c2ccc3c(c2)COC3=O)c(OCC2(C(=O)OC3CCOCC3)CCC2)c1OC] | tetrahydropyran-4-yl 1-[[2,3-dimethoxy-6-(1-oxo-3H-isobenzofuran-5-yl)phenoxy]methyl]cyclobutanecarboxylate |

| Compound | Structure | Compound name |
|---|---|---|
| 842 | 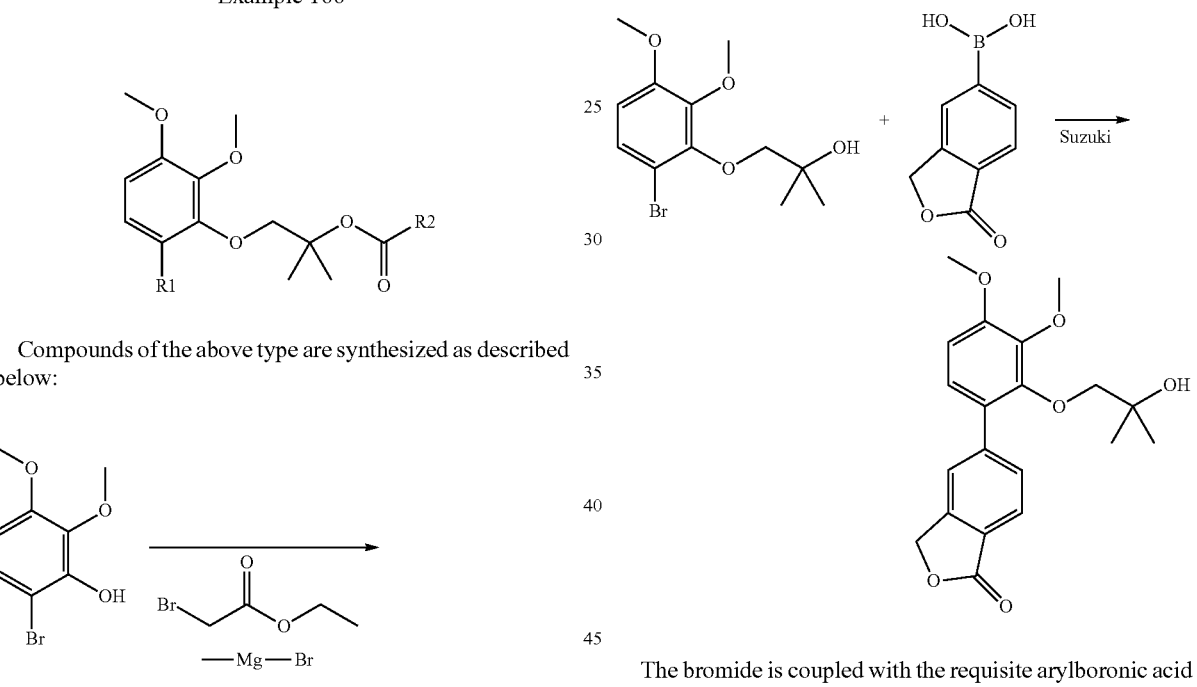 | cycloheptyl 1-[[2,3-dimethoxy-6-(1-oxo-3H-isobenzofuran-5-yl)phenoxy]methyl]cyclobutanecarboxylate |

Example 166

Compounds of the above type are synthesized as described below:

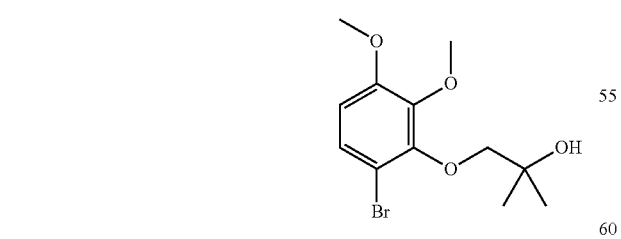

6-bromo-2,3-methoxyphenol is prepared as described in example 169. 6-bromo-2,3-methoxyphenol is alkylated with ethyl bromoacetate in dimethylformamide using potassium carbonate at room temperature. The resulting ester is treated with Methyl Grignard in diethyl ether at room temperature to give the tertiary carbinol.

The bromide is coupled with the requisite arylboronic acid by Suzuki coupling in methanol, using 10% Palladium(bis-triphenylphosphine)dichloride and sodium acetate with conventional heating or microwave heating to give the biaryl compound. The alcohol is acylated upon treatment with an acid chloride in acetonitrile at room temperature using pyridine as a base or as a catalyst.

Example 167

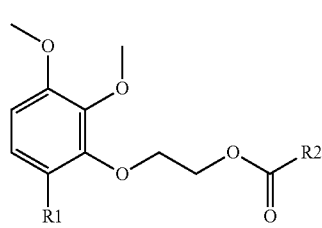

413

Compounds of the above type are synthesized as described below:

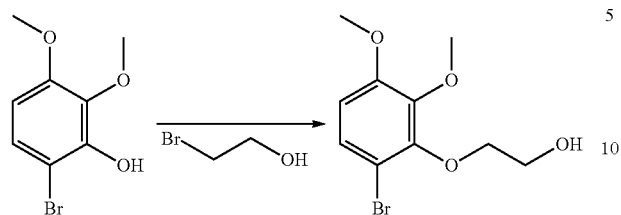

6-bromo-2,3-methoxyphenol is alkylated with bromethanol in dimethylformamide using potassium carbonate as a base under heating.

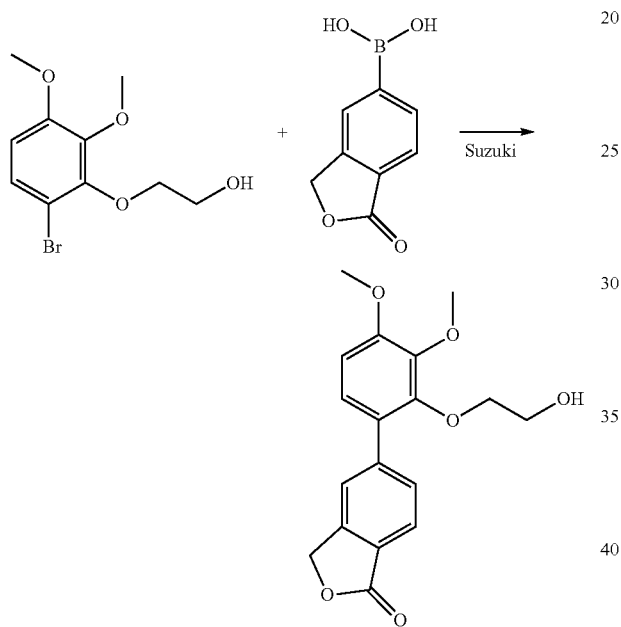

The bromide is coupled with the requisite arylboronic acid by Suzuki coupling in methanol, using 10% Palladium(bis-triphenylphosphine)dichloride and sodium acetate by conventional heating or microwave heating to give the biaryl compound.

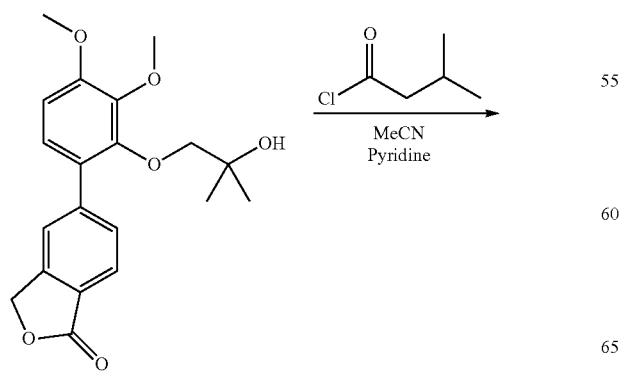

414

-continued

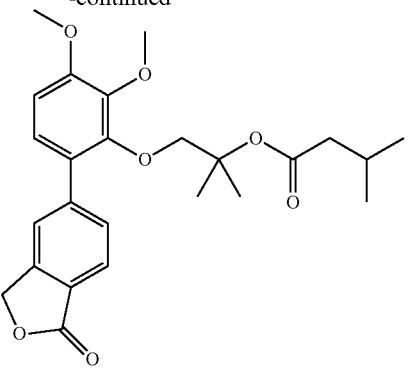

The alcohol is acylated by treatment with an acid chloride in acetonitrile with pyridine as a base.

Example 168

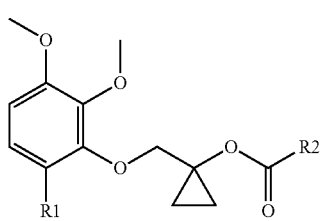

Compounds of the above type may be synthesized as described below (ref. Shevchuk, T. A. and Kulinkovich, O. G. *Russian Journal of Organic Chemistry* (Translation of Zhurnal Organicheskoi Khimii), 36(4), 491-495; 2000)

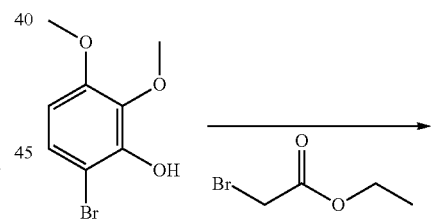

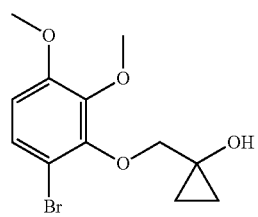

6-bromo-2,3-methoxyphenol is alkylated with ethyl bromoacetate in dimethylformamide using potassium carbonate as a base. The resulting ester is treated with Ethyl Grignard and Titanium tetraisopropoxide in diethyl ether on warming from −60° C. to room temperature to give the cyclopropanol.

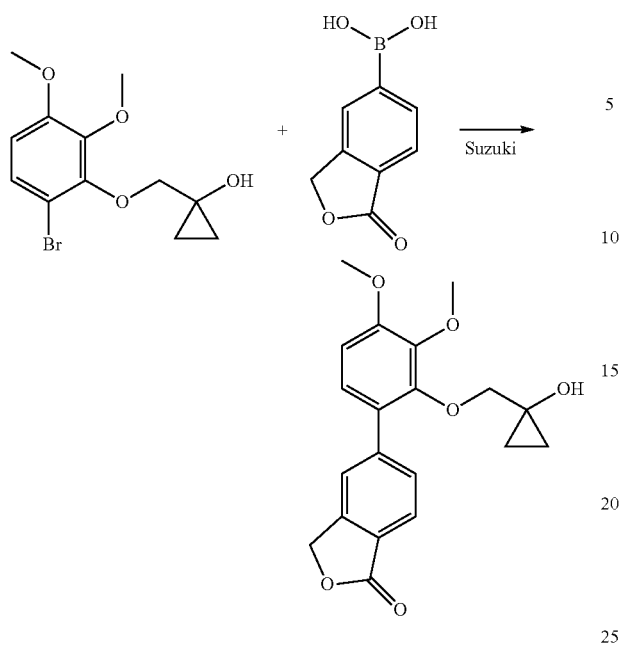

The bromide is coupled with the requisite arylboronic acid by Suzuki coupling in methanol, using 10% Palladium(bis-triphenylphosphine)dichloride and sodium acetate, with conventional heating or microwave heating to give the biaryl product. The alcohol is acylated upon treatment with an acid chloride in acetonitrile at room temperature using pyridine either as a base or a catalyst.

Compounds 843-1184 are prepared according either to example 166, example 167 or example 168

| Compound | Structure | Compound name |
|---|---|---|
| 843 | 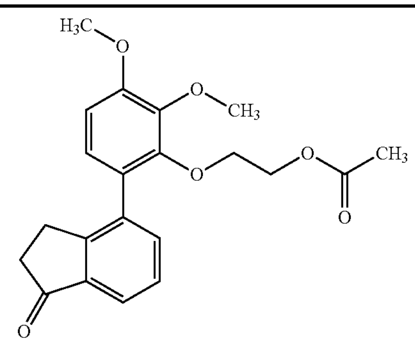 | 2-[2,3-dimethoxy-6-(1-oxoindan-4-yl)phenoxy]ethyl acetate |
| 844 | 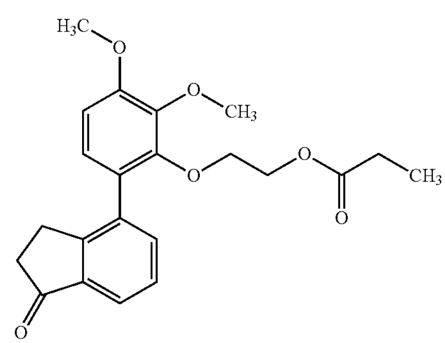 [SMILES: CCC(=O)OCCOc1c(-c2cccc3c2CCC3=O)ccc(OC)c1OC] | 2-[2,3-dimethoxy-6-(1-oxoindan-4-yl)phenoxy]ethyl propanoate |

-continued
| Compound | Structure | Compound name |
|---|---|---|
| 845 | 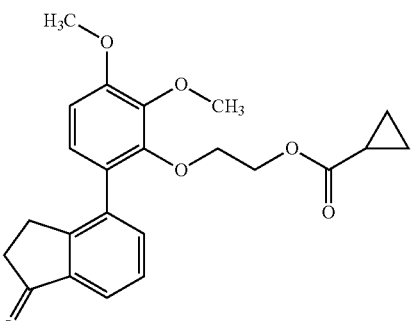 | 2-[2,3-dimethoxy-6-(1-oxoindan-4-yl)phenoxy]ethyl cyclopropanecarboxylate |
| 846 | 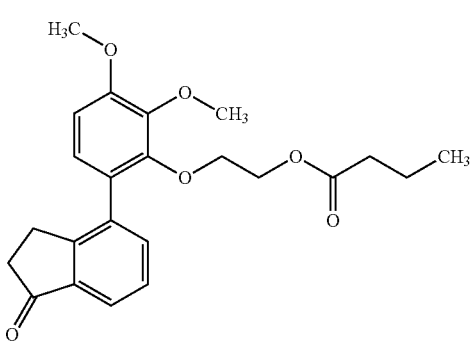 [SMILES: CCCC(=O)OCCOc1c(-c2cccc3c2CCC3=O)ccc(OC)c1OC] | 2-[2,3-dimethoxy-6-(1-oxoindan-4-yl)phenoxy]ethyl butanoate |
| 847 | 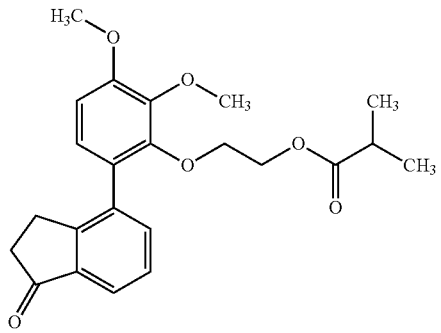 [SMILES: COc1ccc(-c2cccc3c2CCC3=O)c(OCCOC(=O)C(C)C)c1OC] | 2-[2,3-dimethoxy-6-(1-oxoindan-4-yl)phenoxy]ethyl 2-methylpropanoate |
| 848 | 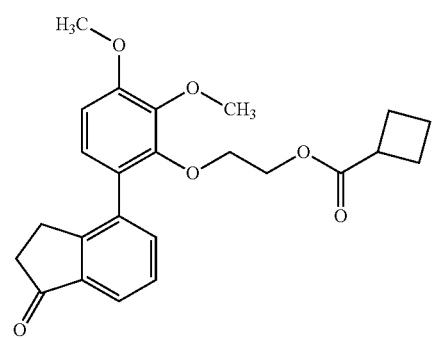 [SMILES: COc1ccc(-c2cccc3c2CCC3=O)c(OCCOC(=O)C2CCC2)c1OC] | 2-[2,3-dimethoxy-6-(1-oxoindan-4-yl)phenoxy]ethyl cyclobutanecarboxylate |

-continued
| Compound | Structure | Compound name |
|---|---|---|
| 849 | 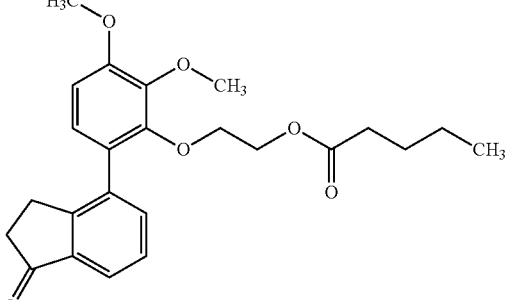 | 2-[2,3-dimethoxy-6-(1-oxoindan-4-yl)phenoxy]ethyl pentanoate |
| 850 | 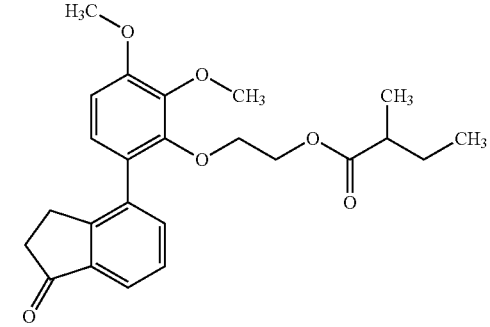 [SMILES: CCC(C)C(=O)OCCOc1c(-c2cccc3c2CCC3=O)ccc(OC)c1OC] | 2-[2,3-dimethoxy-6-(1-oxoindan-4-yl)phenoxy]ethyl 2-methylbutanoate |
| 851 | 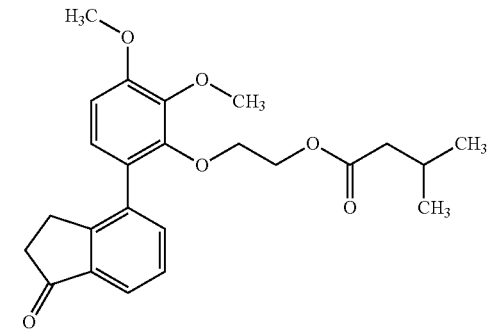 [SMILES: COc1ccc(-c2cccc3c2CCC3=O)c(OCCOC(=O)CC(C)C)c1OC] | 2-[2,3-dimethoxy-6-(1-oxoindan-4-yl)phenoxy]ethyl 3-methylbutanoate |
| 852 | 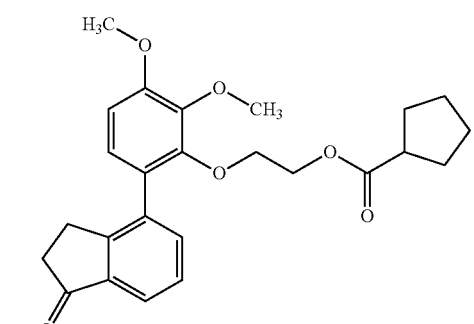 | 2-[2,3-dimethoxy-6-(1-oxoindan-4-yl)phenoxy]ethyl cyclopentanecarboxylate |

-continued
| Compound | Structure | Compound name |
|---|---|---|
| 853 | 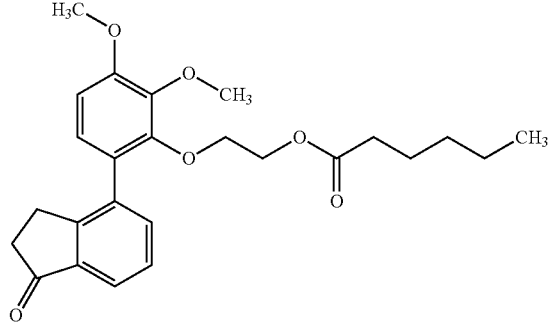 [SMILES: CCCCCC(=O)OCCOc1c(-c2cccc3c2CCC3=O)ccc(OC)c1OC] | 2-[2,3-dimethoxy-6-(1-oxoindan-4-yl)phenoxy]ethyl hexanoate |
| 854 | 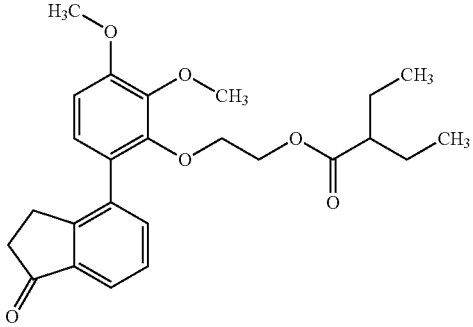 [SMILES: CCC(CC)C(=O)OCCOc1c(-c2cccc3c2CCC3=O)ccc(OC)c1OC] | 2-[2,3-dimethoxy-6-(1-oxoindan-4-yl)phenoxy]ethyl 2-ethylbutanoate |
| 855 | 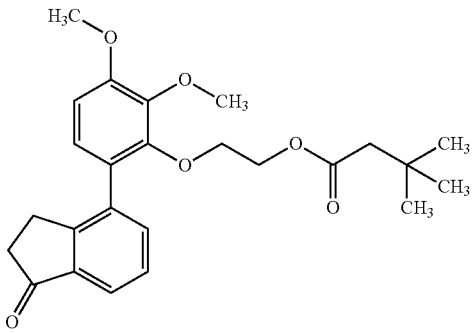 [SMILES: COc1ccc(-c2cccc3c2CCC3=O)c(OCCOC(=O)CC(C)(C)C)c1OC] | 2-[2,3-dimethoxy-6-(1-oxoindan-4-yl)phenoxy]ethyl 3,3-dimethylbutanoate |
| 856 | 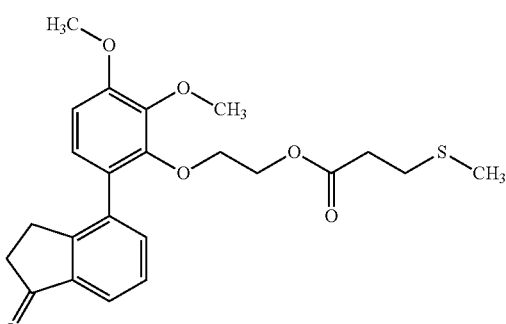 | 2-[2,3-dimethoxy-6-(1-oxoindan-4-yl)phenoxy]ethyl 3-methylsulfanylpropanoate |

-continued

| Compound | Structure | Compound name |
|---|---|---|
| 857 | 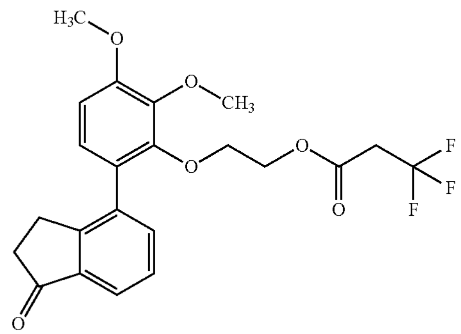 [SMILES: COc1ccc(-c2cccc3c2CCC3=O)c(OCCOC(=O)CC(F)(F)F)c1OC] | 2-[2,3-dimethoxy-6-(1-oxoindan-4-yl)phenoxy]ethyl 3,3,3-trifluoropropanoate |
| 858 | 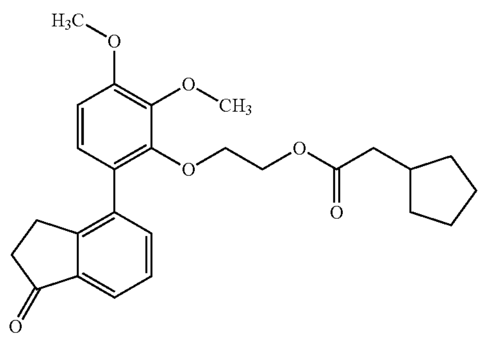 [SMILES: COc1ccc(-c2cccc3c2CCC3=O)c(OCCOC(=O)CC2CCCC2)c1OC] | 2-[2,3-dimethoxy-6-(1-oxoindan-4-yl)phenoxy]ethyl 2-cyclopentylacetate |
| 859 | 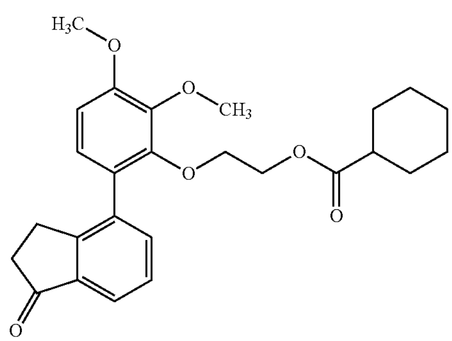 [SMILES: COc1ccc(-c2cccc3c2CCC3=O)c(OCCOC(=O)C2CCCCC2)c1OC] | 2-[2,3-dimethoxy-6-(1-oxoindan-4-yl)phenoxy]ethyl cyclohexanecarboxylate |
| 860 | 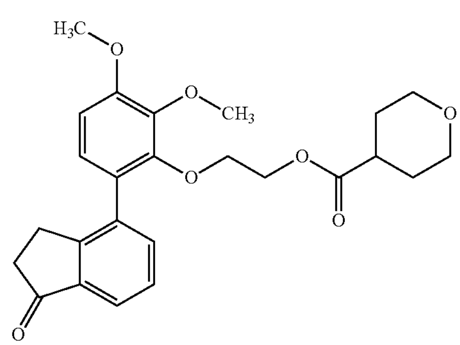 [SMILES: COc1ccc(-c2cccc3c2CCC3=O)c(OCCOC(=O)C2CCOCC2)c1OC] | 2-[2,3-dimethoxy-6-(1-oxoindan-4-yl)phenoxy]ethyl tetrahydropyran-4-carboxylate |

| Compound | Structure | Compound name |
|---|---|---|
| 861 | 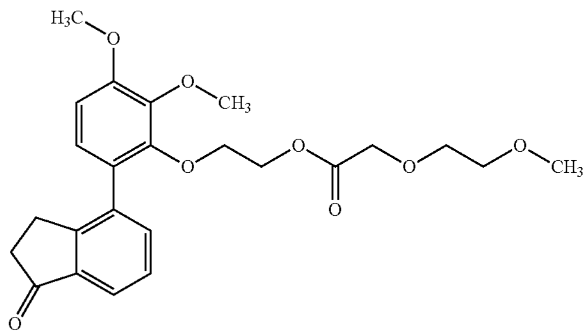 [SMILES: COCCOCC(=O)OCCOc1c(-c2cccc3c2CCC3=O)ccc(OC)c1OC] | 2-[2,3-dimethoxy-6-(1-oxoindan-4-yl)phenoxy]ethyl 2-(2-methoxyethoxy)acetate |
| 862 | 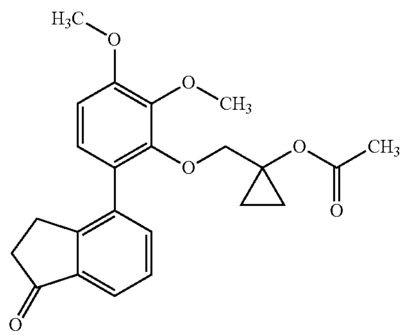 [SMILES: COc1ccc(-c2cccc3c2CCC3=O)c(OCC2(OC(C)=O)CC2)c1OC] | [1-[[2,3-dimethoxy-6-(1-oxoindan-4-yl)phenoxy]methyl]cyclopropyl] acetate |
| 863 | 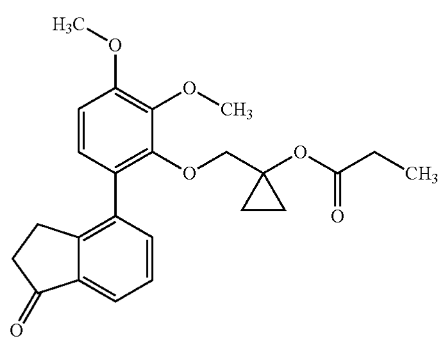 [SMILES: CCC(=O)OC1(COc2c(-c3cccc4c3CCC4=O)ccc(OC)c2OC)CC1] | [1-[[2,3-dimethoxy-6-(1-oxoindan-4-yl)phenoxy]methyl]cyclopropyl] propanoate |
| 864 | 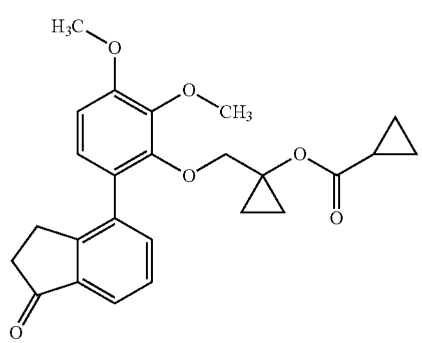 [SMILES: COc1ccc(-c2cccc3c2CCC3=O)c(OCC2(OC(=O)C3CC3)CC2)c1OC] | [1-[[2,3-dimethoxy-6-(1-oxoindan-4-yl)phenoxy]methyl]cyclopropyl] cyclopropanecarboxylate |

-continued

| Compound | Structure | Compound name |
|---|---|---|
| 865 | 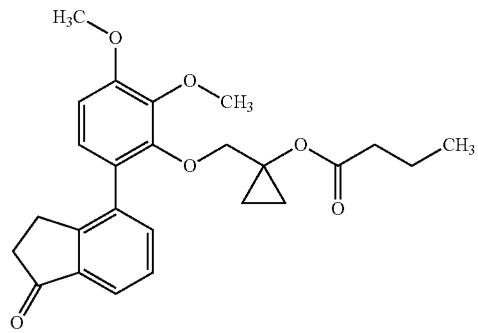 [SMILES: CCCC(=O)OC1(COc2c(-c3cccc4c3CCC4=O)ccc(OC)c2OC)CC1] | [1-[[2,3-dimethoxy-6-(1-oxoindan-4-yl)phenoxy]methyl]cyclopropyl] butanoate |
| 866 | 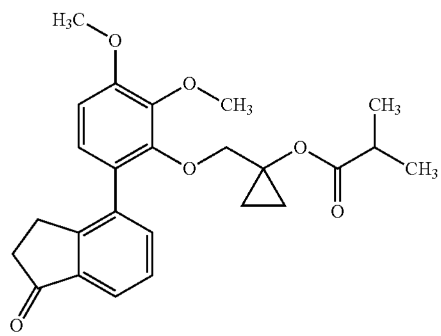 [SMILES: COc1ccc(-c2cccc3c2CCC3=O)c(OCC2(OC(=O)C(C)C)CC2)c1OC] | [1-[[2,3-dimethoxy-6-(1-oxoindan-4-yl)phenoxy]methyl]cyclopropyl] 2-methylpropanoate |
| 867 | 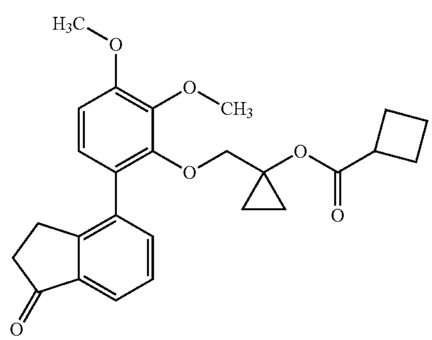 [SMILES: COc1ccc(-c2cccc3c2CCC3=O)c(OCC2(OC(=O)C3CCC3)CC2)c1OC] | [1-[[2,3-dimethoxy-6-(1-oxoindan-4-yl)phenoxy]methyl]cyclopropyl] cyclobutanecarboxylate |
| 868 | 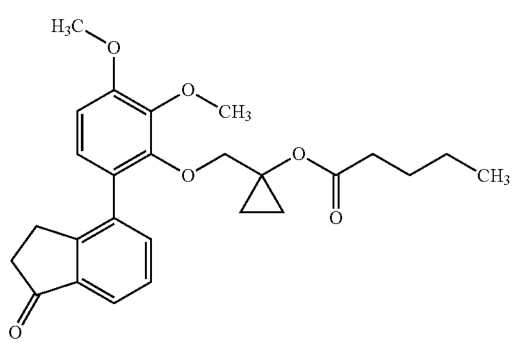 [SMILES: CCCCC(=O)OC1(COc2c(-c3cccc4c3CCC4=O)ccc(OC)c2OC)CC1] | [1-[[2,3-dimethoxy-6-(1-oxoindan-4-yl)phenoxy]methyl]cyclopropyl] pentanoate |

| Compound | Structure | Compound name |
|---|---|---|
| 869 | 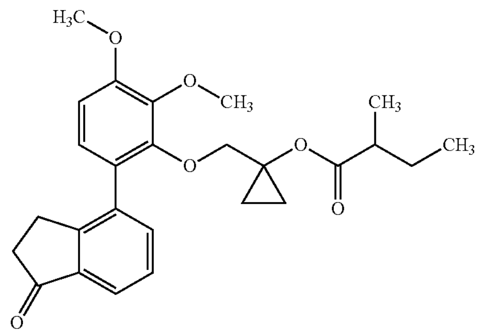 [SMILES: CCC(C)C(=O)OC1(COc2c(-c3cccc4c3CCC4=O)ccc(OC)c2OC)CC1] | [1-[[2,3-dimethoxy-6-(1-oxoindan-4-yl)phenoxy]methyl]cyclopropyl] 2-methylbutanoate |
| 870 | 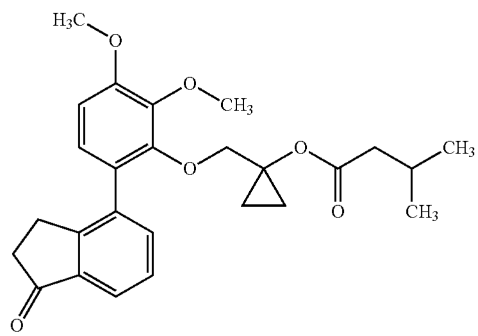 [SMILES: COc1ccc(-c2cccc3c2CCC3=O)c(OCC2(OC(=O)CC(C)C)CC2)c1OC] | [1-[[2,3-dimethoxy-6-(1-oxoindan-4-yl)phenoxy]methyl]cyclopropyl] 3-methylbutanoate |
| 871 | 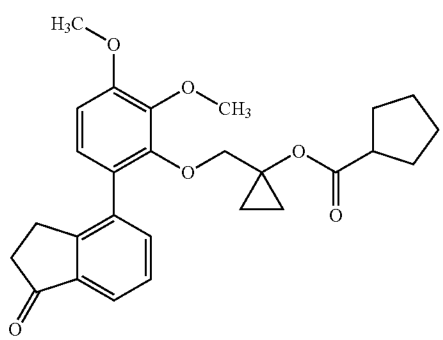 [SMILES: COc1ccc(-c2cccc3c2CCC3=O)c(OCC2(OC(=O)C3CCCC3)CC2)c1OC] | [1-[[2,3-dimethoxy-6-(1-oxoindan-4-yl)phenoxy]methyl]cyclopropyl] cyclopentanecarboxylate |
| 872 | 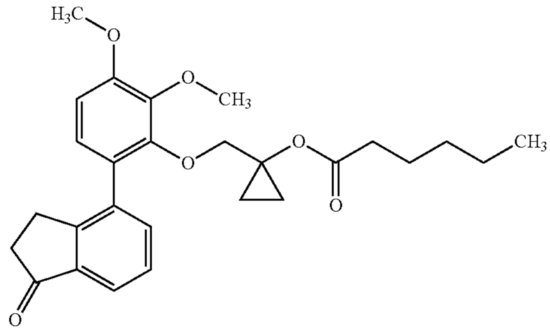 [SMILES: CCCCCC(=O)OC1(COc2c(-c3cccc4c3CCC4=O)ccc(OC)c2OC)CC1] | [1-[[2,3-dimethoxy-6-(1-oxoindan-4-yl)phenoxy]methyl]cyclopropyl] hexanoate |

-continued

| Compound | Structure | Compound name |
|---|---|---|
| 873 | 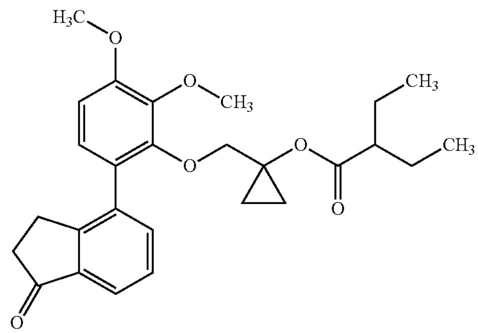 [SMILES: CCC(CC)C(=O)OC1(COc2c(-c3cccc4c3CCC4=O)ccc(OC)c2OC)CC1] | [1-[[2,3-dimethoxy-6-(1-oxoindan-4-yl)phenoxy]methyl]cyclopropyl] 2-ethylbutanoate |
| 874 | 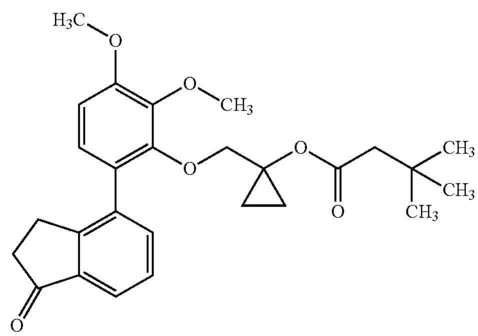 [SMILES: COc1ccc(-c2cccc3c2CCC3=O)c(OCC2(OC(=O)CC(C)(C)C)CC2)c1OC] | [1-[[2,3-dimethoxy-6-(1-oxoindan-4-yl)phenoxy]methyl]cyclopropyl] 3,3-dimethylbutanoate |
| 875 | 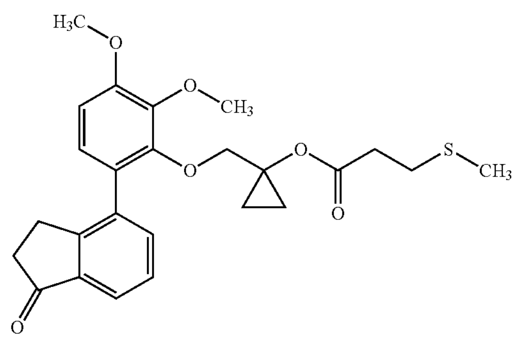 [SMILES: COc1ccc(-c2cccc3c2CCC3=O)c(OCC2(OC(=O)CCSC)CC2)c1OC] | [1-[[2,3-dimethoxy-6-(1-oxoindan-4-yl)phenoxy]methyl]cyclopropyl] 3-methylsulfanylpropanoate |
| 876 | 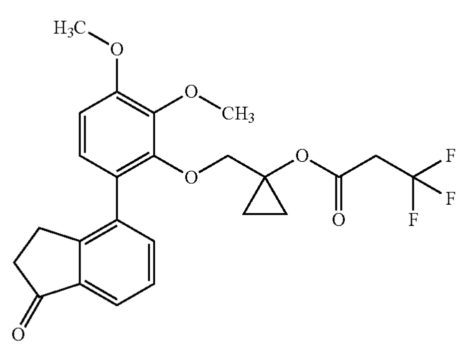 [SMILES: COc1ccc(-c2cccc3c2CCC3=O)c(OCC2(OC(=O)CC(F)(F)F)CC2)c1OC] | [1-[[2,3-dimethoxy-6-(1-oxoindan-4-yl)phenoxy]methyl]cyclopropyl] 3,3,3-trifluoropropanoate |

-continued

| Compound | Structure | Compound name |
|---|---|---|
| 877 | 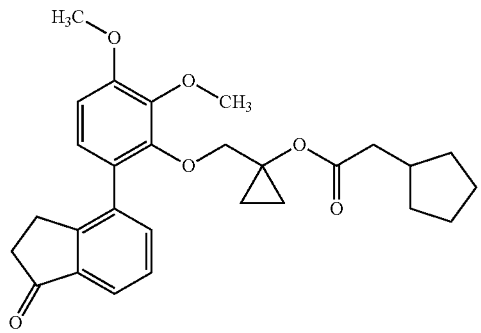 [SMILES: COc1ccc(-c2cccc3c2CCC3=O)c(OCC2(OC(=O)CC3CCCC3)CC2)c1OC] | [1-[[2,3-dimethoxy-6-(1-oxoindan-4-yl)phenoxy]methyl]cyclopropyl] 2-cyclopentylacetate |
| 878 | 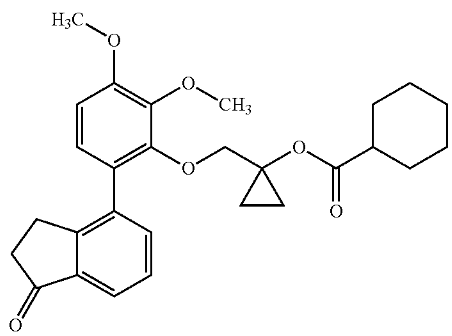 [SMILES: COc1ccc(-c2cccc3c2CCC3=O)c(OCC2(OC(=O)C3CCCCC3)CC2)c1OC] | [1-[[2,3-dimethoxy-6-(1-oxoindan-4-yl)phenoxy]methyl]cyclopropyl] cyclohexanecarboxylate |
| 879 | 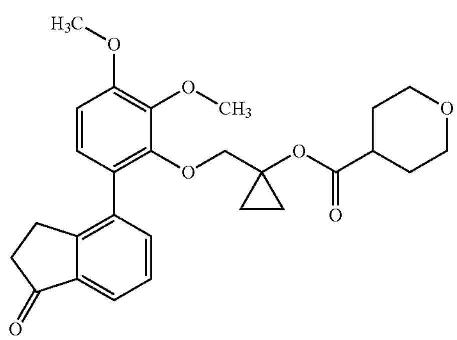 [SMILES: COc1ccc(-c2cccc3c2CCC3=O)c(OCC2(OC(=O)C3CCOCC3)CC2)c1OC] | [1-[[2,3-dimethoxy-6-(1-oxoindan-4-yl)phenoxy]methyl]cyclopropyl] tetrahydropyran-4-carboxylate |
| 880 | 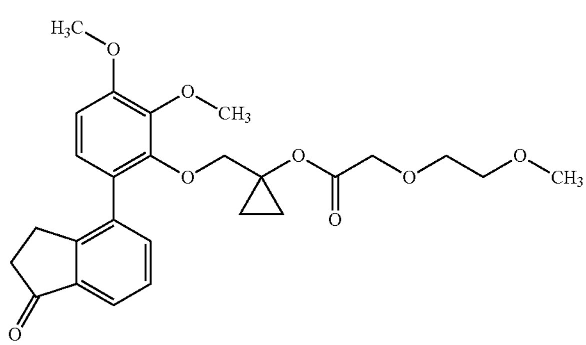 [SMILES: COCCOCC(=O)OC1(COc2c(-c3cccc4c3CCC4=O)ccc(OC)c2OC)CC1] | [1-[[2,3-dimethoxy-6-(1-oxoindan-4-yl)phenoxy]methyl]cyclopropyl] 2-(2-methoxyethoxy)acetate |

| Compound | Structure | Compound name |
|---|---|---|
| 881 | 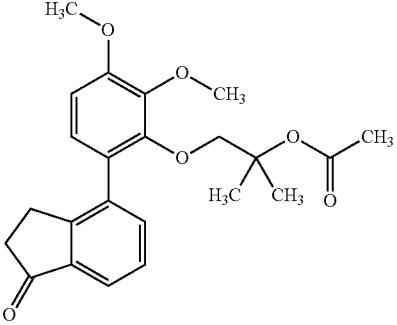 [SMILES: COc1ccc(-c2cccc3c2CCC3=O)c(OCC(C)(C)OC(C)=O)c1OC] | [2-[2,3-dimethoxy-6-(1-oxoindan-4-yl)phenoxy]-1,1-dimethyl-ethyl] acetate |
| 882 | 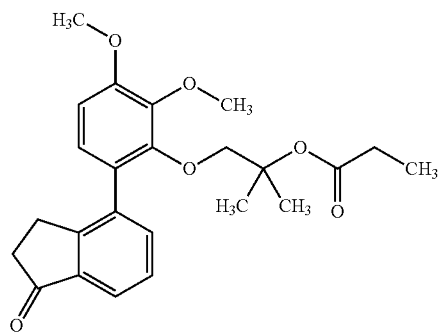 [SMILES: CCC(=O)OC(C)(C)COc1c(-c2cccc3c2CCC3=O)ccc(OC)c1OC] | [2-[2,3-dimethoxy-6-(1-oxoindan-4-yl)phenoxy]-1,1-dimethyl-ethyl] propanoate |
| 883 | 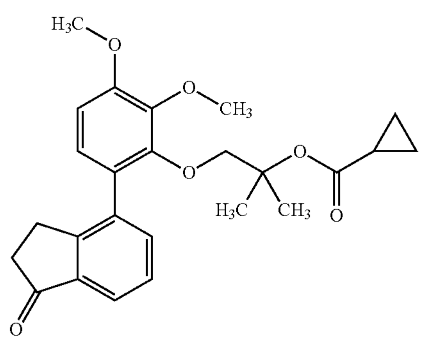 [SMILES: COc1ccc(-c2cccc3c2CCC3=O)c(OCC(C)(C)OC(=O)C2CC2)c1OC] | [2-[2,3-dimethoxy-6-(1-oxoindan-4-yl)phenoxy]-1,1-dimethyl-ethyl] cyclopropanecarboxylate |
| 884 | 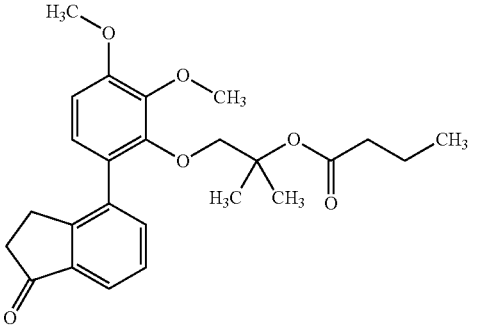 [SMILES: CCCC(=O)OC(C)(C)COc1c(-c2cccc3c2CCC3=O)ccc(OC)c1OC] | [2-[2,3-dimethoxy-6-(1-oxoindan-4-yl)phenoxy]-1,1-dimethyl-ethyl] butanoate |

-continued

| Compound | Structure | Compound name |
|---|---|---|
| 885 | 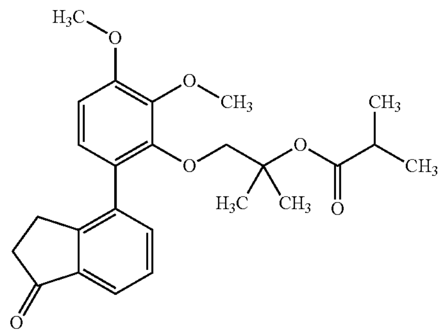 [SMILES: COc1ccc(-c2cccc3c2CCC3=O)c(OCC(C)(C)OC(=O)C(C)C)c1OC] | [2-[2,3-dimethoxy-6-(1-oxoindan-4-yl)phenoxy]-1,1-dimethyl-ethyl] 2-methylpropanoate |
| 886 | 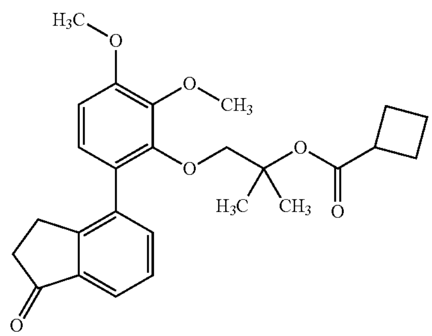 [SMILES: COc1ccc(-c2cccc3c2CCC3=O)c(OCC(C)(C)OC(=O)C2CCC2)c1OC] | [2-[2,3-dimethoxy-6-(1-oxoindan-4-yl)phenoxy]-1,1-dimethyl-ethyl] 2-cyclobutanecarboxylate |
| 887 | 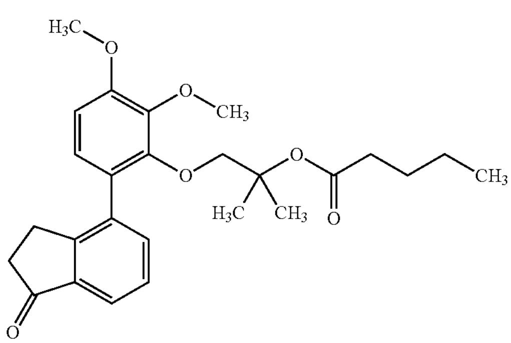 [SMILES: CCCCC(=O)OC(C)(C)COc1c(-c2cccc3c2CCC3=O)ccc(OC)c1OC] | [2-[2,3-dimethoxy-6-(1-oxoindan-4-yl)phenoxy]-1,1-dimethyl-ethyl] pentanoate |
| 888 | 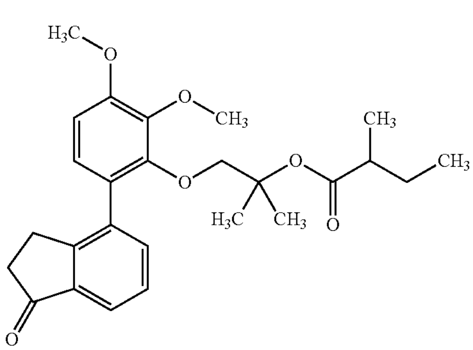 [SMILES: CCC(C)C(=O)OC(C)(C)COc1c(-c2cccc3c2CCC3=O)ccc(OC)c1OC] | [2-[2,3-dimethoxy-6-(1-oxoindan-4-yl)phenoxy]-1,1-dimethyl-ethyl] 2-methylbutanoate |

-continued

| Compound | Structure | Compound name |
|---|---|---|
| 889 | 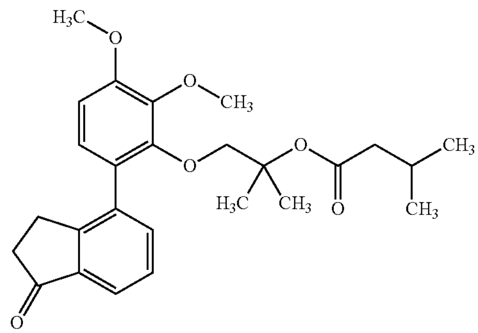 [SMILES: COc1ccc(-c2cccc3c2CCC3=O)c(OCC(C)(C)OC(=O)CC(C)C)c1OC] | [2-[2,3-dimethoxy-6-(1-oxoindan-4-yl)phenoxy]-1,1-dimethyl-ethyl] 3-methylbutanoate |
| 890 | 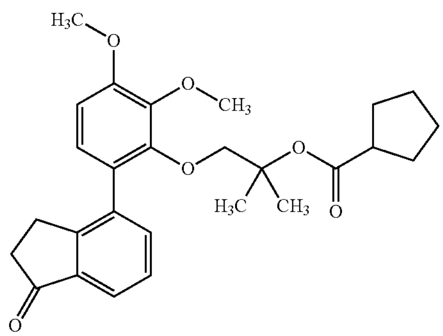 [SMILES: COc1ccc(-c2cccc3c2CCC3=O)c(OCC(C)(C)OC(=O)C2CCCC2)c1OC] | [2-[2,3-dimethoxy-6-(1-oxoindan-4-yl)phenoxy]-1,1-dimethyl-ethyl] cyclopropanecarboxylate |
| 891 | 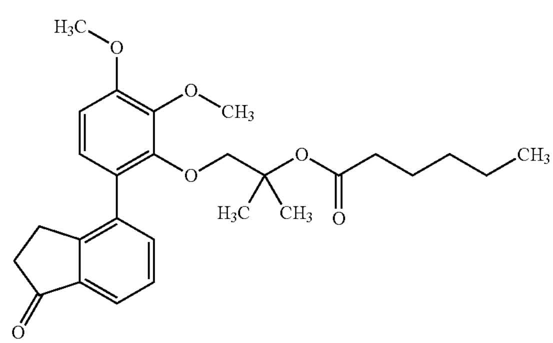 [SMILES: CCCCCC(=O)OC(C)(C)COc1c(-c2cccc3c2CCC3=O)ccc(OC)c1OC] | [2-[2,3-dimethoxy-6-(1-oxoindan-4-yl)phenoxy]-1,1-dimethyl-ethyl] hexanoate |
| 892 | 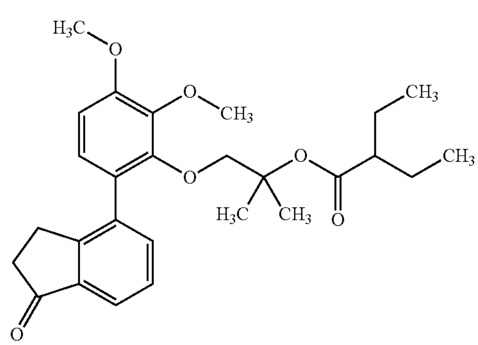 [SMILES: CCC(CC)C(=O)OC(C)(C)COc1c(-c2cccc3c2CCC3=O)ccc(OC)c1OC] | [2-[2,3-dimethoxy-6-(1-oxoindan-4-yl)phenoxy]-1,1-dimethyl-ethyl] 2-ethylbutanoate |

-continued

| Compound | Structure | Compound name |
| --- | --- | --- |
| 893 | 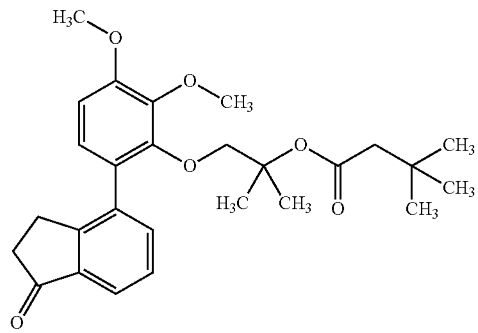 [SMILES: COc1ccc(-c2cccc3c2CCC3=O)c(OCC(C)(C)OC(=O)CC(C)(C)C)c1OC] | [2-[2,3-dimethoxy-6-(1-oxoindan-4-yl)phenoxy]-1,1-dimethyl-ethyl] 3,3-dimethylbutanoate |
| 894 | | [2-[2,3-dimethoxy-6-(1-oxoindan-4-yl)phenoxy]-1,1-dimethyl-ethyl] 3-methylsulfanylpropanoate |
| 894 | | [2-[2,3-dimethoxy-6-(1-oxoindan-4-yl)phenoxy]-1,1-dimethyl-ethyl] 3,3,3-trifluoropropanoate |
| 896 | 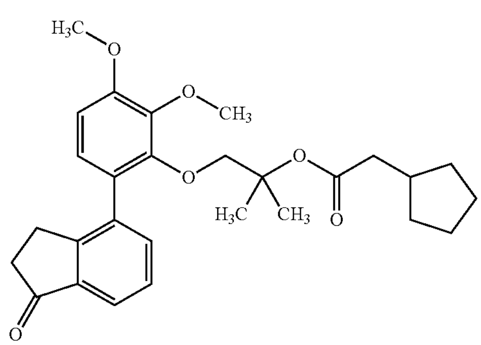 [SMILES: COc1ccc(-c2cccc3c2CCC3=O)c(OCC(C)(C)OC(=O)CC2CCCC2)c1OC] | [2-[2,3-dimethoxy-6-(1-oxoindan-4-yl)phenoxy]-1,1-dimethyl-ethyl] 2-cyclopentylacetate |

| Compound | Structure | Compound name |
|---|---|---|
| 897 | 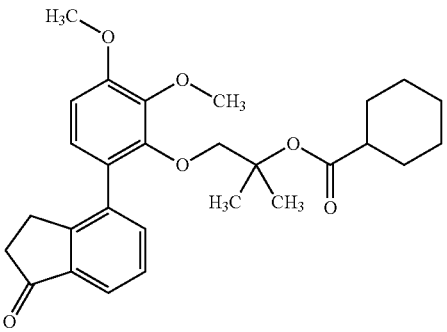 [SMILES: COc1ccc(-c2cccc3c2CCC3=O)c(OCC(C)(C)OC(=O)C2CCCCC2)c1OC] | [2-[2,3-dimethoxy-6-(1-oxoindan-4-yl)phenoxy]-1,1-dimethyl-ethyl] cyclohexanecarboxylate |
| 898 | 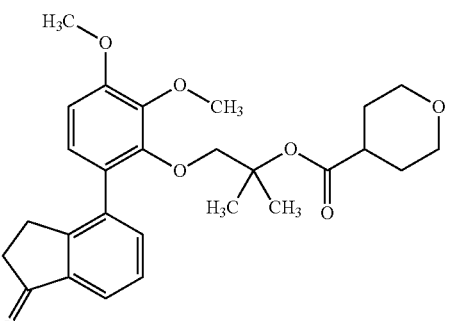 | [2-[2,3-dimethoxy-6-(1-oxoindan-4-yl)phenoxy]-1,1-dimethyl-ethyl] tetrahydropyran-4-carboxylate |
| 899 | 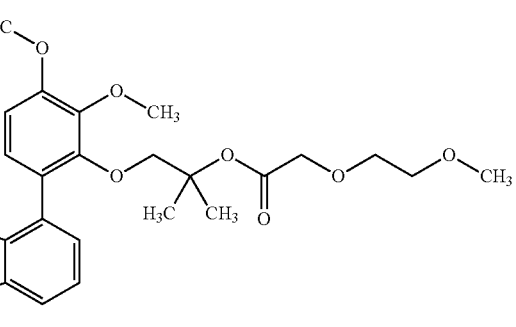 | [2-[2,3-dimethoxy-6-(1-oxoindan-4-yl)phenoxy]-1,1-dimethyl-ethyl] 2-(2-methoxyethoxy)acetate |
| 900 | 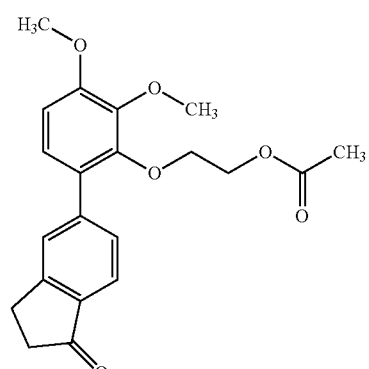 | 2-[2,3-dimethoxy-6-(1-oxoindan-5-yl)phenoxy]ethyl acetate |

-continued

| Compound | Structure | Compound name |
|---|---|---|
| 901 | 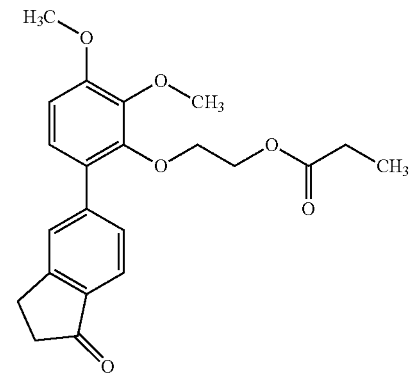 [SMILES: CCC(=O)OCCOc1c(-c2ccc3c(c2)CCC3=O)ccc(OC)c1OC] | 2-[2,3-dimethoxy-6-(1-oxoidan-5-yl)phenoxy]ethyl propanoate |
| 902 | 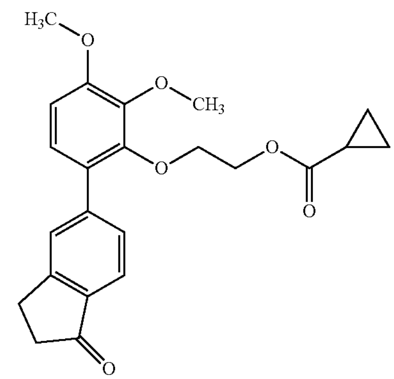 [SMILES: COc1ccc(-c2ccc3c(c2)CCC3=O)c(OCCOC(=O)C2CC2)c1OC] | 2-[2,3-dimethoxy-6-(1-oxoindan-5-yl)phenoxy]ethyl cyclopropanecarboxylate |
| 903 | 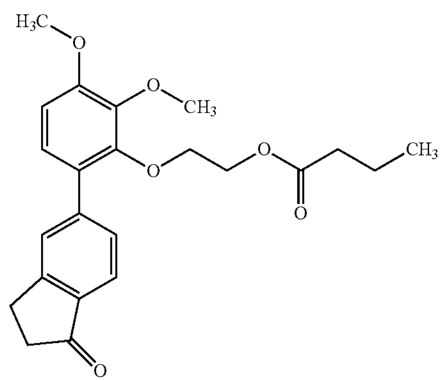 [SMILES: CCCC(=O)OCCOc1c(-c2ccc3c(c2)CCC3=O)ccc(OC)c1OC] | 2-[2,3-dimethoxy-6-(1-oxoindan-5-yl)phenoxy]ethyl butanoate |
| 904 | 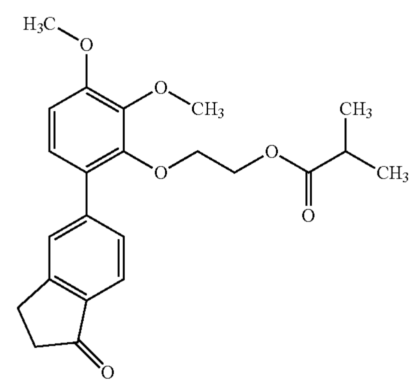 [SMILES: COc1ccc(-c2ccc3c(c2)CCC3=O)c(OCCOC(=O)C(C)C)c1OC] | 2-[2,3-dimethoxy-6-(1-oxoindan-5-yl)phenoxy]ethyl 2-methylpropanoate |

-continued
| Compound | Structure | Compound name |
|---|---|---|
| 905 | 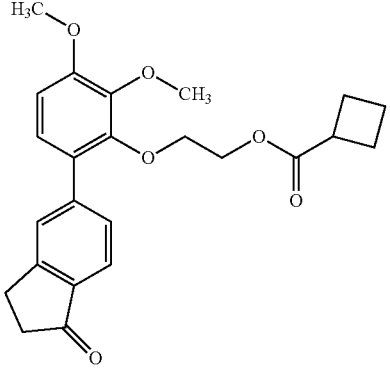 [SMILES: COc1ccc(-c2ccc3c(c2)CCC3=O)c(OCCOC(=O)C2CCC2)c1OC] | 2-[2,3-dimethoxy-6-(1-oxoindan-5-yl)phenoxy]ethyl cyclobutanecarboxylate |
| 906 | 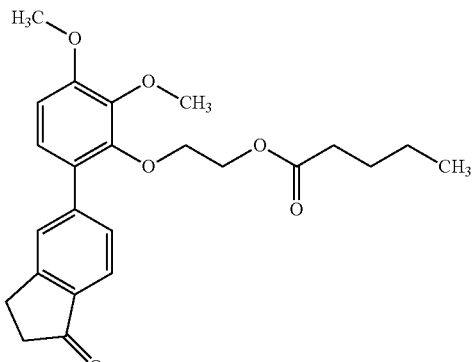 | 2-[2,3-dimethoxy-6-(1-oxoindan-5-yl)phenoxy]ethyl pentanoate |
| 907 | 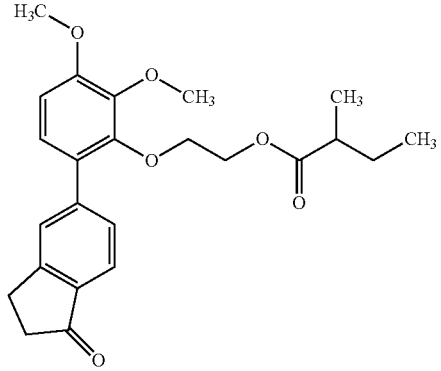 [SMILES: CCC(C)C(=O)OCCOc1c(-c2ccc3c(c2)CCC3=O)ccc(OC)c1OC] | 2-[2,3-dimethoxy-6-(1-oxoindan-5-yl)phenoxy]ethyl 2-methylbutanoate |
| 908 | 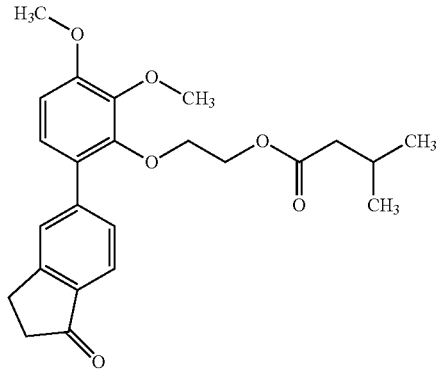 [SMILES: COc1ccc(-c2ccc3c(c2)CCC3=O)c(OCCOC(=O)CC(C)C)c1OC] | 2-[2,3-dimethoxy-6-(1-oxoindan-5-yl)phenoxy]ethyl 3-methylbutanoate |

| Compound | Structure | Compound name |
| --- | --- | --- |
| 909 | 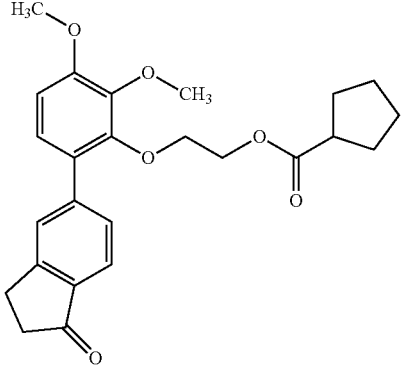 [SMILES: COc1ccc(-c2ccc3c(c2)CCC3=O)c(OCCOC(=O)C2CCCC2)c1OC] | 2-[2,3-dimethoxy-6-(1-oxoindan-5-yl)phenoxy]ethyl cyclopentanecarboxylate |
| 910 | 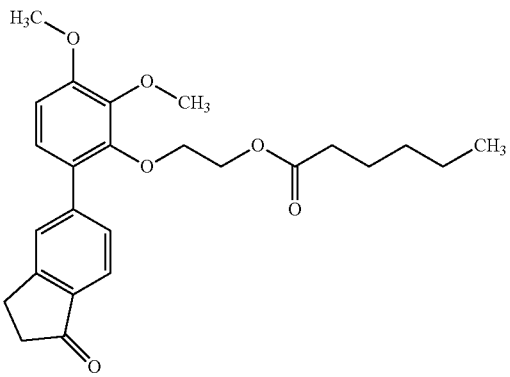 [SMILES: CCCCCC(=O)OCCOc1c(-c2ccc3c(c2)CCC3=O)ccc(OC)c1OC] | 2-[2,3-dimethoxy-6-(1-oxoindan-5-yl)phenoxy]ethyl hexanoate |
| 911 | 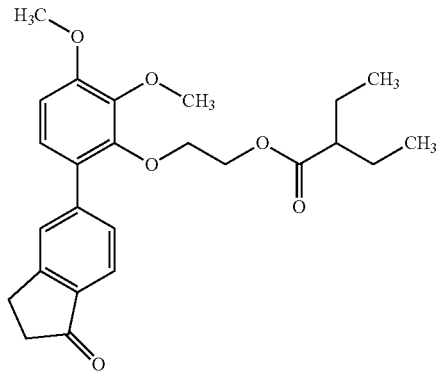 [SMILES: CCC(CC)C(=O)OCCOc1c(-c2ccc3c(c2)CCC3=O)ccc(OC)c1OC] | 2-[2,3-dimethoxy-6-(1-oxoindan-5-yl)phenoxy]ethyl 2-ethylbutanoate |
| 912 | 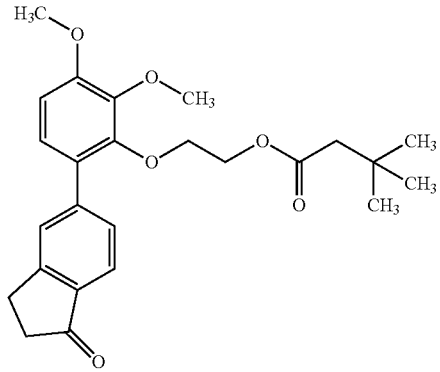 [SMILES: COc1ccc(-c2ccc3c(c2)CCC3=O)c(OCCOC(=O)CC(C)(C)C)c1OC] | 2-[2,3-dimethoxy-6-(1-oxoindan-5-yl)phenoxy]ethyl 3,3-dimethylbutanoate |

-continued

| Compound | Structure | Compound name |
|---|---|---|
| 913 | 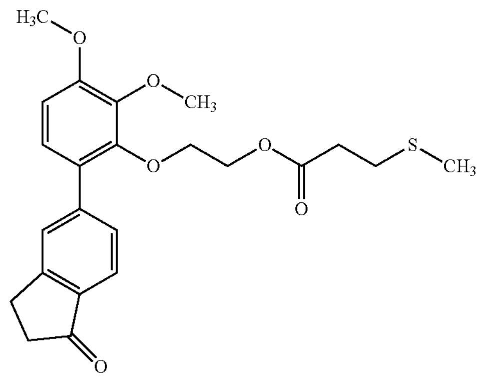 [SMILES: COc1ccc(-c2ccc3c(c2)CCC3=O)c(OCCOC(=O)CCSC)c1OC] | 2-[2,3-dimethoxy-6-(1-oxoindan-5-yl)phenoxy]ethyl 3-methylsulfanylpropanoate |
| 914 | 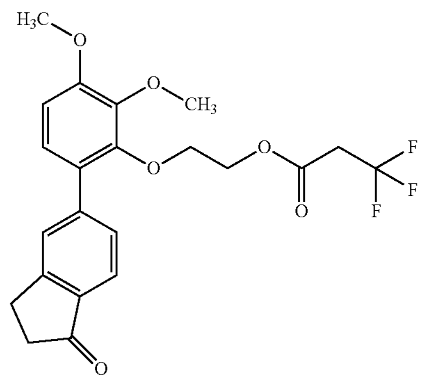 [SMILES: COc1ccc(-c2ccc3c(c2)CCC3=O)c(OCCOC(=O)CC(F)(F)F)c1OC] | 2-[2,3-dimethoxy-6-(1-oxoindan-5-yl)phenoxy]ethyl 3,3,3-trifluoropropanoate |
| 915 | 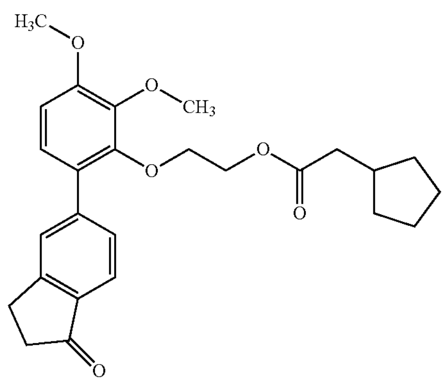 [SMILES: COc1ccc(-c2ccc3c(c2)CCC3=O)c(OCCOC(=O)CC2CCCC2)c1OC] | 2-[2,3-dimethoxy-6-(1-oxoindan-5-yl)phenoxy]ethyl 2-cyclopentylacetate |
| 916 | 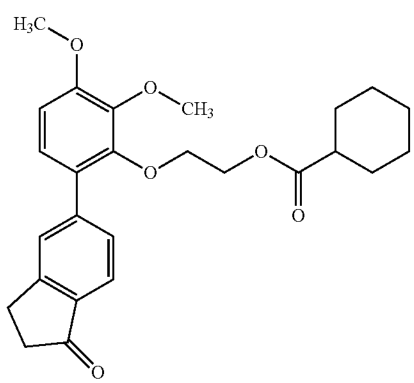 [SMILES: COc1ccc(-c2ccc3c(c2)CCC3=O)c(OCCOC(=O)C2CCCCC2)c1OC] | 2-[2,3-dimethoxy-6-(1-oxoindan-5-yl)phenoxy]ethyl cyclohexanecarboxylate |

| Compound | Structure | Compound name |
|---|---|---|
| 917 | 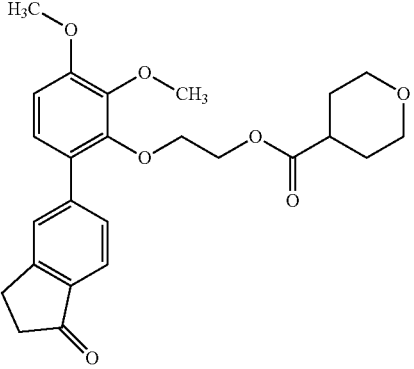 | 2-[2,3-dimethoxy-6-(1-oxoindan-5-yl)phenoxy]ethyl tetrahydrofuran-4-carboxylate |
| 918 | 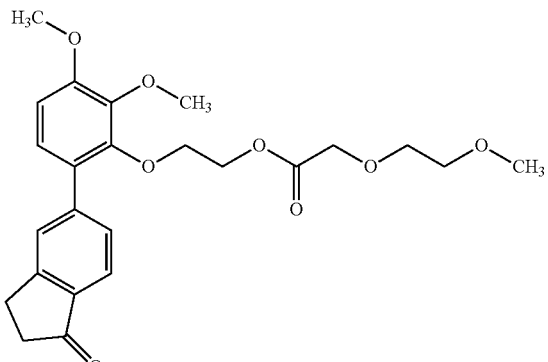 | 2-[2,3-dimethoxy-6-(1-oxoidan-5-yl)phenoxy]ethyl 2-(2-methoxyethoxy)acetate |
| 919 | 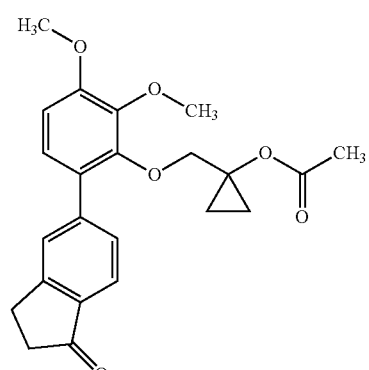 | [1-[[2,3-dimethoxy-6-(1-oxoindan-5-yl)phenoxy]methyl]cyclopropyl] acetate |
| 920 | 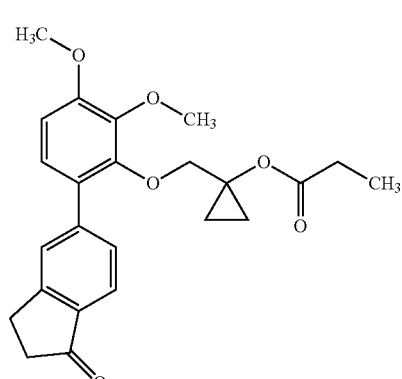 | [1-[[2,3-dimethoxy-6-(1-oxoindan-5-yl)phenoxy]methyl]cyclopropyl] propanoate |

| Compound | Structure | Compound name |
|---|---|---|
| 921 | 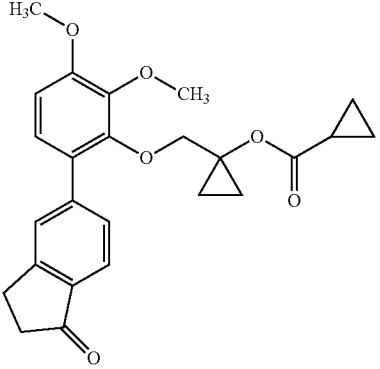 [SMILES: COc1ccc(-c2ccc3c(c2)CCC3=O)c(OCC2(OC(=O)C3CC3)CC2)c1OC] | [1-[[2,3-dimethoxy-6-(1-oxoindan-5-yl)phenoxy]methyl]cyclopropyl] cyclopropanecarboxylate |
| 922 | 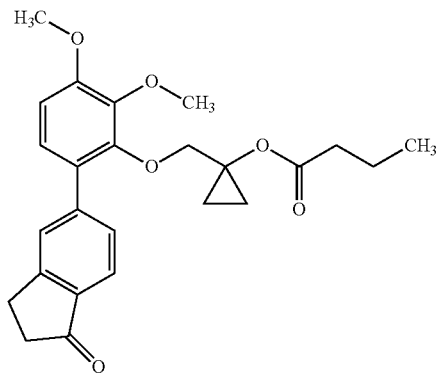 [SMILES: CCCC(=O)OC1(COc2c(-c3ccc4c(c3)CCC4=O)ccc(OC)c2OC)CC1] | [1-[[2,3-dimethoxy-6-(1-oxoindan-5-yl)phenoxy]methyl]cyclopropyl] butanoate |
| 923 | 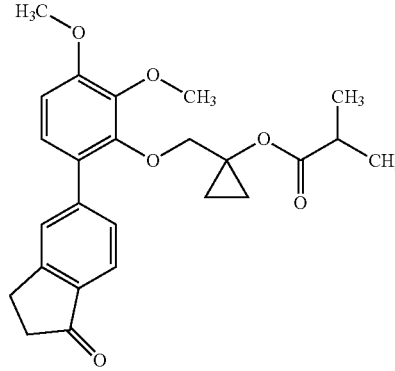 | [1-[[2,3-dimethoxy-6-(1-oxoindan-5-yl)phenoxy]methyl]cyclopropyl] 2-methylpropanoate |
| 924 | 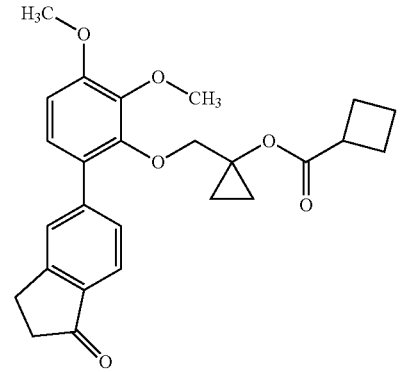 [SMILES: COc1ccc(-c2ccc3c(c2)CCC3=O)c(OCC2(OC(=O)C3CCC3)CC2)c1OC] | [1-[[2,3-dimethoxy-6-(1-oxoindan-5-yl)phenoxy]methyl]cyclopropyl] cyclobutanecarboxylate |

-continued

| Compound | Structure | Compound name |
|---|---|---|
| 925 | 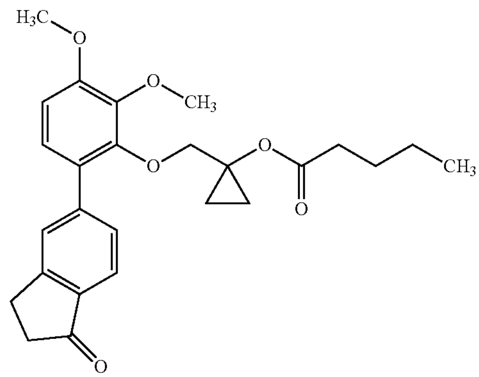 [SMILES: CCCCC(=O)OC1(COc2c(-c3ccc4c(c3)CCC4=O)ccc(OC)c2OC)CC1] | [1-[[2,3-dimethoxy-6-(1-oxoindan-5-yl)phenoxy]methyl]cyclopropyl] pentanoate |
| 926 | 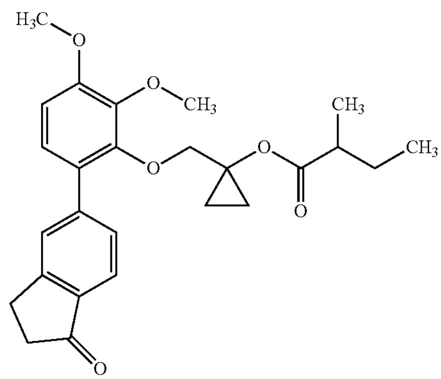 [SMILES: CCC(C)C(=O)OC1(COc2c(-c3ccc4c(c3)CCC4=O)ccc(OC)c2OC)CC1] | [1-[[2,3-dimethoxy-6-(1-oxoindan-5-yl)phenoxy]methyl]cyclopropyl] 2-methylbutanoate |
| 927 | 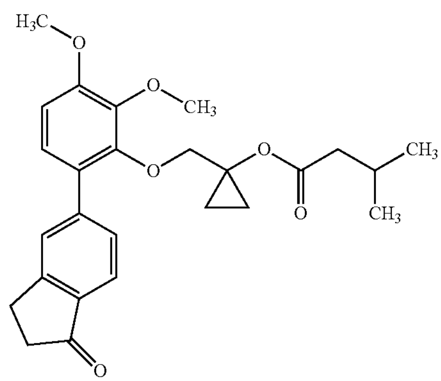 [SMILES: COc1ccc(-c2ccc3c(c2)CCC3=O)c(OCC2(OC(=O)CC(C)C)CC2)c1OC] | [1-[[2,3-dimethoxy-6-(1-oxoindan-5-yl)phenoxy]methyl]cyclopropyl] 3-methylbutanoate |
| 928 | 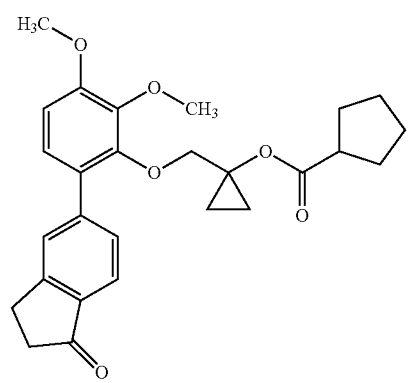 [SMILES: COc1ccc(-c2ccc3c(c2)CCC3=O)c(OCC2(OC(=O)C3CCCC3)CC2)c1OC] | [1-[[2,3-dimethoxy-6-(1-oxoindan-5-yl)phenoxy]methyl]cyclopropyl] cyclopentanecarboxylate |

-continued

| Compound | Structure | Compound name |
|---|---|---|
| 929 | 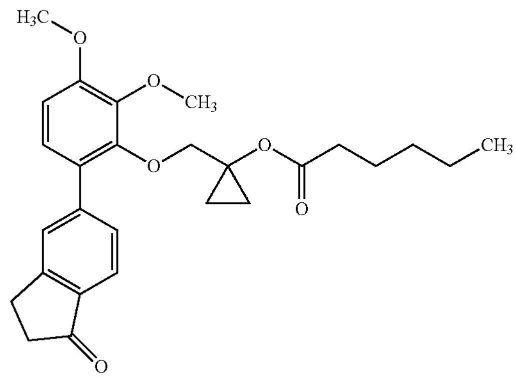 [SMILES: CCCCCC(=O)OC1(COc2c(-c3ccc4c(c3)CCC4=O)ccc(OC)c2OC)CC1] | [1-[[2,3-dimethoxy-6-(1-oxoindan-5-yl)phenoxy]methyl]cyclopropyl] hexanoate |
| 930 | 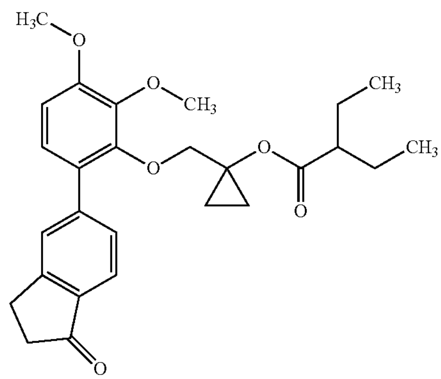 [SMILES: CCC(CC)C(=O)OC1(COc2c(-c3ccc4c(c3)CCC4=O)ccc(OC)c2OC)CC1] | [1-[[2,3-dimethoxy-6-(1-oxoindan-5-yl)phenoxy]methyl]cyclopropyl] 2-ethylbutanoate |
| 931 | 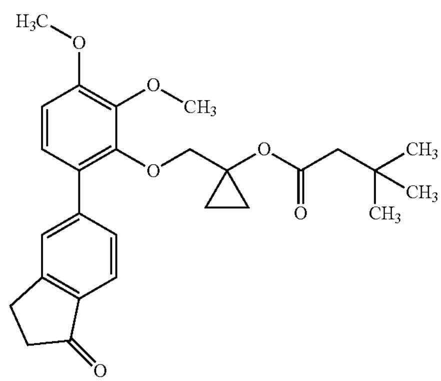 [SMILES: COc1ccc(-c2ccc3c(c2)CCC3=O)c(OCC2(OC(=O)CC(C)(C)C)CC2)c1OC] | [1-[[2,3-dimethoxy-6-(1-oxoindan-5-yl)phenoxy]methyl]cyclopropyl] 3,3-dimethylbutanoate |
| 932 | 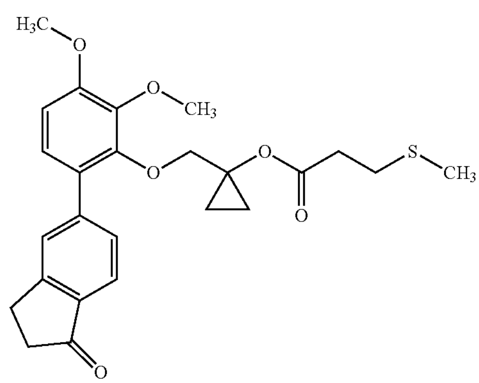 [SMILES: COc1ccc(-c2ccc3c(c2)CCC3=O)c(OCC2(OC(=O)CCSC)CC2)c1OC] | [1-[[2,3-dimethoxy-6-(1-oxoindan-5-yl)phenoxy]methyl]cyclopropyl]-3-methylsulfanylpropanoate |

| Compound | Structure | Compound name |
|---|---|---|
| 933 | 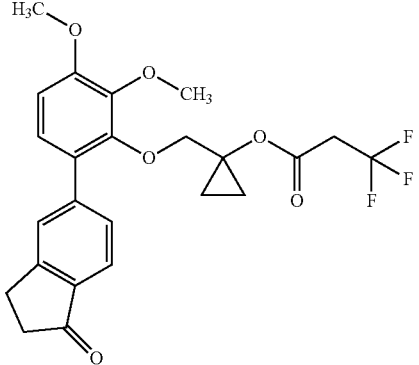 [SMILES: COc1ccc(-c2ccc3c(c2)CCC3=O)c(OCC2(OC(=O)CC(F)(F)F)CC2)c1OC] | [1-[[2,3-dimethoxy-6-(1-oxoindan-5-yl)phenoxy]methyl]cyclopropyl] 3,3,3-trifluoropropanoate |
| 934 | 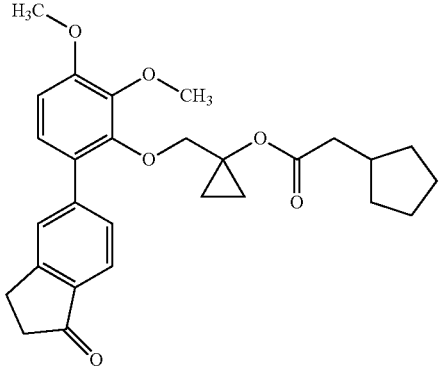 [SMILES: COc1ccc(-c2ccc3c(c2)CCC3=O)c(OCC2(OC(=O)CC3CCCC3)CC2)c1OC] | [1-[[2,3-dimethoxy-6-(1-oxoindan-5-yl)phenoxy]methyl]cyclopropyl] 2-cyclopentylacetate |
| 935 | 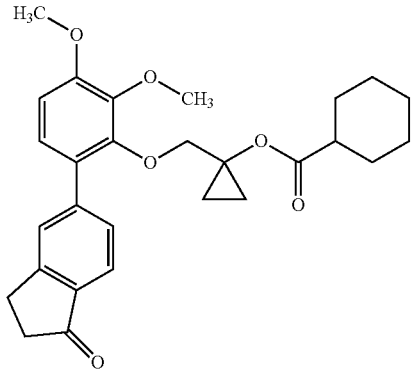 [SMILES: COc1ccc(-c2ccc3c(c2)CCC3=O)c(OCC2(OC(=O)C3CCCCC3)CC2)c1OC] | [1-[[2,3-dimethoxy-6-(1-oxoindan-5-yl)phenoxy]methyl]cyclopropyl] cyclohexanecarboxylate |
| 936 | 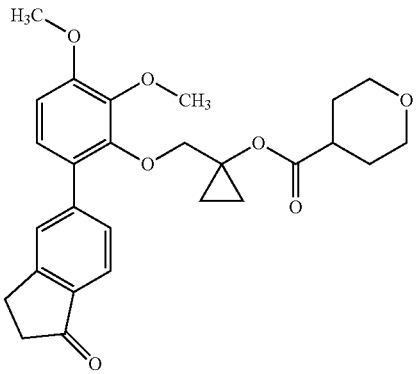 | [1-[[2,3-dimethoxy-6-(1-oxoindan-5-yl)phenoxy]methyl]cyclopropyl] tetrahydropyran-4-carboxylate |

| Compound | Structure | Compound name |
|---|---|---|
| 937 | 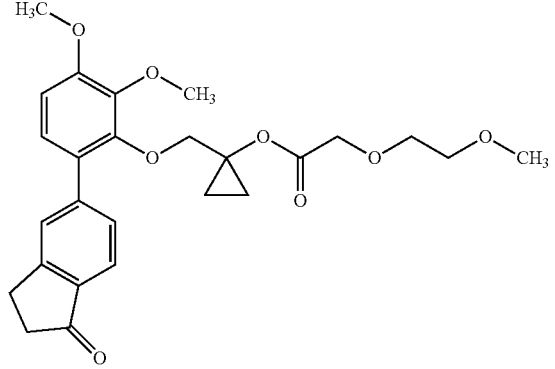 [SMILES: COCCOCC(=O)OC1(COc2c(-c3ccc4c(c3)CCC4=O)ccc(OC)c2OC)CC1] | [1-[[2,3-dimethoxy-6-(1-oxoindan-5-yl)phenoxy]methyl]cyclopropyl] 2-(2-methoxyethoxy)acetate |
| 938 | 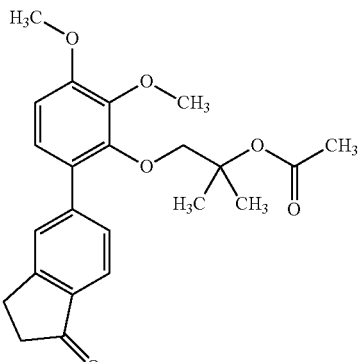 | [2-[2,3-dimethoxy-6-(1-oxoindan-5-yl)phenoxy]-1,1-dimethyl-ethyl] acetate |
| 939 | 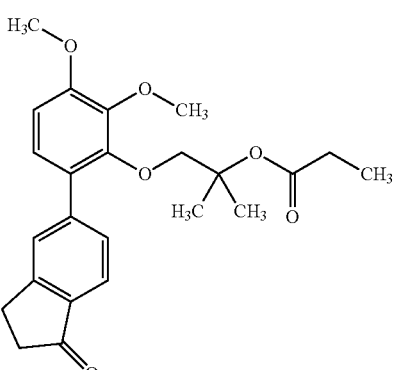 | [2-[2,3-dimethoxy-6-(1-oxoindan-5-yl)phenoxy]-1,1-dimethyl-ethyl] propanoate |
| 940 | 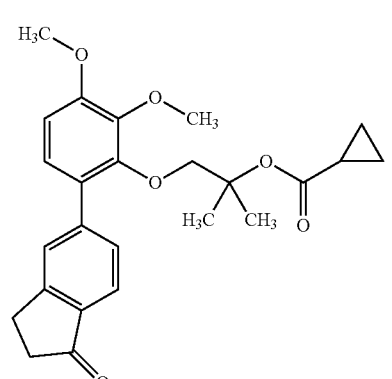 | [2-[2,3-dimethoxy-6-(1-oxoindan-5-yl)phenoxy]-1,1-dimethyl-ethyl] cyclopropanecarboxylate |

| Compound | Structure | Compound name |
|---|---|---|
| 941 | 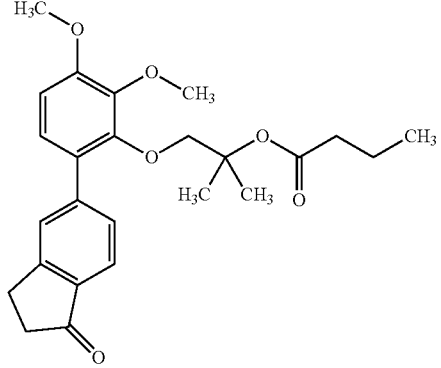 | [2-[2,3-dimethoxy-6-(1-oxoindan-5-yl)phenoxy]-1,1-dimethyl-ethyl] butanoate |
| 942 | 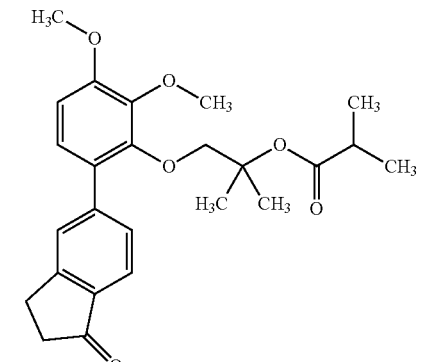 | [2-[2,3-dimethoxy-6-(1-oxoindan-5-yl)phenoxy]-1,1-dimethyl-ethyl] 2-methylpropanoate |
| 943 | 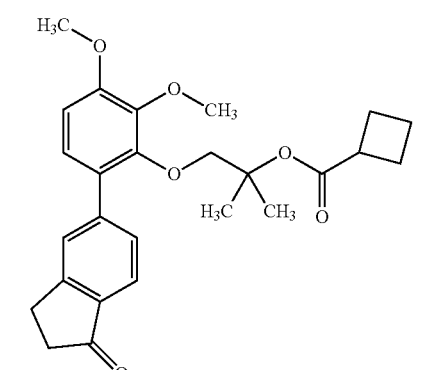 | [2-[2,3-dimethoxy-6-(1-oxoindan-5-yl)phenoxy]-1,1-dimethyl-ethyl] cyclobutanecarboxylate |
| 944 | 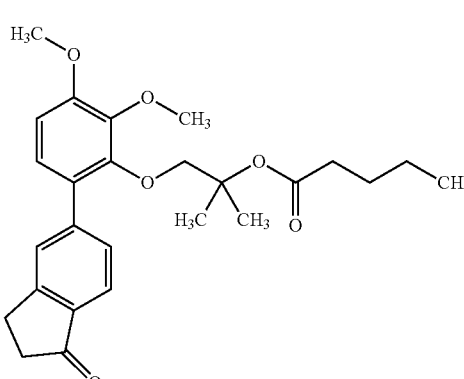 | [2-[2,3-dimethoxy-6-(1-oxoindan-5-yl)phenoxy]-1,1-dimethyl-ethyl] pentanoate |

-continued
| Compound | Structure | Compound name |
|---|---|---|
| 945 | 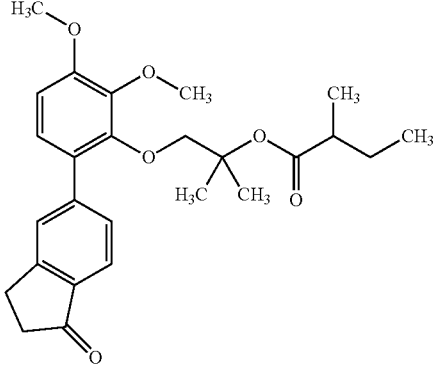 | [2-[2,3-dimethoxy-6-(1-oxoindan-5-yl)phenoxy]-1,1-dimethyl-ethyl] 2-methylbutanoate |
| 946 | 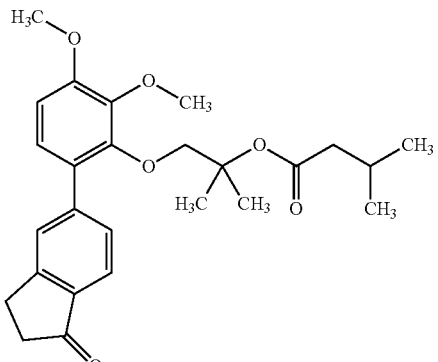 | [2-[2,3-dimethoxy-6-(1-oxoindan-5-yl)phenoxy]-1,1-dimethyl-ethyl] 3-methylbutanoate |
| 947 | 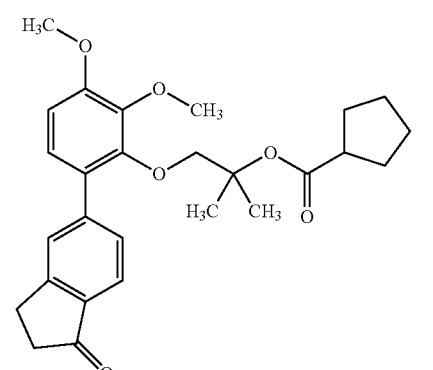 | [2-[2,3-dimethoxy-6-(1-oxoindan-5-yl)phenoxy]-1,1-dimethyl-ethyl] cyclopentanecarboxylate |
| 948 | 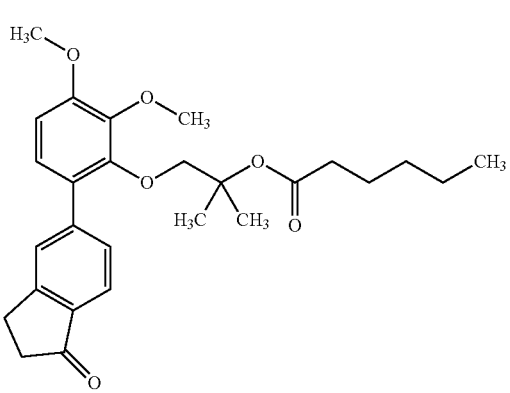 | [2-[2,3-dimethoxy-6-(1-oxoindan-5-yl)phenoxy]-1,1-dimethyl-ethyl] hexanoate |

| Compound | Structure | Compound name |
|---|---|---|
| 949 | 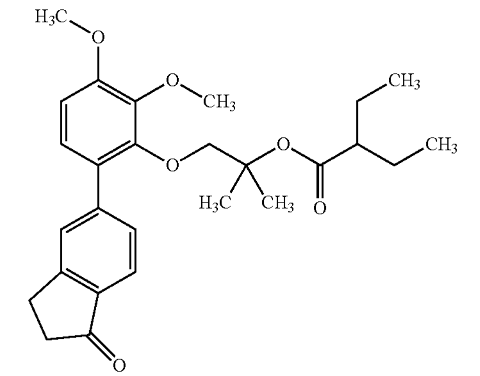 | [2-[2,3-dimethoxy-6-(1-oxoindan-5-yl)phenoxy]-1,1-dimethyl-ethyl] 2-ethylbutanoate |
| 950 | 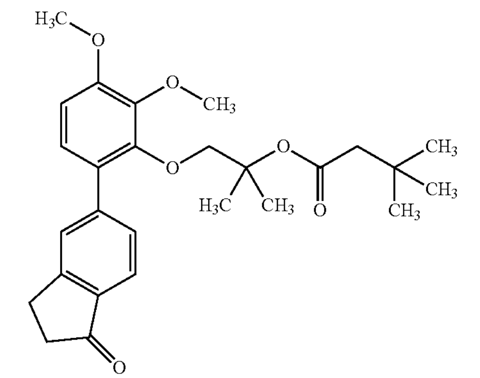 | [2-[2,3-dimethoxy-6-(1-oxoindan-5-yl)phenoxy]-1,1-dimethyl-ethyl] 3,3-dimethylbutanoate |
| 951 | 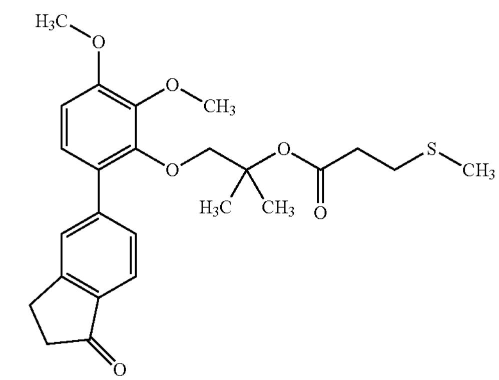 | [2-[2,3-dimethoxy-6-(1-oxoindan-5-yl)phenoxy]-1,1-dimethyl-ethyl] 3-methylsulfanylpropanoate |
| 952 | 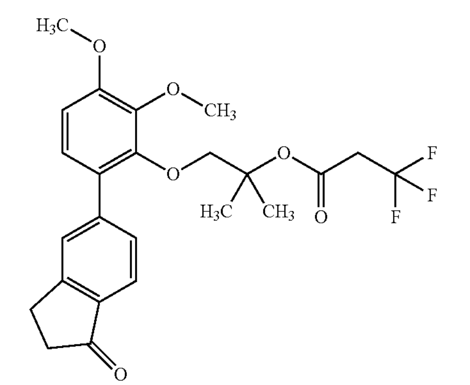 | [2-[2,3-dimethoxy-6-(1-oxoindan-5-yl)phenoxy]-1,1-dimethyl-ethyl] 3,3,3-trifluoropropanoate |

-continued
| Compound | Structure | Compound name |
|---|---|---|
| 953 | 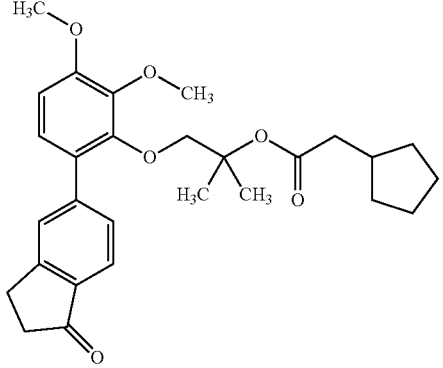 | [2-[2,3-dimethoxy-6-(1-oxoindan-5-yl)phenoxy]-1,1-dimethyl-ethyl] 2-cyclopentylacetate |
| 954 | 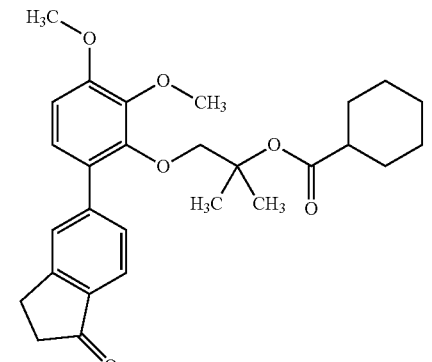 | [2-[2,3-dimethoxy-6-(1-oxoindan-5-yl)phenoxy]-1,1-dimethyl-ethyl] cyclohexanecarboxylate |
| 955 | 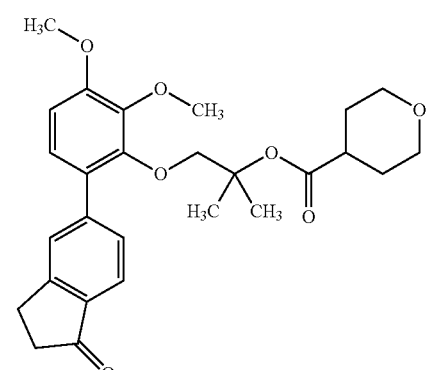 | [2-[2,3-dimethoxy-6-(1-oxoindan-5-yl)phenoxy]-1,1-dimethyl-ethyl] tetrahydropyran-4-carboxylate |
| 956 | 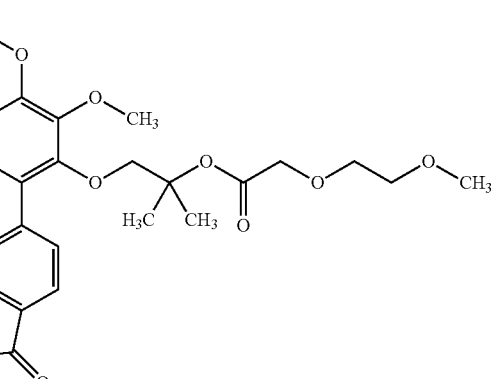 | [2-[2,3-dimethoxy-6-(1-oxoindan-5-yl)phenoxy]-1,1-dimethyl-ethyl] 2-(2-methoxyethoxy)acetate |

| Compound | Structure | Compound name |
|---|---|---|
| 957 | 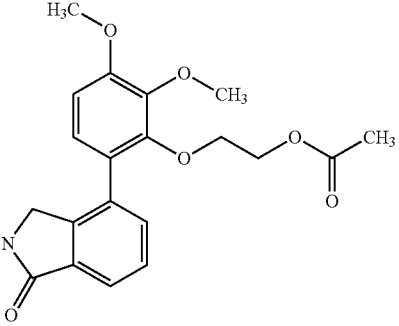 [SMILES: COc1ccc(-c2cccc3c2CNC3=O)c(OCCOC(C)=O)c1OC] | 2-[2,3-dimethoxy-6-(1-oxoisoindolin-4-yl)phenoxy]ethyl acetate |
| 958 | 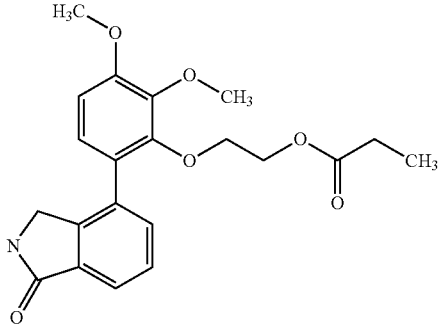 | 2-[2,3-dimethoxy-6-(1-oxoisoindolin-4-yl)phenoxy]ethyl propanoate |
| 959 | 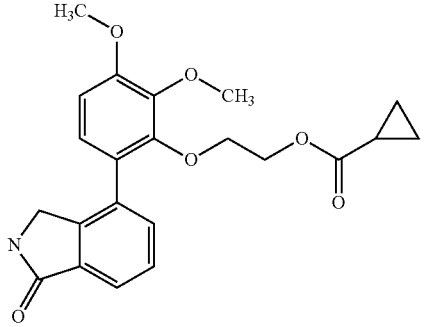 [SMILES: COc1ccc(-c2cccc3c2CNC3=O)c(OCCOC(=O)C2CC2)c1OC] | 2-[2,3-dimethoxy-6-(1-oxoisoindolin-4-yl)phenoxy]ethyl cyclopropanecarboxylate |
| 960 | 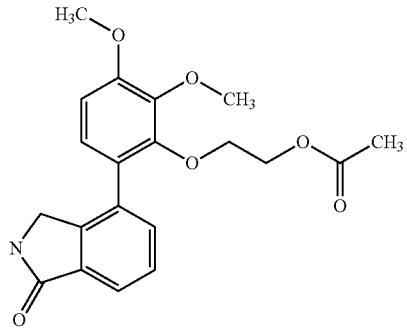 | 2-[2,3-dimethoxy-6-(1-oxoisoindolin-4-yl)phenoxy]ethyl butanoate |

-continued
| Compound | Structure | Compound name |
|---|---|---|
| 961 | 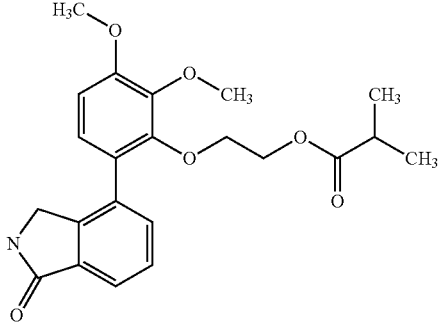 | 2-[2,3-dimethoxy-6-(1-oxoisoindolin-4-yl)phenoxy]ethyl 2-methylpropanoate |
| 962 | 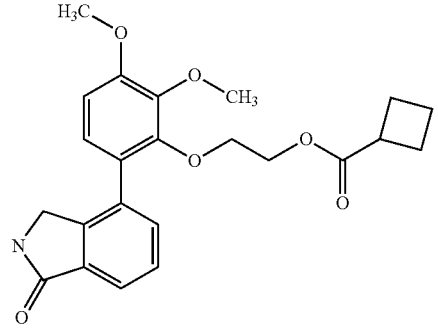 | 2-[2,3-dimethoxy-6-(1-oxoisoindolin-4-yl)phenoxy]ethyl cyclobutanecarboxylate |
| 963 | 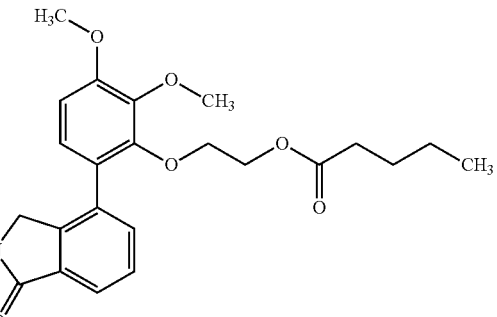 | 2-[2,3-dimethoxy-6-(1-oxoisoindolin-4-yl)phenoxy]ethyl pentanoate |
| 964 | 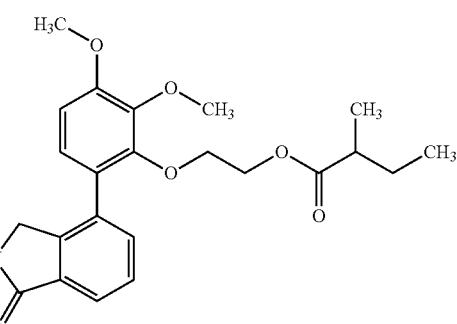 | 2-[2,3-dimethoxy-6-(1-oxoisoindolin-4-yl)phenoxy]ethyl 2-methylbutanoate |

-continued
| Compound | Structure | Compound name |
|---|---|---|
| 965 | 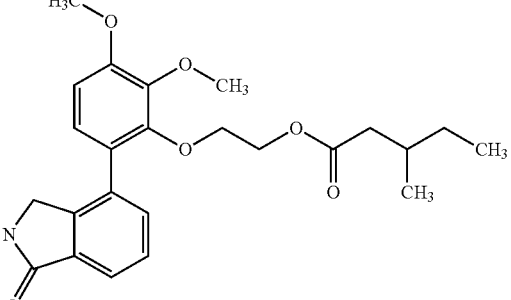 | 2-[2,3-dimethoxy-6-(1-oxoisoindolin-4-yl)phenoxy]ethyl 3-methylbutanoate |
| 966 | 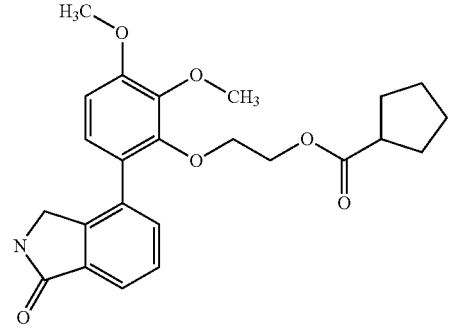 | 2-[2,3-dimethoxy-6-(1-oxoisoindolin-4-yl)phenoxy]ethyl cyclopentanecarboxylate |
| 967 | 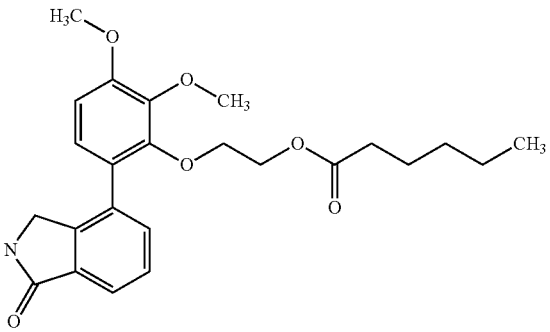 | 2-[2,3-dimethoxy-6-(1-oxoisoindolin-4-yl)phenoxy]ethyl hexanoate |
| 968 | 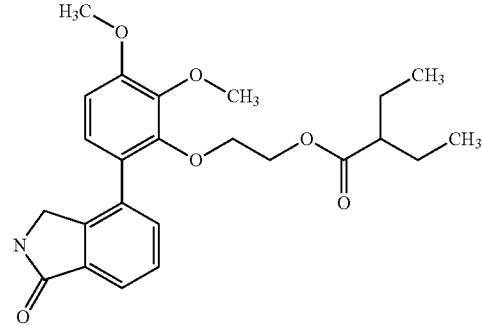 | 2-[2,3-dimethoxy-6-(1-oxoisoindolin-4-yl)phenoxy]ethyl 2-ethylbutanoate |

-continued

| Compound | Structure | Compound name |
|---|---|---|
| 969 | 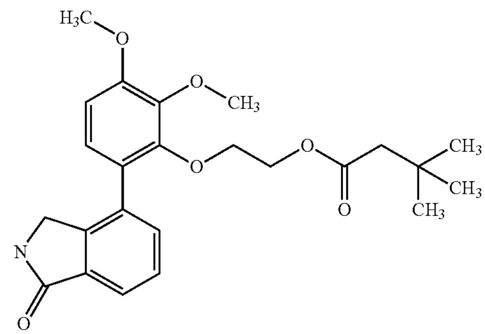 | 2-[2,3-dimethoxy-6-(1-oxoisoindolin-4-yl)phenoxy]ethyl 3,3-dimethyl-butanoate |
| 970 | 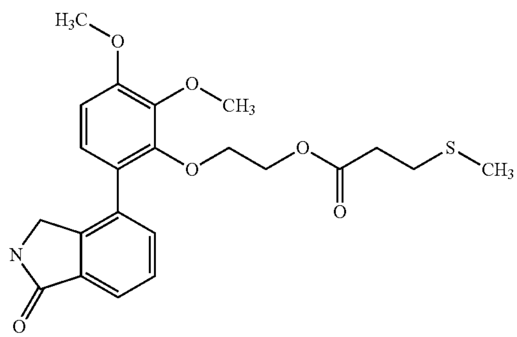 | 2-[2,3-dimethoxy-6-(1-oxoisoindolin-4-yl)phenoxy]ethyl 3-methylsulfanylpropanoate |
| 971 | 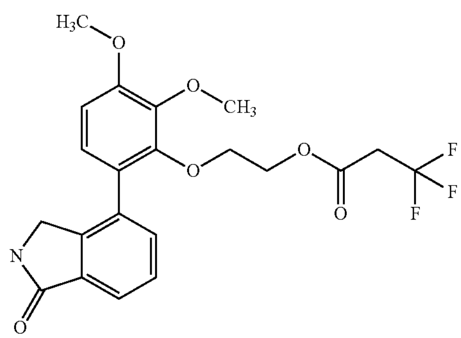 | 2-[2,3-dimethoxy-6-(1-oxoisoindolin-4-yl)phenoxy]ethyl 3,3,3-trifluoropropanoate |
| 972 | 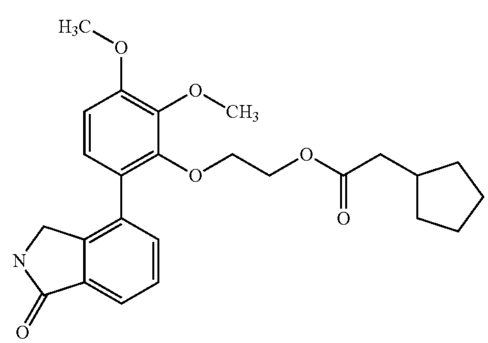 | 2-[2,3-dimethoxy-6-(1-oxoisoindolin-4-yl)phenoxy]ethyl 2-cyclopentylacetate |

| Compound | Structure | Compound name |
|---|---|---|
| 973 | 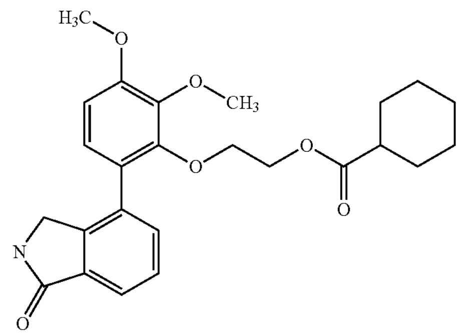 | 2-[2,3-dimethoxy-6-(1-oxoisoindolin-4-yl)phenoxy]ethyl cyclohexanecarboxylate |
| 974 | 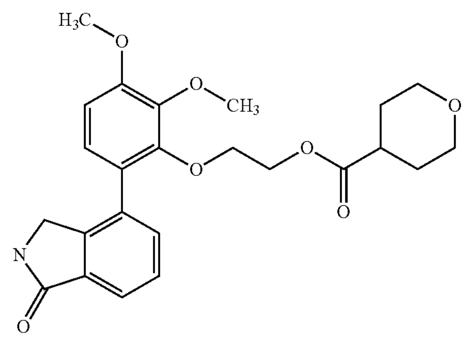 | 2-[2,3-dimethoxy-6-(1-oxoisoindolin-4-yl)phenoxy]ethyl tetrahydropyran-4-carboxylate |
| 975 | 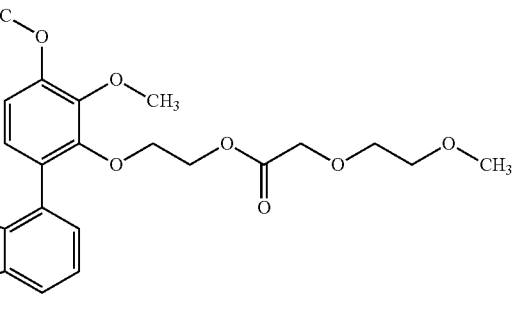 | 2-[2,3-dimethoxy-6-(1-oxoisoindolin-4-yl)phenoxy]ethyl 2-(2-methoxyethoxy)acetate |
| 976 | 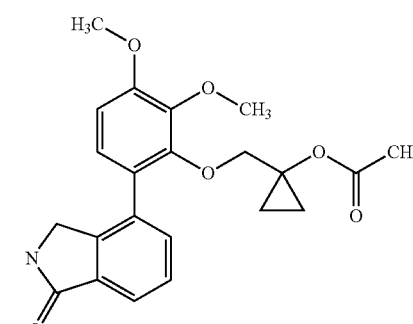 | [1-[[2,3-dimethoxy-6-(1-oxoisoindolin-4-yl)phenoxy]methyl]cyclopropyl] acetate |

-continued

| Compound | Structure | Compound name |
|---|---|---|
| 977 | 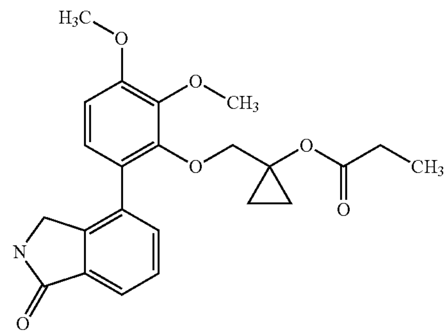 | [1-[[2,3-dimethoxy-6-(1-oxoisoindolin-4-yl)phenoxy]methyl]cyclopropyl] propanoate |
| 978 | 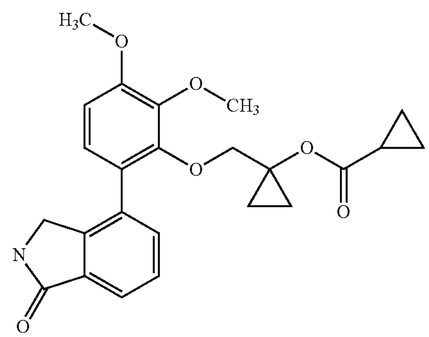 [SMILES: COc1ccc(-c2cccc3c2CNC3=O)c(OCC2(OC(=O)C3CC3)CC2)c1OC] | [1-[[2,3-dimethoxy-6-(1-oxoisoindolin-4-yl)phenoxy]methyl]cyclopropyl] cyclopropanecarboxylate |
| 979 | 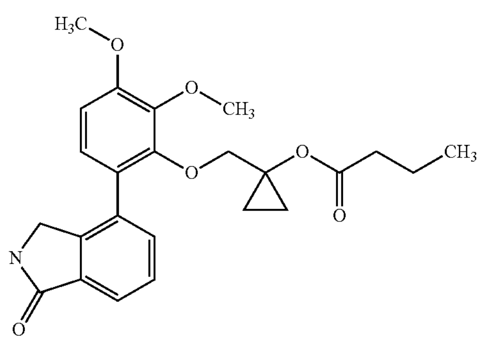 | [1-[[2,3-dimethoxy-6-(1-oxoisoindolin-4-yl)phenoxy]methyl]cyclopropyl] butanoate |
| 980 | 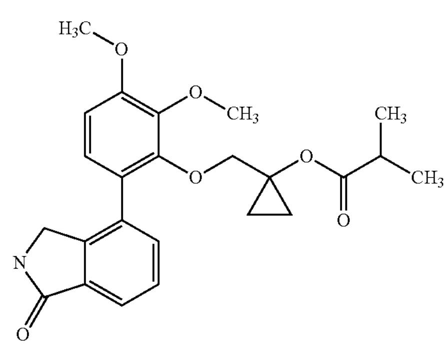 | [1-[[2,3-dimethoxy-6-(1-oxoisoindolin-4-yl)phenoxy]methyl]cyclopropyl] 2-methylpropanoate |

| Compound | Structure | Compound name |
|---|---|---|
| 981 | 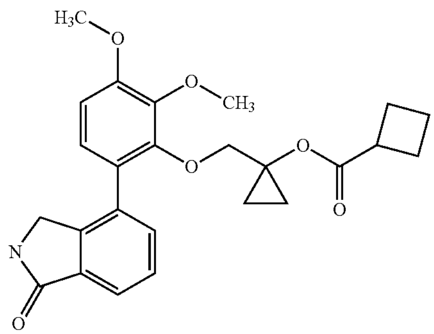 | [1-[[2,3-dimethoxy-6-(1-oxoisoindolin-4-yl)phenoxy]methyl]cyclopropyl] cyclobutanecarboxylate |
| 982 | 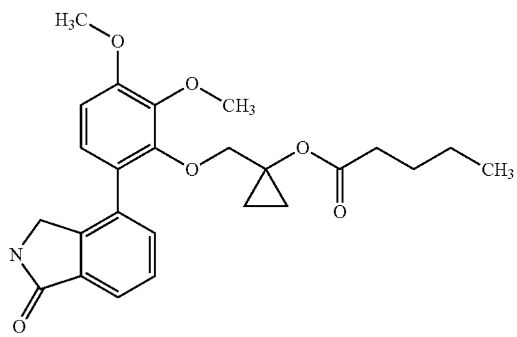 | [1-[[2,3-dimethoxy-6-(1-oxoisoindolin-4-yl)phenoxy]methyl]cyclopropyl] pentanoate |
| 983 | 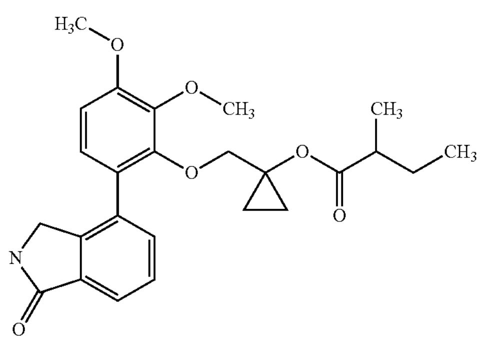 | [1-[[2,3-dimethoxy-6-(1-oxoisoindolin-4-yl)phenoxy]methyl]cyclopropyl] 2-methylbutanoate |
| 984 | 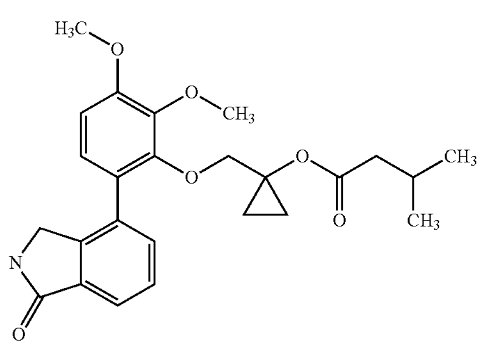 | [1-[[2,3-dimethoxy-6-(1-oxoisoindolin-4-yl)phenoxy]methyl]cyclopropyl] 3-methylbutanoate |

| Compound | Structure | Compound name |
|---|---|---|
| 985 | 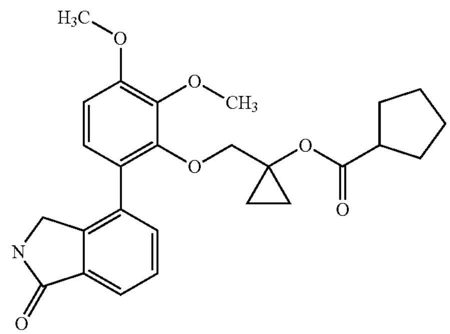 | [1-[[2,3-dimethoxy-6-(1-oxoisoindolin-4-yl)phenoxy]methyl]cyclopropyl] cyclopentanecarboxylate |
| 986 | 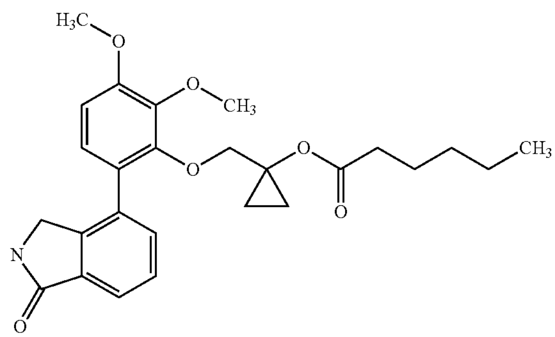 | [1-[[2,3-dimethoxy-6-(1-oxoisoindolin-4-yl)phenoxy]methyl]cyclopropyl] hexanoate |
| 987 | 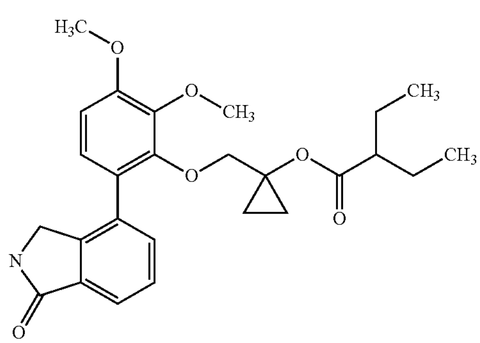 | [1-[[2,3-dimethoxy-6-(1-oxoisoindolin-4-yl)phenoxy]methyl]cyclopropyl] 2-ethylbutanoate |
| 988 | 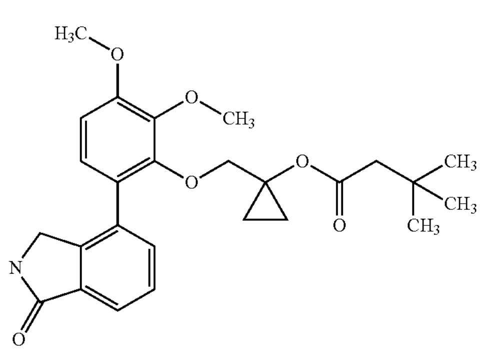 | [1-[[2,3-dimethoxy-6-(1-oxoisoindolin-4-yl)phenoxy]methyl]cyclopropyl] 3,3-dimethylbutanoate |

-continued

| Compound | Structure | Compound name |
|---|---|---|
| 989 | 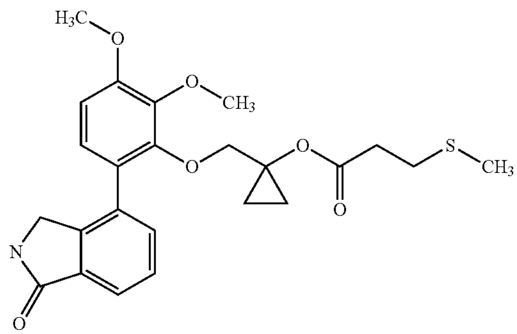 | [1-[[2,3-dimethoxy-6-(1-oxoisoindolin-4-yl)phenoxy]methyl]cyclopropyl] 3-methylsulfanylpropanoate |
| 990 | 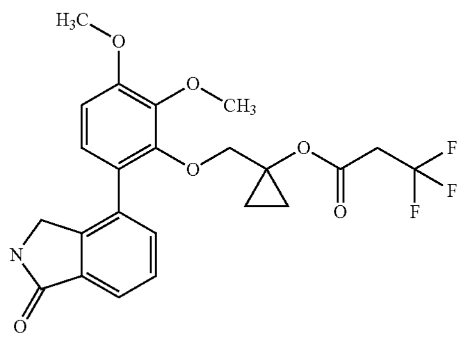 | [1-[[2,3-dimethoxy-6-(1-oxoisoindolin-4-yl)phenoxy]methyl]cyclopropyl] 3,3,3-trifluoropropanoate |
| 991 | 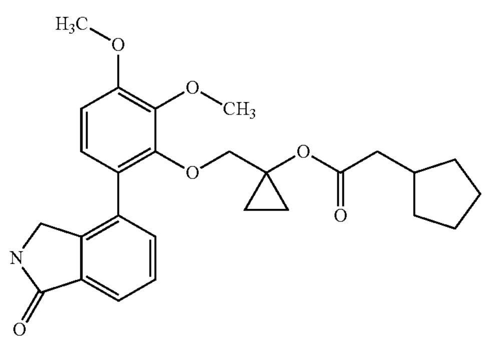 | [1-[[2,3-dimethoxy-6-(1-oxoisoindolin-4-yl)phenoxy]methyl]cyclopropyl] 2-cyclopentylacetate |
| 992 | 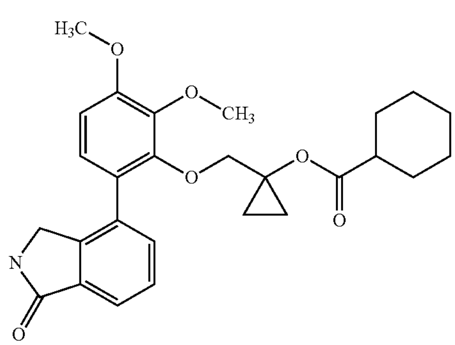 | [1-[[2,3-dimethoxy-6-(1-oxoisoindolin-4-yl)phenoxy]methyl]cyclopropyl] cyclohexanecarboxylate |

| Compound | Structure | Compound name |
|---|---|---|
| 993 | 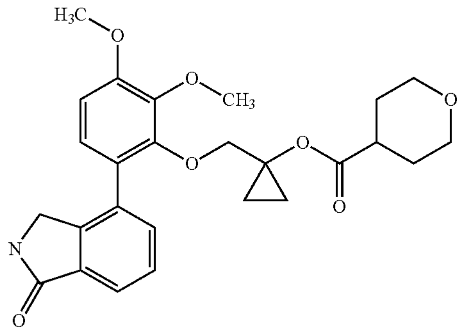 | [1-[[2,3-dimethoxy-6-(1-oxoisoindolin-4-yl)phenoxy]methyl]cyclopropyl] tetrahydropyran-4-carboxylate |
| 994 | 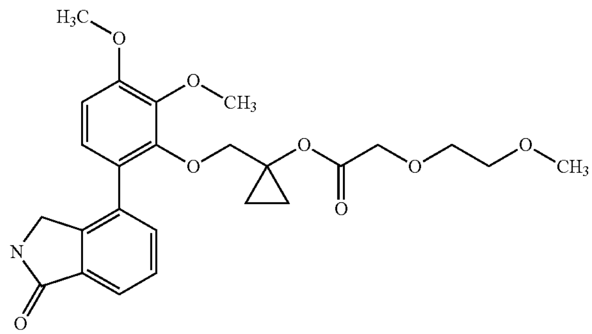 [SMILES: COCCOCC(=O)OC1(COc2c(-c3cccc4c3CNC4=O)ccc(OC)c2OC)CC1] | [1-[[2,3-dimethoxy-6-(1-oxoisoindolin-4-yl)phenoxy]methyl]cyclopropyl] 2-(2-methoxyethoxy)acetate |
| 995 | 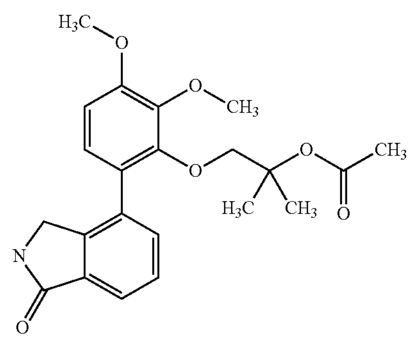 | [2-[2,3-dimethoxy-6-(1-oxoisoindolin-4-yl)phenoxy]-1,1-dimethyl-ethyl] acetate |
| 996 | 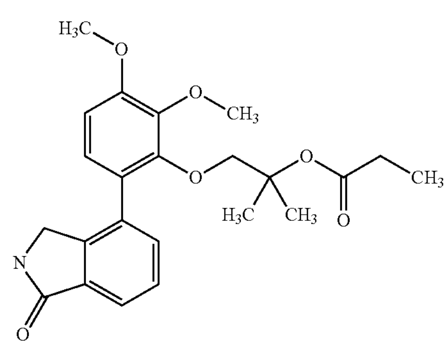 [SMILES: CCC(=O)OC(C)(C)COc1c(-c2cccc3c2CNC3=O)ccc(OC)c1OC] | [2-[2,3-dimethoxy-6-(1-oxoisoindolin-4-yl)phenoxy]-1,1-dimethyl-ethyl] propanoate |

-continued

| Compound | Structure | Compound name |
|---|---|---|
| 997 | 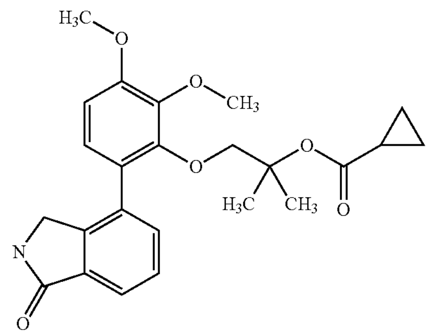 [SMILES: COc1ccc(-c2cccc3c2CNC3=O)c(OCC(C)(C)OC(=O)C2CC2)c1OC] | [2-[2,3-dimethoxy-6-(1-oxoisoindolin-4-yl)phenoxy]-1,1-dimethyl-ethyl] cyclopropanecarboxylate |
| 998 | 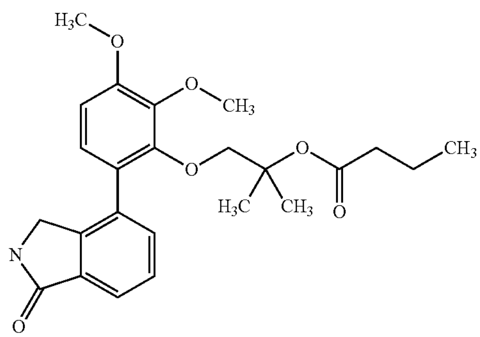 | [2-[2,3-dimethoxy-6-(1-oxoisoindolin-4-yl)phenoxy]-1,1-dimethyl-ethyl] butanoate |
| 999 | 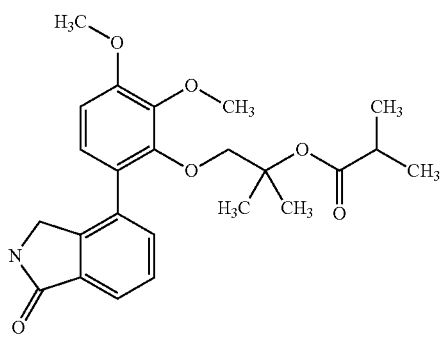 [SMILES: COc1ccc(-c2cccc3c2CNC3=O)c(OCC(C)(C)OC(=O)C(C)C)c1OC] | [2-[2,3-dimethoxy-6-(1-oxoisoindolin-4-yl)phenoxy]-1,1-dimethyl-ethyl] 2-methylpropanoate |
| 1000 | 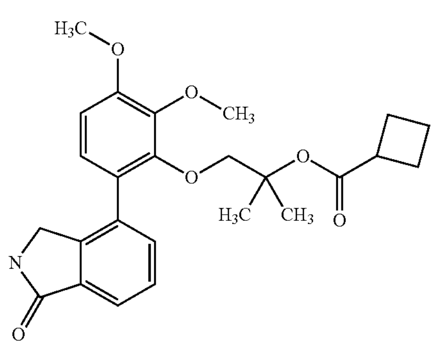 | [2-[2,3-dimethoxy-6-(1-oxoisoindolin-4-yl)phenoxy]-1,1-dimethyl-ethyl] cyclobutanecarboxylate |

-continued

| Compound | Structure | Compound name |
|---|---|---|
| 1001 | 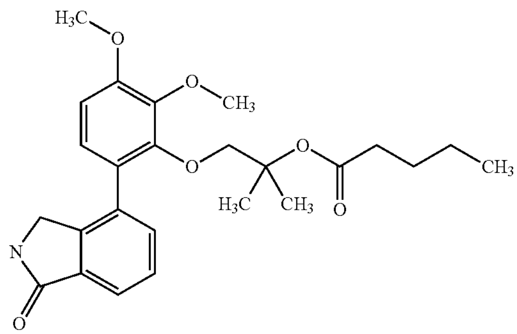 [SMILES: CCCCC(=O)OC(C)(C)COc1c(-c2cccc3c2CNC3=O)ccc(OC)c1OC] | [2-[2,3-dimethoxy-6-(1-oxoisoindolin-4-yl)phenoxy]-1,1-dimethyl-ethyl] pentanoate |
| 1002 | 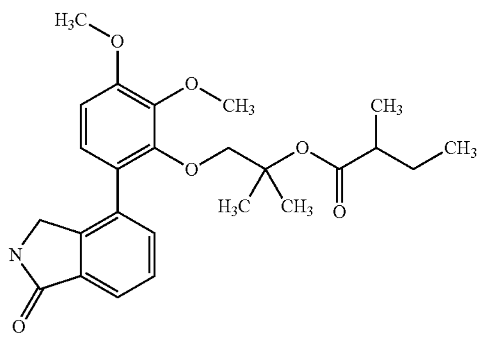 | [2-[2,3-dimethoxy-6-(1-oxoisoindolin-4-yl)phenoxy]-1,1-dimethyl-ethyl] 2-methylbutanoate |
| 1003 | 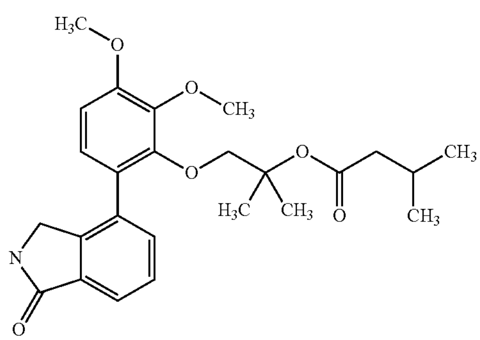 | [2-[2,3-dimethoxy-6-(1-oxoisoindolin-4-yl)phenoxy]-1,1-dimethyl-ethyl] 3-methylbutanoate |
| 1004 | 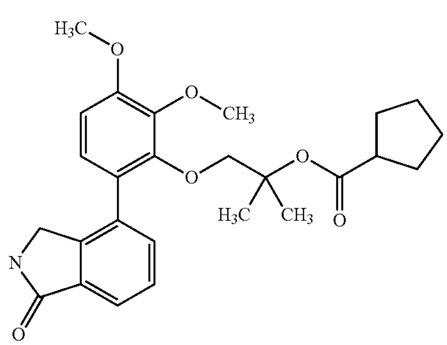 | [2-[2,3-dimethoxy-6-(1-oxoisoindolin-4-yl)phenoxy]-1,1-dimethyl-ethyl] cyclopentanecarboxylate |

| Compound | Structure | Compound name |
|---|---|---|
| 1005 | 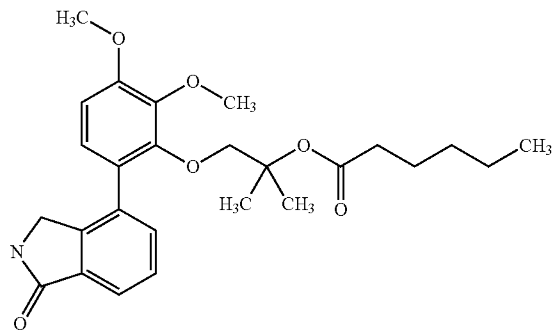 [SMILES: CCCCCC(=O)OC(C)(C)COc1c(-c2cccc3c2CNC3=O)ccc(OC)c1OC] | [2-[2,3-dimethoxy-6-(1-oxoisoindolin-4-yl)phenoxy]-1,1-dimethyl-ethyl] hexanoate |
| 1006 | 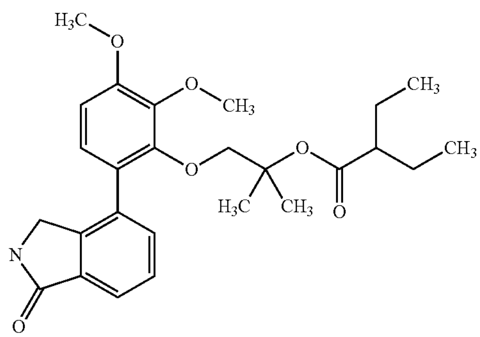 | [2-[2,3-dimethoxy-6-(1-oxoisoindolin-4-yl)phenoxy]-1,1-dimethyl-ethyl] 2-ethylbutanoate |
| 1007 | 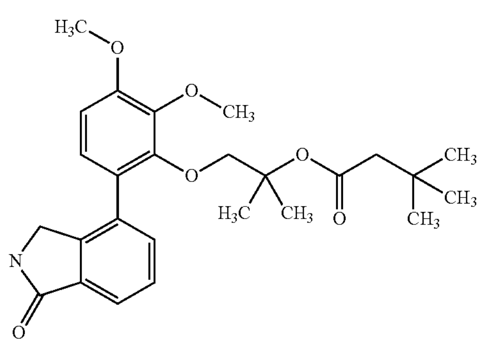 | [2-[2,3-dimethoxy-6-(1-oxoisoindolin-4-yl)phenoxy]-1,1-dimethyl-ethyl] 3,3-dimethylbutanoate |
| 1008 | 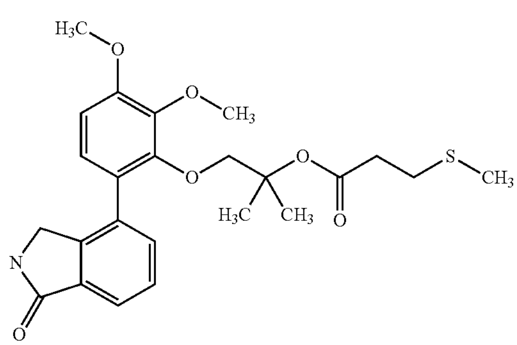 | [2-[2,3-dimethoxy-6-(1-oxoisoindolin-4-yl)phenoxy]-1,1-dimethyl-ethyl] 3-methylsulfanylpropanoate |

| Compound | Structure | Compound name |
|---|---|---|
| 1009 | 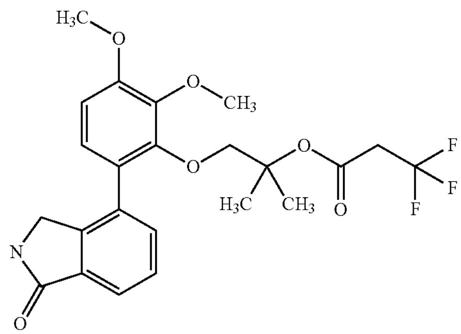 [SMILES: COc1ccc(-c2cccc3c2CNC3=O)c(OCC(C)(C)OC(=O)CC(F)(F)F)c1OC] | [2-[2,3-dimethoxy-6-(1-oxoisoindolin-4-yl)phenoxy]-1,1-dimethyl-ethyl] 3,3,3-trifluoropropanoate |
| 1010 | 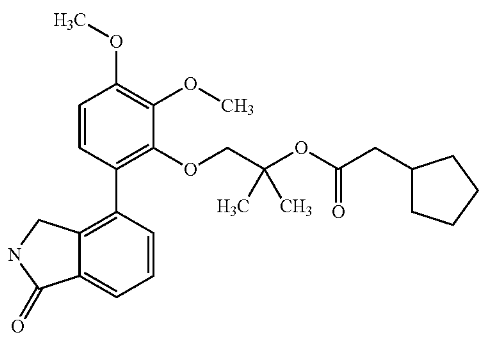 | [2-[2,3-dimethoxy-6-(1-oxoisoindolin-4-yl)phenoxy]-1,1-dimethyl-ethyl] 2-cyclopentylacetate |
| 1011 | 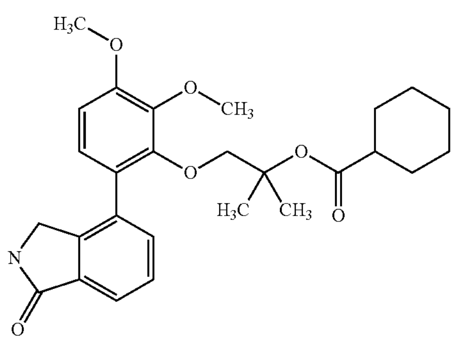 | [2-[2,3-dimethoxy-6-(1-oxoisoindolin-4-yl)phenoxy]-1,1-dimethyl-ethyl] cyclohexanecarboxylate |
| 1012 | 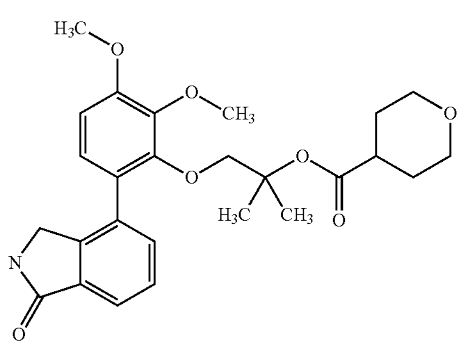 | [2-[2,3-dimethoxy-6-(1-oxoisoindolin-4-yl)phenoxy]-1,1-dimethyl-ethyl] tetrahydropyran-4-carboxylate |

-continued

| Compound | Structure | Compound name |
| --- | --- | --- |
| 1013 | 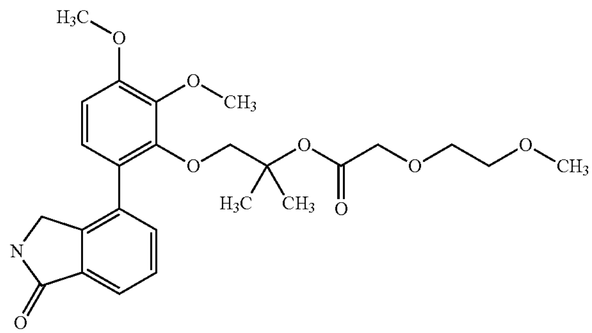 [SMILES: COCCOCC(=O)OC(C)(C)COc1c(-c2cccc3c2CNC3=O)ccc(OC)c1OC] | [2-[2,3-dimethoxy-6-(1-oxoisoindolin-4-yl)phenoxy]-1,1-dimethyl-ethyl] 2-(2-methoxyethoxy)acetate |

| Compound | Structure | IUPAC name |
| --- | --- | --- |
| 1014 | 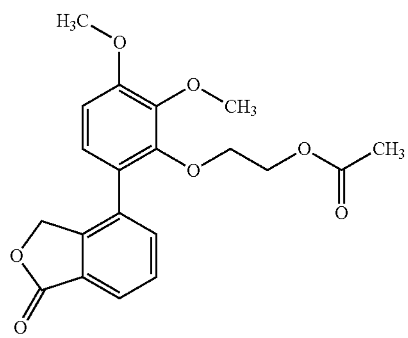 [SMILES: COc1ccc(-c2cccc3c2COC3=O)c(OCCOC(C)=O)c1OC] | 2-[2,3-dimethoxy-6-(1-oxo-3H-isobenzofuran-4-yl)phenoxy]ethyl acetate |
| 1015 | 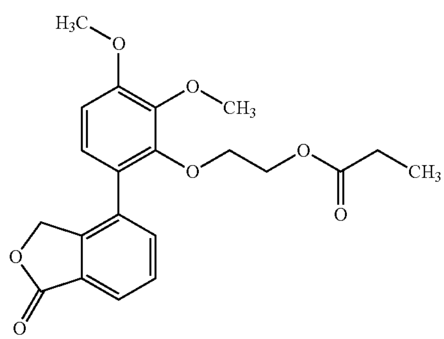 [SMILES: CCC(=O)OCCOc1c(-c2cccc3c2COC3=O)ccc(OC)c1OC] | 2-[2,3-dimethoxy-6-(1-oxo-3H-isobenzofuran-4-yl)phenoxy]ethyl propanoate |
| 1016 | 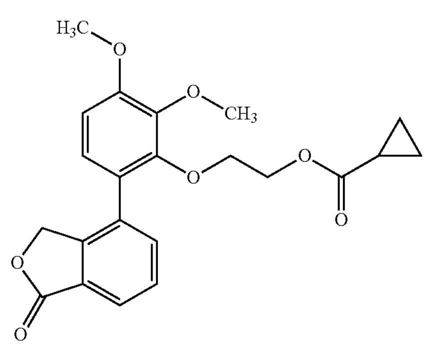 [SMILES: COc1ccc(-c2cccc3c2COC3=O)c(OCCOC(=O)C2CC2)c1OC] | 2-[2,3-dimethoxy-6-(1-oxo-3H-isobenzofuran-4-yl)phenoxy]ethyl cyclopropanecarboxylate |

| Compound | Structure | IUPAC name |
|---|---|---|
| 1017 | 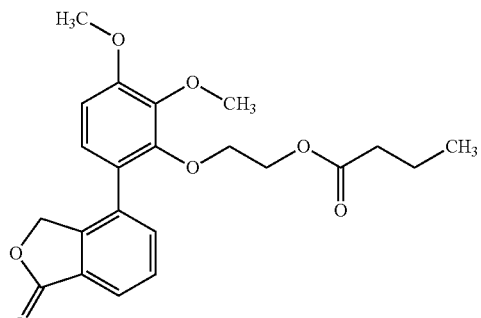 | 2-[2,3-dimethoxy-6-(1-oxo-3H-isobenzofuran-4-yl)phenoxy]ethyl butanoate |
| 1018 | 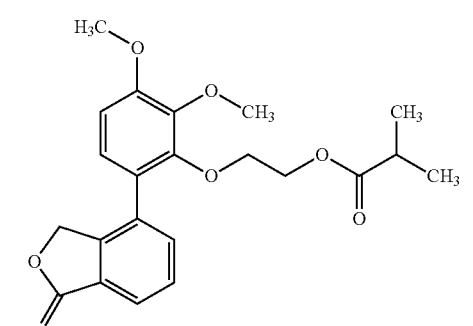 | 2-[2,3-dimethoxy-6-(1-oxo-3H-isobenzofuran-4-yl)phenoxy]ethyl 2-methylpropanoate |
| 1019 | 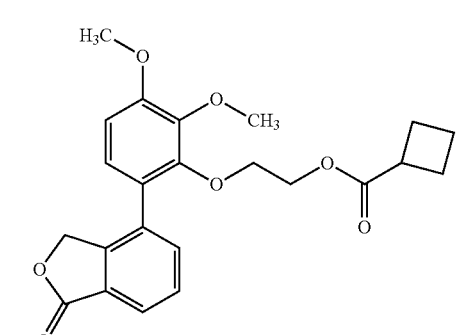 | 2-[2,3-dimethoxy-6-(1-oxo-3H-isobenzofuran-4-yl)phenoxy]ethyl cyclobutanecarboxylate |
| 1020 | 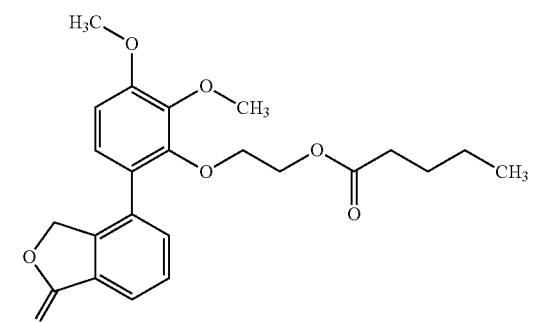 | 2-[2,3-dimethoxy-6-(1-oxo-3H-isobenzofuran-4-yl)phenoxy]ethyl pentanoate |

-continued

| Compound | Structure | IUPAC name |
| --- | --- | --- |
| 1021 | 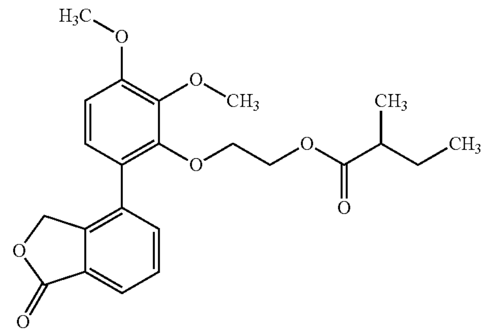 [SMILES: CCC(C)C(=O)OCCOc1c(-c2cccc3c2COC3=O)ccc(OC)c1OC] | 2-[2,3-dimethoxy-6-(1-oxo-3H-isobenzofuran-4-yl)phenoxy]ethyl 2-methylbutanoate |
| 1022 | 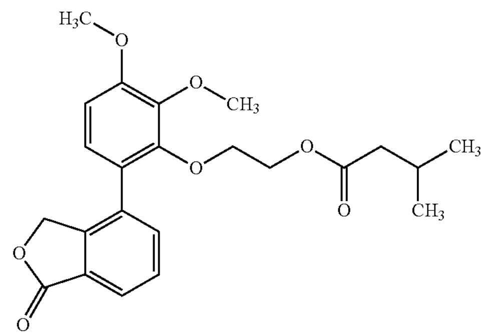 [SMILES: COc1ccc(-c2cccc3c2COC3=O)c(OCCOC(=O)CC(C)C)c1OC] | 2-[2,3-dimethoxy-6-(1-oxo-3H-isobenzofuran-4-yl)phenoxy]ethyl 3-methylbutanoate |
| 1023 | 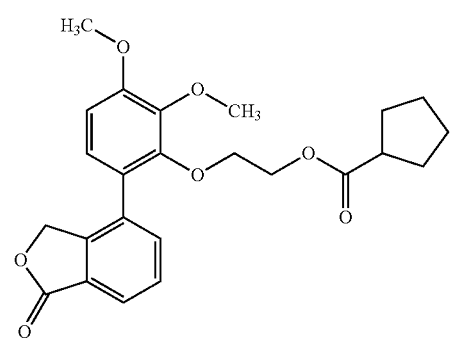 [SMILES: COc1ccc(-c2cccc3c2COC3=O)c(OCCOC(=O)C2CCCC2)c1OC] | 2-[2,3-dimethoxy-6-(1-oxo-3H-isobenzofuran-4-yl)phenoxy]ethyl cyclopentanecarboxylate |
| 1024 | 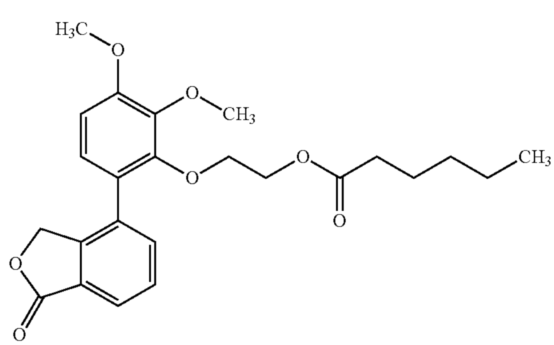 [SMILES: CCCCCC(=O)OCCOc1c(-c2cccc3c2COC3=O)ccc(OC)c1OC] | 2-[2,3-dimethoxy-6-(1-oxo-3H-isobenzofuran-4-yl)phenoxy]ethyl hexanoate |

-continued

| Compound | Structure | IUPAC name |
| --- | --- | --- |
| 1025 | 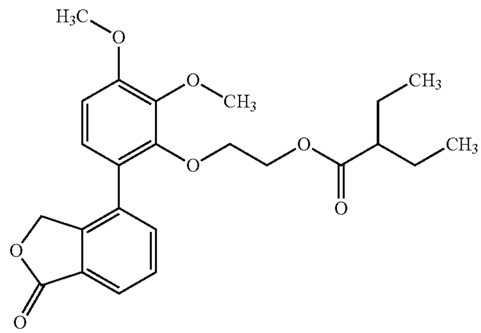 [SMILES: CCC(CC)C(=O)OCCOc1c(-c2cccc3c2COC3=O)ccc(OC)c1OC] | 2-[2,3-dimethoxy-6-(1-oxo-3H-isobenzofuran-4-yl)phenoxy]ethyl 2-ethylbutanoate |
| 1026 | 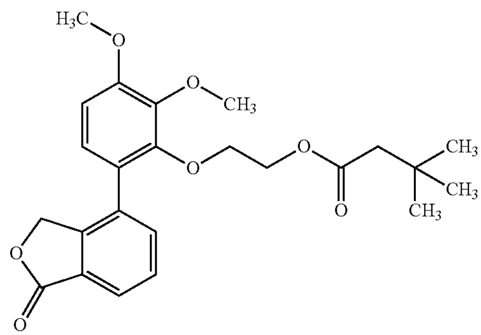 [SMILES: COc1ccc(-c2cccc3c2COC3=O)c(OCCOC(=O)CC(C)(C)C)c1OC] | 2-[2,3-dimethoxy-6-(1-oxo-3H-isobenzofuran-4-yl)phenoxy]ethyl 3,3-dimethylbutanoate |
| 1027 | 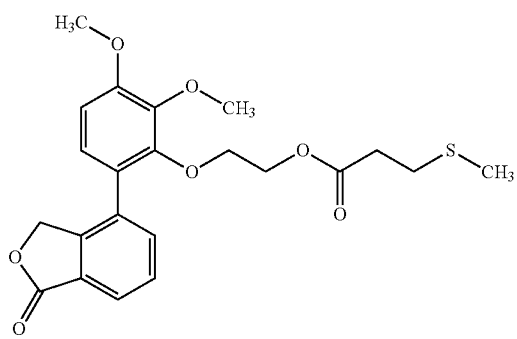 [SMILES: COc1ccc(-c2cccc3c2COC3=O)c(OCCOC(=O)CCSC)c1OC] | 2-[2,3-dimethoxy-6-(1-oxo-3H-isobenzofuran-4-yl)phenoxy]ethyl 3-methylsulfanylpropanoate |
| 1028 | 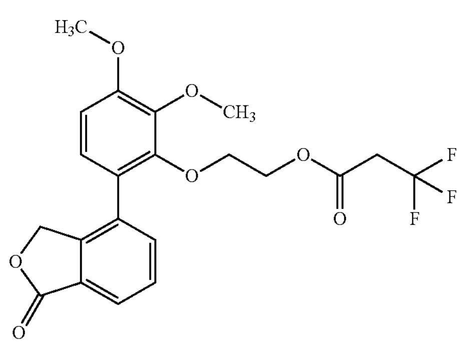 [SMILES: COc1ccc(-c2cccc3c2COC3=O)c(OCCOC(=O)CC(F)(F)F)c1OC] | 2-[2,3-dimethoxy-6-(1-oxo-3H-isobenzofuran-4-yl)phenoxy]ethyl 3,3,3-trifluoropropanoate |

-continued
| Compound | Structure | IUPAC name |
|---|---|---|
| 1029 | 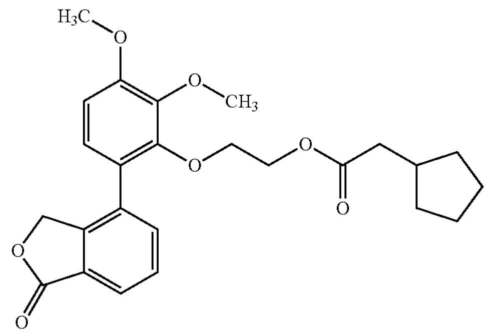 [SMILES: COc1ccc(-c2cccc3c2COC3=O)c(OCCOC(=O)CC2CCCC2)c1OC] | 2-[2,3-dimethoxy-6-(1-oxo-3H-isobenzofuran-4-yl)phenoxy]ethyl 2-cyclopentylacetate |
| 1030 | 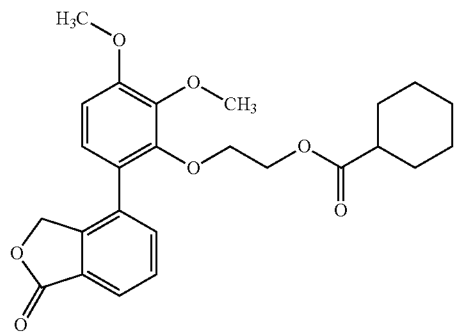 [SMILES: COc1ccc(-c2cccc3c2COC3=O)c(OCCOC(=O)C2CCCCC2)c1OC] | 2-[2,3-dimethoxy-6-(1-oxo-3H-isobenzofuran-4-yl)phenoxy]ethyl cyclohexanecarboxylate |
| 1031 | 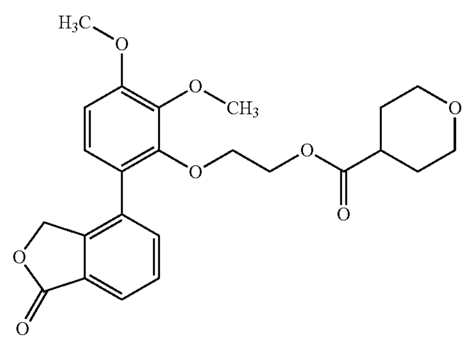 [SMILES: COc1ccc(-c2cccc3c2COC3=O)c(OCCOC(=O)C2CCOCC2)c1OC] | 2-[2,3-dimethoxy-6-(1-oxo-3H-isobenzofuran-4-yl)phenoxy]ethyl tetrahydropyran-4-carboxylate |
| 1032 | 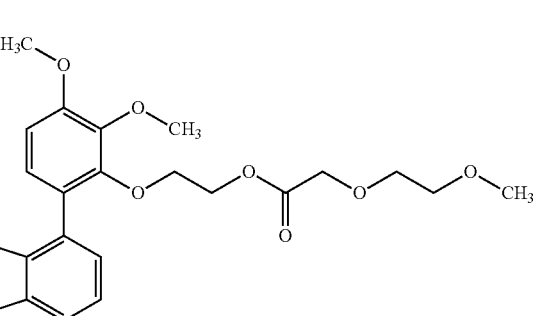 | 2-[2,3-dimethoxy-6-(1-oxo-3H-isobenzofuran-4-yl)phenoxy]ethyl 2-(2-methoxyethoxy)acetate |

-continued

| Compound | Structure | IUPAC name |
|---|---|---|
| 1033 | 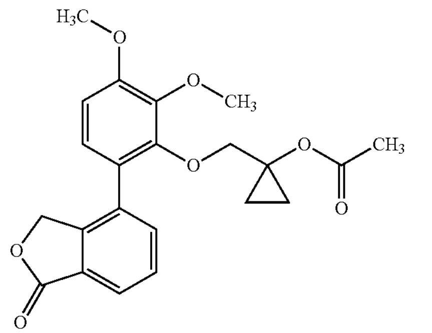 [SMILES: COc1ccc(-c2cccc3c2COC3=O)c(OCC2(OC(C)=O)CC2)c1OC] | [1-[[2,3-dimethoxy-6-(1-oxo-3H-isobenzofuran-4-yl)phenoxy]methyl]cyclopropyl]acetate |
| 1034 | 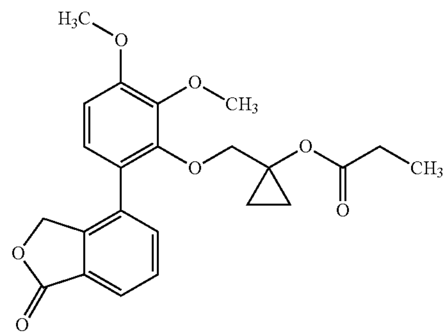 [SMILES: CCC(=O)OC1(COc2c(-c3cccc4c3COC4=O)ccc(OC)c2OC)CC1] | [1-[[2,3-dimethoxy-6-(1-oxo-3H-isobenzofuran-4-yl)phenoxy]methyl]cyclopropyl]propanoate |
| 1035 | 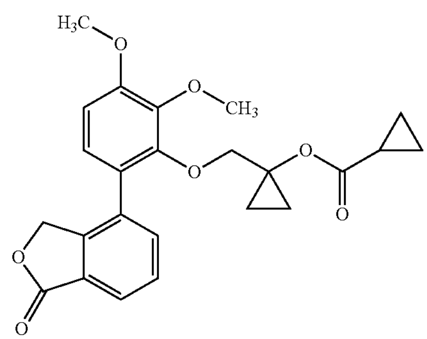 [SMILES: COc1ccc(-c2cccc3c2COC3=O)c(OCC2(OC(=O)C3CC3)CC2)c1OC] | [1-[[2,3-dimethoxy-6-(1-oxo-3H-isobenzofuran-4-yl)phenoxy]methyl]cyclopropyl] cyclopropanecarboxylate |
| 1036 | 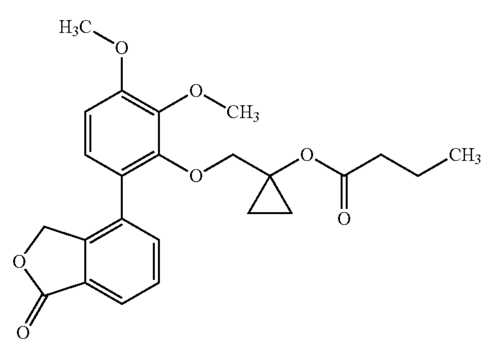 [SMILES: CCCC(=O)OC1(COc2c(-c3cccc4c3COC4=O)ccc(OC)c2OC)CC1] | [1-[[2,3-dimethoxy-6-(1-oxo-3H-isobenzofuran-4-yl)phenoxy]methyl]cyclopropyl]butanoate |

-continued

| Compound | Structure | IUPAC name |
|---|---|---|
| 1037 | 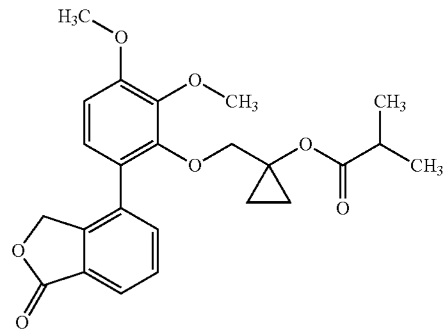 [SMILES: COc1ccc(-c2cccc3c2COC3=O)c(OCC2(OC(=O)C(C)C)CC2)c1OC] | [1-[[2,3-dimethoxy-6-(1-oxo-3H-isobenzofuran-4-yl)phenoxy]methyl]cyclopropyl]2-methylpropanoate |
| 1038 | 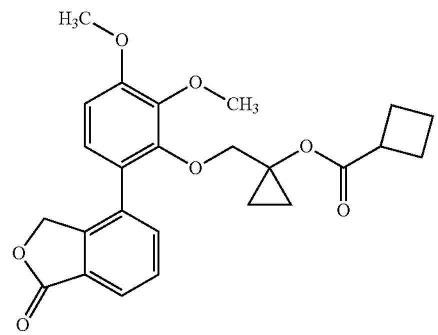 [SMILES: COc1ccc(-c2cccc3c2COC3=O)c(OCC2(OC(=O)C3CCC3)CC2)c1OC] | [1-[[2,3-dimethoxy-6-(1-oxo-3H-isobenzofuran-4-yl)phenoxy]methyl]cyclopropyl]cyclobutanecarboxylate |
| 1039 | 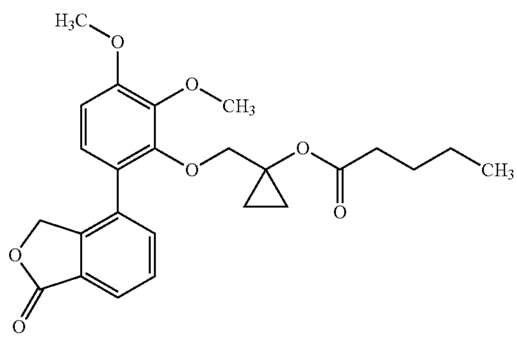 [SMILES: CCCCC(=O)OC1(COc2c(-c3cccc4c3COC4=O)ccc(OC)c2OC)CC1] | [1-[[2,3-dimethoxy-6-(1-oxo-3H-isobenzofuran-4-yl)phenoxy]methyl]cyclopropyl]pentanoate |
| 1040 | 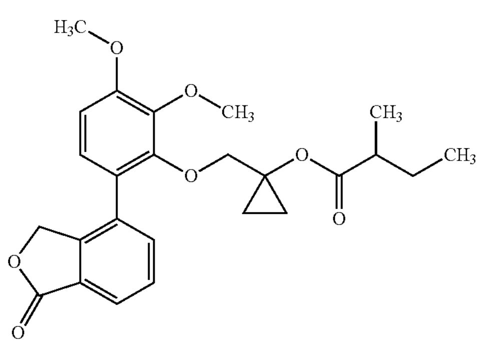 [SMILES: CCC(C)C(=O)OC1(COc2c(-c3cccc4c3COC4=O)ccc(OC)c2OC)CC1] | [1-[[2,3-dimethoxy-6-(1-oxo-3H-isobenzofuran-4-yl)phenoxy]methyl]cyclopropyl]2-methylbutanoate |

-continued

| Compound | Structure | IUPAC name |
|---|---|---|
| 1041 | 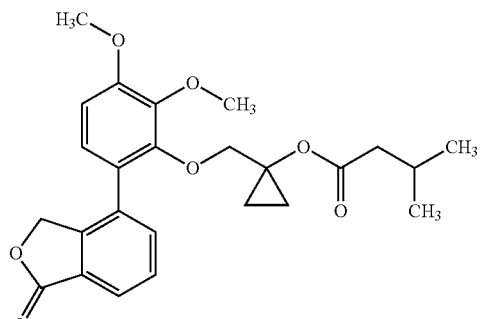 | [1-[[2,3-dimethoxy-6-(1-oxo-3H-isobenzofuran-4-yl)phenoxy]methyl]cyclopropyl]3-methylbutanoate |
| 1042 | 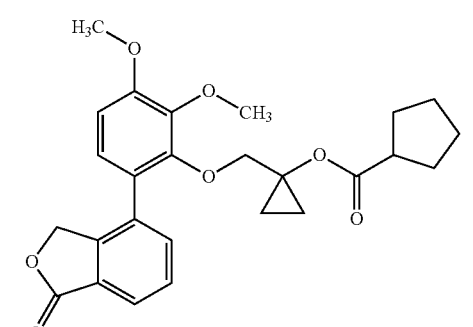 | [1-[[2,3-dimethoxy-6-(1-oxo-3H-isobenzofuran-4-yl)phenoxy]methyl]cyclopropyl] cyclopentanecarboxylate |
| 1043 | 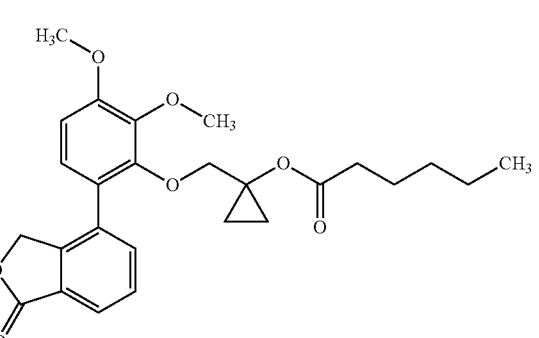 | [1-[[2,3-dimethoxy-6-(1-oxo-3H-isobenzofuran-4-yl)phenoxy]methyl]cyclopropyl]hexanoate |
| 1044 | 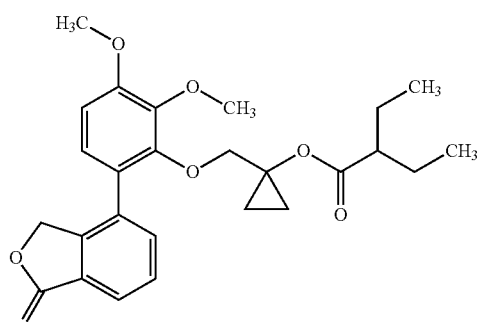 | [1-[[2,3-dimethoxy-6-(1-oxo-3H-isobenzofuran-4-yl)phenoxy]methyl]cyclopropyl]2-ethylbutanoate |

| Compound | Structure | IUPAC name |
| --- | --- | --- |
| 1045 | 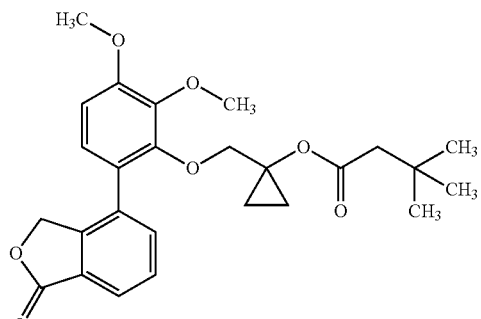 | [1-[[2,3-dimethoxy-6-(1-oxo-3H-isobenzofuran-4-yl)phenoxy]methyl]cyclopropyl]3,3-dimethylbutanoate |
| 1046 | 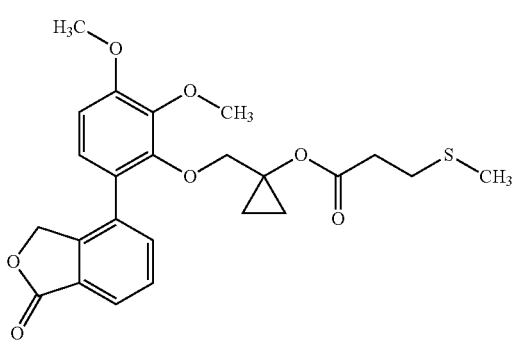 [SMILES: COc1ccc(-c2cccc3c2COC3=O)c(OCC2(OC(=O)CCSC)CC2)c1OC] | [1-[[2,3-dimethoxy-6-(1-oxo-3H-isobenzofuran-4-yl)phenoxy]methyl]cyclopropyl]3-methylsulfanylpropanoate |
| 1047 | 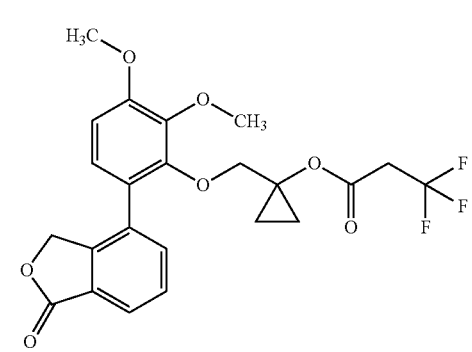 [SMILES: COc1ccc(-c2cccc3c2COC3=O)c(OCC2(OC(=O)CC(F)(F)F)CC2)c1OC] | [1-[[2,3-dimethoxy-6-(1-oxo-3H-isobenzofuran-4-yl)phenoxy]methyl]cyclopropyl]3,3,3-trifluoropropanoate |
| 1048 | 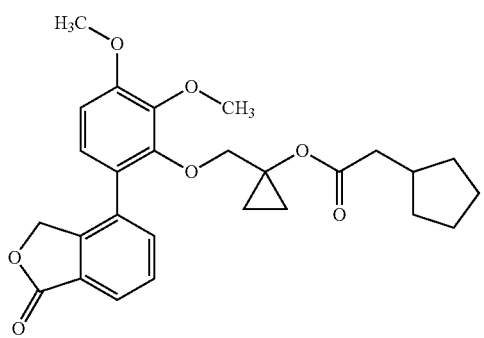 [SMILES: COc1ccc(-c2cccc3c2COC3=O)c(OCC2(OC(=O)CC3CCCC3)CC2)c1OC] | [1-[[2,3-dimethoxy-6-(1-oxo-3H-isobenzofuran-4-yl)phenoxy]methyl]cyclopropyl]2-cyclopentylacetate |

-continued

| Compound | Structure | IUPAC name |
| --- | --- | --- |
| 1049 | 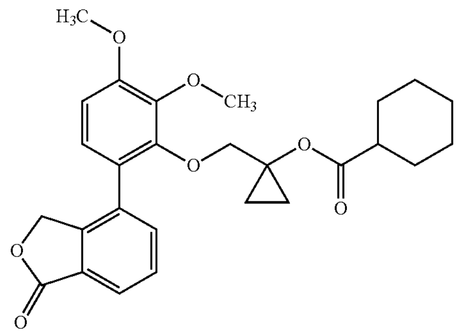 [SMILES: COc1ccc(-c2cccc3c2COC3=O)c(OCC2(OC(=O)C3CCCCC3)CC2)c1OC] | [1-[[2,3-dimethoxy-6-(1-oxo-3H-isobenzofuran-4-yl)phenoxy]methyl]cyclopropyl] cyclohexanecarboxylate |
| 1050 | 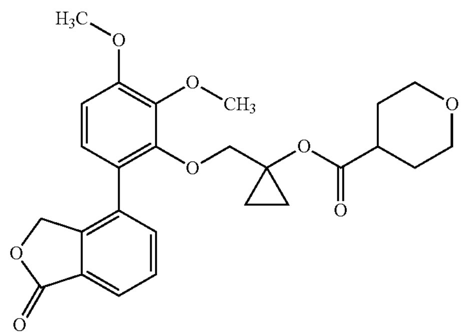 [SMILES: COc1ccc(-c2cccc3c2COC3=O)c(OCC2(OC(=O)C3CCOCC3)CC2)c1OC] | [1-[[2,3-dimethoxy-6-(1-oxo-3H-isobenzofuran-4-yl)phenoxy]methyl]cyclopropyl]tetrahydropyran-4-carboxylate |
| 1051 | 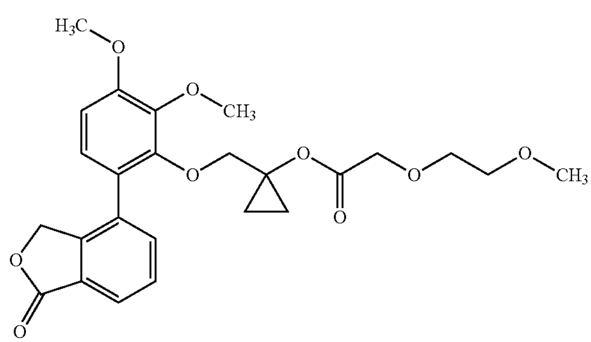 [SMILES: COCCOCC(=O)OC1(COc2c(-c3cccc4c3COC4=O)ccc(OC)c2OC)CC1] | [1-[[2,3-dimethoxy-6-(1-oxo-3H-isobenzofuran-4-yl)phenoxy]nethyl]cyclopropyl]2-(2-methoxyethoxy)acetate |
| 1052 | 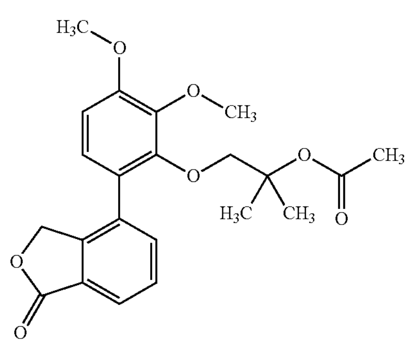 [SMILES: COc1ccc(-c2cccc3c2COC3=O)c(OCC(C)(C)OC(C)=O)c1OC] | [2-[2,3-dimethoxy-6-(1-oxo-3H-isobenzofuran-4-yl)phenoxy]-1,1-dimethyl-ethyl]acetate |

| Compound | Structure | IUPAC name |
|---|---|---|
| 1053 | 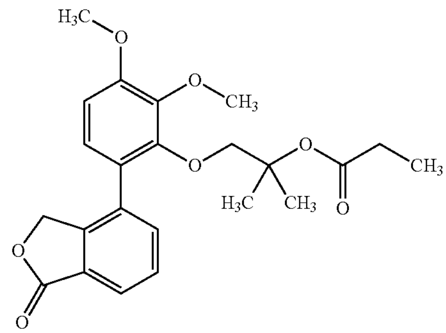 [SMILES: CCC(=O)OC(C)(C)COc1c(-c2cccc3c2COC3=O)ccc(OC)c1OC] | [2-[2,3-dimethoxy-6-(1-oxo-3H-isobenzofuran-4-yl)phenoxy]-1,1-dimethyl-ethyl]propanoate |
| 1054 | 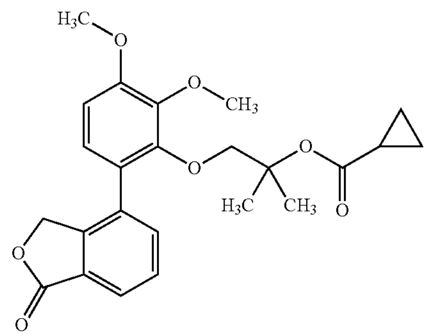 [SMILES: COc1ccc(-c2cccc3c2COC3=O)c(OCC(C)(C)OC(=O)C2CC2)c1OC] | [2-[2,3-dimethoxy-6-(1-oxo-3H-isobenzofuran-4-yl)phenoxy]-1,1-dimethyl-ethyl] cyclopropanecarboxylate |
| 1055 | 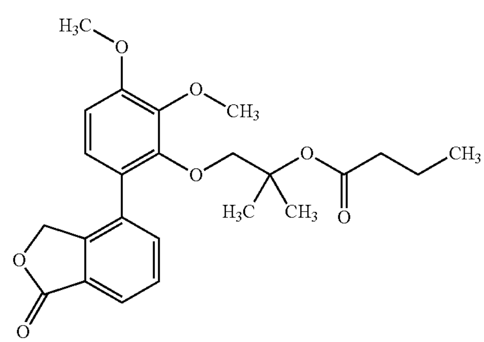 [SMILES: CCCC(=O)OC(C)(C)COc1c(-c2cccc3c2COC3=O)ccc(OC)c1OC] | [2-[2,3-dimethoxy-6-(1-oxo-3H-isobenzofuran-4-yl)phenoxy]-1,1-dimethyl-ethyl]butanoate |
| 1056 | 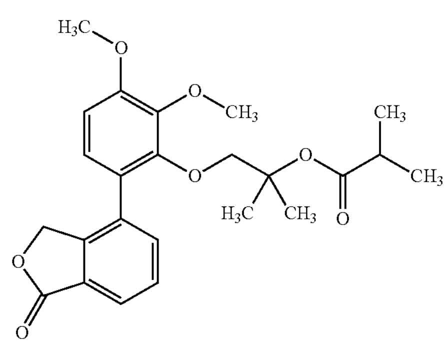 [SMILES: COc1ccc(-c2cccc3c2COC3=O)c(OCC(C)(C)OC(=O)C(C)C)c1OC] | [2-[2,3-dimethoxy-6-(1-oxo-3H-isobenzofuran-4-phenoxy]-1,1-dimethyl-ethyl]2-methylpropanoate |

| Compound | Structure | IUPAC name |
|---|---|---|
| 1057 | 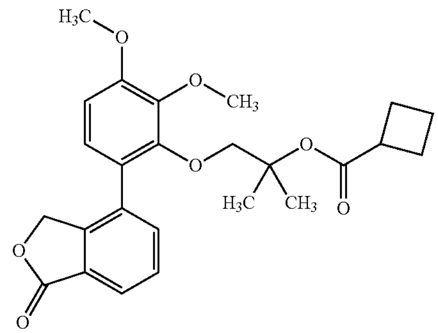 [SMILES: COc1ccc(-c2cccc3c2COC3=O)c(OCC(C)(C)OC(=O)C2CCC2)c1OC] | [2-[2,3-dimethoxy-6-(1-oxo-3H-isobenzofuran-4-yl)phenoxy]-1,1-dimethyl-ethyl]cyclobutane-carboxylate |
| 1058 | 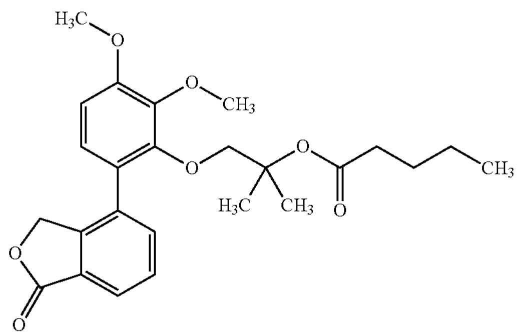 [SMILES: CCCCC(=O)OC(C)(C)COc1c(-c2cccc3c2COC3=O)ccc(OC)c1OC] | [2-[2,3-dimethoxy-6-(1-oxo-3H-isobenzofuran-4-yl)phenoxy]-1,1-dimethyl-ethyl]pentanoate |
| 1059 | 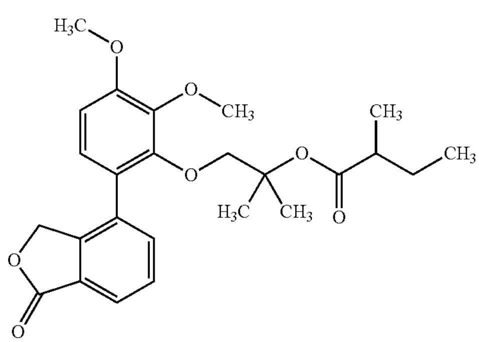 [SMILES: CCC(C)C(=O)OC(C)(C)COc1c(-c2cccc3c2COC3=O)ccc(OC)c1OC] | [2-[2,3-dimethoxy-6-(1-oxo-3H-isobenzofuran-4-yl)phenoxy]-1,1-dimethyl-ethyl]2-methylbutanoate |
| 1060 | 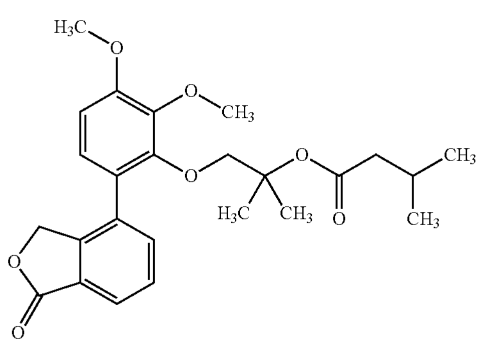 [SMILES: COc1ccc(-c2cccc3c2COC3=O)c(OCC(C)(C)OC(=O)CC(C)C)c1OC] | [2-[2,3-dimethoxy-6-(1-oxo-3H-isobenzofuran-4-yl)phenoxy]-1,1-dimethyl-ethyl]3-methylbutanoate |

-continued

| Compound | Structure | IUPAC name |
| --- | --- | --- |
| 1061 | 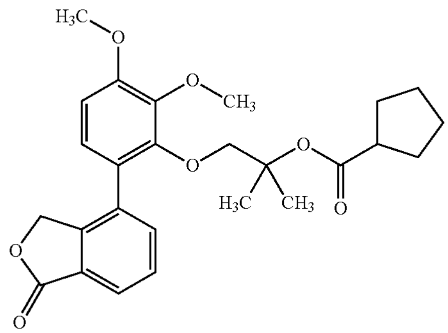 [SMILES: COc1ccc(-c2cccc3c2COC3=O)c(OCC(C)(C)OC(=O)C2CCCC2)c1OC] | [2-[2,3-dimethoxy-6-(1-oxo-3H-isobenzofuran-4-yl)phenoxy]-1,1-dimethyl-ethyl] cyclopentanecarboxylate |
| 1062 | 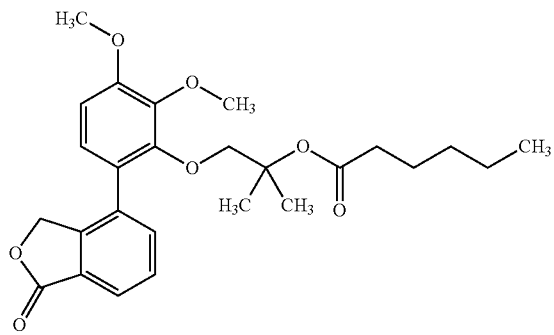 [SMILES: CCCCCC(=O)OC(C)(C)COc1c(-c2cccc3c2COC3=O)ccc(OC)c1OC] | [2-[2,3-dimethoxy-6-(1-oxo-3H-isobenzofuran-4-yl)phenoxy]-1,1-dimethyl-ethyl]hexanoate |
| 1063 | 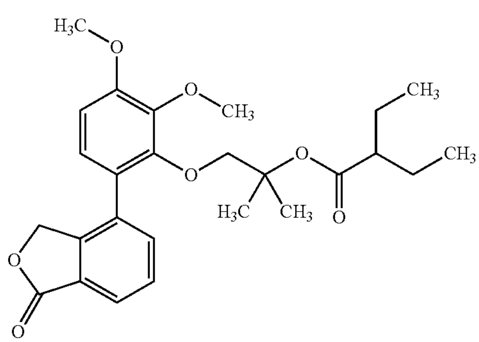 [SMILES: CCC(CC)C(=O)OC(C)(C)COc1c(-c2cccc3c2COC3=O)ccc(OC)c1OC] | [2-[2,3-dimethoxy-6-(1-oxo-3H-isobenzofuran-4-yl)phenoxy]-1,1-dimethyl-ethyl]2-ethylbutanoate |
| 1064 | 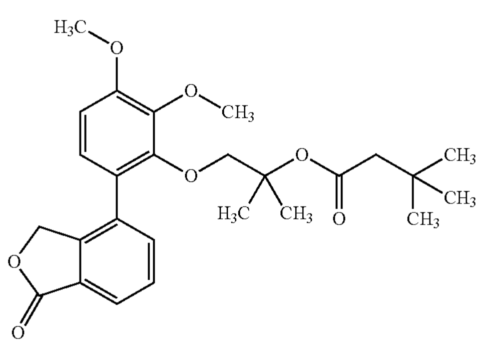 [SMILES: COc1ccc(-c2cccc3c2COC3=O)c(OCC(C)(C)OC(=O)CC(C)(C)C)c1OC] | [2-[2,3-dimethoxy-6-(1-oxo-3H-isobenzofuran-4-yl)phenoxy]-1,1-dimethyl-ethyl]3,3-dimethylbutanoate |

-continued

| Compound | Structure | IUPAC name |
|---|---|---|
| 1065 | 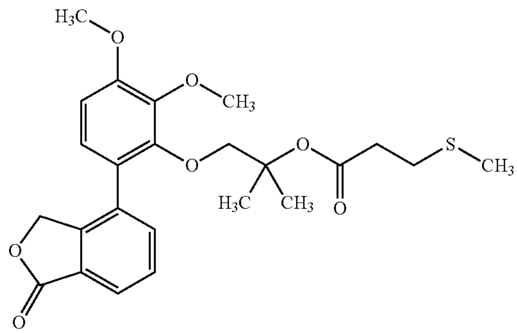 [SMILES: COc1ccc(-c2cccc3c2COC3=O)c(OCC(C)(C)OC(=O)CCSC)c1OC] | [2-[2,3-dimethoxy-6-(1-oxo-3H-isobenzofuran-4-yl)phenoxy]-1,1-dimethyl-ethyl]3-methylsulfanylpropanoate |
| 1066 | 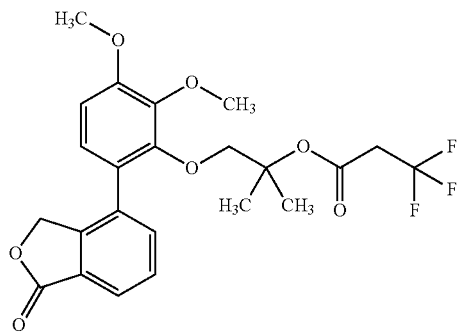 [SMILES: COc1ccc(-c2cccc3c2COC3=O)c(OCC(C)(C)OC(=O)CC(F)(F)F)c1OC] | [2-[2,3-dimethoxy-6-(1-oxo-3H-isobenzofuran-4-yl)phenoxy]-1,1-dimethyl-ethyl]3,3,3-trifluoropropanoate |
| 1067 | 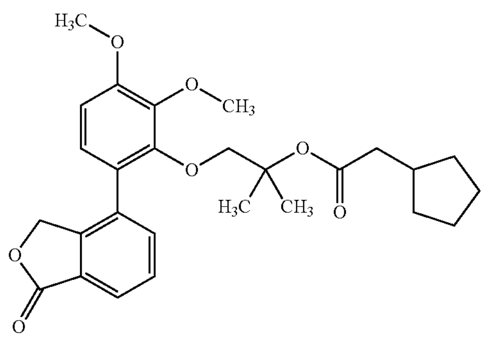 [SMILES: COc1ccc(-c2cccc3c2COC3=O)c(OCC(C)(C)OC(=O)CC2CCCC2)c1OC] | [2-[2,3-dimethoxy-6-(1-oxo-3H-isobenzofuran-4-yl)phenoxy]-1,1-dimethyl-ethyl] 2-cyclopentylacetate |
| 1068 | 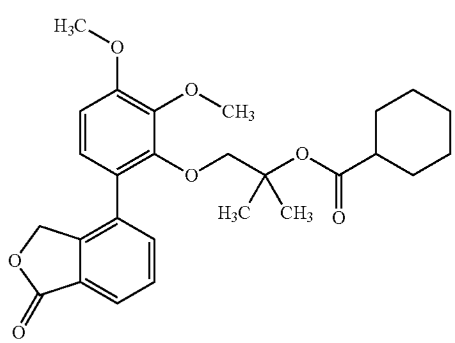 [SMILES: COc1ccc(-c2cccc3c2COC3=O)c(OCC(C)(C)OC(=O)C2CCCCC2)c1OC] | [2-[2,3-dimethoxy-6-(1-oxo-3H-isobenzofuran-4-yl)phenoxy]-1,1-dimethyl-ethyl] cyclohexanecarboxylate |

-continued

| Compound | Structure | IUPAC name |
|---|---|---|
| 1069 | 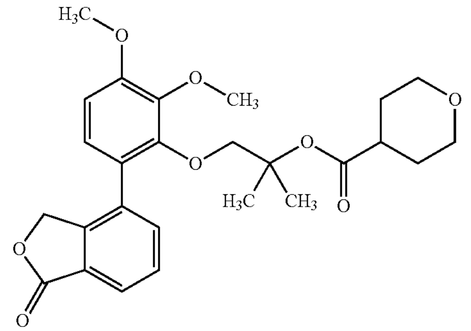 [SMILES: COc1ccc(-c2cccc3c2COC3=O)c(OCC(C)(C)OC(=O)C2CCOCC2)c1OC] | [2-[2,3-dimethoxy-6-(1-oxo-3H-isobenzofuran-4-yl)phenoxy]-1,1-dimethyl-ethyl]tetrahydropyran-4-carboxylate |
| 1070 | 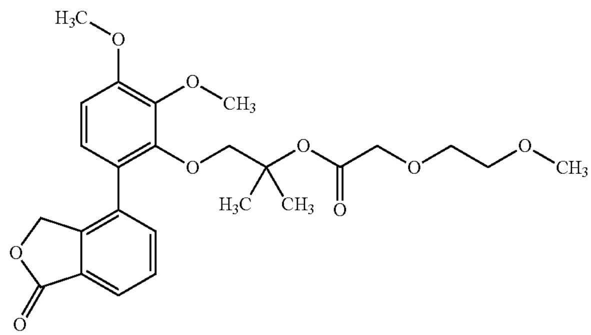 [SMILES: COCCOCC(=O)OC(C)(C)COc1c(-c2cccc3c2COC3=O)ccc(OC)c1OC] | [2-[2,3-dimethoxy-6-(1-oxo-3H-isobenzofuran-4-yl)phenoxy]-1,1-dimethyl-ethyl]2-(2-methoxyethoxy)acetate |

| Compound | Structure | Compound name |
|---|---|---|
| 1071 | 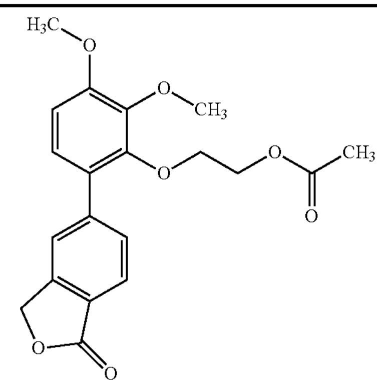 | 2-[2,3-dimethoxy-6-(1-oxo-3H-isobenzofuran-5-yl)phenoxy]ethyl acetate |
| 1072 | 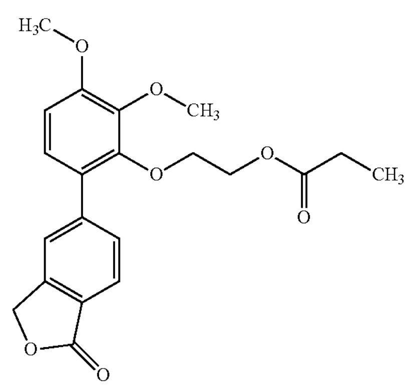 [SMILES: CCC(=O)OCCOc1c(-c2ccc3c(c2)COC3=O)ccc(OC)c1OC] | 2-[2,3-dimethoxy-6-(1-oxo-3H-isobenzofuran-5-yl)phenoxy]ethyl propanoate |

| Compound | Structure | Compound name |
|---|---|---|
| 1073 | 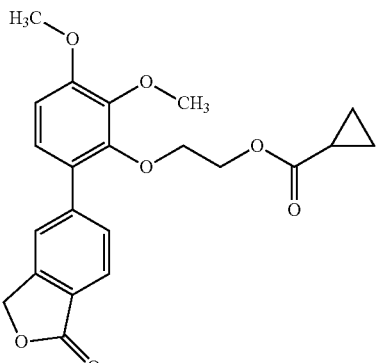 | 2-[2,3-dimethoxy-6-(1-oxo-3H-isobenzofuran-5-yl)phenoxy]ethyl cyclopropanecarboxylate |
| 1074 | 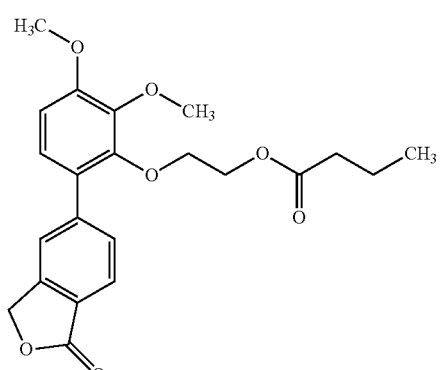 | 2-[2,3-dimethoxy-6-(1-oxo-3H-isobenzofuran-5-yl)phenoxy]ethyl butanoate |
| 1075 | 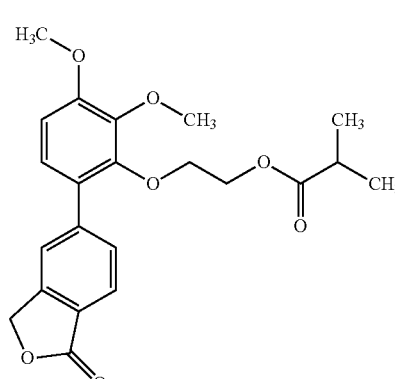 | 2-[2,3-dimethoxy-6-(1-oxo-3H-isobenzofuran-5-yl)phenoxy]ethyl 2-methylpropanoate |
| 1076 | 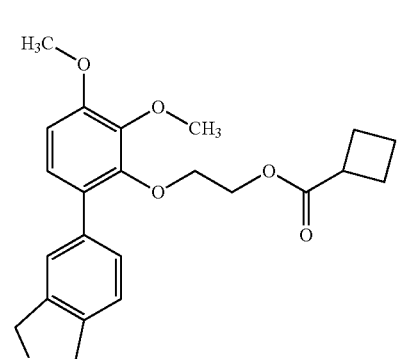 | 2-[2,3-dimethoxy-6-(1-oxo-3H-isobenzofuran-5-yl)phenoxy]ethyl cyclobutanecarboxylate |

-continued
| Compound | Structure | Compound name |
|---|---|---|
| 1077 | 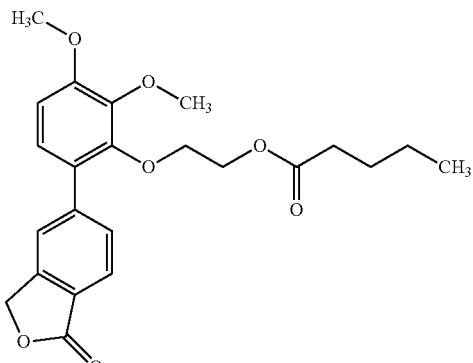 | 2-[2,3-dimethoxy-6-(1-oxo-3H-isobenzofuran-5-yl)phenoxy]ethyl pentanoate |
| 1078 | 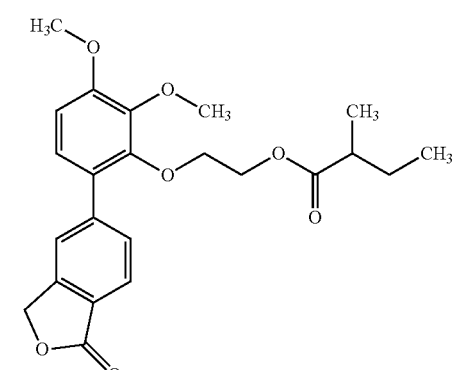 | 2-[2,3-dimethoxy-6-(1-oxo-3H-isobenzofuran-5-yl)phenoxy]ethyl 2-methylbutanoate |
| 1079 | 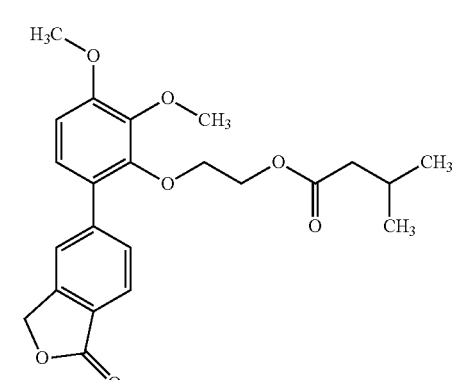 | 2-[2,3-dimethoxy-6-(1-oxo-3H-isobenzofuran-5-yl)phenoxy]ethyl 3-methylbutanoate |
| 1080 | 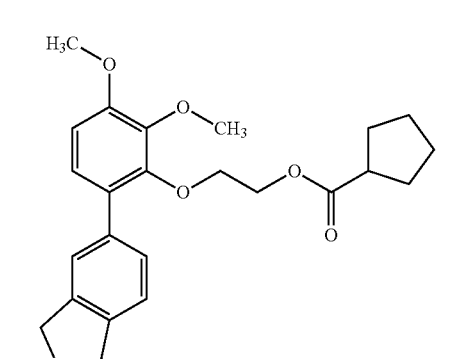 | 2-[2,3-dimethoxy-6-(1-oxo-3H-isobenzofuran-5-yl)phenoxy]ethyl cyclopentanecarboxylate |

| Compound | Structure | Compound name |
|---|---|---|
| 1081 | 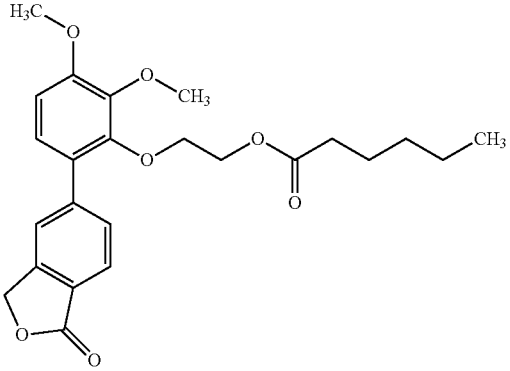 [SMILES: CCCCCC(=O)OCCOc1c(-c2ccc3c(c2)COC3=O)ccc(OC)c1OC] | 2-[2,3-dimethoxy-6-(1-oxo-3H-isobenzofuran-5-yl)phenoxy]ethyl hexanoate |
| 1082 | 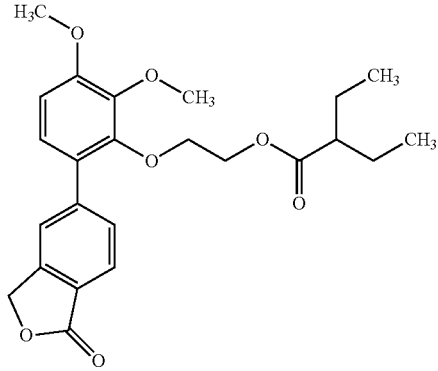 | 2-[2,3-dimethoxy-6-(1-oxo-3H-isobenzofuran-5-yl)phenoxy]ethyl 2-ethylbutanoate |
| 1083 | 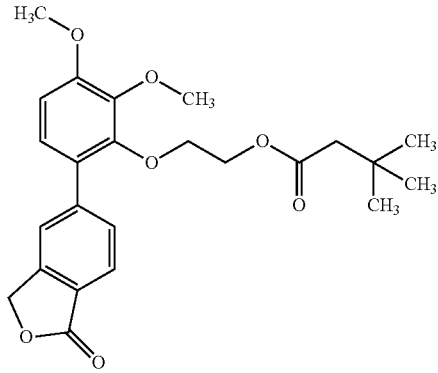 [SMILES: COc1ccc(-c2ccc3c(c2)COC3=O)c(OCCOC(=O)CC(C)(C)C)c1OC] | 2-[2,3-dimethoxy-6-(1-oxo-3H-isobenzofuran-5-yl)phenoxy]ethyl 3,3-dimethylbutanoate |
| 1084 | 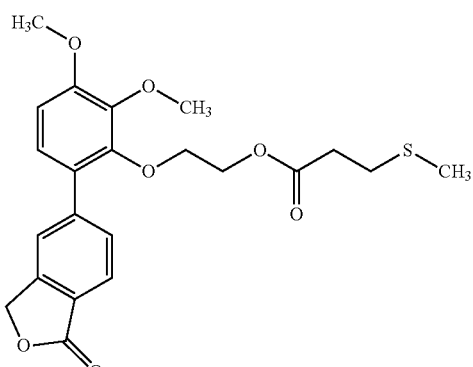 | 2-[2,3-dimethoxy-6-(1-oxo-3H-isobenzofuran-5-yl)phenoxy]ethyl 3-methylsulfanylpropanoate |

| Compound | Structure | Compound name |
|---|---|---|
| 1085 | 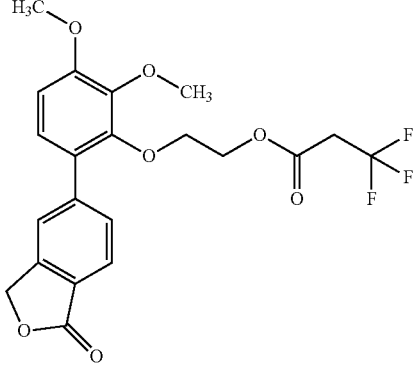 [SMILES: COc1ccc(-c2ccc3c(c2)COC3=O)c(OCCOC(=O)CC(F)(F)F)c1OC] | 2-[2,3-dimethoxy-6-(1-oxo-3H-isobenzofuran-5-yl)phenoxy]ethyl 3,3,3-trifluoropropanoate |
| 1086 | 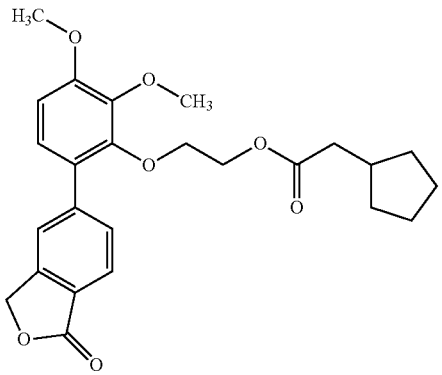 | 2-[2,3-dimethoxy-6-(1-oxo-3H-isobenzofuran-5-yl)phenoxy]ethyl 2-cyclopentylacetate |
| 1087 | 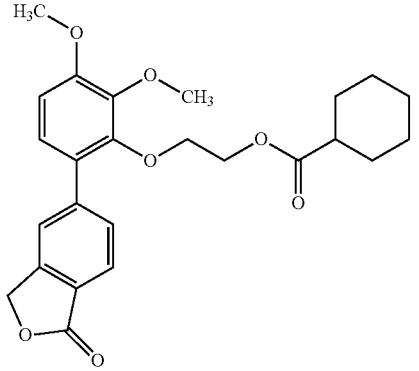 [SMILES: COc1ccc(-c2ccc3c(c2)COC3=O)c(OCCOC(=O)C2CCCCC2)c1OC] | 2-[2,3-dimethoxy-6-(1-oxo-3H-isobenzofuran-5-yl)phenoxy]ethyl cyclohexanecarboxylate |
| 1088 | 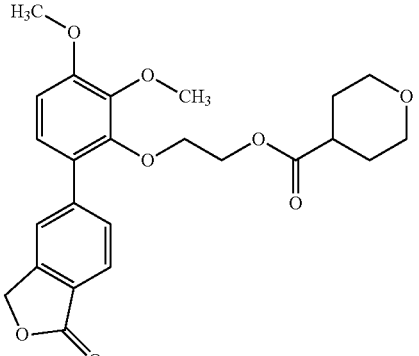 | 2-[2,3-dimethoxy-6-(1-oxo-3H-isobenzofuran-5-yl)phenoxy]ethyl tetrahydropyran-4-carboxylate |

-continued

| Compound | Structure | Compound name |
|---|---|---|
| 1089 | 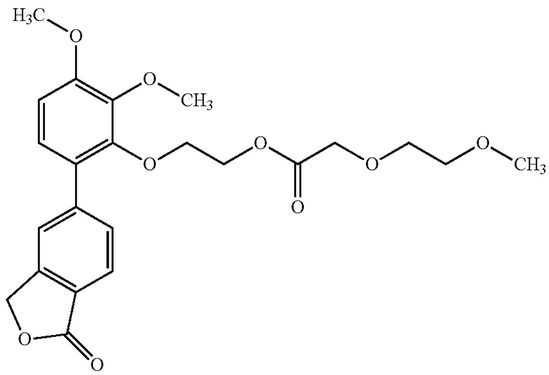 | 2-[2,3-dimethoxy-6-(1-oxo-3H-isobenzofuran-5-yl)phenoxy]ethyl 2-(2-methoxyethoxy)acetate |
| 1090 | 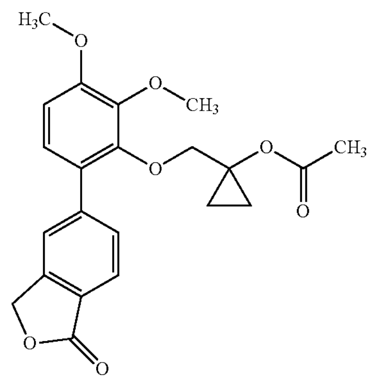 | [1-[[2,3-dimethoxy-6-(1-oxo-3H-isobenzofuran-5-yl)phenoxy]methyl]cyclopropyl] acetate |
| 1091 | 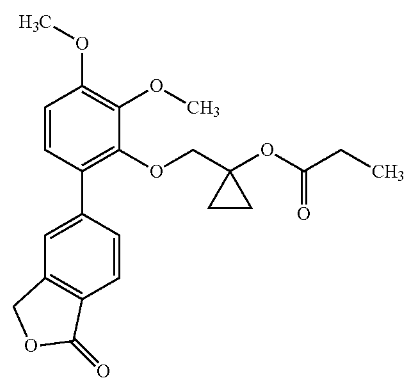 | [1-[[2,3-dimethoxy-6-(1-oxo-3H-isobenzofuran-5-yl)phenoxy]methyl]cyclopropyl] propanoate |
| 1092 | 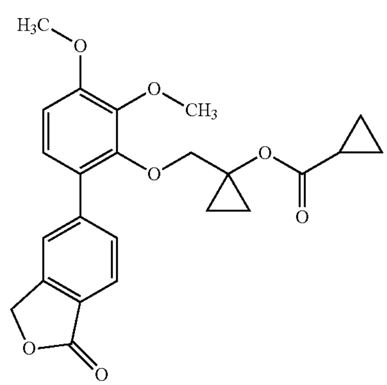 | [1-[[2,3-dimethoxy-6-(1-oxo-3H-isobenzofuran-5-yl)phenoxy]methyl]cyclopropyl] cyclopropanecarboxylate |

-continued

| Compound | Structure | Compound name |
|---|---|---|
| 1093 | 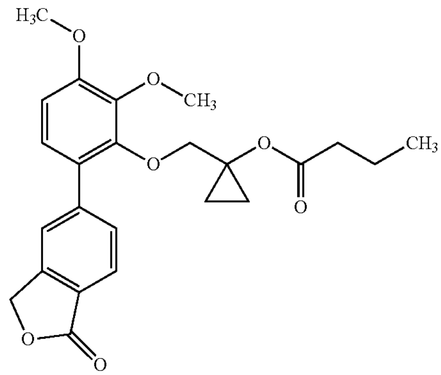 | [1-[[2,3-dimethoxy-6-(1-oxo-3H-isobenzofuran-5-yl)phenoxy]methyl]cyclopropyl] butanoate |
| 1094 | 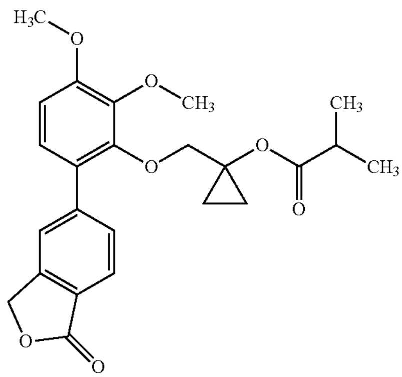 [SMILES: COc1ccc(-c2ccc3c(c2)COC3=O)c(OCC2(OC(=O)C(C)C)CC2)c1OC] | [1-[[2,3-dimethoxy-6-(1-oxo-3H-isobenzofuran-5-yl)phenoxy]methyl]cyclopropyl]2-methylpropanoate |
| 1095 | 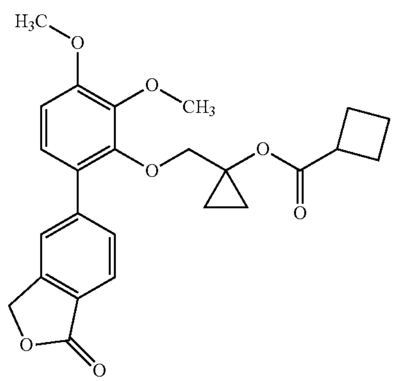 [SMILES: COc1ccc(-c2ccc3c(c2)COC3=O)c(OCC2(OC(=O)C3CCC3)CC2)c1OC] | [1-[[2,3-dimethoxy-6-(1-oxo-3H-isobenzofuran-5-yl)phenoxy]methyl]cyclopropyl] cyclobutanecarboxylate |
| 1096 | 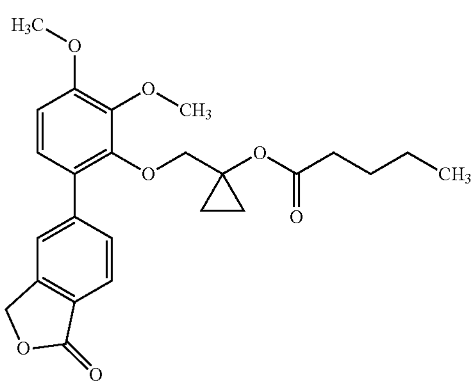 | [1-[[2,3-dimethoxy-6-(1-oxo-3H-isobenzofuran-5-yl)phenoxy]methyl]cyclopropyl] pentanoate |

-continued

| Compound | Structure | Compound name |
| --- | --- | --- |
| 1097 | 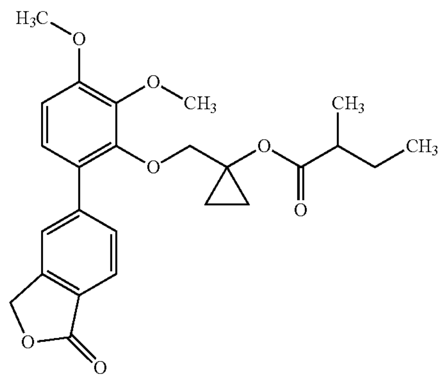 | [1-[[2,3-dimethoxy-6-(1-oxo-3H-isobenzofuran-5-yl)phenoxy]methyl]cyclopropyl] 2-methylbutanoate |
| 1098 | 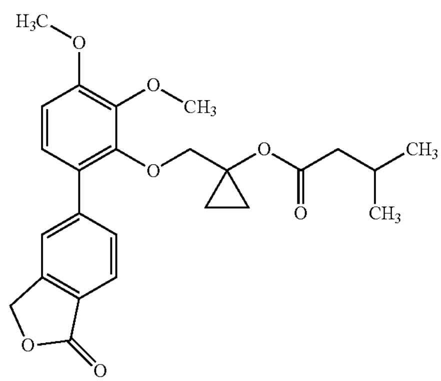 [SMILES: COc1ccc(-c2ccc3c(c2)COC3=O)c(OCC2(OC(=O)CC(C)C)CC2)c1OC] | [1-[[2,3-dimethoxy-6-(1-oxo-3H-isobenzofuran-5-yl)phenoxy]methyl]cyclopropyl] 3-methylbutanoate |
| 1099 | 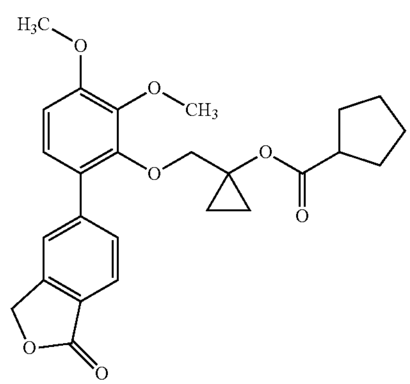 | [1-[[2,3-dimethoxy-6-(1-oxo-3H-isobenzofuran-5-yl)phenoxy]methyl]cyclopropyl] cyclopentanecarboxylate |
| 1100 | 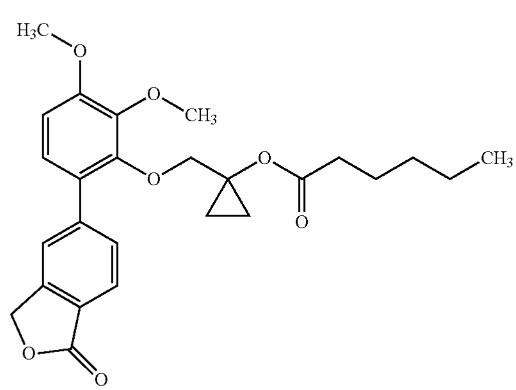 | [1-[[2,3-dimethoxy-6-(1-oxo-3H-isobenzofuran-5-yl)phenoxy]methyl]cyclopropyl] hexanoate |

-continued

| Compound | Structure | Compound name |
|---|---|---|
| 1101 | 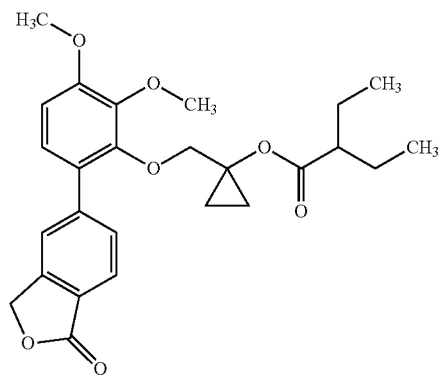 | [1-[[2,3-dimethoxy-6-(1-oxo-3H-isobenzofuran-5-yl)phenoxy]methyl]cyclopropyl] 2-ethylbutanoate |
| 1102 | 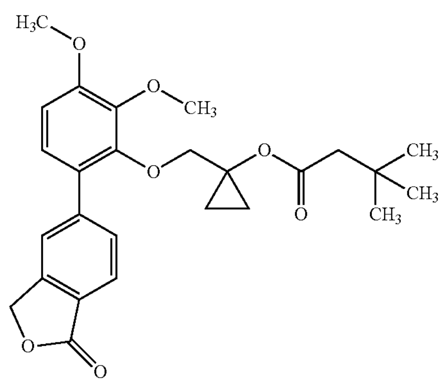 [SMILES: COc1ccc(-c2ccc3c(c2)COC3=O)c(OCC2(OC(=O)CC(C)(C)C)CC2)c1OC] | [1-[[2,3-dimethoxy-6-(1-oxo-3H-isobenzofuran-5-yl)phenoxy]methyl]cyclopropyl] 3,3-dimethylbutanoate |
| 1103 | 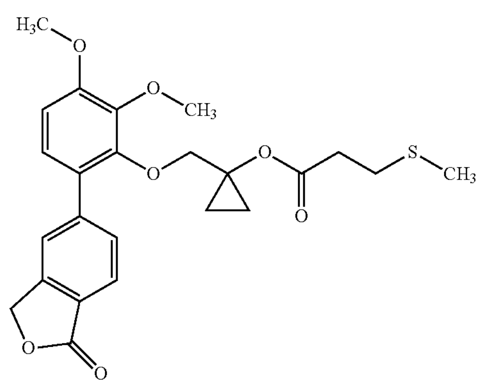 | [1-[[2,3-dimethoxy-6-(1-oxo-3H-isobenzofuran-5-yl)phenoxy]methyl]cyclopropyl] 3-methylsulfanylpropanoate |
| 1104 | 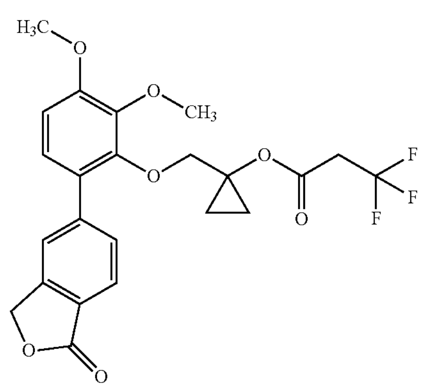 | [1-[[2,3-dimethoxy-6-(1-oxo-3H-isobenzofuran-5-yl)phenoxy]methyl]cyclopropyl] 3,3,3-trifluoropropanoate |

-continued

| Compound | Structure | Compound name |
|---|---|---|
| 1105 | 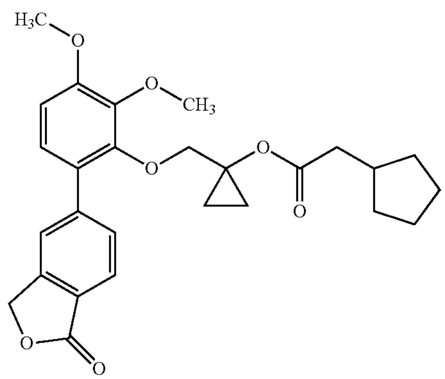 | [1-[[2,3-dimethoxy-6-(1-oxo-3H-isobenzofuran-5-yl)phenoxy]methyl]cyclopropyl] 2-cyclopentylacetate |
| 1106 | 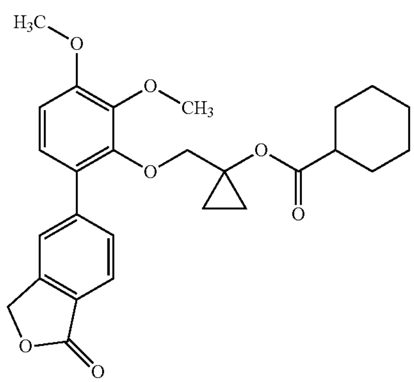 [SMILES: COc1ccc(-c2ccc3c(c2)COC3=O)c(OCC2(OC(=O)C3CCCCC3)CC2)c1OC] | [1-[[2,3-dimethoxy-6-(1-oxo-3H-isobenzofuran-5-yl)phenoxy]methyl]cyclopropyl] cyclohexanecarboxylate |
| 1107 | 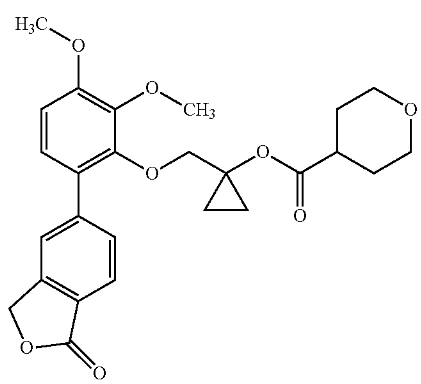 [SMILES: COc1ccc(-c2ccc3c(c2)COC3=O)c(OCC2(OC(=O)C3CCOCC3)CC2)c1OC] | [1-[[2,3-dimethoxy-6-(1-oxo-3H-isobenzofuran-5-yl)phenoxy]methyl]cyclopropyl] tetrahydropyran-4-carboxylate |
| 1108 | 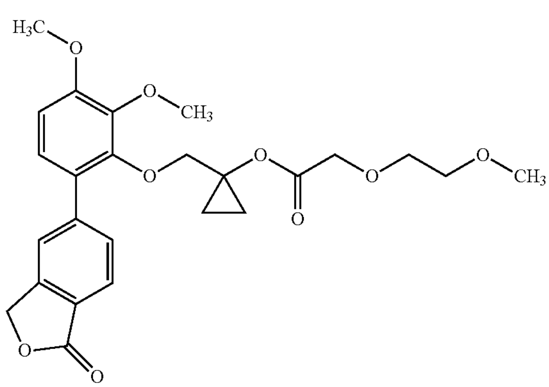 | [1-[[2,3-dimethoxy-6-(1-oxo-3H-isobenzofuran-5-yl)phenoxy]methyl]cyclopropyl] 2-(2-methoxyethoxy)acetate |

-continued
| Compound | Structure | Compound name |
|---|---|---|
| 1109 | 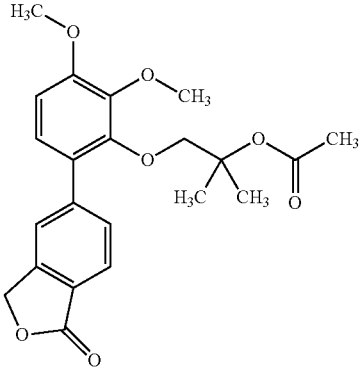 | [2-[2,3-dimethoxy-6-(1-oxo-3H-isobenzofuran-5-yl)phenoxy]-1,1-dimethyl-ethyl] acetate |
| 1110 | 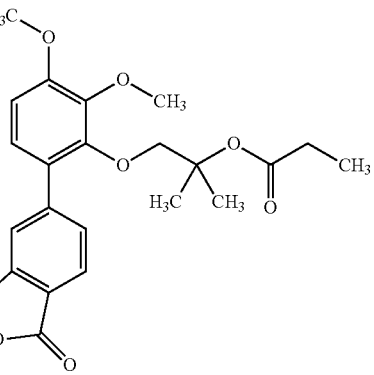 | [2-[2,3-dimethoxy-6-(1-oxo-3H-isobenzofuran-5-yl)phenoxy]-1,1-dimethyl-ethyl] propanoate |
| 1111 | 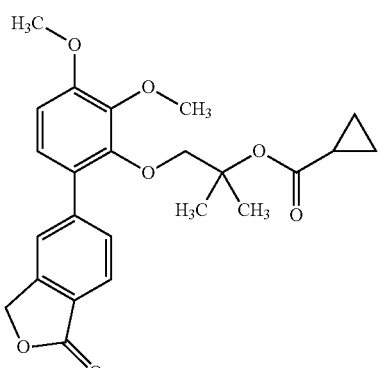 | [2-[2,3-dimethoxy-6-(1-oxo-3H-isobenzofuran-5-yl)phenoxy]-1,1-dimethyl-ethyl] cyclopropanecarboxylate |
| 1112 | 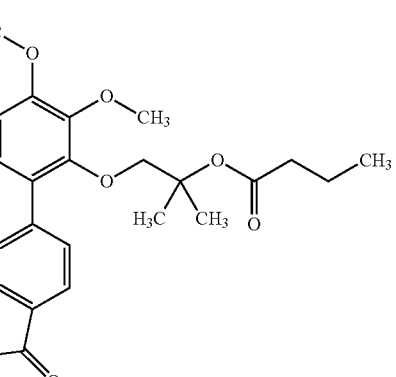 | [2-[2,3-dimethoxy-6-(1-oxo-3H-isobenzofuran-5-yl)phenoxy]-1,1-dimethyl-ethyl] butanoate |

| Compound | Structure | Compound name |
|---|---|---|
| 1113 | 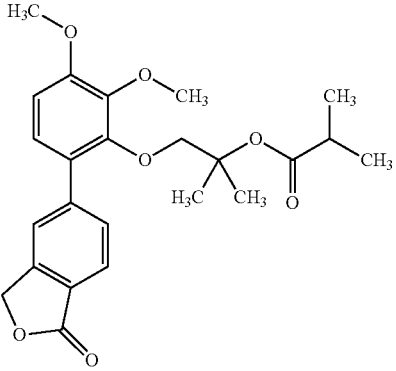 | [2-[2,3-dimethoxy-6-(1-oxo-3H-isobenzofuran-5-yl)phenoxy]-1,1-dimethyl-ethyl] 2-methylpropanoate |
| 1114 | 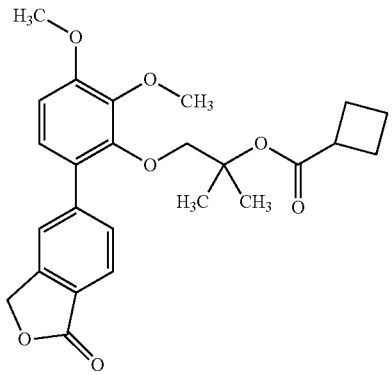 | [2-[2,3-dimethoxy-6-(1-oxo-3H-isobenzofuran-5-yl)phenoxy]-1,1-dimethyl-ethyl] cyclobutanecarboxylate |
| 1115 | 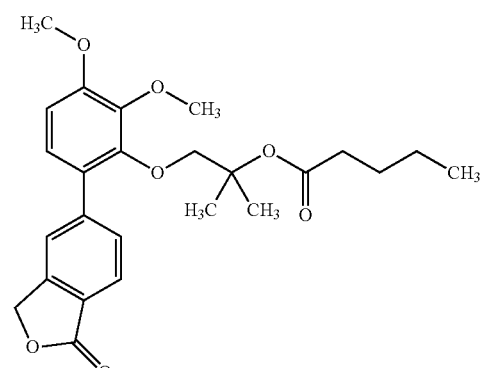 | [2-[2,3-dimethoxy-6-(1-oxo-3H-isobenzofuran-5-yl)phenoxy]-1,1-dimethyl-ethyl] pentanoate |
| 1116 | 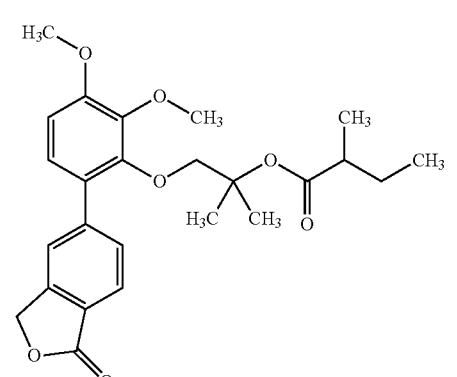 | [2-[2,3-dimethoxy-6-(1-oxo-3H-isobenzofuran-5-yl)phenoxy]-1,1-dimethyl-ethyl] 2-methylbutanoate |

| Compound | Structure | Compound name |
|---|---|---|
| 1117 | 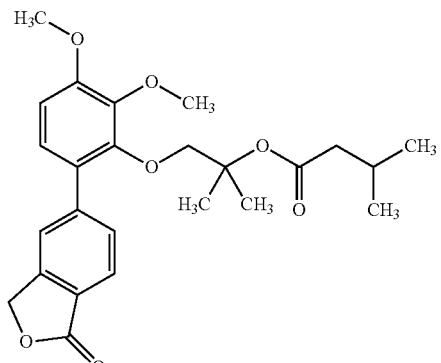 | [2-[2,3-dimethoxy-6-(1-oxo-3H-isobenzofuran-5-yl)phenoxy]-1,1-dimethyl-ethyl] 3-methylbutanoate |
| 1118 | 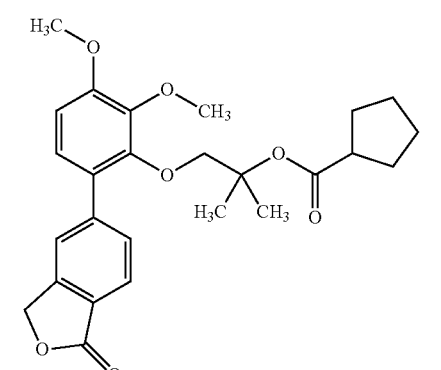 | [2-[2,3-dimethoxy-6-(1-oxo-3H-isobenzofuran-5-yl)phenoxy]-1,1-dimethyl-ethyl] cyclopentanecarboxylate |
| 1119 | 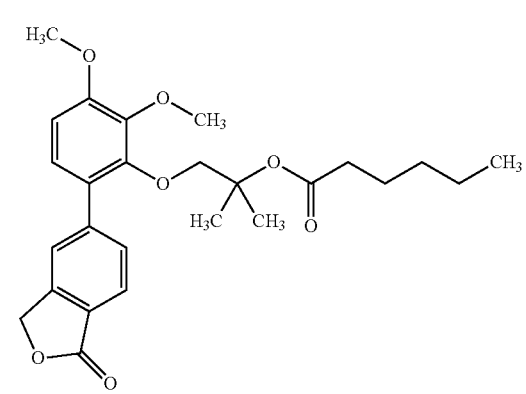 | [2-[2,3-dimethoxy-6-(1-oxo-3H-isobenzofuran-5-yl)phenoxy]-1,1-dimethyl-ethyl] hexanoate |
| 1120 | 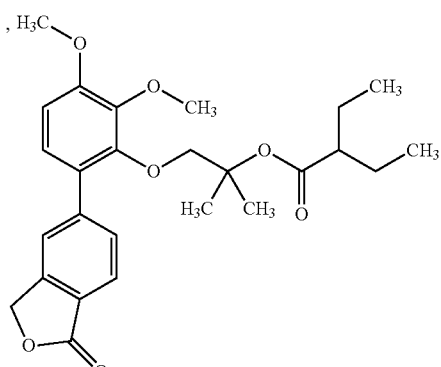 | [2-[2,3-dimethoxy-6-(1-oxo-3H-isobenzofuran-5-yl)phenoxy]-1,1-dimethyl-ethyl] 2-ethylbutanoate |

-continued

| Compound | Structure | Compound name |
|---|---|---|
| 1121 | 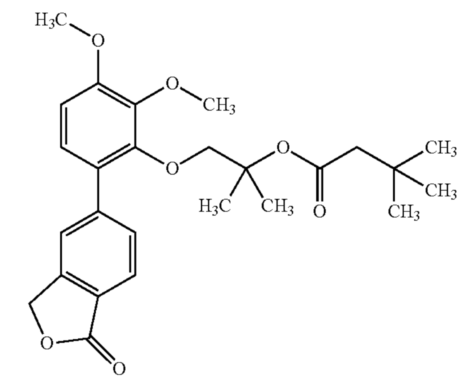 | [2-[2,3-dimethoxy-6-(1-oxo-3H-isobenzofuran-5-yl)phenoxy]-1,1-dimethyl-ethyl] 3,3-dimethylbutanoate |
| 1122 | 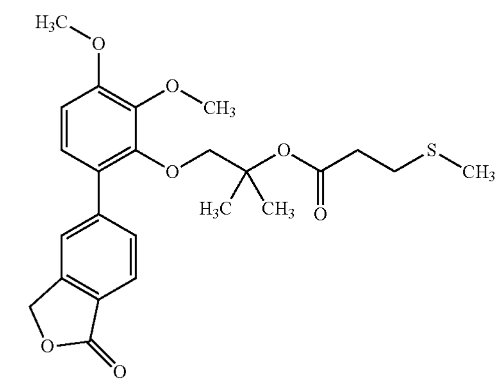 | [2-[2,3-dimethoxy-6-(1-oxo-3H-isobenzofuran-5-yl)phenoxy]-1,1-dimethyl-ethyl] 3-methylsulfanylpropanoate |
| 1123 | 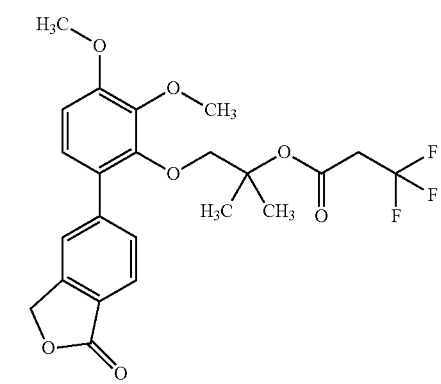 | [2-[2,3-dimethoxy-6-(1-oxo-3H-isobenzofuran-5-yl)phenoxy]-1,1-dimethyl-ethyl] 3,3,3-trifluoropropanoate |
| 1124 | 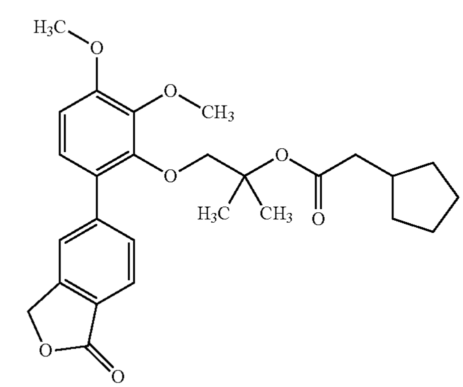 | [2-[2,3-dimethoxy-6-(1-oxo-3H-isobenzofuran-5-yl)phenoxy]-1,1-dimethyl-ethyl] 2-cyclopentylacetate |

| Compound | Structure | Compound name |
|---|---|---|
| 1125 | 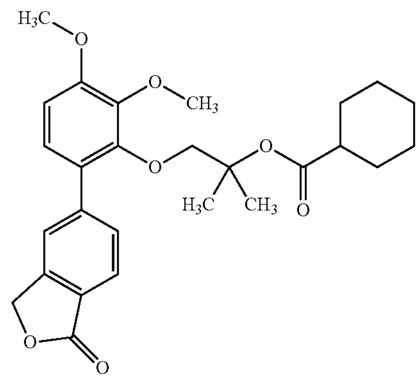 | [2-[2,3-dimethoxy-6-(1-oxo-3H-isobenzofuran-5-yl)phenoxy]-1,1-dimethyl-ethyl] cyclohexanecarboxylate |
| 1126 | 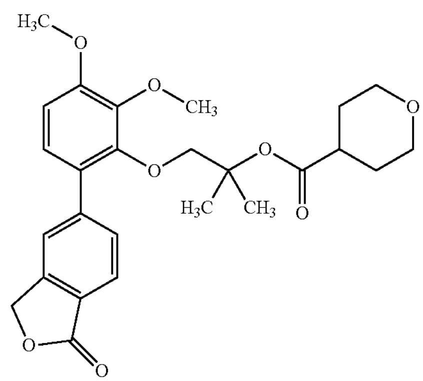 | [2-[2,3-dimethoxy-6-(1-oxo-3H-isobenzofuran-5-yl)phenoxy]-1,1-dimethyl-ethyl] tetrahydropyran-4-carboxylate |
| 1127 | 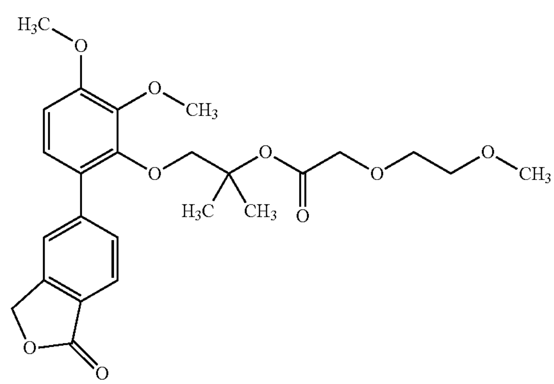 | [2-[2,3-dimethoxy-6-(1-oxo-3H-isobenzofuran-5-yl)phenoxy]-1,1-dimethyl-ethyl] 2-(2-methoxyethoxy)acetate |
| 1128 | 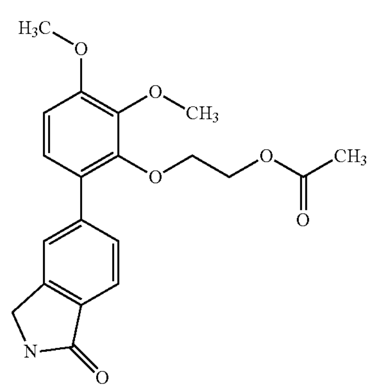 | 2-[2,3-dimethoxy-6-(1-oxoisoindolin-5-yl)phenoxy]ethyl acetate |

| Compound | Structure | Compound name |
|---|---|---|
| 1129 | 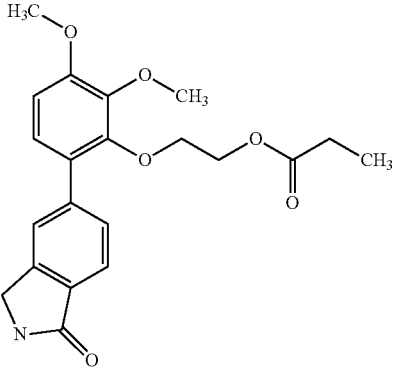 | 2-[2,3-dimethoxy-6-(1-oxoisoindolin-5-yl)phenoxy]ethyl propanoate |
| 1130 | 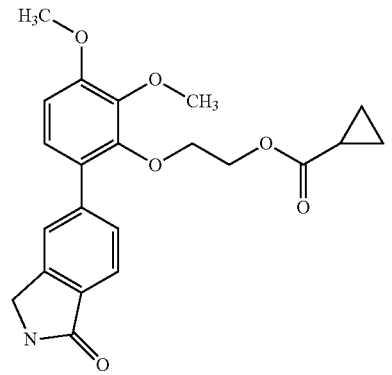 | 2-[2,3-dimethoxy-6-(1-oxoisoindolin-5-yl)phenoxy]ethyl cyclopropanecarboxylate |
| 1131 | 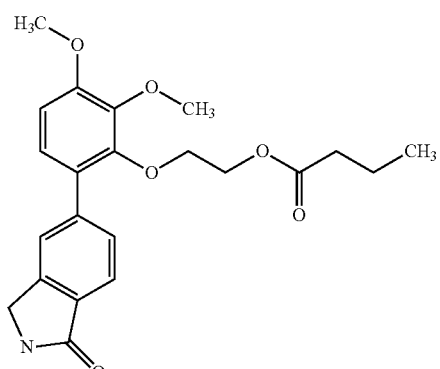 | 2-[2,3-dimethoxy-6-(1-oxoisoindolin-5-yl)phenoxy]ethyl butanoate |
| 1132 | 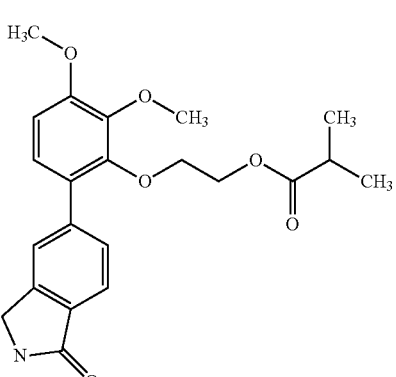 | 2-[2,3-dimethoxy-6-(1-oxoisoindolin-5-yl)phenoxy]ethyl 2-methylpropanoate |

| Compound | Structure | Compound name |
|---|---|---|
| 1133 | 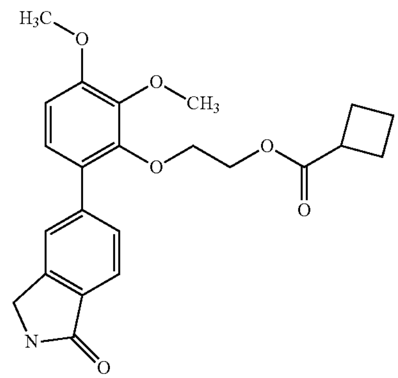 | 2-[2,3-dimethoxy-6-(1-oxoisoindolin-5-yl)phenoxy]ethyl cyclobutanecarboxylate |
| 1134 | 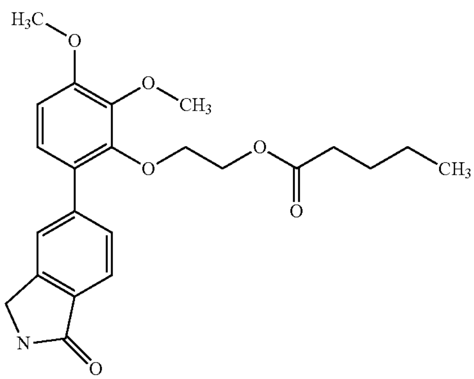 | 2-[2,3-dimethoxy-6-(1-oxoisoindolin-5-yl)phenoxy]ethyl pentanoate |
| 1135 | 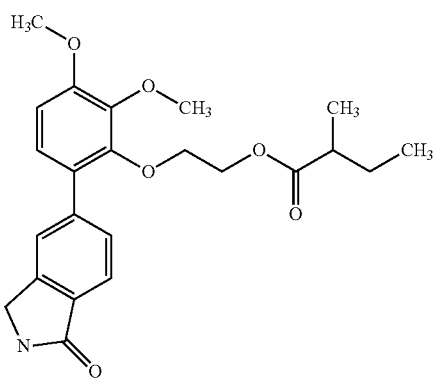 | 2-[2,3-dimethoxy-6-(1-oxoisoindolin-5-yl)phenoxy]ethyl 2-methylbutanoate |
| 1136 | 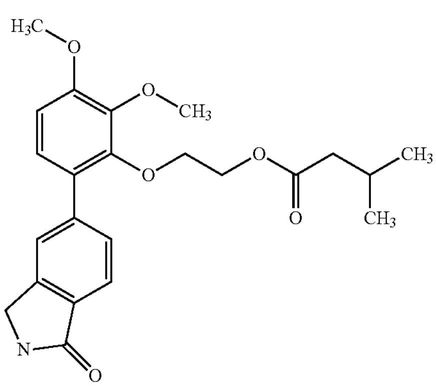 | 2-[2,3-dimethoxy-6-(1-oxoisoindolin-5-yl)phenoxy]ethyl 3-methylbutanoate |

| Compound | Structure | Compound name |
|---|---|---|
| 1137 | 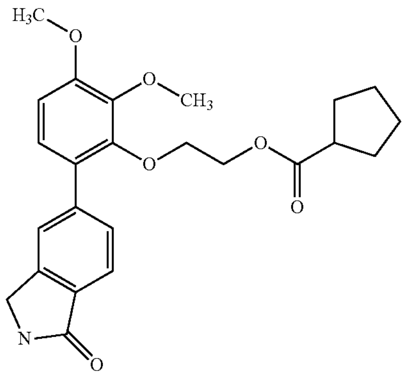 | 2-[2,3-dimethoxy-6-(1-oxoisoindolin-5-yl)phenoxy]ethyl cyclopentanecarboxylate |
| 1138 | 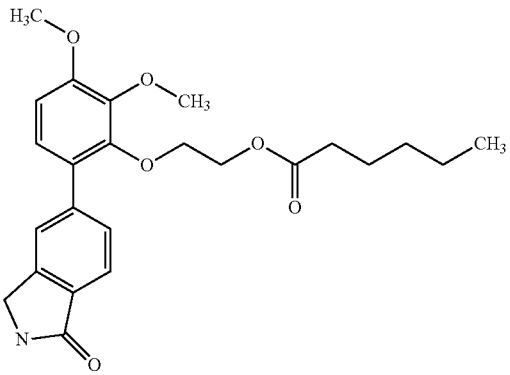 | 2-[2,3-dimethoxy-6-(1-oxoisoindolin-5-yl)phenoxy]ethyl hexanoate |
| 1139 | 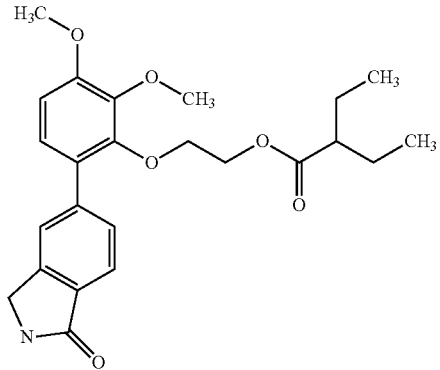 | 2-[2,3-dimethoxy-6-(1-oxoisoindolin-5-yl)phenoxy]ethyl 2-ethylbutanoate |
| 1140 | 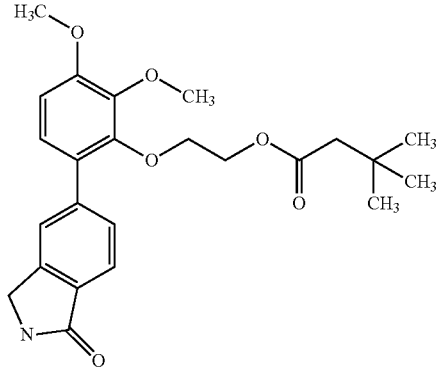 | 2-[2,3-dimethoxy-6-(1-oxoisoindolin-5-yl)phenoxy]ethyl 3,3-dimethylbutanoate |

| Compound | Structure | Compound name |
|---|---|---|
| 1141 | 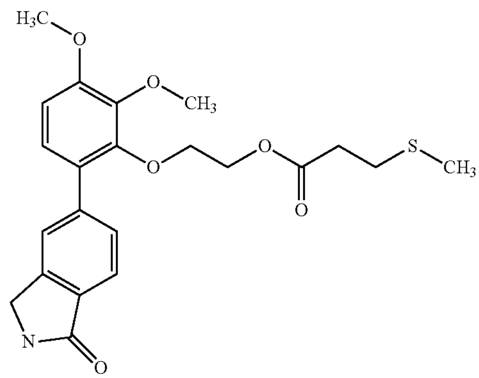 | 2-[2,3-dimethoxy-6-(1-oxoisoindolin-5-yl)phenoxy]ethyl 3-methylsulfanylpropanoate |
| 1142 | 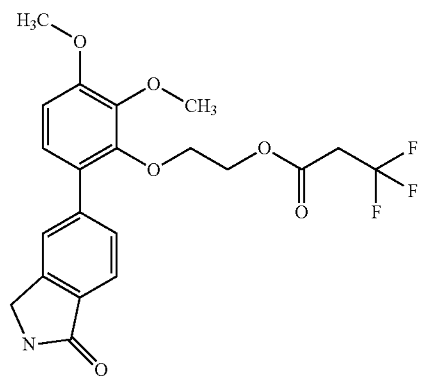 | 2-[2,3-dimethoxy-6-(1-oxoisoindolin-5-yl)phenoxy]ethyl 3,3,3-trifluoropropanoate |
| 1143 | 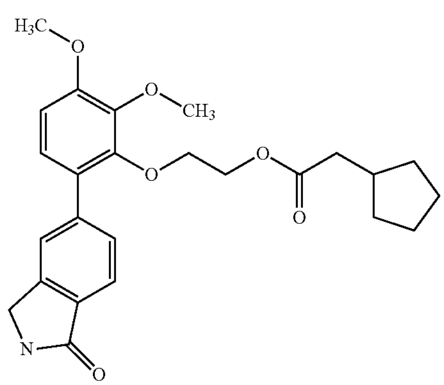 | 2-[2,3-dimethoxy-6-(1-oxoisoindolin-5-yl)phenoxy]ethyl 2-cyclopentylacetate |
| 1144 | 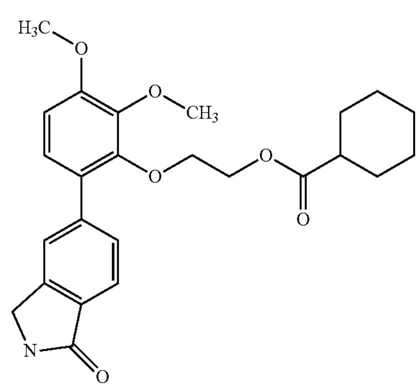 | 2-[2,3-dimethoxy-6-(1-oxoisoindolin-5-yl)phenoxy]ethyl cyclohexanecarboxylate |

| Compound | Structure | Compound name |
|---|---|---|
| 1145 | 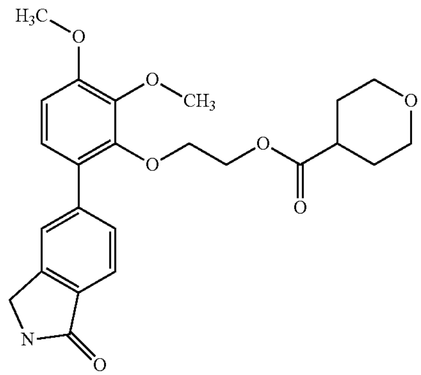 | 2-[2,3-dimethoxy-6-(1-oxoisoindolin-5-yl)phenoxy]ethyl tetrahydropyran-4-carboxylate |
| 1146 | 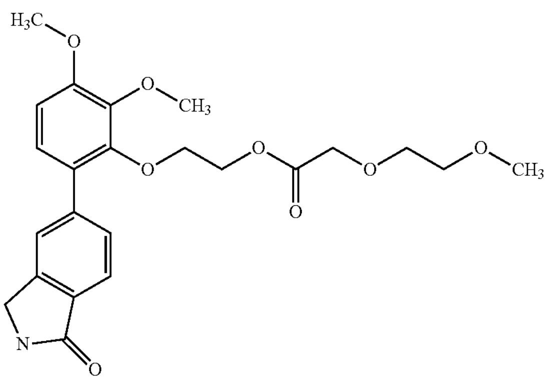 | 2-[2,3-dimethoxy-6-(1-oxoisoindolin-5-yl)phenoxy]ethyl 2-(2-methoxyethoxy)acetate |
| 1147 | 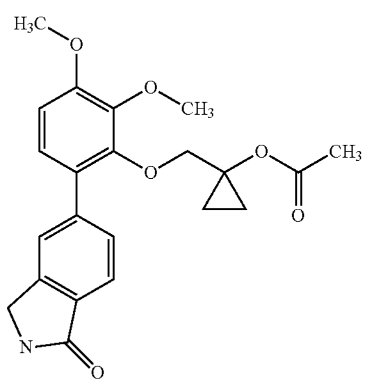 | [1-[[2,3-dimethoxy-6-(1-oxoisoindolin-5-yl)phenoxy]methyl]cyclopropyl] acetate |
| 1148 | 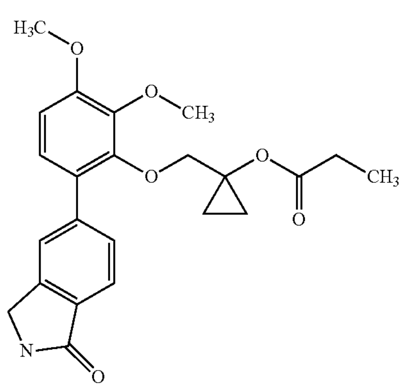 | [1-[[2,3-dimethoxy-6-(1-oxoisoindolin-5-yl)phenoxy]methyn cyclopropyl] propanoate |

-continued

| Compound | Structure | Compound name |
|---|---|---|
| 1149 | 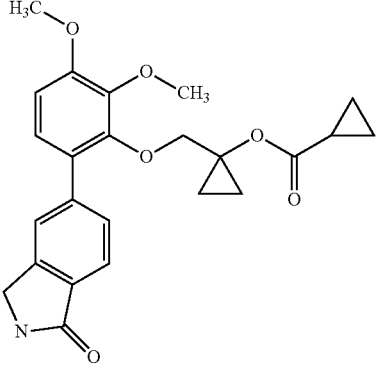 | [1-[[2,3-dimethoxy-6-(1-oxoisoindolin-5-yl)phenoxy]methyl]cyclopropyl] cyclopropanecarboxylate |
| 1150 | 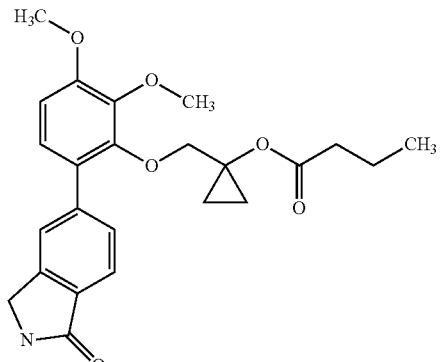 | [1-[[2,3-dimethoxy-6-(1-oxoisoindolin-5-yl)phenoxy]methyl]cyclopropyl] butanoate |
| 1151 | 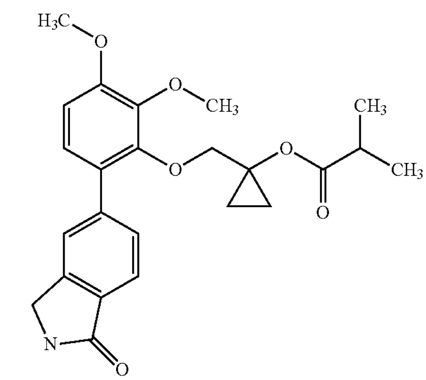 | [1-[[2,3-dimethoxy-6-(1-oxoisoindolin-5-yl)phenoxy]methyl]cyclopropyl] 2-methylpropanoate |
| 1152 | 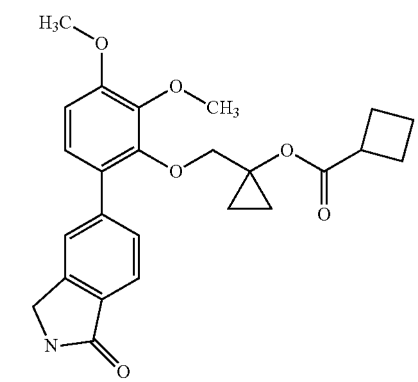 | [1-[[2,3-dimethoxy-6-(1-oxoisoindolin-5-yl)phenoxy]methyl]cyclopropyl] cyclobutanecarboxylate |

| Compound | Structure | Compound name |
|---|---|---|
| 1153 | 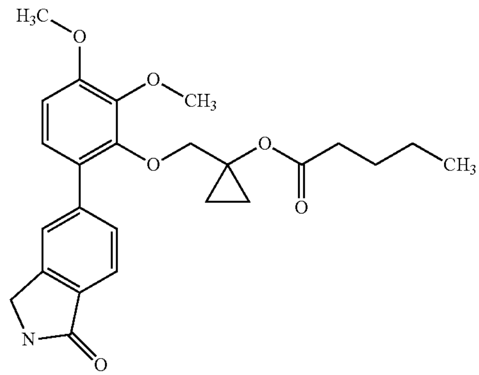 | [1-[[2,3-dimethoxy-6-(1-oxoisoindolin-5-yl)phenoxy]methyl]cyclopropyl] pentanoate |
| 1154 | 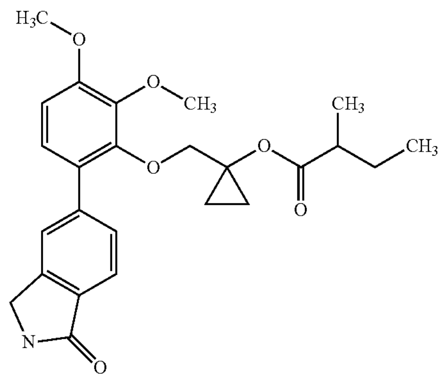 | [1-[[2,3-dimethoxy-6-(1-oxoisoindolin-5-yl)phenoxy]methyl]cyclopropyl] 2-methylbutanoate |
| 1155 | 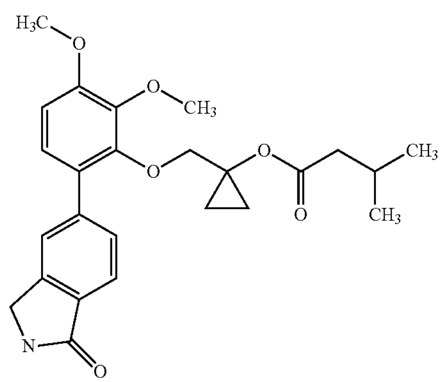 | [1-[[2,3-dimethoxy-6-(1-oxoisoindolin-5-yl)phenoxy]methyl]cyclopropyl] 3-methylbutanoate |
| 1156 | 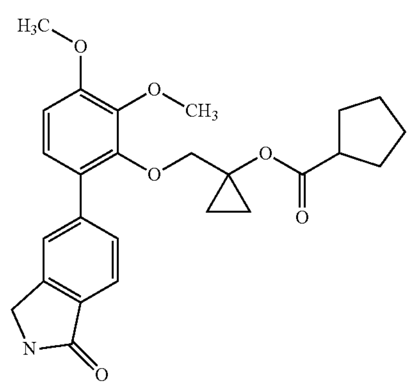 | [1-[[2,3-dimethoxy-6-(1-oxoisoindolin-5-yl)phenoxy]methyl]cyclopropyl] cyclopentanecarboxylate |

-continued
| Compound | Structure | Compound name |
|---|---|---|
| 1157 | 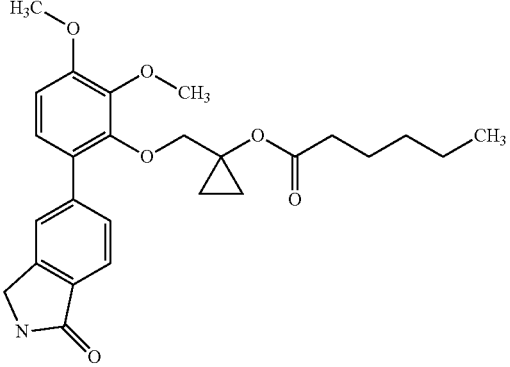 | [1-[[2,3-dimethoxy-6-(1-oxoisoindolin-5-yl)phenoxy]methyl]cyclopropyl] hexanoate |
| 1158 | 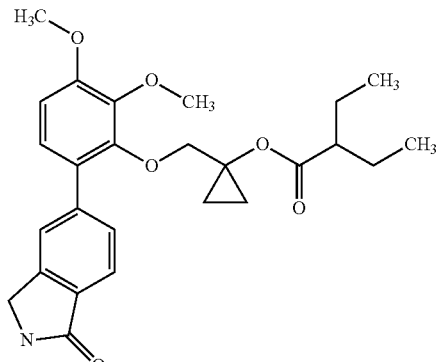 | [1-[[2,3-dimethoxy-6-(1-oxoisoindolin-5-yl)phenoxy]methyl]cyclopropyl] 2-ethylbutanoate |
| 1159 | 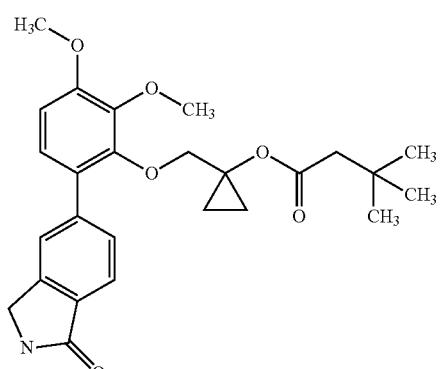 | [1-[[2,3-dimethoxy-6-(1-oxoisoindolin-5-yl)phenoxy]methyl]cyclopropyl] 3,3-dimethylbutanoate |
| 1160 | 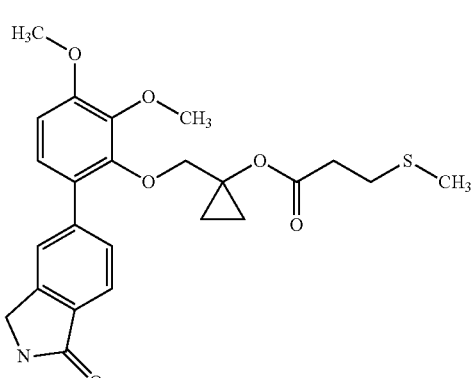 | [1-[[2,3-dimethoxy-6-(1-oxoisoindolin-5-yl)phenoxy]methyl]cyclopropyl] 3-methylsulfanylpropanoate |

-continued

| Compound | Structure | Compound name |
|---|---|---|
| 1161 | 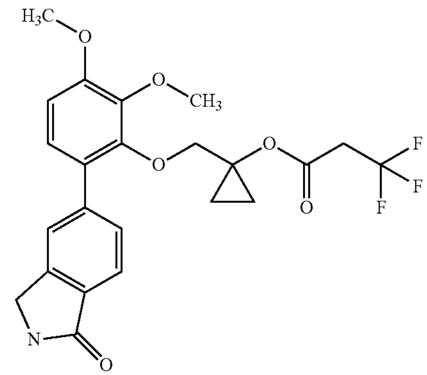 | [1-[[2,3-dimethoxy-6-(1-oxoisoindolin-5-yl)phenoxy]methyl]cyclopropyl] 3,3,3-trifluoropropanoate |
| 1162 | 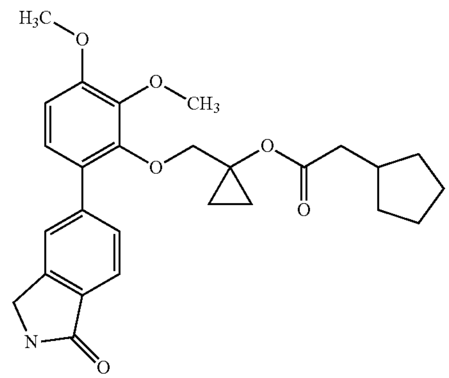 | [1-[[2,3-dimethoxy-6-(1-oxoisoindolin-5-yl)phenoxy]methyl]cyclopropyl] 2-cyclopentylacetate |
| 1163 | 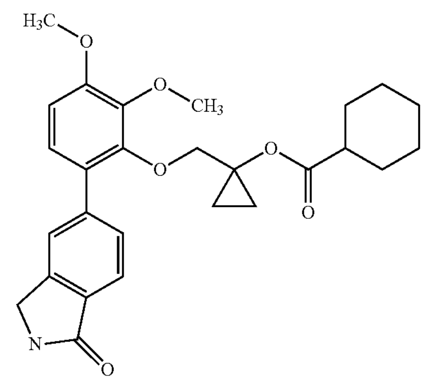 | [1-[[2,3-dimethoxy-6-(1-oxoisoindolin-5-yl)phenoxy]methyl]cyclopropyl] cyclohexanecarboxylate |
| 1164 | 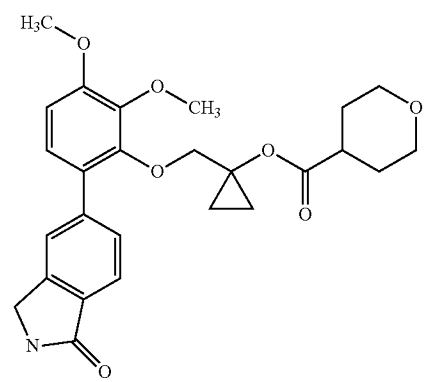 | [1-[[2,3-dimethoxy-6-(1-oxoisoindolin-5-yl)phenoxy]methyl]cyclopropyl] tetrahydropyran-4-carboxylate |

| Compound | Structure | Compound name |
|---|---|---|
| 1165 | 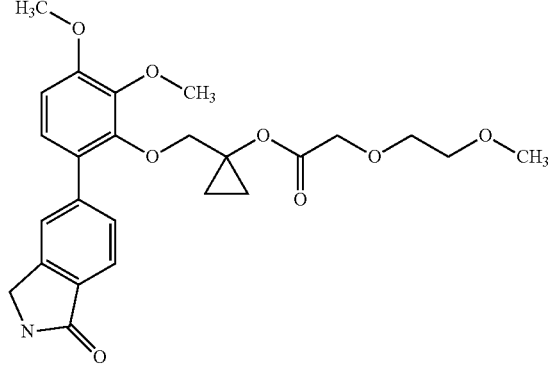 | [1-[[2,3-dimethoxy-6-(1-oxoisoindolin-5-yl)phenoxy]methyl]cyclopropyl] 2-(2-methoxyethoxy)acetate |
| 1166 | 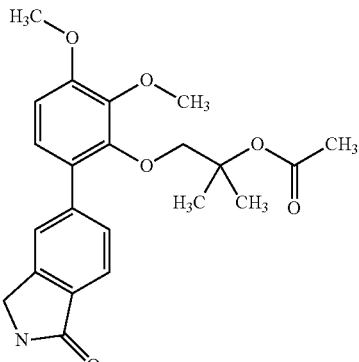 | [2-[2,3-dimethoxy-6-(1-oxoisoindolin-5-yl)phenoxy]-1,1-dimethyl-ethyl] acetate |
| 1167 | 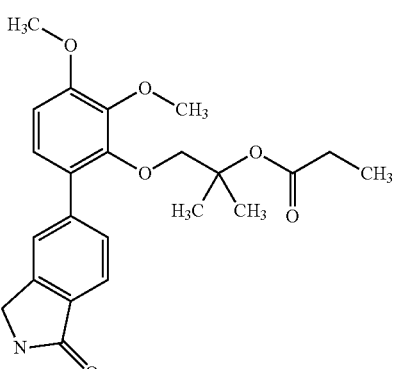 | [2-[2,3-dimethoxy-6-(1-oxoisoindolin-5-yl)phenoxy]-1,1-dimethyl-ethyl] propanoate |
| 1168 | 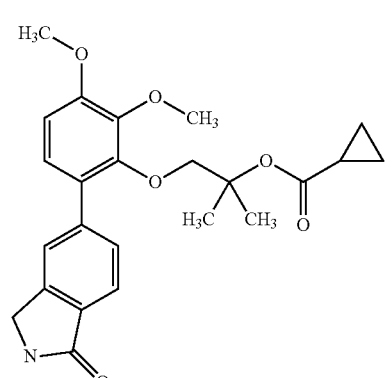 | [2-[2,3-dimethoxy-6-(1-oxoisoindolin-5-yl)phenoxy]-1,1-dimethyl-ethyl] cyclopropanecarboxylate |

-continued

| Compound | Structure | Compound name |
|---|---|---|
| 1169 | 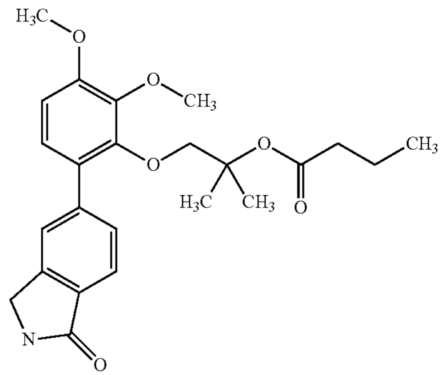 [SMILES: CCCC(=O)OC(C)(C)COc1c(-c2ccc3c(c2)COC3=O)ccc(OC)c1OC] | [2-[2,3-dimethoxy-6-(1-oxoisoindolin-5-yl)phenoxy]-1,1-dimethyl-ethyl] butanoate |
| 1170 | 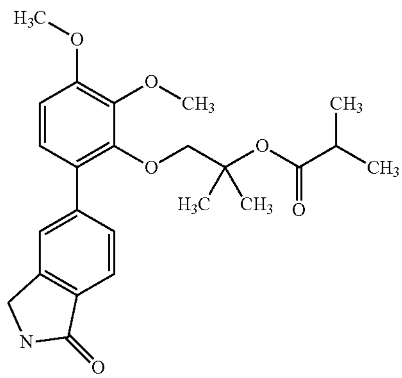 [SMILES: COc1ccc(-c2ccc3c(c2)COC3=O)c(OCC(C)(C)OC(=O)C(C)C)c1OC] | [2-[2,3-dimethoxy-6-(1-oxoisoindolin-5-yl)phenoxy]-1,1-dimethyl-ethyl] 2-methylpropanoate |
| 1171 | 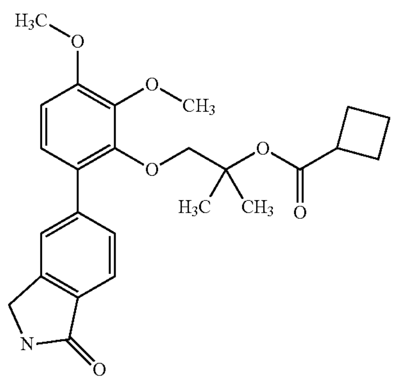 [SMILES: COc1ccc(-c2ccc3c(c2)COC3=O)c(OCC(C)(C)OC(=O)C2CCC2)c1OC] | [2-[2,3-dimethoxy-6-(1-oxoisoindolin-5-yl)phenoxy]-1,1-dimethyl-ethyl] cyclobutanecarboxylate |
| 1172 | 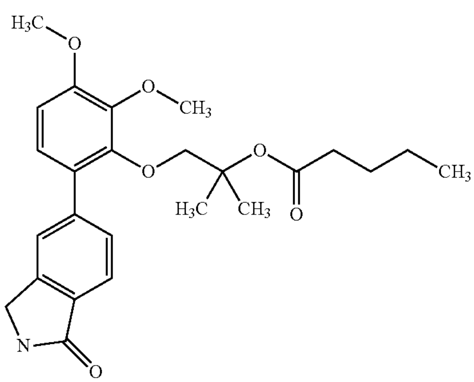 [SMILES: CCCCC(=O)OC(C)(C)COc1c(-c2ccc3c(c2)COC3=O)ccc(OC)c1OC] | [2-[2,3-dimethoxy-6-(1-oxoisoindolin-5-yl)phenoxy]-1,1-dimethyl-ethyl] pentanoate |

-continued

| Compound | Structure | Compound name |
|---|---|---|
| 1173 | 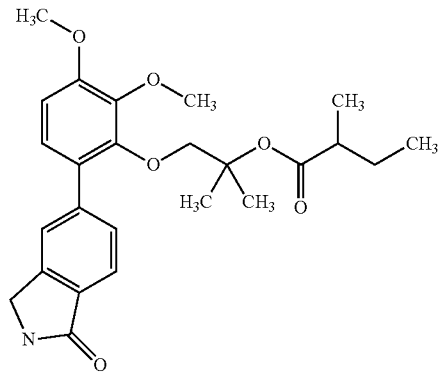 [SMILES: CCC(C)C(=O)OC(C)(C)COc1c(-c2ccc3c(c2)COC3=O)ccc(OC)c1OC] | [2-[2,3-dimethoxy-6-(1-oxoisoindolin-5-yl)phenoxy]-1,1-dimethyl-ethyl] 2-methylbutanoate |
| 1174 | 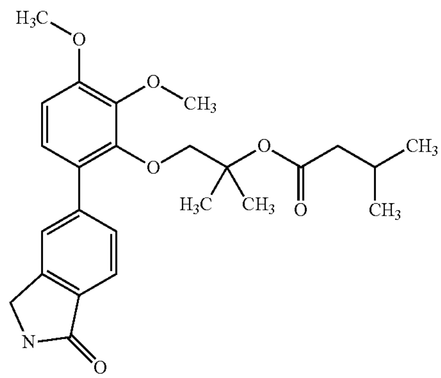 [SMILES: COc1ccc(-c2ccc3c(c2)COC3=O)c(OCC(C)(C)OC(=O)CC(C)C)c1OC] | [2-[2,3-dimethoxy-6-(1-oxoisoindolin-5-yl)phenoxy]-1,1-dimethyl-ethyl] 3-methylbutanoate |
| 1175 | 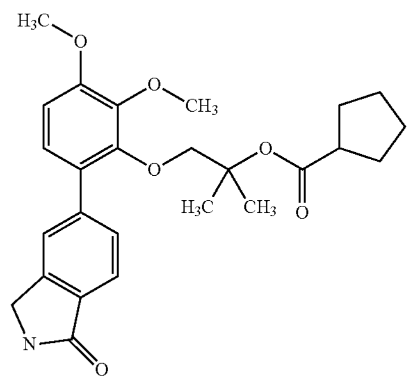 [SMILES: COc1ccc(-c2ccc3c(c2)COC3=O)c(OCC(C)(C)OC(=O)C2CCCC2)c1OC] | [2-[2,3-dimethoxy-6-(1-oxoisoindolin-5-yl)phenoxy]-1,1-dimethyl-ethyl] cyclopentanecarboxylate |
| 1176 | 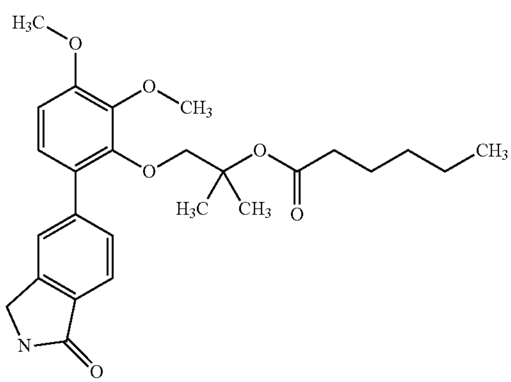 [SMILES: CCCCCC(=O)OC(C)(C)COc1c(-c2ccc3c(c2)COC3=O)ccc(OC)c1OC] | [2-[2,3-dimethoxy-6-(1-oxoisoindolin-5-yl)phenoxy]-1,1-dimethyl-ethyl] hexanoate |

-continued

| Compound | Structure | Compound name |
|---|---|---|
| 1177 | 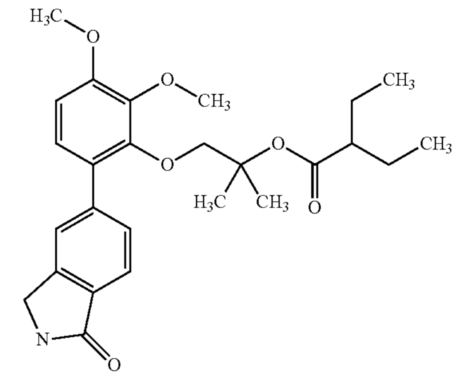 [SMILES: CCC(CC)C(=O)OC(C)(C)COc1c(-c2ccc3c(c2)COC3=O)ccc(OC)c1OC] | [2-[2,3-dimethoxy-6-(1-oxoisoindolin-5-yl)phenoxy]-1,1-dimethyl-ethyl] 2-ethylbutanoate |
| 1178 | 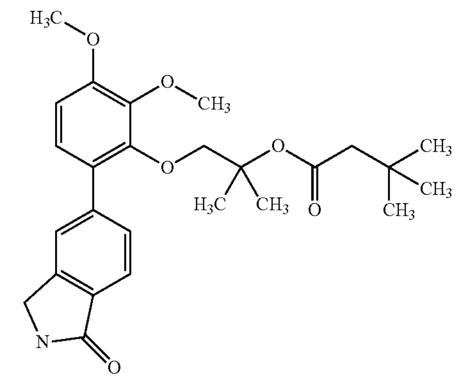 [SMILES: COc1ccc(-c2ccc3c(c2)COC3=O)c(OCC(C)(C)OC(=O)CC(C)(C)C)c1OC] | [2-[2,3-dimethoxy-6-(1-oxoisoindolin-5-yl)phenoxy]-1,1-dimethyl-ethyl] 3,3-dimethylbutanoate |
| 1179 | 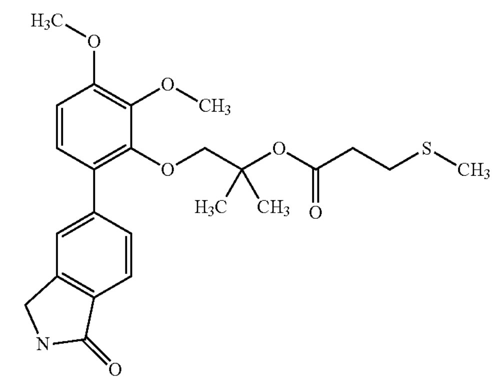 [SMILES: COc1ccc(-c2ccc3c(c2)COC3=O)c(OCC(C)(C)OC(=O)CCSC)c1OC] | [2-[2,3-dimethoxy-6-(1-oxoisoindolin-5-yl)phenoxy]-1,1-dimethyl-ethyl] 3-methylsulfanylpropanoate |
| 1180 | 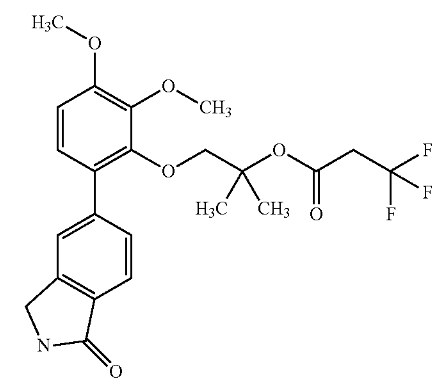 [SMILES: COc1ccc(-c2ccc3c(c2)COC3=O)c(OCC(C)(C)OC(=O)CC(F)(F)F)c1OC] | [2-[2,3-dimethoxy-6-(1-oxoisoindolin-5-yl)phenoxy]-1,1-dimethyl-ethyl] 3,3,3-trifluoropropanoate |

| Compound | Structure | Compound name |
|---|---|---|
| 1181 | 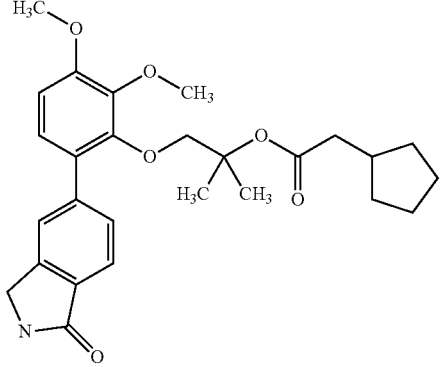 [SMILES: COc1ccc(-c2ccc3c(c2)COC3=O)c(OCC(C)(C)OC(=O)CC2CCCC2)c1OC] | [2-[2,3-dimethoxy-6-(1-oxoisoindolin-5-yl)phenoxy]-1,1-dimethyl-ethyl] 2-cyclopentylacetate |
| 1182 | 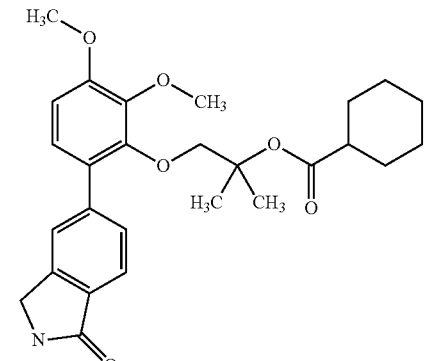 | [2-[2,3-dimethoxy-6-(1-oxoisoindolin-5-yl)phenoxy]-1,1-dimethyl-ethyl] cyclohexanecarboxylate |
| 1183 | 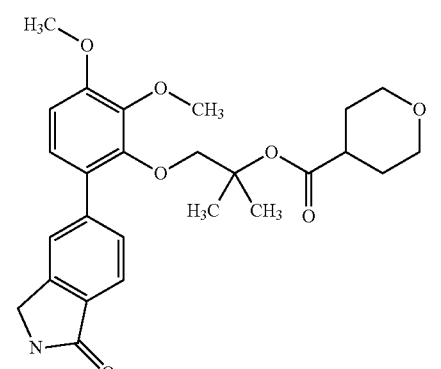 | [2-[2,3-dimethoxy-6-(1-oxoisoindolin-5-yl)phenoxy]-1,1-dimethyl-ethyl] tetrahydropyran-4-carboxylate |
| 1184 | 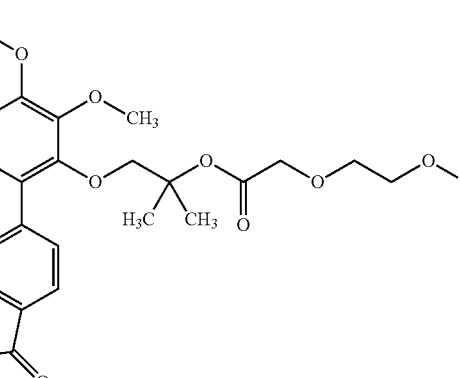 | [2-[2,3-dimethoxy-6-(1-oxoisoindolin-5-yl)phenoxy]-1,1-dimethyl-ethyl] 2-(2-methoxyethoxy)acetate |

Example 169

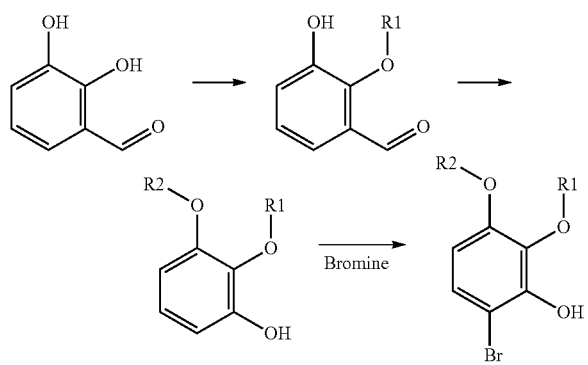

2,3-dihydroxybenzaldehyde is deuteromethylated in position 2 and 3 (ref. Staveris, S. et al *Journal of Labelled Compounds and Radiopharmaceuticals,* 23(1), 51-7; 1986) employing bis-deuteromethyl sulphate, in combination with potassium carbonate in acetone, or in acetonitrile, or in DMF. In the same manner, the 2,3-dimethylated product is prepared using dimethyl sulphate or methyl iodide under the same conditions. Selective methylation or deuteromethylation ortho to the carbonyl is achieved with methyl iodide or deuteromethyl iodide, combined with potassium bicarbonate in DMF by the method of Lowell, Andrew N. et. al. *Tetrahedron,* 66(30), 5573-5582; 2010, followed by methylation or deuteromethylation of the remaining phenolic hydroxyl group. In this fashion, products are obtained that are deuteromethylated selectively at the 2- or 3-position, respectively.

The compound is oxidised (ref. Roy, Amrita et. al. *Synthetic Communications,* 29(21), 3781-3791; 1999) using hydrogen peroxide and boric acid in a mixed solvent of water and THF to give the di-alkylated phenol. Bromination ortho to the phenol is performed with bromine in carbontetrachloride (ref. Sargent, Melvyn V. Journal of the Chemical Society, Perkin Transactions 1 (11), 2553-63; 1987).

The deuterated bromo-phenols are coupled with the appropriate boronic acid esters by Suzuki coupling, as for example described for the preparation of compounds 303-307. Alternatively they are converted into the corresponding boronic acid as described for 6-bromo-2,3-dimethoxyphenol in preparation 1 and subsequently converted into the deuterated analogues of compounds 303-307 as described in preparations 3-7. The introduction of the substituents in position R3 is performed as described in the preparation of the analogous non-deuterated compounds.

Compounds 1185-1292 are prepared as described in example 169

| Compound | Structure | Compound name |
|---|---|---|
| 1185 | 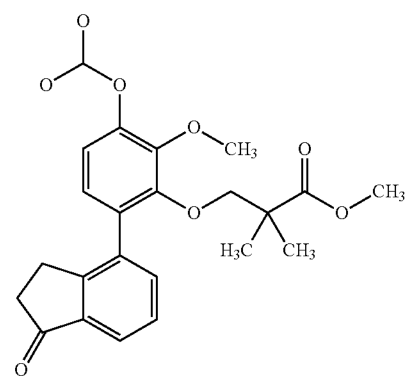 [SMILES: COC(=O)C(C)(C)COc1c(-c2cccc3c2CCC3=O)ccc(OC(O)O)c1OC] | methyl 3-[3-(dideuteriomethoxy)-2-methoxy-6-(1-oxoindan-4-yl)phenoxy]-2,2-dimethyl-propanoate |
| 1186 | 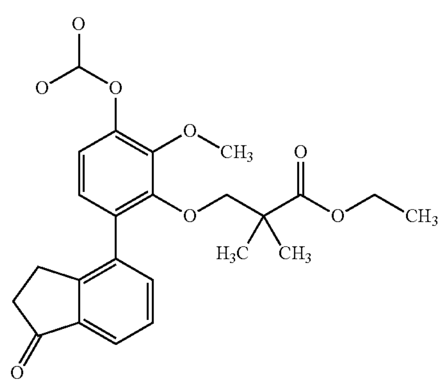 [SMILES: CCOC(=O)C(C)(C)COc1c(-c2cccc3c2CCC3=O)ccc(OC(O)O)c1OC] | ethyl 3-[3-(dideuteriomethoxy)-2-methoxy-6-(1-oxoindan-4-yl)phenoxy]-2,2-dimethyl-propanoate |

-continued

| Compound | Structure | Compound name |
|---|---|---|
| 1187 | 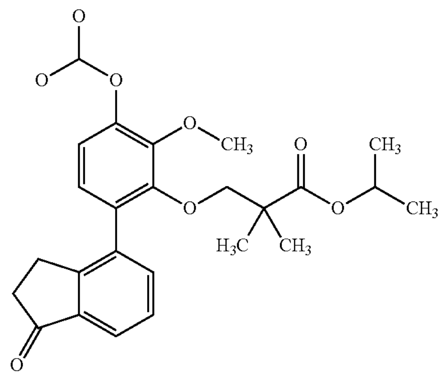 [SMILES: COc1c(OC(O)O)ccc(-c2cccc3c2CCC3=O)c1OCC(C)(C)C(=O)OC(C)C] | isopropyl 3-[3-(dideuteriomethoxy)-2-methoxy-6-(1-oxoindan-4-4-yl)phenoxy]-2,2-dimethyl-propanoate |
| 1188 | 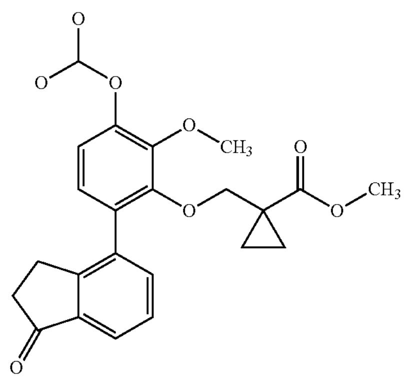 [SMILES: COC(=O)C1(COc2c(-c3cccc4c3CCC4=O)ccc(OC(O)O)c2OC)CC1] | methyl 1-[[3-(dideuteriomethoxy)-2-methoxy-6-(1-oxoindan-4-yl)phenoxy]methyl]cyclopropanecarboxylate |
| 1189 | 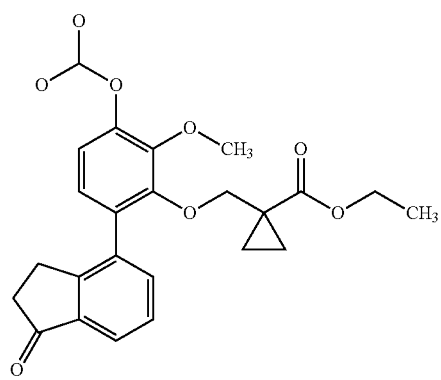 [SMILES: CCOC(=O)C1(COc2c(-c3cccc4c3CCC4=O)ccc(OC(O)O)c2OC)CC1] | ethyl 1-[[3-(dideuteriomethoxy)-2-methoxy-6-(1-oxoindan-4-yl)phenoxy]methyl]cyclopropanecarboxylate |
| 1190 | 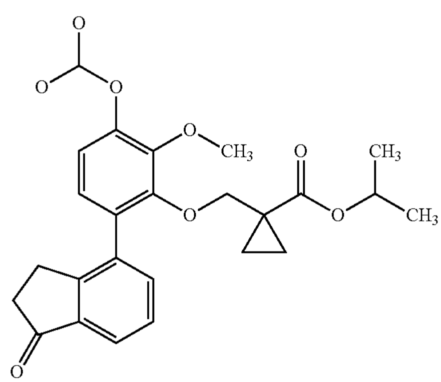 [SMILES: COc1c(OC(O)O)ccc(-c2cccc3c2CCC3=O)c1OCC1(C(=O)OC(C)C)CC1] | isopropyl 1-[[3-(dideuteriomethoxy)-2-methoxy-6-(1-oxoindan-4-yl)phenoxy]methyl]cyclopropanecarboxylate |

-continued

| Compound | Structure | Compound name |
|---|---|---|
| 1191 | 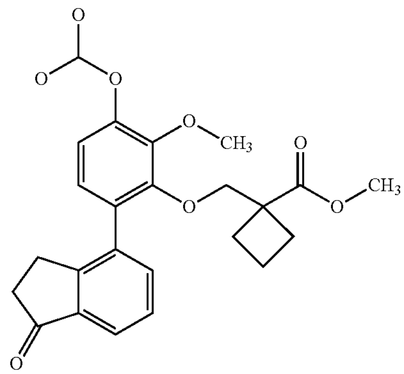 [SMILES: COC(=O)C1(COc2c(-c3cccc4c3CCC4=O)ccc(OC(O)O)c2OC)CCC1] | methyl 1-[[3-(dideuteriomethoxy)-2-methoxy-6-(1-oxoindan-4-yl)phenoxy]methyl]cyclobutanecarboxylate |
| 1192 | 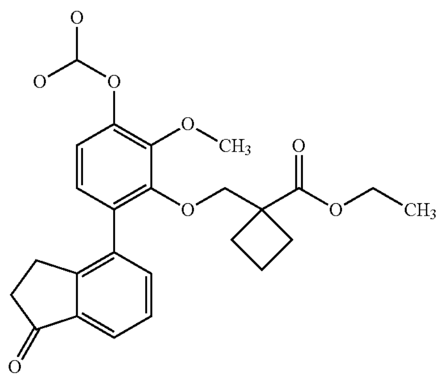 [SMILES: CCOC(=O)C1(COc2c(-c3cccc4c3CCC4=O)ccc(OC(O)O)c2OC)CCC1] | ethyl 1-[[3-(dideuteriomethoxy)-2-methoxy-6-(1-oxoindan-4-yl)phenoxy]methyl]cyclobutanecarboxylate |
| 1193 | 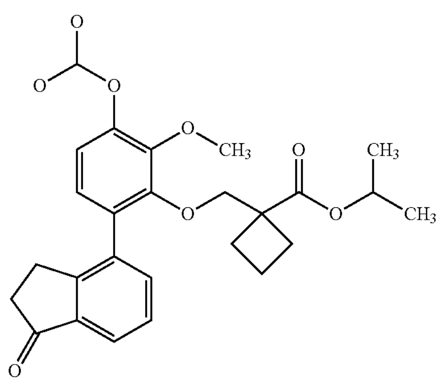 [SMILES: COc1c(OC(O)O)ccc(-c2cccc3c2CCC3=O)c1OCC1(C(=O)OC(C)C)CCC1] | isopropyl 1-[[3-(dideuteriomethoxy)-2-methoxy-6-(1-oxoindan-4-yl)phenoxy]methyl]cyclobutanecarboxylate |
| 1194 | 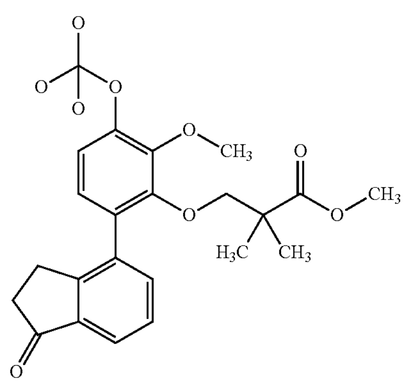 [SMILES: COC(=O)C(C)(C)COc1c(-c2cccc3c2CCC3=O)ccc(OC(O)(O)O)c1OC] | methyl 3-[2-methoxy-6-(1-oxoindan-4-yl)-3-(trideuteriomethoxy)phenoxy]-2,2-dimethyl-propanoate |

| Compound | Structure | Compound name |
|---|---|---|
| 1195 | 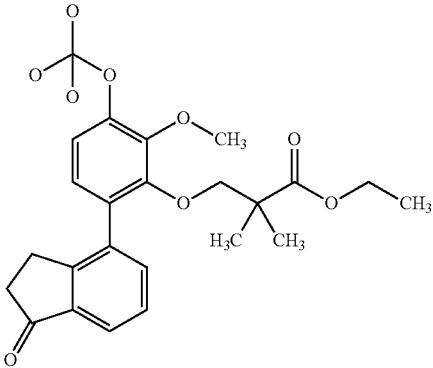 [SMILES: CCOC(=O)C(C)(C)COc1c(-c2cccc3c2CCC3=O)ccc(OC(O)(O)O)c1OC] | ethyl 3-[2-methoxy-6-(1-oxoindan-4-yl)-3-(trideuteriomethoxy)phenoxy]-2,2-dimethyl-propanoate |
| 1196 | 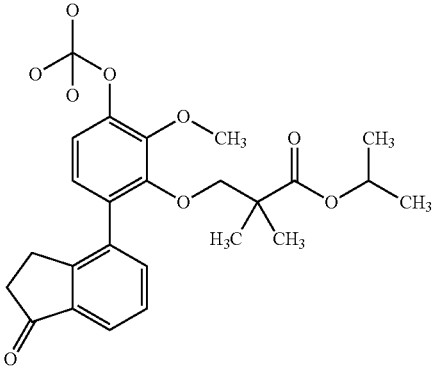 [SMILES: COc1c(OC(O)(O)O)ccc(-c2cccc3c2CCC3=O)c1OCC(C)(C)C(=O)OC(C)C] | isopropyl 3-[2-methoxy-6-(1-oxoindan-4-yl)-3-(trideuteriomethoxy)phenoxy]-2,2-dimethyl-propanoate |
| 1197 | 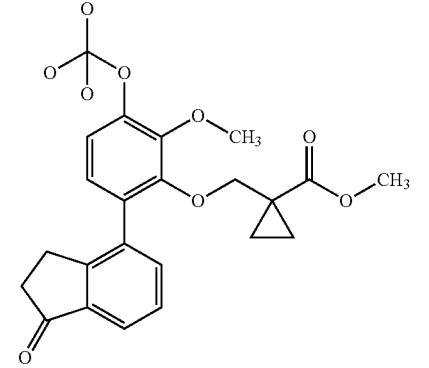 [SMILES: COC(=O)C1(COc2c(-c3cccc4c3CCC4=O)ccc(OC(O)(O)O)c2OC)CC1] | methyl 1-[[2-methoxy-6-(1-oxoindan-4-yl)-3-(trideuteriomethoxy)phenoxy]methyl]cyclopropanecarboxylate |
| 1198 | 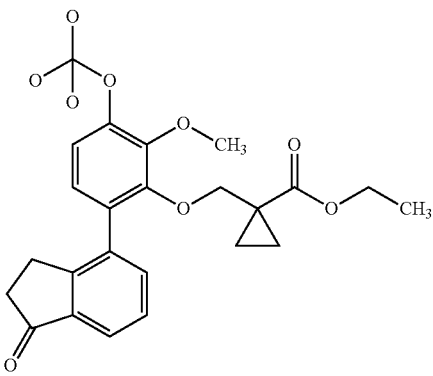 [SMILES: CCOC(=O)C1(COc2c(-c3cccc4c3CCC4=O)ccc(OC(O)(O)O)c2OC)CC1] | ethyl 1-[[2-methoxy-6-(1-oxoindan-4-yl)-3-(trideuteriomethoxy)phenoxy]methyl]cyclopropanecarboxylate |

-continued

| Compound | Structure | Compound name |
|---|---|---|
| 1199 | 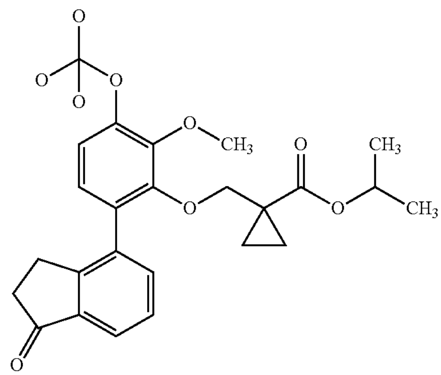 [SMILES: COc1c(OC(O)(O)O)ccc(-c2cccc3c2CCC3=O)c1OCC1(C(=O)OC(C)C)CC1] | isopropyl 1-[[2-methoxy-6-(1-oxoindan-4-yl)-3-(trideuteriomethoxy)phenoxy]methyl]cyclopropanecarboxylate |
| 1200 | 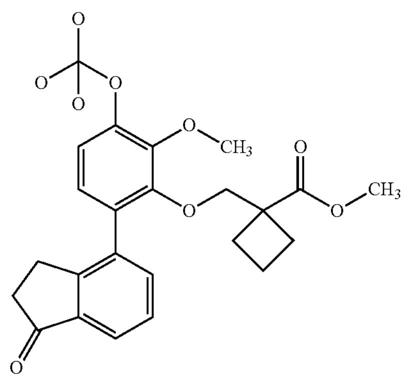 [SMILES: COC(=O)C1(COc2c(-c3cccc4c3CCC4=O)ccc(OC(O)(O)O)c2OC)CCC1] | methyl 1-[[2-methoxy-6-(1-oxoindan-4-yl)-3-(trideuteriomethoxy)phenoxy]methyl]cyclobutanecarboxylate |
| 1201 | 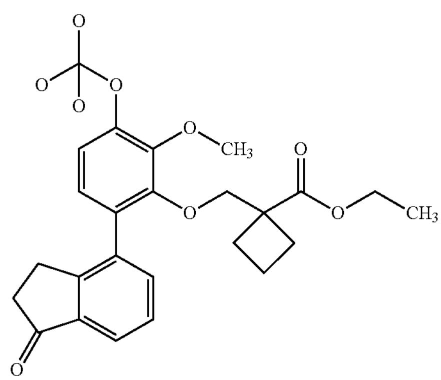 [SMILES: CCOC(=O)C1(COc2c(-c3cccc4c3CCC4=O)ccc(OC(O)(O)O)c2OC)CCC1] | ethyl 1-[[2-methoxy-6-(1-oxoindan-4-yl)-3-(trideuteriomethoxy)phenoxy]methyl]cyclobutanecarboxylate |
| 1202 | 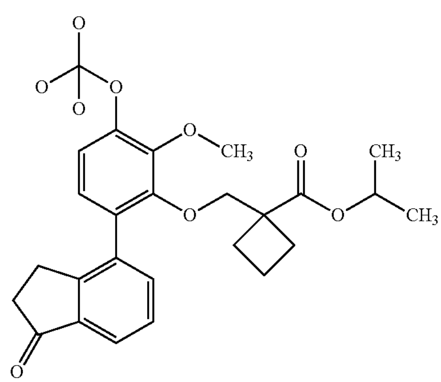 [SMILES: COc1c(OC(O)(O)O)ccc(-c2cccc3c2CCC3=O)c1OCC1(C(=O)OC(C)C)CCC1] | isopropyl 1-[[2-methoxy-6-(1-oxoindan-4-yl)-3-(trideuteriomethoxy)phenoxy]methyl]cyclobutanecarboxylate |

| Compound | Structure | Compound name |
|---|---|---|
| 1203 | 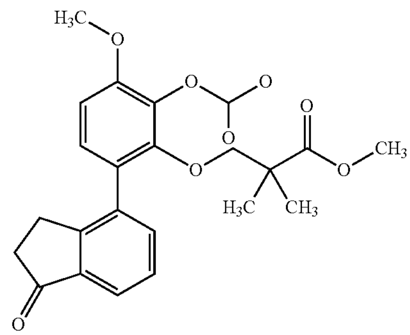 [SMILES: COC(=O)C(C)(C)COc1c(-c2cccc3c2CCC3=O)ccc(OC)c1OC(O)O] | methyl 3-[2-(dideuteriomethoxy)-3-methoxy-6-(1-oxoindan-4-yl)phenoxy]-2,2-dimethyl-propanoate |
| 1204 | 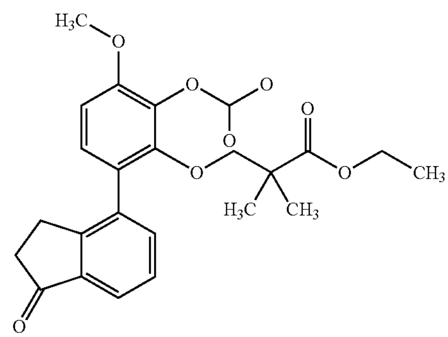 [SMILES: CCOC(=O)C(C)(C)COc1c(-c2cccc3c2CCC3=O)ccc(OC)c1OC(O)O] | ethyl 3-[2-(dideuteriomethoxy)-3-methoxy-6-(1-oxoindan-4-yl)phenoxy]-2,2-dimethyl-propanoate |
| 1205 | 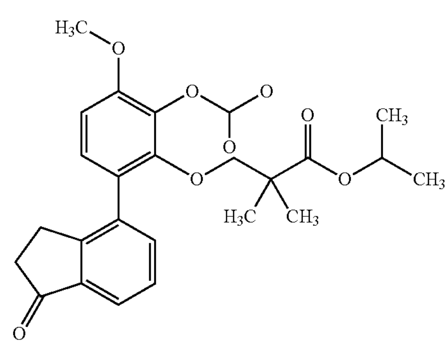 [SMILES: COc1ccc(-c2cccc3c2CCC3=O)c(OCC(C)(C)C(=O)OC(C)C)c1OC(O)O] | isopropyl 3-[2-(dideuteriomethoxy)-3-methoxy-6-(1-oxoindan-4-yl)phenoxy]-2,2-dimethyl-propanoate |
| 1206 | 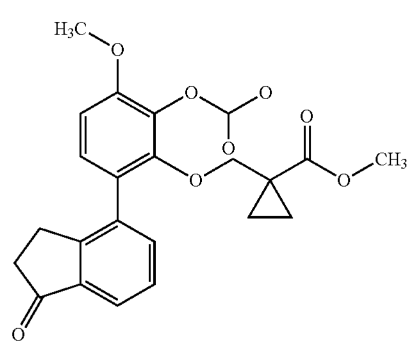 [SMILES: COC(=O)C1(COc2c(-c3cccc4c3CCC4=O)ccc(OC)c2OC(O)O)CC1] | methyl 1-[[2-(dideuteriomethoxy)-3-methoxy-6-(1-oxoindan-4-yl)phenoxy]methyl]cyclopropanecarboxylate |

| Compound | Structure | Compound name |
|---|---|---|
| 1207 | 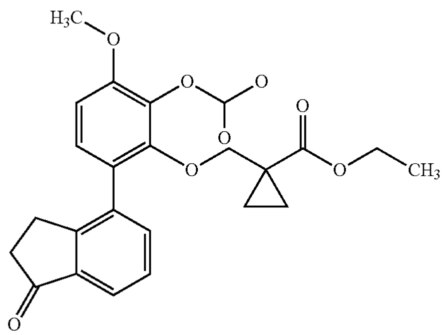 [SMILES: CCOC(=O)C1(COc2c(-c3cccc4c3CCC4=O)ccc(OC)c2OC(O)O)CC1] | ethyl 1-[[2-(dideuteriomethoxy)-3-methoxy-6-(1-oxoindan-4-yl)phenoxy]methyl]cyclopropanecarboxylate |
| 1208 | 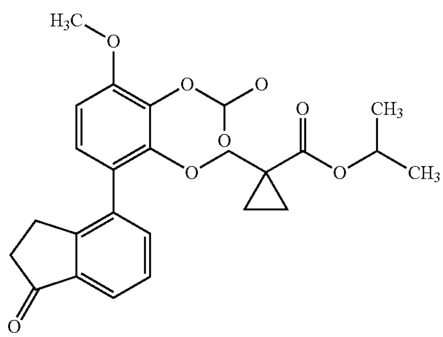 [SMILES: COc1ccc(-c2cccc3c2CCC3=O)c(OCC2(C(=O)OC(C)C)CC2)c1OC(O)O] | isopropyl 1-[[2-(dideuteriomethoxy)-3-methoxy-6-(1-oxoindan-4-yl)phenoxy]methyl]cyclopropanecarboxylate |
| 1209 | 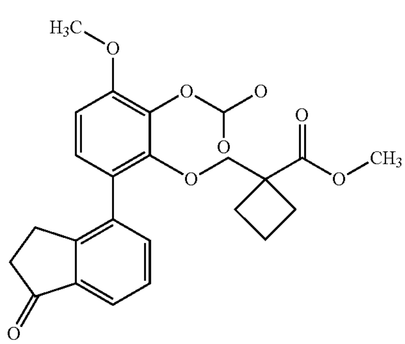 [SMILES: COC(=O)C1(COc2c(-c3cccc4c3CCC4=O)ccc(OC)c2OC(O)O)CCC1] | methyl 1-[[2-(dideuteriomethoxy)-3-methoxy-6-(1-oxoindan-4-yl)phenoxy]methyl]cyclobutanecarboxylate |
| 1210 | 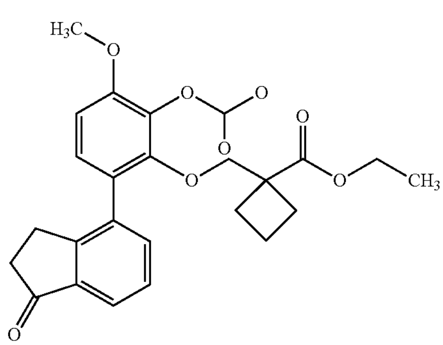 [SMILES: CCOC(=O)C1(COc2c(-c3cccc4c3CCC4=O)ccc(OC)c2OC(O)O)CCC1] | ethyl 1-[[2-(dideuteriomethoxy)-3-methoxy-6-(1-oxoindan-4-yl)phenoxy]methyl]cyclobutanecarboxylate |

| Compound | Structure | Compound name |
| --- | --- | --- |
| 1211 | 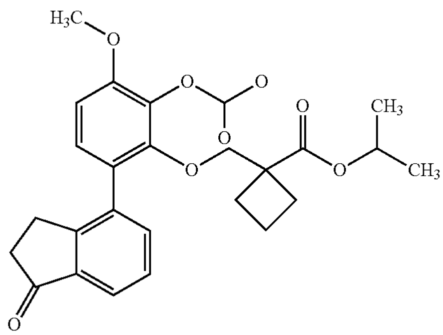 [SMILES: COc1ccc(-c2cccc3c2CCC3=O)c(OCC2(C(=O)OC(C)C)CCC2)c1OC(O)O] | isopropyl 1-[[2-(dideuteriomethoxy)-3-methoxy-6-(1-oxoindan-4-yl)phenoxy]methyl]cyclobutanecarboxylate |
| 1212 | 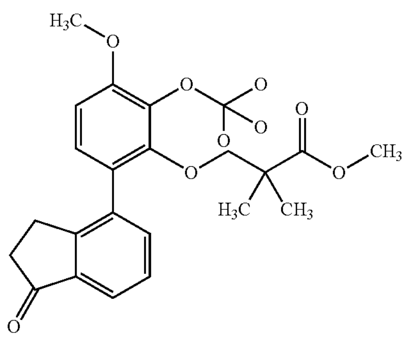 [SMILES: COC(=O)C(C)(C)COc1c(-c2cccc3c2CCC3=O)ccc(OC)c1OC(O)(O)O] | methyl 3-[3-methoxy-6-(1-oxoindan-4-yl)-2-(trideuteriomethoxy)phenoxy]-2,2-dimethyl-propanoate |
| 1213 | 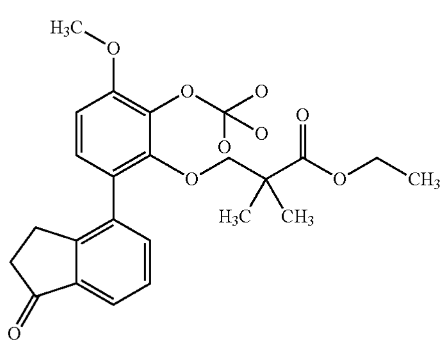 [SMILES: CCOC(=O)C(C)(C)COc1c(-c2cccc3c2CCC3=O)ccc(OC)c1OC(O)(O)O] | ethyl 3-[3-methoxy-6-(1-oxoindan-4-yl)-2-(trideuteriomethoxy)phenoxy]-2,2-dimethyl-propanoate |
| 1214 | 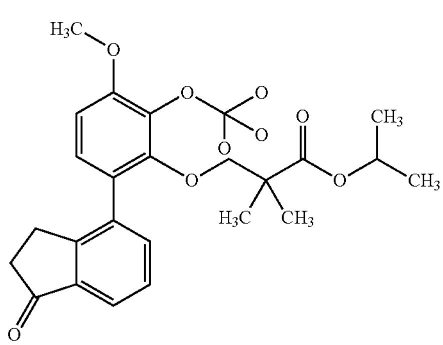 [SMILES: COc1ccc(-c2cccc3c2CCC3=O)c(OCC(C)(C)C(=O)OC(C)C)c1OC(O)(O)O] | isopropyl 3-[3-methoxy-6-(1-oxoindan-4-yl)-2-(trideuteriomethoxy)phenoxy]-2,2-dimethyl-propanoate |

-continued

| Compound | Structure | Compound name |
|---|---|---|
| 1215 | 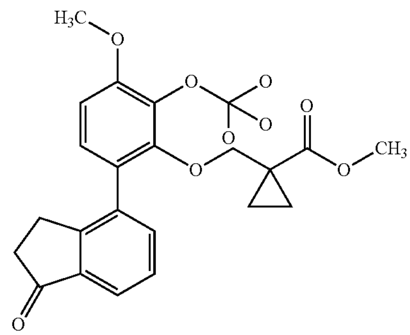 [SMILES: COC(=O)C1(COc2c(-c3cccc4c3CCC4=O)ccc(OC)c2OC(O)(O)O)CC1] | methyl 1-[[3-methoxy-6-(1-oxoindan-4-yl)-2-(trideuteriomethoxy)phenoxy]methyl]cyclopropanecarboxylate |
| 1216 | 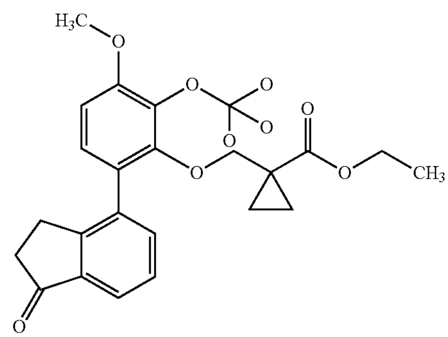 [SMILES: CCOC(=O)C1(COc2c(-c3cccc4c3CCC4=O)ccc(OC)c2OC(O)(O)O)CC1] | ethyl 1-[[3-methoxy-6-(1-oxoindan-4-yl)-2-(trideuteriomethoxy)phenoxy]methyl]cyclopropanecarboxylate |
| 1217 | 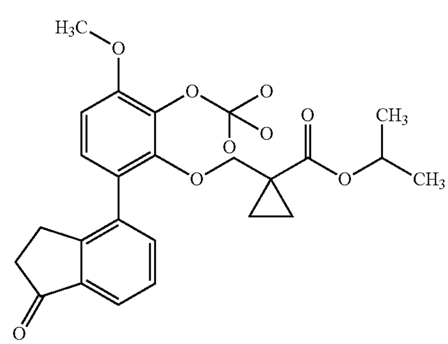 [SMILES: COc1ccc(-c2cccc3c2CCC3=O)c(OCC2(C(=O)OC(C)C)CC2)c1OC(O)(O)O] | isopropyl 1-[[3-methoxy-6-(1-oxoindan-4-yl)-2-trideuteriomethoxy)phenoxy]methyl]cyclopropanecarboxylate |
| 1218 | 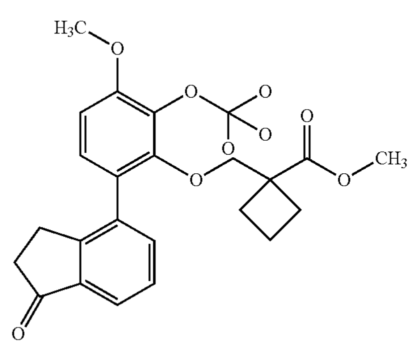 [SMILES: COC(=O)C1(COc2c(-c3cccc4c3CCC4=O)ccc(OC)c2OC(O)(O)O)CCC1] | methyl 1-[[3-methoxy-6-(1-oxoindan-4-yl)-2-(trideuteriomethoxy)phenoxy]methyl]cyclobutanecarboxylate |

| Compound | Structure | Compound name |
| --- | --- | --- |
| 1219 | 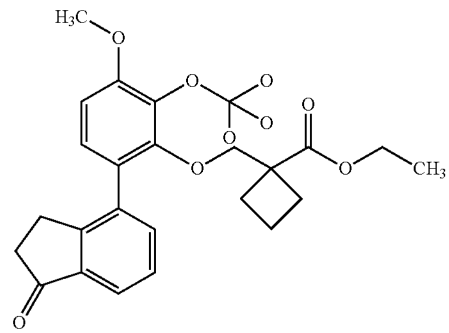 [SMILES: CCOC(=O)C1(COc2c(-c3cccc4c3CCC4=O)ccc(OC)c2OC(O)(O)O)CCC1] | ethyl 1-[[3-methoxy-6-(1-oxoindan-4-yl)-2-(trideuteriomethoxy)phenoxy]methyl]cyclobutanecarboxylate |
| 1220 | 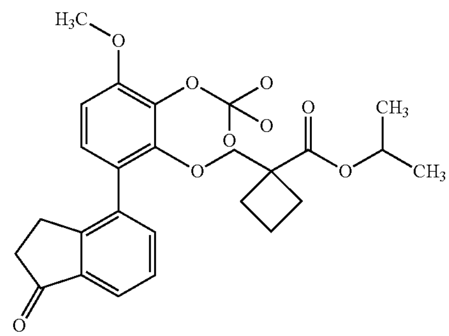 [SMILES: COc1ccc(-c2cccc3c2CCC3=O)c(OCC2(C(=O)OC(C)C)CCC2)c1OC(O)(O)O] | isopropyl 1-[[3-methoxy-6-(1-oxoindan-4-yl)-2-(trideuteriomethoxy)phenoxy]methyl]cyclobutanecarboxylate |
| 1221 | 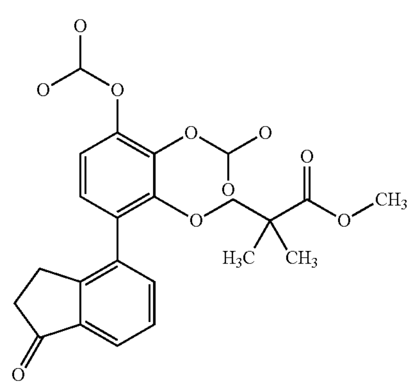 [SMILES: COC(=O)C(C)(C)COc1c(-c2cccc3c2CCC3=O)ccc(OC(O)O)c1OC(O)O] | methyl 3-[2,3-bis(dideuteriomethoxy)-6-(1-oxoindan-4-yl)phenoxy]-2,2-dimethyl-propanoate |
| 1222 | 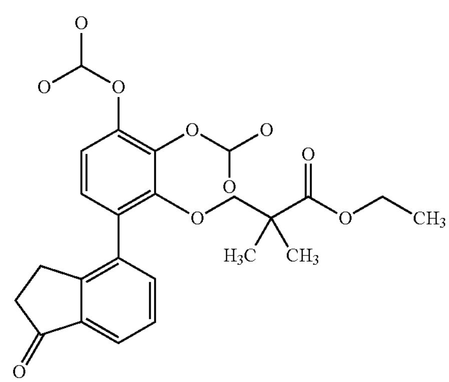 [SMILES: CCOC(=O)C(C)(C)COc1c(-c2cccc3c2CCC3=O)ccc(OC(O)O)c1OC(O)O] | ethyl 3-[2,3-bis(dideuteriomethoxy)-6-(1-oxoindan-4-yl)phenoxy]-2,2-dimethyl-propanoate |

-continued

| Compound | Structure | Compound name |
|---|---|---|
| 1223 | 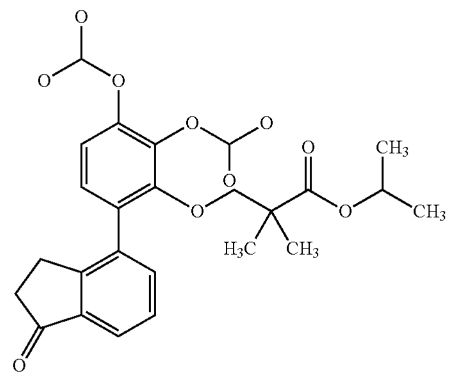 [SMILES: CC(C)OC(=O)C(C)(C)COc1c(-c2cccc3c2CCC3=O)ccc(OC(O)O)c1OC(O)O] | isopropyl 3-[2,3-bis(dideuteriomethoxy)-6-(1-oxoindan-4-yl)phenoxy]-2,2-dimethyl-propanoate |
| 1224 | 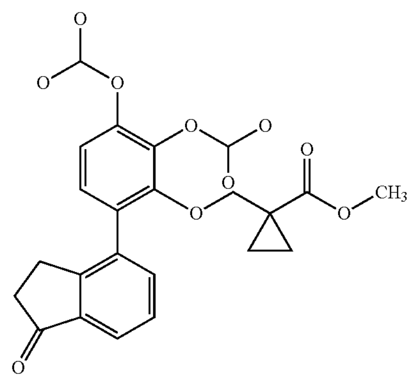 [SMILES: COC(=O)C1(COc2c(-c3cccc4c3CCC4=O)ccc(OC(O)O)c2OC(O)O)CC1] | methyl 1-[[2,3-bis(dideuteriomethoxy)-6-(1-oxoindan-4-yl)phenoxy]methyl]cyclopropanecarboxylate |
| 1225 | 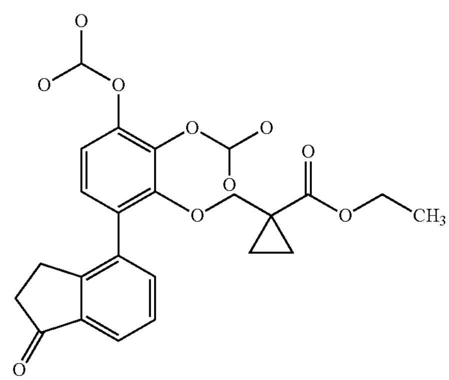 [SMILES: CCOC(=O)C1(COc2c(-c3cccc4c3CCC4=O)ccc(OC(O)O)c2OC(O)O)CC1] | ethyl 1-[[2,3-bis(dideuteriomethoxy)-6-(1-oxoindan-4-yl)phenoxy]methyl]cyclopropanecarboxylate |
| 1226 | 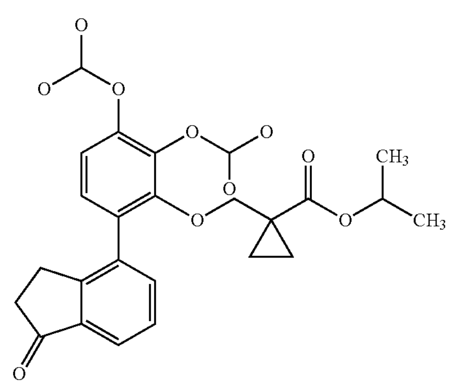 [SMILES: CC(C)OC(=O)C1(COc2c(-c3cccc4c3CCC4=O)ccc(OC(O)O)c2OC(O)O)CC1] | isopropyl 1-[[2,3-bis(dideuteriomethoxy)-6-(1-oxoindan-4-yl)phenoxy]methyl]cyclopropanecarboxylate |

-continued

| Compound | Structure | Compound name |
|---|---|---|
| 1227 | 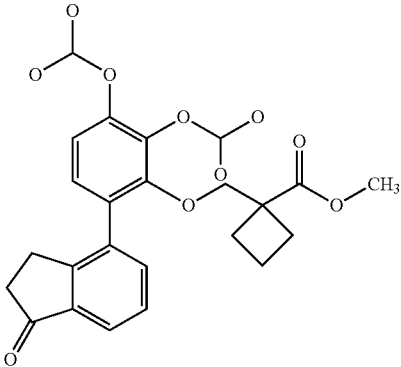 [SMILES: COC(=O)C1(COc2c(-c3cccc4c3CCC4=O)ccc(OC(O)O)c2OC(O)O)CCC1] | methyl 1-[[2,3-bis(dideuteriomethoxy)-6-(1-oxoindan-4-yl)phenoxy]methyl]cyclobutanecarboxylate |
| 1228 | 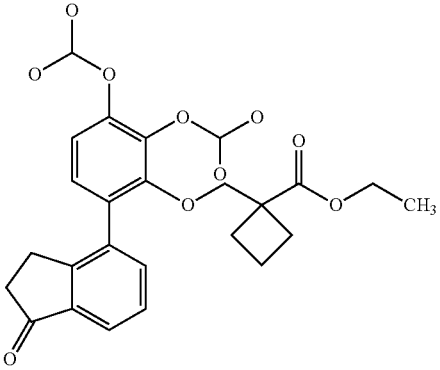 [SMILES: CCOC(=O)C1(COc2c(-c3cccc4c3CCC4=O)ccc(OC(O)O)c2OC(O)O)CCC1] | ethyl 1-[[2,3-bis(dideuteriomethoxy)-6-(1-oxoindan-4-yl)phenoxy]methyl]cyclobutanecarboxylate |
| 1229 | 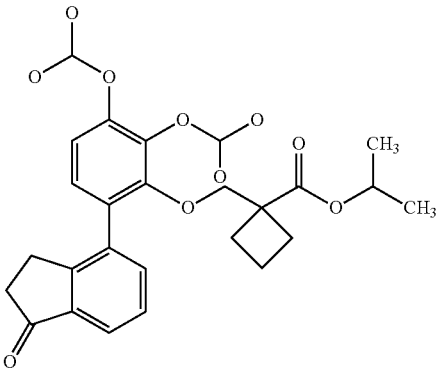 [SMILES: CC(C)OC(=O)C1(COc2c(-c3cccc4c3CCC4=O)ccc(OC(O)O)c2OC(O)O)CCC1] | isopropyl 1-[[2,3-bis(dideuteriomethoxy)-6-(1-oxoindan-4-yl)phenoxy]methyl]cyclobutanecarboxylate |
| 1230 | 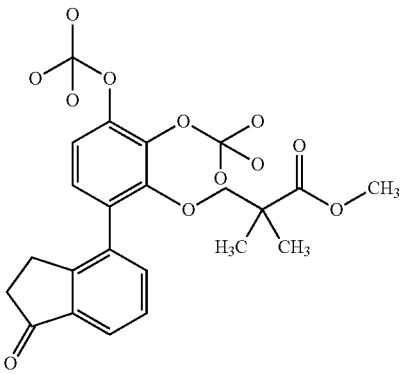 [SMILES: COC(=O)C(C)(C)COc1c(-c2cccc3c2CCC3=O)ccc(OC(O)(O)O)c1OC(O)(O)O] | methyl 2,2-dimethyl-3-[6-(1-oxoindan-4-yl)-2,3-bis(trideuteriomethoxy)phenoxy]propanoate |

-continued

| Compound | Structure | Compound name |
|---|---|---|
| 1231 | 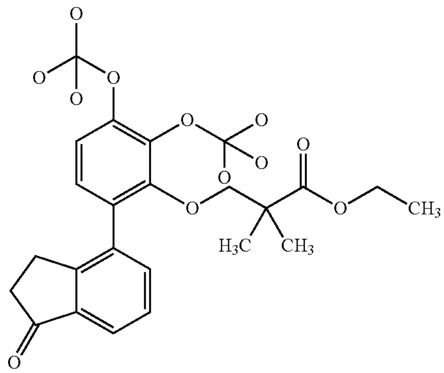 [SMILES: CCOC(=O)C(C)(C)COc1c(-c2cccc3c2CCC3=O)ccc(OC(O)(O)O)c1OC(O)(O)O] | ethyl 2,2-dimethyl-3-[6-(1-oxoindan-4-yl)-2,3-bis(trideuteriomethoxy)phenoxy]propanoate |
| 1232 | 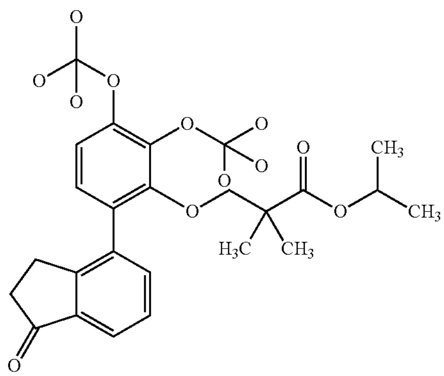 [SMILES: CC(C)OC(=O)C(C)(C)COc1c(-c2cccc3c2CCC3=O)ccc(OC(O)(O)O)c1OC(O)(O)O] | isopropyl 2,2-dimethyl-3-[6-(1-oxoindan-4-yl)-2,3-bis(trideuteriomethoxy)phenoxy]propanoate |
| 1233 | 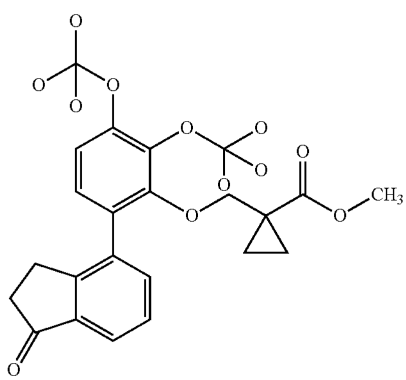 [SMILES: COC(=O)C1(COc2c(-c3cccc4c3CCC4=O)ccc(OC(O)(O)O)c2OC(O)(O)O)CC1] | methyl 1-[[6-(1-oxoindan-4-yl)-2,3-bis(trideuteriomethoxy)phenoxy]methyl]cyclopropanecarboxylate |
| 1234 | 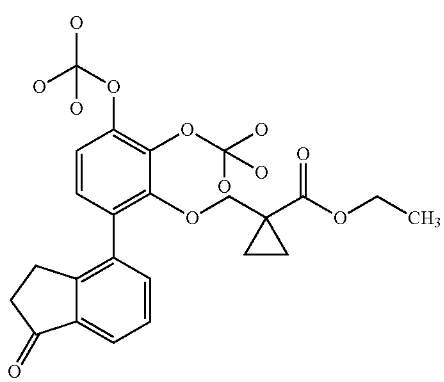 [SMILES: CCOC(=O)C1(COc2c(-c3cccc4c3CCC4=O)ccc(OC(O)(O)O)c2OC(O)(O)O)CC1] | ethyl 1-[[6-(1-oxoindan-4-yl)-2,3-bis(trideuteriomethoxy)phenoxy]methyl]cyclopropanecarboxylate |

-continued

| Compound | Structure | Compound name |
| --- | --- | --- |
| 1235 | 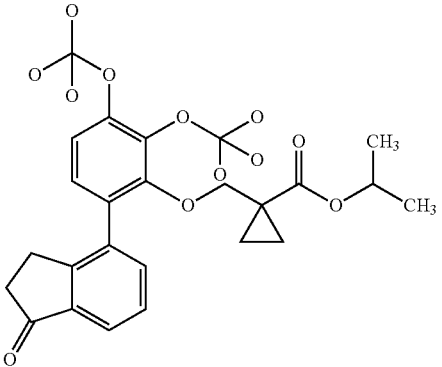 [SMILES: CC(C)OC(=O)C1(COc2c(-c3cccc4c3CCC4=O)ccc(OC(O)(O)O)c2OC(O)(O)O)CC1] | isopropyl 1-[[6-(1-oxoindan-4-yl)-2,3-bis(trideuteriomethoxy)phenoxy]methyl]cyclopropanecarboxylate |
| 1236 | 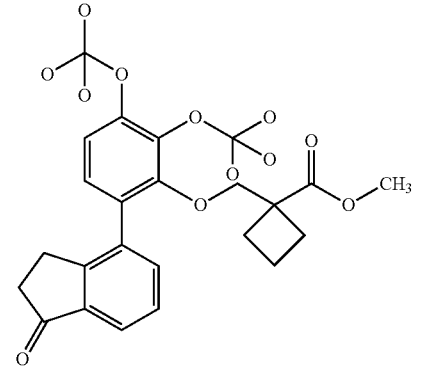 [SMILES: COC(=O)C1(COc2c(-c3cccc4c3CCC4=O)ccc(OC(O)(O)O)c2OC(O)(O)O)CCC1] | methyl 1-[[6-(1-oxoindan-4-yl)-2,3-bis(trideuteriomethoxy)phenoxy]methyl]cyclobutanecarboxylate |
| 1237 | 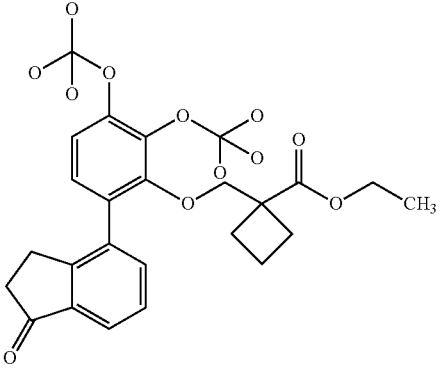 [SMILES: CCOC(=O)C1(COc2c(-c3cccc4c3CCC4=O)ccc(OC(O)(O)O)c2OC(O)(O)O)CCC1] | ethyl 1-[[6-(1-oxoindan-4-yl)-2,3-bis(trideuteriomethoxy)phenoxy]methyl]cyclobutanecarboxylate |
| 1238 | 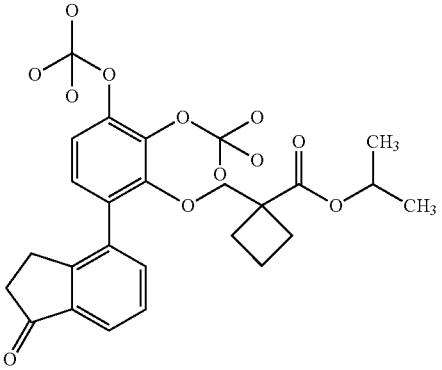 [SMILES: CC(C)OC(=O)C1(COc2c(-c3cccc4c3CCC4=O)ccc(OC(O)(O)O)c2OC(O)(O)O)CCC1] | isopropyl 1-[[6-(1-oxoindan-4-yl)-2,3-bis(trideuteriomethoxy)phenoxy]methyl]cyclobutanecarboxylate |

-continued
| Compound | Structure | Compound name |
|---|---|---|
| 1239 | 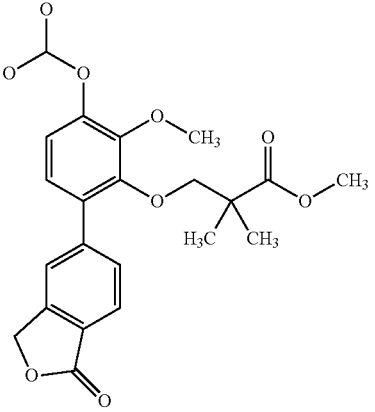 [SMILES: COC(=O)C(C)(C)COc1c(-c2ccc3c(c2)COC3=O)ccc(OC(O)O)c1OC] | methyl 3-[3-(dideuteriomethoxy)-2-methoxy-6-(1-oxo-3H-isobenzofuran-5-yl)phenoxy]-2,2-dimethyl-propanoate |
| 1240 | 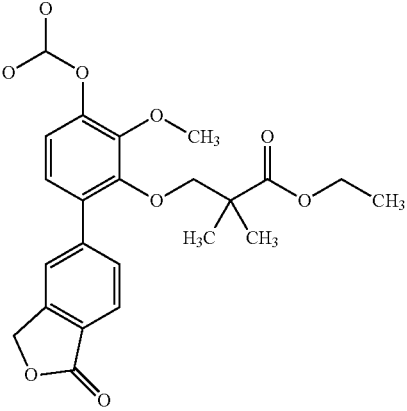 [SMILES: CCOC(=O)C(C)(C)COc1c(-c2ccc3c(c2)COC3=O)ccc(OC(O)O)c1OC] | ethyl 3-[3-(dideuteriomethoxy)-2-methoxy-6-(1-oxo-3H-isobenzofuran-5-yl)phenoxy]-2,2-dimethyl-propanoate |
| 1241 | 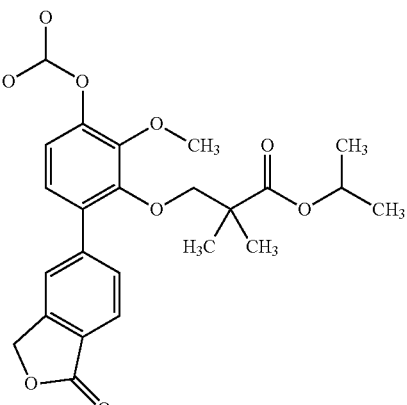 | isopropyl 3-[3-(dideuteriomethoxy)-2-methoxy-6-(1-oxo-3H-isobenzofuran-5-yl)phenoxy]-2,2-dimethyl-propanoate |

-continued

| Compound | Structure | Compound name |
|---|---|---|
| 1242 | 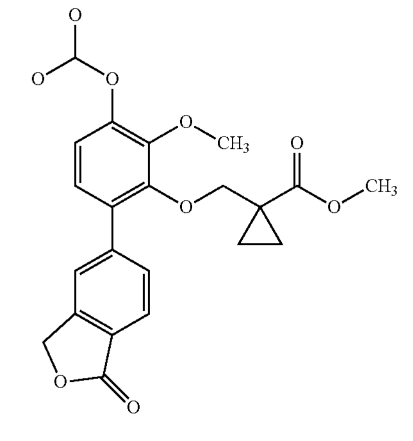 [SMILES: COC(=O)C1(COc2c(-c3ccc4c(c3)COC4=O)ccc(OC(O)O)c2OC)CC1] | methyl 1-[[3-(dideuteriomethoxy)-2-methoxy-6-(1-oxo-3H-isobenzofuran-5-yl)phenoxy]methyl]cyclopropanecarboxylate |
| 1243 | 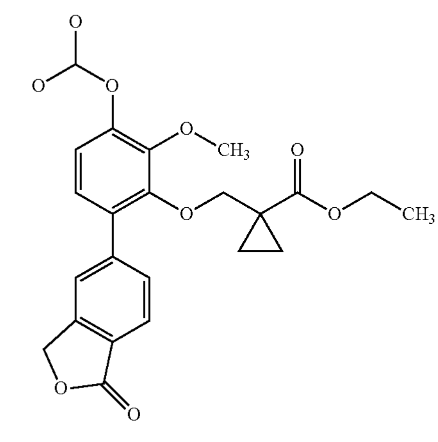 [SMILES: CCOC(=O)C1(COc2c(-c3ccc4c(c3)COC4=O)ccc(OC(O)O)c2OC)CC1] | ethyl 1-[[3-(dideuteriomethoxy)-2-methoxy-6-(1-oxo-3H-isobenzofuran-5-yl)phenoxy]methyl]cyclopropanecarboxylate |
| 1244 | 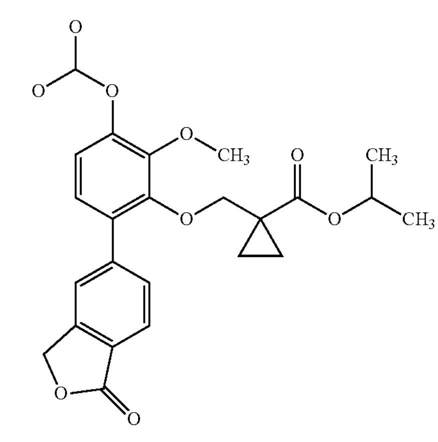 [SMILES: COc1c(OC(O)O)ccc(-c2ccc3c(c2)COC3=O)c1OCC1(C(=O)OC(C)C)CC1] | isopropyl 1-[[3-(dideuteriomethoxy)-2-methoxy-6-(1-oxo-3H-isobenzofuran-5-yl)phenoxy]methyl]cyclopropanecarboxylate |

-continued

| Compound | Structure | Compound name |
|---|---|---|
| 1245 | 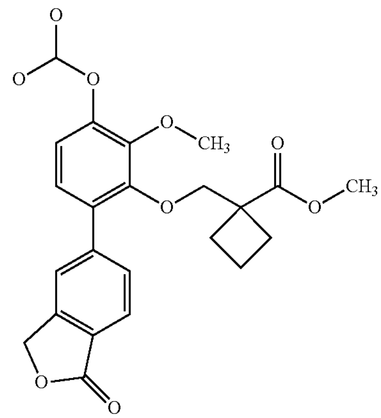 [SMILES: COC(=O)C1(COc2c(-c3ccc4c(c3)COC4=O)ccc(OC(O)O)c2OC)CCC1] | methyl 1-[[3-(dideuteriomethoxy)-2-methoxy-6-(1-oxo-3H-isobenzofuran-5-yl)phenoxy]methyl]cyclobutanecarboxylate |
| 1246 | 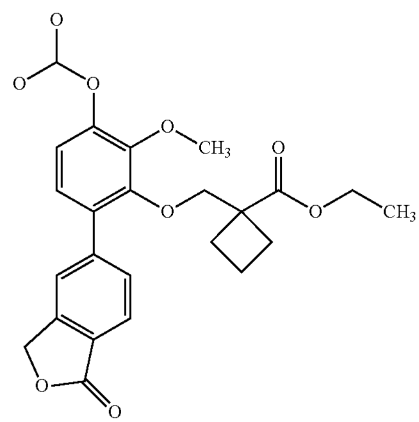 [SMILES: CCOC(=O)C1(COc2c(-c3ccc4c(c3)COC4=O)ccc(OC(O)O)c2OC)CCC1] | ethyl 1-[[3-(dideuteriomethoxy)-2-methoxy-6-(1-oxo-3H-isobenzofuran-5-yl)phenoxy]methyl]cyclobutanecarboxylate |
| 1247 | 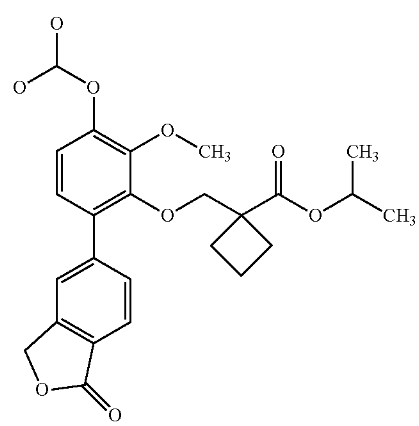 [SMILES: COc1c(OC(O)O)ccc(-c2ccc3c(c2)COC3=O)c1OCC1(C(=O)OC(C)C)CCC1] | isopropyl 1-[[3-(dideuteriomethoxy)-2-methoxy-6-(1-oxo-3H-isobenzofuran-5-yl)phenoxy]methyl]cyclobutanecarboxylate |

-continued

| Compound | Structure | Compound name |
|---|---|---|
| 1248 | 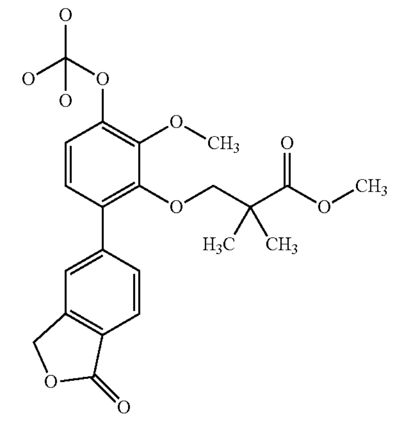 [SMILES: COC(=O)C(C)(C)COc1c(-c2ccc3c(c2)COC3=O)ccc(OC(O)(O)O)c1OC] | methyl 3-[2-methoxy-6-(1-oxo-3H-isobenzofuran-5-yl)-3-(trideuteriomethoxy)phenoxy]-2,2-dimethyl-propanoate |
| 1249 | 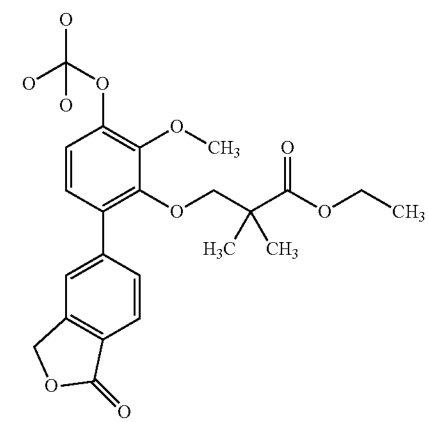 [SMILES: CCOC(=O)C(C)(C)COc1c(-c2ccc3c(c2)COC3=O)ccc(OC(O)(O)O)c1OC] | ethyl 3-[2-methoxy-6-(1-oxo-3H-isobenzofuran-5-yl)-3-(trideuteriomethoxy)phenoxy]-2,2-dimethyl-propanoate |
| 1250 | 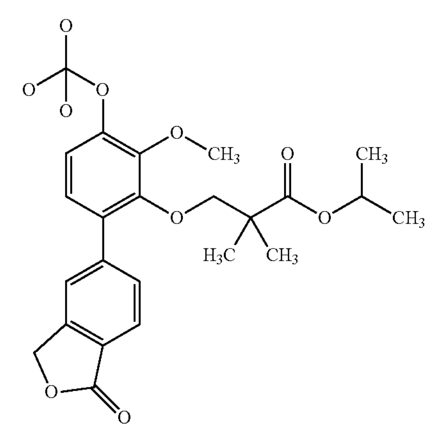 [SMILES: COc1c(OC(O)(O)O)ccc(-c2ccc3c(c2)COC3=O)c1OCC(C)(C)C(=O)OC(C)C] | isopropyl 3-[2-methoxy-6-(1-oxo-3H-isobenzofuran-5-yl)-3-(trideuteriomethoxy)phenoxy]-2,2-dimethyl-propanoate |

-continued

| Compound | Structure | Compound name |
|---|---|---|
| 1251 | 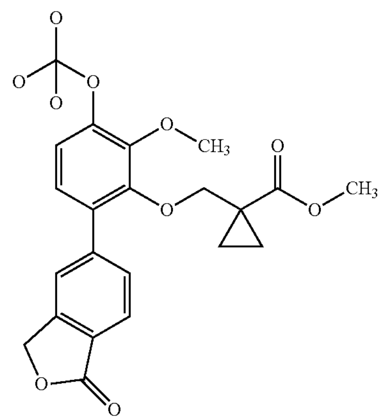 [SMILES: COC(=O)C1(COc2c(-c3ccc4c(c3)COC4=O)ccc(OC(O)(O)O)c2OC)CC1] | methyl 1-[[2-methoxy-6-(1-oxo-3H-isobenzofuran-5-yl)-3-(trideuteriomethoxy)phenoxy]methyl]cyclopropanecarboxylate |
| 1252 | 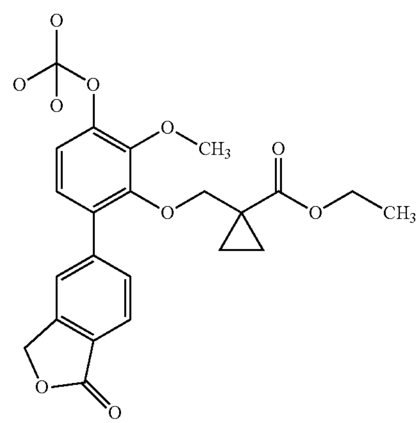 [SMILES: CCOC(=O)C1(COc2c(-c3ccc4c(c3)COC4=O)ccc(OC(O)(O)O)c2OC)CC1] | ethyl 1-[[2-methoxy-6-(1-oxo-3H-isobenzofuran-5-yl)-3-(trideuteriomethoxy)phenoxy]methyl]cyclopropanecarboxylate |
| 1253 | 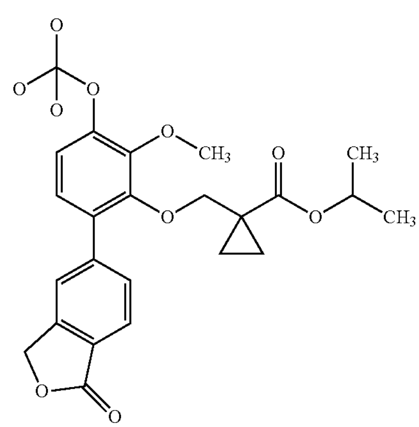 [SMILES: COc1c(OC(O)(O)O)ccc(-c2ccc3c(c2)COC3=O)c1OCC1(C(=O)OC(C)C)CC1] | isopropyl 1-[[2-methoxy-6-(1-oxo-3H-isobenzofuran-5-yl)-3-(trideuteriomethoxy)phenoxy]methyl]cyclopropanecarboxylate |

-continued

| Compound | Structure | Compound name |
|---|---|---|
| 1254 | 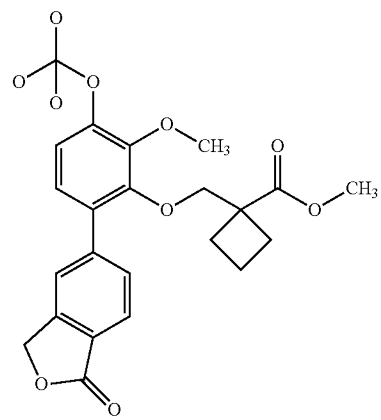 [SMILES: COC(=O)C1(COc2c(-c3ccc4c(c3)COC4=O)ccc(OC(O)(O)O)c2OC)CCC1] | methyl 1-[[2-methoxy-6-(1-oxo-3H-isobenzofuran-5-yl)-3-(trideuteriomethoxy)phenoxy]methyl]cyclobutanecarboxylate |
| 1255 | 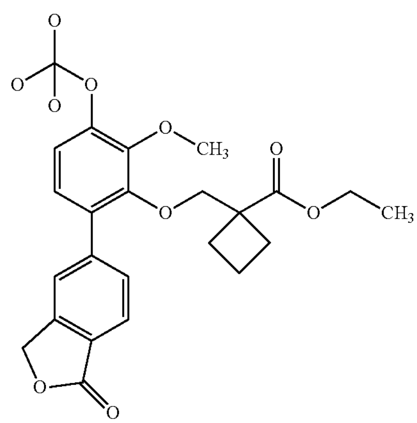 [SMILES: CCOC(=O)C1(COc2c(-c3ccc4c(c3)COC4=O)ccc(OC(O)(O)O)c2OC)CCC1] | ethyl 1-[[2-methoxy-6-(1-oxo-3H-isobenzofuran-5-yl)-3-(trideuteriomethoxy)phenoxy]methyl]cyclobutanecarboxylate |
| 1256 | 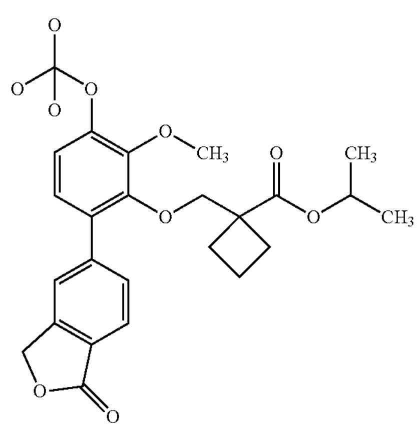 [SMILES: COc1c(OC(O)(O)O)ccc(-c2ccc3c(c2)COC3=O)c1OCC1(C(=O)OC(C)C)CCC1] | isopropyl 1-[[2-methoxy-6-(1-oxo-3H-isobenzofuran-5-yl)-3-(trideuteriomethoxy)phenoxy]methyl]cyclobutanecarboxylate |

-continued

| Compound | Structure | Compound name |
| --- | --- | --- |
| 1257 | 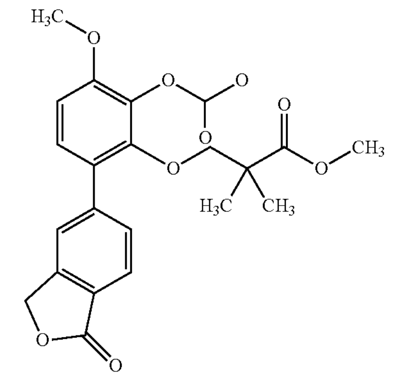 [SMILES: COC(=O)C(C)(C)COc1c(-c2ccc3c(c2)COC3=O)ccc(OC)c1OC(O)O] | methyl 3-[2-(dideuteriomethoxy)-3-methoxy-6-(1-oxo-3H-isobenzofuran-5-yl)phenoxy]-2,2-dimethyl-propanoate |
| 1258 | 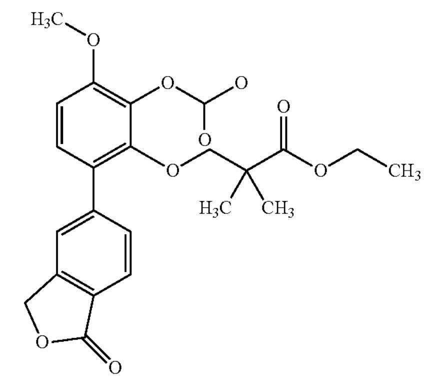 [SMILES: CCOC(=O)C(C)(C)COc1c(-c2ccc3c(c2)COC3=O)ccc(OC)c1OC(O)O] | ethyl 3-[2-(dideuteriomethoxy)-3-methoxy-6-(1-oxo-3H-isobenzofuran-5-yl)phenoxy]-2,2-dimethyl-propanoate |
| 1259 | 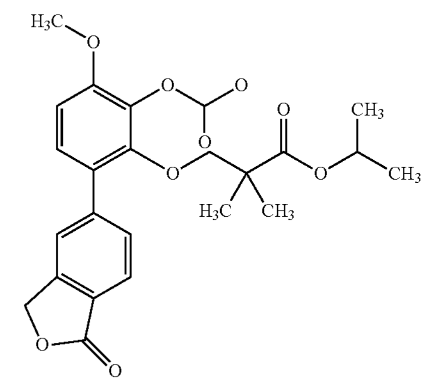 [SMILES: COc1ccc(-c2ccc3c(c2)COC3=O)c(OCC(C)(C)C(=O)OC(C)C)c1OC(O)O] | isopropyl 3-[2-(dideuteriomethoxy)-3-methoxy-6-(1-oxo-3H-isobenzofuran-5-yl)phenoxy]-2,2-dimethyl-propanoate |
| 1260 | 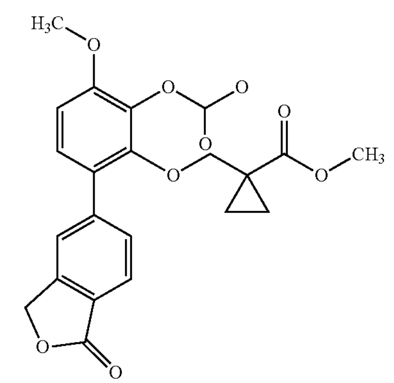 [SMILES: COC(=O)C1(COc2c(-c3ccc4c(c3)COC4=O)ccc(OC)c2OC(O)O)CC1] | methyl 1-[[2-(dideuteriomethoxy)-3-methoxy-6-(1-oxo-3H-isobenzofuran-5-yl)phenoxy]methyl]cyclopropanecarboxylate |

-continued

| Compound | Structure | Compound name |
| --- | --- | --- |
| 1261 | 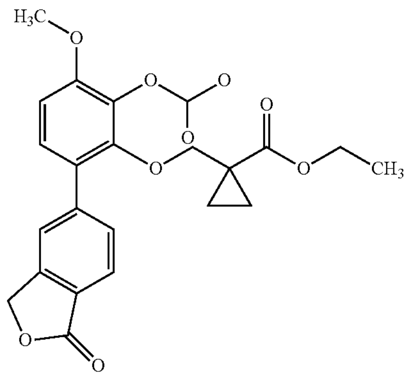 [SMILES: CCOC(=O)C1(COc2c(-c3ccc4c(c3)COC4=O)ccc(OC)c2OC(O)O)CC1] | ethyl 1-[[2-(dideuteriomethoxy)-3-methoxy-6-(1-oxo-3H-isobenzofuran-5-yl)phenoxy]methyl]cyclopropanecarboxylate |
| 1262 | 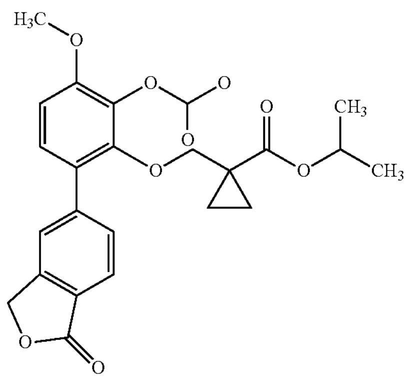 [SMILES: COc1ccc(-c2ccc3c(c2)COC3=O)c(OCC2(C(=O)OC(C)C)CC2)c1OC(O)O] | isopropyl 1-[[2-(dideuteriomethoxy)-3-methoxy-6-(1-oxo-3H-isobenzofuran-5-yl)phenoxy]methyl]cyclopropanecarboxylate |
| 1263 | 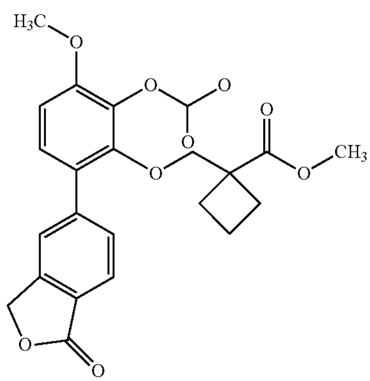 [SMILES: COC(=O)C1(COc2c(-c3ccc4c(c3)COC4=O)ccc(OC)c2OC(O)O)CCC1] | methyl 1-[[2-(dideuteriomethoxy)-3-methoxy-6-(1-oxo-3H-isobenzofuran-5-yl)phenoxy]methyl]cyclobutanecarboxylate |
| 1264 | 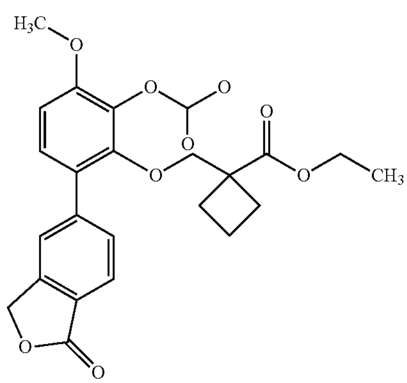 [SMILES: CCOC(=O)C1(COc2c(-c3ccc4c(c3)COC4=O)ccc(OC)c2OC(O)O)CCC1] | ethyl 1-[[2-(dideuteriomethoxy)-3-methoxy-6-(1-oxo-3H-isobenzofuran-5-yl)phenoxy]methyl]cyclobutanecarboxylate |

| Compound | Structure | Compound name |
|---|---|---|
| 1265 | 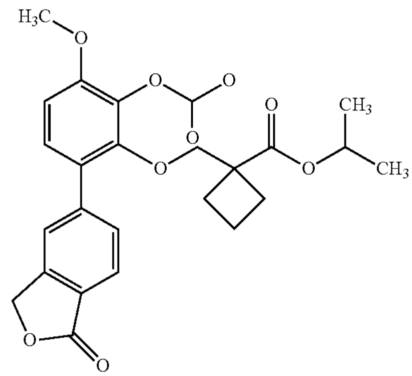 [SMILES: COc1ccc(-c2ccc3c(c2)COC3=O)c(OCC2(C(=O)OC(C)C)CCC2)c1OC(O)O] | isopropyl 1-[[2-(dideuteriomethoxy)-3-methoxy-6-(1-oxo-3H-isobenzofuran-5-yl)phenoxy]methyl]cyclobutanecarboxylate |
| 1266 | 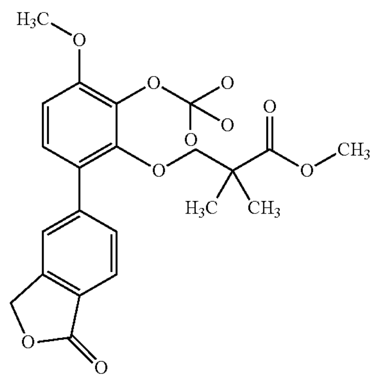 [SMILES: COC(=O)C(C)(C)COc1c(-c2ccc3c(c2)COC3=O)ccc(OC)c1OC(O)(O)O] | methyl 3-[3-methoxy-6-(1-oxo-3H-isobenzofuran-5-yl)-2-(trideuteriomethoxy)phenoxy]-2,2-dimethyl-propanoate |
| 1267 | 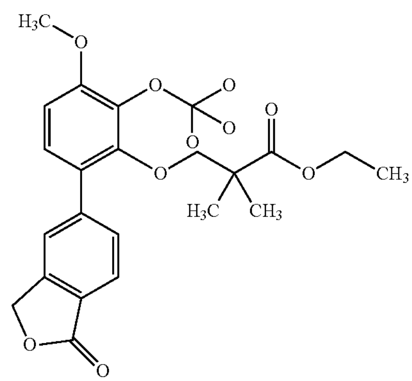 [SMILES: CCOC(=O)C(C)(C)COc1c(-c2ccc3c(c2)COC3=O)ccc(OC)c1OC(O)(O)O] | ethyl 3-[3-methoxy-6-(1-oxo-3H-isobenzofuran-5-yl)-2-(trideuteriomethoxy)phenoxy]-2,2-dimethyl-propanoate |
| 1268 | 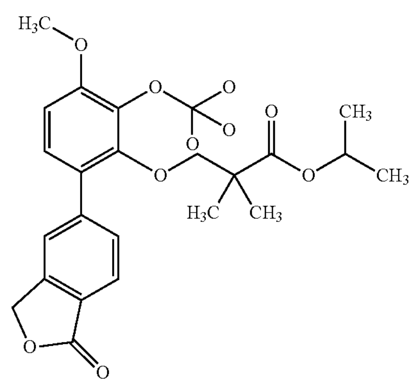 [SMILES: COc1ccc(-c2ccc3c(c2)COC3=O)c(OCC(C)(C)C(=O)OC(C)C)c1OC(O)(O)O] | isopropyl 3-[3-methoxy-6-(1-oxo-3H-isobenzofuran-5-yl)-2-(trideuteriomethoxy)phenoxy]-2,2-dimethyl-propanoate |

-continued

| Compound | Structure | Compound name |
|---|---|---|
| 1269 | 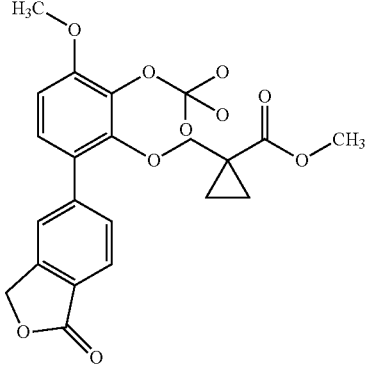 [SMILES: COC(=O)C1(COc2c(-c3ccc4c(c3)COC4=O)ccc(OC)c2OC(O)(O)O)CC1] | methyl 1-[[3-methoxy-6-(1-oxo-3H-isobenzofuran-5-yl)-2-(trideuteriomethoxy)phenoxy]methyl]cyclopropanecarboxylate |
| 1270 | 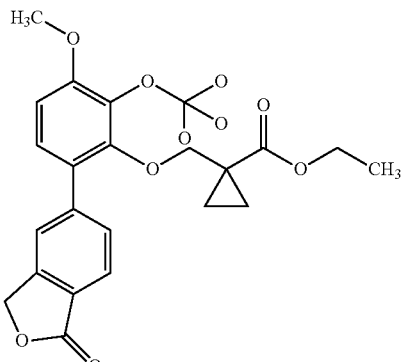 | ethyl 1-[[3-methoxy-6-(1-oxo-3H-isobenzofuran-5-yl)-2-(trideuteriomethoxy)phenoxy]methyl]cyclopropanecarboxylate |
| 1271 | 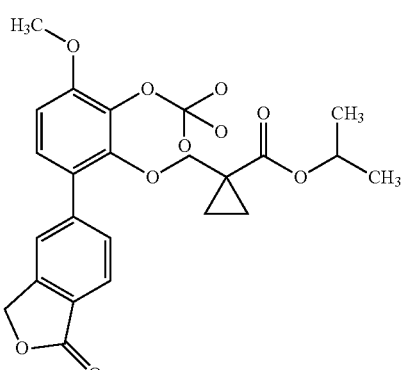 | isopropyl 1-[[3-methoxy-6-(1-oxo-3H-isobenzofuran-5-yl)-2-(trideuteriomethoxy)phenoxy]methyl]cyclopropanecarboxylate |
| 1272 | 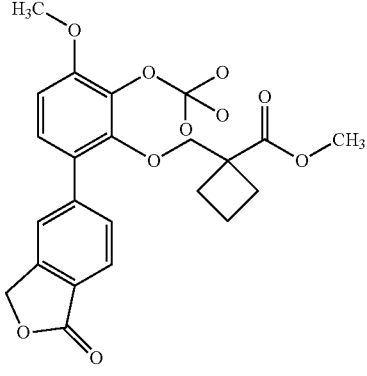 [SMILES: COC(=O)C1(COc2c(-c3ccc4c(c3)COC4=O)ccc(OC)c2OC(O)(O)O)CCC1] | methyl 1-[[3-methoxy-6-(1-oxo-3H-isobenzofuran-5-yl)-2-(trideuteriomethoxy)phenoxy]methyl]cyclobutanecarboxylate |

-continued

| Compound | Structure | Compound name |
|---|---|---|
| 1273 | 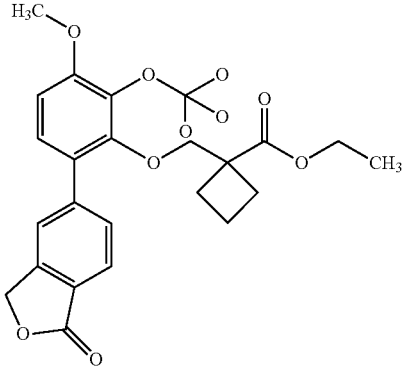 [SMILES: CCOC(=O)C1(COc2c(-c3ccc4c(c3)COC4=O)ccc(OC)c2OC(O)(O)O)CCC1] | ethyl 1-[[3-methoxy-6-(1-oxo-3H-isobenzofuran-5-yl)-2-(trideuteriomethoxy)phenoxy]methyl]cyclobutanecarboxylate |
| 1274 | 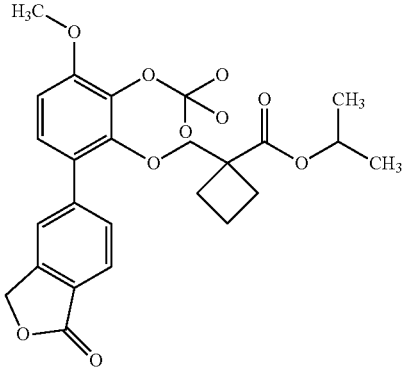 [SMILES: COc1ccc(-c2ccc3c(c2)COC3=O)c(OCC2(C(=O)OC(C)C)CCC2)c1OC(O)(O)O] | isopropyl 1-[[3-methoxy-6-(1-oxo-3H-isobenzofuran-5-yl)-2-(trideuteriomethoxy)phenoxy]methyl]cyclobutanecarboxylate |
| 1275 | 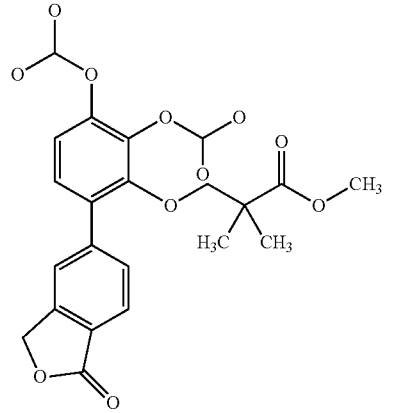 [SMILES: COC(=O)C(C)(C)COc1c(-c2ccc3c(c2)COC3=O)ccc(OC(O)O)c1OC(O)O] | methyl 3-[2,3-bis(dideuteriomethoxy)-6-(1-oxo-3H-isobenzofuran-5-yl)phenoxy]-2,2-dimethyl-propanoate |
| 1276 | 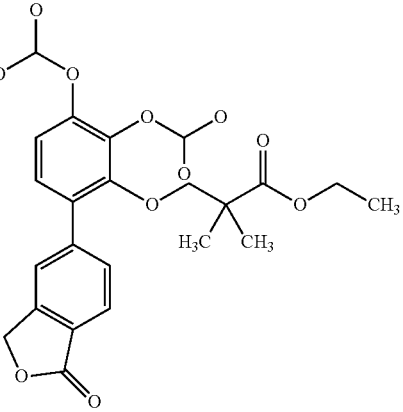 | ethyl 3-[2,3-bis(dideuteriomethoxy)-6-(1-oxo-3H-isobenzofuran-5-yl)phenoxy]-2,2-dimethyl-propanoate |

-continued
| Compound | Structure | Compound name |
|---|---|---|
| 1277 | 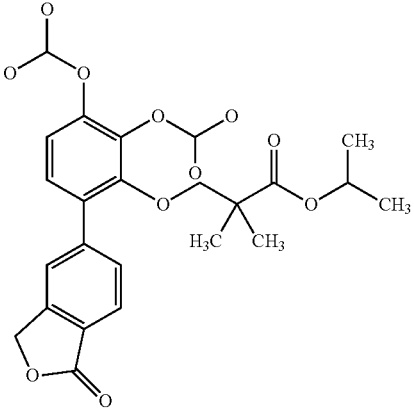 [SMILES: CC(C)OC(=O)C(C)(C)COc1c(-c2ccc3c(c2)COC3=O)ccc(OC(O)O)c1OC(O)O] | isopropyl 3-[2,3-bis(dideuteriomethoxy)-6-(1-oxo-3H-isobenzofuran-5-yl)phenoxy]-2,2-dimethyl-propanoate |
| 1278 | 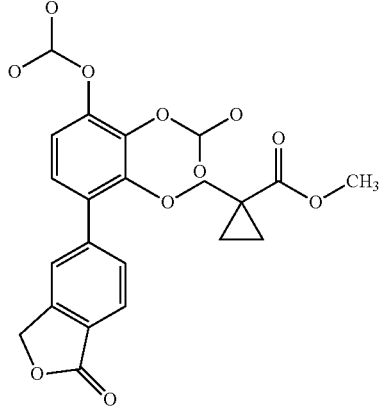 [SMILES: COC(=O)C1(COc2c(-c3ccc4c(c3)COC4=O)ccc(OC(O)O)c2OC(O)O)CC1] | methyl 1-[[2,3-bis(dideuteriomethoxy)-6-(1-oxo-3H-isobenzofuran-5-yl)phenoxy]methyl]cyclopropanecarboxylate |
| 1279 | 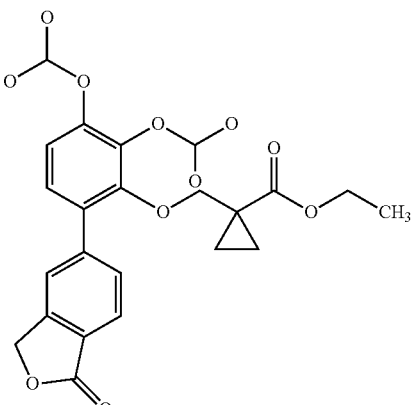 | ethyl 1-[[2,3-bis(dideuteriomethoxy)-6-(1-oxo-3H-isobenzofuran-5-yl)phenoxy]methyl]cyclopropanecarboxylate |

-continued

| Compound | Structure | Compound name |
|---|---|---|
| 1280 | 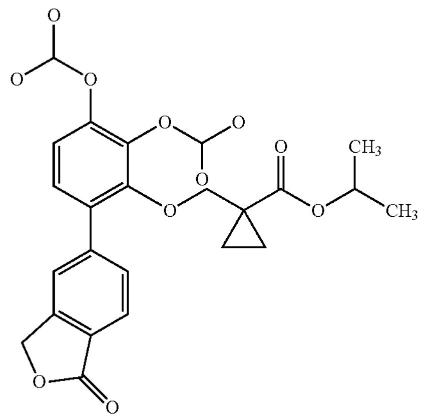 [SMILES: CC(C)OC(=O)C1(COc2c(-c3ccc4c(c3)COC4=O)ccc(OC(O)O)c2OC(O)O)CC1] | isopropyl 1-[[2,3-bis(dideuteriomethoxy)-6-(1-oxo-3H-isobenzofuran-5-yl)phenoxy]methyl]cyclopropanecarboxylate |
| 1281 | 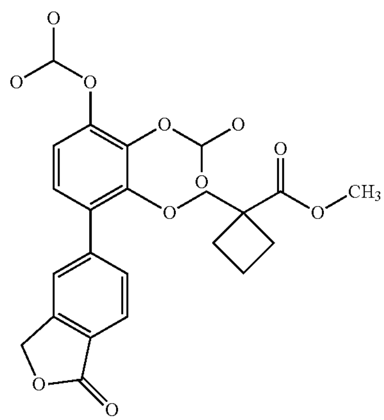 [SMILES: COC(=O)C1(COc2c(-c3ccc4c(c3)COC4=O)ccc(OC(O)O)c2OC(O)O)CCC1] | methyl 1-[[2,3-bis(dideuteriomethoxy)-6-(1-oxo-3H-isobenzofuran-5-yl)phenoxy]methyl]cyclobutanecarboxylate |
| 1282 | 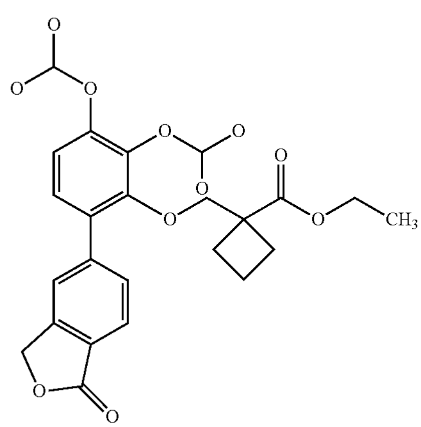 [SMILES: CCOC(=O)C1(COc2c(-c3ccc4c(c3)COC4=O)ccc(OC(O)O)c2OC(O)O)CCC1] | ethyl 1-[[2,3-bis(dideuteriomethoxy)-6-(1-oxo-3H-isobenzofuran-5-yl)phenoxy]methyl]cyclobutanecarboxylate |

| Compound | Structure | Compound name |
|---|---|---|
| 1283 | 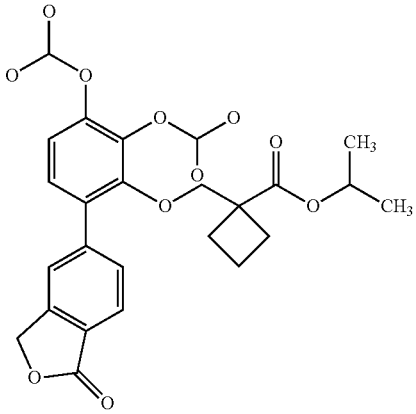 [SMILES: CC(C)OC(=O)C1(COc2c(-c3ccc4c(c3)COC4=O)ccc(OC(O)O)c2OC(O)O)CCC1] | isopropyl 1-[[2,3-bis(dideuteriomethoxy)-6-(1-oxo-3H-isobenzofuran-5-yl)phenoxy]methyl]cyclobutanecarboxylate |
| 1284 | 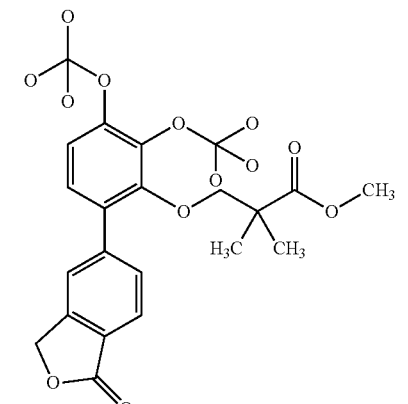 | methyl 2,2-dimethyl-3-[6-(1-oxo-3H-isobenzofuran-5-yl)-2,3-bis(trideuteriomethoxy)phenoxy]propanoate |
| 1285 | 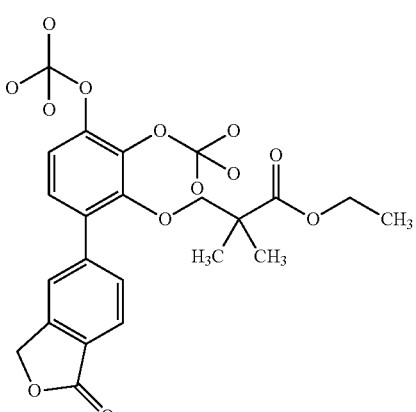 | ethyl 2,2-dimethyl-3-[6-(1-oxo-3H-isobenzofuran-5-yl)-2,3-bis(trideuteriomethoxy)phenoxy]propanoate |

-continued

| Compound | Structure | Compound name |
|---|---|---|
| 1286 | 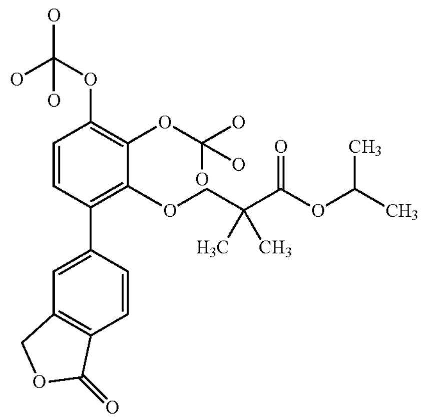 [SMILES: CC(C)OC(=O)C(C)(C)COc1c(-c2ccc3c(c2)COC3=O)ccc(OC(O)(O)O)c1OC(O)(O)O] | isopropyl 2,2-dimethyl-3-[6-(1-oxo-3H-isobenzofuran-5-yl)-2,3-bis(trideuteriomethoxy)phenoxy]propanoate |
| 1287 | 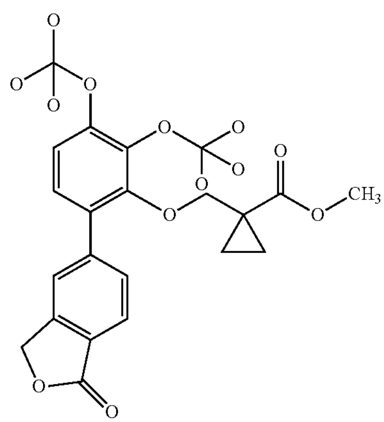 [SMILES: COC(=O)C1(COc2c(-c3ccc4c(c3)COC4=O)ccc(OC(O)(O)O)c2OC(O)(O)O)CC1] | methyl 1-[[6-(1-oxo-3H-isobenzofuran-5-yl)-2,3-bis(trideuteriomethoxy)phenoxy]methyl]cyclopropanecarboxylate |
| 1288 | 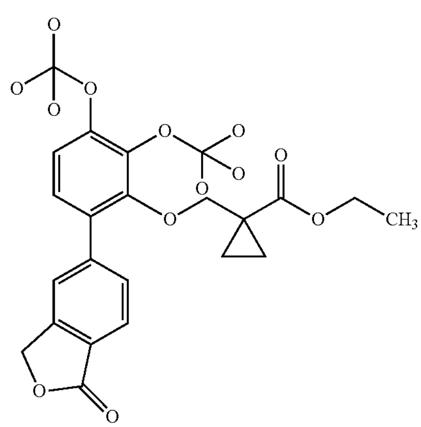 [SMILES: CCOC(=O)C1(COc2c(-c3ccc4c(c3)COC4=O)ccc(OC(O)(O)O)c2OC(O)(O)O)CC1] | ethyl 1-[[6-(1-oxo-3H-isobenzofuran-5-yl)-2,3-bis(trideuteriomethoxy) phenoxy]methyl]cyclopropanecarboxylate |

-continued

| Compound | Structure | Compound name |
|---|---|---|
| 1289 | 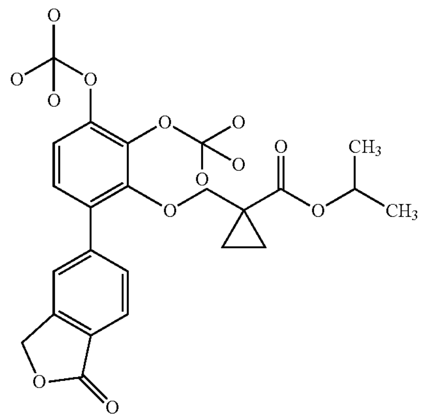 [SMILES: CC(C)OC(=O)C1(COc2c(-c3ccc4c(c3)COC4=O)ccc(OC(O)(O)O)c2OC(O)(O)O)CC1] | isopropyl 1-[[6-(1-oxo-3H-isobenzofuran-5-yl)-2,3-bis(trideuteriomethoxy)phenoxy]methyl]cyclopropanecarboxylate |
| 1290 | 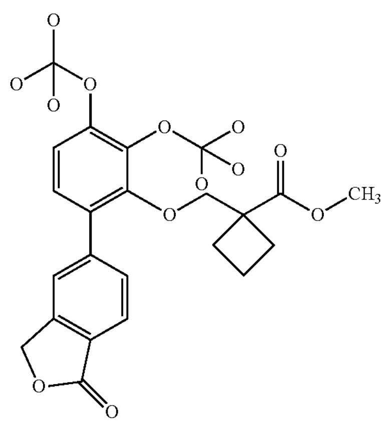 [SMILES: COC(=O)C1(COc2c(-c3ccc4c(c3)COC4=O)ccc(OC(O)(O)O)c2OC(O)(O)O)CCC1] | methyl 1-[[6-(1-oxo-3H-isobenzofuran-5-yl)-2,3-bis(trideuteriomethoxy)phenoxy]methyl]cyclobutanecarboxylate |
| 1291 | 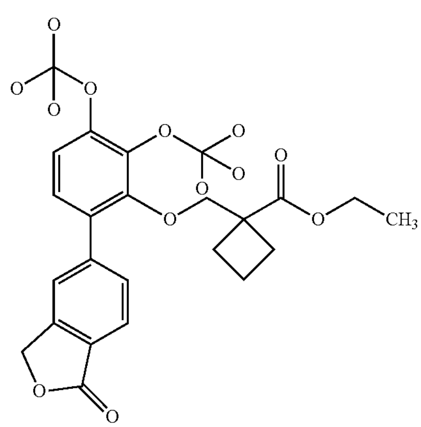 [SMILES: CCOC(=O)C1(COc2c(-c3ccc4c(c3)COC4=O)ccc(OC(O)(O)O)c2OC(O)(O)O)CCC1] | ethyl 1-[[6-(1-oxo-3H-isobenzofuran-5-yl)-2,3-bis(trideuteriomethoxy)phenoxy]methyl]cyclobutanecarboxylate |

-continued

| Compound | Structure | Compound name |
|---|---|---|
| 1292 | 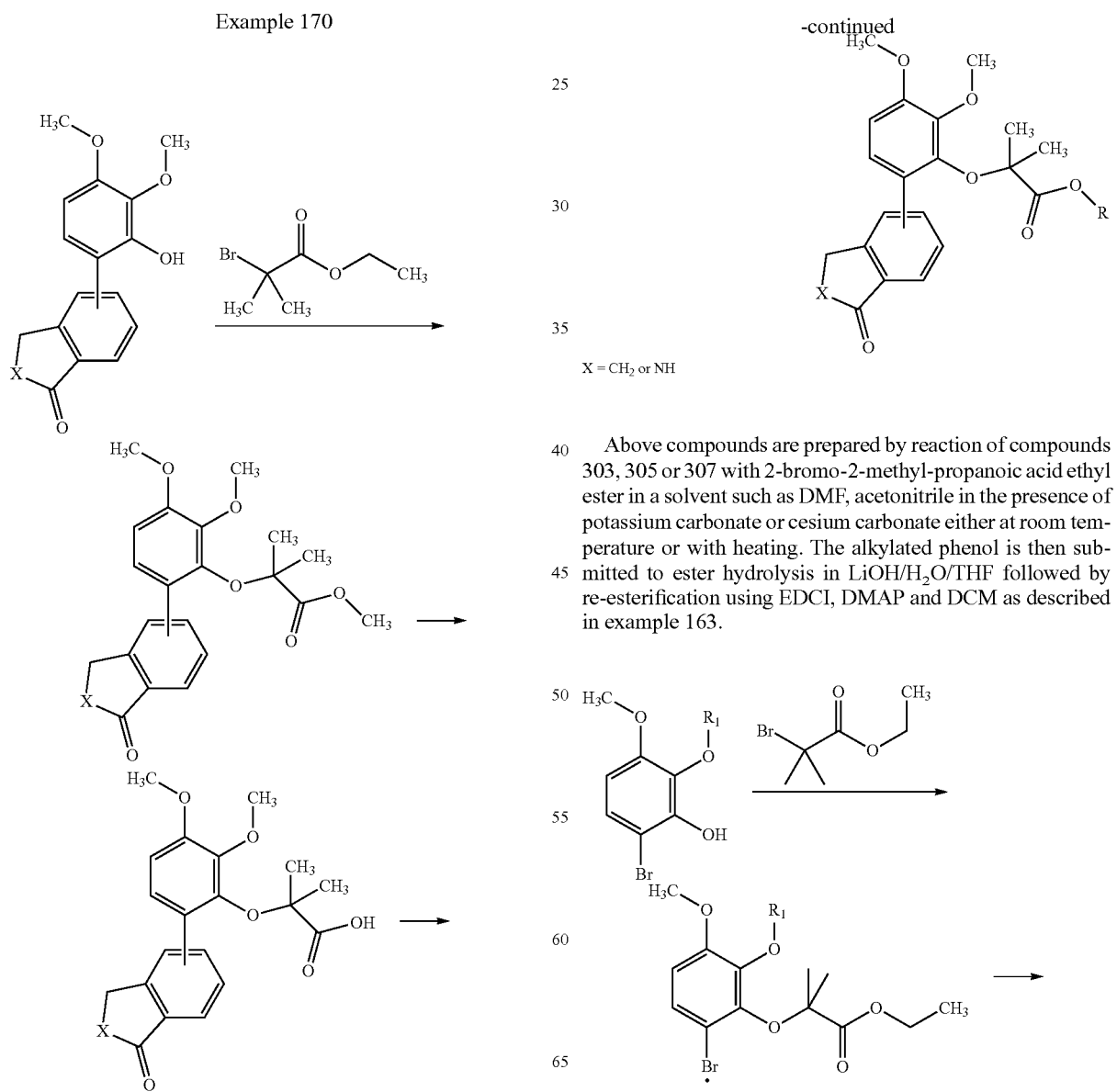 | isopropyl 1-[[6-(1-oxo-3H-isobenzofuran-5-yl)-2,3-bis(trideuteriomethoxy)phenoxy]methyl]cyclobutanecarboxylate |

Example 170

X = CH₂ or NH

Above compounds are prepared by reaction of compounds 303, 305 or 307 with 2-bromo-2-methyl-propanoic acid ethyl ester in a solvent such as DMF, acetonitrile in the presence of potassium carbonate or cesium carbonate either at room temperature or with heating. The alkylated phenol is then submitted to ester hydrolysis in LiOH/H₂O/THF followed by re-esterification using EDCI, DMAP and DCM as described in example 163.

649
-continued

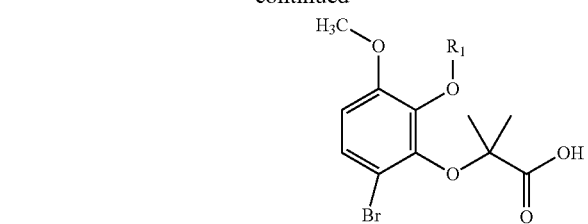

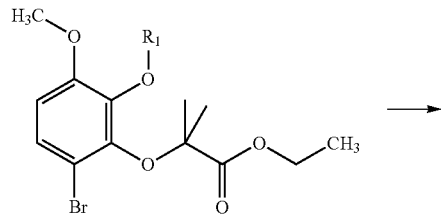

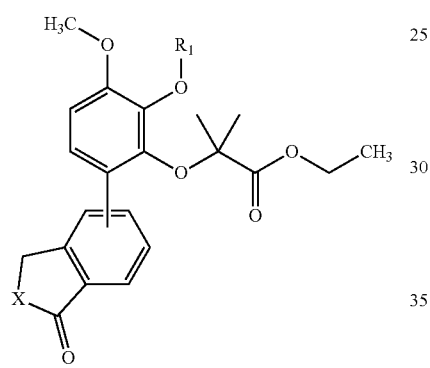

R1 = Methyl, Ethyl
X = CH2 or NH

Alternatively the compounds are prepared in analogy with the synthesis described in example 88, starting from 6-bromo-2,3-dimethoxyphenol and 2-bromo-2-methyl-propanoic acid ethyl ester. The amide synthesis in example 88 is replaced with an ester synthesis as described above Example 171

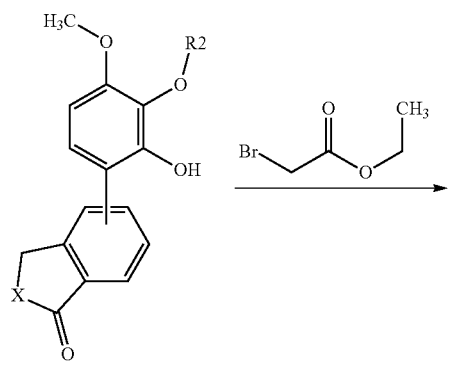

650
-continued

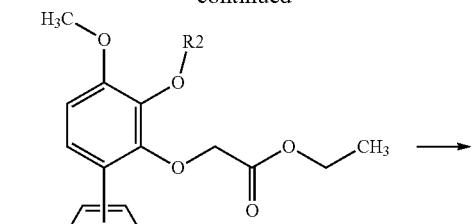

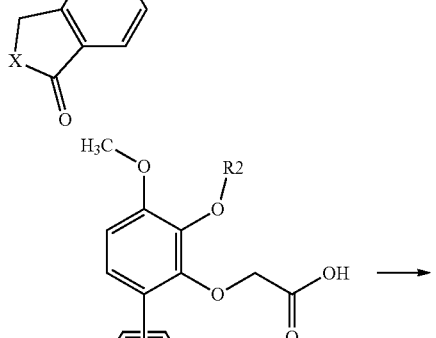

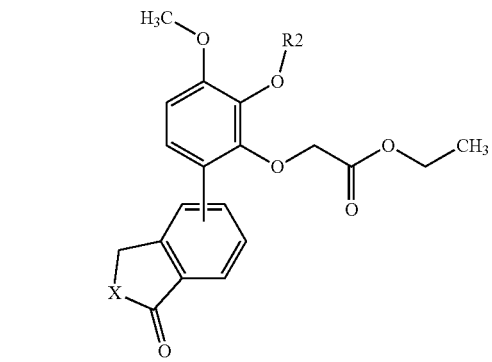

R2 = Methyl, Ethyl
X = CH2 or NH

Above compounds are prepared by reaction of compounds 303, 305 or 307 with 2-bromo-acetic acid ethyl ester in a solvent such as DMF, acetonitrile in the presence of potassium carbonate or cesium carbonate either at room temperature or with heating. The alkylated phenol is then submitted to ester hydrolysis in LiOH/H$_2$O/THF followed by re-esterification using EDCI, DMAP and DCM as described in example 163. Alternatively the synthesis is performed as described in example 153, replacing the amide synthesis by an ester synthesis as described above.

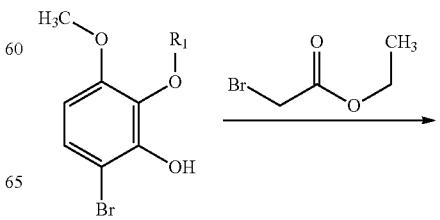

-continued

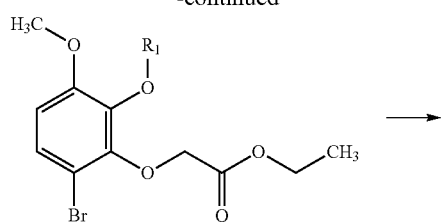

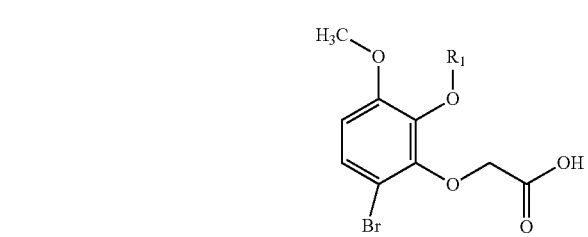

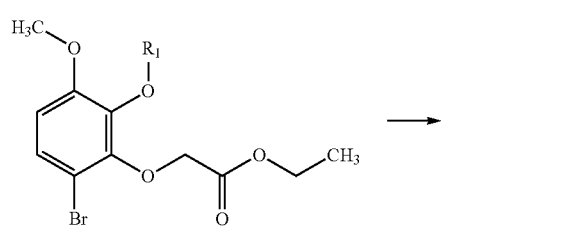

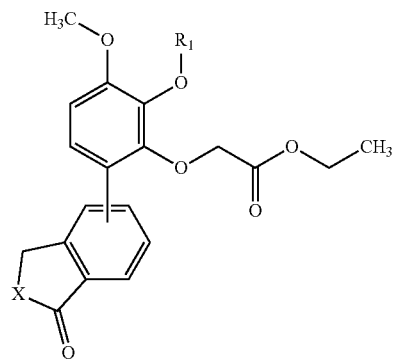

R1 = Methyl, Ethyl
X = CH₂ or NH

Or, alternatively the compounds are prepared in analogy with the synthesis described in example 88, starting from 6-bromo-2,3-dimethoxyphenol and 2-bromo-acetic acid ethyl ester. The amide synthesis in example 88 is replaced with an ester synthesis as described above If R2 is ethyl, the starting material is prepared as described for the preparation of compound 321 in preparation 21, replacing cyclopropylmethyl bromide with ethyl bromide or ethyl iodide and coupling the bromide with the appropriate boronic acid ester.

Example 172

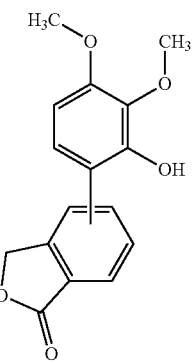 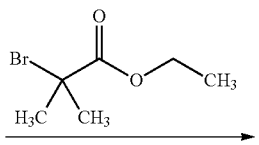

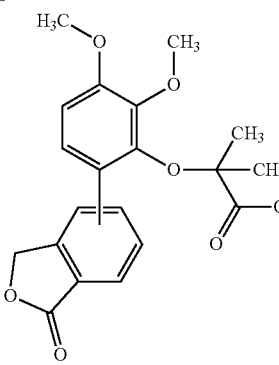

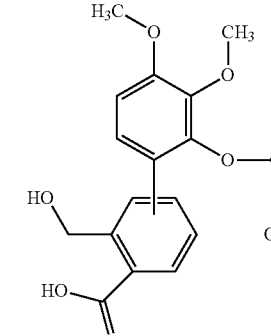

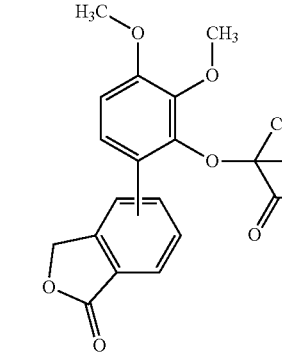

653

-continued

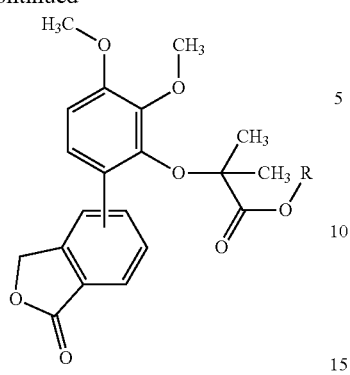

Above compounds are prepared as described in example 165, only replacing the Mitsunobu reaction with an alkylation of the phenol using 2-bromo-2-methyl-propanoic acid ethyl ester in a solvent such as DMF, acetonitrile in the presence of potassium carbonate or cesium carbonate either at room temperature or with heating Example 173

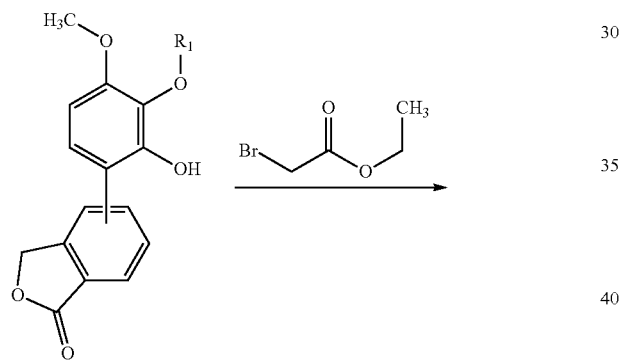

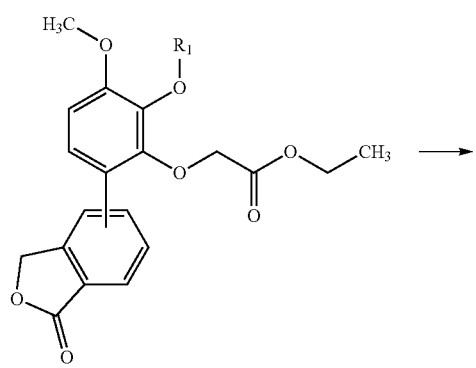

654

-continued

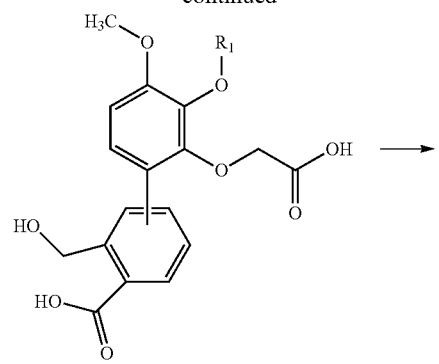

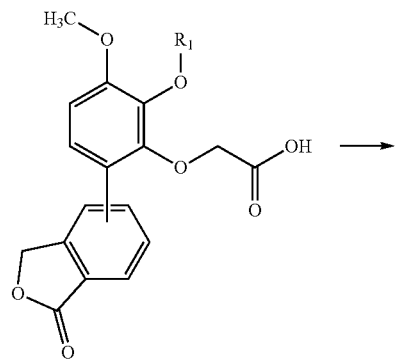

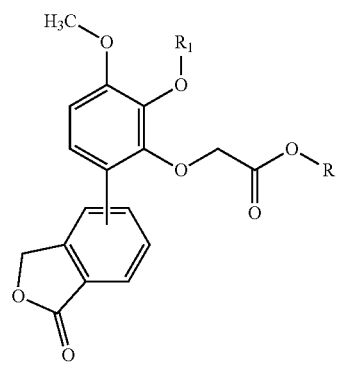

R1 = Methyl, Ethyl

Above compounds are prepared as described in example 165, only replacing the Mitsunobu reaction with an alkylation of the phenol using 2-bromo-acetic acid ethyl ester in a solvent such as DMF, acetonitrile in the presence of potassium carbonate or cesium carbonate either at room temperature or with heating Example 174

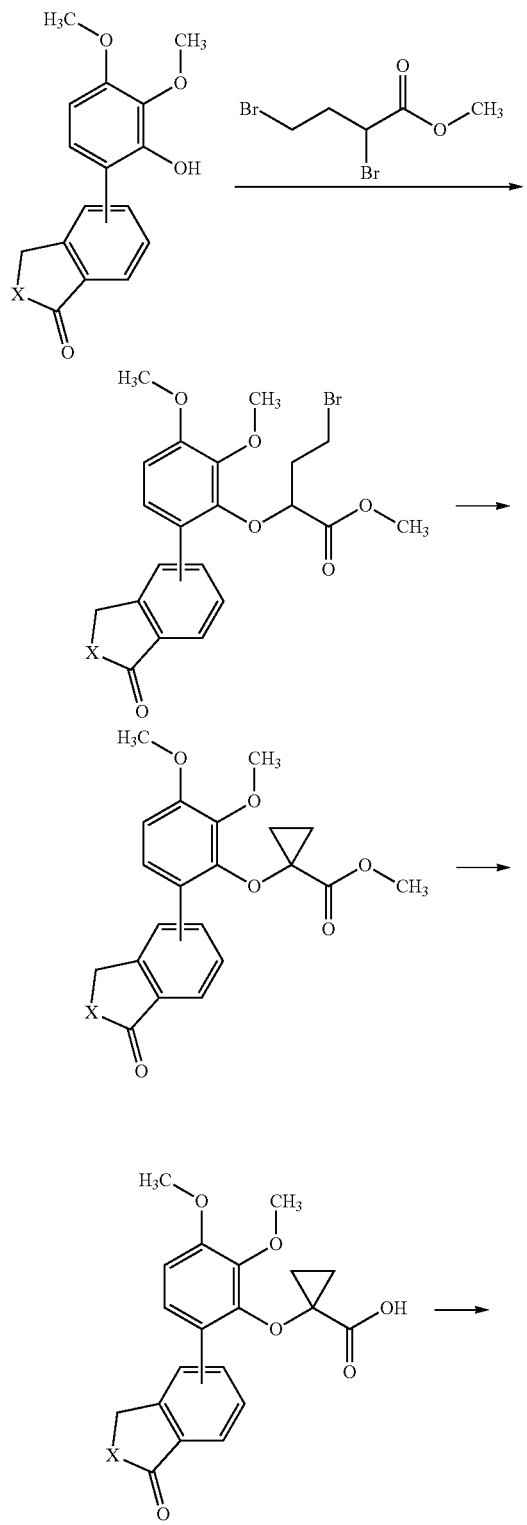

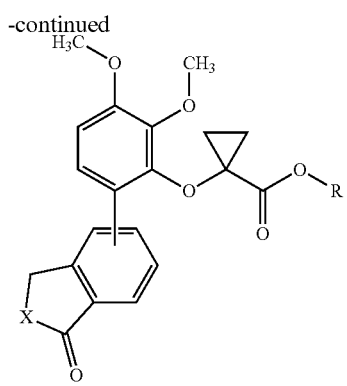

X = CH₂ or NH

Above compounds are prepared starting from compounds 303, 305 or 307. To the solution of the phenol in DMF methyl 2,4-dibromobutyrate and potassium carbonate is added. After stirring the reaction mixture is poured on ethyl acetate and 1 M aqueous hydrochloric acid and extracted. The organic phases are washed with brine, dried over magnesium sulfate, filtered and evaporated. The residue is purified by column chromatography on silica gel.

The residue is dissolved in tetrahydrofuran and cooled to −15.deg. C. and potassium tert-butoxide is added. The cooling bath was removed and the reaction is stirred at room temperature. The solution is poured on ethyl acetate and aqueous hydrochloric acid, extracted and the phases were separated.

The organic layer is washed with brine and the aqueous layers are extracted with ethyl acetate. The combined organic layers are dried over magnesium sulfate, filtered and evaporated. The residue is purified by column chromatography on silica to afford the cyclopropyl derivative. The subsequent esterhydrolysis and re-esterification is performed as described in example 163

Alternatively, the compounds are prepared starting from 6-bromo-2,3-dimethoxyphenol. To the solution of the phenol in DMF methyl 2,4-dibromobutyrate and potassium carbonate is added. After stirring the reaction mixture is poured on ethyl acetate and 1 M aqueous hydrochloric acid and extracted. The organic phases are washed with brine, dried over magnesium sulfate, filtered and evaporated. The residue is purified by column chromatography on silica gel.

The residue is dissolved in tetrahydrofuran and cooled to −15.deg. C. and potassium tert-butoxide is added. The cooling bath was removed and the reaction is stirred at room temperature. The solution is poured on ethyl acetate and aqueous hydrochloric acid, extracted and the phases were separated.

The organic layer is washed with brine and the aqueous layers are extracted with ethyl acetate. The combined organic layers are dried over magnesium sulfate, filtered and evaporated. The residue is purified by column chromatography on silica to afford the cyclopropyl derivative. The subsequent esterhydrolysis and re-esterification is performed as described in example 163. The bromide is coupled with the appropriate boronic acid ester by Suzuki coupling as described in example 88 to afford the biaryl product.

Example 175

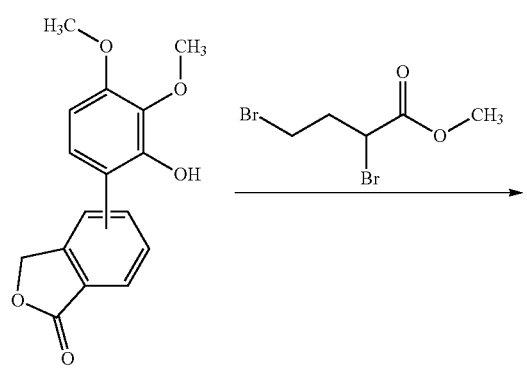

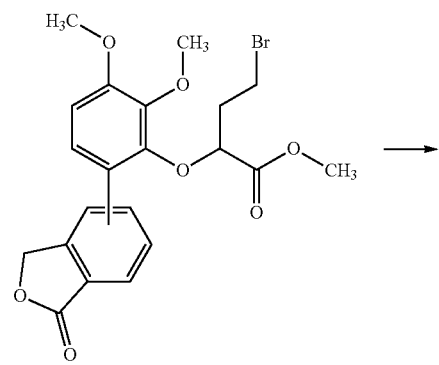

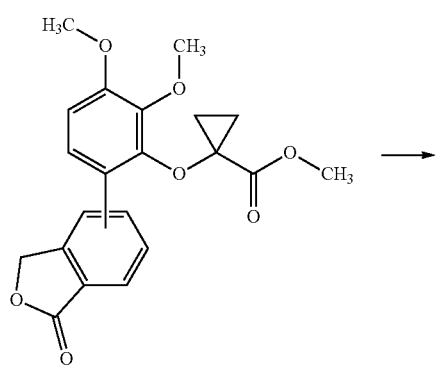

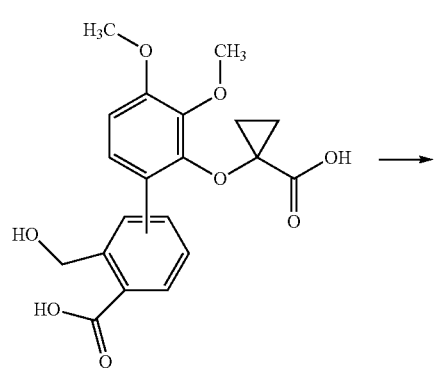

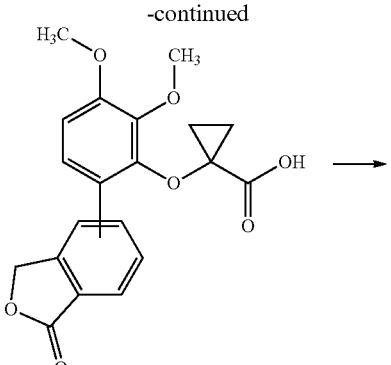

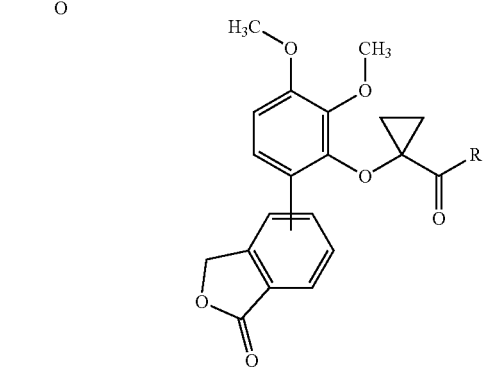

Above compounds are prepared starting from compounds 303, 305 or 307. To the solution of the phenol in DMF methyl 2,4-dibromobutyrate and potassium carbonate is added. After stirring the reaction mixture is poured on ethyl acetate and 1 M aqueous hydrochloric acid and extracted. The organic phases are washed with brine, dried over magnesium sulfate, filtered and evaporated. The residue is purified by column chromatography on silica gel.

The residue is dissolved in tetrahydrofuran and cooled to −15.deg. C. and potassium tert-butoxide is added. The cooling bath was removed and the reaction is stirred at room temperature. The solution is poured on ethyl acetate and aqueous hydrochloric acid, extracted and the phases were separated.

The organic layer is washed with brine and the aqueous layers are extracted with ethyl acetate. The combined organic layers are dried over magnesium sulfate, filtered and evaporated. The residue is purified by column chromatography on silica to afford the cyclopropyl derivative. The subsequent esterhydrolysis, lactone formation and re-esterification is performed as described in example 165.

Example 176

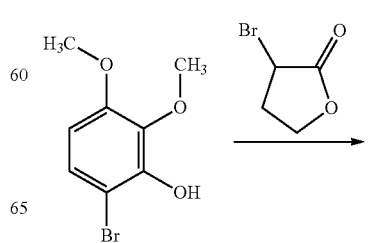

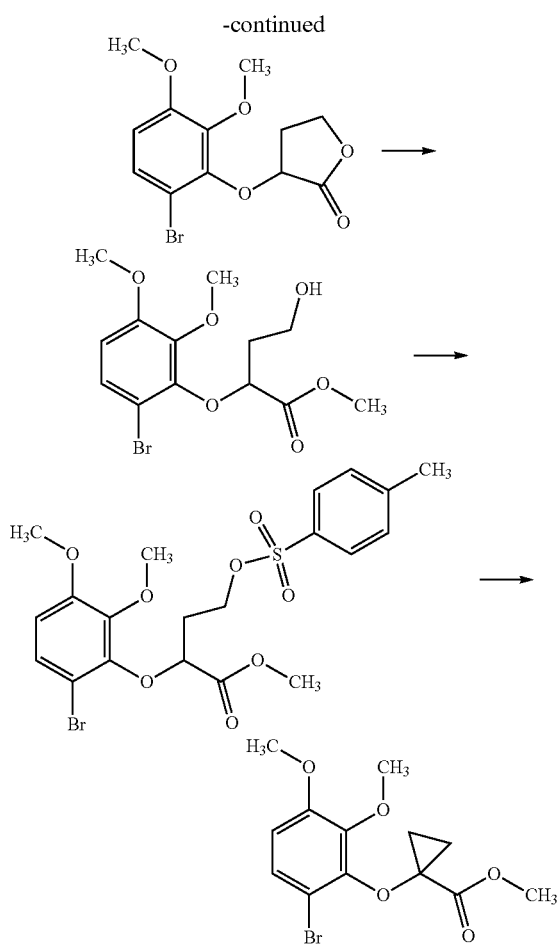

The cyclopropyl derivatives can alternatively be prepared as outlined above.

A mixture of 3-bromo-dihydro-furan-2-one, 6-bromo-2,3-dimethoxyphenol and potassium carbonate in a solvent such as DMF, acetonitrile or 2-butan-one reacts either at room temperature or with heating. The mixture is stirred until completion. After removing solvents, the residue is partitioned between H₂O and EtOAc and the aqueous layer is extracted with EtOAc. The combined organic layers were dried (MgSO₄) and purified by column chromatography To a solution of the lacton in MeOH at room temperature NaOMe is added. The resulting mixture is stirred at room temperature or with heating until reaction is finished and quenched with aqueous NH₄Cl. The mixture was extracted with EtOAc. The organic extracts is dried (MgSO₄) and concentrated. The crude product is purified by column chromatography.

To a solution of the alcohol, methanesulfonyl chloride or p-toluenesulfonyl chloride in a solvent such as CH₂Cl₂, THF or DMF at room temperature is added a base such as Et₃N, DIPEA or potassium carbonate. The resulting mixture is stirred either at room temperature or with heating. The reaction is partitioned between H₂O and EtOAc and the aqueous layer is extracted with EtOAc. The combined organic layers is dried (MgSO₄) and purified by column chromatography.

To a solution of the product in a solvent such as THF, DMF or DMSO at 0.deg. C. under N₂ is added a base such as t-BuOK, NaH MeONa. The resulting mixture is stirred at 0.deg. C. or with heating until the reaction is complet and acidified with HCl aq. The reaction is extracted with EtOAc. The combined organic layers are dried (MgSO₄) and concentrated. The crude product is purified by column. (ref. US2007244094)

The bromide is coupled with the appropriate boronic aced ester by Suzuki coupling as for example described in example 88 to afford the biaryl products.

Compounds 1294-1558 are prepared according to example 170, 171, 172, 173, 174, 175 or 176.

| Compound | Structure | Compound name |
|---|---|---|
| 1294 | 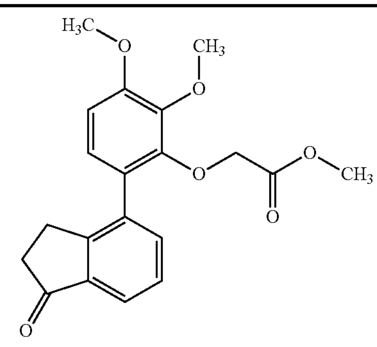 | methyl 2-[2,3-dimethoxy-6-(1-oxoindan-4-yl)phenoxy]acetate |
| 1295 | 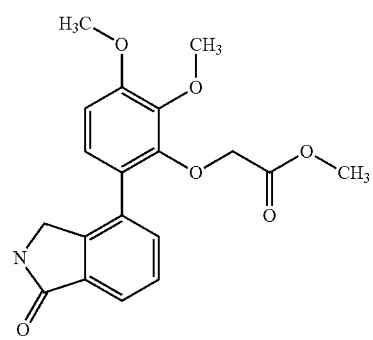 [SMILES: COC(=O)COc1c(-c2cccc3c2CNC3=O)ccc(OC)c1OC] | methyl 2-[2,3-dimethoxy-6-(1-oxoisoindolin-4-yl)phenoxy]acetate |

| Compound | Structure | Compound name |
|---|---|---|
| 1296 | 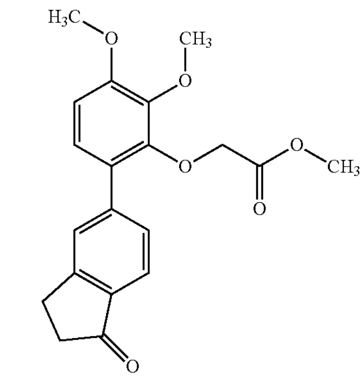 [SMILES: COC(=O)COc1c(-c2ccc3c(c2)CCC3=O)ccc(OC)c1OC] | methyl 2-[2,3-dimethoxy-6-(1-oxoindan-5-yl)phenoxy]acetate |
| 1297 | 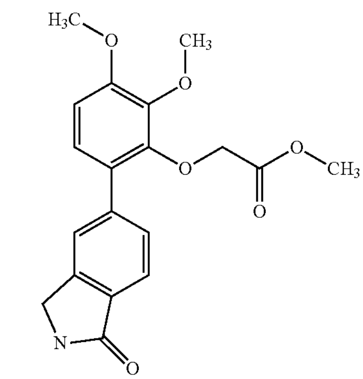 [SMILES: COC(=O)COc1c(-c2ccc3c(c2)CNC3=O)ccc(OC)c1OC] | methyl 2-[2,3-dimethoxy-6-(1-oxoisoindolin-5-yl)phenoxy]acetate |
| 1298 | 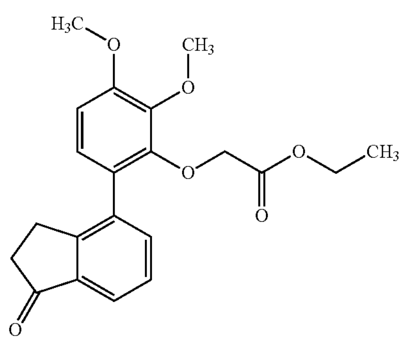 [SMILES: CCOC(=O)COc1c(-c2cccc3c2CCC3=O)ccc(OC)c1OC] | ethyl 2-[2,3-dimethoxy-6-(1-oxoindan-4-yl)phenoxy]acetate |
| 1299 | 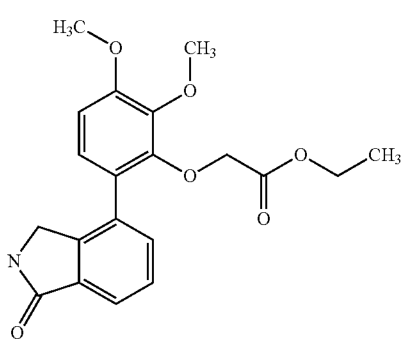 [SMILES: CCOC(=O)COc1c(-c2cccc3c2CNC3=O)ccc(OC)c1OC] | ethyl 2-[2,3-dimethoxy-6-(1-oxoisoindolin-4-yl)phenoxy]acetate |

-continued

| Compound | Structure | Compound name |
|---|---|---|
| 1300 | 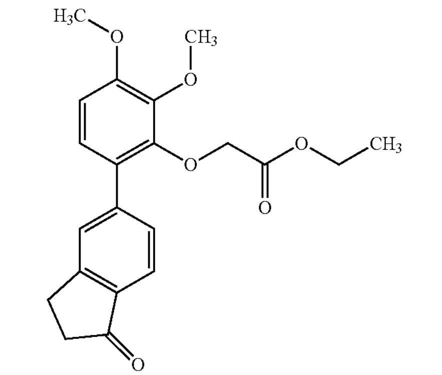 [SMILES: CCOC(=O)COc1c(-c2ccc3c(c2)CCC3=O)ccc(OC)c1OC] | ethyl 2-[2,3-dimethoxy-6-(1-oxoindan-5-yl)phenoxy]acetate |
| 1301 | 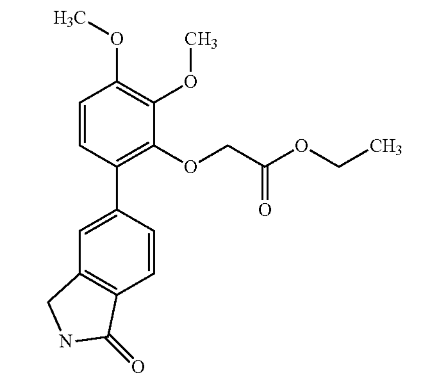 [SMILES: CCOC(=O)COc1c(-c2ccc3c(c2)CNC3=O)ccc(OC)c1OC] | ethyl 2-[2,3-dimethoxy-6-(1-oxoisoindolin-5-yl)phenoxy]acetate |
| 1302 | 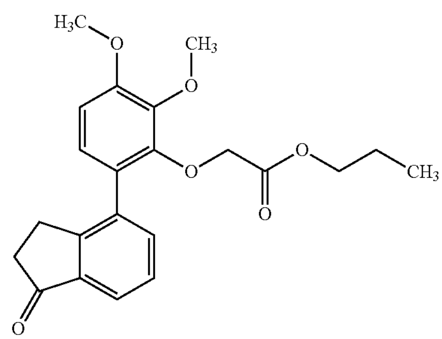 [SMILES: CCCOC(=O)COc1c(-c2cccc3c2CCC3=O)ccc(OC)c1OC] | propyl 2-[2,3-dimethoxy-6-(1-oxoindan-4-yl)phenoxy]acetate |
| 1303 | 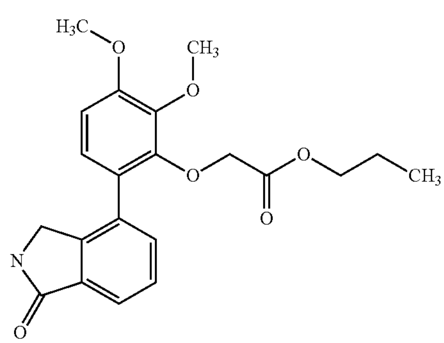 | propyl 2-[2,3-dimethoxy-6-(1-oxoisoindolin-4-yl)phenoxy]acetate |

-continued

| Compound | Structure | Compound name |
|---|---|---|
| 1304 | 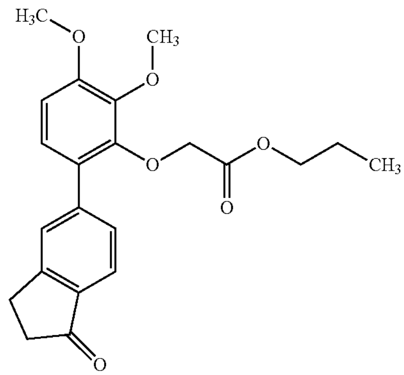 [SMILES: CCCOC(=O)COc1c(-c2ccc3c(c2)CCC3=O)ccc(OC)c1OC] | propyl 2-[2,3-dimethoxy-6-(1-oxoindan-5-yl)phenoxy]acetate |
| 1305 | 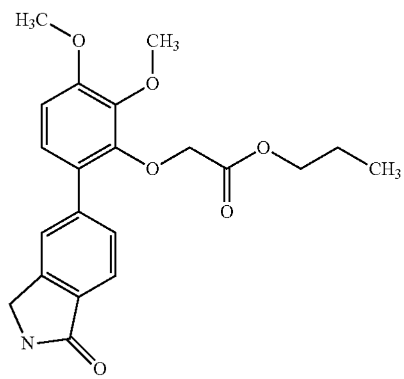 [SMILES: CCCOC(=O)COc1c(-c2ccc3c(c2)CNC3=O)ccc(OC)c1OC] | propyl 2-[2,3-dimethoxy-6-(1-oxoisoindolin-5-yl)phenoxy]acetate |
| 1306 | 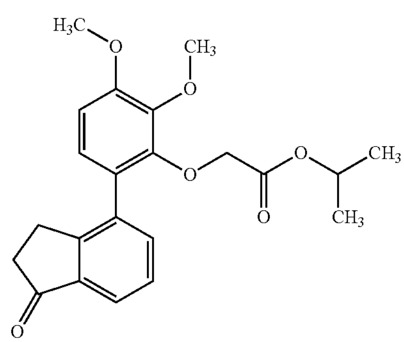 [SMILES: COc1ccc(-c2cccc3c2CCC3=O)c(OCC(=O)OC(C)C)c1OC] | isopropyl 2-[2,3-dimethoxy-6-(1-oxoindan-4-yl)phenoxy]acetate |
| 1307 | 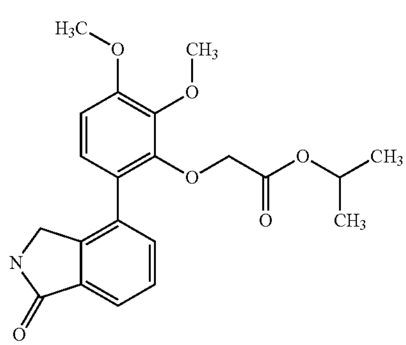 [SMILES: COc1ccc(-c2cccc3c2CNC3=O)c(OCC(=O)OC(C)C)c1OC] | isopropyl 2-[2,3-dimethoxy-6-(1-oxoisoindolin-4-yl)phenoxy]acetate |

| Compound | Structure | Compound name |
|---|---|---|
| 1308 | 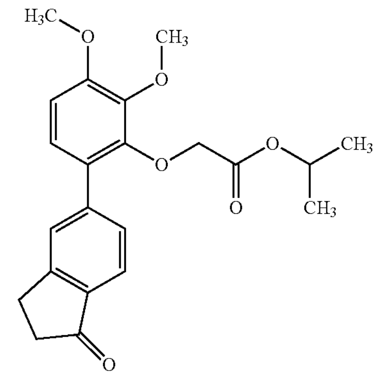 [SMILES: COc1ccc(-c2ccc3c(c2)CCC3=O)c(OCC(=O)OC(C)C)c1OC] | isopropyl 2-[2,3-dimethoxy-6-(1-oxoindan-5-yl)phenoxy]acetate |
| 1309 | 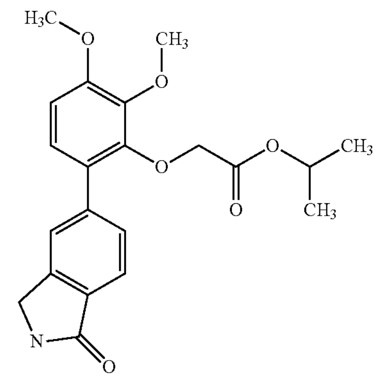 [SMILES: COc1ccc(-c2ccc3c(c2)CNC3=O)c(OCC(=O)OC(C)C)c1OC] | isopropyl 2-[2,3-dimethoxy-6-(1-oxoisoindolin-5-yl)phenoxy]acetate |
| 1310 | 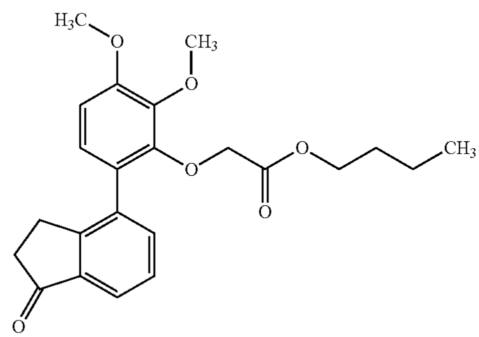 [SMILES: CCCCOC(=O)COc1c(-c2cccc3c2CCC3=O)ccc(OC)c1OC] | butyl 2-[2,3-dimethoxy-6-(1-oxoindan-4-yl)phenoxy]acetate |
| 1311 | 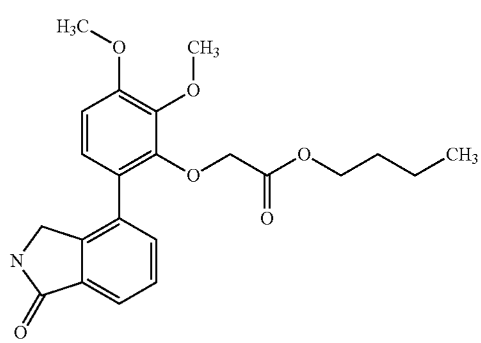 [SMILES: CCCCOC(=O)COc1c(-c2cccc3c2CNC3=O)ccc(OC)c1OC] | butyl 2-[2,3-dimethoxy-6-(1-oxoisoindolin-4-yl)phenoxy]acetate |

-continued
| Compound | Structure | Compound name |
|---|---|---|
| 1312 | 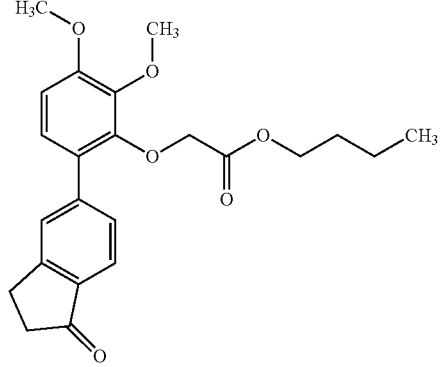 [SMILES: CCCCOC(=O)COc1c(-c2ccc3c(c2)CCC3=O)ccc(OC)c1OC] | butyl 2-[2,3-dimethoxy-6-(1-oxoindan-5-yl)phenoxy]acetate |
| 1313 | 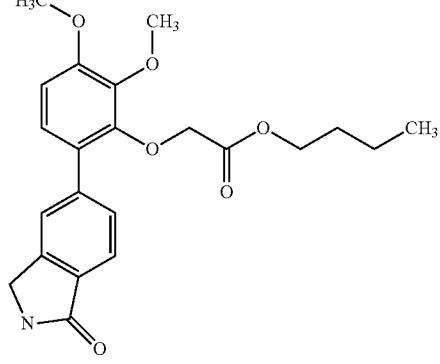 | butyl 2-[2,3-dimethoxy-6-(1-oxoisoindolin-5-yl)phenoxy]acetate |
| 1314 | 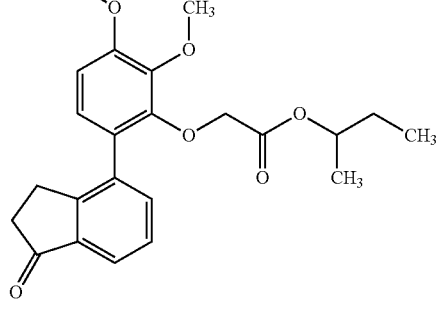 | sec-butyl 2-[2,3-dimethoxy-6-(1-oxoindan-4-yl)phenoxy]acetate |
| 1315 | 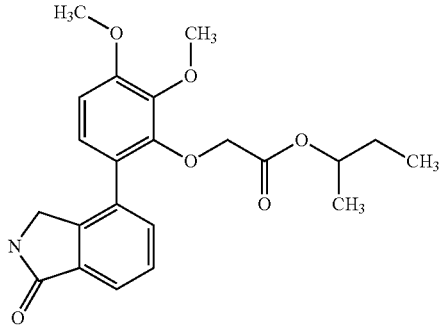 [SMILES: CCC(C)OC(=O)COc1c(-c2cccc3c2CCC3=O)ccc(OC)c1OC] | sec-butyl 2-[2,3-dimethoxy-6-(1-oxoisoindolin-4-yl)phenoxy]acetate |

-continued

| Compound | Structure | Compound name |
|---|---|---|
| 1316 | 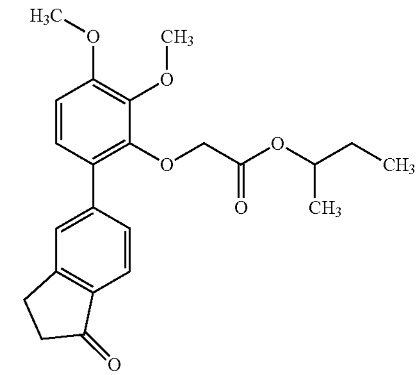 [SMILES: CCC(C)OC(=O)COc1c(-c2ccc3c(c2)CCC3=O)ccc(OC)c1OC] | sec-butyl 2-[2,3-dimethoxy-6-(1-oxoindan-5-yl)phenoxy]acetate |
| 1317 | 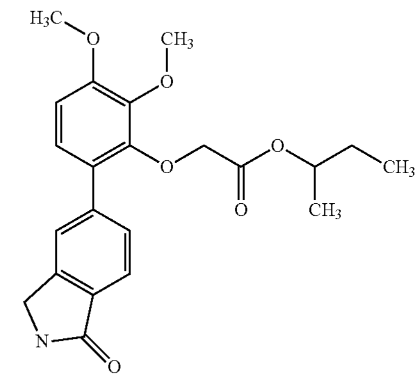 [SMILES: CCC(C)OC(=O)COc1c(-c2ccc3c(c2)CNC3=O)ccc(OC)c1OC] | sec-butyl 2-[2,3-dimethoxy-6-(1-oxoisoindolin-5-yl)phenoxy]acetate |
| 1318 | 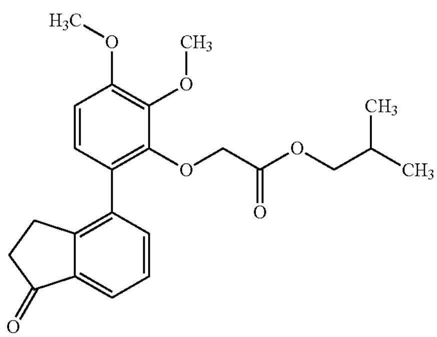 [SMILES: COc1ccc(-c2cccc3c2CCC3=O)c(OCC(=O)OCC(C)C)c1OC] | isobutyl 2-[2,3-dimethoxy-6-(1-oxoindan-4-yl)phenoxy]acetate |
| 1319 | 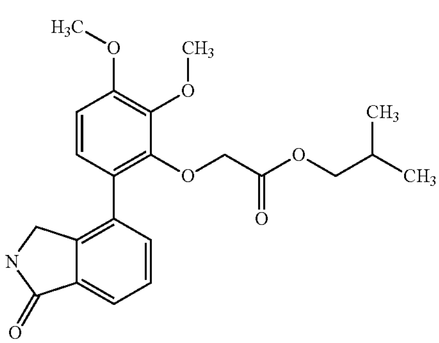 [SMILES: COc1ccc(-c2cccc3c2CNC3=O)c(OCC(=O)OCC(C)C)c1OC] | isobutyl 2-[2,3-dimethoxy-6-(1-oxoisoindolin-4-yl)phenoxy]acetate |

| Compound | Structure | Compound name |
|---|---|---|
| 1320 | 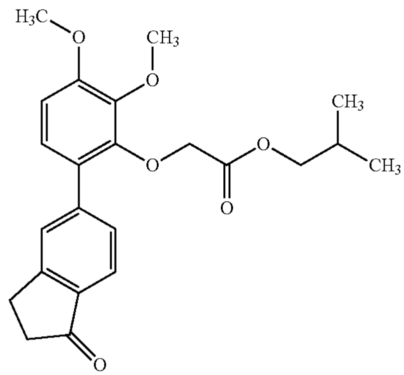 [SMILES: COc1ccc(-c2ccc3c(c2)CCC3=O)c(OCC(=O)OCC(C)C)c1OC] | isobutyl 2-[2,3-dimethoxy-6-(1-oxoindan-5-yl)phenoxy]acetate |
| 1321 | 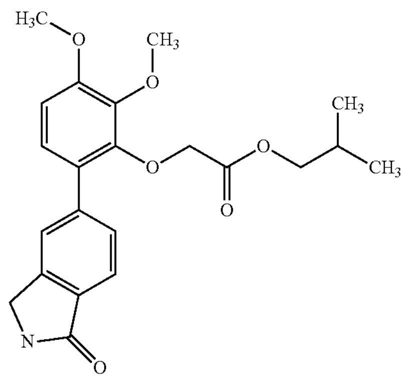 | isobutyl 2-[2,3-dimethoxy-6-(1-oxoisoindolin-5-yl)phenoxy]acetate |
| 1322 | 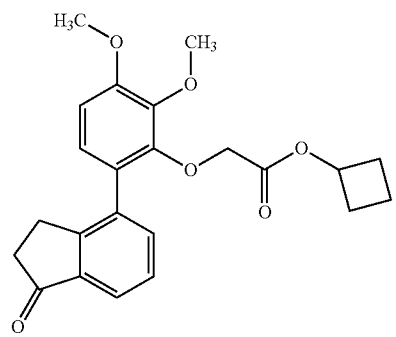 [SMILES: COc1ccc(-c2cccc3c2CCC3=O)c(OCC(=O)OC2CCC2)c1OC] | cyclobutyl 2-[2,3-dimethoxy-6-(1-oxoindan-4-yl)phenoxy]acetate |
| 1323 | 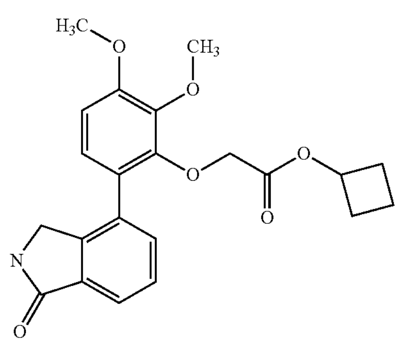 [SMILES: COc1ccc(-c2cccc3c2CNC3=O)c(OCC(=O)OC2CCC2)c1OC] | cyclobutyl 2-[2,3-dimethoxy-6-(1-oxoisoindolin-4-yl)phenoxy]acetate |

| Compound | Structure | Compound name |
|---|---|---|
| 1324 | 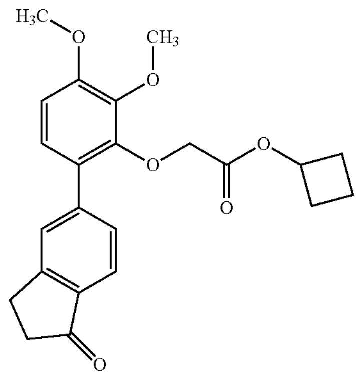 [SMILES: COc1ccc(-c2ccc3c(c2)CCC3=O)c(OCC(=O)OC2CCC2)c1OC] | cyclobutyl 2-[2,3-dimethoxy-6-(1-oxoindan-5-yl)phenoxy]acetate |
| 1325 | 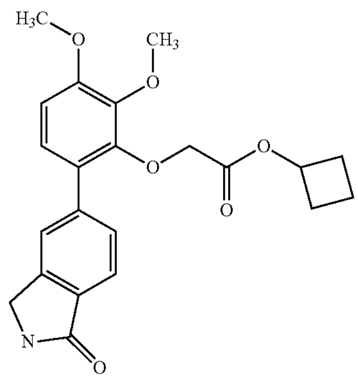 [SMILES: COc1ccc(-c2ccc3c(c2)CNC3=O)c(OCC(=O)OC2CCC2)c1OC] | cyclobutyl 2-[2,3-dimethoxy-6-(1-oxoisoindolin-5-yl)phenoxy]acetate |
| 1326 | 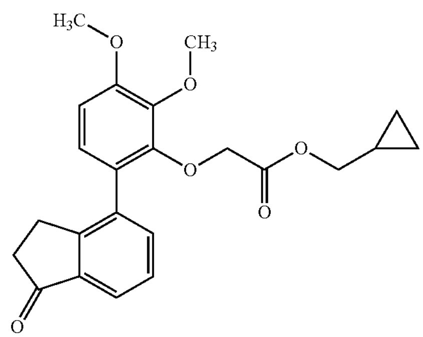 [SMILES: COc1ccc(-c2cccc3c2CCC3=O)c(OCC(=O)OCC2CC2)c1OC] | cyclopropylmethyl 2-[2,3-dimethoxy-6-(1-oxoindan-4-yl)phenoxy]acetate |
| 1327 | 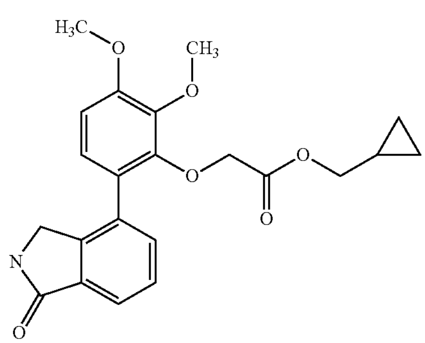 [SMILES: COc1ccc(-c2cccc3c2CNC3=O)c(OCC(=O)OCC2CC2)c1OC] | cyclopropylmethyl 2-[2,3-dimethoxy-6-(1-oxoisoindolin-4-yl)phenoxy]acetate |

-continued

| Compound | Structure | Compound name |
|---|---|---|
| 1328 | 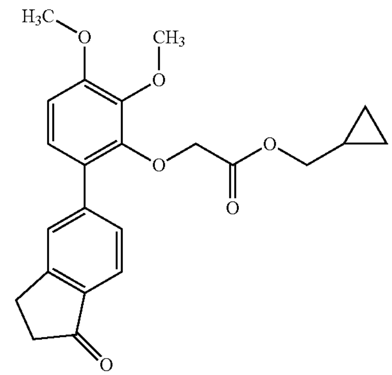 [SMILES: COc1ccc(-c2ccc3c(c2)CCC3=O)c(OCC(=O)OCC2CC2)c1OC] | cyclopropylmethyl 2-[2,3-dimethoxy-6-(1-oxoindan-5-yl)phenoxy]acetate |
| 1329 | 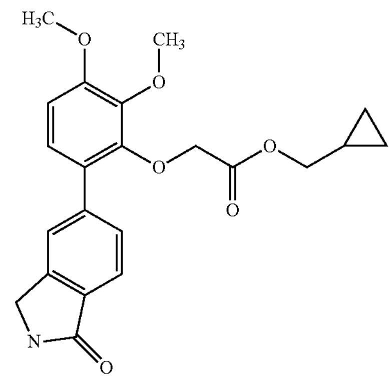 | cyclopropylmethyl 2-[2,3-dimethoxy-6-(1-oxoisoindolin-5-yl)phenoxy]acetate |
| 1330 | 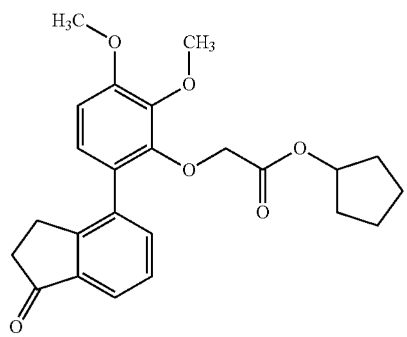 [SMILES: COc1ccc(-c2cccc3c2CCC3=O)c(OCC(=O)OC2CCCC2)c1OC] | cyclopentyl 2-[2,3-dimethoxy-6-(1-oxoindan-4-yl)phenoxy]acetate |
| 1331 | 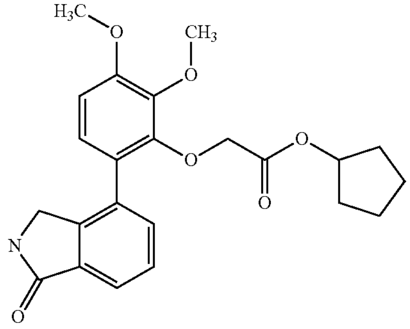 | cyclopentyl 2-[2,3-dimethoxy-6-(1-oxoisoindolin-4-yl)phenoxy]acetate |

-continued

| Compound | Structure | Compound name |
|---|---|---|
| 1332 | 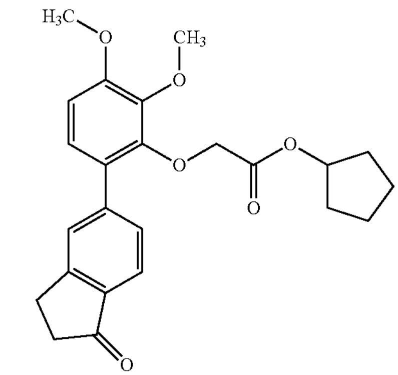 | cyclopentyl 2-[2,3-dimethoxy-6-(1-oxoindan-5-yl)phenoxy]acetate |
| 1333 | 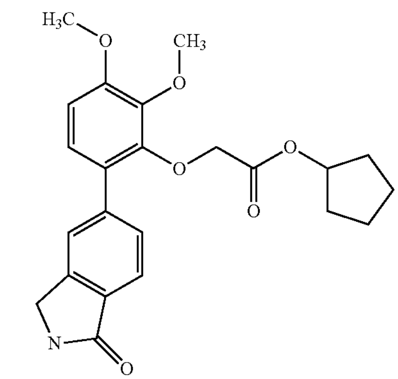 [SMILES: COc1ccc(-c2ccc3c(c2)CNC3=O)c(OCC(=O)OC2CCCC2)c1OC] | cyclopentyl 2-[2,3-dimethoxy-6-(1-oxoisoindolin-5-yl)phenoxy]acetate |
| 1334 | 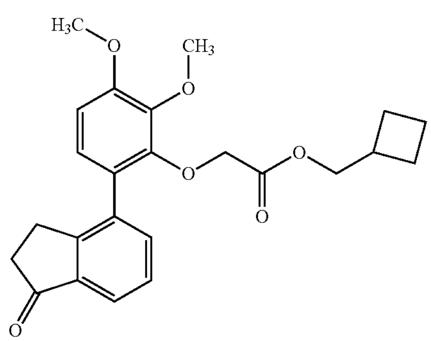 [SMILES: COc1ccc(-c2cccc3c2CCC3=O)c(OCC(=O)OCC2CCC2)c1OC] | cyclobutylmethyl 2-[2,3-dimethoxy-6-(1-oxoindan-4-yl)phenoxy]acetate |
| 1335 | 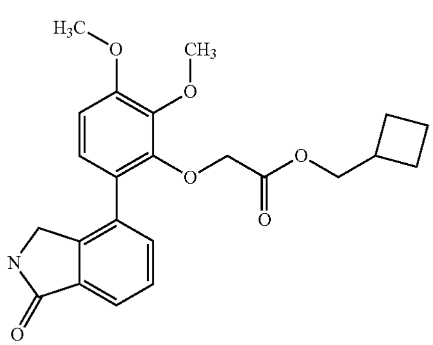 [SMILES: COc1ccc(-c2cccc3c2CNC3=O)c(OCC(=O)OCC2CCC2)c1OC] | cyclobutylmethyl 2-[2,3-dimethoxy-6-(1-oxoisoindolin-4-yl)phenoxy]acetate |

| Compound | Structure | Compound name |
|---|---|---|
| 1336 | 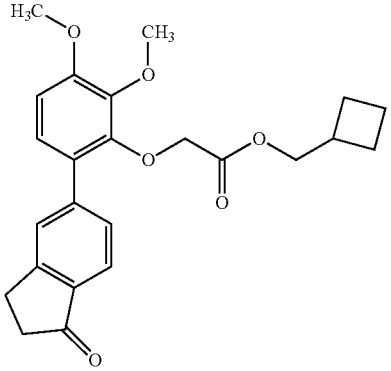 [SMILES: COc1ccc(-c2ccc3c(c2)CCC3=O)c(OCC(=O)OCC2CCC2)c1OC] | cyclobutylmethyl 2-[2,3-dimethoxy-6-(1-oxoindan-5-yl)phenoxy]acetate |
| 1337 | 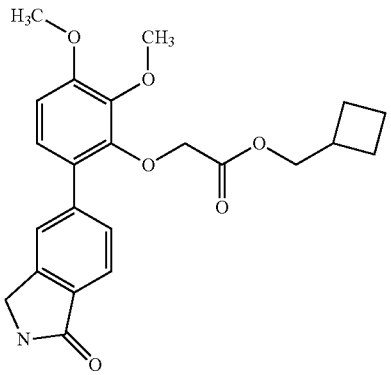 | cyclobutylmethyl 2-[2,3-dimethoxy-6-(1-oxoisoindolin-5-yl)phenoxy]acetate |
| 1338 | 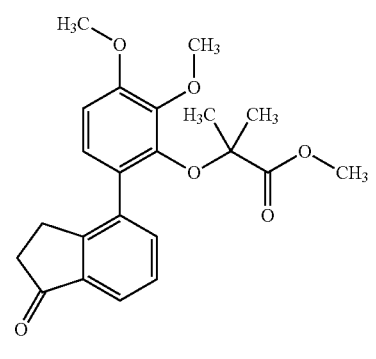 [SMILES: COC(=O)C(C)(C)Oc1c(-c2cccc3c2CCC3=O)ccc(OC)c1OC] | methyl 2-[2,3-dimethoxy-6-(1-oxoindan-4-yl)phenoxy]-2-methyl-propanoate |
| 1339 | 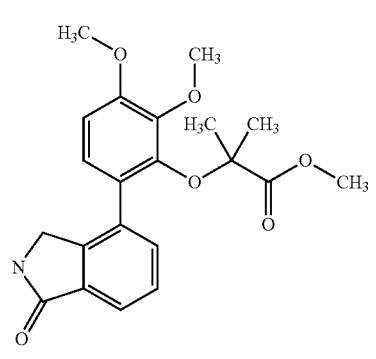 | methyl 2-[2,3-dimethoxy-6-(1-oxoisoindolin-4-yl)phenoxy]-2-methyl-propanoate |

| Compound | Structure | Compound name |
|---|---|---|
| 1340 | 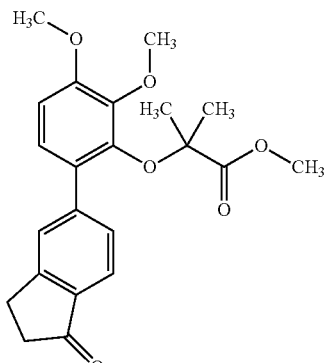 | methyl 2-[2,3-dimethoxy-6-(1-oxoindan-5-yl)phenoxy]-2-methyl-propanoate |
| 1341 | 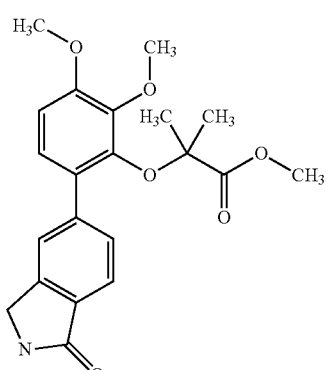 | methyl 2-[2,3-dimethoxy-6-(1-oxoisoindolin-5-yl)phenoxy]-2-methyl-propanoate |
| 1342 | 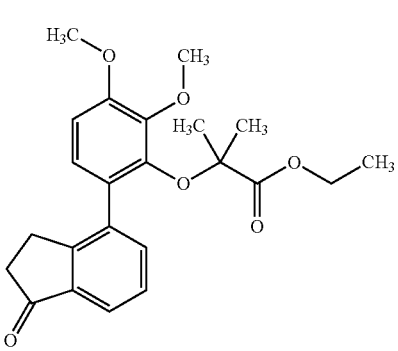 [SMILES: CCOC(=O)C(C)(C)Oc1c(-c2cccc3c2CCC3=O)ccc(OC)c1OC] | ethyl 2-[2,3-dimethoxy-6-(1-oxoindan-4-yl)phenoxy]-2-methyl-propanoate |
| 1343 | 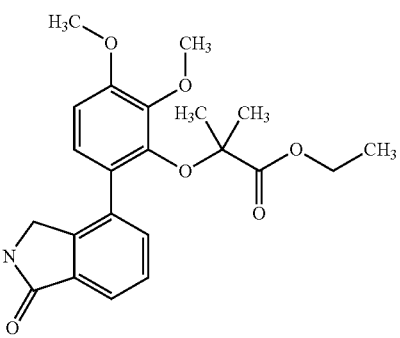 [SMILES: CCOC(=O)C(C)(C)Oc1c(-c2cccc3c2CNC3=O)ccc(OC)c1OC] | ethyl 2-[2,3-dimethoxy-6-(1-oxoisoindolin-4-yl)phenoxy]-2-methyl-propanoate |

| Compound | Structure | Compound name |
|---|---|---|
| 1344 | 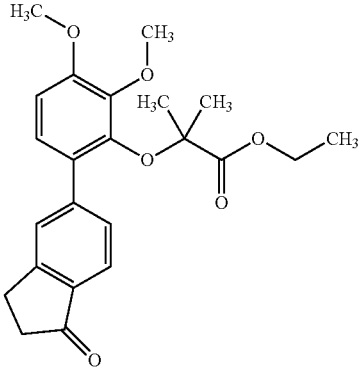 [SMILES: CCOC(=O)C(C)(C)Oc1c(-c2ccc3c(c2)CCC3=O)ccc(OC)c1OC] | ethyl 2-[2,3-dimethoxy-6-(1-oxoindan-5-yl)phenoxy]-2-methyl-propanoate |
| 1345 | 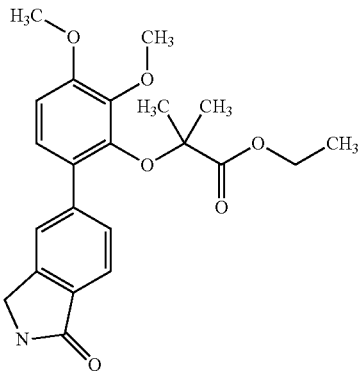 [SMILES: CCOC(=O)C(C)(C)Oc1c(-c2ccc3c(c2)CNC3=O)ccc(OC)c1OC] | ethyl 2-[2,3-dimethoxy-6-(1-oxoisoindolin-5-yl)phenoxy]-2-methyl-propanoate |
| 1346 | 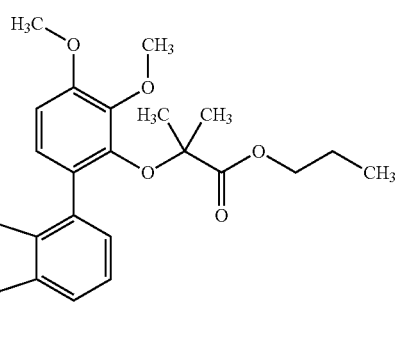 | propyl 2-[2,3-dimethoxy-6-(1-oxoindan-4-yl)phenoxy]-2-methyl-propanoate |
| 1347 | 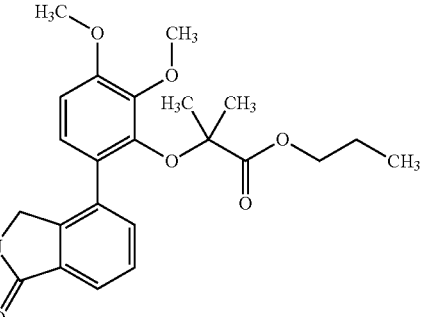 | propyl 2-[2,3-dimethoxy-6-(1-oxoisoindolin-4-yl)phenoxy]-2-methyl-propanoate |

| Compound | Structure | Compound name |
|---|---|---|
| 1348 | 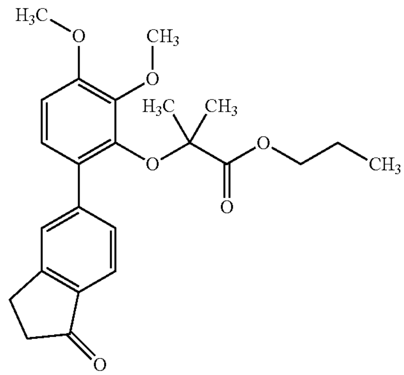 [SMILES: CCCOC(=O)C(C)(C)Oc1c(-c2ccc3c(c2)CCC3=O)ccc(OC)c1OC] | propyl 2-[2,3-dimethoxy-6-(1-oxoindan-5-yl)phenoxy]-2-methyl-propanoate |
| 1349 | 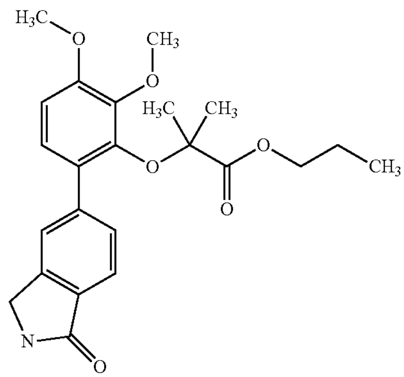 [SMILES: CCCOC(=O)C(C)(C)Oc1c(-c2ccc3c(c2)CNC3=O)ccc(OC)c1OC] | propyl 2-[2,3-dimethoxy-6-(1-oxoisoindolin-5-yl)phenoxy]-2-methyl-propanoate |
| 1350 | 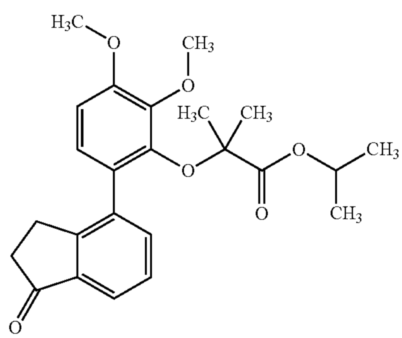 [SMILES: COc1ccc(-c2cccc3c2CCC3=O)c(OC(C)(C)C(=O)OC(C)C)c1OC] | isopropyl 2-[2,3-dimethoxy-6-(1-oxoindan-4-yl)phenoxy]-2-methyl-propanoate |
| 1351 | 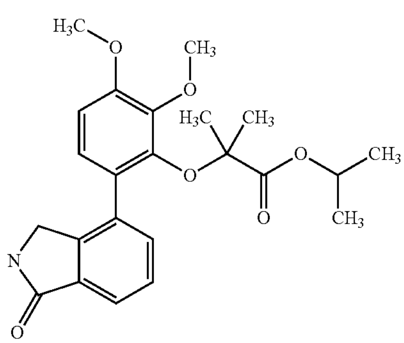 [SMILES: COc1ccc(-c2cccc3c2CNC3=O)c(OC(C)(C)C(=O)OC(C)C)c1OC] | isopropyl 2-[2,3-dimethoxy-6-(-1 oxoisoindolin-4-yl)phenoxy]-2-methyl-propanoate |

-continued

| Compound | Structure | Compound name |
|---|---|---|
| 1352 | 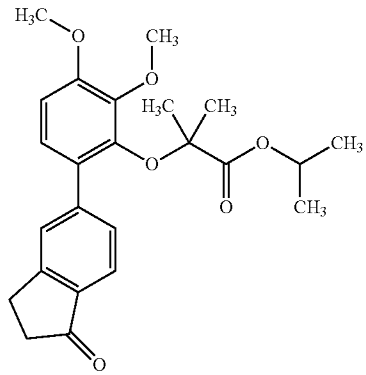 [SMILES: COc1ccc(-c2ccc3c(c2)CCC3=O)c(OC(C)(C)C(=O)OC(C)C)c1OC] | isopropyl 2-[2,3-dimethoxy-6-(1-oxoindan-5-yl)phenoxy]-2-methyl-propanoate |
| 1353 | 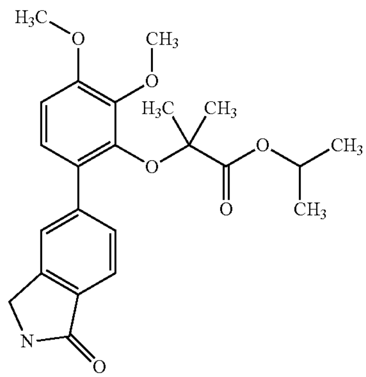 [SMILES: COc1ccc(-c2ccc3c(c2)CNC3=O)c(OC(C)(C)C(=O)OC(C)C)c1OC] | isopropyl 2-[2,3-dimethoxy-6-(1-oxoisoindolin-5-yl)phenoxy]-2-methyl-propanoate |
| 1354 | 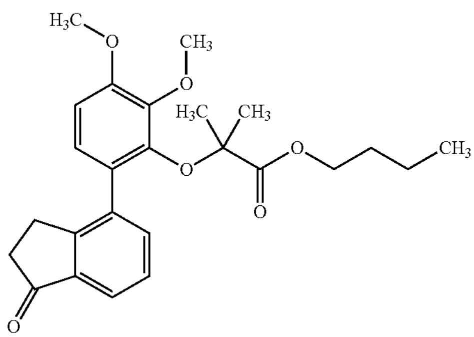 [SMILES: CCCCOC(=O)C(C)(C)Oc1c(-c2cccc3c2CCC3=O)ccc(OC)c1OC] | butyl 2-[2,3-dimethoxy-6-(1-oxoindan-4-yl)phenoxy]-2-methyl-propanoate |
| 1355 | 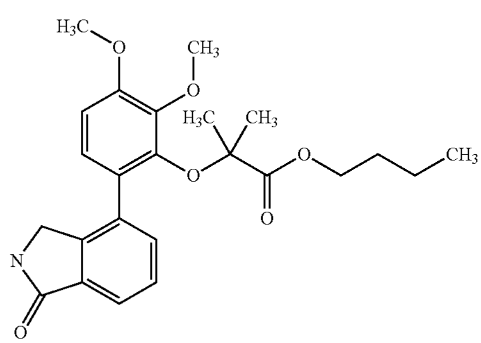 [SMILES: CCCCOC(=O)C(C)(C)Oc1c(-c2cccc3c2CNC3=O)ccc(OC)c1OC] | butyl 2-[2,3-dimethoxy-6-(1-oxoisoindolin-4-yl)phenoxy]-2-methyl-propanoate |

| Compound | Structure | Compound name |
|---|---|---|
| 1356 | 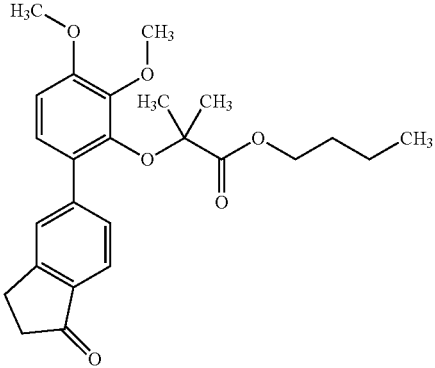 [SMILES: CCCCOC(=O)C(C)(C)Oc1c(-c2ccc3c(c2)CCC3=O)ccc(OC)c1OC] | butyl 2-[2,3-dimethoxy-6-(1-oxoindan-5-yl)phenoxy]-2-methyl-propanoate |
| 1357 | 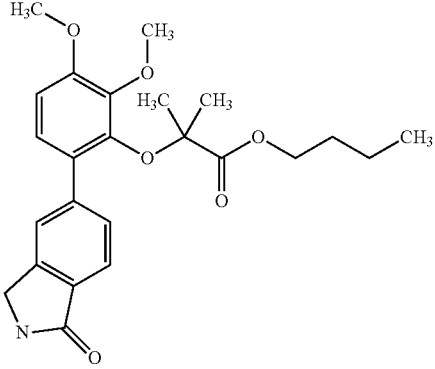 | butyl 2-[2,3-dimethoxy-6-(1-oxoisoindolin-5-yl)phenoxy]-2-methyl-propanoate |
| 1358 | 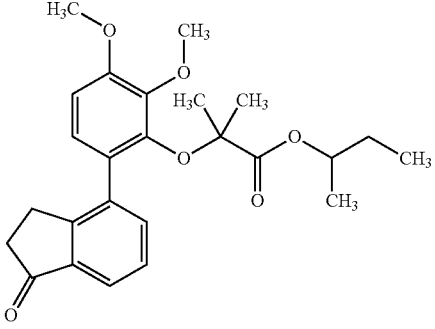 [SMILES: CCC(C)OC(=O)C(C)(C)Oc1c(-c2cccc3c2CCC3=O)ccc(OC)c1OC] | sec-butyl 2-[2,3-dimethoxy-6-(1-oxoindan-4-yl)phenoxy]-2-methyl-propanoate |
| 1359 | 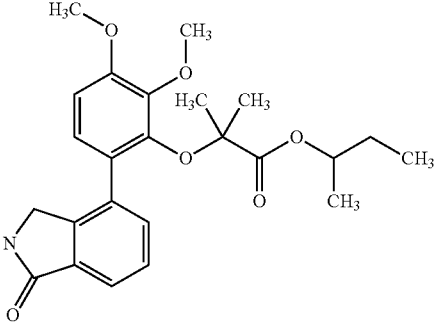 | sec-butyl 2-[2,3-dimethoxy-6-(1-oxoisoindolin-4-yl)phenoxy]-2-methyl-propanoate |

| Compound | Structure | Compound name |
|---|---|---|
| 1360 | 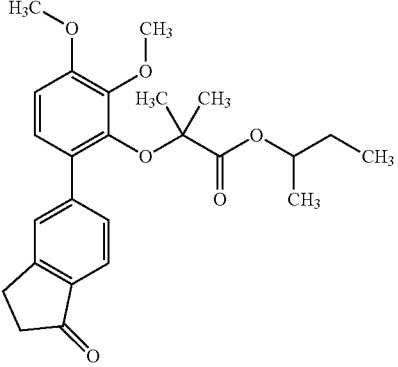 [SMILES: CCC(C)OC(=O)C(C)(C)Oc1c(-c2ccc3c(c2)CCC3=O)ccc(OC)c1OC] | sec-butyl 2-[2,3-dimethoxy-6-(1-oxoindan-5-yl)phenoxy]-2-methyl-propanoate |
| 1361 | 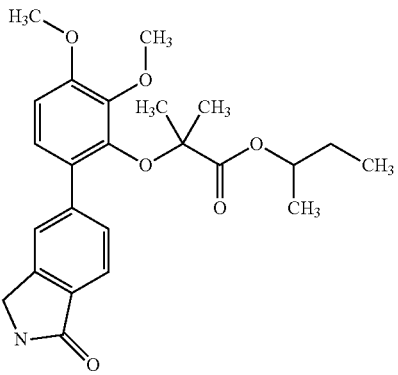 [SMILES: CCC(C)OC(=O)C(C)(C)Oc1c(-c2ccc3c(c2)CNC3=O)ccc(OC)c1OC] | sec-butyl 2-[2,3-dimethoxy-6-(1-oxoisoindolin-5-yl)phenoxy]-2-methyl-propanoate |
| 1362 | 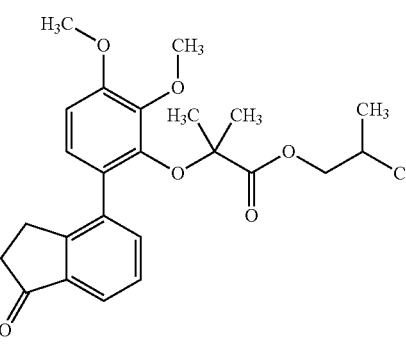 | isobutyl 2-[2,3-dimethoxy-6-(1-oxoindan-4-yl)phenoxy]-2-methyl-propanoate |
| 1363 | 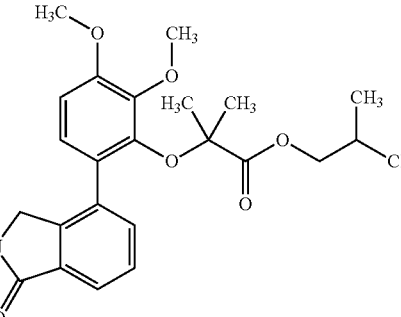 | isobutyl 2-[2,3-dimethoxy-6-(1-oxoisoindolin-4-yl)phenoxy]-2-methyl-propanoate |

-continued

| Compound | Structure | Compound name |
|---|---|---|
| 1364 | 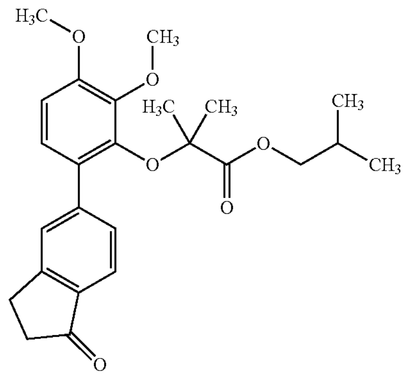 [SMILES: COc1ccc(-c2ccc3c(c2)CCC3=O)c(OC(C)(C)C(=O)OCC(C)C)c1OC] | isobutyl 2-[2,3-dimethoxy-6-(1-oxoindan-5-yl)phenoxy]-2-methyl-propanoate |
| 1365 | 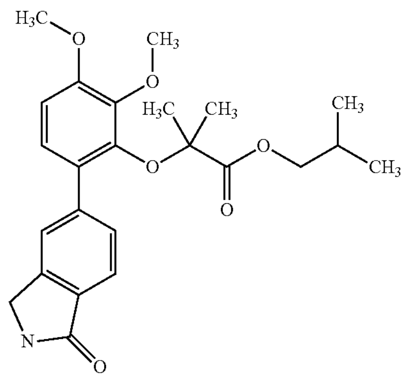 [SMILES: COc1ccc(-c2ccc3c(c2)CNC3=O)c(OC(C)(C)C(=O)OCC(C)C)c1OC] | isobutyl 2-[2,3-dimethoxy-6-(1-oxoisoindolin-5-yl)phenoxy]-2-methyl-propanoate |
| 1366 | 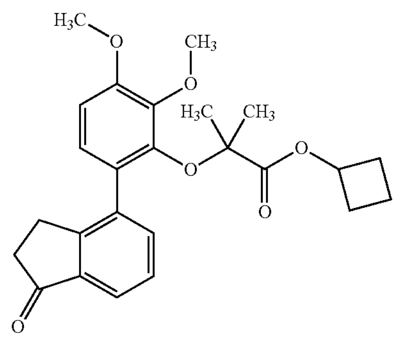 [SMILES: COc1ccc(-c2cccc3c2CCC3=O)c(OC(C)(C)C(=O)OC2CCC2)c1OC] | cyclobutyl 2-[2,3-dimethoxy-6-(1-oxoindan-4-yl)phenoxy]-2-methyl-propanoate |
| 1367 | 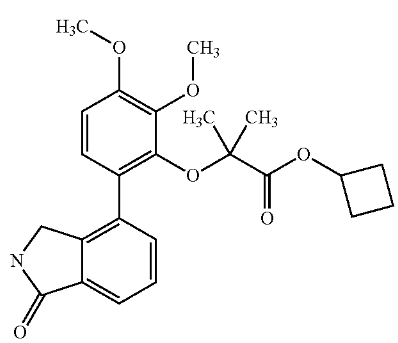 [SMILES: COc1ccc(-c2cccc3c2CNC3=O)c(OC(C)(C)C(=O)OC2CCC2)c1OC] | cyclobutyl 2-[2,3-dimethoxy-6-(1-oxoisoindolin-4-yl)phenoxy]-2-methyl-propanoate |

-continued

| Compound | Structure | Compound name |
|---|---|---|
| 1368 | 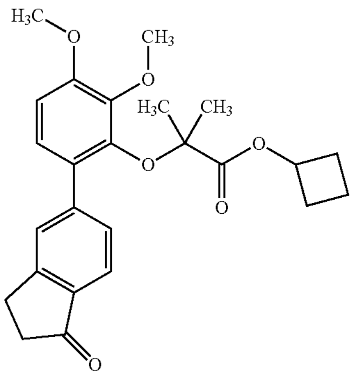 [SMILES: COc1ccc(-c2ccc3c(c2)CCC3=O)c(OC(C)(C)C(=O)OC2CCC2)c1OC] | cyclobutyl 2-[2,3-dimethoxy-6-(1-oxoindan-5-yl)phenoxy]-2-methyl-propanoate |
| 1369 | 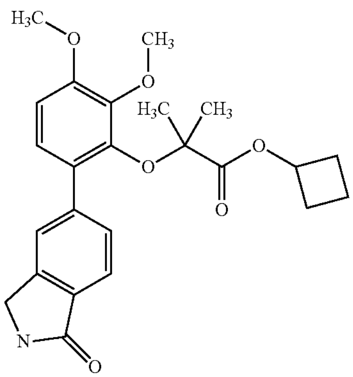 [SMILES: COc1ccc(-c2ccc3c(c2)CNC3=O)c(OC(C)(C)C(=O)OC2CCC2)c1OC] | cyclobutyl 2-[2,3-dimethoxy-6-(1-oxoisoindolin-5-yl)phenoxy]-2-methyl-propanoate |
| 1370 | 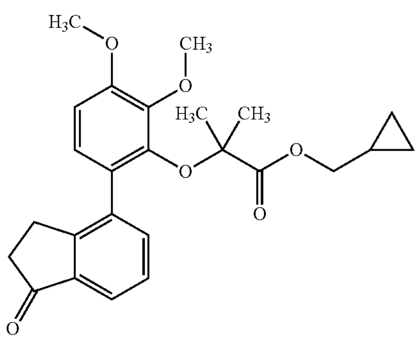 [SMILES: COc1ccc(-c2cccc3c2CCC3=O)c(OC(C)(C)C(=O)OCC2CC2)c1OC] | cyclopropylmethyl 2-[2,3-dimethoxy-6-(1-oxoindan-4-yl)phenoxy]-2-methyl-propanoate |
| 1371 | 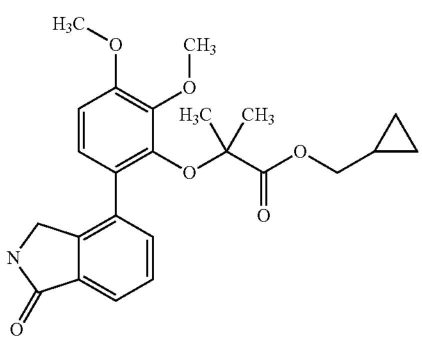 [SMILES: COc1ccc(-c2cccc3c2CNC3=O)c(OC(C)(C)C(=O)OCC2CC2)c1OC] | cyclopropylmethyl 2-[2,3-dimethoxy-6-(1-oxoisoindolin-4-yl)phenoxy]-2-methyl-propanoate |

-continued

| Compound | Structure | Compound name |
|---|---|---|
| 1372 | 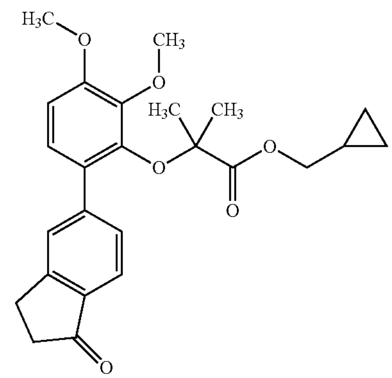 [SMILES: COc1ccc(-c2ccc3c(c2)CCC3=O)c(OC(C)(C)C(=O)OCC2CC2)c1OC] | cyclopropylmethyl 2-[2,3-dimethoxy-6-(1-oxoindan-5-yl)phenoxy]-2-methyl-propanoate |
| 1373 | 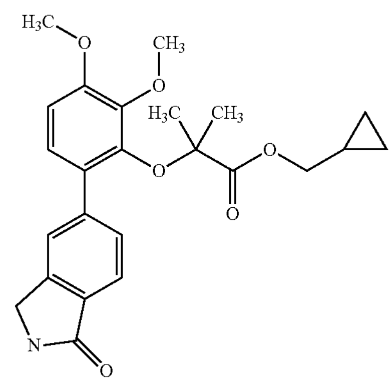 [SMILES: COc1ccc(-c2ccc3c(c2)CNC3=O)c(OC(C)(C)C(=O)OCC2CC2)c1OC] | cyclopropylmethyl 2-[2,3-dimethoxy-6-(1-oxoisoindolin-5-yl)phenoxy]-2-methyl-propanoate |
| 1374 | 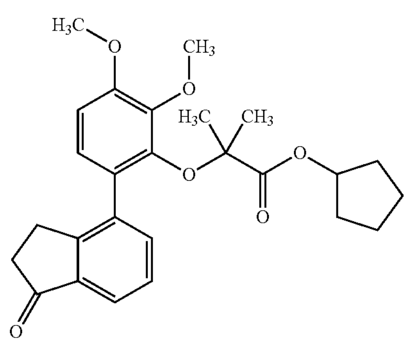 [SMILES: COc1ccc(-c2cccc3c2CCC3=O)c(OC(C)(C)C(=O)OC2CCCC2)c1OC] | cyclopentyl 2-[2,3-dimethoxy-6-(1-oxoindan-4-yl)phenoxy]-2-methyl-propanoate |
| 1375 | 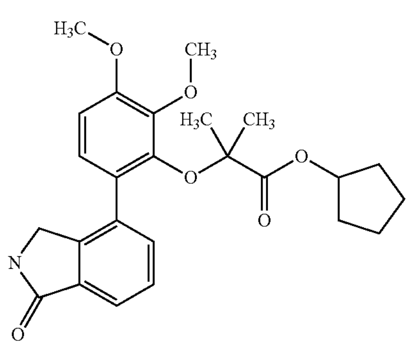 | cyclopentyl 2-[2,3-dimethoxy-6-(1-oxoisoindolin-4-yl)phenoxy]-2-methyl-propanoate |

| Compound | Structure | Compound name |
|---|---|---|
| 1376 | 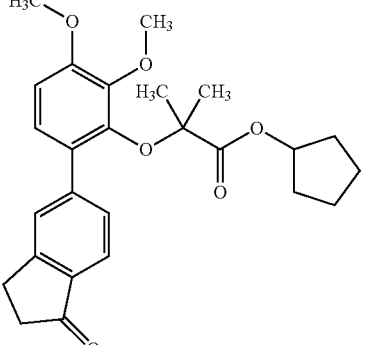 | cylcopentyl 2-[2,3-dimethoxy-6-(1-oxoindan-5-yl)phenoxy]-2-methyl-propanoate |
| 1377 | 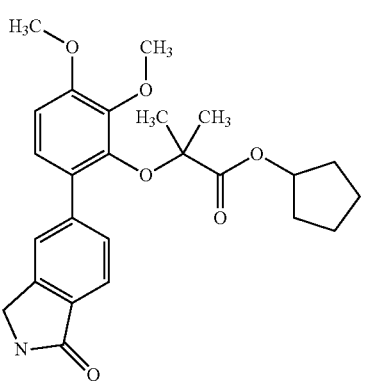 [SMILES: COc1ccc(-c2ccc3c(c2)CNC3=O)c(OC(C)(C)C(=O)OC2CCCC2)c1OC] | cyclopentyl 2-[2,3-dimethoxy-6-(1-oxoisoindolin-5-yl)phenoxy]-2-methyl-propanoate |
| 1378 | 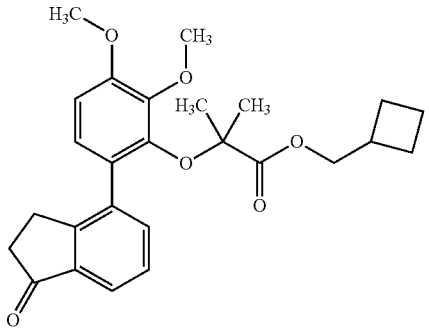 [SMILES: COc1ccc(-c2cccc3c2CCC3=O)c(OC(C)(C)C(=O)OCC2CCC2)c1OC] | cyclobutylmethyl 2-[2,3-dimethoxy-6-(1-oxoindan-4-yl)phenoxy]-2-methyl-propanoate |
| 1379 | 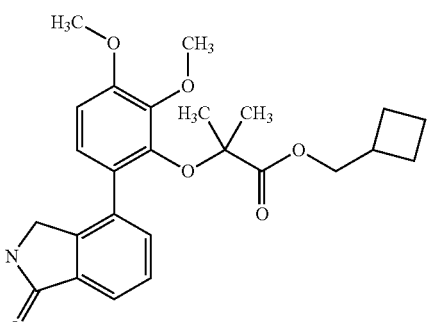 | cyclobutylmethyl 2-[2,3-dimethoxy-6-(1-oxoisoindolin-4-yl)phenoxy]-2-methyl-propanoate |

-continued

| Compound | Structure | Compound name |
|---|---|---|
| 1380 | 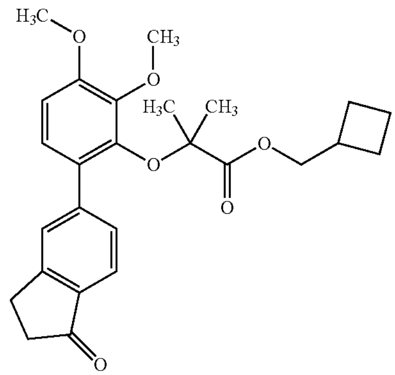 [SMILES: COc1ccc(-c2ccc3c(c2)CCC3=O)c(OC(C)(C)C(=O)OCC2CCC2)c1OC] | cyclobutylmethyl 2-[2,3-dimethoxy-6-(1-oxoindan-5-yl)phenoxy]-2-methyl-propanoate |
| 1381 | 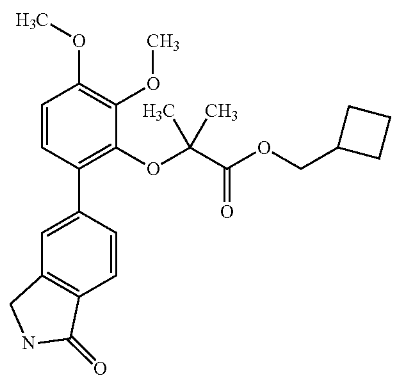 [SMILES: COc1ccc(-c2ccc3c(c2)CNC3=O)c(OC(C)(C)C(=O)OCC2CCC2)c1OC] | cyclobutylmethyl 2-[2,3-dimethoxy-6-(1-oxoisoindolin-5-yl)phenoxy]-2-methyl-propanoate |
| 1382 | 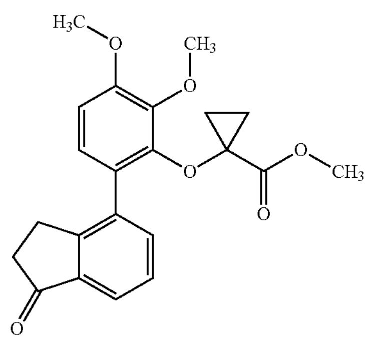 [SMILES: COC(=O)C1(Oc2c(-c3cccc4c3CCC4=O)ccc(OC)c2OC)CC1] | methyl 1-[2,3-dimethoxy-6-(1-oxoindan-4-yl)phenoxy]cyclopropanecarboxylate |
| 1383 | 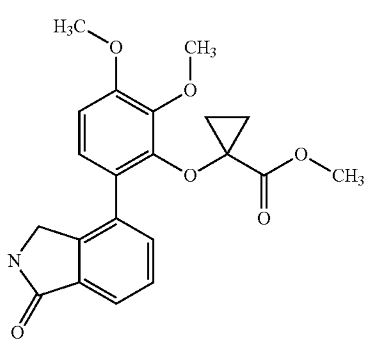 [SMILES: COC(=O)C1(Oc2c(-c3cccc4c3CNC4=O)ccc(OC)c2OC)CC1] | methyl 1-[2,3-dimethoxy-6-(1-oxoisoindolin-4-yl)phenoxy]cyclopropanecarboxylate |

-continued

| Compound | Structure | Compound name |
|---|---|---|
| 1384 | 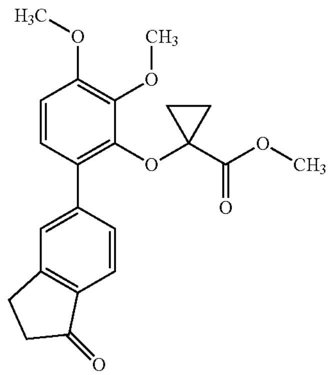 [SMILES: COC(=O)C1(Oc2c(-c3ccc4c(c3)CCC4=O)ccc(OC)c2OC)CC1] | methyl 1-[2,3-dimethoxy-6-(1-oxoindan-5-yl)phenoxy]cyclopropanecarboxylate |
| 1385 | 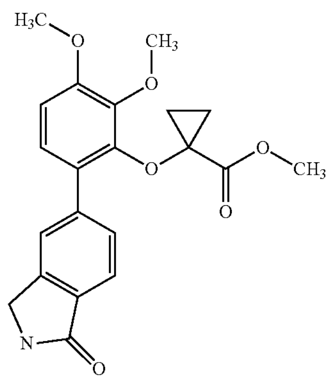 [SMILES: COC(=O)C1(Oc2c(-c3ccc4c(c3)CNC4=O)ccc(OC)c2OC)CC1] | methyl 1-[2,3-dimethoxy-6-(1-oxoisoindolin-5-yl)phenoxy]cyclopropanecarboxylate |
| 1386 | 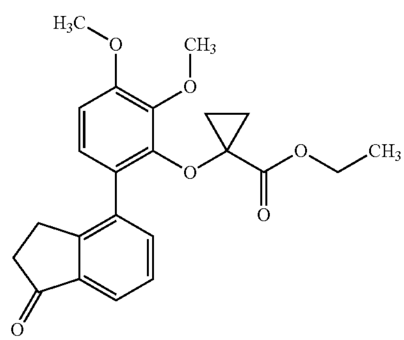 [SMILES: CCOC(=O)C1(Oc2c(-c3cccc4c3CCC4=O)ccc(OC)c2OC)CC1] | ethyl 1-[2,3-dimethoxy-6-(1-oxoindan-4-yl)phenoxy]cyclopropanecarboxylate |
| 1387 | 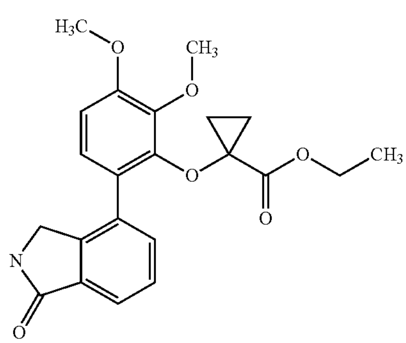 [SMILES: CCOC(=O)C1(Oc2c(-c3cccc4c3CNC4=O)ccc(OC)c2OC)CC1] | ethyl 1-[2,3-dimethoxy-6-(1-oxoisoindolin-4-yl)phenoxy]cyclopropanecarboxylate |

-continued

| Compound | Structure | Compound name |
|---|---|---|
| 1388 | 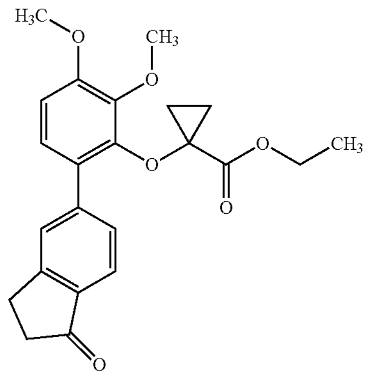 [SMILES: CCOC(=O)C1(Oc2c(-c3ccc4c(c3)CCC4=O)ccc(OC)c2OC)CC1] | ethyl 1-[2,3-dimethoxy-6-(1-oxoindan-5-yl)phenoxy]cyclopropanecarboxylate |
| 1389 | 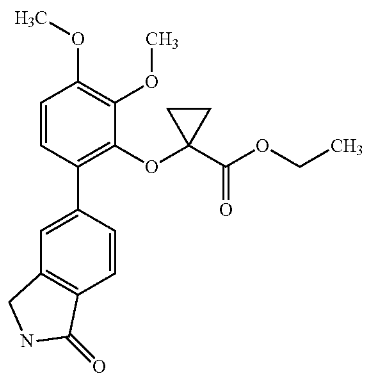 [SMILES: CCOC(=O)C1(Oc2c(-c3ccc4c(c3)CNC4=O)ccc(OC)c2OC)CC1] | ethyl 1-[2,3-dimethoxy-6-(1-oxoisoindolin-5-yl)phenoxy]cyclopropanecarboxylate |
| 1390 | 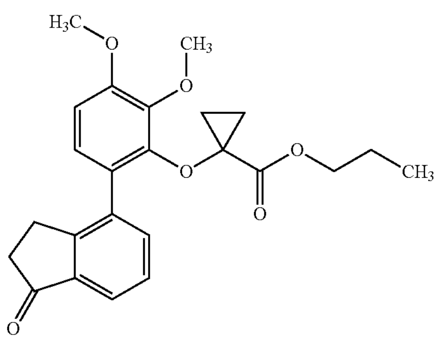 [SMILES: CCCOC(=O)C1(Oc2c(-c3cccc4c3CCC4=O)ccc(OC)c2OC)CC1] | propyl 1-[2,3-dimethoxy-6-(1-oxoindan-4-yl)phenoxy]cyclopropanecarboxylate |
| 1391 | 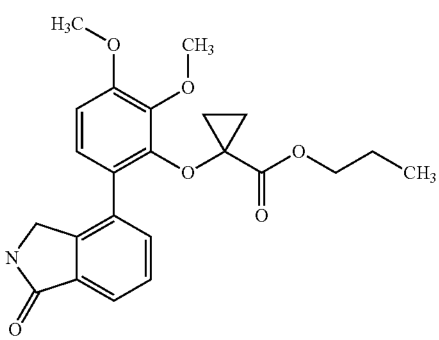 | propyl 1-[2,3-dimethoxy-6-(1-oxoisoindolin-4-yl)phenoxy]cyclopropanecarboxylate |

-continued
| Compound | Structure | Compound name |
|---|---|---|
| 1392 | 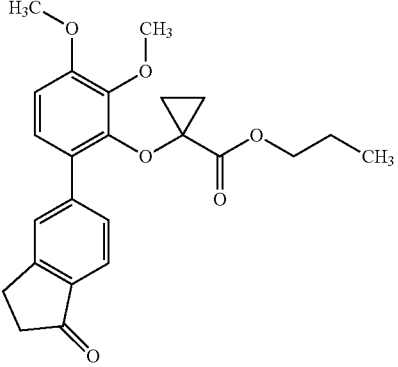 [SMILES: CCCOC(=O)C1(Oc2c(-c3ccc4c(c3)CCC4=O)ccc(OC)c2OC)CC1] | propyl 1-[2,3-dimethoxy-6-(1-oxoindan-5-yl)phenoxy]cyclopropanecarboxylate |
| 1393 | 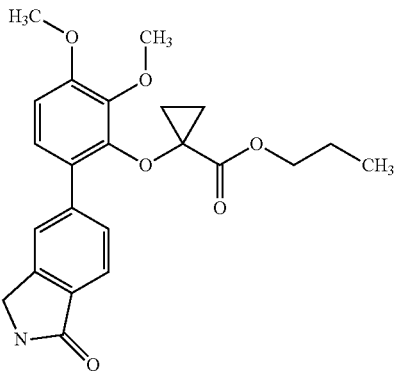 [SMILES: CCCOC(=O)C1(Oc2c(-c3ccc4c(c3)CNC4=O)ccc(OC)c2OC)CC1] | propyl 1-[2,3-dimethoxy-6-(1-oxoisoindolin-5-yl)phenoxy]cyclopropanecarboxylate |
| 1394 | 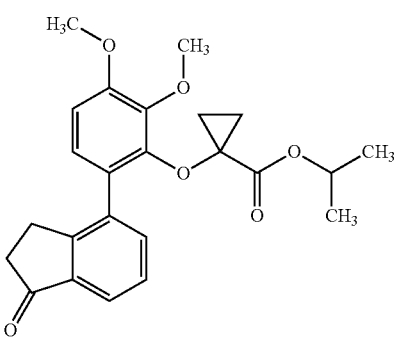 [SMILES: COc1ccc(-c2cccc3c2CCC3=O)c(OC2(C(=O)OC(C)C)CC2)c1OC] | isopropyl 1-[2,3-dimethoxy-6-(1-oxoindan-4-yl)phenoxy]cyclopropanecarboxylate |
| 1395 | 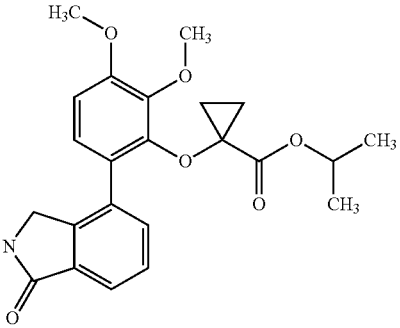 [SMILES: COc1ccc(-c2cccc3c2CNC3=O)c(OC2(C(=O)OC(C)C)CC2)c1OC] | isopropyl 1-[2,3-dimethoxy-6-(1-oxoisoindolin-4-yl)phenoxy]cyclopropanecarboxylate |

| Compound | Structure | Compound name |
|---|---|---|
| 1396 | 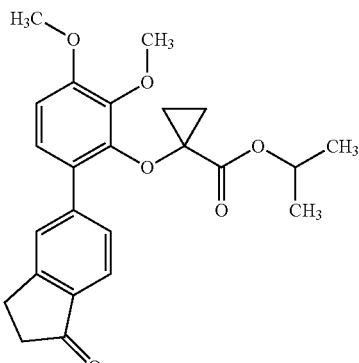 | isopropyl 1-[2,3-dimethoxy-6-(1-oxoindan-5-yl)phenoxy]cyclopropanecarboxylate |
| 1397 | 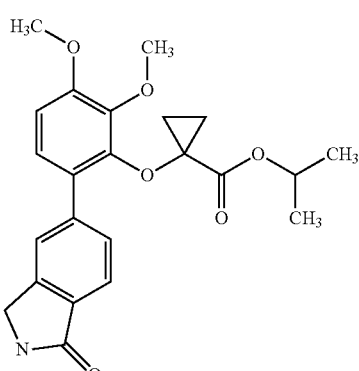 | isopropyl 1-[2,3-dimethoxy-6-(1-oxoisoindolin-5-yl)phenoxy]cyclopropanecarboxylate |
| 1398 | 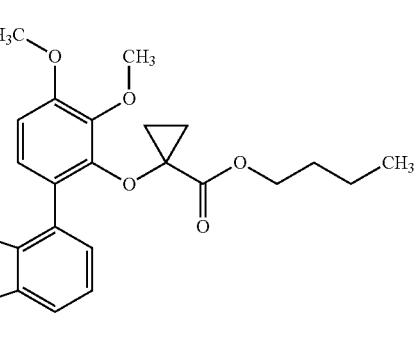 | butyl 1-[2,3-dimethoxy-6-(1-oxoindan-4-yl)phenoxy]cyclopropanecarboxylate |
| 1399 | 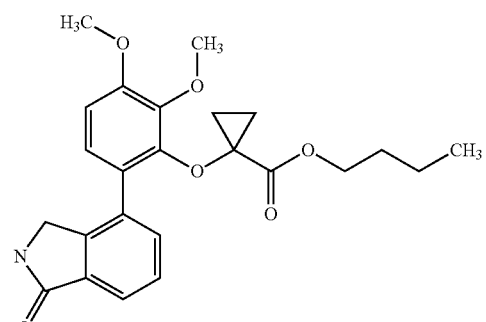 | butyl 1-[2,3-dimethoxy-6-(1-oxoisoindolin-4-yl)phenxoy]cyclopropanecarboxylate |

| Compound | Structure | Compound name |
|---|---|---|
| 1400 | 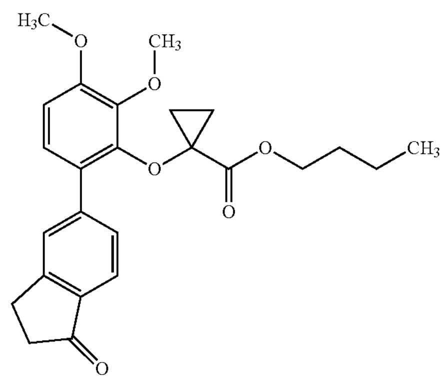 [SMILES: CCCCOC(=O)C1(Oc2c(-c3ccc4c(c3)CCC4=O)ccc(OC)c2OC)CC1] | butyl 1-[2,3-dimethoxy-6-(1-oxoindan-5-yl)phenoxy]cyclopropanecarboxylate |
| 1401 | 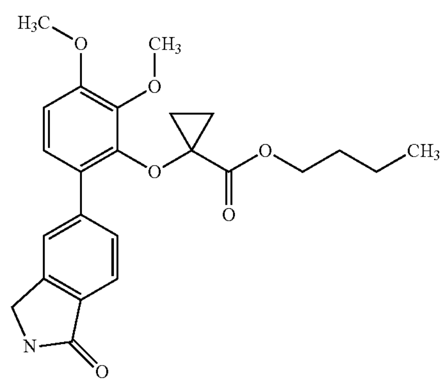 [SMILES: CCCCOC(=O)C1(Oc2c(-c3ccc4c(c3)CNC4=O)ccc(OC)c2OC)CC1] | butyl 1-[2,3-dimethoxy-6-(1-oxoisoindolin-5-yl)phenoxy]cyclopropanecarboxylate |
| 1402 | 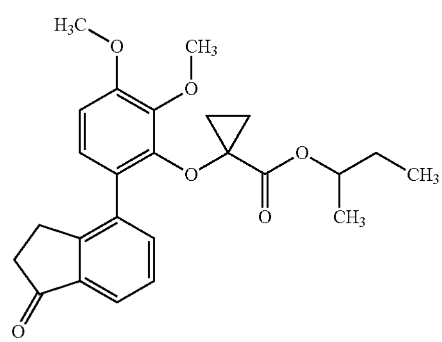 [SMILES: CCC(C)OC(=O)C1(Oc2c(-c3cccc4c3CCC4=O)ccc(OC)c2OC)CC1] | sec-butyl 1-[2,3-dimethoxy-6-(1-oxoindan-4-yl)phenoxy]cyclopropanecarboxylate |
| 1403 | 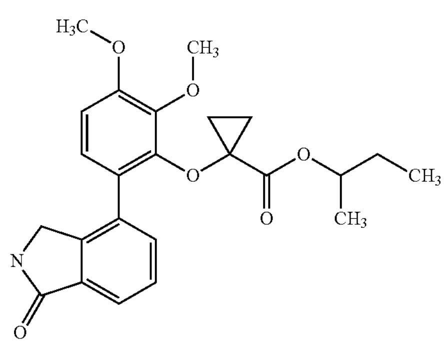 | sec-butyl 1-[2,3-dimethoxy-6-(1-oxoisoindolin-4-yl)phenoxy]cyclopropanecarboxylate |

-continued

| Compound | Structure | Compound name |
|---|---|---|
| 1404 | 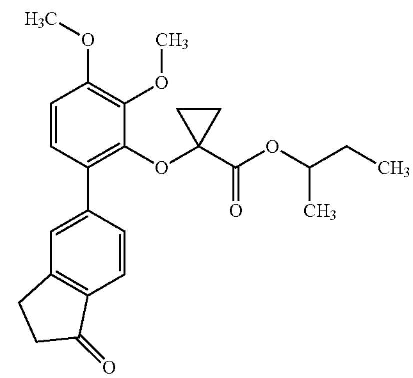 [SMILES: CCC(C)OC(=O)C1(Oc2c(-c3ccc4c(c3)CCC4=O)ccc(OC)c2OC)CC1] | sec-butyl 1-[2,3-dimethoxy-6-(1-oxoindan-5-yl)phenoxy]cyclopropanecarboxylate |
| 1405 | 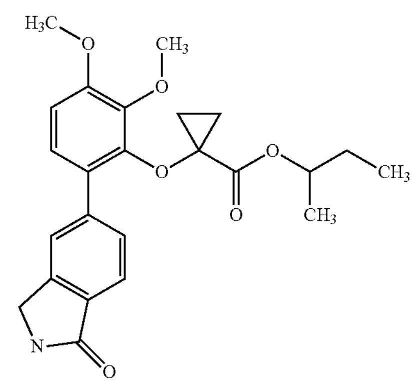 [SMILES: CCC(C)OC(=O)C1(Oc2c(-c3ccc4c(c3)CNC4=O)ccc(OC)c2OC)CC1] | sec-butyl 1-[2,3-dimethoxy-6-(1-oxoisoindolin-5-yl)phenoxy]cyclopropanecarboxylate |
| 1406 | 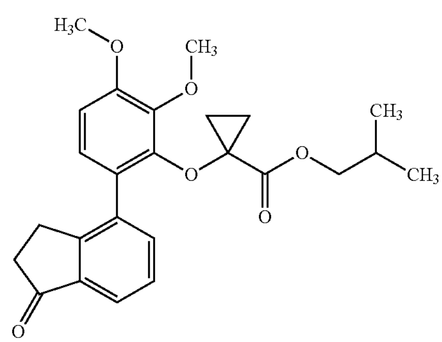 [SMILES: COc1ccc(-c2cccc3c2CCC3=O)c(OC2(C(=O)OCC(C)C)CC2)c1OC] | isobutyl 1-[2,3-dimethoxy-6-(1-oxoindan-4-yl)phenoxy]cyclopropanecarboxylate |
| 1407 | 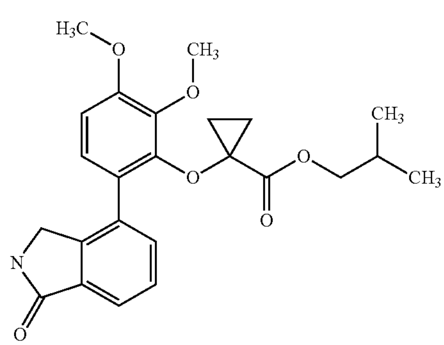 [SMILES: COc1ccc(-c2cccc3c2CNC3=O)c(OC2(C(=O)OCC(C)C)CC2)c1OC] | isobutyl 1-[2,3-dimethoxy-6-(1-oxoisoindolin-4-yl)phenoxy]cyclopropanecarboxylate |

-continued

| Compound | Structure | Compound name |
|---|---|---|
| 1408 | 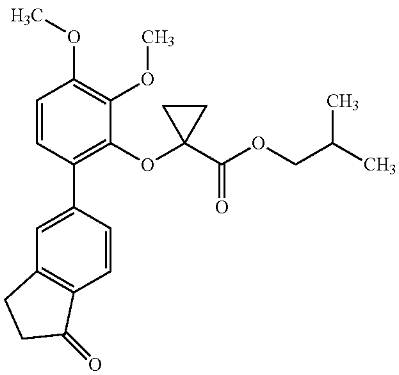 [SMILES: COc1ccc(-c2ccc3c(c2)CCC3=O)c(OC2(C(=O)OCC(C)C)CC2)c1OC] | isobutyl 1-[2,3-dimethoxy-6-(1-oxoindan-5-yl)phenoxy]cyclopropanecarboxylate |
| 1409 | 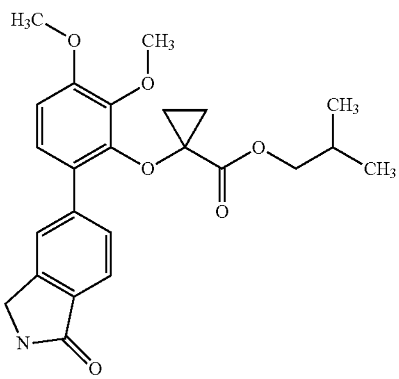 | isobutyl 1-[2,3-dimethoxy-6-(1-oxoisoindolin-5-yl)phenoxy]cyclopropanecarboxylate |
| 1410 | 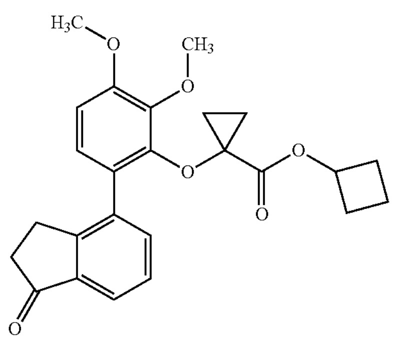 [SMILES: COc1ccc(-c2cccc3c2CCC3=O)c(OC2(C(=O)OC3CCC3)CC2)c1OC] | cyclobutyl 1-[2,3-dimethoxy-6-(1-oxoindan-4-yl)phenoxy]cyclopropanecarboxylate |
| 1411 | 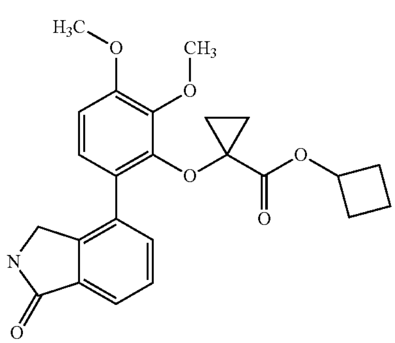 [SMILES: COc1ccc(-c2cccc3c2CNC3=O)c(OC2(C(=O)OC3CCC3)CC2)c1OC] | cyclobutyl 1-[2,3-dimethoxy-6-(1-oxoisoindolin-4-yl)phenoxy]cyclopropanecarboxylate |

-continued
| Compound | Structure | Compound name |
|---|---|---|
| 1412 | 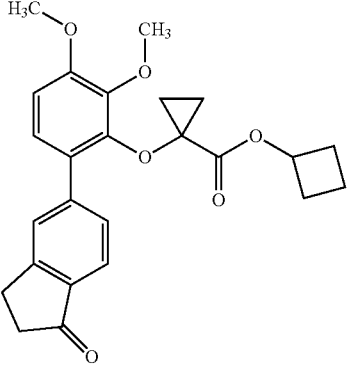 | cyclobutyl 1-[2,3-dimethoxy-6-(1-oxoindan-5-yl)phenoxy]cyclopropanecarboxylate |
| 1413 | 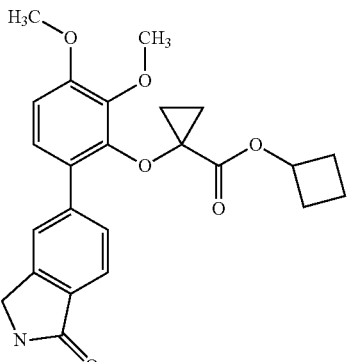 | cyclobutyl 1-[2,3-dimethoxy-6-(1-oxoisoindolin-5-yl)phenoxy]cyclopropanecarboxylate |
| 1414 | 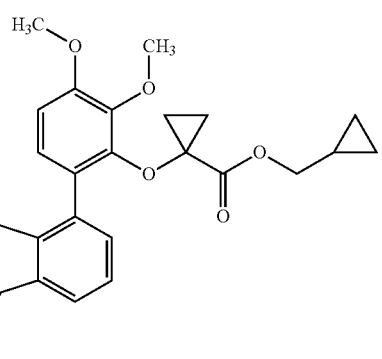 | cyclopropylmethyl 1-[2,3-dimethoxy-6-(1-oxoindan-4-yl)phenoxy]cyclopropanecarboxylate |
| 1415 | 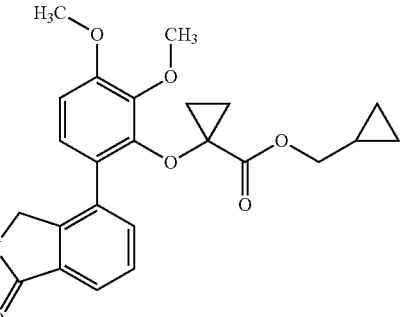 | cyclopropylmethyl 1-[2,3-dimethoxy-6-(1-oxoisoindolin-4-yl)phenoxy]cyclopropanecarboxylate |

| Compound | Structure | Compound name |
|---|---|---|
| 1416 | 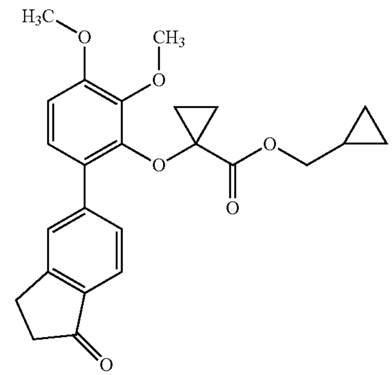 [SMILES: COc1ccc(-c2ccc3c(c2)CCC3=O)c(OC2(C(=O)OCC3CC3)CC2)c1OC] | cyclopropylmethyl 1-[2,3-dimethoxy-6-(1-oxoindan-5-yl)phenoxy]cyclopropanecarboxylate |
| 1417 | 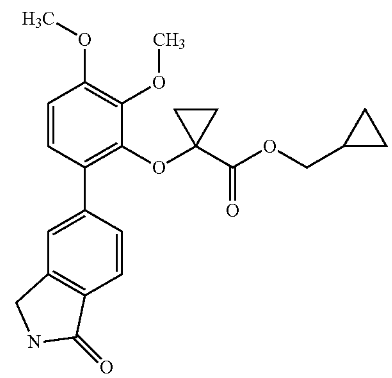 | cyclopropylmethyl 1-[2,3-dimethoxy-6-(1-oxoisoindolin-5-yl)phenoxy]cyclopropanecarboxylate |
| 1418 | 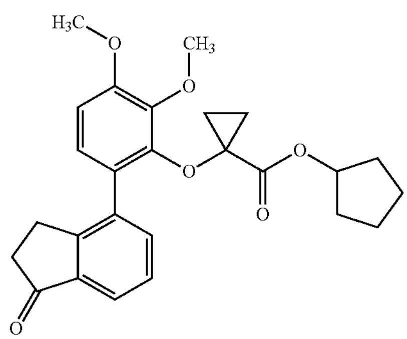 [SMILES: COc1ccc(-c2cccc3c2CCC3=O)c(OC2(C(=O)OC3CCCC3)CC2)c1OC] | cyclopentyl 1-[2,3-dimethoxy-6-(1-oxoindan-4-yl)phenoxy]cyclopropanecarboxylate |
| 1419 | 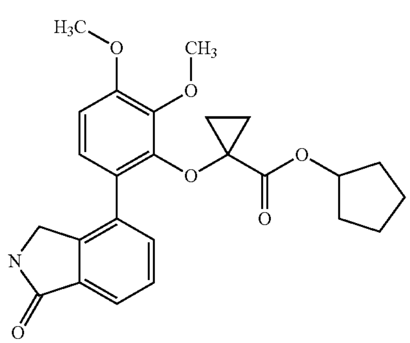 | cyclopentyl 1-[2,3-dimethoxy-6-(1-oxoisoindolin-4-yl)phenoxy]cyclopropanecarboxylate |

-continued

| Compound | Structure | Compound name |
|---|---|---|
| 1420 | 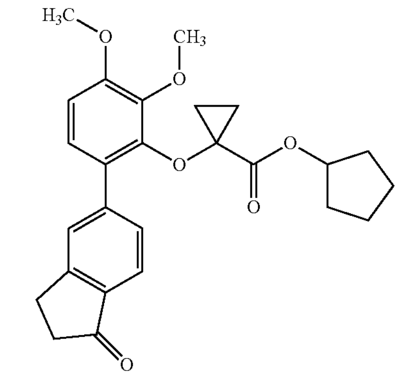 [SMILES: COc1ccc(-c2ccc3c(c2)CCC3=O)c(OC2(C(=O)OC3CCCC3)CC2)c1OC] | cyclopentyl 1-[2,3-dimethoxy-6-(1-oxoindan-5-yl)phenoxy]cyclopropanecarboxylate |
| 1421 | 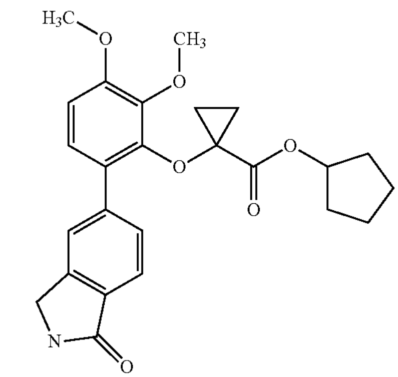 [SMILES: COc1ccc(-c2ccc3c(c2)CNC3=O)c(OC2(C(=O)OC3CCCC3)CC2)c1OC] | cyclopentyl 1-[2,3-dimethoxy-6-(1-oxoindolin-5-yl)phenxoy]cyclopropanecarboxylate |
| 1422 | 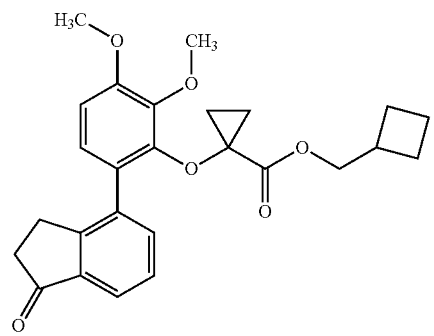 [SMILES: COc1ccc(-c2cccc3c2CCC3=O)c(OC2(C(=O)OCC3CCC3)CC2)c1OC] | cyclobutylmethyl 1-[2,3-dimethoxy-6-(1-oxoindan-4-yl)phenoxy]cyclopropanecarboxylate |
| 1423 | 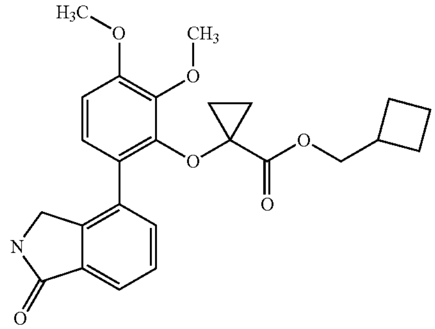 [SMILES: COc1ccc(-c2cccc3c2CNC3=O)c(OC2(C(=O)OCC3CCC3)CC2)c1OC] | cyclobutylmethyl 1-[2,3-dimethoxy-6-(1-oxoisoindolin-4-yl)phenoxy]cyclopropanecarboxylate |

| Compound | Structure | Compound name |
|---|---|---|
| 1424 | 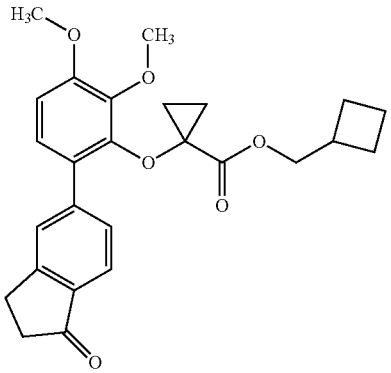 | cyclobutylmethyl 1-[2,3-dimethoxy-6-(1-oxoindan-5-yl)phenoxy]cyclopropanecarboxylate |
| 1425 | 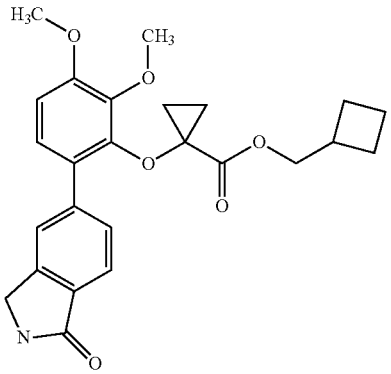 | cyclobutylmethyl 1-[2,3-dimethoxy-6-(1-oxoisoindolin-5-yl)phenoxy]cyclopropanecarboxylate |
| 1426 | 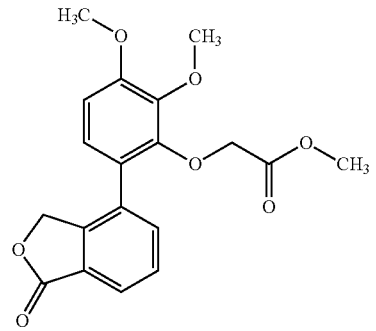 | methyl 2-[2,3-dimethoxy-6-(1-oxo-3H-isobenzofuran-4-yl)phenoxy]acetate |
| 1427 | 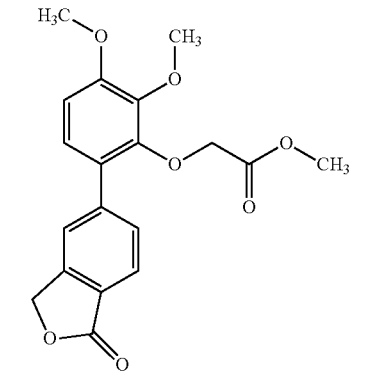 | methyl 2-[2,3-dimethoxy-6-(1-oxo-3H-isobenzofuran-5-yl)phenoxy]acetate |

-continued

| Compound | Structure | Compound name |
|---|---|---|
| 1428 | 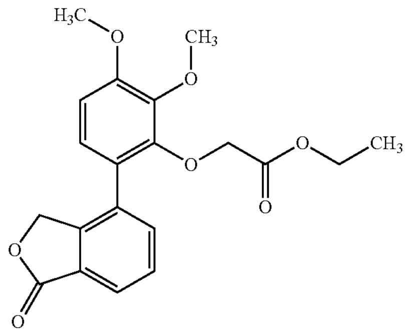 | ethyl 2-[2,3-dimethoxy-6-(1-oxo-3H-isobenzofuran-4-yl)phenoxy]acetate |
| 1429 | 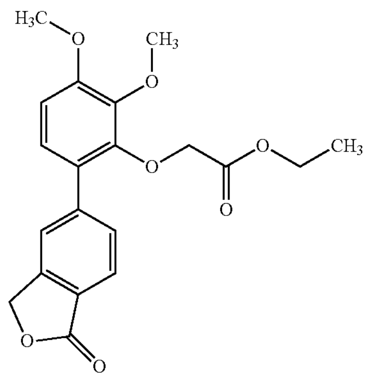 | ethyl 2-[2,3-dimethoxy-6-(1-oxo-3H-isobenzofuran-5-yl)phenoxy]acetate |
| 1430 | 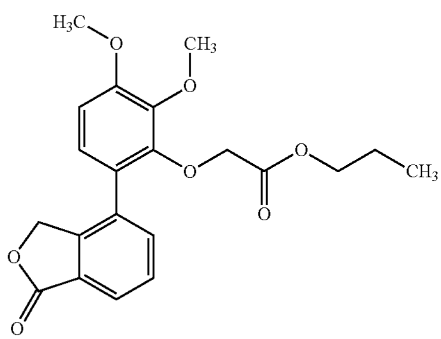 [SMILES: CCCOC(=O)COc1c(-c2cccc3c2COC3=O)ccc(OC)c1OC] | propyl 2-[2,3-dimethoxy-6-(1-oxo-3H-isobenzofuran-4-yl)phenoxy]acetate |
| 1431 | 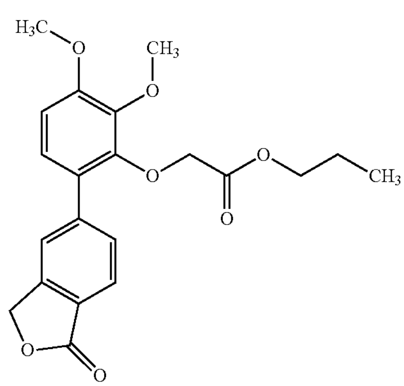 | propyl 2-[2,3-dimethoxy-6-(1-oxo-3H-isobenzofuran-5-yl)phenoxy]acetate |

-continued

| Compound | Structure | Compound name |
|---|---|---|
| 1432 | 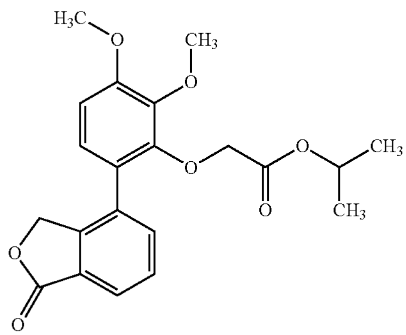 [SMILES: COc1ccc(-c2cccc3c2COC3=O)c(OCC(=O)OC(C)C)c1OC] | isopropyl 2-[2,3-dimethoxy-6-(1-oxo-3H-isobenzofuran-4-yl)phenoxy]acetate |
| 1433 | 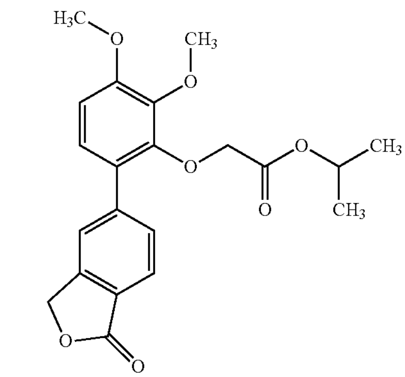 | isopropyl 2-[2,3-dimethoxy-6-(1-oxo-3H-isobenzofuran-5-yl)phenoxy]acetate |
| 1434 | 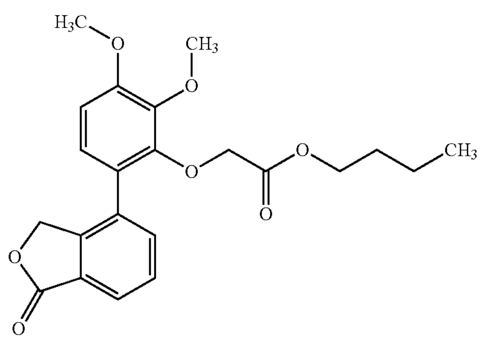 [SMILES: CCCCOC(=O)COc1c(-c2cccc3c2COC3=O)ccc(OC)c1OC] | butyl 2-[2,3-dimethoxy-6-(1-oxo-3H-isobenzofuran-4-yl)phenoxy]acetate |
| 1435 | 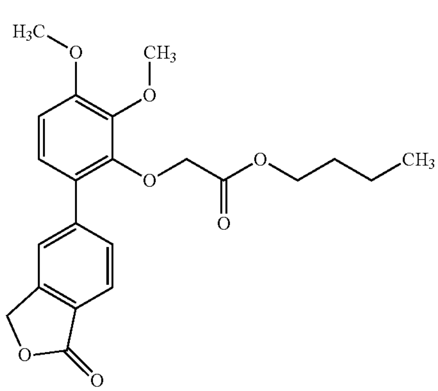 | butyl 2-[2,3-dimethoxy-6-(1-oxo-3H-isobenzofuran-5-yl)phenoxy]acetate |

| Compound | Structure | Compound name |
|---|---|---|
| 1436 | 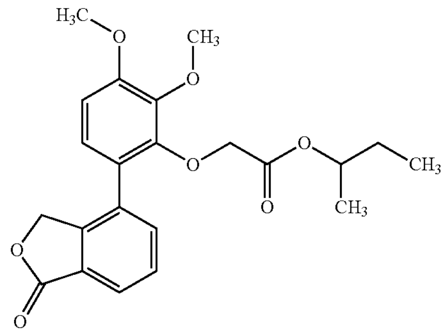 [SMILES: CCC(C)OC(=O)COc1c(-c2cccc3c2COC3=O)ccc(OC)c1OC] | sec-butyl 2-[2,3-dimethoxy-6-(1-oxo-3H-isobenzofuran-4-yl)phenoxy]acetate |
| 1437 | 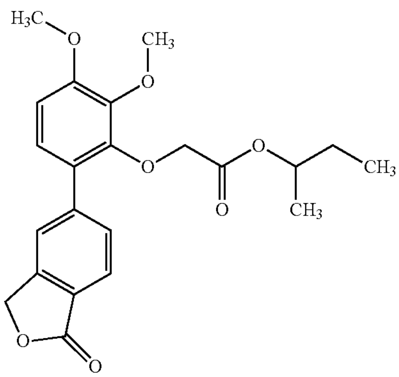 | sec-butyl 2-[2,3-dimethoxy-6-(1-oxo-3H-isobenzofuran-5-yl)phenoxy]acetate |
| 1438 | 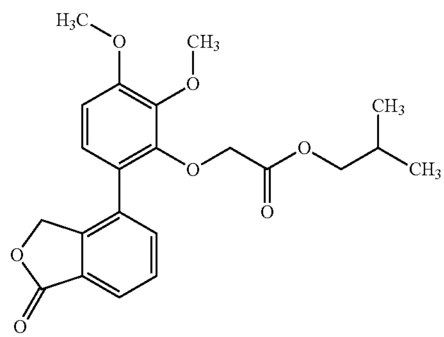 | isobutyl 2-[2,3-dimethoxy-6-(1-oxo-3H-isobenzofuran-4-yl)phenoxy]acetate |
| 1439 | 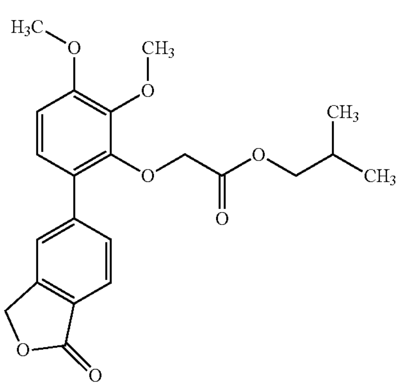 [SMILES: COc1ccc(-c2ccc3c(c2)COC3=O)c(OCC(=O)OCC(C)C)c1OC] | isobutyl 2-[2,3-dimethoxy-6-(1-oxo-3H-isobenzofuran-5-yl)phenoxy]acetate |

-continued

| Compound | Structure | Compound name |
|---|---|---|
| 1440 | 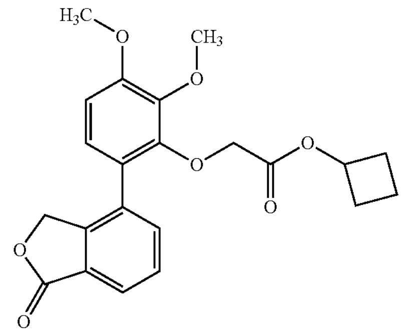 | cyclobutyl 2-[2,3-dimethoxy-6-(1-oxo-3H-isobenzofuran-4-yl)phenoxy]acetate |
| 1441 | 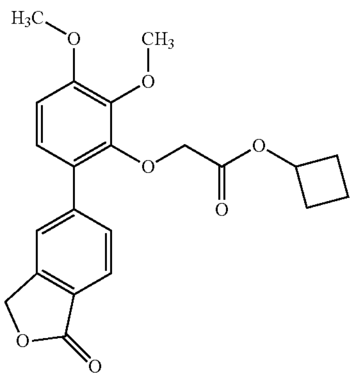 [SMILES: COc1ccc(-c2ccc3c(c2)COC3=O)c(OCC(=O)OC2CCC2)c1OC] | cyclobutyl 2-[2,3-dimethoxy-6-(1-oxo-3H-isobenzofuran-5-yl)phenoxy]acetate |
| 1442 | 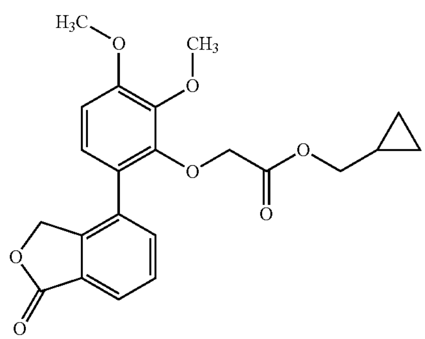 [SMILES: COc1ccc(-c2cccc3c2COC3=O)c(OCC(=O)OCC2CC2)c1OC] | cyclopropylmethyl 2-[2,3-dimethoxy-6-(1-oxo-3H-isobenzofuran-4-yl)phenoxy]acetate |
| 1443 | 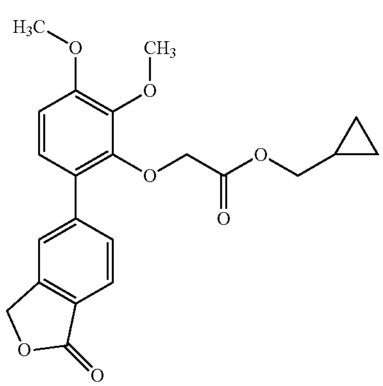 [SMILES: COc1ccc(-c2ccc3c(c2)COC3=O)c(OCC(=O)OCC2CC2)c1OC] | cyclopropylmethyl 2-[2,3-dimethoxy-6-(1-oxo-3H-isobenzofuran-5-yl)phenoxy]acetate |

-continued

| Compound | Structure | Compound name |
|---|---|---|
| 1444 | 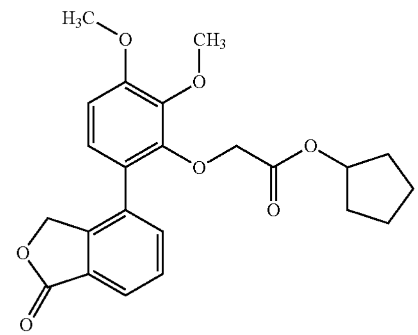 [SMILES: COc1ccc(-c2cccc3c2COC3=O)c(OCC(=O)OC2CCCC2)c1OC] | cyclopentyl 2-[2,3-dimethoxy-6-(1-oxo-3H-isobenzofuran-4-yl)phenoxy]acetate |
| 1445 | 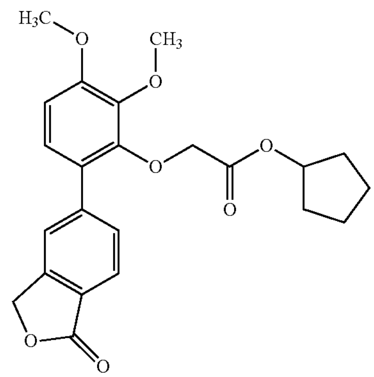 | cyclopentyl 2-[2,3-dimethoxy-6-(1-oxo-3H-isobenzofuran-5-yl)phenoxy]acetate |
| 1446 | 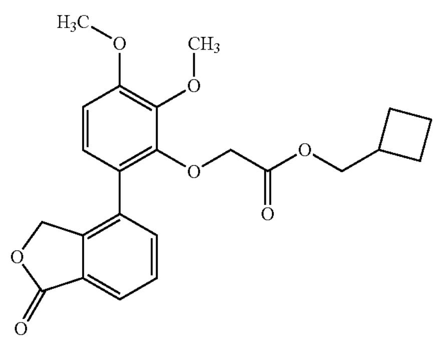 | cyclobutylmethyl 2-[2,3-dimethoxy-6-(1-oxo-3H-isobenzofuran-4-yl)phenoxy]acetate |
| 1447 | 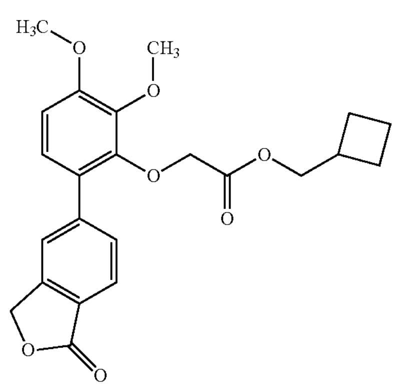 [SMILES: COc1ccc(-c2ccc3c(c2)COC3=O)c(OCC(=O)OCC2CCC2)c1OC] | cyclobutylmethyl 2-[2,3-dimethoxy-6-(1-oxo-3H-isobenzofuran-5-yl)phenoxy]acetate |

| Compound | Structure | Compound name |
|---|---|---|
| 1448 | 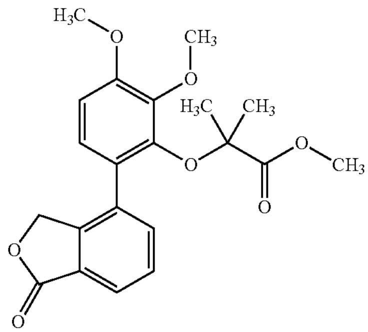 | methyl 2-[2,3-dimethoxy-6-(1-oxo-3H-isobenzoufuran-4-yl)phenoxy]-2-methyl-propanoate |
| 1449 | 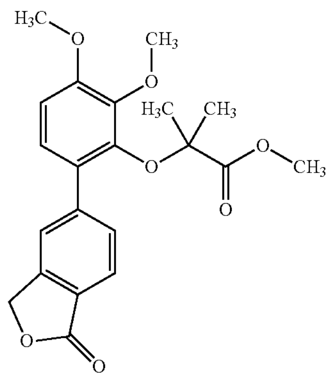 [SMILES: COC(=O)C(C)(C)Oc1c(-c2ccc3c(c2)COC3=O)ccc(OC)c1OC] | methyl 2-[2,3-dimethoxy-6-(1-oxo-3H-isobenzofuran-5-yl)phenoxy]-2-methyl-propanoate |
| 1450 | 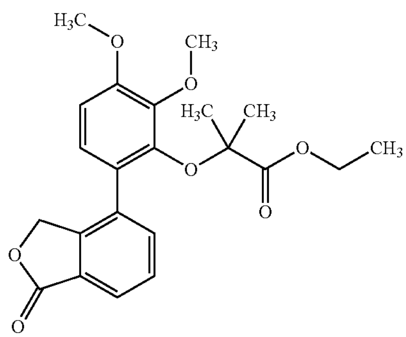 | ethyl 2-[2,3-dimethoxy-6-(1-oxo-3H-isobenzofuran-4-yl)phenoxy]-2-methyl-propanoate |
| 1451 | 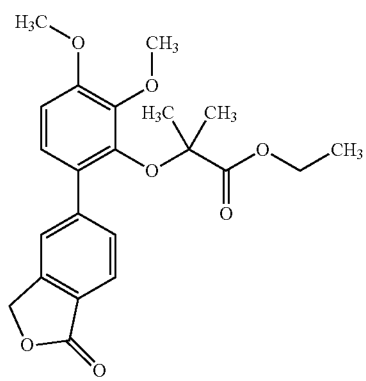 | ethyl 2-[2,3-dimethoxy-6-(1-oxo-3H-isobenzofuran-5-yl)phenoxy]-2-methyl-propanoate |

| Compound | Structure | Compound name |
|---|---|---|
| 1452 | 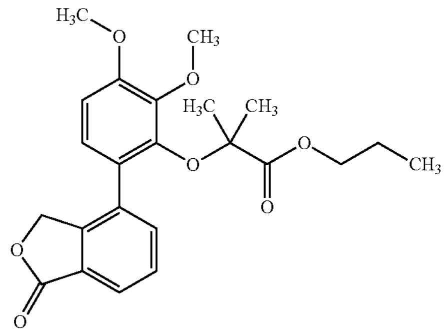 | propyl 2-[2,3-dimethoxy-6-(1-oxo-3H-isobenzofuran-4-yl)phenoxy]-2-methyl-propanoate |
| 1453 | 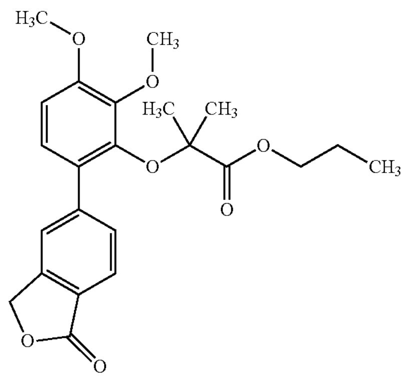 [SMILES: CCCOC(=O)C(C)(C)Oc1c(-c2ccc3c(c2)COC3=O)ccc(OC)c1OC] | propyl 2-[2,3-dimethoxy-6-(1-oxo-3H-isobenzofuran-5-yl)phenoxy]-2-methyl-propanoate |
| 1454 | 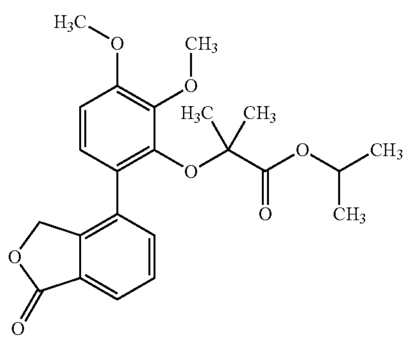 | isopropyl 2-[2,3-dimethoxy-6-(1-oxo-3H-isobenzofuran-4-yl)phenoxy]-2-methyl-propanoate |
| 1455 | 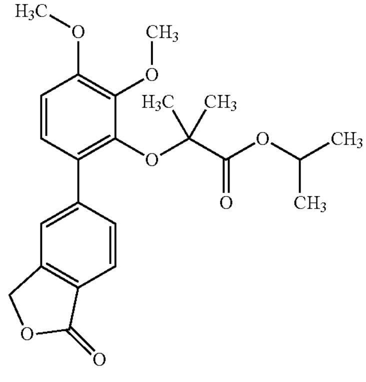 | isopropyl 2-[2,3-dimethoxy-6-(1-oxo-3H-isobenzofuran-5-yl)phenoxy]-2-methyl-propanoate |

| Compound | Structure | Compound name |
|---|---|---|
| 1456 | 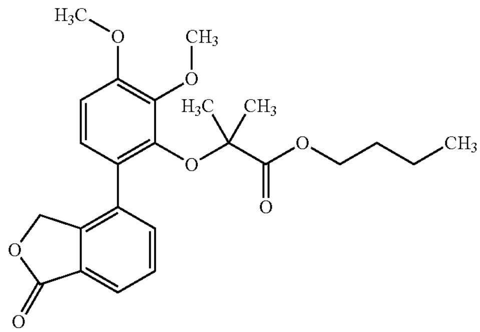 [SMILES: CCCCOC(=O)C(C)(C)Oc1c(-c2cccc3c2COC3=O)ccc(OC)c1OC] | butyl 2-[2,3-dimethoxy-6-(1-oxo-3H-isobenzofuran-4-yl)phenoxy]-2-methyl-propanoate |
| 1457 | 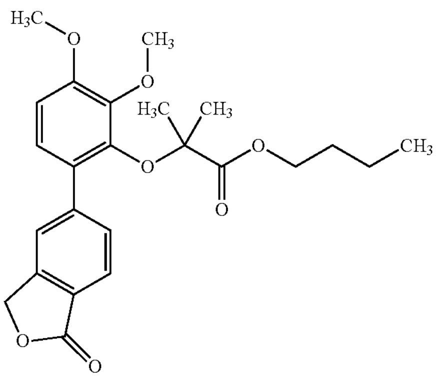 | butyl 2-[2,3-dimethoxy-6-(1-oxo-3H-isobenzofuran-5-yl)phenoxy]-2-methyl-propanoate |
| 1458 | 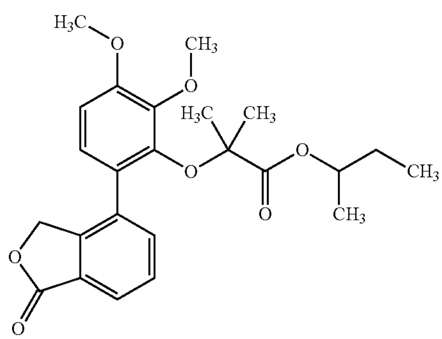 [SMILES: CCC(C)OC(=O)C(C)(C)Oc1c(-c2cccc3c2COC3=O)ccc(OC)c1OC] | sec-butyl 2-[2,3-dimethoxy-6-(1-oxo-3H-isobenzofuran-4-yl)phenoxy]-2-methyl-propanoate |
| 1459 | 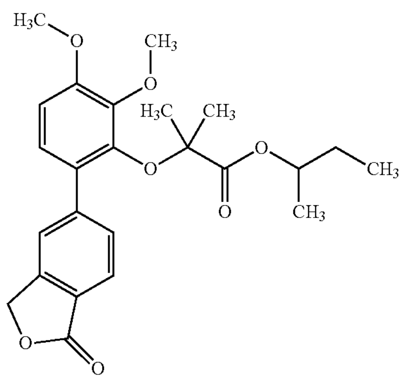 | sec-butyl 2-[2,3-dimethoxy-6-(1-oxo-3H-isobenzofuran-5-yl)phenoxy]-2-methyl-propanoate |

| Compound | Structure | Compound name |
|---|---|---|
| 1460 | 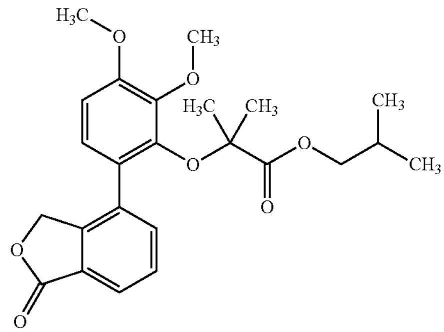 [SMILES: COc1ccc(-c2cccc3c2COC3=O)c(OC(C)(C)C(=O)OCC(C)C)c1OC] | isobutyl 2-[2,3-dimethoxy-6-(1-oxo-3H-isobenzofuran-4-yl)phenoxy]-2-methyl-propanoate |
| 1461 | 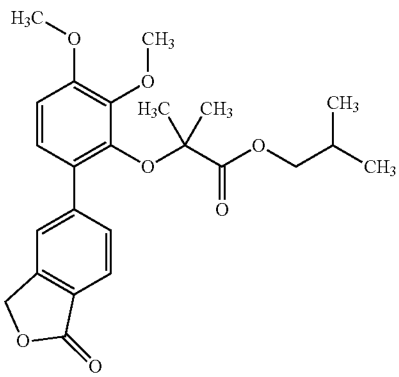 | isobutyl 2-[2,3-dimethoxy-6-(1-oxo-3H-isobenzofuran-5-yl)phenoxy]-2-methyl-propanoate |
| 1462 | 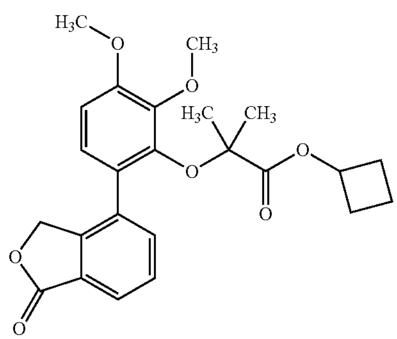 | cyclobutyl 2-[2,3-dimethoxy-6-(1-oxo-3H-isobenzofuran-4-yl)phenoxy]-2-methyl-propanoate |
| 1463 | 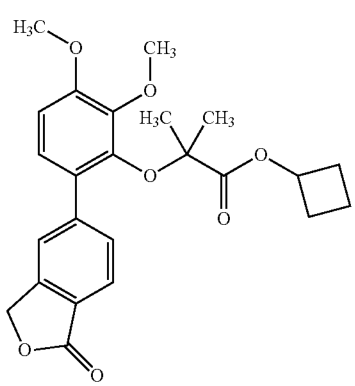 | cyclobutyl 2-[2,3-dimethoxy-6-(1-oxo-3H-isobenzofuran-5-yl)phenoxy]-2-methyl-propanoate |

| Compound | Structure | Compound name |
|---|---|---|
| 1464 | 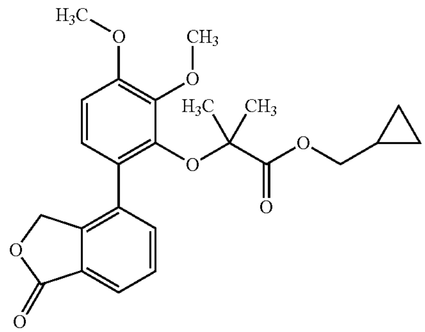 | cyclopropylmethyl 2-[2,3-dimethoxy-6-(1-oxo-3H-isobenzofuran-4-yl)phenoxy]-2-methyl-propanoate |
| 1465 | 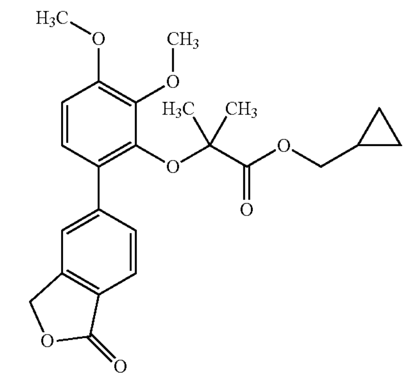 [SMILES: COc1ccc(-c2ccc3c(c2)COC3=O)c(OC(C)(C)C(=O)OCC2CC2)c1OC] | cyclopropylmethyl 2-[2,3-dimethoxy-6-(1-oxo-3H-isobenzofuran-5-yl)phenoxy]-2-methyl-propanoate |
| 1466 | 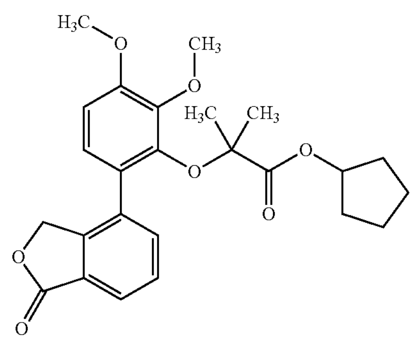 [SMILES: COc1ccc(-c2cccc3c2COC3=O)c(OC(C)(C)C(=O)OC2CCCC2)c1OC] | cyclopentyl 2-[2,3-dimethoxy-6-(1-oxo-3H-isobenzofuran-4-yl)phenoxy]-2-methyl-propanoate |
| 1467 | 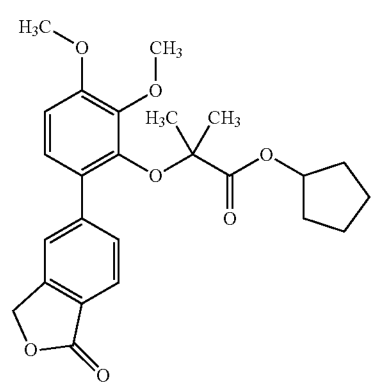 | cyclopentyl 2-[2,3-dimethoxy-6-(1-oxo-3H-isobenzofuran-5-yl)phenoxy]-2-methyl-propanoate |

-continued

| Compound | Structure | Compound name |
|---|---|---|
| 1468 | 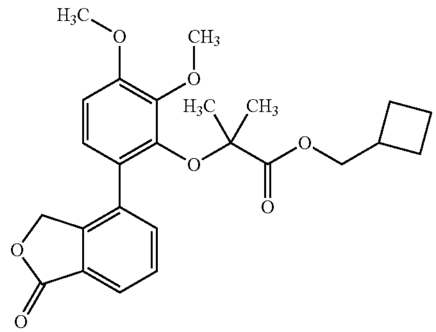 | cyclobutylmethyl 2-[2,3-dimethoxy-6-(1-oxo-3H-isobenzofuran-4-yl)phenoxy]-2-methyl-propanoate |
| 1469 | 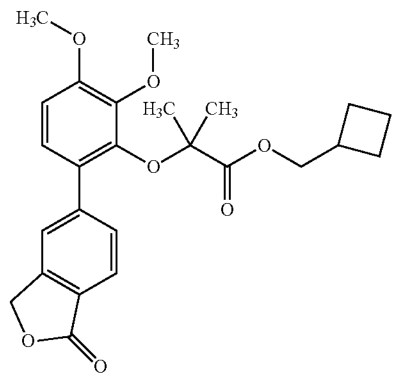 [SMILES: COc1ccc(-c2ccc3c(c2)COC3=O)c(OC(C)(C)C(=O)OCC2CCC2)c1OC] | cyclobutylmethyl 2-[2,3-dimethoxy-6-(1-oxo-3H-isobenzofuran-5-yl)phenoxy]-2-methyl-propanoate |
| 1470 | 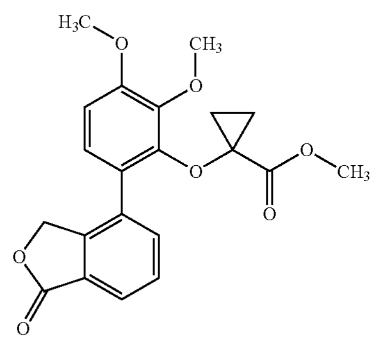 [SMILES: COC(=O)C1(Oc2c(-c3cccc4c3COC4=O)ccc(OC)c2OC)CC1] | methyl 1-[2,3-dimethoxy-6-(1-oxo-3H-isobenzofuran-4-yl)phenoxy]cyclopropanecarboxylate |
| 1471 | 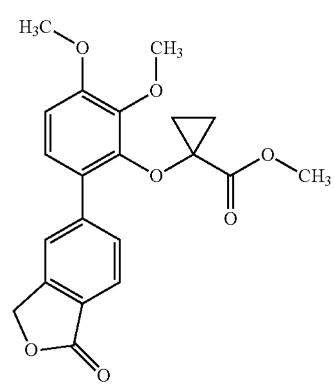 | methyl 1-[2,3-dimethoxy-6-(1-oxo-3H-isobenzofuran-5-yl)phenoxy]cyclopropanecarboxylate |

-continued

| Compound | Structure | Compound name |
|---|---|---|
| 1472 | 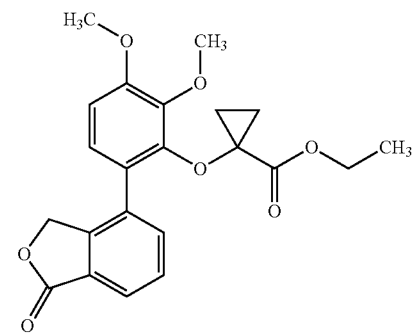 | ethyl 1-[2,3-dimethoxy-6-(1-oxo-3H-isobenzofuran-4-yl)phenoxy]cyclopropanecarboxylate |
| 1473 | 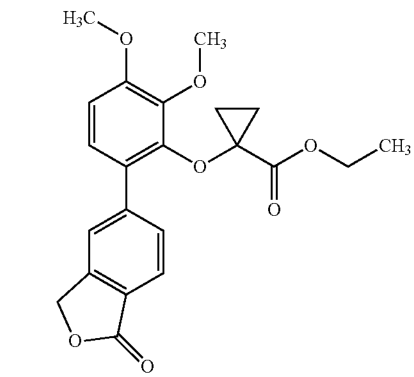 | ethyl 1-[2,3-dimethxoy-6-(1-oxo-3H-isobenzofuran-5-yl)phenoxy]cyclopropanecarboxylate |
| 1474 | 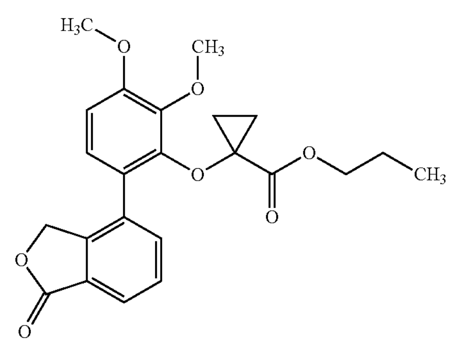 [SMILES: CCCOC(=O)C1(Oc2c(-c3cccc4c3COC4=O)ccc(OC)c2OC)CC1] | propyl 1-[2,3-dimethoxy-6-(1-oxo-3H-isobenzofuran-4-yl)phenoxy]cyclopropanecarboxylate |
| 1475 | 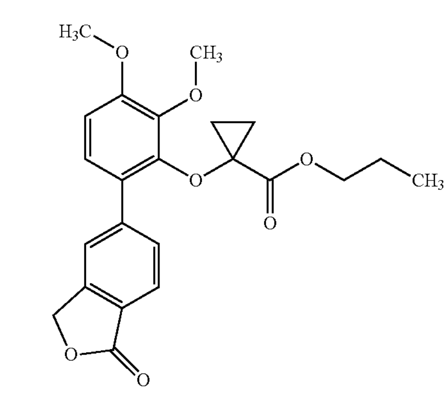 | propyl 1-[2,3-dimethoxy-6-(1-oxo-3H-isobenzofuran-5-yl)phenoxy]cyclopropanecarboxylate |

-continued

| Compound | Structure | Compound name |
|---|---|---|
| 1476 | 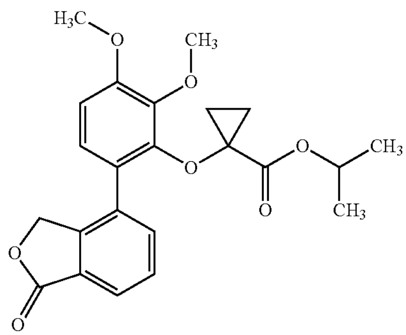 | isopropyl 1-[2,3-dimethoxy-6-(1-oxo-3H-isobenzofuran-4-yl)phenoxy]cyclopropanecarboxylate |
| 1477 | 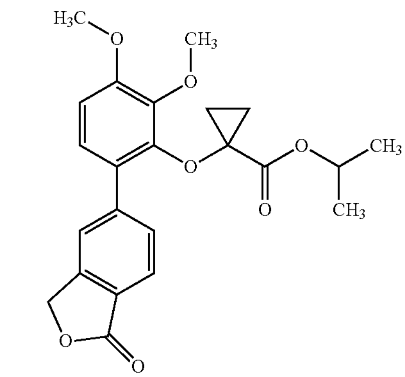 | isopropyl 1-[2,3-dimethoxy-6-(1-oxo-3H-isobenzofuran-5-yl)phenoxy]cyclopropanecarboxylate |
| 1478 | 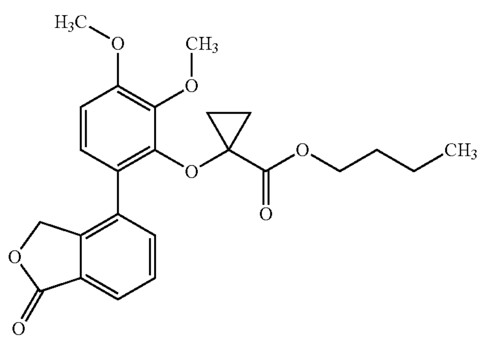 [SMILES: CCCCOC(=O)C1(Oc2c(-c3cccc4c3COC4=O)ccc(OC)c2OC)CC1] | butyl 1-[2,3-dimethoxy-6-(1-oxo-3H-isobenzofuran-4-yl)phenoxy]cyclopropanecarboxylate |
| 1479 | 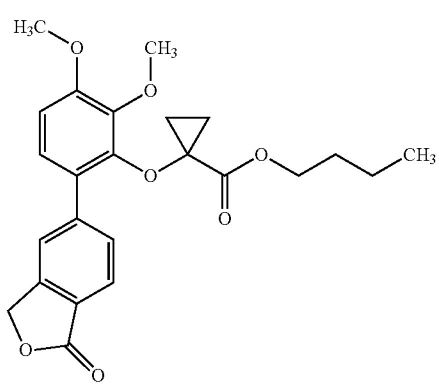 | butyl 1-[2,3-dimethoxy-6-(1-oxo-3H-isobenzofuran-5-yl)phenoxy]cyclopropanecarboxylate |

-continued

| Compound | Structure | Compound name |
|---|---|---|
| 1480 | 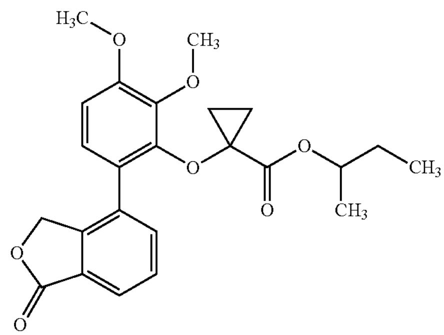 [SMILES: CCC(C)OC(=O)C1(Oc2c(-c3cccc4c3COC4=O)ccc(OC)c2OC)CC1] | sec-butyl 1-[2,3-dimethoxy-6-(1-oxo-3H-isobenzofuran-4-yl)phenoxy]cyclopropanecarboxylate |
| 1481 | 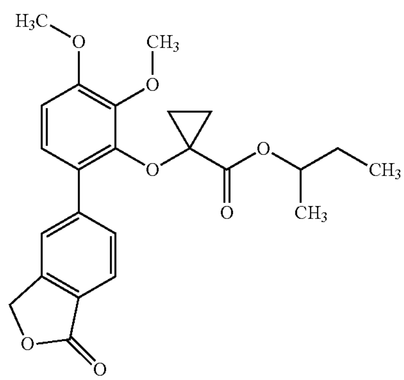 | sec-butyl 1-[2,3-dimethoxy-6-(1-oxo-3H-isobenzofuran-5-yl)phenoxy]cyclopropanecarboxylate |
| 1482 | 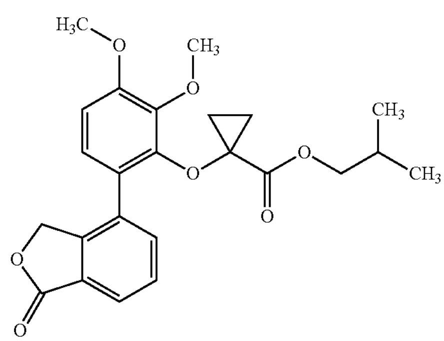 | isobutyl 1-[2,3-dimethoxy-6-(1-oxo-3H-isobenzofuran-4-yl)phenoxy]cyclopropanecarboxylate |
| 1483 | 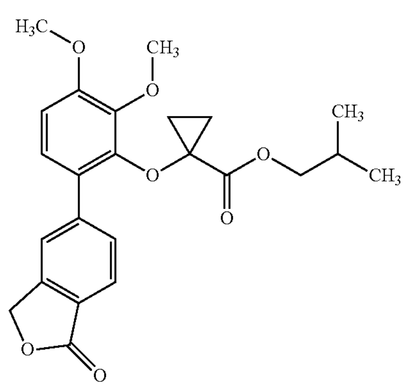 [SMILES: COc1ccc(-c2ccc3c(c2)COC3=O)c(OC2(C(=O)OCC(C)C)CC2)c1OC] | isobutyl 1-[2,3-dimethoxy-6-(1-oxo-3H-isobenzofuran-5-yl)phenxoxy]cyclopropanecarboxylate |

| Compound | Structure | Compound name |
|---|---|---|
| 1484 | 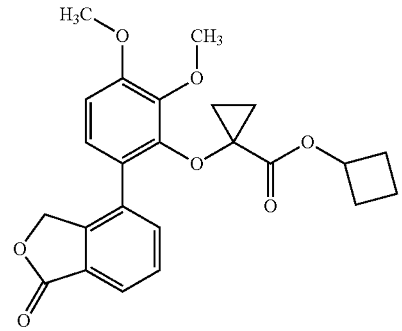 | cyclobutyl 1-[2,3-dimethoxy-6-(1-oxo-3H-isobenzofuran-4-yl)phenoxy]cyclopropanecarboxylate |
| 1485 | 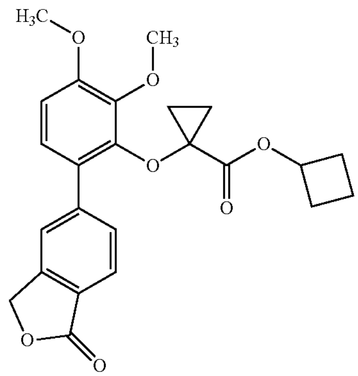 [SMILES: COc1ccc(-c2ccc3c(c2)COC3=O)c(OC2(C(=O)OC3CCC3)CC2)c1OC] | cyclobutyl 1-[2,3-dimethoxy-6-(1-oxo-3H-isobenzofuran-5-yl)phenoxy]cyclopropanecarboxylate |
| 1486 | 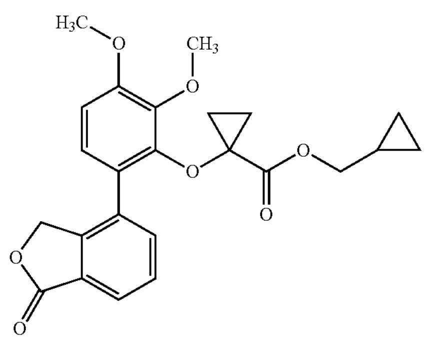 [SMILES: COc1ccc(-c2cccc3c2COC3=O)c(OC2(C(=O)OCC3CC3)CC2)c1OC] | cyclopropylmethyl 1-[2,3-dimethoxy-6-(1-oxo-3H-isobenzofuran-4-yl)phenoxy]cyclopropanecarboxylate |
| 1487 | 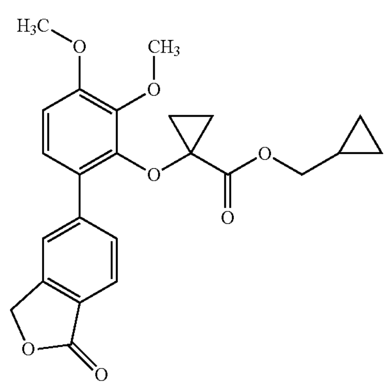 [SMILES: COc1ccc(-c2ccc3c(c2)COC3=O)c(OC2(C(=O)OCC3CC3)CC2)c1OC] | cyclopropylmethyl 1-[2,3-dimethoxy-6-(1-oxo-3H-isobenzofuran-5-yl)phenoxy]cyclopropanecarboxylate |

| Compound | Structure | Compound name |
|---|---|---|
| 1488 | 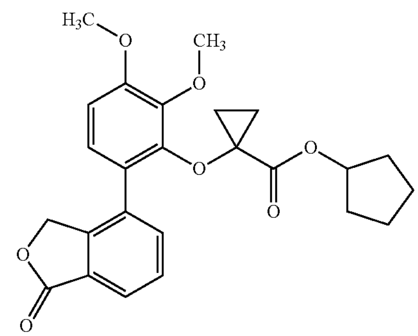 [SMILES: COc1ccc(-c2cccc3c2COC3=O)c(OC2(C(=O)OC3CCCC3)CC2)c1OC] | cyclopentyl 1-[2,3-dimethoxy-6-(1-oxo-3H-isobenzofuran-4-yl)phenoxy]cyclopropanecarboxylate |
| 1489 | 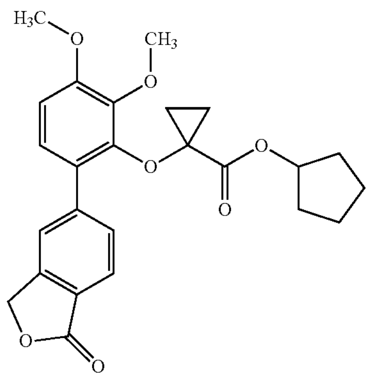 | cyclopentyl 1-[2,3-dimethoxy-6-(1-oxo-3H-isobenzofuran-5-yl)phenoxy]cyclopropanecarboxylate |
| 1490 | 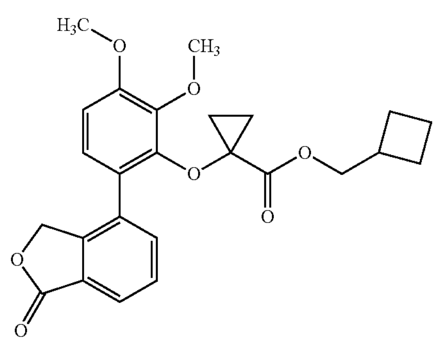 | cyclobutylmethyl 1-[2,3-dimethoxy-6-(1-oxo-3H-isobenzofuran-4-yl)phenoxy]cyclopropanecarboxylate |
| 1491 | 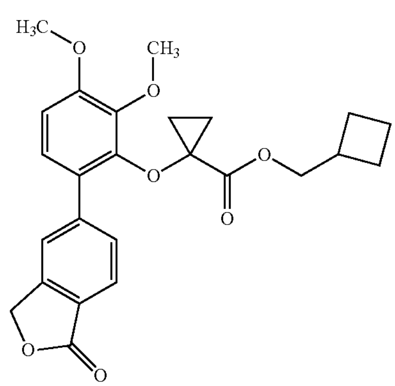 [SMILES: COc1ccc(-c2ccc3c(c2)COC3=O)c(OC2(C(=O)OCC3CCC3)CC2)c1OC] | cyclobutylmethyl 1-[2,3-dimethoxy-6-(1-oxo-3H-isobenzofuran-5-yl)phenoxy]cyclopropanecarboxylate |

-continued

| Compound | Structure | Compound name |
|---|---|---|
| 1492 | 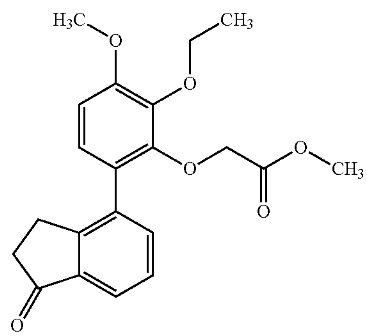 [SMILES: CCOc1c(OC)ccc(-c2cccc3c2CCC3=O)c1OCC(=O)OC] | methyl 2-[2-ethoxy-3-methoxy-6-(1-oxoindan-4-yl)phenoxy]acetate |
| 1493 | 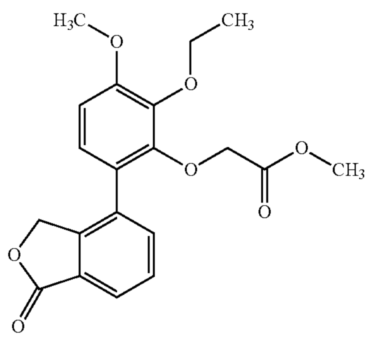 [SMILES: CCOc1c(OC)ccc(-c2cccc3c2COC3=O)c1OCC(=O)OC] | methyl 2-[2-ethoxy-3-methoxy-6-(1-oxoisoindolin-4-yl)phenoxy]acetate |
| 1494 | 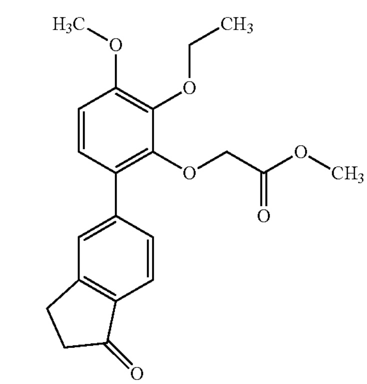 [SMILES: CCOc1c(OC)ccc(-c2ccc3c(c2)CCC3=O)c1OCC(=O)OC] | methyl 2-[2-ethoxy-3-methoxy-6-(1-oxoindan-5-yl)phenoxy]acetate |
| 1495 | 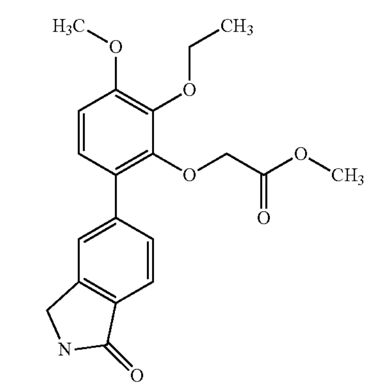 | methyl 2-[2-ethoxy-3-methoxy-6-(1-oxoisoindolin-5-yl)phenoxy]acetate |

-continued

| Compound | Structure | Compound name |
|---|---|---|
| 1496 | 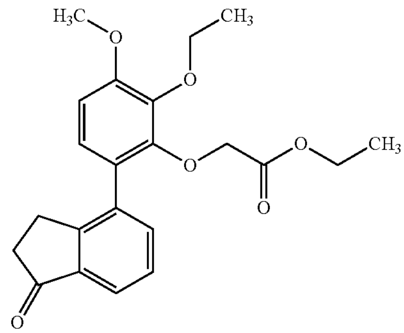 [SMILES: CCOC(=O)COc1c(-c2cccc3c2CCC3=O)ccc(OC)c1OCC] | ethyl 2-[2-ethoxy-3-methoxy-6-(1-oxoindan-4-yl)phenoxy]acetate |
| 1497 | 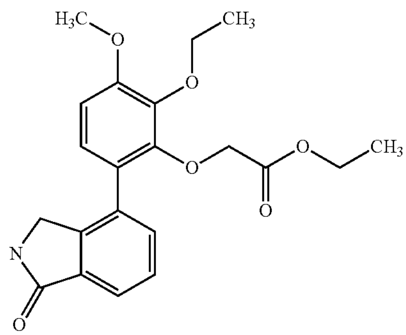 [SMILES: CCOC(=O)COc1c(-c2cccc3c2CNC3=O)ccc(OC)c1OCC] | ethyl 2-[2-ethoxy-3-methoxy-6-(1-oxoisoindolin-4-yl)phenoxy]acetate |
| 1498 | 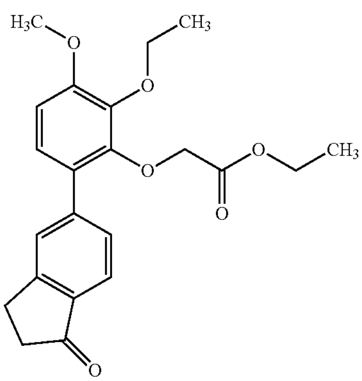 [SMILES: CCOC(=O)COc1c(-c2ccc3c(c2)CCC3=O)ccc(OC)c1OCC] | ethyl 2-[2-ethoxy-3-methoxy-6-(1-oxoindan-5-yl)phenoxy]acetate |
| 1499 | 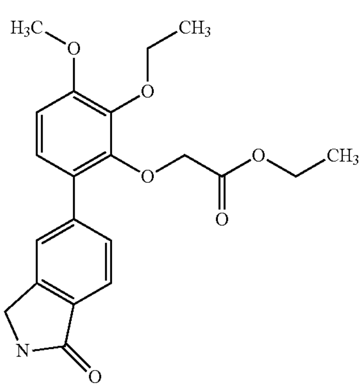 | ethyl 2-[2-ethoxy-3-methoxy-6-(1-oxoisoindolin-5-yl)phenoxy]acetate |

| Compound | Structure | Compound name |
|---|---|---|
| 1500 | 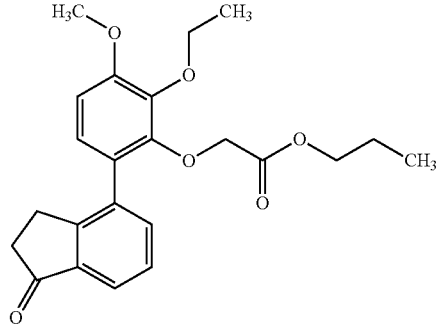 [SMILES: CCCOC(=O)COc1c(-c2cccc3c2CCC3=O)ccc(OC)c1OCC] | propyl 2-[2-ethoxy-3-methoxy-6-(1-oxoindan-4-yl)phenoxy]acetate |
| 1501 | 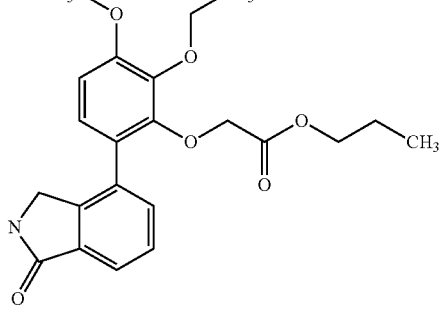 | propyl 2-[2-ethoxy-3-methoxy-6-(1-oxoisoindolin-4-yl)phenoxy]acetate |
| 1502 | 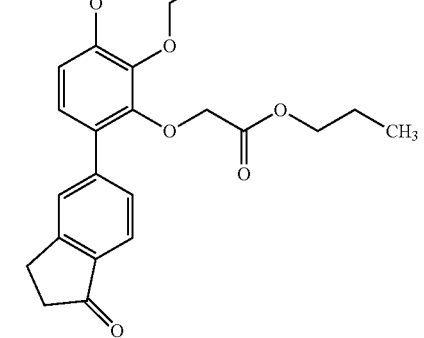 | propyl 2-[2-ethoxy-3-methoxy-6-(1-oxoindan-5-yl)phenoxy]acetate |
| 1503 | 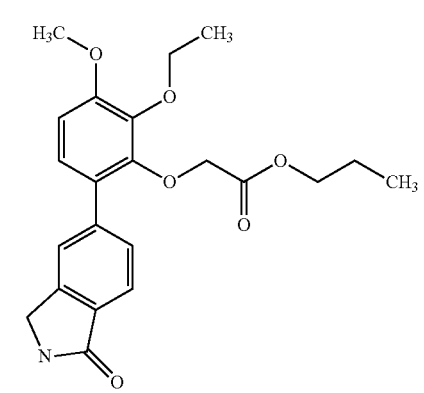 | propyl 2-[2-ethoxy-3-methoxy-6-(1-oxoisoindolin-5-yl)phenoxy]acetate |

| Compound | Structure | Compound name |
|---|---|---|
| 1504 | 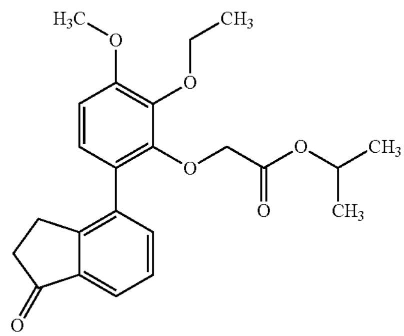 [SMILES: CCOc1c(OC)ccc(-c2cccc3c2CCC3=O)c1OCC(=O)OC(C)C] | isopropyl 2-[2-ethoxy-3-methoxy-6-(1-oxoindan-4-yl)phenoxy]acetate |
| 1505 | 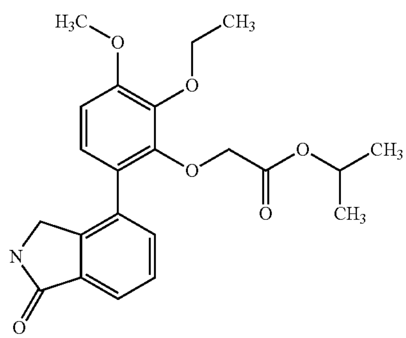 [SMILES: CCOc1c(OC)ccc(-c2cccc3c2CNC3=O)c1OCC(=O)OC(C)C] | isopropyl 2-[2-ethoxy-3-methoxy-6-(1-oxoisoindolin-4-yl)phenoxy]acetate |
| 1506 | 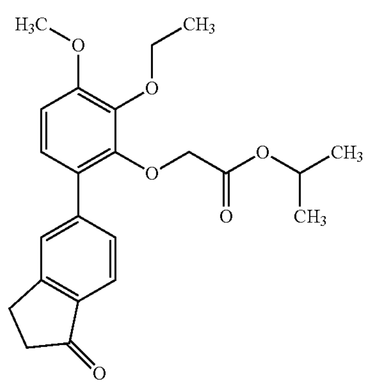 [SMILES: CCOc1c(OC)ccc(-c2ccc3c(c2)CCC3=O)c1OCC(=O)OC(C)C] | isopropyl 2-[2-ethoxy-3-methoxy-6-(1-oxoindan-5-yl)phenoxy]acetate |
| 1507 | 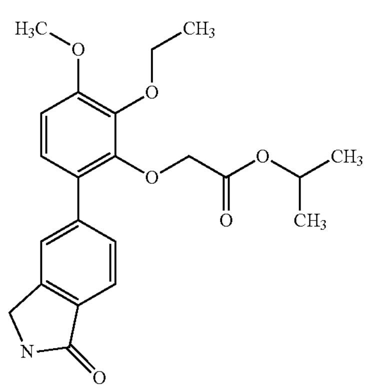 | isopropyl 2-[2-ethoxy-3-methoxy-6-(1-oxoisoindolin-5-yl)phenoxy]acetate |

| Compound | Structure | Compound name |
|---|---|---|
| 1508 | 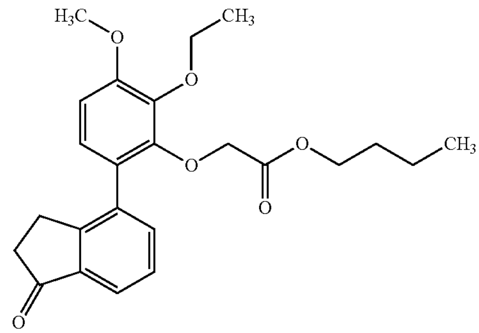 [SMILES: CCCCOC(=O)COc1c(-c2cccc3c2CCC3=O)ccc(OC)c1OCC] | butyl 2-[2-ethoxy-3-methoxy-6-(1-oxoindan-4-yl)phenoxy]acetate |
| 1509 | 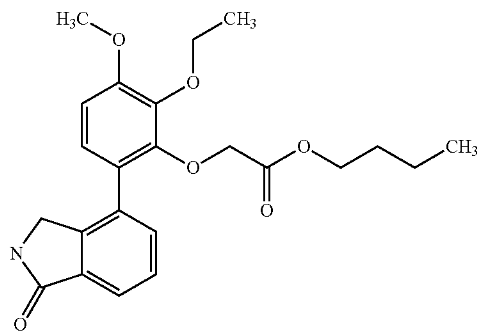 [SMILES: CCCCOC(=O)COc1c(-c2cccc3c2CNC3=O)ccc(OC)c1OCC] | butyl 2-[2-ethoxy-3-methoxy-6-(1-oxoisoindolin-4-yl)phenoxy]acetate |
| 1510 | 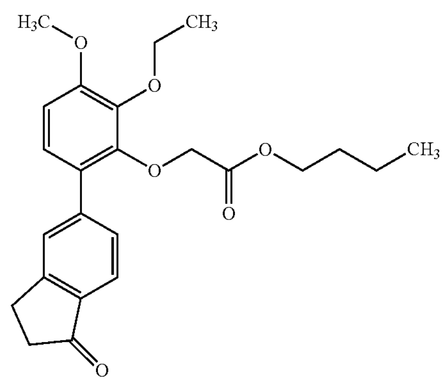 [SMILES: CCCCOC(=O)COc1c(-c2ccc3c(c2)CCC3=O)ccc(OC)c1OCC] | butyl 2-[2-ethoxy-3-methoxy-6-(1-oxoindan-5-yl)phenoxy]acetate |
| 1511 | 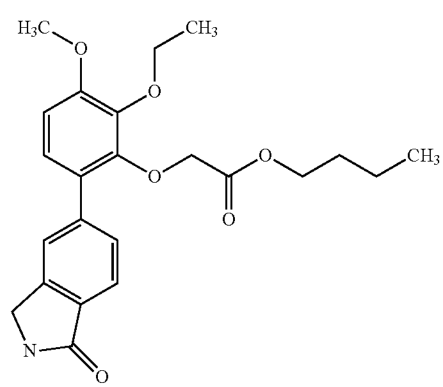 | butyl 2-[2-ethoxy-3-methoxy-6-(1-oxoisoindolin-5-yl)phenoxy]acetate |

-continued
| Compound | Structure | Compound name |
|---|---|---|
| 1512 | 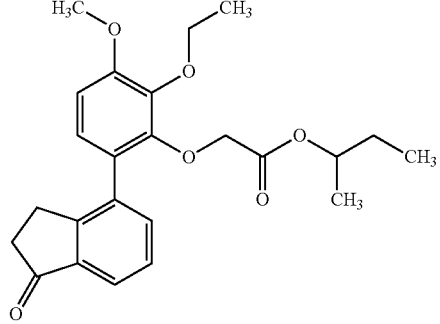 [SMILES: CCOc1c(OC)ccc(-c2cccc3c2CCC3=O)c1OCC(=O)OC(C)CC] | sec-butyl 2-[2-ethoxy-3-methoxy-6-(1-oxoindan-4-yl)phenoxy]acetate |
| 1513 | 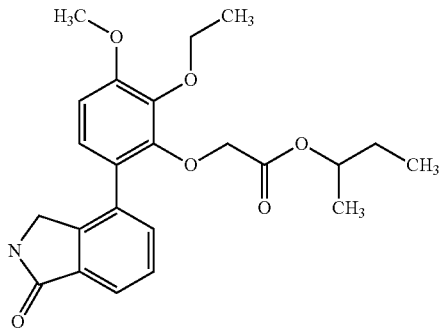 | sec-butyl 2-[2-ethoxy-3-methoxy-6-(1-oxoisoindolin-4-yl)phenoxy]acetate |
| 1514 | 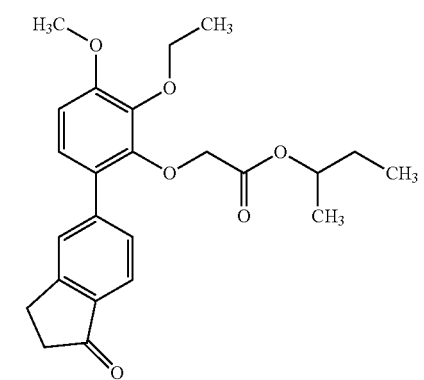 [SMILES: CCOc1c(OC)ccc(-c2ccc3c(c2)CCC3=O)c1OCC(=O)OC(C)CC] | sec-butyl 2-[2-ethoxy-3-methxoy-6-(1-oxoindan-5-yl)phenoxy]acetate |
| 1516 | 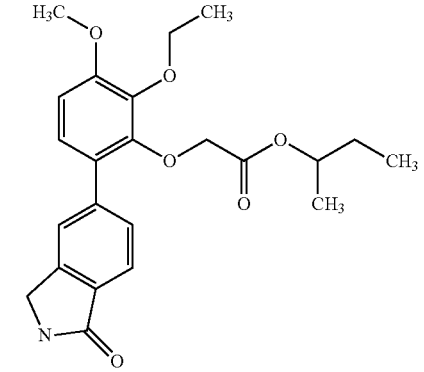 | sec-butyl 2-[2-ethoxy-3-methoxy-6-(1-oxoisoindolin-5-yl)phenoxy]acetate |

| Compound | Structure | Compound name |
|---|---|---|
| 1517 | 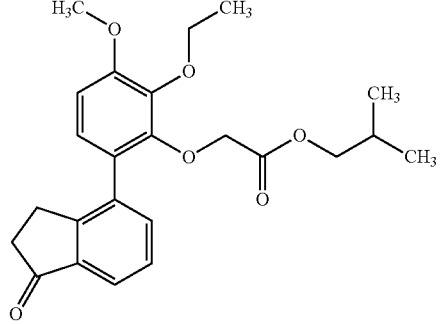 [SMILES: CCOc1c(OC)ccc(-c2cccc3c2CCC3=O)c1OCC(=O)OCC(C)C] | isobutyl 2-[2-ethoxy-3-methoxy-6-(1-oxoindan-4-yl)phenoxy]acetate |
| 1518 | 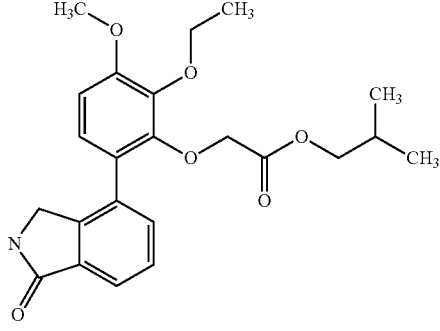 | isobutyl 2-[2-ethoxy-3-methoxy-6-(1-oxoisoindolin-4-yl)phenoxy]acetate |
| 1519 | 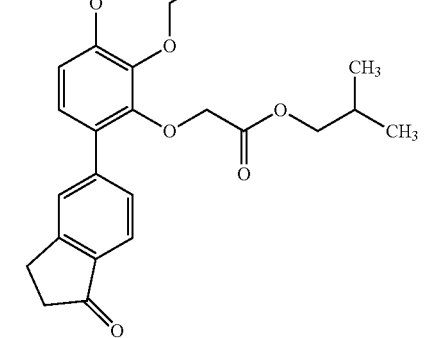 | isobutyl 2-[2-ethoxy-3-methoxy-6-(1-oxoindan-5-yl)phenoxy]acetate |
| 1520 | 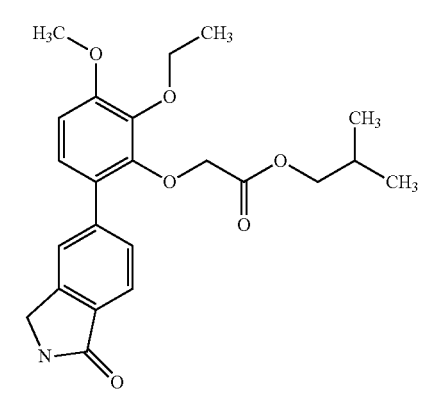 [SMILES: CCOc1c(OC)ccc(-c2ccc3c(c2)CCC3=O)c1OCC(=O)OCC(C)C] | isobutyl 2-[2-ethoxy-3-methoxy-6-(1-oxoisoindolin-5-yl)phenoxy]acetate |

-continued

| Compound | Structure | Compound name |
|---|---|---|
| 1521 | 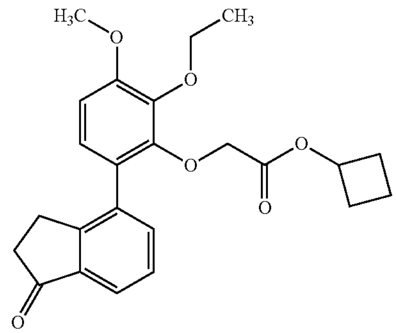 [SMILES: CCOc1c(OC)ccc(-c2cccc3c2CCC3=O)c1OCC(=O)OC1CCC1] | cyclobutyl 2-[2-ethoxy-3-methoxy-6-(1-oxoindan-4-yl)phenoxy]acetate |
| 1522 | 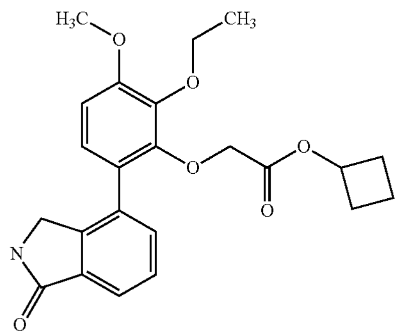 [SMILES: CCOc1c(OC)ccc(-c2cccc3c2CNC3=O)c1OCC(=O)OC1CCC1] | cyclobutyl 2-[2-ethoxy-3-methoxy-6-(1-oxoisoindolin-4-yl)phenoxy]acetate |
| 1523 | 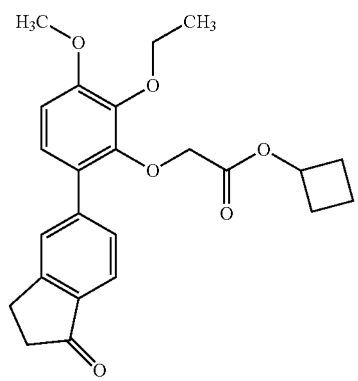 [SMILES: CCOc1c(OC)ccc(-c2ccc3c(c2)CCC3=O)c1OCC(=O)OC1CCC1] | cyclobutyl 2-[2-ethoxy-3-methoxy-6-(1-oxoindan-5-yl)phenoxy]acetate |
| 1524 | 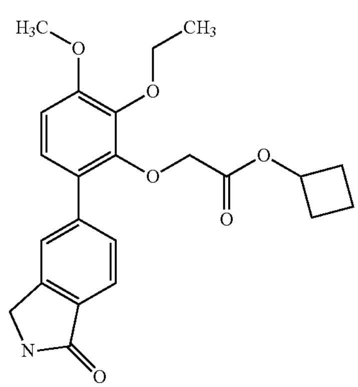 [SMILES: CCOc1c(OC)ccc(-c2ccc3c(c2)CNC3=O)c1OCC(=O)OC1CCC1] | cyclobutyl 2-[2-ethoxy-3-methoxy-6-(1-oxoisoindolin-5-yl)phenoxy]acetate |

| Compound | Structure | Compound name |
|---|---|---|
| 1525 | 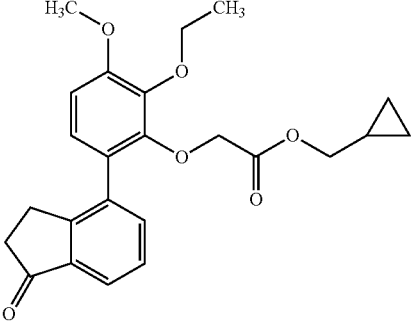 [SMILES: CCOc1c(OC)ccc(-c2cccc3c2CCC3=O)c1OCC(=O)OCC1CC1] | cyclopropylmethyl 2-[2-ethoxy-3-methoxy-6-(1-oxoindan-4-yl)phenoxy]acetate |
| 1526 | 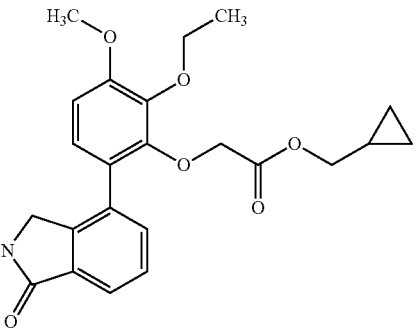 [SMILES: CCOc1c(OC)ccc(-c2cccc3c2CNC3=O)c1OCC(=O)OCC1CC1] | cyclopropylmethyl 2-[2-ethoxy-3-methoxy-6-(1-oxoisoindolin-4-yl)phenoxy]acetate |
| 1527 | 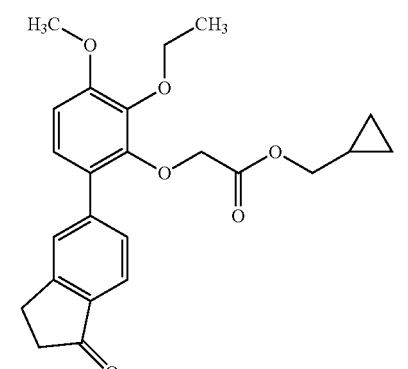 | cyclopropylmethyl 2-[2-ethoxy-3-methoxy-6-(1-oxoindan-5-yl)phenoxy]acetate |
| 1528 | 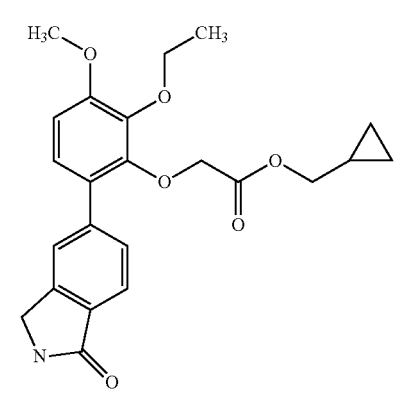 [SMILES: CCOc1c(OC)ccc(-c2ccc3c(c2)CCC3=O)c1OCC(=O)OCC1CC1] | cyclopropylmethyl 2-[2-ethoxy-3-methoxy-6-(1-oxoisoindolin-5-yl)phenoxy]acetate |

-continued

| Compound | Structure | Compound name |
|---|---|---|
| 1529 | 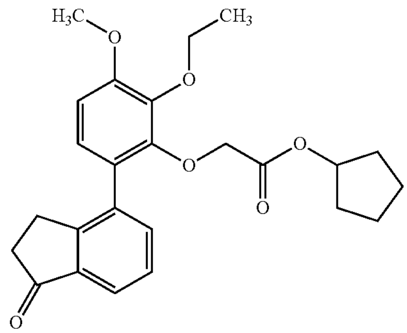 [SMILES: CCOc1c(OC)ccc(-c2cccc3c2CCC3=O)c1OCC(=O)OC1CCCC1] | cyclopentyl 2-[2-ethoxy-3-methoxy-6-(1-oxoindan-4-yl)phenoxy]acetate |
| 1530 | 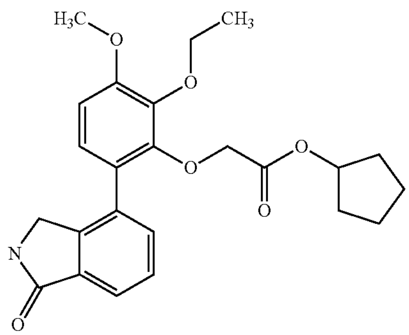 [SMILES: CCOc1c(OC)ccc(-c2cccc3c2CNC3=O)c1OCC(=O)OC1CCCC1] | cyclopentyl 2-[2-ethoxy-3-methoxy-6-(1-oxoisoindolin-4-yl)phenoxy]acetate |
| 1531 | 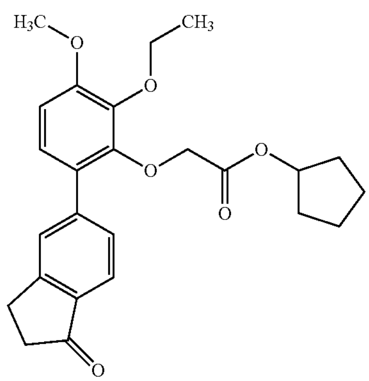 [SMILES: CCOc1c(OC)ccc(-c2ccc3c(c2)CCC3=O)c1OCC(=O)OC1CCCC1] | cyclopentyl 2-[2-ethoxy-3-methoxy-6-(1-oxoindan-5-yl)phenoxy]acetate |
| 1532 | 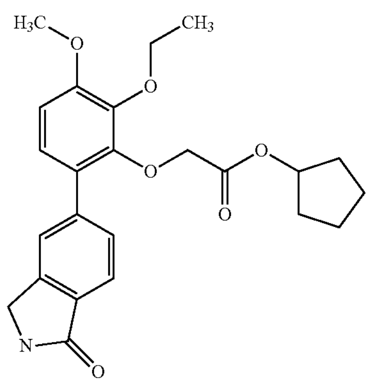 [SMILES: CCOc1c(OC)ccc(-c2ccc3c(c2)CNC3=O)c1OCC(=O)OC1CCCC1] | cyclopentyl 2-[2-ethoxy-3-methoxy-6-(1-oxoisoindolin-5-yl)phenoxy]acetate |

| Compound | Structure | Compound name |
|---|---|---|
| 1533 | 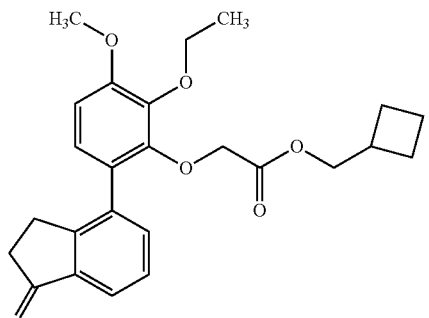 | cyclobutylmethyl 2-[2-ethoxy-3-methoxy-6-(1-oxoindan-4-yl)phenoxy]acetate |
| 1534 | 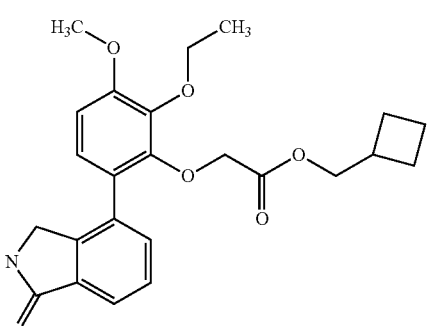 | cyclobutylmethyl 2-[2-ethoxy-3-methoxy-6-(1-oxoisoindolin-4-yl)phenoxy]acetate |
| 1535 | 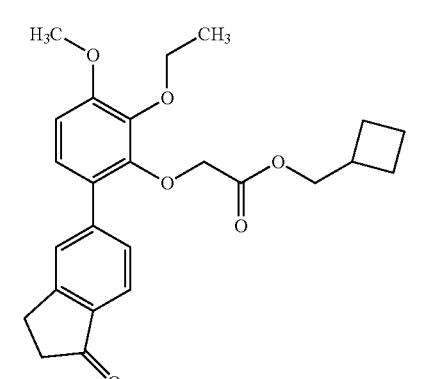 | cyclobutylmethyl 2-[2-ethoxy-3-methoxy-6-(1-oxoindan-5-yl)phenoxy]acetate |
| 1536 | 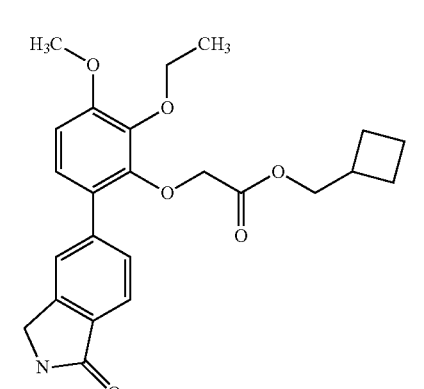 | cyclobutylmethyl 2-[2-ethoxy-3-methoxy-6-(1-oxoisoindolin-5-yl)phenoxy]acetate |

-continued

| Compound | Structure | Compound name |
|---|---|---|
| 1537 | 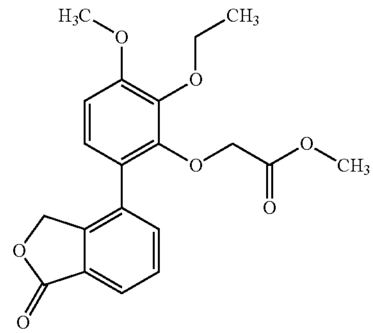 [SMILES: CCOc1c(OC)ccc(-c2cccc3c2COC3=O)c1OCC(=O)OC] | methyl 2-[2-ethoxy-3-methoxy-6-(1-oxo-3H-isobenzofuran-4-yl)phenoxy]acetate |
| 1538 | 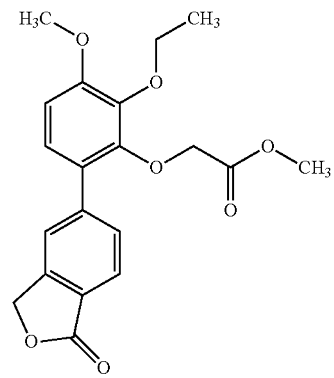 [SMILES: CCOc1c(OC)ccc(-c2ccc3c(c2)COC3=O)c1OCC(=O)OC] | methyl 2-[2-ethoxy-3-methoxy-6-(1-oxo-3H-isobenzofuran-5-yl)phenoxy]acetate |
| 1539 | 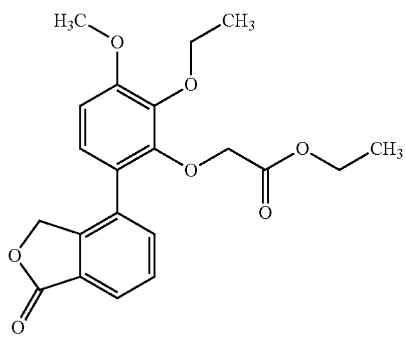 | ethyl 2-[2-ethoxy-3-methoxy-6-(1-oxo-3H-isobenzofuran-4-yl)phenoxy]acetate |
| 1540 | 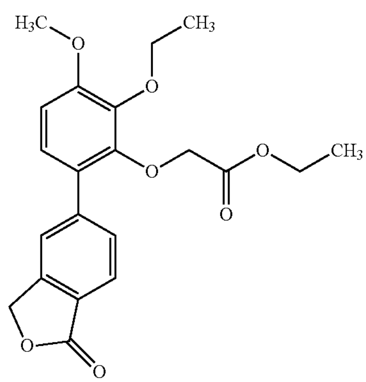 [SMILES: CCOC(=O)COc1c(-c2ccc3c(c2)COC3=O)ccc(OC)c1OCC] | ethyl 2-[2-ethoxy-3-methoxy-6-(1-oxo-3H-isobenzofuran-5-yl)phenoxy]acetate |

-continued
| Compound | Structure | Compound name |
|---|---|---|
| 1541 | 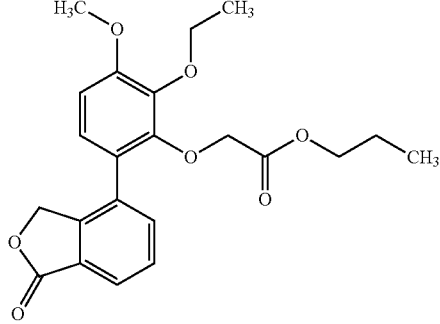 | propyl 2-[2-ethoxy-3-methoxy-6-(1-oxo-3H-isobenzofuran-4-yl)phenoxy]acetate |
| 1542 | 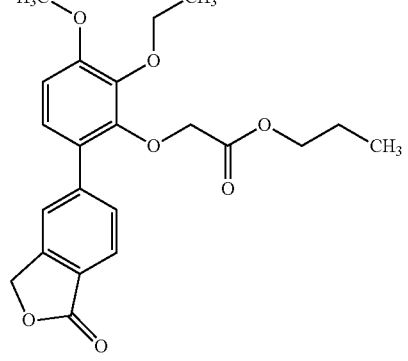 | propyl 2-[2-ethoxy-3-methoxy-6-(1-oxo-3H-isobenzofuran-5-yl)phenoxy]acetate |
| 1543 | 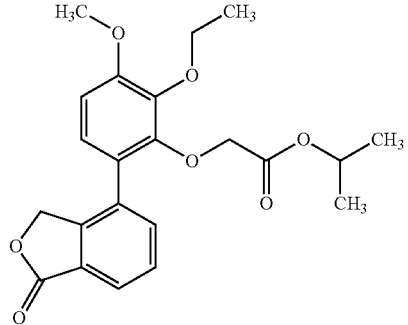 | isopropyl 2-[2-ethoxy-3-methoxy-6-(1-oxo-3H-isobenzofuran-4-yl)phenoxy]acetate |
| 1544 | 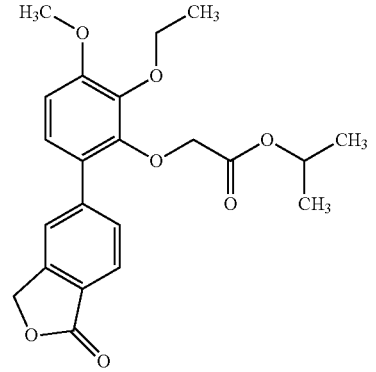 [SMILES: CCOc1c(OC)ccc(-c2ccc3c(c2)COC3=O)c1OCC(=O)OC(C)C] | isopropyl 2-[2-ethoxy-3-methoxy-6-(1-oxo-3H-isobenzofuran-5-yl)phenoxy]acetate |

-continued

| Compound | Structure | Compound name |
|---|---|---|
| 1545 | 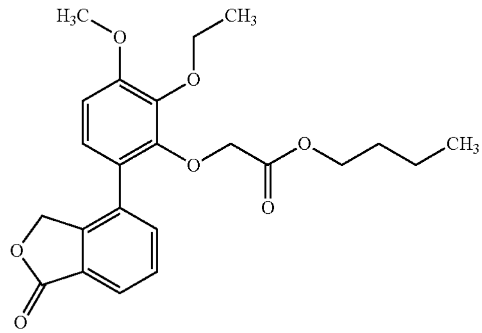 | butyl 2-[2-ethoxy-3-methoxy-6-(1-oxo-3H-isobenzofuran-4-yl)phenoxy]acetate |
| 1546 | 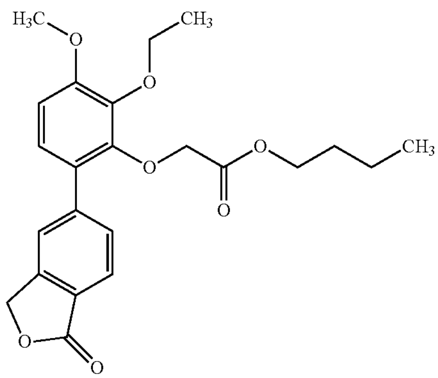 [SMILES: CCCCOC(=O)COc1c(-c2ccc3c(c2)COC3=O)ccc(OC)c1OCC] | butyl 2-[2-ethoxy-3-methoxy-6-(1-oxo-3H-isobenzofuran-5-yl)phenoxy]acetate |
| 1547 | 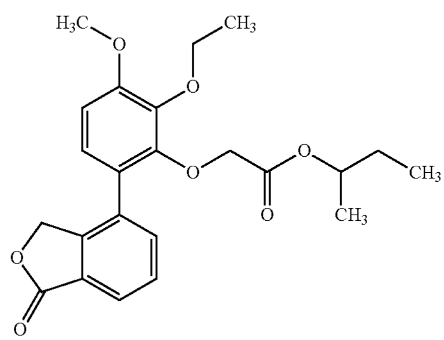 | sec-butyl 2-[2-ethoxy-3-methoxy-6-(1-oxo-3H-isobenzofuran-4-yl)phenoxy]acetate |
| 1548 | 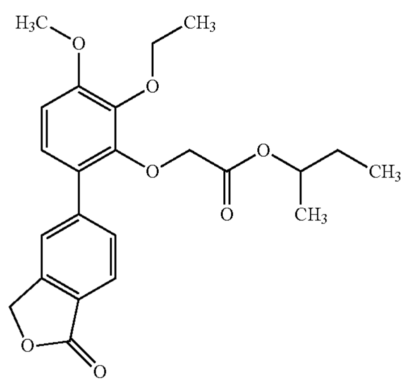 [SMILES: CCOc1c(OC)ccc(-c2ccc3c(c2)COC3=O)c1OCC(=O)OC(C)CC] | sec-butyl 2-[2-ethoxy-3-methoxy-6-(1-oxo-3H-isobenzofuran-5-yl)phenoxy]acetate |

-continued

| Compound | Structure | Compound name |
|---|---|---|
| 1549 | 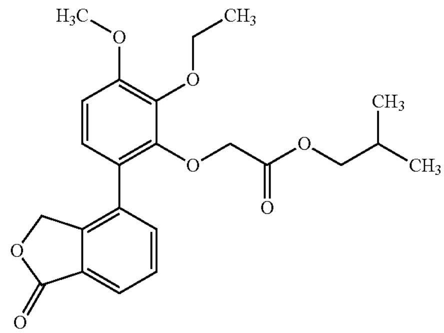 [SMILES: CCOc1c(OC)ccc(-c2cccc3c2COC3=O)c1OCC(=O)OCC(C)C] | isobutyl 2-[2-ethoxy-3-methoxy-6-(1-oxo-3H-isobenzofuran-4-yl)phenoxy]acetate |
| 1550 | 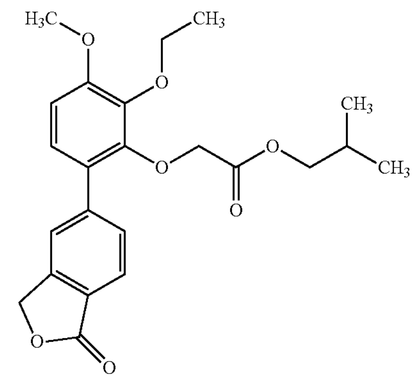 [SMILES: CCOc1c(OC)ccc(-c2ccc3c(c2)COC3=O)c1OCC(=O)OCC(C)C] | isobutyl 2-[2-ethoxy-3-methoxy-6-(1-oxo-3H-isobenzofuran-5-yl)phenoxy]acetate |
| 1551 | 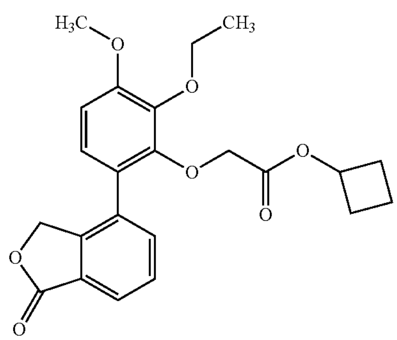 | cyclobutyl 2-[2-ethoxy-3-methoxy-6-(1-oxo-3H-isobenzofuran-4-yl)phenoxy]acetate |
| 1552 | 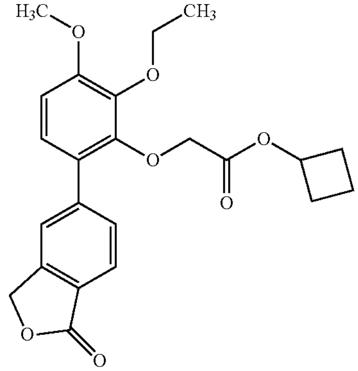 [SMILES: CCOc1c(OC)ccc(-c2ccc3c(c2)COC3=O)c1OCC(=O)OC1CCC1] | cyclobutyl 2-[2-ethoxy-3-methoxy-6-(1-oxo-3H-isobenzofuran-5-yl)phenoxy]acetate |

-continued

| Compound | Structure | Compound name |
|---|---|---|
| 1553 | 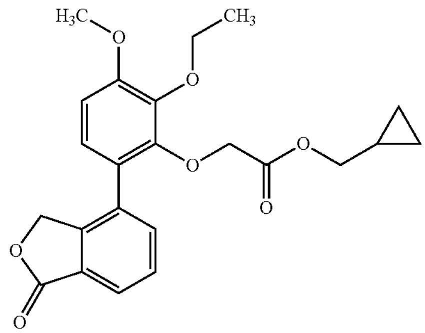 | cyclopropylmethyl 2-[2-ethoxy-3-methoxy-6-(1-oxo-3H-isobenzofuran-4-yl)phenoxy]acetate |
| 1554 | 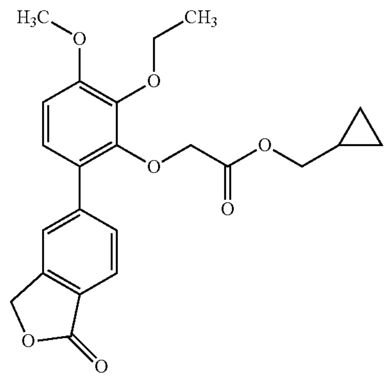 | cyclopropylmethyl 2-[2-ethoxy-3-methoxy-6-(1-oxo-3H-isobenzofuran-5-yl)phenoxy]acetate |
| 1555 | 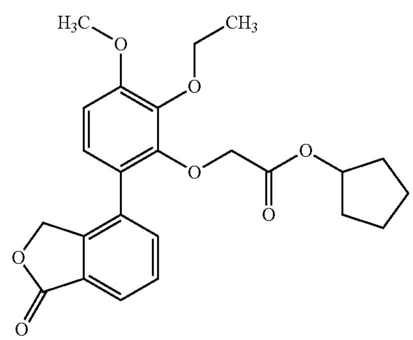 [SMILES: CCOc1c(OC)ccc(-c2cccc3c2COC3=O)c1OCC(=O)OC1CCCC1] | cyclopentyl 2-[2-ethoxy-3-methoxy-6-(1-oxo-3H-isobenzofuran-4-yl)phenoxy]acetate |
| 1556 | 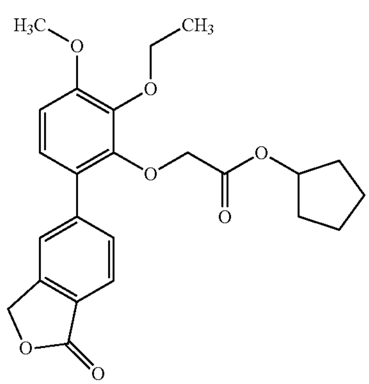 [SMILES: CCOc1c(OC)ccc(-c2ccc3c(c2)COC3=O)c1OCC(=O)OC1CCCC1] | cyclopentyl 2-[2-ethoxy-3-methoxy-6-(1-oxo-3H-isobenzofuran-5-yl)phenoxy]acetate |

-continued

| Compound | Structure | Compound name |
|---|---|---|
| 1557 | 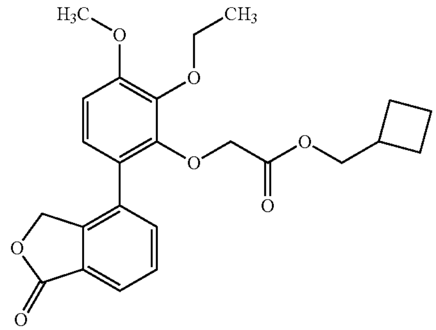 | cyclobutylmethyl 2-[2-ethoxy-3-methoxy-6-(1-oxo-3H-isobenzofuran-4-yl)phenoxy]acetate |
| 1558 | 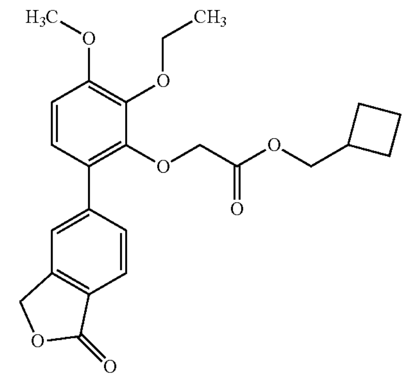 | cyclobutylmethyl 2-[2-ethoxy-3-methoxy-6-(1-oxo-3H-isobenzofuran-5-yl)phenoxy]acetate |

Example 177

PDE4 assay

Human recombinant PDE4 (Genbank accession no NM_006203) was incubated for 1 hour with the test compound at concentrations up to 10 µM, with cAMP ($1 \times 10^{-5}$M), and with a low amount (0.021 MBq) of radioactively labelled cAMP. At the end of the incubation, the cleavage of the substrate was evaluated by the binding of the AMP product to SPA beads, which generate chemoluminescence when bound to the radioactive tracer. The AMP product inhibited the binding of the radioactive tracer to the beads, and the luminescent signal was competed.

The results were calculated as the molar concentrations resulting in 50% inhibition of the substrate cleavage compared to controls samples, and are expressed as a range of $IC_{50}$ (M).

The compounds of the present invention were tested in the PDE4 assay.

Compounds for which $IC_{50}$ values are <100 nM in the PDE4 assay are:

Compounds 101-118, 120-128, 130-150, 152-158, 160-163, 165-166, 169-170, 174-175, 177-181, 183-190, 192-198, 200-206, 210-211, 213, 215-219, 221-222, 225-243, 245-253, 256-261, 264-266, 268-270, 287-299, 400-417, 421-422, 428, 429, 433, 434, 466, 483, 484, 520, 522, 523, 528, 532, 535, 536.

PDE4 $IC_{50}$ ranges

\* indicates that $IC_{50}$ values are ≥500 nM

\*\* indicates that $IC_{50}$ values are ≥100 and <500 nM

\*\*\* indicates that $IC_{50}$ values are <100 nM

| Compound name and number | PDE4 $IC_{50}$ range |
|---|---|
| 4-[3,4-Dimethoxy-2-(3-methyl-butoxy)-phenyl]-indan-1-one (Compound 101) | \*\*\* |
| 4-(2-Cyclobutylmethoxy-3,4-dimethoxy-phenyl)-indan-1-one (Compound 102) | \*\*\* |
| 4-[2-(4-Methanesulfonyl-benzyloxy)-3,4-dimethoxy-phenyl]-indan-1-one (Compound 103) | \*\*\* |
| 4-[2-(3-Hydroxymethyl-oxetan-3-ylmethoxy)-3,4-dimethoxy-phenyl]-indan-1-one (Compound 104) | \*\*\* |
| 4-[2-(3,3-Dimethyl-butoxy)-3,4-dimethoxy-phenyl]-indan-1-one (Compound 105) | \*\*\* |
| 4-[2,3-Dimethoxy-6-(1-oxo-indan-4-yl)-phenoxymethyl]-benzamide (Compound 106) | \*\*\* |
| 4-[2-(3-Hydroxy-2,2-dimethyl-propoxy)-3,4-dimethoxy-phenyl]-indan-1-one (Compound 107 | \*\*\* |

| Compound name and number | PDE4 IC$_{50}$ range |
|---|---|
| 4-[2,3-Dimethoxy-6-(1-oxo-indan-4-yl)-phenoxymethyl]-N-methyl-benzamide (Compound 108) | *** |
| 4-[2,3-Dimethoxy-6-(1-oxo-indan-4-yl)-phenoxymethyl]-N,N-dimethyl-benzamide (Compound 109) | *** |
| 3-[2,3-Dimethoxy-6-(1-oxo-indan-4-yl)-phenoxymethyl]-N,N-dimethyl-benzamide (Compound 110 | *** |
| 3-[2,3-Dimethoxy-6-(1-oxo-indan-4-yl)-phenoxymethyl]-N,N-dimethyl-benzenesulfonamide (Compound 111) | *** |
| 4-[2,3-Dimethoxy-6-(1-oxo-indan-4-yl)-phenoxymethyl]-benzenesulfonamide (Compound 112) | *** |
| 4-[2-(3-Methanesulfonyl-benzyloxy)-3,4-dimethoxy-phenyl]-indan-1-one (Compound 113) | *** |
| 3-[2,3-Dimethoxy-6-(1-oxo-indan-4-yl)-phenoxymethyl]-benzamide (Compound 114) | *** |
| 4-[2-(4-Methanesulfonyl-benzyloxy)-3,4-dimethoxy-phenyl]-3H-isobenzofuran-1-one (Compound 115) | *** |
| 4-[2,3-Dimethoxy-6-(1-oxo-1,3-dihydro-isobenzofuran-4-yl)-phenoxymethyl]-benzamide (Compound 116) | *** |
| 4-[2,3-Dimethoxy-6-(1-oxo-1,3-dihydro-isobenzofuran-4-yl)-phenoxymethyl]-N-methyl-benzamide (Compound 117) | *** |
| 4-[2,3-Dimethoxy-6-(1-oxo-1,3-dihydro-isobenzofuran-4-yl)-phenoxymethyl]-N,N-dimethyl-benzamide (Compound 118) | *** |
| 4-[2-(3-Hydroxymethyl-oxetan-3-ylmethoxy)-3,4-dimethoxy-phenyl]-3H-isobenzofuran-1-one (Compound 119) | ** |
| 5-[3,4-Dimethoxy-2-(3-methyl-butoxy)-phenyl]-indan-1-one (Compound 120) | *** |
| 5-[2-(2,2-Dimethyl-propoxy)-3,4-dimethoxy-phenyl]-indan-1-one (Compound 121) | *** |
| 5-(2-Cyclobutylmethoxy-3,4-dimethoxy-phenyl)-indan-1-one (Compound 122) | *** |
| 5-[2-(3,3-Dimethyl-butoxy)-3,4-dimethoxy-phenyl]-indan-1-one (Compound 123) | *** |
| 4-[2,3-Dimethoxy-6-(1-oxo-indan-5-yl)-phenoxymethyl]-benzamide (Compound 124) | *** |
| 5-[2-(3-Hydroxy-2,2-dimethyl-propoxy)-3,4-dimethoxy-phenyl]-indan-1-one (Compound 125) | *** |
| 4-[2,3-Dimethoxy-6-(1-oxo-indan-5-yl)-phenoxymethyl]-N-methyl-benzamide (Compound 126) | *** |
| 4-[2,3-Dimethoxy-6-(1-oxo-indan-5-yl)-phenoxymethyl]-N,N-dimethyl-benzamide (Compound 127) | *** |
| 3-[2,3-Dimethoxy-6-(1-oxo-indan-5-yl)-phenoxymethyl]-N,N-dimethyl-benzamide (Compound 128) | *** |
| 5-[2-(3-Hydroxymethyl-oxetan-3-ylmethoxy)-3,4-dimethoxy-phenyl]-indan-1-one (Compound 129) | ** |
| 5-[2-(4-Methanesulfonyl-benzyloxy)-3,4-dimethoxy-phenyl]-indan-1-one (Compound 130) | *** |
| 5-[3,4-Dimethoxy-2-(3-methyl-butoxy)-phenyl]-3H-isobenzofuran-1-one (Compound 131) | *** |
| 5-[2-(2,2-Dimethyl-propoxy)-3,4-dimethoxy-phenyl]-3H-isobenzofuran-1-one (Compound 132) | *** |
| 5-(2-Cyclobutylmethoxy-3,4-dimethoxy-phenyl)-3H-isobenzofuran-1-one (Compound 133) | *** |
| 5-[2-(3-Hydroxymethyl-oxetan-3-ylmethoxy)-3,4-dimethoxy-phenyl]-3H-isobenzofuran-1-one (Compound 134) | *** |
| 5-[2-(3,3-Dimethyl-butoxy)-3,4-dimethoxy-phenyl]-3H-isobenzofuran-1-one (Compound 135) | *** |
| 4-[2,3-Dimethoxy-6-(1-oxo-1,3-dihydro-isobenzofuran-5-yl)-phenoxymethyl]-benzamide (Compound 136) | *** |
| 5-[2-(3-Hydroxy-2,2-dimethyl-propoxy)-3,4-dimethoxy-phenyl]-3H-isobenzofuran-1-one (Compound 137) | *** |
| 4-[2,3-Dimethoxy-6-(1-oxo-1,3-dihydro-isobenzofuran-5-yl)-phenoxymethyl]-N-methyl-benzamide (Compound 138) | *** |
| 4-[2,3-Dimethoxy-6-(1-oxo-1,3-dihydro-isobenzofuran-5-yl)-phenoxymethyl]-N,N-dimethyl-benzamide (Compound 139) | *** |
| 3-[2,3-Dimethoxy-6-(1-oxo-1,3-dihydro-isobenzofuran-5-yl)-phenoxymethyl]-N,N-dimethyl-benzamide (Compound 140) | *** |
| 4-[2,3-Dimethoxy-6-(1-oxo-1,3-dihydro-isobenzofuran-5-yl)-phenoxymethyl]-benzenesulfonamide (Compound 141) | *** |
| 5-[2-(4-Methanesulfonyl-benzyloxy)-3,4-dimethoxy-phenyl]-3H-isobenzofuran-1-one (Compound 142) | *** |
| 5-[2-(3-Methanesulfonyl-benzyloxy)-3,4-dimethoxy-phenyl]-3H-isobenzofuran-1-one (Compound 143) | *** |
| 3-[2,3-Dimethoxy-6-(1-oxo-1,3-dihydro-isobenzofuran-5-yl)-phenoxymethyl]-benzenesulfonamide (Compound 144) | *** |
| 3-[2,3-Dimethoxy-6-(1-oxo-1,3-dihydro-isobenzofuran-5-yl)-phenoxymethyl]-N,N-dimethyl-benzenesulfonamide (Compound 145) | *** |

| Compound name and number | PDE4 IC$_{50}$ range |
|---|---|
| 3-[2,3-Dimethoxy-6-(1-oxo-1,3-dihydro-isobenzofuran-5-yl)-phenoxymethyl]-benzamide (Compound 146) | *** |
| 5-[3,4-Dimethoxy-2-(3-methyl-butoxy)-phenyl]-2,3-dihydro-isoindol-1-one (Compound 147) | *** |
| 5-[2-(2,2-Dimethyl-propoxy)-3,4-dimethoxy-phenyl]-2,3-dihydro-isoindol-1-one (Compound 148) | *** |
| 5-(2-Cyclobutylmethoxy-3,4-dimethoxy-phenyl)-2,3-dihydro-isoindol-1-one (Compound 149) | *** |
| 5-[2-(4-Methanesulfonyl-benzyloxy)-3,4-dimethoxy-phenyl]-2,3-dihydro-isoindol-1-one (Compound 150) | *** |
| 5-[2-(3-Hydroxymethyl-oxetan-3-ylmethoxy)-3,4-dimethoxy-phenyl]-2,3-dihydro-isoindol-1-one (Compound 151) | ** |
| 5-[2-(3,3-Dimethyl-butoxy)-3,4-dimethoxy-phenyl]-2,3-dihydro-isoindol-1-one (Compound 152) | *** |
| 4-[2,3-Dimethoxy-6-(1-oxo-2,3-dihydro-1H-isoindol-5-yl)-phenoxymethyl]-benzamide (Compound 153) | *** |
| 5-[2-(3-Hydroxy-2,2-dimethyl-propoxy)-3,4-dimethoxy-phenyl]-2,3-dihydro-isoindol-1-one (Compound 154) | *** |
| 4-[2,3-Dimethoxy-6-(1-oxo-2,3-dihydro-1H-isoindol-5-yl)-phenoxymethyl]-N-methyl-benzamide (Compound 155) | *** |
| 4-[2,3-Dimethoxy-6-(1-oxo-2,3-dihydro-1H-isoindol-5-yl)-phenoxymethyl]-N,N-dimethyl-benzamide (Compound 156) | *** |
| 3-[2,3-Dimethoxy-6-(1-oxo-2,3-dihydro-1H-isoindol-5-yl)-phenoxymethyl]-N,N-dimethyl-benzamide (Compound 157) | *** |
| 3-[2,3-Dimethoxy-6-(1-oxo-2,3-dihydro-1H-isoindol-5-yl)-phenoxymethyl]-benzenesulfonamide (Compound 158) | *** |
| 3-[2,3-Dimethoxy-6-(1-oxo-2,3-dihydro-1H-isoindol-5-yl)-phenoxymethyl]-benzamide (Compound 159) | ** |
| 5-[2-(3-Methanesulfonyl-benzyloxy)-3,4-dimethoxy-phenyl]-2,3-dihydro-isoindol-1-one (Compound 160) | *** |
| 4-[2,3-Dimethoxy-6-(1-oxo-2,3-dihydro-1H-isoindol-5-yl)-phenoxymethyl]-benzenesulfonamide (Compound 161) | *** |
| 3-[2,3-Dimethoxy-6-(1-oxo-indan-4-yl)-phenoxy]-2,2-dimethyl-propionic acid methyl ester (Compound 162) | *** |
| 4-[3,4-Dimethoxy-2-(3-methyl-oxetan-3-ylmethoxy)-phenyl]-indan-1-one (Compound 163) | *** |
| 4-[3,4-Dimethoxy-2-(3-methyl-oxetan-3-ylmethoxy)-phenyl]-3H-isobenzofuran-1-one (Compound 164) | ** |
| 3-[2,3-Dimethoxy-6-(1-oxo-indan-5-yl)-phenoxy]-2,2-dimethyl-propionic acid methyl ester (Compound 165) | *** |
| 4-(2-Isobutoxy-3,4-dimethoxy-phenyl)-indan-1-one (Compound 166) | *** |
| 4-(2-Isobutoxy-3,4-dimethoxy-phenyl)-6,7-dimethoxy-indan-1-one (Compound 167) | ** |
| 4-(2-Isobutoxy-3,4-dimethoxy-phenyl)-7-methoxy-indan-1-one (Compound 168) | * |
| 5-(2-Isobutoxy-3,4-dimethoxy-phenyl)-indan-1-one (Compound 169) | *** |
| 5-(2-Isobutoxy-3,4-dimethoxy-phenyl)-3H-isobenzofuran-1-one (Compound 170) | *** |
| 5-(2-Isobutoxy-3,4-dimethoxy-phenyl)-2,3-dimethyl-2,3-dihydro-isoindol-1-one (Compound 171) | * |
| 5-(2-Isobutoxy-3,4-dimethoxy-phenyl)-2-methyl-2,3-dihydro-isoindol-1-one (Compound 172) | * |
| 4-(2-Isobutoxy-3,4-dimethoxy-phenyl)-2,3-dihydro-isoindol-1-one (Compound 173) | ** |
| 5-(2-Isobutoxy-3,4-dimethoxy-phenyl)-2,3-dihydro-isoindol-1-one (Compound 174) | *** |
| 4-(2-Isobutoxy-3,4-dimethoxy-phenyl)-3H-isobenzofuran-1-one (Compound 175) | *** |
| 6-(2-Isobutoxy-3,4-dimethoxy-phenyl)-benzofuran-3-one (Compound 176) | ** |
| 4-[2-(1-Hydroxymethyl-cyclopropylmethoxy)-3,4-dimethoxy-phenyl]-indan-1-one (Compound 177) | *** |
| 4-[3,4-Dimethoxy-2-(1-methoxymethyl-cyclopropylmethoxy)-phenyl]-indan-1-one (Compound 178) | *** |
| Ethyl-carbamic acid 1-[2,3-dimethoxy-6-(1-oxo-indan-4-yl)-phenoxymethyl]-cyclopropylmethyl ester (Compound 179) | *** |
| Isopropyl-carbamic acid 1-[2,3-dimethoxy-6-(1-oxo-indan-4-yl)-phenoxymethyl]-cyclopropylmethyl ester (Compound 180) | *** |
| Benzyl-carbamic acid 1-[2,3-dimethoxy-6-(1-oxo-indan-4-yl)-phenoxymethyl]-cyclopropylmethyl ester (Compound 181) | *** |
| 4-[2-(1-Aminomethyl-cyclopropylmethoxy)-3,4-dimethoxy-phenyl]-indan-1-one (Compound 182) | |
| N-{1-[2,3-Dimethoxy-6-(1-oxo-indan-4-yl)-phenoxymethyl]-cyclopropylmethyl}-isobutyramide (Compound 183) | *** |
| N-{1-[2,3-Dimethoxy-6-(1-oxo-indan-4-yl)-phenoxymethyl]-cyclopropylmethyl}-butyramide (Compound 184) | *** |

| Compound name and number | PDE4 IC$_{50}$ range |
|---|---|
| N-{1-[2,3-Dimethoxy-6-(1-oxo-indan-4-yl)-phenoxymethyl]-cyclopropylmethyl}-acetamide (Compound 185) | *** |
| {1-[2,3-Dimethoxy-6-(1-oxo-indan-4-yl)-phenoxymethyl]-cyclopropylmethyl}-carbamic acid ethyl ester (Compound 186) | *** |
| {1-[2,3-Dimethoxy-6-(1-oxo-indan-4-yl)-phenoxymethyl]-cyclopropylmethyl}-carbamic acid isopropyl ester (Compound 187) | *** |
| {1-[2,3-Dimethoxy-6-(1-oxo-indan-4-yl)-phenoxymethyl]-cyclopropylmethyl}-carbamic acid 2-methoxy-ethyl ester (Compound 188) | *** |
| Ethyl-carbamic acid 3-[2,3-dimethoxy-6-(1-oxo-indan-4-yl)-phenoxymethyl]-oxetan-3-ylmethyl ester (Compound 189) | *** |
| 4-[3,4-Dimethoxy-2-(3-methoxymethyl-oxetan-3-ylmethoxy)-phenyl]-indan-1-one (Compound 190) | *** |
| 4-[2-(3-Aminomethyl-oxetan-3-ylmethoxy)-3,4-dimethoxy-phenyl]-indan-1-one (Compound 191) | |
| N-{3-[2,3-Dimethoxy-6-(1-oxo-indan-4-yl)-phenoxymethyl]-oxetan-3-ylmethyl}-acetamide (Compound 192) | *** |
| N-{3-[2,3-Dimethoxy-6-(1-oxo-indan-4-yl)-phenoxymethyl]-oxetan-3-ylmethyl}-isobutyramide (Compound 193) | *** |
| N-{3-[2,3-Dimethoxy-6-(1-oxo-indan-4-yl)-phenoxymethyl]-oxetan-3-ylmethyl}-butyramide (Compound 194) | *** |
| N-{3-[2,3-Dimethoxy-6-(1-oxo-indan-4-yl)-phenoxymethyl]-oxetan-3-ylmethyl}-2-methoxy-acetamide (Compound 195) | *** |
| {3-[2,3-Dimethoxy-6-(1-oxo-indan-4-yl)-phenoxymethyl]-oxetan-3-ylmethyl}-carbamic acid ethyl ester (Compound 196) | *** |
| {3-[2,3-Dimethoxy-6-(1-oxo-indan-4-yl)-phenoxymethyl]-oxetan-3-ylmethyl}-carbamic acid isopropyl ester (Compound 197) | *** |
| {3-[2,3-Dimethoxy-6-(1-oxo-indan-4-yl)-phenoxymethyl]-oxetan-3-ylmethyl}-carbamic acid 2-methoxy-ethyl ester (Compound 198) | *** |
| 3-[2,3-Dimethoxy-6-(1-oxo-indan-4-yl)-phenoxy]-2,2-dimethyl-propionic acid (Compound 199) | |
| 3-[2,3-Dimethoxy-6-(1-oxo-indan-4-yl)-phenoxy]-2,2,N-trimethyl-propionamide (Compound 200) | *** |
| 3-[2,3-Dimethoxy-6-(1-oxo-indan-4-yl)-phenoxy]-N-ethyl-2,2-dimethyl-propionamide (Compound 201) | *** |
| 3-[2,3-Dimethoxy-6-(1-oxo-indan-4-yl)-phenoxy]-2,2,N,N-tetramethyl-propionamide (Compound 202) | *** |
| N-Cyclopropyl-3-[2,3-dimethoxy-6-(1-oxo-indan-4-yl)-phenoxy]-2,2-dimethyl-propionamide (Compound 203) | *** |
| 4-[2-(2,2-Dimethyl-3-morpholin-4-yl-3-oxo-propoxy)-3,4-dimethoxy-phenyl]-indan-1-one (Compound 204) | *** |
| 3-[2,3-Dimethoxy-6-(1-oxo-indan-5-yl)-phenoxy]-2,2-dimethyl-propionic acid (Compound 205) | |
| 3-[2,3-Dimethoxy-6-(1-oxo-indan-5-yl)-phenoxy]-2,2,N-trimethyl-propionamide (Compound 206) | *** |
| 3-[2,3-Dimethoxy-6-(1-oxo-indan-5-yl)-phenoxy]-2,2,N,N-tetramethyl-propionamide (Compound 207) | ** |
| 3-[2,3-Dimethoxy-6-(1-oxo-indan-5-yl)-phenoxy]-N-isopropyl-2,2-dimethyl-propionamide (Compound 208) | * |
| 3-[2,3-Dimethoxy-6-(1-oxo-indan-5-yl)-phenoxy]-2,2-dimethyl-N-propyl-propionamide (Compound 209) | ** |
| Ethyl-carbamic acid 3-[2,3-dimethoxy-6-(1-oxo-1,3-dihydro-isobenzofuran-5-yl)-phenoxy]-2,2-dimethyl-propyl ester (Compound 210) | *** |
| Ethyl-carbamic acid 3-[2,3-dimethoxy-6-(1-oxo-indan-4-yl)-phenoxy]-2,2-dimethyl-propyl ester (Compound 211) | *** |
| Ethyl-carbamic acid 3-[2,3-dimethoxy-6-(1-oxo-2,3-dihydro-1H-isoindol-5-yl)-phenoxy]-2,2-dimethyl-propyl ester (Compound 212) | * |
| Ethyl-carbamic acid 3-[2,3-dimethoxy-6-(1-oxo-1,3-dihydro-isobenzofuran-5-yl)-phenoxymethyl]-oxetan-3-ylmethyl ester (Compound 213) | *** |
| Ethyl-carbamic acid 3-[2,3-dimethoxy-6-(1-oxo-2,3-dihydro-1H-isoindol-5-yl)-phenoxymethyl]-oxetan-3-ylmethyl ester (Compound 214) | * |
| 5-[3,4-Dimethoxy-2-(3-methoxymethyl-oxetan-3-ylmethoxy)-phenyl]-3H-isobenzofuran-1-one (Compound 215) | *** |
| 5-[3,4-Dimethoxy-2-(3-methoxymethyl-oxetan-3-ylmethoxy)-phenyl]-2,3-dihydro-isoindol-1-one (Compound 216) | *** |
| 4-[3,4-Dimethoxy-2-(3-methoxy-2,2-dimethyl-propoxy)-phenyl]-indan-1-one (Compound 217) | *** |
| 5-[3,4-Dimethoxy-2-(3-methoxy-2,2-dimethyl-propoxy)-phenyl]-3H-isobenzofuran-1-one (Compound 218) | *** |
| 5-[3,4-Dimethoxy-2-(3-methoxy-2,2-dimethyl-propoxy)-phenyl]-2,3-dihydro-isoindol-1-one (Compound 219) | *** |

The invention claimed is:
1. A compound of general formula I

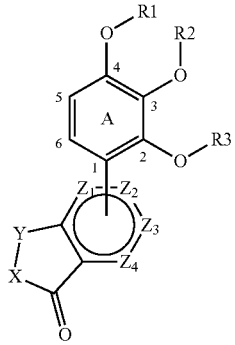

wherein R1 is alkyl, deuterioalkyl, alkenyl, alkynyl, cycloalkyl, heterocycloalkyl, or alkylcarbonyl, each of which is optionally substituted with one or more substituents selected from halogen, cyano, alkyl, alkoxy, hydroxy, and oxo;

R2 represents alkyl, deuterioalkyl, alkenyl, alkynyl, cycloalkyl, heterocycloalkyl, cycloalkylalkyl, heterocycloalkylalkyl, arylalkyl, alkoxycarbonylalkyl, alkylcarbonyl, arylcarbonyl, or alkoxyalkyl, each of which is optionally substituted by one or more, same or different substituents selected from R4;

R3 represents alkyl, alkenyl, alkynyl, alkylaryl, arylalkyl, cycloalkyl, heterocycloalkyl, cycloalkylalkyl, heterocycloalkylalkyl, alkylcycloalkylalkyl, alkylheterocycloalkylalkyl, alkylalkoxycarbonyl, alkoxycarbonylalkyl, alkylcarbonyl, arylcarbonyl, alkoxyalkyl, heterocycloalkylcarbonyl, cycloalkylcarbonyl, heteroarylcarbonyl, alkoxyalkylcarbonyl, cycloalkoxycarbonylalkyl or cycloalkoxyalkyl, each of which is optionally substituted by one or more, same or different substituents selected from R4;

R4 represents oxo, halogen, cyano, hydroxy or nitro; or
R4 represents alkylaryl, alkyl, alkenyl, cycloalkenyl, alkynyl, haloalkyl, cycloalkyl, heterocycloalkenyl, heterocycloalkyl, hydroxyalkyl, alkoxyalkyl, aryl or heteroaryl, each of which is optionally substituted by one or more, same or different substituents selected from R7; or
R4 represents, —NRaRb, —ORa, —SRa, —SO$_2$Ra, —S(O)Ra, —SO$_2$NRaRb, —NRa SO$_2$Rb, —OC(O)NRaRb, —NRaC(O)ORb, —NRaC(O)NRbRc, —NRaC(O)Rb, —C(O)NRaRb, —C(O)Ra, OC(O)Ra, OC(O)ORa, C(O)ORa, —P(O)RaRb, —P(O)(ORa)ORb, —OP(O)RaRb, —OP(O)(ORa)ORb or —NRaS(O)$_2$NRbRc;

R7 represents halogen, hydroxy, oxo or cyano; or
R7 represents alkyl, cycloalkyl, heterocycloalkyl, aryl or heteroaryl, each of which is optionally substituted by one or more, same or different substituents selected from R8;

or R7 represents —ORd, —SRd, —SO$_2$Rd, —SO$_2$NRdRe, —NRd SO$_2$Re, —NRdC(O)Re, —C(O)NRdRe, OC(O)Re, —C(O)ORd, —OC(O)ORe or —NRdC(O)ORe;

R8 represents alkyl, oxo, hydroxy, halogen, alkoxy or haloalkyl;

Ra, Rb and Rc independently represents hydrogen; or
Ra, Rb and Rc independently represents alkylaryl, alkyl, alkenyl, cycloalkenyl, alkynyl, haloalkyl, cycloalkyl, heterocycloalkenyl, heterocycloalkyl, hydroxyalkyl, alkoxyalkyl, aryl or heteroaryl, each of which is optionally substituted by one or more, same or different substituents selected from R7;

Rd and Re independently represents hydrogen; or
Rd and Re independently represents alkyl, alkenyl, cycloalkyl, cycloalkenyl, alkynyl, haloalkyl, heterocycloalkenyl, heterocycloalkyl, aryl, heteroaryl or hydroxyalkyl, each of which is optionally substituted by one or more, same or different substituents selected from R8;

position 1 of ring A is connected to either $Z_1$ or $Z_2$;

X and Y are CRfRg, NRh, O or S, wherein Rf and Rg independently represent H, halogen, cyano, hydroxy, alkyl, alkoxy, haloalkyl, or haloalkoxy; and Rh represents hydrogen, alkyl or haloalkyl; with the proviso that at least one of X and Y represents CRfRg;

$Z_1$, $Z_2$, $Z_3$ and $Z_4$ independently are CRi or N, wherein Ri represents a bond, hydrogen, alkyl, halogen, alkoxy, cyano, haloalkyl, haloalkoxy, or hydroxy; with the proviso that when position 1 of ring A is connected to $Z_1$ then $Z_1$ is CRi; and when position 1 of ring A is connected to $Z_2$ then $Z_2$ is CRi;

and pharmaceutically acceptable and physiologically cleavable esters, pharmaceutically acceptable salts, hydrates, N-oxides or solvates thereof;

with the proviso that when R1=R2=R3=CH$_3$, X=Y=—CH$_2$—, position 1 of ring A is connected to $Z_2$, then at least one of $Z_1$, $Z_3$, and $Z_4$ is different from CH; and with the proviso that when R1=R2=R3=CH$_3$, X=Y=—CH$_2$—, position 1 of ring A is connected to $Z_1$, Z4 is CRi, then Ri is different from methoxy; and with the proviso that when R1=R2=CH$_3$, R3=benzyl, position 1 of ring A is connected to $Z_2$, $Z_1$ is N, $Z_3$=$Z_4$=CRi, Ri=CH$_3$, X=O, Y=CRfRg, Rf=H, then Rg is different from CH$_3$.

2. A compound of general formula I according to claim 1

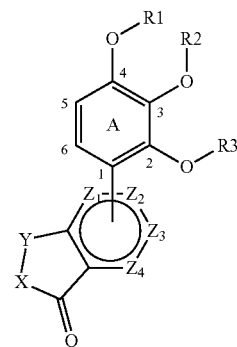

wherein R1 is alkyl, alkenyl, alkynyl, cycloalkyl, heterocycloalkyl, or alkylcarbonyl, each of which is optionally substituted with one or more substituents selected from halogen, cyano, alkyl, alkoxy, hydroxy, and oxo;

R2 represents alkyl, alkenyl, alkynyl, cycloalkyl, heterocycloalkyl, cycloalkylalkyl, heterocycloalkylalkyl, arylalkyl, alkoxycarbonylalkyl, alkylcarbonyl, arylcarbonyl, or alkoxyalkyl, each of which is optionally substituted by one or more, same or different substituents selected from R4;

R3 represents alkyl, alkenyl, alkynyl, alkylaryl, arylalkyl, cycloalkyl, heterocycloalkyl, cycloalkylalkyl, heterocycloalkylalkyl, alkylcycloalkylalkyl, alkylheterocycloalkylalkyl, alkylalkoxycarbonyl, alkoxycarbonylalkyl, alkylcarbonyl, arylcarbonyl, or alkoxyalkyl, each of which is optionally substituted by one or more, same or different substituents selected from R4;

R4 represents oxo, halogen, cyano, hydroxy or nitro; or R4 represents alkylaryl, alkyl, alkenyl, cycloalkenyl, alkynyl, haloalkyl, cycloalkyl, heterocycloalkenyl, heterocycloalkyl, hydroxyalkyl, alkoxyalkyl, aryl or heteroaryl, each of which is optionally substituted by one or more, same or different substituents selected from R7;

or R4 represents, —NRaRb, —ORa, —SRa, —SO$_2$Ra, —S(O)Ra, —SO$_2$NRaRb, —NRaSO$_2$Rb, —OC(O)NRaRb, —NRaC(O)ORb, —NRaC(O)NRbRc, —NRaC(O)Rb, —C(O)NRaRb, —C(O)Ra, OC(O)Ra, OC(O)ORa, or C(O)ORa;

R7 represents halogen, hydroxy, or oxo; or

R7 represents alkyl, cycloalkyl, heterocycloalkyl, aryl or heteroaryl each of which is optionally substituted by one or more, same or different substituents selected from R8; or R7 represents —ORd, —SO$_2$Rd, —SO$_2$NRdRe, —NRdSO$_2$Re, —NRdC(O)Re, —C(O)NRdRe, OC(O)Re, or —C(O)ORd;

R8 represents alkyl, oxo, hydroxy, halogen, alkoxy or haloalkyl;

Ra, Rb, and Rc independently represents hydrogen; or

Ra, Rb and Rc independently represents alkylaryl, alkyl, alkenyl, cycloalkenyl, alkynyl, haloalkyl, cycloalkyl, heterocycloalkenyl, heterocycloalkyl, hydroxyalkyl, alkoxyalkyl, aryl or heteroaryl, each of which is optionally substituted by one or more, same or different substituents selected from R7;

Rd and Re independently represents hydrogen; or

Rd and Re independently represents alkyl, alkenyl, cycloalkyl, cycloalkenyl, alkynyl, haloalkyl, heterocycloalkenyl, heterocycloalkyl, aryl, heteroaryl or hydroxyalkyl, each of which is optionally substituted by one or more, same or different substituents selected from R8;

position 1 of ring A is connected to either $Z_1$ or $Z_2$;

X and Y are CRfRg, NRh, O or S, wherein Rf and Rg independently represent H, halogen, cyano, hydroxy, alkyl, alkoxy, haloalkyl, or haloalkoxy; and Rh represents hydrogen, alkyl or haloalkyl; with the proviso that at least one of X and Y represents CRfRg;

$Z_1$, $Z_2$, $Z_3$ and $Z_4$ independently are CRi or N, wherein Ri represents a bond, hydrogen, alkyl, halogen, alkoxy, cyano, haloalkyl, haloalkoxy, or hydroxy; with the proviso that when position 1 of ring A is connected to $Z_1$ then $Z_1$ is CRi; and when position 1 of ring A is connected to $Z_2$ then $Z_2$ is CRi;

and pharmaceutically acceptable and physiologically cleavable esters, pharmaceutically acceptable salts, hydrates, N-oxides or solvates thereof;

with the proviso that when R1=R2=R3=CH$_3$, X=Y=CH$_2$—, position 1 of ring A is connected to $Z_2$, then at least one of $Z_1$, $Z_3$, and $Z_4$ is different from CH; and with the proviso that when R1=R2=R3=CH$_3$, X=Y=CH$_2$—, position 1 of ring A is connected to $Z_1$, Z4 is CRi, then Ri is different from methoxy; and with the proviso that when R1=R2=CH$_3$, R3=benzyl, position 1 of ring A is connected to $Z_2$, $Z_1$ is N, $Z_3$=$Z_4$=CRi, Ri=CH$_3$, X=O, Y=CRfRg, Rf =H, then Rg is different from CH$_3$.

3. The compound according to claim 1 of the general formula Ia

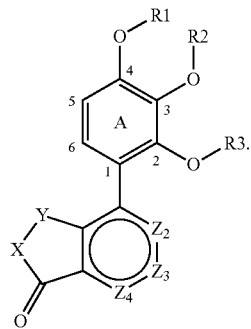

4. The compound according to claim 1 of the general formula Ib

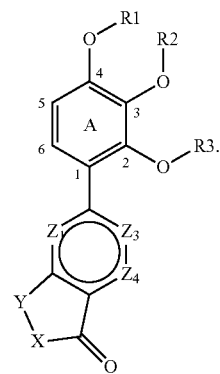

5. The compound of general formula I according to claim 1, wherein:

R1 is alkyl, deuterioalkyl, cycloalkyl, or alkylcarbonyl, each of which is optionally substituted with one or more substituents selected from halogen, alkoxy, and oxo;

R2 represents alkyl, deuterioalkyl, cycloalkyl, heterocycloalkyl, cycloalkylalkyl, heterocycloalkylalkyl, or arylalkyl, each of which is optionally substituted by one or more, same or different substituents selected from R4;

R3 represents alkyl, arylalkyl, cycloalkyl, cycloalkylalkyl, heterocycloalkylalkyl, alkylcycloalkylalkyl, alkylheterocycloalkylalkyl, alkoxyalkylcarbonyl, cycloalkoxycarbonylalkyl, alkylcarbonyl, cycloalkylcarbonyl, or alkoxycarbonylalkyl, each of which is optionally substituted by one or more, same or different substituents selected from R4;

R4 represents oxo, halogen, cyano, or hydroxy; or

R4 represents alkyl, cycloalkyl, heterocycloalkyl, aryl or heteroaryl, each of which is optionally substituted by one or more, same or different substituents selected from R7;

or R4 represents, —NRaRb, —ORa, —SO$_2$Ra, —S(O)Ra, —SO$_2$NRaRb, —NRaSO$_2$Rb, —OC(O)NRaRb, —NRaC(O)ORb, —NRaC(O)Rb, —C(O)NRaRb, —OC(O)Ra, or C(O)ORa;

R7 represents cyano, halogen or hydroxy; or

R7 represents alkyl or heterocycloalkyl, each of which is optionally substituted by one or more, same or different substituents selected from R8; or R7 represents —ORd, —SRd, —SO$_2$Rd, —SO$_2$NRdRe, —NRdSO$_2$Re, —NRdC(O)Re, —C(O)NRdRe, OC(O)Re, or —C(O)ORd;

R8 represents alkyl, hydroxy, or halogen;
Ra, Rb, and Rc independently represents hydrogen; or
Ra, Rb and Rc independently represents alkyl, cycloalkyl, heterocycloalkyl, aryl or heteroaryl, each of which is optionally substituted by one or more, same or different substituents selected from R7;
Rd and Re independently represents hydrogen; or
Rd and Re independently represents alkyl, cycloalkyl, heterocycloalkyl, aryl, or heteroaryl, each of which is optionally substituted by one or more, same or different substituents selected from R8;
position 1 of ring A is connected to either $Z_1$ or $Z_2$;
X and Y are CRfRg, NRh, O or S, wherein Rf and Rg independently represent H, halogen, cyano, alkyl, or alkoxy; and Rh represents hydrogen or alkyl; with the proviso that at least one of X and Y represents CRfRg;
$Z_1$, $Z_2$, $Z_3$ and $Z_4$ independently are CRi or N, wherein Ri represents a bond, hydrogen, alkyl, halogen, or alkoxy;
with the proviso that when position 1 of ring A is connected to $Z_1$ then $Z_1$ is CRi; and when position 1 of ring A is connected to $Z_2$ then $Z_2$ is CRi.

6. The compound according to claim 1, wherein R1 is methyl, ethyl or difluoromethyl.

7. The compound according to claim 1, wherein R2 is methyl, ethyl, cyclopropylmethyl, isobutyl or difluoromethyl.

8. The compound according to claim 1, wherein R3 is alkyl, arylalkyl, cycloalkylalkyl, heterocycloalkylalkyl, alkylcycloalkylalkyl, alkylheterocycloalkylalkyl, alkoxyalkylcarbonyl, cycloalkoxycarbonylalkyl, alkylcarbonyl, cycloalkylcarbonyl, or alkoxycarbonylalkyl, each of which is optionally substituted by one or more, same or different substituents selected from R4.

9. The compound according to claim 8, wherein R3 is isobutyl, neopentyl, benzyl, 1-methyl-cyclopropylmethyl, 3-methyl-oxetan-3-ylmethyl, 3,3-dimethylbutyl, isopentyl, cyclobutylmethyl, or 1-methyl-cyclobutylmethyl, each of which is optionally substituted by one or more, same or different substituents selected from R4.

10. The compound according to claim 1, wherein R4 is selected from the group consisting of hydroxy, —NRaRb, —ORa, —SO₂Ra, —OC(O)NRaRb, —OC(O)Ra, —C(O)NRaRb, —SO₂NRaRb, —NRaSO₂Rb, —NRaC(O)ORb, —NRaC(O)Rb, and C(O)ORa.

11. The compound according to claim 1, wherein Ra, Rb and Rc independently represent hydrogen or alkyl, wherein said alkyl is optionally substituted by one or more substituents selected from halogen, hydroxy and alkoxy.

12. The compound according to claim 11, wherein Ra, Rb and Re independently represent hydrogen or ($C_1$-$C_5$) alkyl, wherein said alkyl is optionally substituted by ($C_1$-$C_5$) alkoxy.

13. The compound according to claim 1, wherein X is CRfRg, NRh, or O.

14. The compound according to claim 1, wherein Y is CRfRg.

15. The compound according to claim 1, wherein Rf, Rg and Rh independently represent hydrogen or alkyl.

16. The compound according to claim 15, wherein Rf, Rg and Rh independently represent hydrogen or ($C_1$-$C_2$) alkyl.

17. The compound according to claim 1, wherein $Z_1$, $Z_2$, $Z_3$ and $Z_4$ independently are CRi.

18. The compound according to claim 1, wherein Ri represents a bond, hydrogen, or alkoxy.

19. The compound according to claim 1, wherein Ri represents a bond, hydrogen or methoxy.

20. The compound according to claim 1, selected from:
4-[3,4-dimethoxy-2-(3-methyl-butoxy)-phenyl]-indan-1-one (Compound 101);
4-(2-cyclobutylmethoxy-3,4-dimethoxy-phenyl)-indan-1-one (Compound 102);
4-[2-(4-methanesulfonyl-benzyloxy)-3,4-dimethoxy-phenyl]-indan-1-one (Compound 103);
4-[2-(3-hydroxymethyl-oxetan-3-ylmethoxy)-3,4-dimethoxy-phenyl]-indan-1-one (Compound 104);
4[2-(3,3-dimethyl-butoxy)-3,4-dimethoxy-phenyl]-indan-1-one (Compound 105); 4-[2,3-Dimethoxy-6-(1-oxo-indan-4-yl)-phenoxymethyl]-benzamide (Compound 106);
4-[2-(3-hydroxy-2,2-dimethyl-propoxy)-3,4-dimethoxy-phenyl]-indan-1-one (Compound 107);
4-[2,3-dimethoxy-6-(1-oxo-indan-4-yl)-phenoxymethyl]-N-methyl-benzamide (Compound 108);
4-[2,3-dimethoxy-6-(1-oxo-indan-4-yl)-phenoxymethyl]-N,N-dimethyl-benzamide (Compound 109);
3-[2,3-dimethoxy-6-(1-oxo-indan-4-yl)-phenoxymethyl]-N,N-dimethyl-benzamide (Compound 110);
3-[2,3-dimethoxy-6-(1-oxo-indan-4-yl)-phenoxymethyl]-N,N-dimethyl-benzenesulfonamide (Compound 111);
4-[2,3-dimethoxy-6-(1-oxo-indan-4-yl)-phenoxymethyl]-benzenesulfonamide (Compound 112);
4[2-(3-methanesulfonyl-benzyloxy)-3,4-dimethoxy-phenyl]-indan-1-one (Compound 113);
3-[2,3-dimethoxy-6-(1-oxo-indan-4-yl)-phenoxymethyl]-benzamide (Compound 114);
4-[2-(4-methanesulfonyl-benzyloxy)-3,4-dimethoxy-phenyl]-3H-isobenzofuran-1-one (Compound 115);
4-[2,3-dimethoxy-6-(1-oxo-1,3-dihydro-isobenzofuran-4-yl)-phenoxymethyl]-benzamide (Compound 116);
4-[2,3-dimethoxy-6-(1-oxo-1,3-dihydro-isobenzofuran-4-yl)-phenoxymethyl]-N-methyl-benzamide (Compound 117);
4-[2,3-dimethoxy-6-(1-oxo-1,3-dihydro-isobenzofuran-4-yl)-phenoxymethyl]-N,N-dimethyl-benzamide (Compound 118);
4-[2-(3-hydroxymethyl-oxetan-3-ylmethoxy)-3,4-dimethoxy-phenyl]-3H-isobenzofuran-1-one (Compound 119);
5-[3,4-dimethoxy-2-(3-methyl-butoxy)-phenyl]-indan-1-one (Compound 120);
5[2-(2,2-dimethyl-propoxy)-3,4-dimethoxy-phenyl]-indan-1-one (Compound 121);
5-(2-cyclobutylmethoxy-3,4-dimethoxy-phenyl)-indan-1-one (Compound 122);
5-[2-(3,3-dimethyl-butoxy)-3,4-dimethoxy-phenyl]-indan-1-one (Compound 123);
4-[2,3-dimethoxy-6-(1-oxo-indan-5-yl)-phenoxymethyl]-benzamide (Compound 124);
5-[2-(3-hydroxy-2,2-dimethyl-propoxy)-3,4-dimethoxy-phenyl]-indan-1-one (Compound 125);
4-[2,3-dimethoxy-6-(1-oxo-indan-5-yl)-phenoxymethyl]-N-methyl-benzamide (Compound 126);
4-[2,3-dimethoxy-6-(1-oxo-indan-5-yl)-phenoxymethyl]-N,N-dimethyl-benzamide (Compound 127);
3-[2,3-dimethoxy-6-(1-oxo-indan-5-yl)-phenoxymethyl]-N,N-dimethyl-benzamide (Compound 128);
5-[2-(3-hydroxymethyl-oxetan-3-ylmethoxy)-3,4-dimethoxy-phenyl]-indan-1-one (Compound 129) 5-[2-(4-methanesulfonyl-benzyloxy)-3,4-dimethoxy-phenyl]-indan-1-one (Compound 130);
5-[3,4-dimethoxy-2-(3-methyl-butoxy)-phenyl]-3H-isobenzofuran-1-one (Compound 131);

5-[2-(2,2-dimethyl-propoxy)-3,4-dimethoxy-phenyl]-3H-isobenzofuran-1-one (Compound 132);
5-(2-cyclobutylmethoxy-3,4-dimethoxy-phenyl)-3H-isobenzofuran-1-one (Compound 133);
5-[2-(3-hydroxymethyl-oxetan-3-ylmethoxy)-3,4-dimethoxy-phenyl]-3H-isobenzofuran-1-one (Compound 134);
5-[2-(3,3-dimethyl-butoxy)-3,4-dimethoxy-phenyl]-3H-isobenzofuran-1-one (Compound 135);
4-[2,3-dimethoxy-6-(1-oxo-1,3-dihydro-isobenzofuran-5-yl)-phenoxymethyl]-benzamide (Compound 136);
5-[2-(3-hydroxy-2,2-dimethyl-propoxy)-3,4-dimethoxy-phenyl]-3H-isobenzofuran-1-one (Compound 137);
4-[2,3-dimethoxy-6-(1-oxo-1,3-dihydro-isobenzofuran-5-yl)-phenoxymethyl]-N-methyl-benzamide (Compound 138);
4-[2,3-dimethoxy-6-(1-oxo-1,3-dihydro-isobenzofuran-5-yl)-phenoxymethyl]-N,N-dimethyl-benzamide (Compound 139);
3-[2,3-dimethoxy-6-(1-oxo-1,3-dihydro-isobenzofuran-5-yl)-phenoxymethyl]-N,N-dimethyl-benzamide (Compound 140);
4-[2,3-dimethoxy-6-(1-oxo-1,3-dihydro-isobenzofuran-5-yl)-phenoxymethyl]-benzenesulfonamide (Compound 141);
5-[2-(4-methanesulfonyl-benzyloxy)-3,4-dimethoxy-phenyl]-3H-isobenzofuran-1-one (Compound 142);
5-[2-(3-methanesulfonyl-benzyloxy)-3,4-dimethoxy-phenyl]-3H-isobenzofuran-1-one (Compound 143);
3-[2,3-dimethoxy-6-(1-oxo-1,3-dihydro-isobenzofuran-5-yl)-phenoxymethyl]-benzenesulfonamide (Compound 144);
3-[2,3-dimethoxy-6-(1-oxo-1,3-dihydro-isobenzofuran-5-yl)-phenoxymethyl]-N,N-dimethyl-benzenesulfonamide (Compound 145);
3-[2,3-dimethoxy-6-(1-oxo-1,3-dihydro-isobenzofuran-5-yl)-phenoxymethyl]-benzamide (Compound 146);
5-[3,4-dimethoxy-2-(3-methyl-butoxy)-phenyl]-2,3-dihydro-isoindol-1-one (Compound 147);
5-[2-(2,2-dimethyl-propoxy)-3,4-dimethoxy-phenyl]-2,3-dihydro-isoindol-1-one (Compound 148);
5-(2-cyclobutylmethoxy-3,4-dimethoxy-phenyl)-2,3-dihydro-isoindol-1-one (Compound 149);
5-[2-(4-methanesulfonyl-benzyloxy)-3,4-dimethoxy-phenyl]-2,3-dihydro-isoindol-1-1-one (Compound 150);
5-[2-(3-hydroxymethyl-oxetan-3-ylmethoxy)-3,4-dimethoxy-phenyl]-2,3-dihydro-isoindol-1-1-one (Compound 151);
5-[2-(3,3-dimethyl-butoxy)-3,4-dimethoxy-phenyl]-2,3-dihydro-isoindol-1-1-one (Compound 152);
4-[2,3-dimethoxy-6-(1-oxo-2,3-dihydro-1H-isoindol-5-yl)-phenoxymethyl]-benzamide (Compound 153);
5-[2-(3-hydroxy-2,2-dimethyl-propoxy)-3,4-dimethoxy-phenyl]-2,3-dihydro-isoindol-1-1-one (Compound 154);
4-[2,3-dimethoxy-6-(1-oxo-2,3-dihydro-1H-isoindol-5-yl)-phenoxymethyl]-N-methyl-benzamide (Compound 155);
4-[2,3-dimethoxy-6-(1-oxo-2,3-dihydro-1H-isoindol-5-yl)-phenoxymethyl]-N,N-dimethyl-benzamide (Compound 156);
3-[2,3-dimethoxy-6-(1-oxo-2,3-dihydro-1H-isoindol-5-yl)-phenoxymethyl]-N,N-dimethyl-benzamide (Compound 157);
3-[2,3-dimethoxy-6-(1-oxo-2,3-dihydro-1H-isoindol-5-yl)-phenoxymethyl]-benzenesulfonamide (Compound 158);
3-[2,3-dimethoxy-6-(1-oxo-2,3-dihydro-1H-isoindol-5-yl)-phenoxymethyl]-benzamide (Compound 159);
5-[2-(3-methanesulfonyl-benzyloxy)-3,4-dimethoxy-phenyl]-2,3-dihydro-isoindol-1-1-one (Compound 160);
4-[2,3-dimethoxy-6-(1-oxo-2,3-dihydro-1H-isoindol-5-yl)-phenoxymethyl]-benzenesulfonamide (Compound 161);
3-[2,3-dimethoxy-6-(1-oxo-indan-4-yl)-phenoxy]-2,2-dimethyl-propionic acid methyl ester (Compound 162);
4-[3,4-dimethoxy-2-(3-methyl-oxetan-3-ylmethoxy)-phenyl]-indan-1-one (Compound 163);
4-[3,4-dimethoxy-2-(3-methyl-oxetan-3-ylmethoxy)-phenyl]-3H-isobenzofuran-1-one (Compound 164);
3-[2,3-dimethoxy-6-(1-oxo-indan-5-yl)-phenoxy]-2,2-dimethyl-propionic acid methyl ester (Compound 165);
4-(2-isobutoxy-3,4-dimethoxy-phenyl)-indan-1-one (Compound 166);
4-(2-isobutoxy-3,4-dimethoxy-phenyl)-6,7-dimethoxy-indan-1-one (Compound 167);
4-(2-isobutoxy-3,4-dimethoxy-phenyl)-7-methoxy-indan-1-one (Compound 168);
5-(2-isobutoxy-3,4-dimethoxy-phenyl)-indan-1-one (Compound 169);
5-(2-isobutoxy-3,4-dimethoxy-phenyl)-3H-isobenzofuran-1-one (Compound 170);
5-(2-isobutoxy-3,4-dimethoxy-phenyl)-2,3-dimethyl-2,3-dihydro-isoindol-1-one (Compound 171);
5-(2-isobutoxy-3,4-dimethoxy-phenyl)-2-methyl-2,3-dihydro-isoindol-1-one (Compound 172);
4-(2-isobutoxy-3,4-dimethoxy-phenyl)-2,3-dihydro-isoindol-1-one (Compound 173);
5-(2-isobutoxy-3,4-dimethoxy-phenyl)-2,3-dihydro-isoindol-1-one (Compound 174);
4-(2-isobutoxy-3,4-dimethoxy-phenyl)-3H-isobenzofuran-1-one (Compound 175);
6-(2-isobutoxy-3,4-dimethoxy-phenyl)-benzofuran-3-one (Compound 176);
4-[2-(1-hydroxymethyl-cyclopropylmethoxy)-3,4-dimethoxy-phenyl]-indan-1-one (Compound 177);
4-[3,4-dimethoxy-2-(1-methoxymethyl-cyclopropylmethoxy)-phenyl]-indan-1-one (Compound 178);
ethyl-carbamic acid 1-[2,3-dimethoxy-6-(1-oxo-indan-4-yl)-phenoxymethyl]-cyclopropylmethyl ester (Compound 179);
isopropyl-carbamic acid 1-[2,3-dimethoxy-6-(1-oxo-indan-4-yl)-phenoxymethyl]-cyclopropylmethyl ester (Compound 180);
benzyl-carbamic acid 1-[2,3-dimethoxy-6-(1-oxo-indan-4-yl)-phenoxymethyl]-cyclopropylmethyl ester (Compound 181);
4-[2-(1-aminomethyl-cyclopropylmethoxy)-3,4-dimethoxy-phenyl]-indan-1-one (Compound 182);
N-{1-[2,3-dimethoxy-6-(1-oxo-indan-4-yl)-phenoxymethyl]-cyclopropylmethyl}-isobutyramide (Compound 183);
N-{1-[2,3-dimethoxy-6-(1-oxo-indan-4-yl)-phenoxymethyl]-cyclopropylmethyl}-butyramide (Compound 184);
N-{1-[2,3-dimethoxy-6-(1-oxo-indan-4-yl)-phenoxymethyl]-cyclopropylmethyl}-acetamide (Compound 185);
{1-[2,3-dimethoxy-6-(1-oxo-indan-4-yl)-phenoxymethyl]-cyclopropylmethyl}-carbamic acid ethyl ester (Compound 186);
{1-[2,3-dimethoxy-6-(1-oxo-indan-4-yl)-phenoxymethyl]-cyclopropylmethyl}-carbamic acid isopropyl ester (Compound 187);

{1-[2,3-dimethoxy-6-(1-oxo-indan-4-yl)-phenoxymethyl]-cyclopropylmethyl}-carbamic acid 2-methoxyethyl ester (Compound 188);

ethyl-carbamic acid 3-[2,3-dimethoxy-6-(1-oxo-indan-4-yl)-phenoxymethy]-oxetan-3-ylmethyl ester (Compound 189);

4-[3,4-dimethoxy-2-(3-methoxymethyl-oxetan-3-ylmethoxy)-phenyl]-indan-1-one (Compound 190);

4-[2-(3-aminomethyl-oxetan-3-ylmethoxy)-3,4-dimethoxy-pheny]indan-1-one (Compound 191);

N- {3-[2,3-dimethoxy-6-(1-oxo-indan-4-yl)-phenoxymethyl]-oxetan-3 -ylmethyl } -acetamide (Compound 192);

N- {3-[2,3-dimethoxy-6-(1-oxo-indan-4-yl)-phenoxymethyl]-oxetan-3-ylmethyl}-isobutyramide (Compound 193);

N- {3-[2,3-dimethoxy-6-(1-oxo-indan-4-yl)-phenoxymethyl]-oxetan-3 -ylmethyl}-butyramide (Compound 194);

N- {3[2,3 -dimethoxy-6-(1-oxo-inclan-4-yl)-phenoxymethyl]-oxetan-3 -ylmethyl}1-2-methoxy-acetamide (Compound 195);

{3-[2,3-dimethoxy-6-(1-oxo-indan-4-yl)-phenoxymethyl]-oxetan-3-ylmethyl}-carbamic acid ethyl ester (Compound 196);

{3-[2,3-dimethoxy-6-(1-oxo-indan-4-yl)-phenoxymethyl]-oxetan-3-ylmethyl}-carbamic acid isopropyl ester (Compound 197);

{3-[2,3-dimethoxy-6-(1-oxo-indan-4-yl)-phenoxymethyl]-oxetan-3-ylmethyl}-carbamic acid 2-methoxyethyl ester (Compound 198);

3-[2,3-dimethoxy-6-(1-oxo-indan-4-yl)-phenoxy]-2,2-dimethyl-propionic acid (Compound 199);

3-[2,3-dimethoxy-6-(1-oxo-indan-4-yl)-phenoxy]-2,2,N-trimethyl-propionamide (Compound 200);

3-[2,3-dimethoxy-6-(1-oxo-indan-4-yl)-phenoxy]-N-ethyl-2,2-dimethyl-propionamide (Compound 201);

3-[2,3-dimethoxy-6-(1-oxo-indan-4-yl)-phenoxy]-2,2,N,N-tetramethyl-propionamide (Compound 202);

N-cyclopropyl-3-[2,3-dimethoxy-6-(1-oxo-indan-4-yl)-phenoxy]-2,2-dimethyl-propionamide (Compound 203);

4-[2-(2,2-dimethyl-3-morpholin-4-yl-3-oxo-propoxy)-3,4-dimethoxy-phenyl]-indan-1-one (Compound 204);

3-[2,3-dimethoxy-6-(1-oxo-indan-5-yl)-phenoxy]-2,2-dimethyl-propionic acid (Compound 205);

3-[2,3-dimethoxy-6-(1-oxo-indan-5-yl)-phenoxy]-2,2,N-trimethyl-propionamide (Compound 206);

3-[2,3-dimethoxy-6-(1-oxo-indan-5-yl)-phenoxy]-2,2,N,N-tetramethyl-propionamide (Compound 207);

3-[2,3-dimethoxy-6-(1-oxo-indan-5-yl)-phenoxy]-N-isopropyl-2,2-dimethyl-propionamide (Compound 208);

3-[2,3-dimethoxy-6-(1-oxo-indan-5-yl)-phenoxy]-2,2-dimethyl-N-propyl-propionamide (Compound 209);

ethyl-carbamic acid 3-[2,3-dimethoxy-6-(1-oxo-1,3-dihydro-isobenzofuran-5-yl)-phenoxy]-2,2-dimethyl-propyl ester (Compound 210);

ethyl-carbamic acid 3-[2,3-dimethoxy-6-(1-oxo-indan-4-yl)-phenoxy]-2,2-dimethyl-propyl ester (Compound 211);

ethyl-carbamic acid 3-[2,3-dimethoxy-6-(1-oxo-2,3-dihydro-1H-isoindol-5-yl)-phenoxy]-2,2-dimethyl-propyl ester (Compound 212);

ethyl-carbamic acid 3-[2,3-dimethoxy-6-(1-oxo-1,3-dihydro-isobenzofuran-5-yl)-phenoxymethyl]-oxetan-3-ylmethyl ester (Compound 213);

ethyl-carbamic acid 3-[2,3-dimethoxy-6-(1-oxo-2,3-dihydro-1H-isoindol-5-yl)-phenoxymethyl]-oxetan-3-ylmethyl ester (Compound 214);

5-[3,4-dimethoxy-2-(3-methoxymethyl-oxetan-3-ylmethoxy)-phenyl]-3H-isobenzofuran-1-one (Compound 215);

5-[3,4-dimethoxy-2-(3-methoxymethyl-oxetan-3-ylmethoxy)-phenyl]-2,3-dihydro-isoindol-1-one (Compound 216);

4-[3,4-dimethoxy-2-(3-methoxy-2,2-dimethyl-propoxy)-phenyl]-indan-1-one (Compound 217);

5-[3,4-dimethoxy-2-(3-methoxy-2,2-dimethyl-propoxy)-phenyl]-3H-isobenzofuran-1-one (Compound 218);

5-[3,4-dimethoxy-2-(3-methoxy-2,2-dimethyl-propoxy)-phenyl]-2,3-dihydro-isoindol-1-one (Compound 219);

3-(2,3-dimethoxy-6-(1-oxo-1,3-dihydroisobenzofuran-5-yl)phenoxy)-2,2-dimethylpropanoic acid (Compound 220);

3-(2,3-dimethoxy-6-(1-oxo-1,3-dihydroisobenzofuran-5-yl)phenoxy)-N,2,2-trimethylpropanamide (Compound 221);

3-(2,3-dimethoxy-6-(1-oxo-1,3-dihydroisobenzofuran-5-yl)phenoxy)-N,N,2,2-tetramethylpropanamide (Compound 222);

3-(2,3-dimethoxy-6-(1-oxo-1,3-dihydroisobenzofuran-5-yl)phenoxy)-N-isopropyl-2,2-dimethylpropanamide (Compound 223);

3-(2,3-dimethoxy-6-(1-oxo-1,3-dihydroisobenzofuran-5-yl)phenoxy)-2,2-dimethyl-N-propylpropanamide (Compound 224);

4-(4-difluoromethoxy-2-ethoxy-3-methoxy-phenyl)-indan-1-one (Compound 225);

4-(4-difluoromethoxy-3-methoxy-2-propoxy-phenyl)-indan-1-one (Compound 226);

4-(4-difluoromethoxy-2-isobutoxy-3-methoxy-phenyl)-indan-1-one (Compound 227);

4-[4-difluoromethoxy-2-(3-hydroxy-2,2-dimethyl-propoxy)-3-methoxy-phenyl]-indan-1-one (Compound 228);

4-[4-difluoromethoxy-3-methoxy-2-(3-methoxy-2,2-dimethyl-propoxy)-phenyl]-indan-1-one (Compound 229);

4-[4-difluoromethoxy-2-(3-hydroxymethyl-oxetan-3-ylmethoxy)-3-methoxy-phenyl]-indan-1-one (Compound 230);

4-[4-difluoromethoxy-3-methoxy-2-(3-methoxymethyl-oxetan-3-ylmethoxy)-phenyl]-indan-1-one (Compound 231);

4-[3-difluoromethoxy-2-methoxy-6-(1-oxo-indan-4-yl)-phenoxymethyl]-benzenesulfonamide (Compound 232);

4-[4-difluoromethoxy-2-(4-methanesulfonyl-benzyloxy)-3-methoxy-phenyl]-indan-1-one (Compound 233);

4-((3-(difluoromethoxy)-2-methoxy-6-(1-oxo-2,3-dihydro-1H-inden-4-yl)phenoxy)methyl)benzamide (Compound 234);

5-(4-difluoromethoxy-2-ethoxy-3-methoxy-phenyl)-3H-isobenzofuran-1-one (Compound 235);

5-(4-difluoromethoxy-3-methoxy-2-propoxy-phenyl)-3H-isobenzofuran-1-one (Compound 236);

5-(4-difluoromethoxy-2-isobutoxy-3-methoxy-phenyl)-3H-isobenzofuran-1-one (Compound 237);

5-[4-difuoromethoxy-2-(3-hydroxy-2,2-dimethyl-propoxy)-3-methoxy-phenyl]-3H-isobenzofuran-1-one (Compound 238);

5-[4-difluoromethoxy-3-methoxy-2-(3-methoxy-2,2-dimethyl-propoxy)-phenyl]-3H-isobenzofuran-1-one (Compound 239);
5-[4-difluoromethoxy-2-(3-hydroxymethyl-oxetan-3-ylmethoxy)-3-methoxy-phenyl]-3H-isobenzofuran-1-one (Compound 240);
4-[3-difluoromethoxy-2-hydroxy-6-(1-oxo-1,3-dihydro-isobenzofuran-5-yl)-phenoxymethyl]-benzenesulfonamide (Compound 241);
5-[4-difluoromethoxy-3-hydroxy-2-(4-methanesulfonyl-benzyloxy)-phenyl]-3H-isobenzofuran-1-one (Compound 242);
5-(4-(difluoromethoxy)-3-methoxy-2-((3-(methoxymethyl)oxetan-3-yl)methoxy)pheny)isobenzofuran-1(3H)-one (Compound 243);
5-(4-(difluoromethoxy)-2-ethoxy-3-methoxyphenyl)isoindolin-1-one (Compound 244);
5-(4-(difluoromethoxy)-3-methoxy-2-propoxyphenyl)isoindolin-1-one (Compound 245);
5-(4-(difluoromethoxy)-2-isobutoxy-3-methoxyphenyl)isoindolin-1-one (Compound 246);
5-[4-difluoromethoxy-3-methoxy-2-(3-hydroxy-2,2-dimethyl-propoxy)-phenyl]-2,3-dihydro-isoindol-1-one (Compound 247);
5-[4-difluoromethoxy-3-methoxy-2-(3-methyl-oxetan-3-ylmethoxy)-phenyl]-2,3-dihydro-isoindol-1-one (Compound 248);
5-[4-difluoromethoxy-2-(3-hydroxymethyl-oxetan-3-ylmethoxy)-3-methoxy-phenyl]-2,3-dihydro-isoindol-1-one (Compound 249);
5-[4-difluoromethoxy-3-methoxy-2-(3-methoxymethyl-oxetan-3-ylmethoxy)-phenyl]-2,3-dihydro-isoindol-1-one (Compound 250);
4-[3-difluoromethoxy-2-methoxy-6-(1-oxo-2,3-dihydro-1H-isoindol-5-yl)-phenoxymethyl]-benzenesulfonamide (Compound 251);
5-[4-difluoromethoxy-2-(4-methanesulfonyl-benzyloxy)-3-methoxy-phenyl]-2,3-dihydro-isoindol-1-one (Compound 252);
4-((3-(difluoromethoxy)-2-methoxy-6-(1-oxoisoindolin-5-yl)phenoxy)methyl)benzamide (Compound 253);
2-[3-difluoromethoxy-2-methoxy-6-(1-oxo-2,3-dihydro-1H-isoindol-5-yl)-phenoxy]-N-propyl-acetamide (Compound 254);
4-(2,4-diethoxy-3-methoxyphenyl)-2,3-dihydro-1H-inden-1-one;
4-(4-ethoxy-3-methoxy-2-propoxyphenyl)-2,3-dihydro-1H-inden-1-one (Compound 256);
4-(4-ethoxy-2-isobutoxy-3-methoxyphenyl)-2,3-dihydro-1H-inden-1-one (Compound 257);
4-(4-ethoxy-2-(3-hydroxy-2,2-dimethylpropoxy)-3-methoxyphenyl)-2,3-dihydro-1H-inden-1-one (Compound 258);
4-(4-ethoxy-3-methoxy-2-((3-methyloxetan-3-yl)methoxy)phenyl)-2,3-dihydro-1H-inden-1-one (Compound 259);
4-(4-ethoxy-2-((3-(hydroxymethyl)oxetan-3-yl)methoxy)-3-methoxyphenyl)-2,3-dihydro-1H-inden-1-one (Compound 260);
4-(4-ethoxy-3-methoxy-2-(4-(methylsulfonyl)benzyloxy)phenyl)-2,3-dihydro-1H-inden-1-one (Compound 261);
5-(2,4-diethoxy-3-methoxyphenyl)isobenzofuran-1(3H)-one (Compound 262);
5-(4-ethoxy-2-isobutoxy-3-methoxyphenyl)isobenzofuran-1(3H)-one (Compound 264);
5-(4-ethoxy-2-(3-hydroxy-2,2-dimethylpropoxy)-3-methoxyphenyl)isobenzofuran-1(3H)-one (Compound 265);
5-(4-ethoxy-3-methoxy-2-((3-methyloxetan-3-yl)methoxy)phenyl)isobenzofuran-1(3H)-one (Compound 266);
5-[4-ethoxy-2-(3-hydroxymethyl-oxetan-3-ylmethoxy)-3-methoxy-phenyl]-3H-isobenzofuran-1-one (Compound 267);
5-(4-ethoxy-3-methoxy-2-(4-(methylsulfonyl)benzyloxy)phenyl)isobenzofuran-1(3H)-one (Compound 268);
4-(3-ethoxy-2,4-dimethoxyphenyl)-2,3-dihydro-1H-inden-1-one (Compound 269);
4-(2,4-dimethoxy-3-propoxyphenyl)-2,3-dihydro-1H-inden-1-one (Compound 270);
4-(3-isobutoxy-2,4-dimethoxyphenyl)-2,3-dihydro-1H-inden-1-one (Compound 271);
4-[3-(3-hydroxy-2,2-dimethyl-propoxy)-2,4-dimethoxy-phenyl]-indan-1-one (Compound 272);
4-(2,4-dimethoxy-3((3-methyloxetan-3-yl)methoxyphenyl)-2,3-dihydro-1H-inden-1-one (Compound 273);
4-(3-((3-(hydroxymethyl)oxetan-3-yl)methoxy)-2,4-dimethoxyphenyl)-2,3-dihydro-1H-inden-1-one (Compound 274);
4[2,4-dimethoxy-3-(3-methoxymethyl-oxetan-3-ylmethoxy)-phenyl]-indan-1-one (Compound 275);
4-[2,6-dimethoxy-3-(1-oxo-indan-4-yl)-phenoxymethyl]-benzenesulfonamide (Compound 276);
4-(2,4-dimethoxy-3-(4-(methylsulfonyl)benzyloxy)phenyl)-2,3-dihydro-1H-inden-1-one (Compound 277);
5-(3-ethoxy-2,4-dimethoxy-phenyl)-3H-isobenzofuran-1-one (Compound 278);
5-(2,4-dimethoxy-3-propoxy-phenyl)-3H-isobenzofuran-1-one (Compound 279);
5-(3-isobutoxy-2,4-dimethoxy-phenyl)-3H-isobenzofuran-1-one (Compound 280);
5-[2,4-dimethoxy-3-(3-methyl-oxetan-3-ylmethoxy)-phenyl]-3H-isobenzofuran-1-one (Compound 281);
5-(3-((3-(hydroxymethyl)oxetan-3-yl)methoxy)-2,4-dimethoxyphenyl)isobenzofuran-1(3H)-one (Compound 282);
5-[2,4-dimethoxy-3-(3-methoxymethyl-oxetan-3-ylmethoxy)-phenyl]-3H-isobenzofuran-1-one (Compound 283);
4-[2,6-dimethoxy-3-(1-oxo-1,3-dihydro-isobenzofuran-5-yl)-phenoxymethyl]-benzenesulfonamide (Compound 284);
5-(2,4-dimethoxy-3-(4-(methylsulfonyl)benzyloxy)phenyl)isobenzofuran-1(3H)-one (Compound 285);
4-[2,6-dimethoxy-3-(1-oxo-1,3-dihydro-isobenzofuran-5-yl)-phenoxymethyl]-benzamide (Compound 286);
4-(3-difluoromethoxy-2-ethoxy-4-methoxy-phenyl)-indan-1-one (Compound 287);
4(3-difluoromethoxy-4-methoxy-2-propoxy-phenyl)-indan-1-one (Compound 288);
4-(3-difluoromethoxy-2-isobutoxy-4-methoxy-phenyl)-indan-1-one (Compound 289);
4-[3-difluoromethoxy-2-(3-hydroxymethyl-oxetan-3-ylmethoxy)-4-methoxy-phenyl]-indan-1-one (Compound 290);
4-[3-difluoromethoxy-4-methoxy-2-(3-methoxymethyl-oxetan-3-ylmethoxy)-phenyl]-indan-1-one (Compound 291);
4-[2-difluoromethoxy-3-methoxy-6-(1-oxo-indan-4-yl)-phenoxymethyl]-benzenesulfonamide (Compound 292);

4-[3-difluoromethoxy-2-(4-methanesulfonyl-benzyloxy)-4-methoxy-phenyil]-indan-1-one (Compound 293);
5-(3-difluoromethoxy-2-ethoxy-4-methoxy-phenyl)-3H-isobenzofuran-1-one (Compound 294);
5-(3-difluoromethoxy-4-methoxy-2-propoxy-phenyl)-3H-isobenzofuran-1-one (Compound 295);
5-(3-difluoromethoxy-2-isobutoxy-4-methoxy-phenyl)-3H-isobenzofuran-1-one (Compound 296);
5-[3-difluoromethoxy-4-methoxy-2-(3-methyl-oxetan-3-ylmethoxy)-phenyl]-3H-isobenzofuran-1-one (Compound 297);
5-[3-difluoromethoxy-2-(3-hydroxymethyl-oxetan-3-ylmethoxy)-4-methoxy-phenyl]-3H-isobenzofuran-1-one (Compound 298);
5-[3-difluoromethoxy-4-methoxy-2-(3-methoxymethyl-oxetan-3-ylmethoxy)-phenyl]-3H-isobenzofuran-1-one (Compound 299);
4-((2-(difluoromethoxy)-3-methoxy-6-(1-oxo-1,3-dihydroisobenzofuran-5-yl)phenoxy)methyl)benzenesulfonamide (Compound 400);
5-(3-(difluoromethoxy)-4-methoxy-2-(4-(methylsulfonyl)benzyloxy)phenyl)isobenzofuran-1(3H)-one (Compound 401);
4-((2-(difluoromethoxy)-3-methoxy-6-(1-oxo-1,3-dihydroisobenzofuran-5-yl)phenoxy)methyl)benzamide (Compound 402);
4-(3-cyclopropylmethoxy-2-ethoxy-4-methoxy-phenyl)-indan-1-one (Compound 403);
4-(3-cyclopropylmethoxy-4-methoxy-2-propoxy-phenyl)-indan-1-one (Compound 404);
4-(3-cyclopropylmethoxy-2-isobutoxy-4-methoxy-phenyl)-indan-1-one (Compound 405);
4-[3-cyclopropylmethoxy-4-methoxy-2-(3-methyl-oxetan-3-ylmethoxy)-phenyl]-indan-1-one (Compound 406);
4-[3-cyclopropylmethoxy-2-(3-hydroxymethyl-oxetan-3-ylmethoxy)-4-methoxy-phenyl]-indan-1-one (Compound 407);
4-[3-cyclopropylmethoxy-4-methoxy-2-(3-methoxymethyl-oxetan-3-ylmethoxy)-phenyl]-indan-1-one (Compound 408);
4-[3-cyclopropylmethoxy-2-(4-methanesulfonyl-benzyloxy)-4-methoxy-phenyl]-indan-1-one (Compound 409);
2-[2-cyclopropylmethoxy-3-methoxy-6-(1-oxo-indan-4-yl)-phenoxy]-N-propyl-acetamide (Compound 410);
5-(3-cyclopropylmethoxy-2-ethoxy-4-methoxy-phenyl)-3H-isobenzofuran-1-one (Compound 411);
5-(3-cyclopropylmethoxy-4-methoxy-2-propoxy-phenyl)-3H-isobenzofuran-1-one (Compound 412);
5-(3-cyclopropylmethoxy-2-isobutoxy-4-methoxy-phenyl)-3H-isobenzofuran-1-one (Compound 413);
5-[3-cyclopropylmethoxy-4-methoxy-2-(3-methyl-oxetan-3-ylmethoxy)-phenyl]-3H-isobenzofuran-1-one (Compound 414);
5-[3-cyclopropylmethoxy-2-(3-hydroxymethyl-oxetan-3-ylmethoxy)-4-methoxy-phenyl]-3H-isobenzofuran-1-one (Compound 415);
5-[3-cyclopropylmethoxy-4-methoxy-2-(3-methoxymethyl-oxetan-3-ylmethoxy)-phenyl]-3H-isobenzofuran-1-one (Compound 416);
5-[3-cyclopropylmethoxy-2-(4-methanesulfonyl-benzyloxy)-4-methoxy-phenyl]-3H-isobenzofuran-1-one (Compound 417);
2-(2-(cyclopropylmethoxy)-3-methoxy-6-(1-oxo-1,3-dihydroisobenzofuran-5-yl)phenoxy)-N-propylacetamide (Compound 418);
5-(3-(cyclopropylmethoxy)-2,4-dimethoxyphenyl)-2,3-dihydro-1H-inden-1-one (Compound 419);
5-(3-(cyclopropylmethoxy)-2,4-dimethoxyphenyl)isobenzofuran-1(3H)-one (Compound 420);
Methyl 3-[2,3-dimethoxy-6-(1-oxo-3H-isobenzofuran-4-yl)phenoxy]-2,2-dimethyl-propanoate; (Compound 421);
Methyl 3-[2,3-dimethoxy-6-(1-oxo-3H-isobenzofuran-5-yl)phenoxy]-2,2-dimethyl-propanoate; (Compound 422);
[2,3-dimethoxy-6-(1-oxoindan-4-yl)phenyl] propanoate;
[2,3-dimethoxy-6-(1-oxoindan-4-yl)phenyl] cyclopropanecarboxylate;
[2,3-dimethoxy-6-(1-oxoindan-4-yl)phenyl] 2-methylpropanoate;
[2,3-dimethoxy-6-(1-oxoindan-4-yl)phenyl] butanoate;
[2,3-dimethoxy-6-(1-oxoindan-4-yl)phenyl] cyclobutanecarboxylate;
[2,3-dimethoxy-6-(1-oxoindan-4-yl)phenyl] 2-methylbutanoate;
[2,3-dimethoxy-6-(1-oxoindan-4-yl)phenyl] 3-methylbutanoate;
[2,3-dimethoxy-6-(1-oxoindan-4-yl)phenyl] pentanoate;
[2,3-dimethoxy-6-(1-oxoindan-4-yl)phenyl] cyclopentanecarboxylate;
[2,3-dimethoxy-6-(1-oxoindan-4-yl)phenyl] hexanoate;
[2,3-dimethoxy-6-(1-oxoindan-4-yl)phenyl] 2-ethylbutanoate;
[2,3-dimethoxy-6-(1-oxoindan-4-yl)phenyl] 3,3-dimethylbutanoate;
[2,3-dimethoxy-6-(1-oxoindan-4-yl)phenyl] 3-methylsulfanylpropanoate;
[2,3-dimethoxy-6-(1-oxoindan-4-yl)phenyl] 3,3,3-trifluoropropanoate;
[2,3-dimethoxy-6-(1-oxoindan-4-yl)phenyl] cyclohexanecarboxylate;
[2,3-dimethoxy-6-(1-oxoindan-4-yl)phenyl] 2-cyclopentylacetate;
[2,3-dimethoxy-6-(1-oxoindan-4-yl)phenyl] 2-(2-methoxyethoxy)acetate;
[2,3-dimethoxy-6-(1-oxoindan-4-yl)phenyl] 3-cyclopentylpropanoate;
[2,3-dimethoxy-6-(1-oxoindan-5-yl)phenyl] acetate;
[2,3-dimethoxy-6-(1-oxoindan-5-yl)phenyl] cyclopropanecarboxylate;
[2,3-dimethoxy-6-(1-oxoindan-5-yl)phenyl] butanoate;
[2,3-dimethoxy-6-(1-oxoindan-5-yl)phenyl] 2-methylpropanoate;
[2,3-dimethoxy-6-(1-oxoindan-5-yl)phenyl] cyclobutanecarboxylate;
[2,3-dimethoxy-6-(1-oxoindan-5-yl)phenyl] pentanoate;
[2,3-dimethoxy-6-(1-oxoindan-5-yl)phenyl] 3-methylbutanoate;
[2,3-dimethoxy-6-(1-oxoindan-5-yl)phenyl] 2-methylbutanoate;
[2,3-dimethoxy-6-(1-oxoindan-5-yl)phenyl] cyclopentanecarboxylate;
[2,3-dimethoxy-6-(1-oxoindan-5-yl)phenyl] 2-ethylbutanoate;
[2,3-dimethoxy-6-(1-oxoindan-5-yl)phenyl] hexanoate;
[2,3-dimethoxy-6-(1-oxoindan-5-yl)phenyl] 3,3-dimethylbutanoate;
[2,3-dimethoxy-6-(1-oxoindan-5-yl)phenyl] 3-methylsulfanylpropanoate;
[2,3-dimethoxy-6-(1-oxoindan-5-yl)phenyl] 3,3,3-trifluoropropanoate;

[2,3-dimethoxy-6-(1-oxoindan-5-yl)phenyl] cyclohexanecarboxylate;
[2,3-dimethoxy-6-(1-oxoindan-5-yl)phenyl] 2-cyclopentylacetate;
[2,3-dimethoxy-6-(1-oxoindan-5-yl)phenyl] 2-(2-methoxyethoxy)acetate;
[2,3-dimethoxy-6-(1-oxoindan-5-yl)phenyl] 3-cyclopentylpropanoate;
[2,3-dimethoxy-6-(1-oxo-3H-isobenzofuran-4-yl)phenyl] propanoate;
[2,3-dimethoxy-6-(1-oxo-3H-isobenzofuran-4-yl)phenyl] cyclopropanecarboxylate;
[2,3-dimethoxy-6-(1-oxo-3H-isobenzofuran-4-yl)phenyl] butanoate;
[2,3-dimethoxy-6-(1-oxo-3H-isobenzofuran-4-yl)phenyl] 2-methylpropanoate;
[2,3-dimethoxy-6-(1-oxo-3H-isobenzofuran-4-yl)phenyl] cyclobutanecarboxylate;
[2,3-dimethoxy-6-(1-oxo-3H-isobenzofuran-4-yl)phenyl] pentanoate;
[2,3-dimethoxy-6-(1-oxo-3H-isobenzofuran-4-yl)phenyl] 3-methylbutanoate;
[2,3-dimethoxy-6-(1-oxo-3H-isobenzofuran-4-yl)phenyl] cyclopentanecarboxylate;
[2,3-dimethoxy-6-(1-oxo-3H-isobenzofuran-4-yl)phenyl] 3,3-dimethylbutanoate;
[2,3-dimethoxy-6-(1-oxo-3H-isobenzofuran-4-yl)phenyl] hexanoate;
[2,3-dimethoxy-6-(1-oxo-3H-isobenzofuran-4-yl)phenyl] 2-ethylbutanoate;
[2,3-dimethoxy-6-(1-oxo-3H-isobenzofuran-4-yl)phenyl] 3-methylsulfanylpropanoate;
[2,3-dimethoxy-6-(1-oxo-3H-isobenzofuran-4-yl)phenyl] cyclohexanecarboxylate;
[2,3-dimethoxy-6-(1-oxo-3H-isobenzofuran-4-yl)phenyl] 2-cyclopentylacetate;
[2,3-dimethoxy-6-(1-oxo-3H-isobenzofuran-4-yl)phenyl] 2-(2-methoxyethoxy)acetate;
[2,3-dimethoxy-6-(1-oxo-3H-isobenzofuran-4-yl)phenyl] 3-cyclopentylpropanoate;
[2,3-dimethoxy-6-(1-oxo-3H-isobenzofuran-5-yl)phenyl] acetate;
[2,3-dimethoxy-6-(1-oxo-3H-isobenzofuran-5-yl)phenyl] cyclopropanecarboxylate;
[2,3-dimethoxy-6-(1-oxo-3H-isobenzofuran-5-yl)phenyl] butanoate;
[2,3-dimethoxy-6-(1-oxo-3H-isobenzofuran-5-yl)phenyl] 2-methylpropanoate;
[2,3-dimethoxy-6-(1-oxo-3H-isobenzofuran-5-yl)phenyl] cyclobutanecarboxylate;
[2,3-dimethoxy-6-(1-oxo-3H-isobenzofuran-5-yl)phenyl] 3-methylbutanoate;
[2,3-dimethoxy-6-(1-oxo-3H-isobenzofuran-5-yl)phenyl] pentanoate;
[2,3-dimethoxy-6-(1-oxo-3H-isobenzofuran-5-yl)phenyl] 2-methylbutanoate;
[2,3-dimethoxy-6-(1-oxo-3H-isobenzofuran-5-yl)phenyl] 3,3-dimethylbutanoate;
[2,3-dimethoxy-6-(1-oxo-3H-isobenzofuran-5-yl)phenyl] 2-ethylbutanoate;
[2,3-dimethoxy-6-(1-oxo-3H-isobenzofuran-5-yl)phenyl] 3-methylsulfanylpropanoate;
[2,3-dimethoxy-6-(1-oxo-3H-isobenzofuran-5-yl)phenyl] 2-(2-methoxyethoxy)acetate;
[2,3-dimethoxy-6-(1-oxo-3H-isobenzofuran-5-yl)phenyl] 3-cyclopentylpropanoate;
[2,3-dimethoxy-6-(1-oxoisoindolin-5-yl)phenyl] 2-methylpropanoate;
[2,3-dimethoxy-6-(1-oxoisoindolin-5-yl)phenyl] cyclobutanecarboxylate;
[2,3-dimethoxy-6-(1-oxoisoindolin-5-yl)phenyl] pentanoate;
[2,3-dimethoxy-6-(1-oxoisoindolin-5-yl)phenyl] 3-methylbutanoate;
[2,3-dimethoxy-6-(1-oxoisoindolin-5-yl)phenyl] 2-methylbutanoate;
[2,3-dimethoxy-6-(1-oxoisoindolin-5-yl)phenyl] cyclopentanecarboxylate;
[2,3-dimethoxy-6-(1-oxoisoindolin-5-yl)phenyl] hexanoate;
[2,3-dimethoxy-6-(1-oxoisoindolin-5-yl)phenyl] 3,3-dimethylbutanoate;
[2,3-dimethoxy-6-(1-oxoisoindolin-5-yl)phenyl] 2-ethylbutanoate;
[2,3-dimethoxy-6-(1-oxoisoindolin-5-yl)phenyl] cyclohexanecarboxylate;
[2,3-dimethoxy-6-(1-oxoisoindolin-5-yl)phenyl] 3-cyclopentylpropanoate;
methyl (2R)-3-[2,3-dimethoxy-6-(1-oxoindan-4-yl)phenoxy]-2-methyl-propanoate;
methyl (2S)-3-[2,3-dimethoxy-6-(1-oxoindan-4-yl)phenoxy]-2-methyl-propanoate;
methyl 1-[[2,3-dimethoxy-6-(1-oxoindan-4-yl)phenoxy]methyl]cyclopropanecarboxylate;
ethyl (2S)-3-[2,3-dimethoxy-6-(1-oxoindan-4-yl)phenoxy]-2-methyl-propanoate;
ethyl (2R)-3-[2,3-dimethoxy-6-(1-oxoindan-4-yl)phenoxy]-2-methyl-propanoate;
ethyl 1-[[2,3-dimethoxy-6-(1-oxoindan-4-yl)phenoxy]methyl]cyclopropanecarboxylate;
methyl 1-[[2,3-dimethoxy-6-(1-oxoindan-4-yl)phenoxy]methyl]cyclobutanecarboxylate;
ethyl 3-[2,3-dimethoxy-6-(1-oxoindan-4-yl)phenoxy]-2,2-dimethyl-propanoate;
propyl (2R)-3-[2,3-dimethoxy-6-(1-oxoindan-4-yl)phenoxy]-2-methyl-propanoate;
propyl (2S)-3-[2,3-dimethoxy-6-(1-oxoindan-4-yl)phenoxy]-2-methyl-propanoate;
isopropyl (2S)-3-[2,3-dimethoxy-6-(1-oxoindan-4-yl)phenoxy]-2-methyl-propanoate;
isopropyl (2R)-3-[2,3-dimethoxy-6-(1-oxoindan-4-yl)phenoxy]-2-methyl-propanoate;
propyl 1-[[2,3-dimethoxy-6-(1-oxoindan-4-yl)phenoxy]methyl]cyclopropanecarboxylate;
ethyl 1-[[2,3-dimethoxy-6-(1-oxoindan-4-yl)phenoxy]methyl]cyclobutanecarboxylate;
isopropyl 1-[[2,3-dimethoxy-6-(1-oxoindan-4-yl)phenoxy]methyl]cyclopropanecarboxylate;
propyl 3-[2,3-dimethoxy-6-(1-oxoindan-4-yl)phenoxy]-2,2-dimethyl-propanoate;
isopropyl 3-[2,3-dimethoxy-6-(1-oxoindan-4-yl)phenoxy]-2,2-dimethyl-propanoate;
cyclobutyl 1-[[2,3-dimethoxy-6-(1-oxoindan-4-yl$_p$phenoxy]methyl]cyclopropanecarboxylate;
isobutyl 1-[[2,3-dimethoxy-6-(1-oxoindan-4-yl)phenoxy]methyl]cyclopropanecarboxylate;
propyl 1-[[2,3-dimethoxy-6-(1-oxoindan-4-yl)phenoxy]methyl]cyclobutanecarboxylate;
butyl 1-[[2,3-dimethoxy-6-(1-oxoindan-4-yl)phenoxy]methyl]cyclopropanecarboxylate;
cyclobutyl 3-[2,3-dimethoxy-6-(1-oxoindan-4-yl)phenoxy]-2,2-dimethyl-propanoate;

isopropyl 1-[[2,3-dimethoxy-6-(1-oxoindan-4-yl)phenoxy]methyl]cyclobutanecarboxylate;
butyl 3-[2,3-dimethoxy-6-(1-oxoindan-4-yl)phenoxy]-2,2-dimethyl-propanoate;
isobutyl 3-[2,3-dimethoxy-6-(1-oxoindan-4-yl)phenoxy]-2,2-dimethyl-propanoate;
3-fluoropropyl 1-[[2,3-dimethoxy-6-(1-oxoindan-4-yl)phenoxy]methyl]cyclopropanecarboxylate;
cyclobutyl 1-[[2,3-dimethoxy-6-(1-oxoindan-4-Aphenoxy]methyl]cyclobutanecarboxylate;
cyclopentyl 1-[[2,3-dimethoxy-6-(1-oxoindan-4-yl)phenoxy]methyl]cyclopropanecarboxylate;
cyclobutylmethyl 1-[[2,3-dimethoxy-6-(1-oxoindan-4-yl)phenoxy]methyl]cyclopropanecarboxylate;
cyclopentyl 3-[2,3-dimethoxy-6-(1-oxoindan-4-yl)phenoxy]-2,2-dimethyl-propanoate;
cyclobutylmethyl 3-[2,3-dimethoxy-6-(1-oxoindan-4-yl)phenoxy]-2,2-dimethyl-propanoate;
1-ethylpropyl 1-[[2,3-dimethoxy-6-(1-oxoindan-4-yl)phenoxy]methyl]cyclopropanecarboxylate;
butyl 1-[[2,3-dimethoxy-6-(1-oxoindan-4-yl)phenoxy]methyl]cyclobutanecarboxylate;
2,2-dimethylpropyl 1-[[2,3-dimethoxy-6-(1-oxoindan-4-yl)phenoxy]methyl]cyclopropanecarboxylate;
isobutyl 1-[[2,3-dimethoxy-6-(1-oxoindan-4-yl)phenoxy]methyl]cyclobutanecarboxylate;
2,2-dirnethylpropyl 3-[2,3-dimethoxy-6-(1-oxoindan-4-yl)phenoxy]-2,2-dimethyl-propanoate;
1-ethylpropyl 3-[2,3-dimethoxy-6-(1-oxoindan-4-yl)phenoxy]-2,2-dimethyl-propanoate;
(1-cyano-1-methyl-ethyl) 1-[[2,3-dimethoxy-6-(1-oxoindan-4-yl)phenoxy]methyl]cyclobutanecarboxylate;
cyclohexyl 1-[[2,3-dimethoxy-6-(1-oxoindan-4-yl)phenoxy]methyl]cyclopropanecarboxylate;
cyclopentyl 1-[[2,3-dimethoxy-6-(1-oxoindan-4-yl)phenoxy]methyl]cyclobutanecarboxylate;
1-ethylpropyl 1-[[2,3-dimethoxy-6-(1-oxoindan-4-yl)phenoxy]methyl]cyclobutanecarboxylate;
2,2-dimethylpropyl 1-[[2,3-dimethoxy-6-(1-oxoindan-4-yl)phenoxy]methyl]icyclobutanecarboxylate;
cyclohexyl 3-[2,3-dimethoxy-6-(1-oxoindan-4-yl)phenoxy]-2,2-dimethyl-propanoate; and
cyclohexyl 1-[[2,3-dimethoxy-6-(1-oxoindan-4-yl)phenoxy]methyl]cyclobutanecarboxylate.

21. A pharmaceutical composition comprising a compound according to claim 1 and pharmaceutically acceptable and physiologically cleavable esters, pharmaceutically acceptable salts, hydrates, N-oxides or solvates thereof; together with a pharmaceutically acceptable vehicle or excipient or pharmaceutically acceptable carrier(s).

22. The pharmaceutical composition according to claim 21 further comprising one or more other therapeutically active compound(s).

23. A method for the treatment or amelioration of PDE4-related conditions wherein treatment is effected by the inhibition of PDE4, which comprises administering to a person suffering from at least one of said conditions an effective amount of one or more compounds according to claim 1.

24. The method according to claim 23, wherein the PDE4-related conditions are dermal diseases or conditions.

25. The method according to claim 24, wherein the disease or disorder is selected from proliferative and inflammatory skin disorders.

26. The method according to claim 25, wherein the disease or disorder is selected from psoriasis, cancer, epidermal inflammation, alopecia, skin atrophy, skin aging, dermatitis, urticarial, pruritis and eczema.

27. The method according to claim 25, wherein the disease or disorder is selected from steroid-induced skin atrophy, photo skin aging, atopic dermatitis, seborrheic dermatitis and contact dermatitis.

28. A method of treating or ameliorating dermal diseases or conditions, the method comprising administering to a person suffering from at least one of said diseases an effective amount of one or more compounds according to according to claim 1, optionally together with a pharmaceutically acceptable carrier or one or more excipients, optionally in combination with other therapeutically active compounds.

29. The method according to claim 28, wherein the disease or disorder is selected from proliferative and inflammatory skin disorders.

30. The method according to claim 29, wherein the disease or disorder is selected from psoriasis, cancer, epidermal inflammation, alopecia, skin atrophy, skin aging, dermatitis, urticarial, pruritis and eczema.

31. The method according to claim 29, wherein the disease or disorder is selected from steroid-induced skin atrophy, photo skin aging, atopic dermatitis, seborrheic dermatitis and contact dermatitis.

* * * * *